US012721039B2

(12) United States Patent
Kim et al.

(10) Patent No.: US 12,721,039 B2
(45) Date of Patent: Aug. 25, 2026

(54) COMPOSITION MATERIAL FOR ORGANIC ELECTROLUMINESCENT DEVICE, PLURALITY OF HOST MATERIALS, AND ORGANIC ELECTROLUMINESCENT DEVICE COMPRISING THE SAME

(71) Applicant: DuPont Specialty Materials Korea Ltd., Chungcheongnam-do (KR)

(72) Inventors: Bitnari Kim, Gyeonggi-do (KR); Sang-Hee Cho, Gyeonggi-do (KR); Hyo-Jung Lee, Gyeonggi-do (KR); Hyun-Ju Kang, Gyeonggi-do (KR); Jeong-Eun Yang, Gyeonggi-do (KR); Su-Hyun Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 0 days.

(21) Appl. No.: 18/921,469

(22) Filed: Oct. 21, 2024

(65) Prior Publication Data

US 2025/0127050 A1 Apr. 17, 2025

Related U.S. Application Data

(63) Continuation of application No. 16/981,243, filed as application No. PCT/KR2019/002998 on Mar. 15, 2019, now abandoned.

(30) Foreign Application Priority Data

Mar. 16, 2018 (KR) ........................ 10-2018-0030943
Mar. 12, 2019 (KR) ........................ 10-2019-0028057

(51) Int. Cl.

| | |
|---|---|
| ***H10K 85/60*** | (2023.01) |
| ***C07D 209/94*** | (2006.01) |
| ***C07D 403/10*** | (2006.01) |
| ***C07D 405/04*** | (2006.01) |
| ***C07D 405/10*** | (2006.01) |
| ***C07D 487/04*** | (2006.01) |
| ***C07D 487/16*** | (2006.01) |
| ***C09K 11/02*** | (2006.01) |
| ***C09K 11/06*** | (2006.01) |
| ***H10K 50/11*** | (2023.01) |
| ***H10K 101/00*** | (2023.01) |
| ***H10K 101/10*** | (2023.01) |

(52) U.S. Cl.

CPC ....... *H10K 85/6572* (2023.02); *C07D 209/94* (2013.01); *C07D 403/10* (2013.01); *C07D 405/04* (2013.01); *C07D 405/10* (2013.01); *C07D 487/04* (2013.01); *C07D 487/16* (2013.01); *C09K 11/02* (2013.01); *C09K 11/06* (2013.01); *H10K 85/636* (2023.02); *H10K 85/654* (2023.02); *H10K 85/6574* (2023.02); *C09K 2211/1007* (2013.01); *C09K 2211/1029* (2013.01); *C09K 2211/185* (2013.01); *H10K 50/11* (2023.02); *H10K 2101/10* (2023.02); *H10K 2101/90* (2023.02)

(58) Field of Classification Search

CPC .................................................. H10K 85/6572
See application file for complete search history.

(56) References Cited

U.S. PATENT DOCUMENTS

2017/0170408 A1* 6/2017 Park ...................... H10K 85/40

FOREIGN PATENT DOCUMENTS

KR 20150121337 A * 10/2015 ......... H10K 85/6572

* cited by examiner

*Primary Examiner* — William D Young
(74) *Attorney, Agent, or Firm* — G. Creston Campbell

(57) ABSTRACT

The present disclosure relates to a composition material for an organic electroluminescent device, a plurality of host materials, and an organic electroluminescent device comprising the same. By comprising the composition material for an organic electroluminescent device comprising a specific combination of compounds, an organic electroluminescent device having high luminous efficiency and/or long lifespan characteristics can be produced.

12 Claims, No Drawings

COMPOSITION MATERIAL FOR ORGANIC ELECTROLUMINESCENT DEVICE, PLURALITY OF HOST MATERIALS, AND ORGANIC ELECTROLUMINESCENT DEVICE COMPRISING THE SAME

CLAIM OF BENEFIT OF PRIOR APPLICATION

This application is a continuation of U.S. patent application Ser. No. 16/981,243 filed Sep. 15, 2020, which is the National Stage Entry of PCT/KR2019/002998, filed Mar. 15, 2019, both of which are incorporated by reference herein in their entirety.

TECHNICAL FIELD

The present disclosure relates to a composition material for an organic electroluminescent device, a plurality of host materials, and an organic electroluminescent device comprising the same.

BACKGROUND ART

A small molecular green organic electroluminescent device (OLED) was first developed by Tang, et al., of Eastman Kodak in 1987 by using TPD/ALq3 bi-layer consisting of a light-emitting layer and a charge transport layer. Thereafter, the development of OLEDs was rapidly effected and OLEDs have been commercialized. At present, OLEDs primarily use phosphorescent materials having excellent luminous efficiency in panel implementation. An OLED having high luminous efficiency and/or long lifespan characteristics is required for prolonged use and high resolution of a display.

U.S. Pat. No. 6,902,831 discloses an azulene derivative as an organic electroluminescent compound, and Korean Patent Application Laid-Open Nos. 2016-0022784 and 2017-0001563 disclose an organic electroluminescent device comprising a carbazole derivative and a compound of carbazole-carbazole structure as a plurality of host compounds. However, development for improving performances of an organic electroluminescent device is still required.

DISCLOSURE OF THE INVENTION

Problems to be Solved

The objective of the present disclosure is to provide an organic electroluminescent device having high luminous efficiency and/or long lifespan characteristics, by comprising a composition material for an organic electroluminescent device comprising a specific combination of compounds.

Solution to Problems

The present inventors found that the above objective can be achieved by a composition material for an organic electroluminescent device comprising the compound represented by the following formula 1 and the compound represented by the following formula 2:

(1)

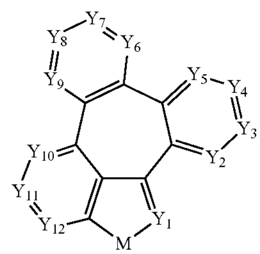

wherein

M represents N-L-$(Ar)_a$, S, or O;

L represents a single bond, a substituted or unsubstituted (C6-C30)arylene, or a substituted or unsubstituted (3- to 30-membered)heteroarylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$Y_1$ to $Y_{12}$, each independently, represent N or $CR_1$;

$R_1$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or adjacent $R_1$'s may be fused with each other to form a substituted or unsubstituted ring; and a represents an integer of 1 to 4, in which if a is an integer of 2 or more, each of Ar may be the same or different;

(2)

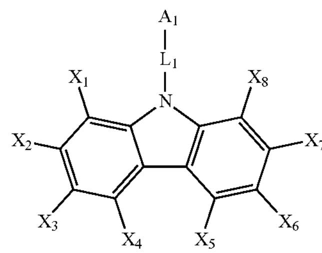

wherein $A_1$ represents a substituted or unsubstituted (C6-C30)aryl, or a substituted or unsubstituted (5- to 30-membered) heteroaryl;

$L_1$ represents a single bond, a substituted or unsubstituted (C6-C30)arylene, or a substituted or unsubstituted (3- to 30-membered)heteroarylene;

$X_1$ to $X_8$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered) heteroaryl, —$NR_5R_6$, or —$SiR_7R_8R_9$; or may be fused with adjacent $X_1$ to $X_8$ to form a ring, with the proviso that any one of $X_1$ to $X_8$ is not a substituted or unsubstituted carbazolyl; and $R_5$ to $R_9$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered) heteroaryl; or may be fused with adjacent $R_5$ to $R_9$ to form a ring.

Effects of the Invention

By using the composition material for an organic electroluminescent device according to the present disclosure, an organic electroluminescent device having high luminous efficiency and/or long lifespan characteristics can be produced.

EMBODIMENTS OF THE INVENTION

Hereinafter, the present disclosure will be described in detail. However, the following description is intended to explain the disclosure, and it is not meant in any way to restrict the scope of the disclosure.

The term "a composition material for an organic electroluminescent device" in the present disclosure means that at least two materials, which may be used in an organic electroluminescent device, are present together or are prepared so as to be present together. Herein, "being present together" means not only that at least two materials are mixed, but also that at least two materials are separated from each other. In addition, the composition material for an organic electroluminescent device is a concept encompassing a material before being comprised in an organic electroluminescent device (for example, before vapor deposition) as well as a material after being comprised in an organic electroluminescent device (for example, after vapor deposition). For example, the composition material for an organic electroluminescent device may comprise at least two among a hole injection material, a hole transport material, a hole auxiliary material, a light-emitting auxiliary material, an electron blocking material, a light-emitting material (a host material and/or a dopant material), an electron buffer material, a hole blocking material, an electron transport material, and an electron injection material. The composition material for an organic electroluminescent device may comprise at least two hole injection materials, at least two hole transport materials, at least two hole auxiliary materials, at least two light-emitting auxiliary materials, at least two electron blocking materials, at least two light-emitting materials (host materials and/or dopant materials), at least two electron buffer materials, at least two hole blocking materials, at least two electron transport materials, and/or at least two electron injection materials. The composition material for an organic electroluminescent device of the present disclosure may be comprised in any layer constituting an organic electroluminescent device. At least two materials comprised in the composition material may be comprised together in one layer or may be comprised in different layers, respectively. When at least two materials are comprised in one layer, they may be mixture-evaporated to form a layer, or may be co-evaporated separately at the same time to form a layer.

The term "a plurality of host materials" in the present disclosure means a host material comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of host materials of the present disclosure may be a combination of at least two host materials, and selectively may further comprise the conventional materials comprised in an organic electroluminescent material. At least two compounds comprised in a plurality of host materials of the present disclosure may be comprised together in one light-emitting layer or may respectively be comprised in different light-emitting layers by the method used in the art. For example, the at least two compounds may be mixture-evaporated or co-evaporated, or may be individually evaporated.

Herein, "(C1-C30)alkyl" is meant to be a linear or branched alkyl having 1 to 30 carbon atoms constituting the chain, in which the number of carbon atoms is preferably 1 to 10, more preferably 1 to 6, and includes methyl, ethyl, n-propyl, isopropyl, n-butyl, isobutyl, tert-butyl, etc. "(C3-C30)cycloalkyl" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms and may be partially saturated, in which the number of ring backbone carbon atoms is preferably 6 to 20, more preferably 6 to 15, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the above aryl may include a phenyl group, a 1-naphthyl group, a 2-naphthyl group, a 1-anthryl group, a 2-anthryl group, a 9-anthryl group, a benzanthryl group, a 1-phenanthryl group, a 2-phenanthryl group, a 3-phenanthryl group, a 4-phenanthryl group, a 9-phenanthryl group, a naphthacenyl group, a pyrenyl group, a 1-chrysenyl group, a 2-chrysenyl group, a 3-chrysenyl group, a 4-chrysenyl group, a 5-chrysenyl group, a 6-chrysenyl group, a benzo[c]phenanthryl group, a benzo[g]chrysenyl group, a 1-triphenylenyl group, a 2-triphenylenyl group, a 3-triphenylenyl group, a 4-triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, an o-terphenyl group, an m-terphenyl-4-yl group, an m-terphenyl-3-yl group, an m-terphenyl-2-yl group, a p-terphenyl-4-yl group, a p-terphenyl-3-yl group, a p-terphenyl-2-yl group, an m-quaterphenyl group, a 3-fluoranthenyl group, a 4-fluoranthenyl group, an 8-fluoranthenyl group, a 9-fluoranthenyl group, a benzofluoranthenyl group, an o-tolyl group, an m-tolyl group, a p-tolyl group, a 2,3-xylyl group, a 3,4-xylyl group, a 2,5-xylyl group, a mesityl group, an o-cumenyl group, an m-cumenyl group, a p-cumenyl group, a p-t-butylphenyl group, a p-(2-phenylpropyl)phenyl group, a 4'-methylbiphenylyl group, a 4"-t-butyl-p-terphenyl-4-yl group, a 9,9-dimethyl-1-fluorenyl group, a 9,9-dimethyl-2-fluorenyl group, a 9,9-dimethyl-3-fluorenyl group, a 9,9-dimethyl-4-fluorenyl group, a 9,9-diphenyl-1-fluorenyl group, a 9,9-diphenyl-2-fluorenyl group, a 9,9-diphenyl-3-fluorenyl group, a 9,9-diphenyl-4-fluorenyl group, etc. "(3- to 50-membered)heteroaryl(ene)" is meant to be an aryl group having at least one, preferably 1 to 4 heteroatoms selected from the group consisting of B, N, O, S, Si, and P, and 3 to 50 ring backbone atoms, in which the number of ring backbone atoms is preferably 3 to 30, more preferably 5 to 20; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzonaphthothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, quinoxazinyl, phenanthridinyl, benzodioxolyl, etc. More specifically, the above heteroaryl may include a 1-pyrrolyl group, a 2-pyrrolyl group, a 3-pyrrolyl group, a pyrazinyl group, a 2-pyridinyl group, a 2-pyrimidinyl group, a 4-pyrimidinyl group, a 5-pyrimidinyl group, a 6-pyrimidinyl group, a 1,2,3-triazin-4-yl group, a 1,2,4-triazin-3-yl group, a 1,3,5-triazin-2-yl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, an azacarbazolyl-1-yl group, an azacarbazolyl-2-yl group, an azacarbazolyl-3-yl group, an azacarbazolyl-4-yl group, an azacarbazolyl-5-yl group, an azacarbazolyl-6-yl group, an azacarbazolyl-7-yl group, an azacarbazolyl-8-yl group, an azacarbazolyl-9-yl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl) pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group. "Halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or functional group, i.e., a substituent. The substituents of the substituted alkyl, the substituted alkoxy, the substituted cycloalkyl, the substituted cycloalkenyl, the substituted heterocycloalkyl, the substituted aryl(ene), the substituted heteroaryl(ene), the substituted trialkylsilyl, the substituted triarylsilyl, the substituted dialkylarylsilyl, the substituted alkyldiarylsilyl, the substituted mono- or di-alkylamino, the substituted mono- or di-arylamino, and the substituted alkylarylamino in Ar, L, $R_1$ to $R_9$, $R_{16}$, $A_1$, $L_1$, and $X_1$ to $X_8$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (3- to 7-membered)heterocycloalkyl; a (C6-C30)aryloxy; a (C6-C30)arylthio; a (3- to 50-membered)heteroaryl unsubstituted or substituted with a (C1-C30)alkyl, a (C6-C30)aryl, and/or a di(C6-C30)arylamino; a (C6-C30)aryl unsubstituted or substituted with a cyano, a (3- to 50-membered)heteroaryl, and/or a tri(C6-C30)arylsily; a tri(C1-C30)alkylsilyl, a tri(C6-C30)arylsilyl; a di(C1-C30) alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl (C6-C30)aryl. Preferably, the substituent may be at least one selected from the group consisting of a (C1-C20)alkyl; a (C6-C25)aryl unsubstituted or substituted with a (C1-C20) alkyl and/or a (3- to 30-membered)heteroaryl; a (3- to 40-membered)heteroaryl unsubstituted or substituted with a (C1-C20)alkyl and/or a (C6-C25)aryl; and a di(C6-C20) arylamino. For example, the substituents may be methyl; tert-butyl; phenyl unsubstituted or substituted with pyridinyl, diphenyltriazinyl, phenylquinoxalinyl, phenylquinazolinyl, biphenylquinazolinyl, dibenzofuranyl and/or dibenzothiophenyl; naphthyl unsubstituted or substituted with diphenyltriazinyl; biphenyl; naphthylphenyl; terphenyl; dimethylfluorenyl; phenylfluorenyl; diphenylfluorenyl; phenanthrenyl; triphenylenyl; pyridinyl; triazinyl substituted with at least one of phenyl and naphthyl; indolyl substituted with diphenyl; benzoimidazole substituted with phenyl; quinolyl; quinazolinyl substituted with phenyl and/or biphenyl; quinoxalinyl substituted with phenyl; carbazolyl unsubstituted or substituted with phenyl; dibenzofuranyl; dibenzothiophenyl; benzocarbazolyl unsubstituted or substituted with phenyl; dibenzocarbazolyl; benzophenanthrothiophenyl; diphenylamino; dimethylfluorenylphenylamino; or a substituted or unsubstituted (16- to 33-membered)heteroaryl containing at least one of nitrogen, oxygen, or sulfur.

In the formulas of the present disclosure, if adjacent substituents are linked to or fused with each other to form a substituted or unsubstituted (3- to 30-membered) ring, the ring may be a mono- or polycyclic, alicyclic or aromatic ring, or the combination thereof, in which the ring may contain at least one heteroatom selected from nitrogen, oxygen, and sulfur. For example, the ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl (ene) may each independently contain at least one heteroatom selected from B, N, O, S, Si, and P. In addition, the heteroatom may be combined with at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri (C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

In formula 1 above, M represents N-L-$(Ar)_a$, S, or O.

In formula 1 above, L represents a single bond, a substituted or unsubstituted (C6-C30)arylene, or a substituted or unsubstituted (3- to 30-membered)heteroarylene; preferably a single bond, a substituted or unsubstituted (C6-C25) arylene, or a substituted or unsubstituted (5- to 25-membered)heteroarylene; and more preferably a single bond, an unsubstituted (C6-C18)arylene, or an unsubstituted (5- to 18-membered)heteroarylene, in which the heteroarylene may contain at least one of nitrogen, oxygen, and sulfur. According to an embodiment of the present disclosure, in formula 1, L may represent a single bond, a substituted or unsubstituted phenylene, a substituted or unsubstituted naphthylene, a substituted or unsubstituted biphenylene, a substituted or unsubstituted pyridylene, a substituted or unsubstituted pyrimidylene, a substituted or unsubstituted triazinylene, a substituted or unsubstituted quinazolinylene, a substituted or unsubstituted quinoxalinylene, a substituted or unsubstituted naphthyridinylene, a substituted or unsubstituted benzoquinazolinylene, a substituted or unsubstituted benzothienopyrimidinylene, a substituted or unsubstituted acenaphthopyrimidinylene, a substituted or unsubstituted (13- to 16-membered)heteroarylene containing at least one of nitrogen, oxygen, and sulfur.

In formula 1 above, Ar represents hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; preferably a substituted or unsubstituted (C6-C25)aryl, a substituted or unsubstituted (5- to 30-membered)heteroaryl, or a substituted or unsubstituted di(C6-C25)arylamino; and more preferably a substituted or unsubstituted (C6-C18)aryl, a substituted or unsubstituted (5- to 25-membered)heteroaryl, or a substituted or unsubstituted di(C6-C18)arylamino.

According to an embodiment of the present disclosure, in formula 1, Ar may represent a substituted or unsubstituted phenyl, a substituted or unsubstituted naphthyl, a substituted or unsubstituted biphenyl, a substituted or unsubstituted terphenyl, a substituted or unsubstituted fluorenyl, a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzothienopyrimidinyl, a substituted or unsubstituted benzothienoquinolinyl, a substituted or unsubstituted benzofuroquinolinyl, a substituted or unsubstituted triaindenyl, a substituted or unsubstituted phenanthroimidazolyl, a substituted or unsubstituted (9- to 25-membered)heteroaryl containing at least one of nitrogen, oxygen, and sulfur, a substituted or unsubstituted diphenylamino, a substituted or unsubstituted phenylbiphenylamino, a substituted or unsubstituted diphenylamino, a substituted or unsubstituted fluorenylphenylamino, or a substituted or unsubstituted fluorenylbiphenylamino.

In formula 1 above, a represents an integer of 1 to 4, preferably 1 or 2. If a is an integer of 2 or more, each of Ar may be the same or different.

In formula 1 above, $Y_1$ to $Y_{12}$, each independently, represent N or $CR_1$. According to an embodiment of the present disclosure, all of $Y_1$ to $Y_{12}$ may represent $CR_1$. According to another embodiment of the present disclosure, at least one of $Y_1$ to $Y_{12}$ may represent N.

Herein, $R_1$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or adjacent $R_1$'s may be fused with each other to form a substituted or unsubstituted ring. Preferably, $R_1$ represents hydrogen, a substituted or unsubstituted (C1-C20)alkyl, a substituted or unsubstituted (C6-C25)aryl, a substituted or unsubstituted (5- to 25-membered)heteroaryl, or a substituted or unsubstituted di(C6-C25)arylamino; or adjacent $R_1$'s may be fused with each other to form a substituted or unsubstituted, mono- or polycyclic, (C3-C25) aromatic ring, in which at least one carbon atom of the formed aromatic ring may be replaced with at least one heteroatom selected from nitrogen, oxygen, and sulfur. More preferably, $R_1$ represents hydrogen, a substituted or unsubstituted (C1-C10)alkyl, a substituted or unsubstituted (C6-C18)aryl, a substituted or unsubstituted (5- to 18-membered)heteroaryl, or a substituted or unsubstituted di(C6-C18)arylamino; or adjacent $R_1$'s may be fused with each other to form a substituted or unsubstituted, mono- or polycyclic, (C5-C18) aromatic ring, in which at least one carbon atom of the formed aromatic ring may be replaced with at least one heteroatom selected from nitrogen, oxygen, and sulfur. According to an embodiment of the present disclosure, $R_1$ may represent hydrogen, a substituted or unsubstituted methyl, a substituted or unsubstituted phenyl, a substituted or unsubstituted naphthyl, a substituted or unsubstituted biphenyl, a substituted or unsubstituted pyridyl, a substituted or unsubstituted pyrimidinyl, a substituted or unsubstituted triazinyl, a substituted or unsubstituted quinazolinyl, a substituted or unsubstituted quinoxalinyl, a substituted or unsubstituted phenylbiphenylamino, etc.

According to an embodiment of the present disclosure, in formula 1, at least an adjacent pair of $Y_1$ to $Y_{12}$ represent $CR_1$, and $R_1$'s of the two adjacent $CR_1$'s are fused with each other to independently form the ring represented by any one of the following formulas 1-11 to 1-15, but are not limited thereto. Herein, $Y_1$ and $Y_2$, $R_5$ and $Y_6$, and $Y_9$ and $Y_{10}$ are also regarded as being adjacent to each other. For example, the formed ring may be a substituted or unsubstituted benzene ring, a naphthalene ring, a furan ring, a thiophene ring, a substituted or unsubstituted pyrrole ring, a pyridine ring, a benzofuran ring, a benzothiophene ring, a substituted or unsubstituted indole ring, a dibenzofuran ring, a dibenzothiophene ring, a substituted or unsubstituted carbazole ring, or a phenanthrene ring, including the rings represented by formulas 1-11 to 1-15.

(1-11)

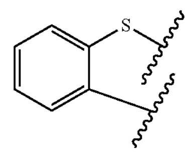

(1-12)

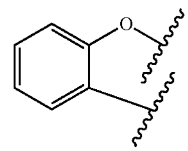

(1-13)

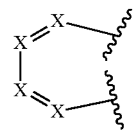

(1-14)

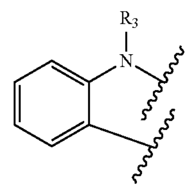

(1-15)

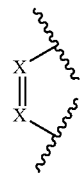

In formulas 1-11 to 1-15 above,  represents a fused site of C and $R_1$ in the adjacent CRI's of formula 1.

In formulas 1-13 to 1-15 above, X represents N or $CR_4$. According to an embodiment of the present disclosure, all X may be $CR_4$. According to another embodiment of the present disclosure, at least one X may be N. $R_4$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino; preferably a substituted or unsubstituted (C6-C25)aryl, or a substituted or unsubstituted (5- to 25-membered)heteroaryl; and more preferably a substituted or unsubstituted (C6-C18)aryl, or a substituted or unsubstituted (5- to 18-membered)heteroaryl.

In formula 1-14 above, $R_3$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; preferably a substituted or unsubstituted (C6-C25)aryl, or a substituted or unsubstituted (5- to 25-membered)heteroaryl; and more preferably a substituted or unsubstituted (C6-C18)aryl, or a substituted or unsubstituted (5- to 18-membered)heteroaryl; for example, phenyl.

The compound represented by formula 1 may be represented by the following formula 1-1 or 1-2.

(1-1)

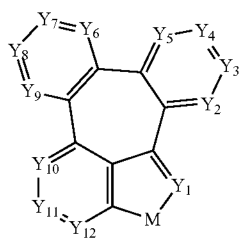

(1-2)

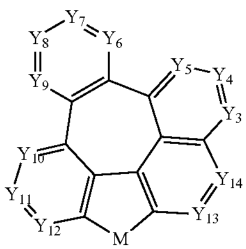

In formulas 1-1 and 1-2 above, M and $Y_2$ to $Y_{12}$ are as defined in formula 1, and $Y_{13}$ and $Y_{14}$, each independently, are as defined for $Y_2$.

In formula 1-1 above, $Y_1$ represents N or $CR_2$, in which $R_2$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino.

In formula 2 above, $A_1$ represents a substituted or unsubstituted (C6-C30)aryl, or a substituted or unsubstituted (5- to 30-membered)heteroaryl; preferably an unsubstituted (C6-C25)aryl, or a (5- to 25-membered)heteroaryl unsubstituted or substituted with a (C6-C30)aryl; and more preferably an unsubstituted (C6-C18)aryl, or a (5- to 18-membered)heteroaryl unsubstituted or substituted with a (C6-C18)aryl. For example, $A_1$ may represent phenyl; naphthyl; biphenyl; terphenyl; triazinyl substituted with at least one of phenyl, naphthyl, and biphenyl; diphenylpyridinyl; phenylquinoline; phenylquinoxaline; phenylquinazolinyl; biphenylquinazolinyl; quinazolinyl substituted with phenylcarbazole; dibenzofuranyl; dibenzothiophenyl; or phenylcarbazolyl.

In formula 2 above, $L_1$ represents a single bond, a substituted or unsubstituted (C6-C30)arylene, or a substituted or unsubstituted (3- to 30-membered)heteroarylene; preferably a single bond, an unsubstituted (C6-C25)arylene, or an unsubstituted (5- to 25-membered)heteroarylene; and more preferably a single bond, an unsubstituted (C6-C18)arylene, or an unsubstituted (5- to 18-membered)heteroarylene. For example, $L_1$ may represent a single bond, phenylene, naphthylene, biphenylene, quinolinylene, quinoxalinylene, quinazolinylene, or carbazolylene.

In formula 2 above, $X_1$ to $X_8$, each independently, represent hydrogen, deuterium, a halogen, a cyano, a carboxyl, a nitro, a hydroxyl, a substituted or unsubstituted (C1-C30) alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $—NR_5R_6$, or $—SiR_7R_8R_9$; or may be fused with adjacent $X_1$ to $X_8$ to form a ring; preferably hydrogen, an unsubstituted (C6-C25)aryl, or an unsubstituted (5- to 25-membered) heteroaryl; or may be fused with adjacent $X_1$ to $X_8$ to form a ring; and more preferably hydrogen, an unsubstituted (C6-C18)aryl, or an unsubstituted (5- to 18-membered) heteroaryl; or may be fused with adjacent $X_1$ to $X_8$ to form a ring. However, any one of $X_1$ to $X_8$ is not a substituted or unsubstituted carbazolyl. For example, $X_1$ to $X_8$, each independently, may represent hydrogen, phenyl, dibenzofuranyl, or dibenzothiophenyl, or may be fused with adjacent $X_1$ to $X_8$ to form a benzene ring, a substituted indole ring, a benzothiophene ring, a benzofuran ring, a substituted benzoindole ring, a naphthofuran ring, a naphthothiophene ring, or an azepine ring. The substituent of the substituted indole ring may be at least one selected from phenyl unsubstituted or substituted with phenyltriazinyl, phenylquinoxalinyl, phenylquinazolinyl, biphenylquinazolinyl, dibenzofuranyl and/or dibenzothiophenyl; an unsubstituted naphthylphenyl; an unsubstituted biphenyl; an unsubstituted terphenyl; quinoxalinyl substituted with phenyl; quinazolinyl substituted with phenyl; and naphthyl substituted with diphenyltriazinyl. The substituent of the substituted benzoindole ring may be at least one selected from phenyl unsubstituted or substituted with benzofuranyl or dibenzothiophenyl; naphthylphenyl; biphenyl; and dibenzofuranyl.

In formula 2 above, $R_5$ to $R_9$, each independently, represent hydrogen, deuterium, a halogen, a cyano, a carboxyl, a nitro, a hydroxyl, a substituted or unsubstituted (C1-C30) alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; or may be fused with adjacent $R_5$ to $R_9$ to form a ring.

The compound represented by formula 2 may be represented by any one of the following formulas 2-1 to 2-8.

(2-1)

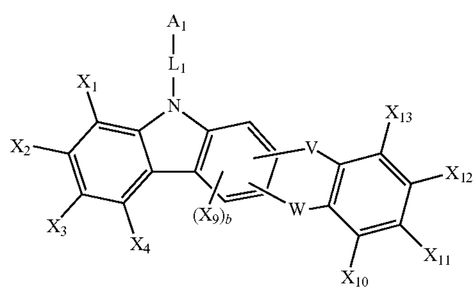

(2-2)

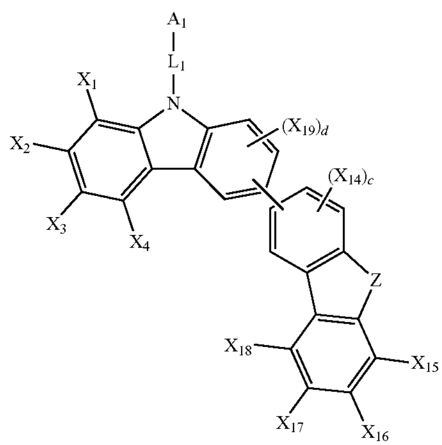

(2-3)

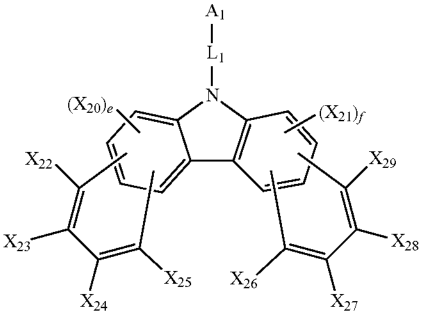

(2-4)

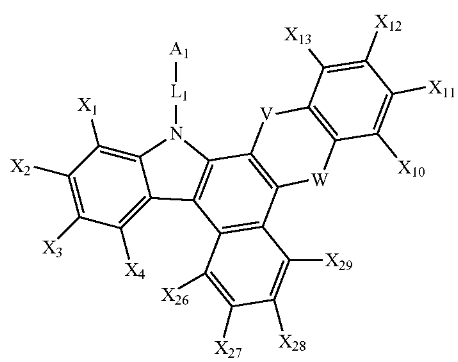

-continued (2-5)

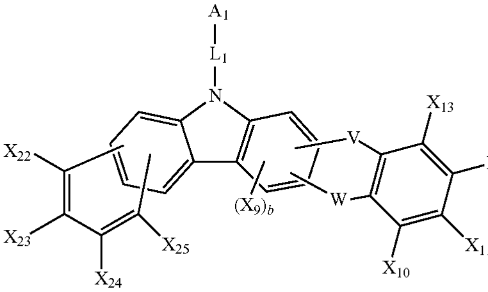

(2-6)

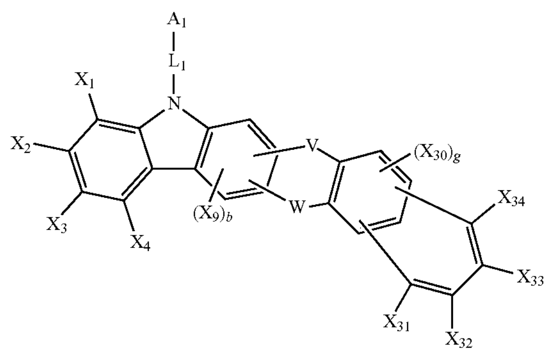

(2-7)

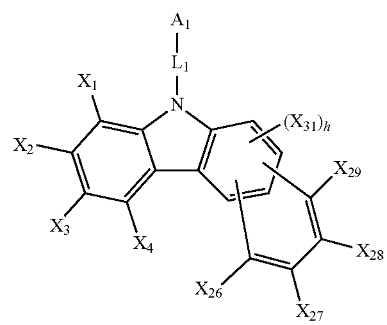

(2-8)

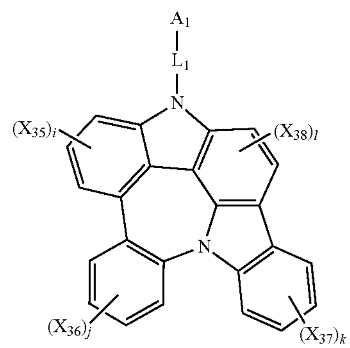

In formulas 2-1 to 2-8 above, $A_1$, $L_1$, and $X_1$ to $X_4$ are as defined in formula 2; $X_9$ to $X_{38}$, each independently, are as defined for $X_1$; b, e, f, g, h, and l, each independently, represent 1 or 2; c, d, and i, each independently, represent an integer of 1 to 3; j and k, each independently, represent an integer of 1 to 4; in which if b to l are an integer of 2 or more, each of $X_9$, $X_{14}$, $X_{19}$, $X_{20}$, $X_{21}$, $X_{30}$, $X_{31}$, and $X_{35}$ to $X_{38}$ may be the same or different. In formula 2-2 above, Z represents O or S.

In formulas 2-1 and 2-4 to 2-6 above, V and W, each independently, represent a single bond, $NR_{16}$, O, or S, with the proviso that both V and W are not a single bond, and both V and W are not $NR_{16}$. According to an embodiment of the present disclosure, one of V and W may represent a single bond, and the other represents $NR_{16}$, O, or S.

$R_{16}$ represents hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30) aryl, or a substituted or unsubstituted (3- to 30-membered) heteroaryl; preferably a (C6-C25)aryl unsubstituted or substituted with a (3- to 30-membered)heteroaryl, or a (5- to 25-membered)heteroaryl unsubstituted or substituted with a (C6-C30)aryl; and more preferably a (C6-C18)aryl unsubstituted or substituted with a (5- to 25-membered)heteroaryl, or a (5- to 18-membered)heteroaryl unsubstituted or substituted with a (C6-C18)aryl. For example, $R_{16}$ may represent phenyl unsubstituted or substituted with diphenyltriazinyl, phenylquinoxalinyl, phenylquinazolinyl, biphenylquinazolinyl, dibenzothiophenyl and/or dibenzofuranyl; naphthyl substituted with diphenyltriazinyl; biphenyl; terphenyl; naphthylphenyl; quinazolinyl substituted with phenyl; or quinoxalinyl substituted with phenyl.

In formulas 2-1 to 2-8 above, $X_1$ to $X_4$, and $X_9$ to $X_{38}$, each independently, represent preferably hydrogen or an unsubstituted (C6-C25)aryl; or may be fused with adjacent $X_1$ to $X_4$ and $X_9$ to $X_{38}$ to form a ring; more preferably represent hydrogen or an unsubstituted (C6-C18)aryl; or may be fused with adjacent $X_1$ to $X_4$ and $X_9$ to $X_{38}$ to form a ring. For example, $X_1$ to $X_4$, and $X_9$ to $X_{30}$, each independently, may represent hydrogen or phenyl; $X_{31}$ to $X_{38}$ may represent hydrogen; $X_1$ and $X_2$, $X_3$ and $X_4$, and adjacent two $X_{21}$'s, each independently, may be fused with each other to form an indole ring substituted with phenyl, or an unsubstituted benzene ring.

The compound represented by formula 1 may be at least one selected from the following compounds, but is not limited thereto.

C-1

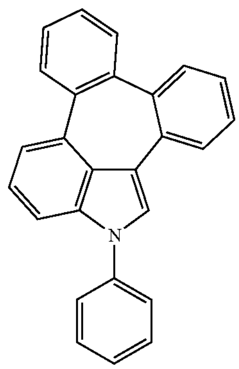

-continued

C-2

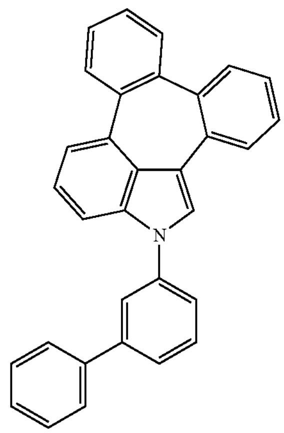

C-3

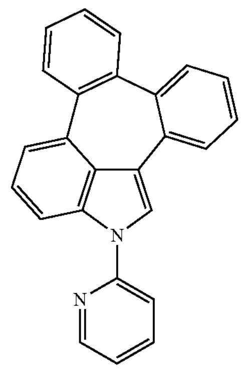

C-4

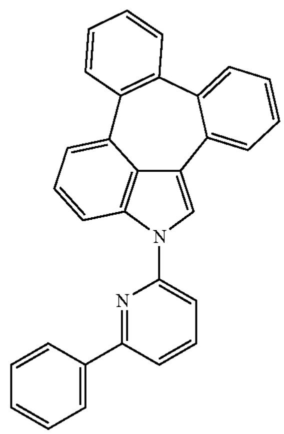

C-5

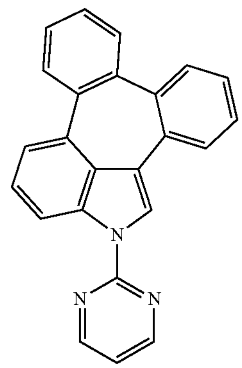

-continued
C-6
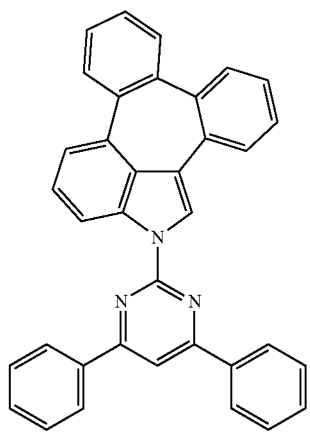
C-7
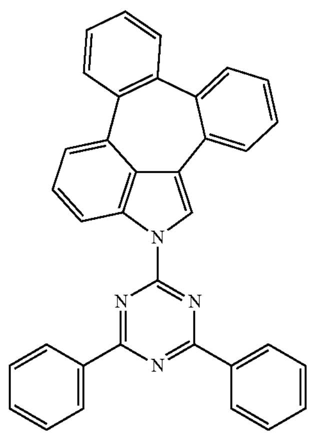
C-8
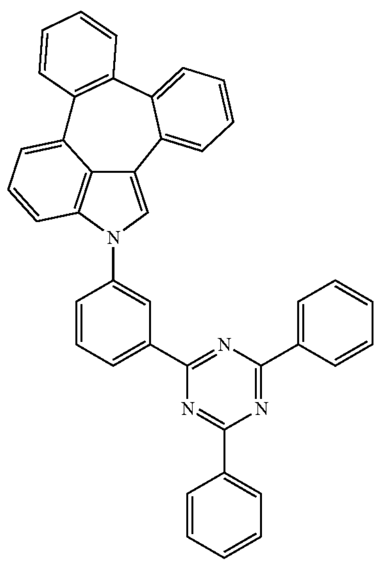
-continued
C-9
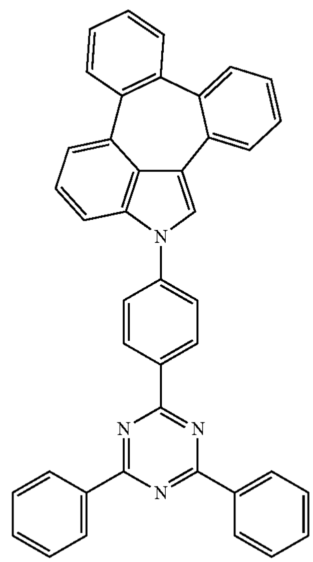
C-10
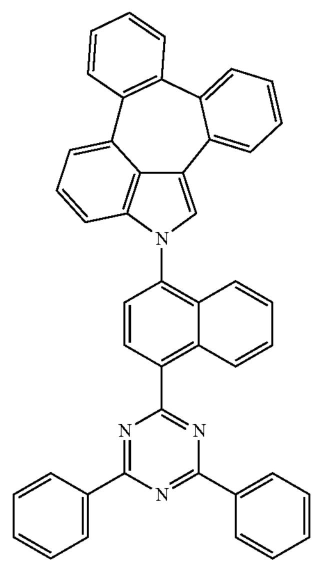
C-11
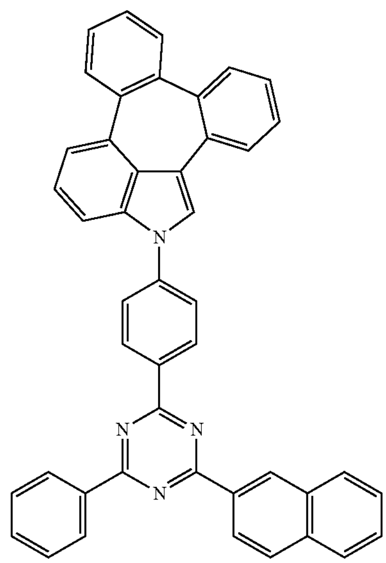

-continued
C-12
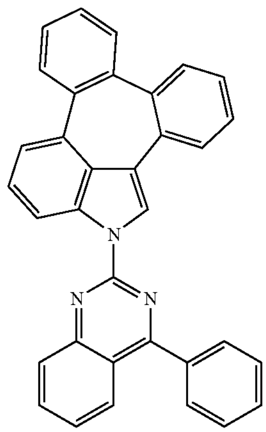
C-13
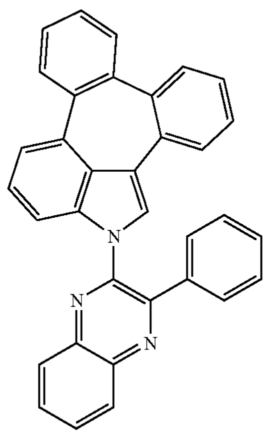
C-14
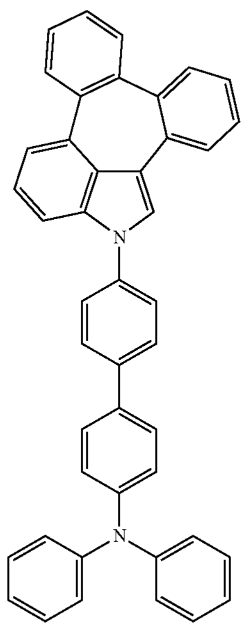
-continued
C-15
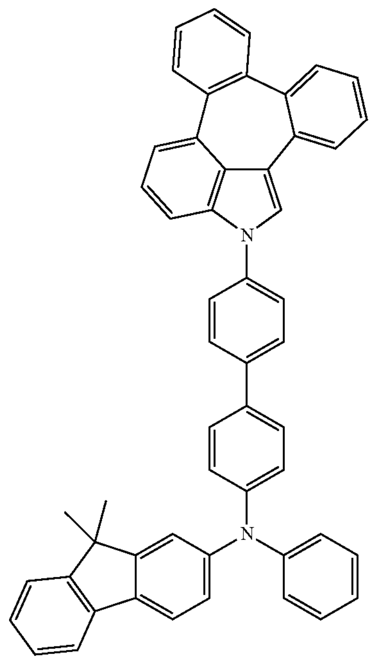
C-16
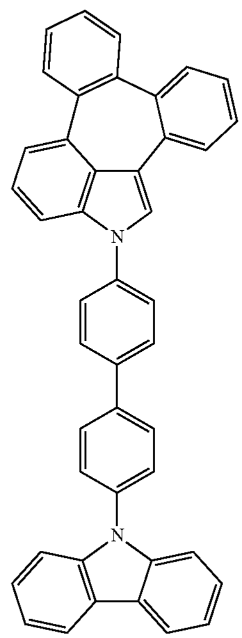
C-17
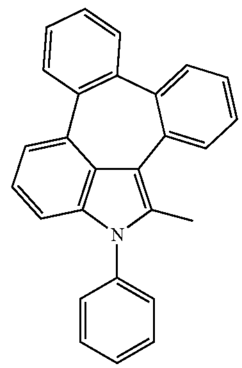

-continued
C-18
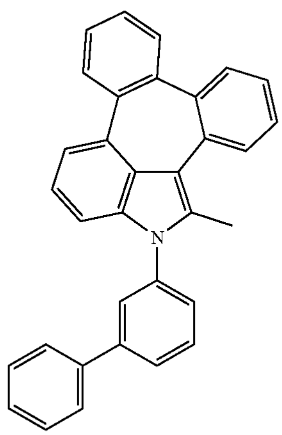
C-19
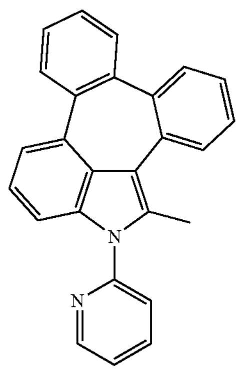
C-20
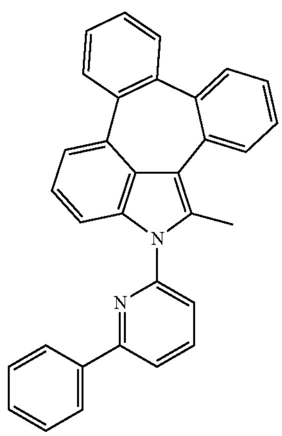
C-21
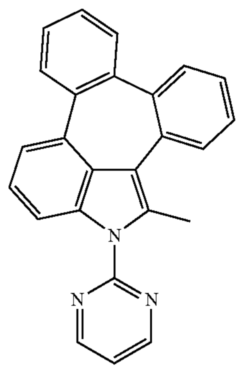
-continued
C-22
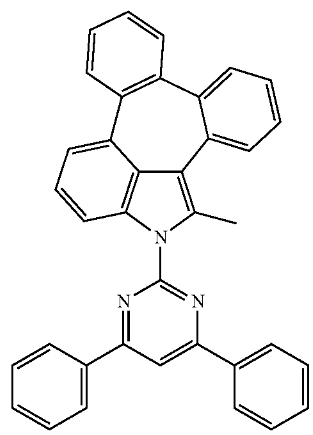
C-23
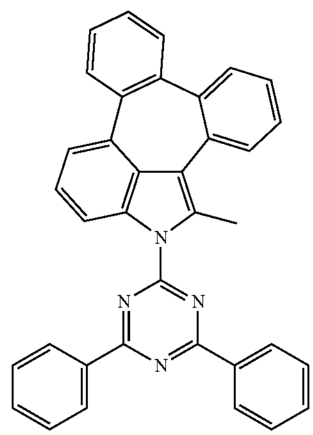
C-24
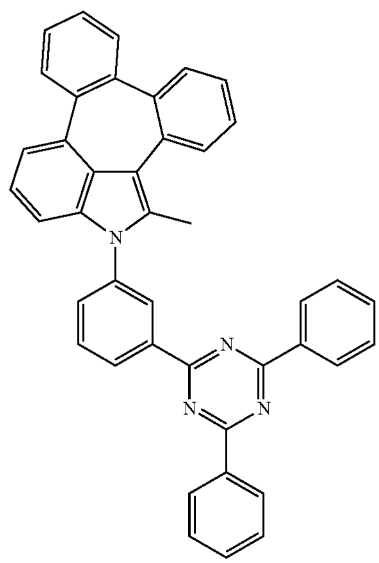

-continued
C-25
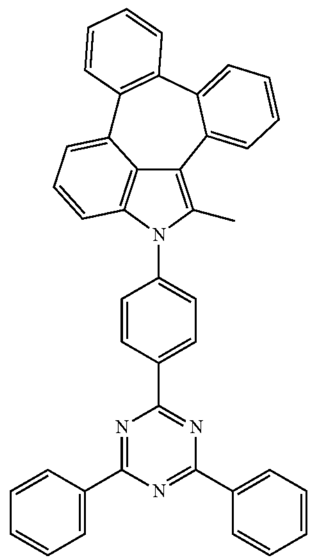
C-26
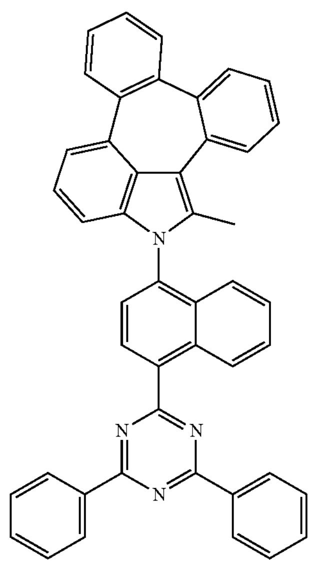
C-27
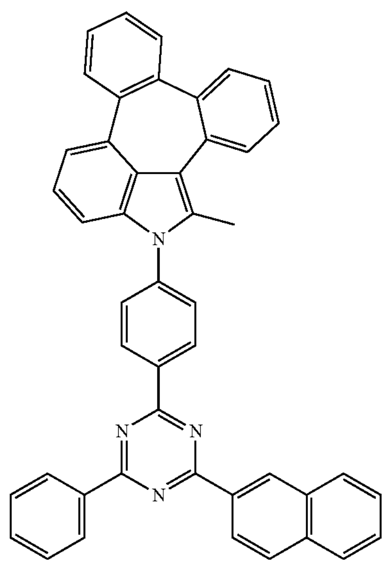
-continued
C-28
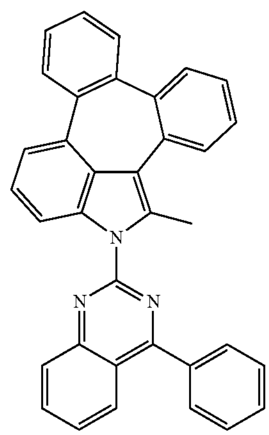
C-29
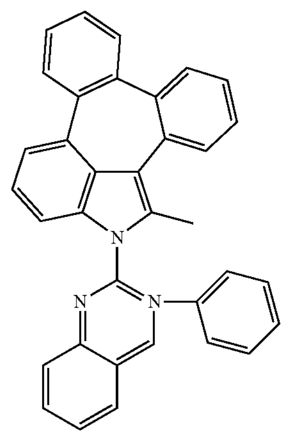
C-30
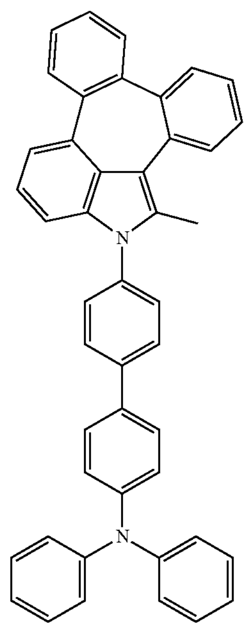

-continued
C-31
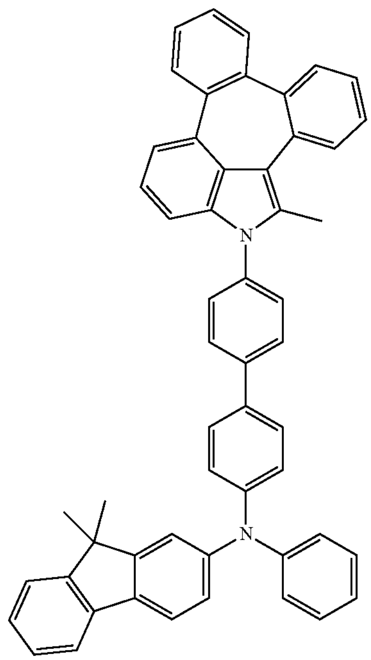
C-32
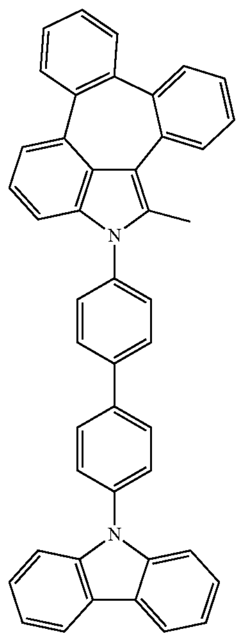
C-33
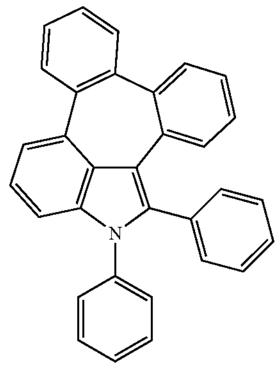
-continued
C-34
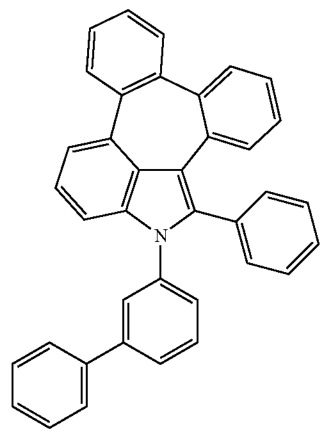
C-35
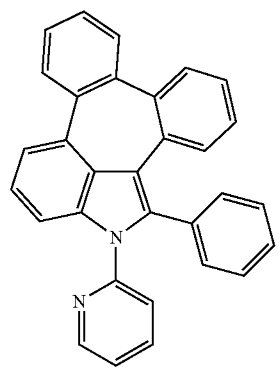
C-36
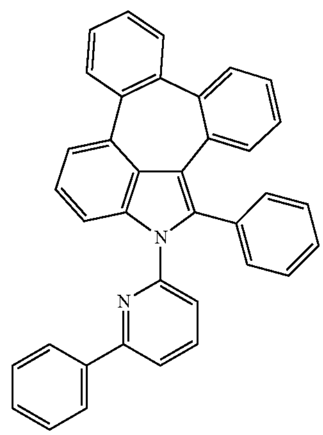
C-37
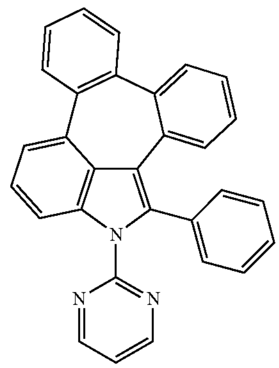

-continued
C-38
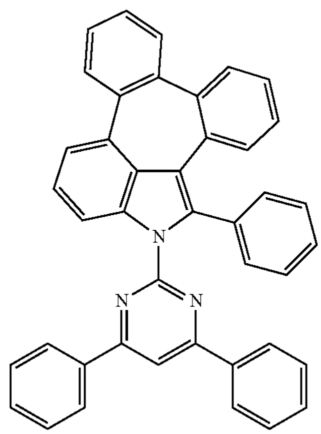
C-39
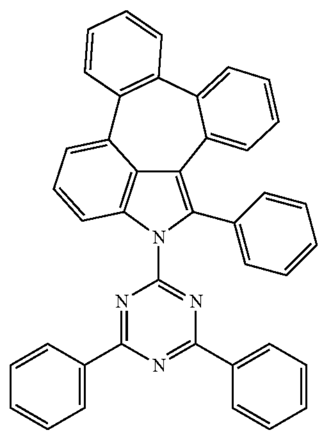
C-40
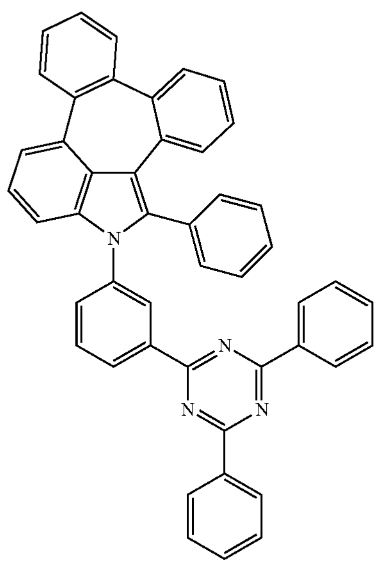
-continued
C-41
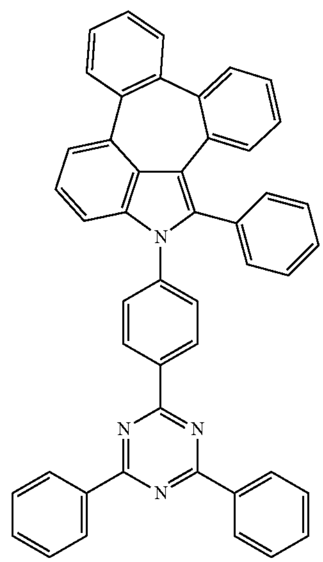
C-42
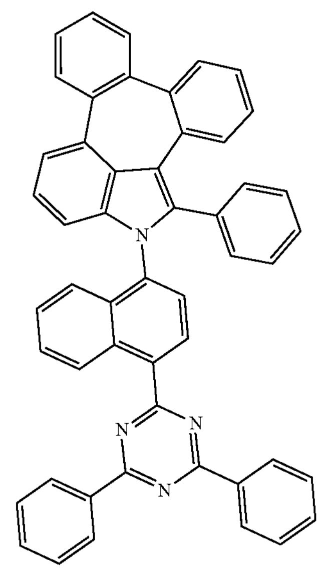

-continued
C-43
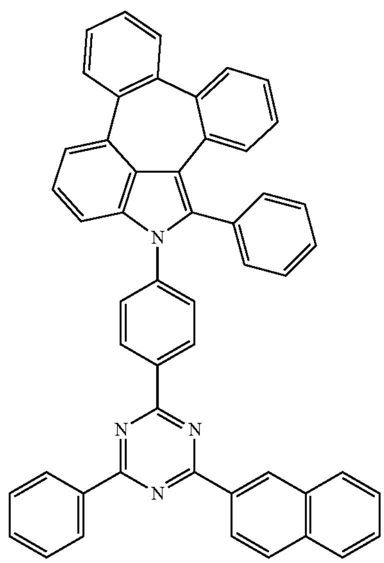
C-44
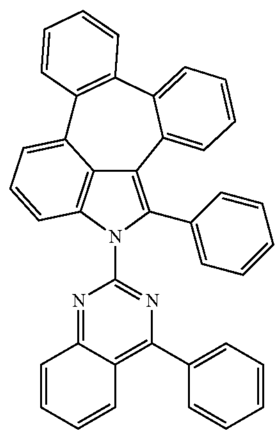
C-45
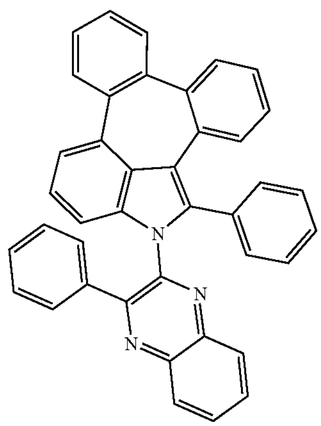
-continued
C-46
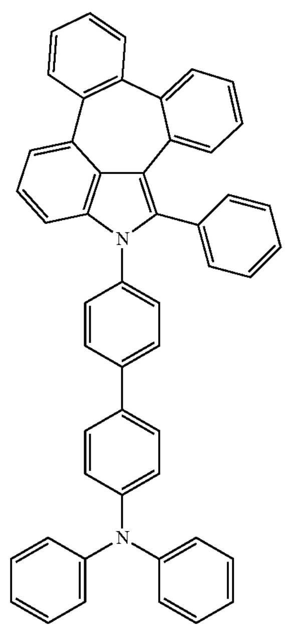
C-47
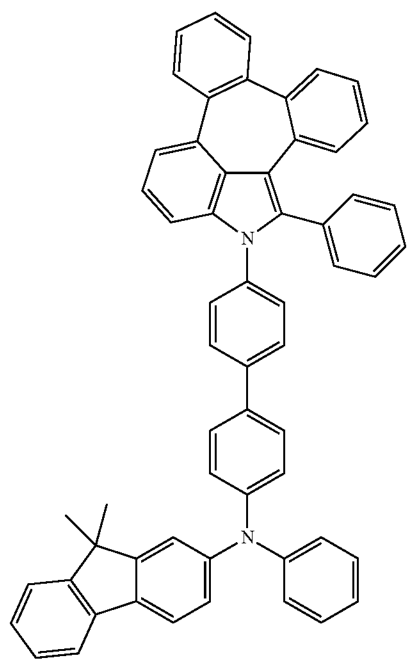

-continued
C-48
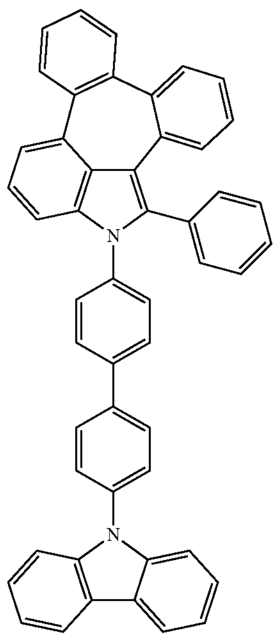
C-49
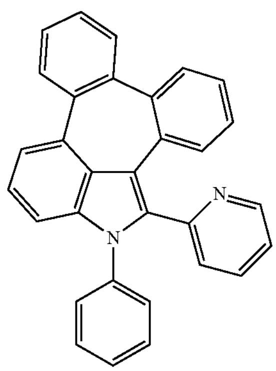
C-50
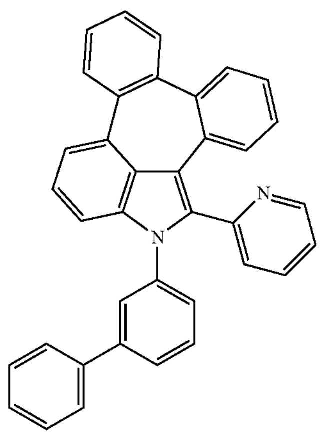
-continued
C-51
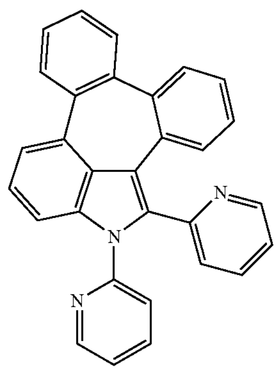
C-52
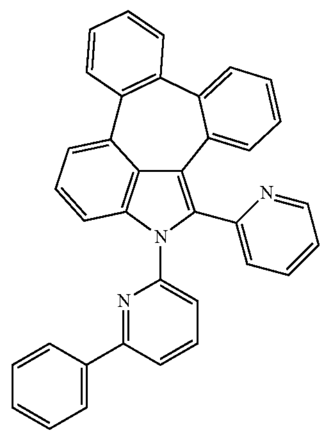
C-53
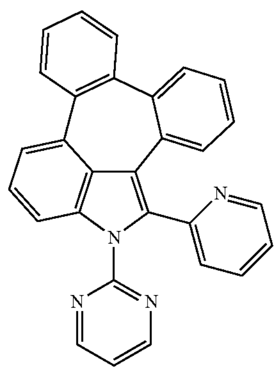
C-54
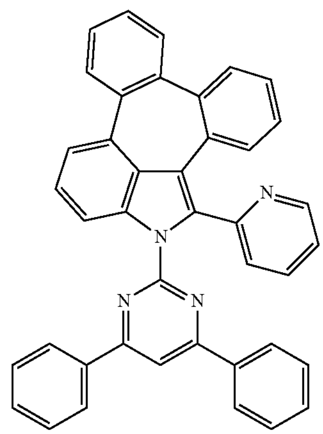

-continued
C-55
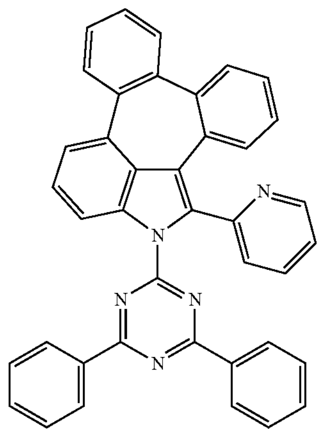
C-56
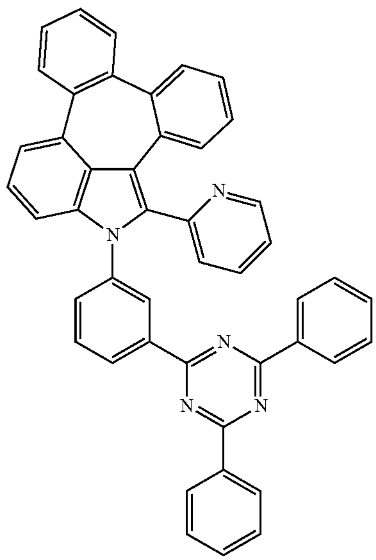
C-57
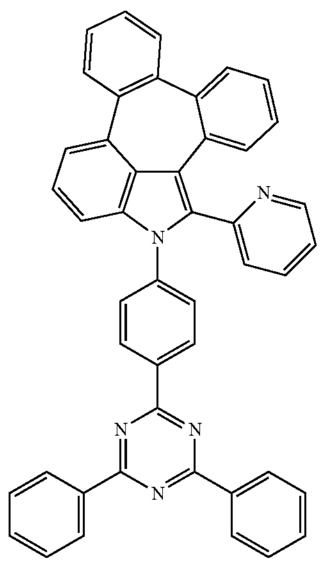
-continued
C-58
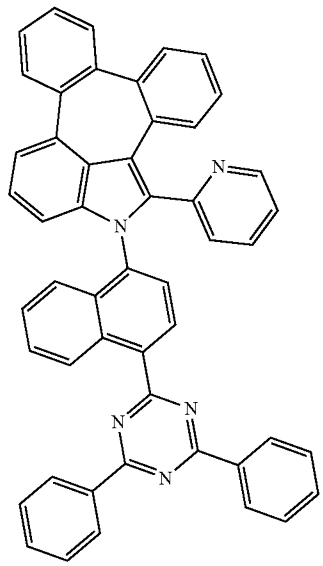
C-59
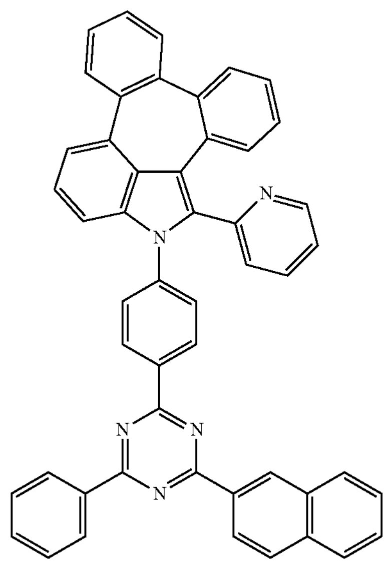
C-60
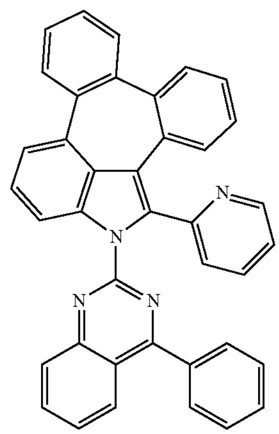

-continued
C-61
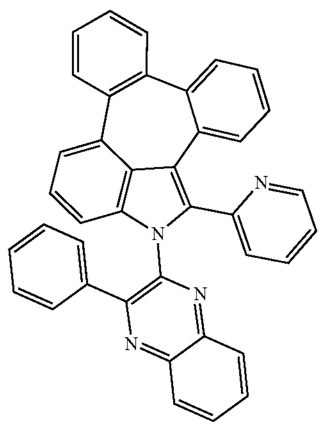
C-62
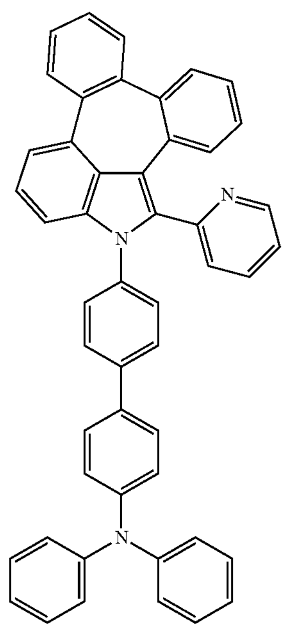
-continued
C-63
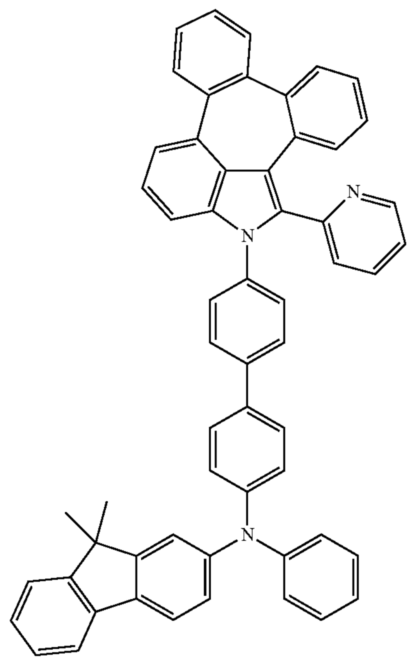
C-64
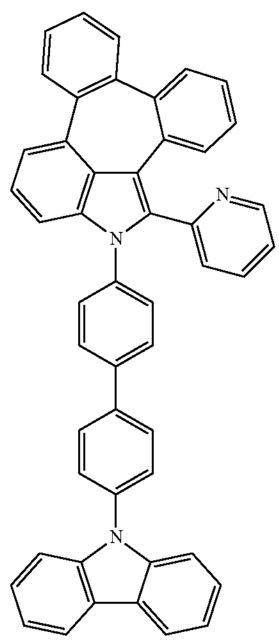
C-65
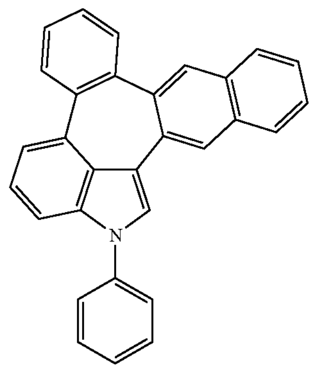

-continued
C-66
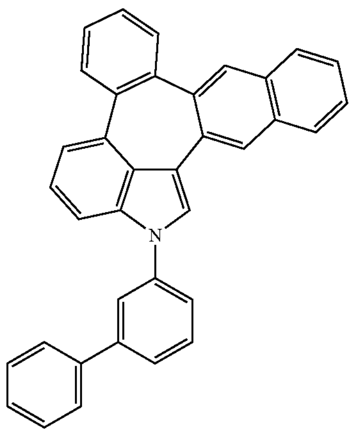
C-67
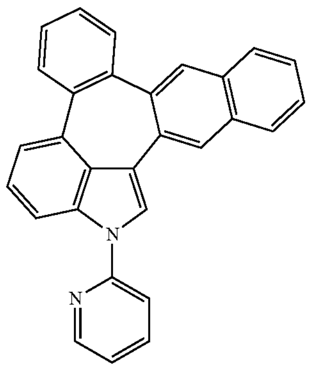
C-68
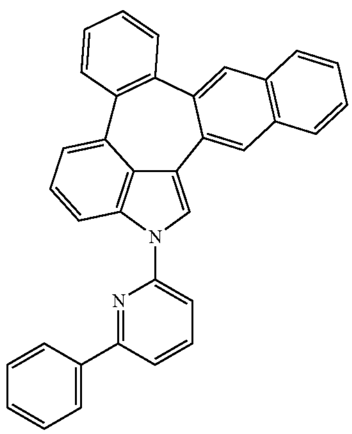
C-69
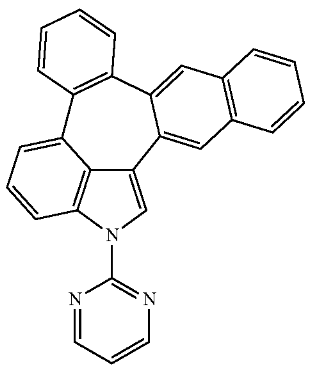
-continued
C-70
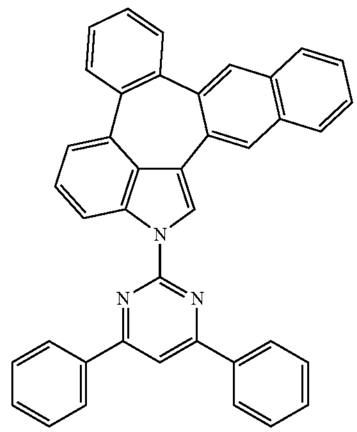
C-71
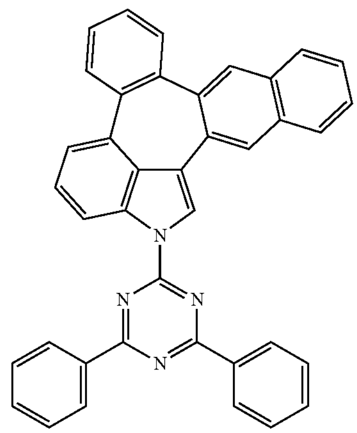
C-72
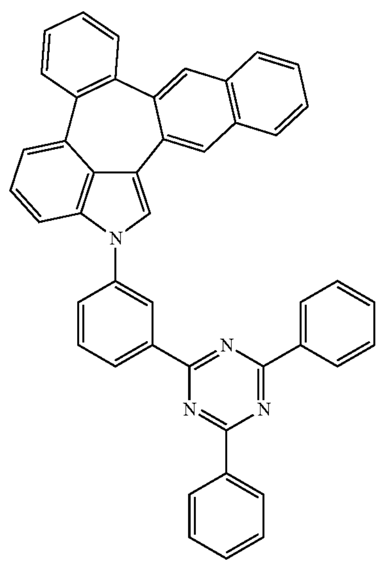

-continued
C-73
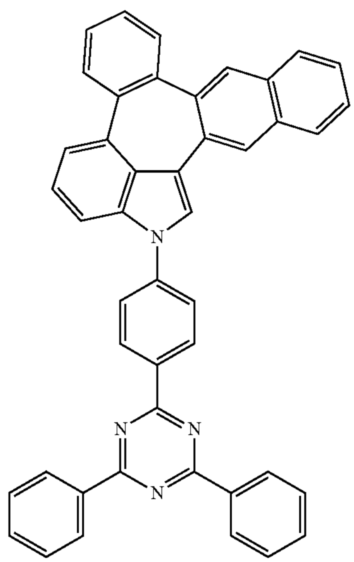
C-74
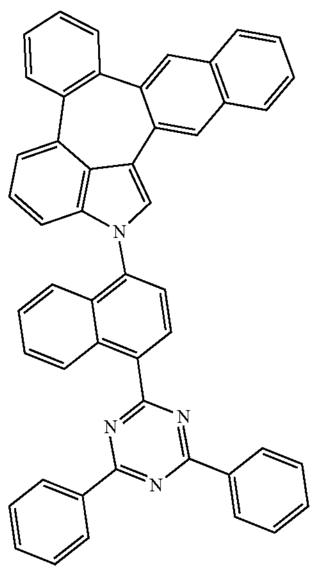
-continued
C-75
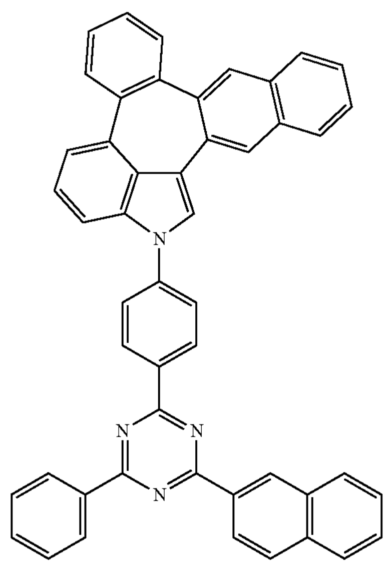
C-76
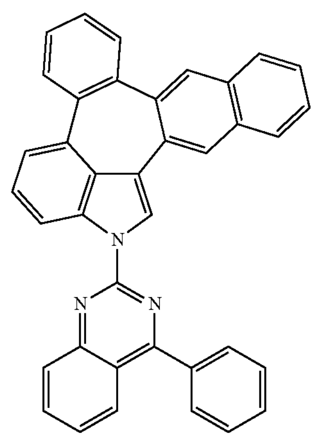
C-77
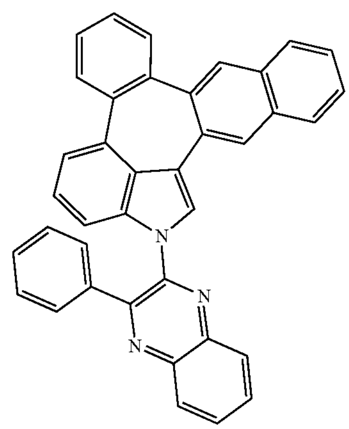

-continued
C-78
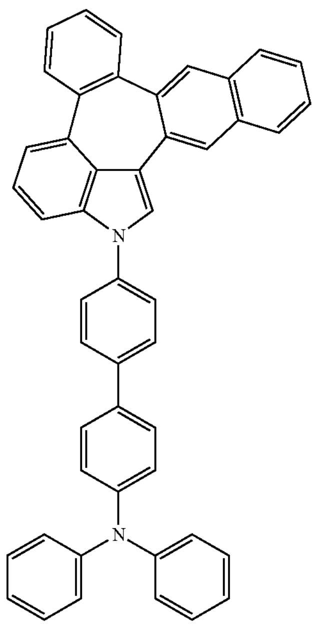
C-79
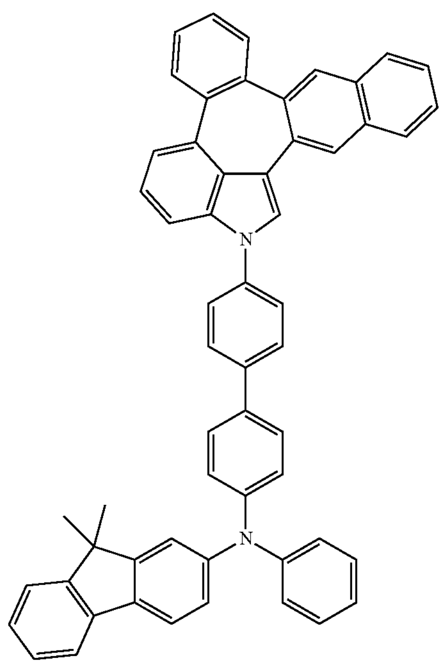
-continued
C-80
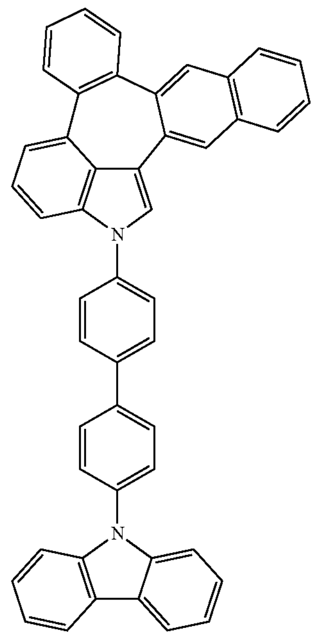
C-81
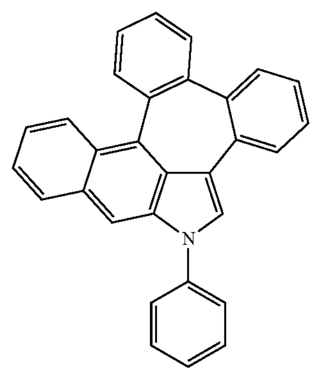
C-82
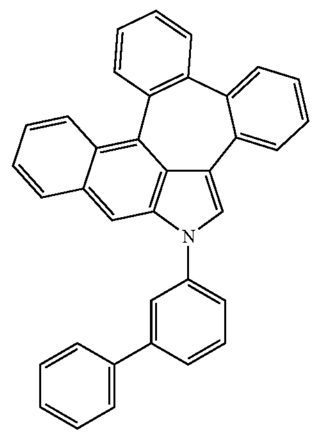

-continued
C-83
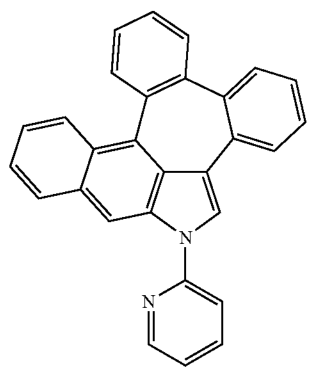
C-84
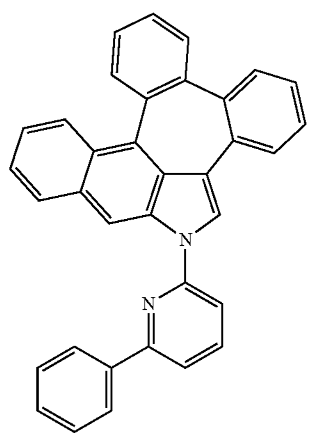
C-85
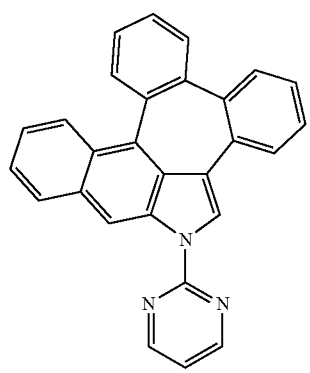
C-86
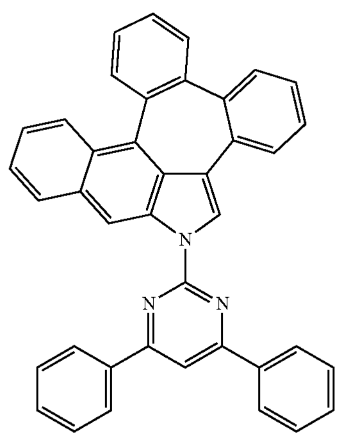
C-87
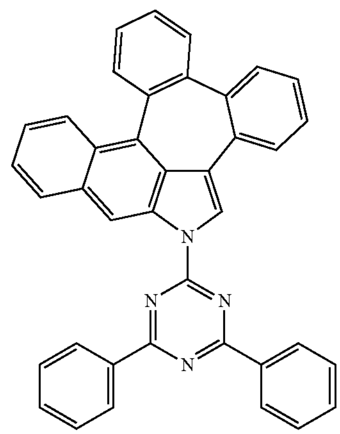
C-88
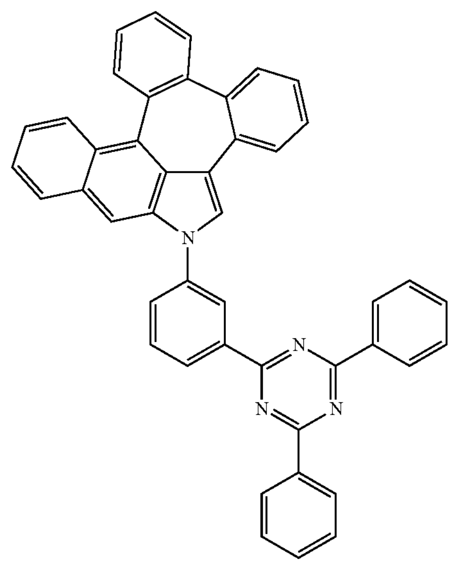
C-89
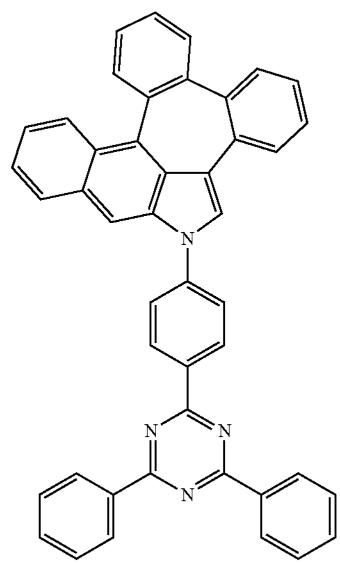

-continued
C-90
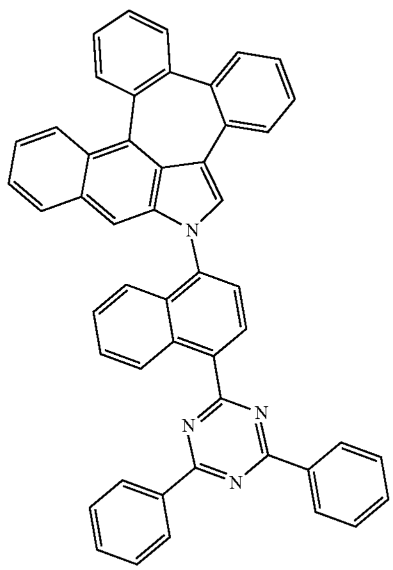
C-91
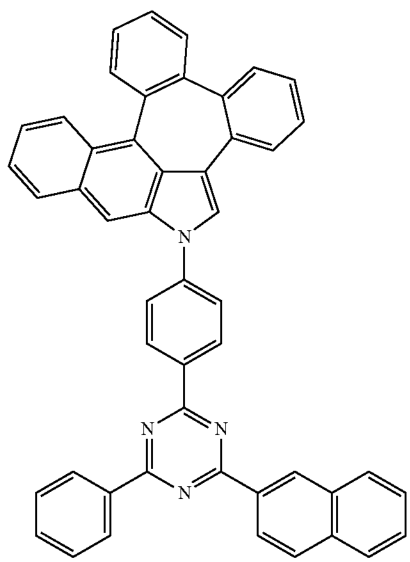
C-92
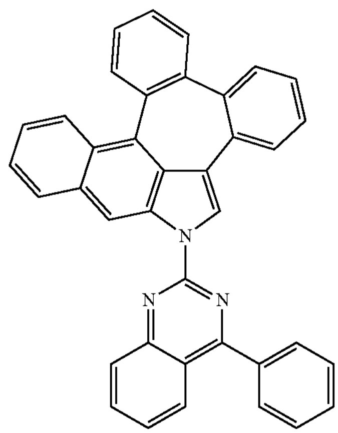
-continued
C-93
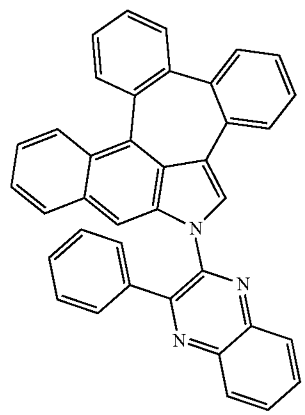
C-94
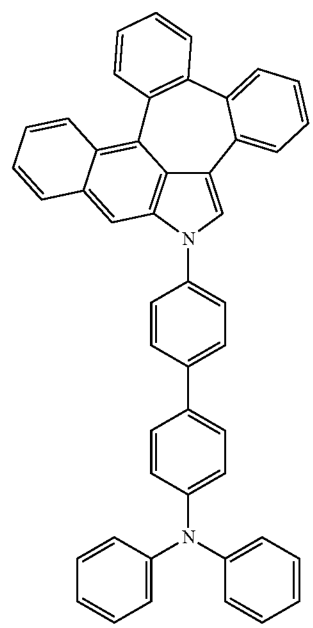

-continued
C-95
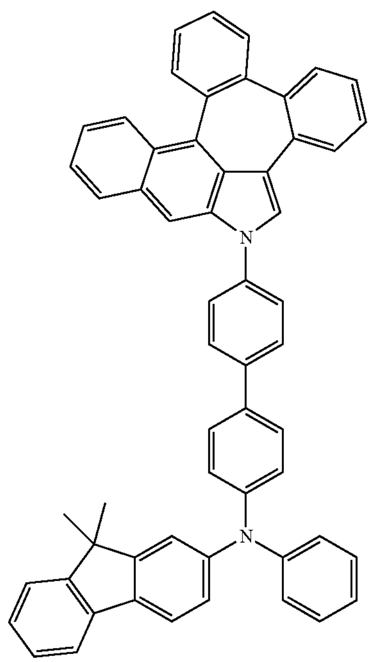
C-96
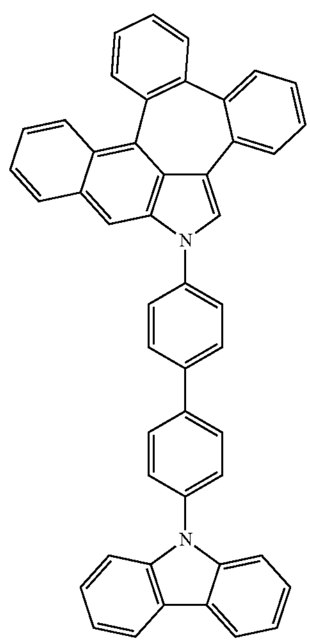
-continued
C-97
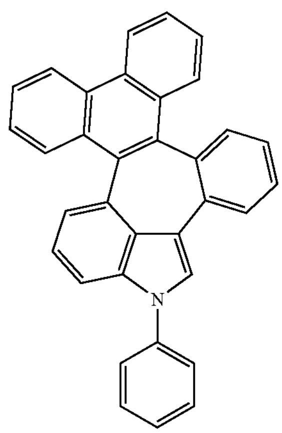
C-98
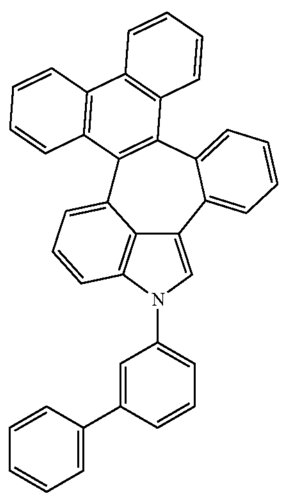
C-99
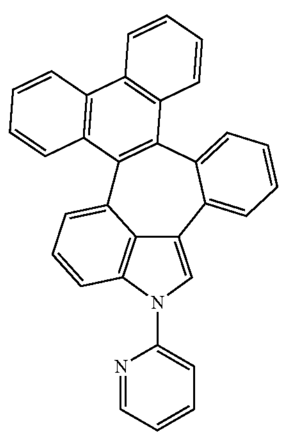

-continued
C-100
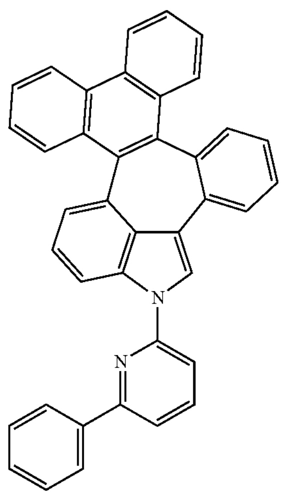
C-101
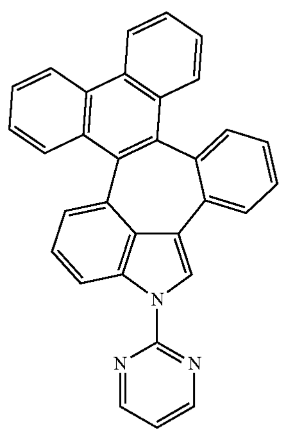
C-102
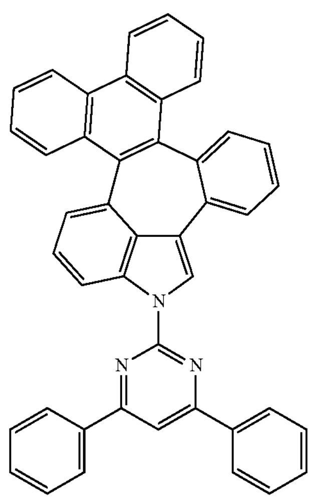
-continued
C-103
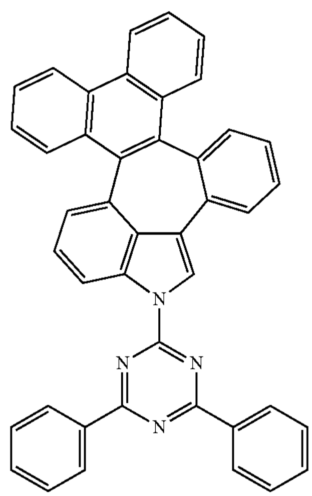
C-104
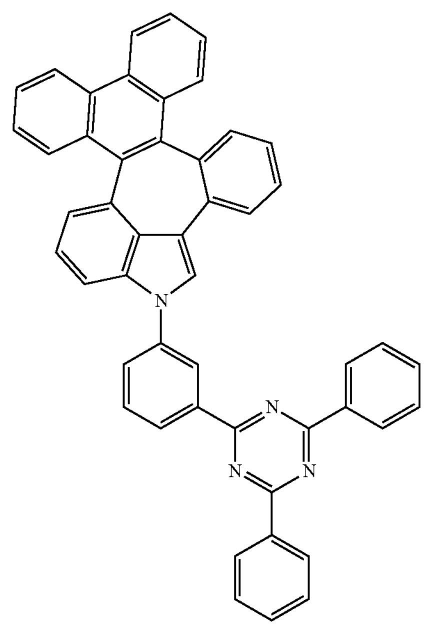

-continued
C-105
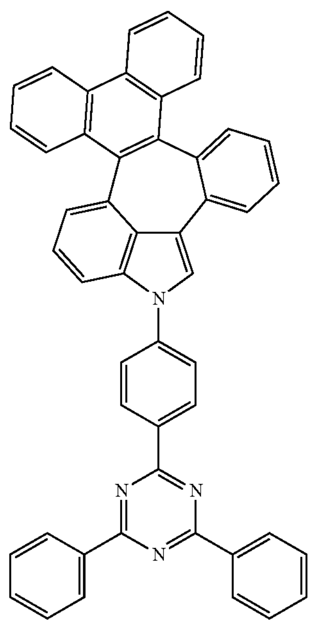
C-106
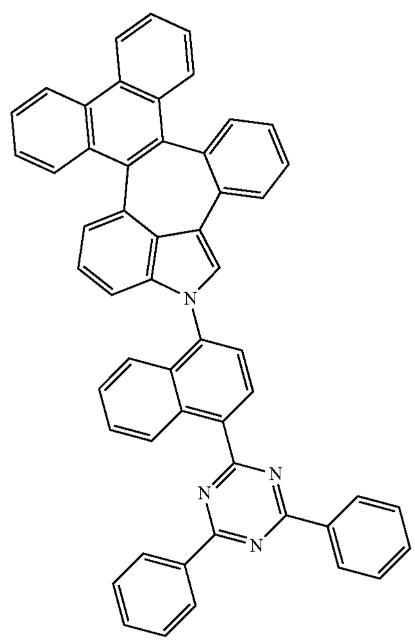
-continued
C-107
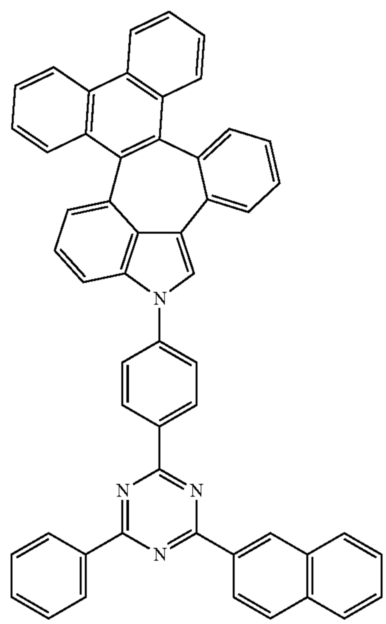
C-108
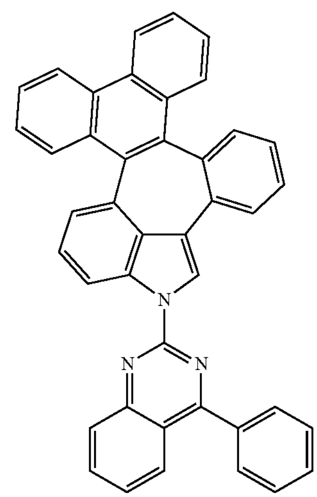
C-109
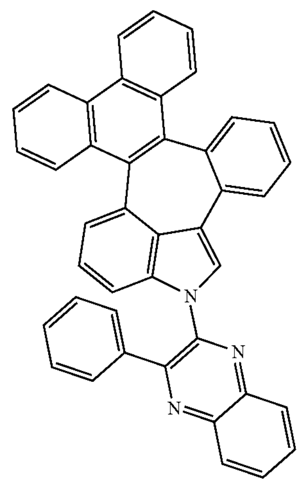

-continued
C-110
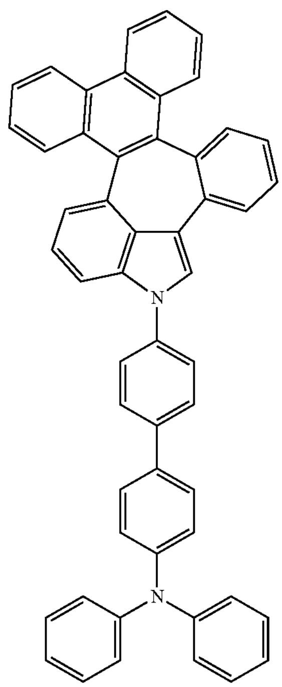
C-111
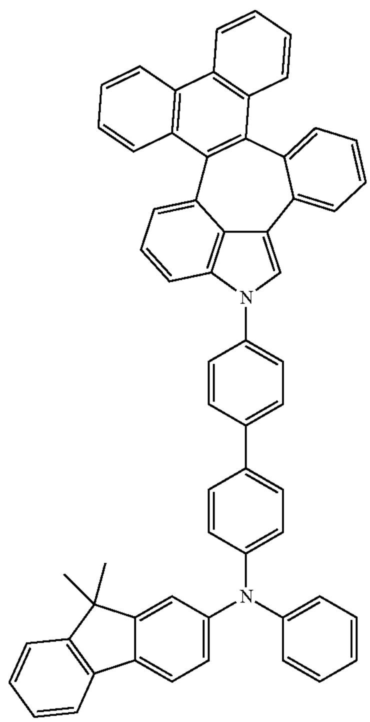
-continued
C-112
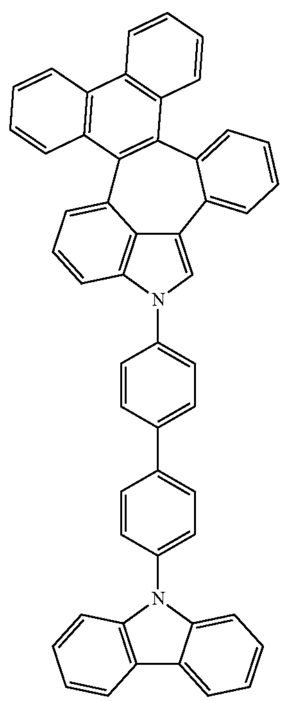
C-113
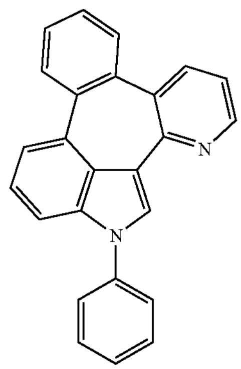
C-114
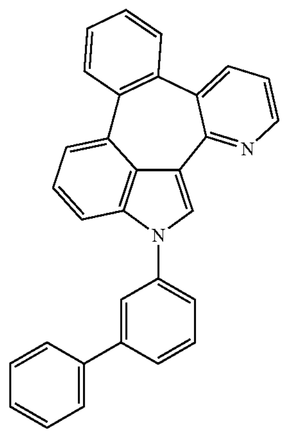

-continued
C-115
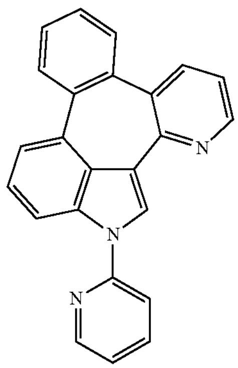
C-116
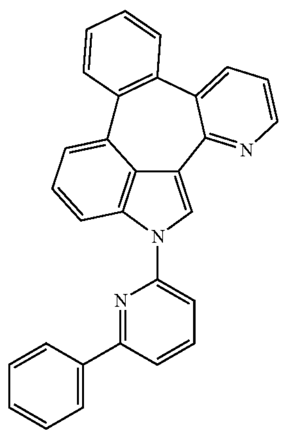
C-117
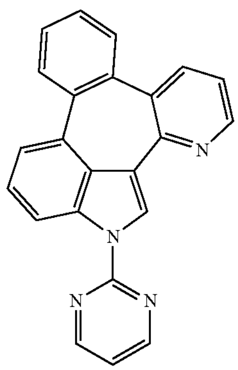
C-118
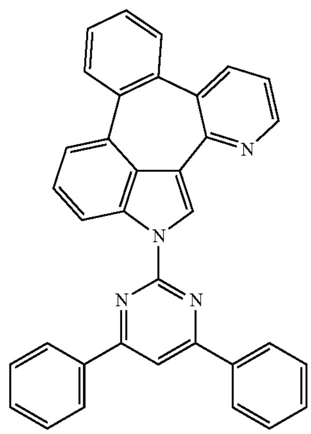
-continued
C-119
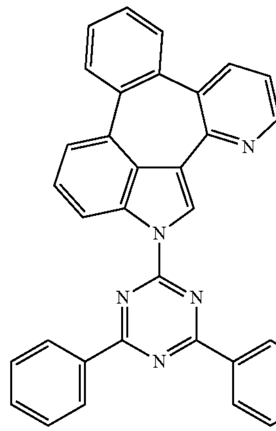
C-120
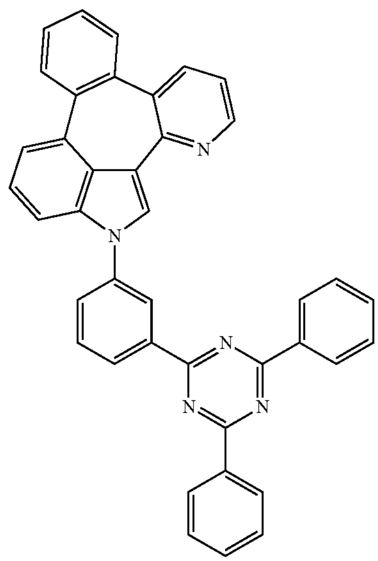
C-121
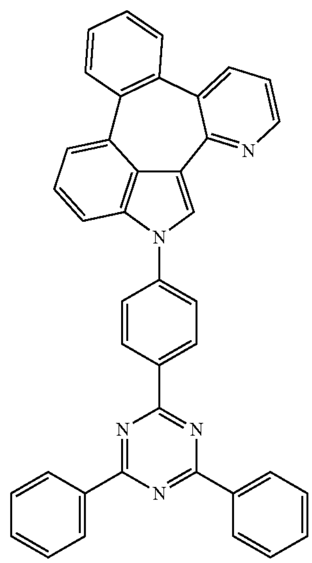

-continued
C-122
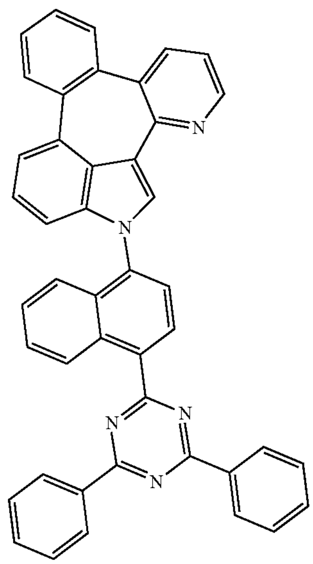
C-123
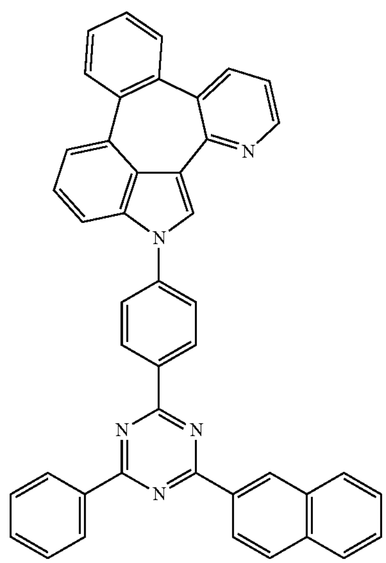
C-124
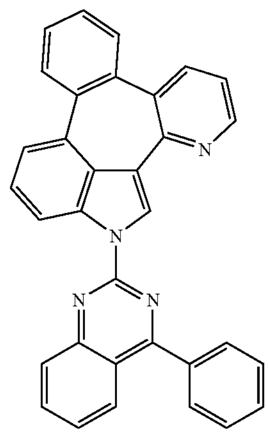
-continued
C-125
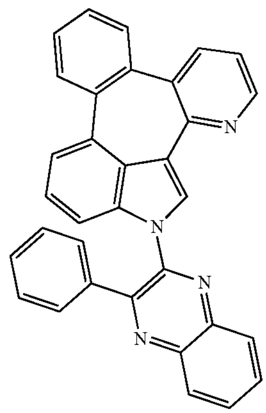
C-126
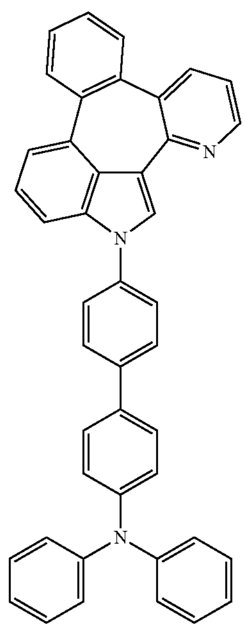

-continued
C-127
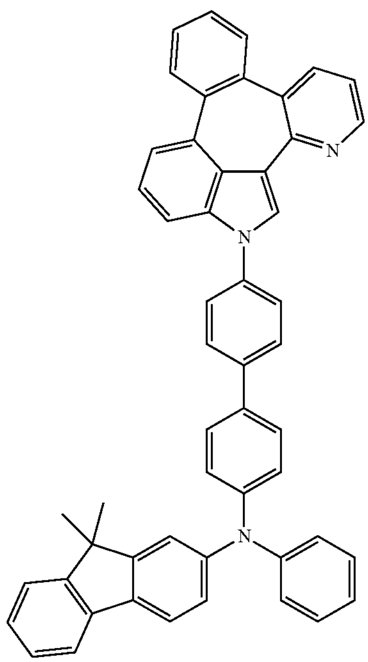
C-128
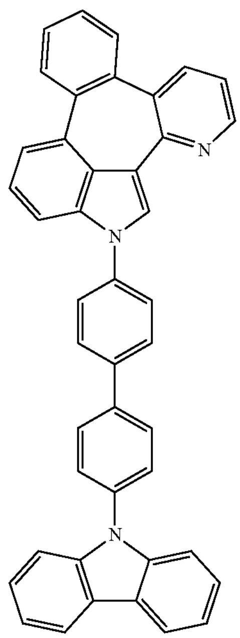
-continued
C-129
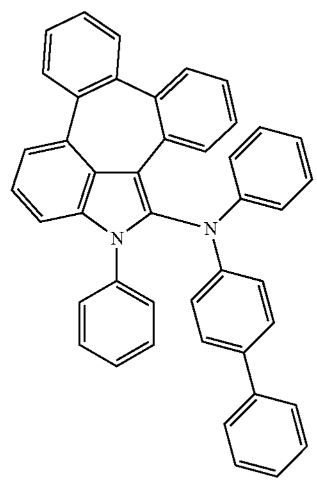
C-130
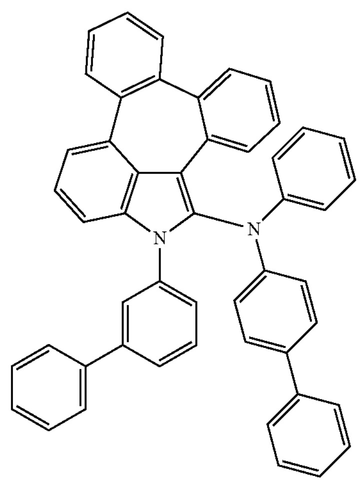
C-131
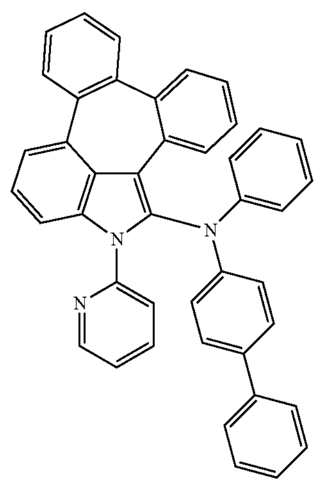

-continued
C-132
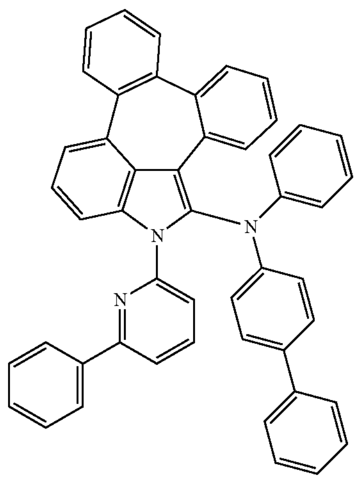
C-133
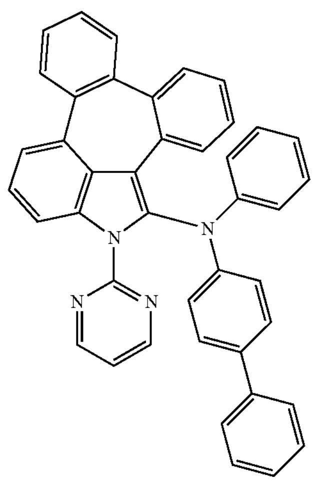
C-134
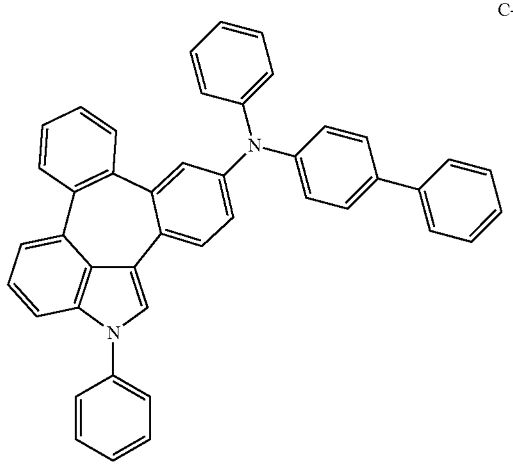
-continued
C-135
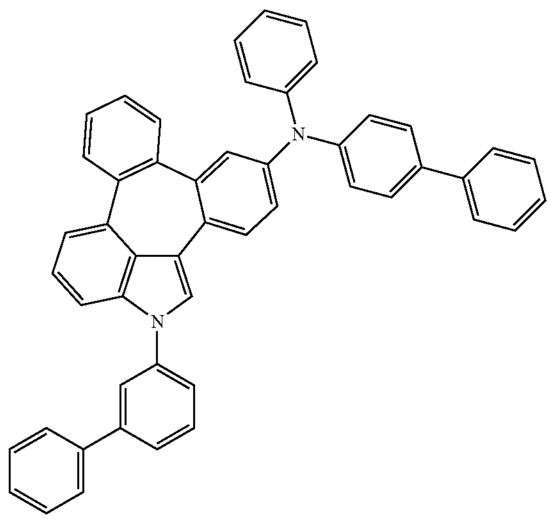
C-136
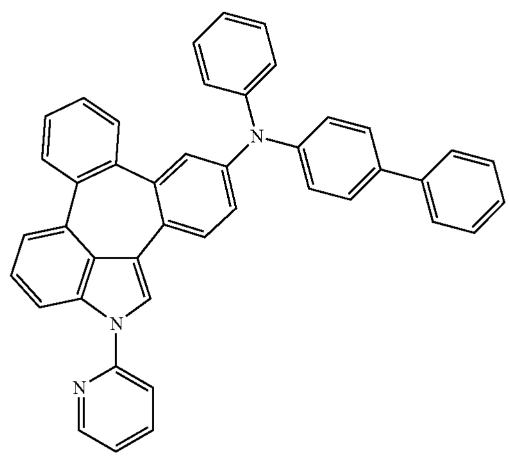
C-137
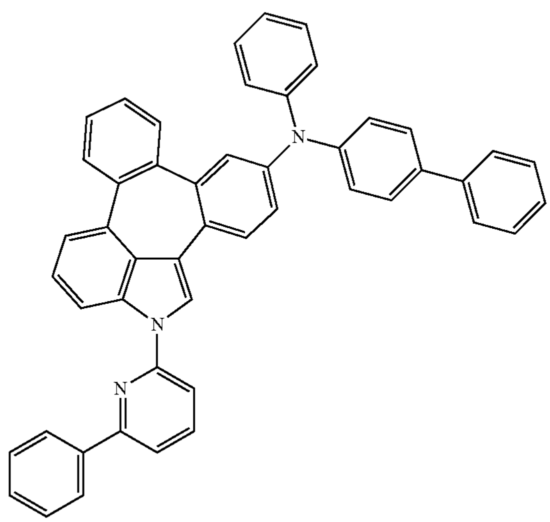

-continued
C-138
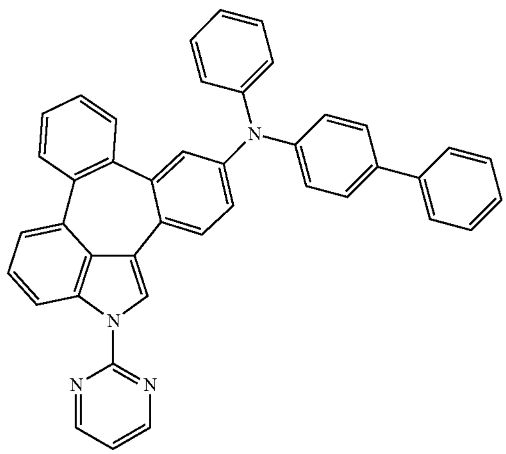
C-139
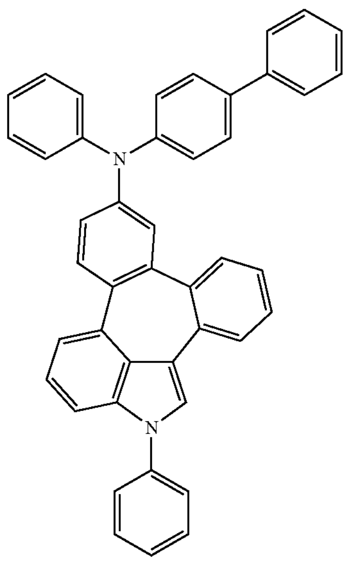
C-140
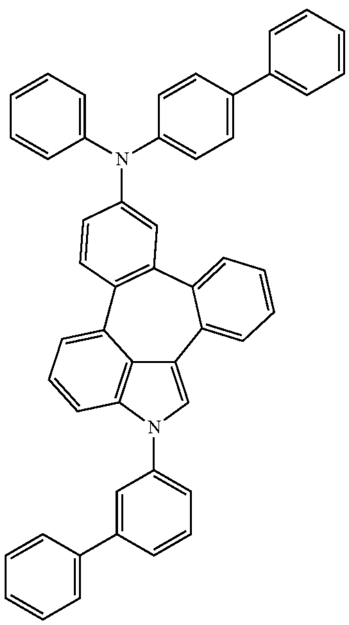
-continued
C-141
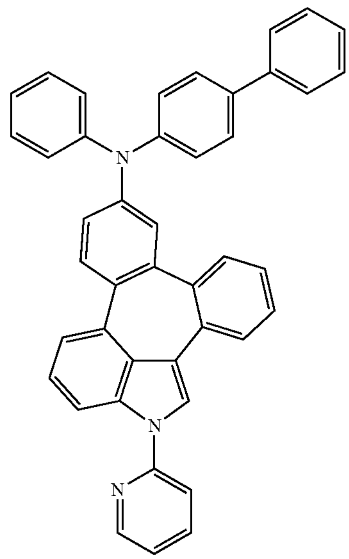
C-142
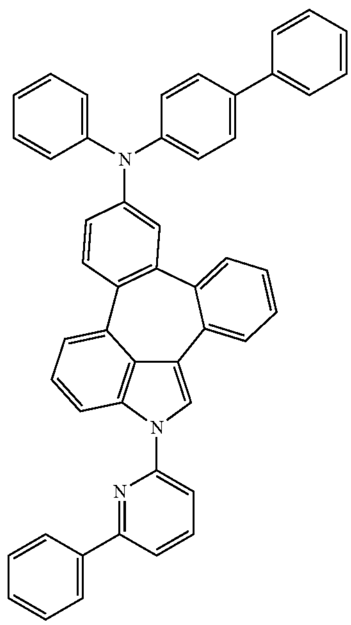

C-143
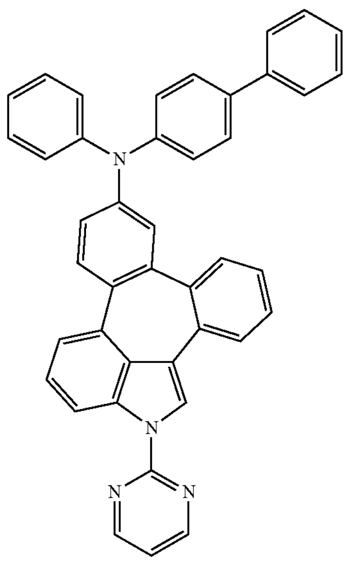
C-144
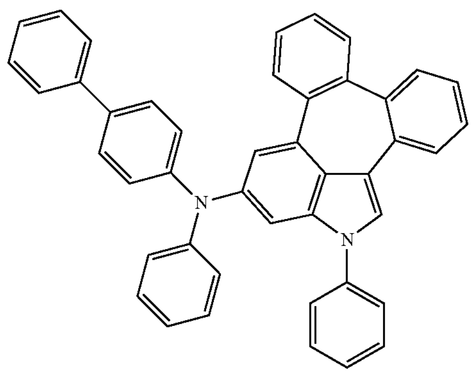
C-145
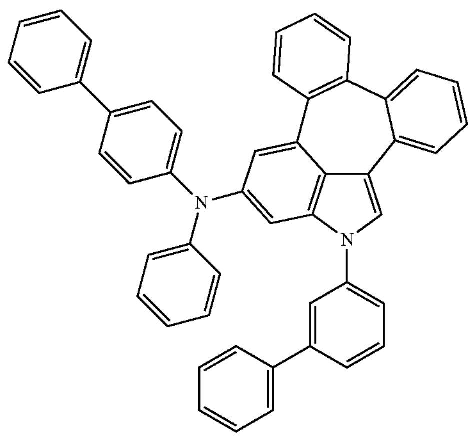
C-146
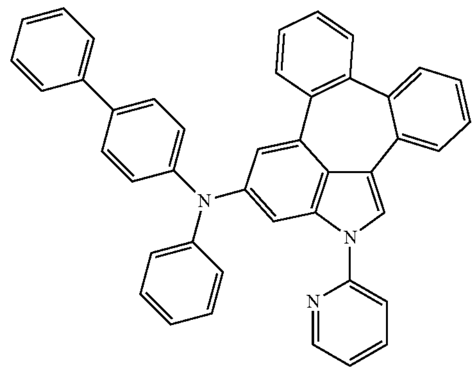
C-147
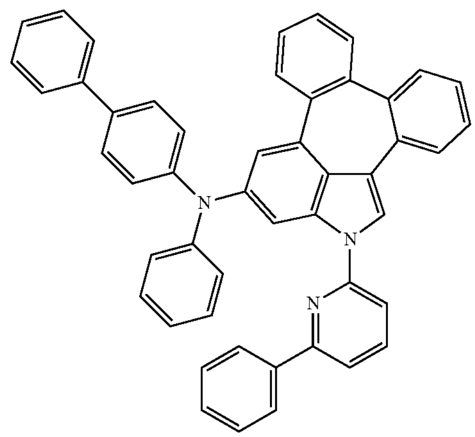
C-148
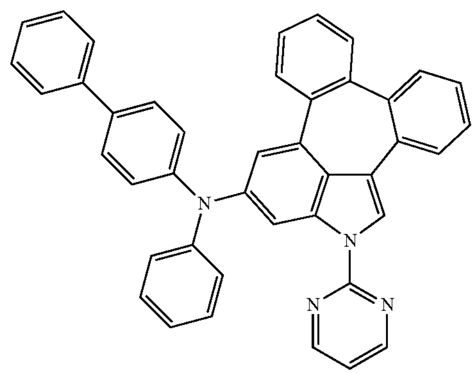
C-149
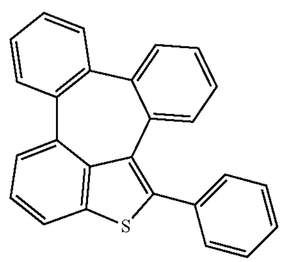

-continued
C-150
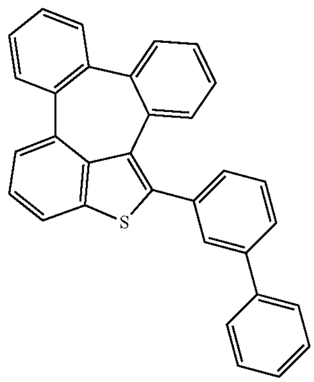
C-151
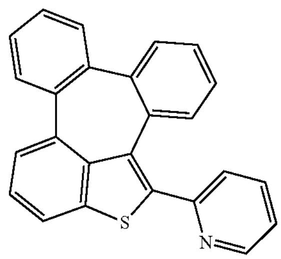
C-152
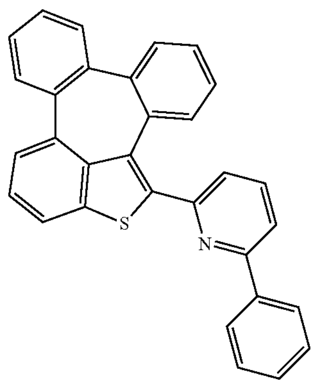
C-153
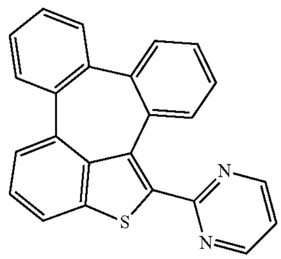
-continued
C-154
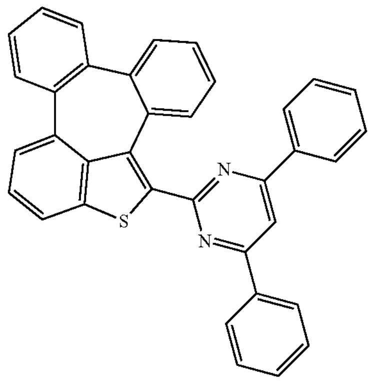
C-155
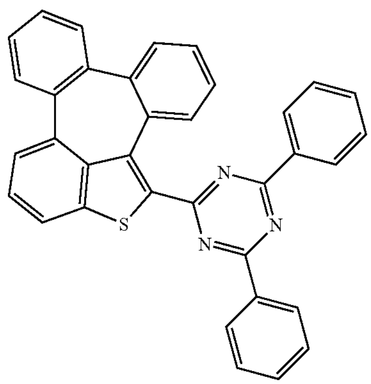
C-156
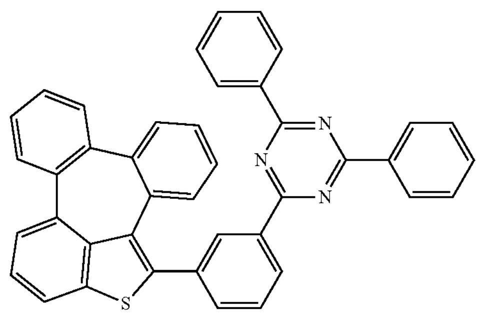
C-157
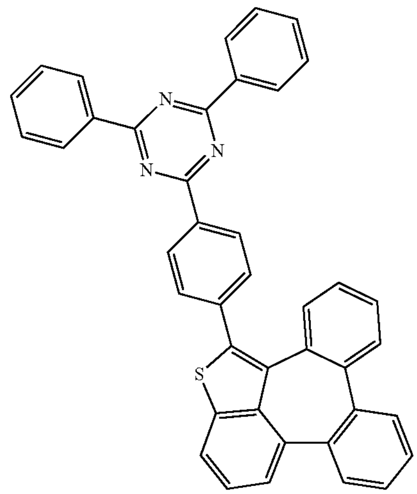

-continued
C-158
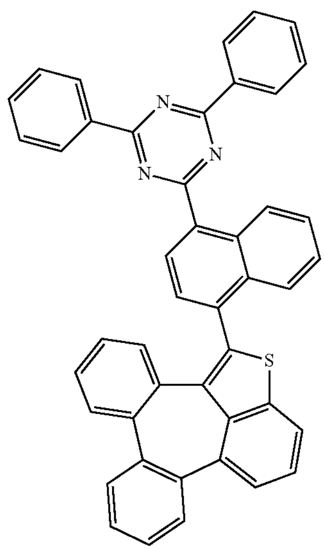
C-159
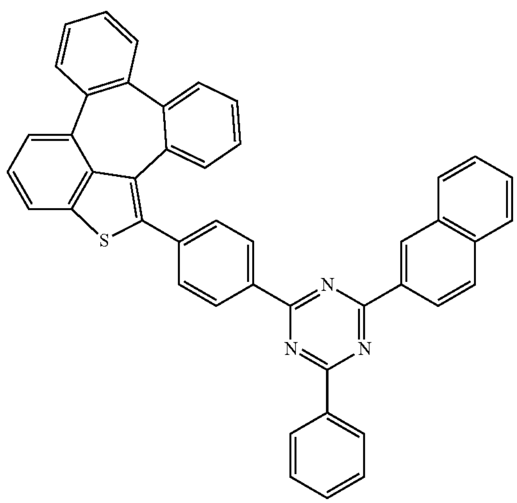
C-160
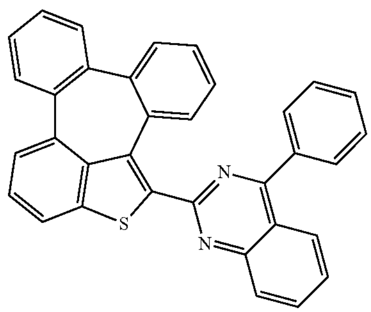
-continued
C-161
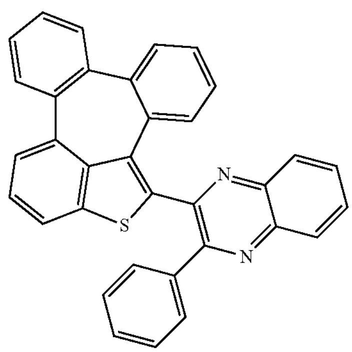
C-162
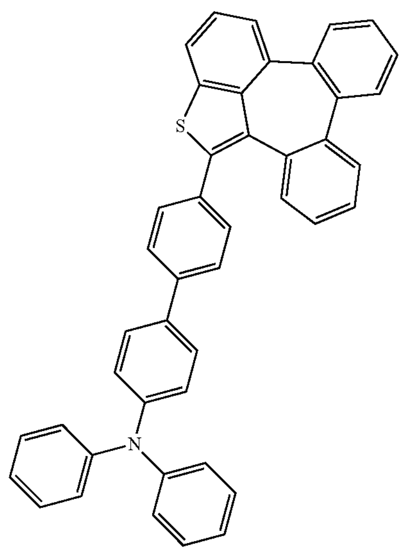
C-163
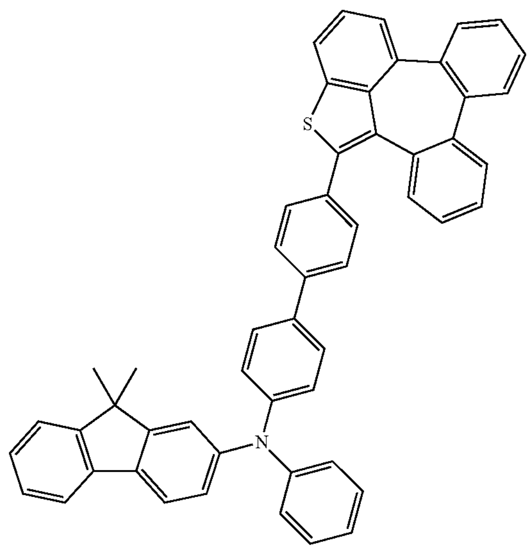

-continued
C-164
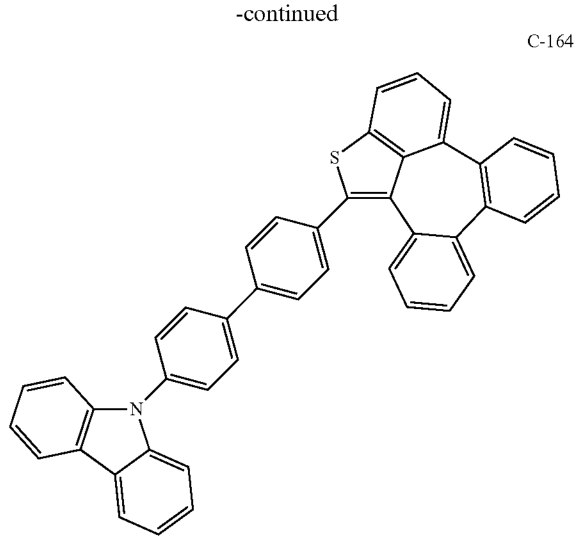
C-165
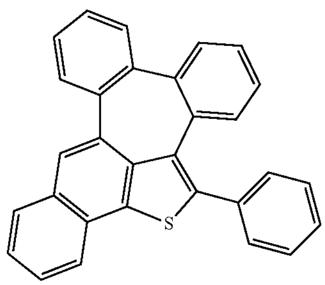
C-166
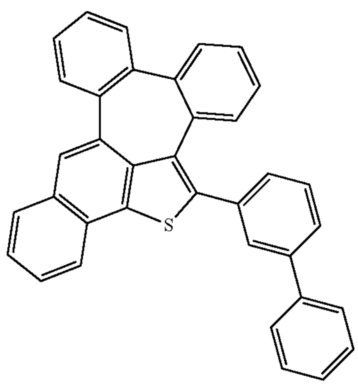
C-167
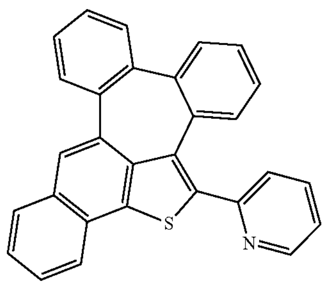
-continued
C-168
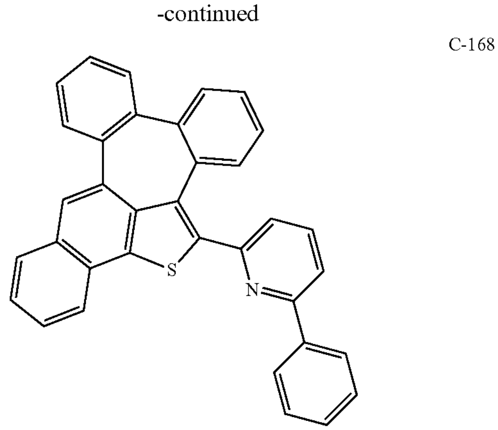
C-169
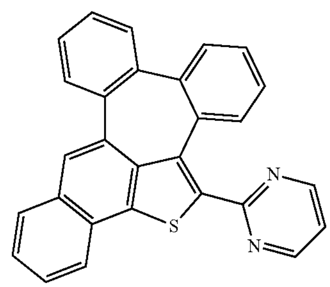
C-170
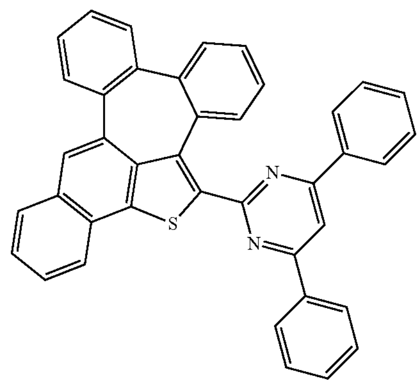
C-171
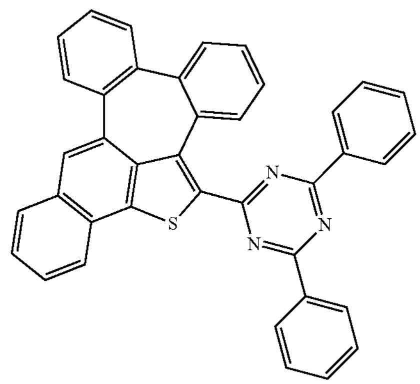

C-172
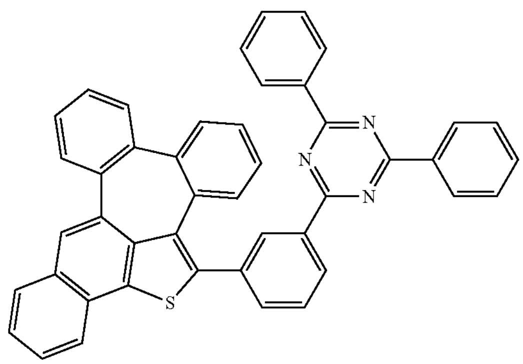
C-173
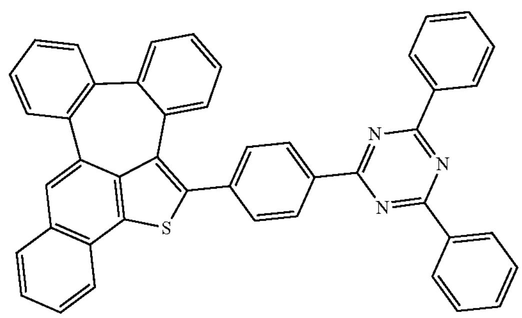
C-174
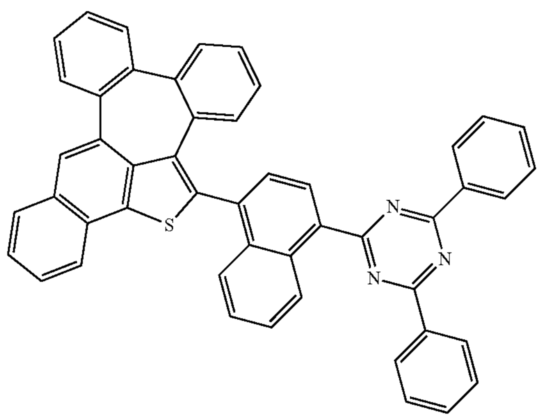
C-175
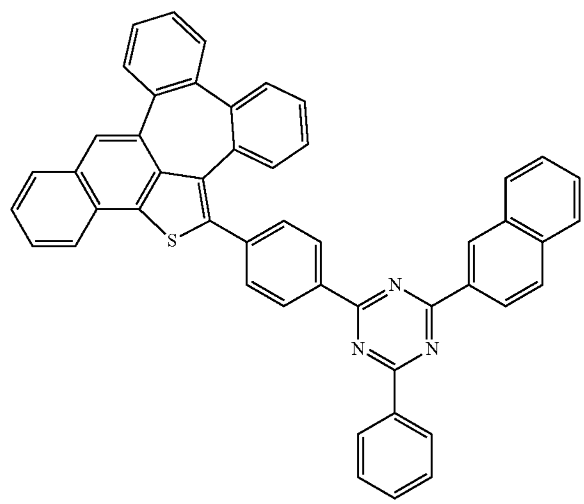
C-176
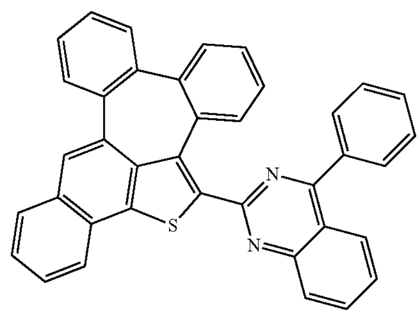
C-177
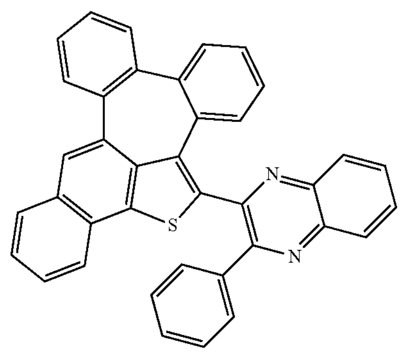

-continued
C-178
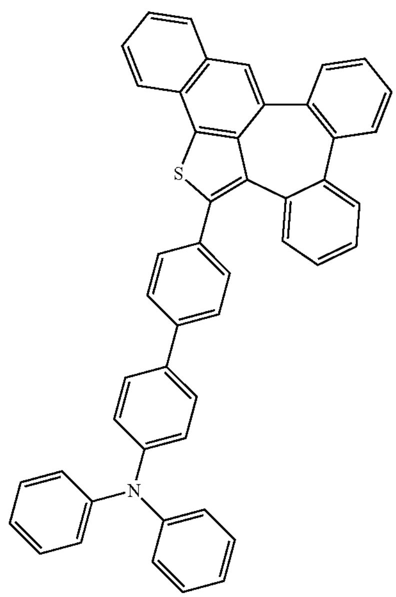
C-179
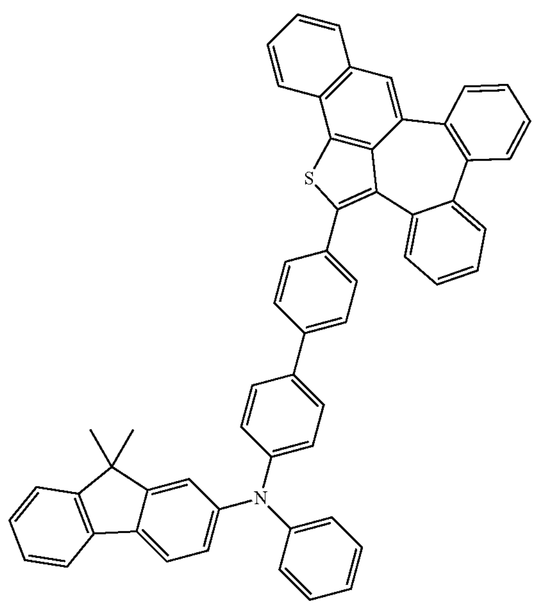
-continued
C-180
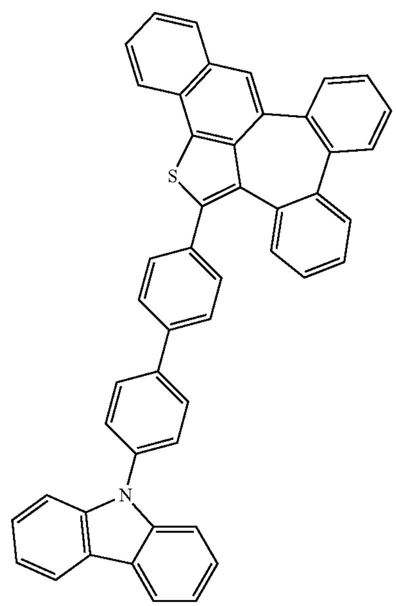
C-181
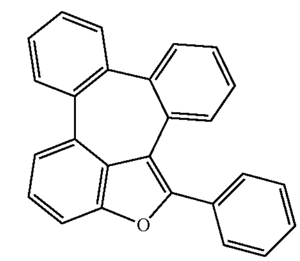
C-182
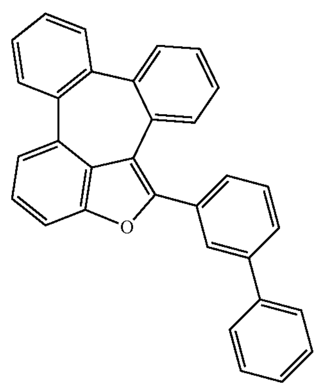
C-183
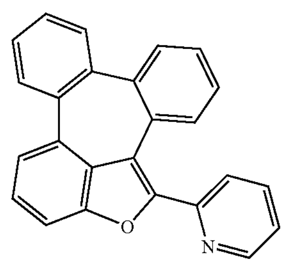

-continued
C-184
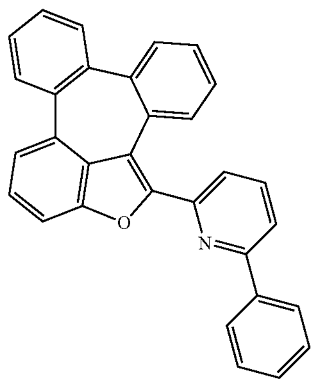
C-185
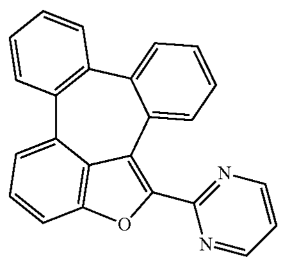
C-186
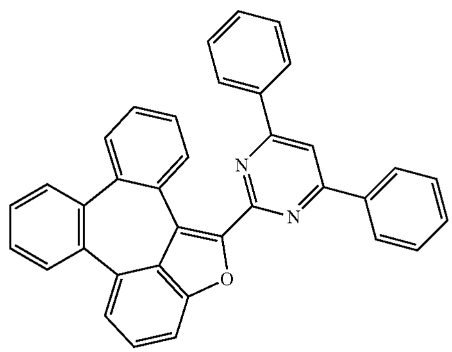
C-187
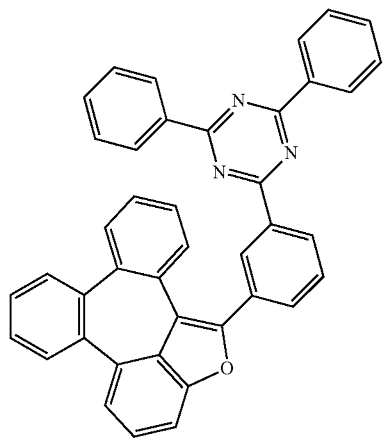
-continued
C-188
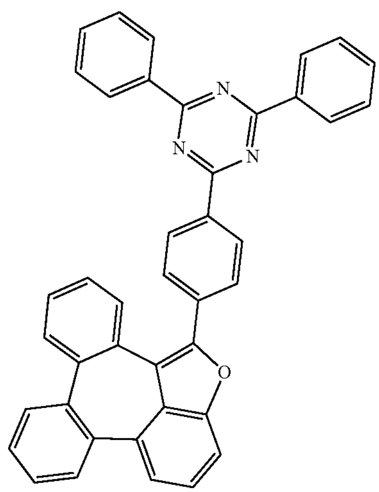
C-189
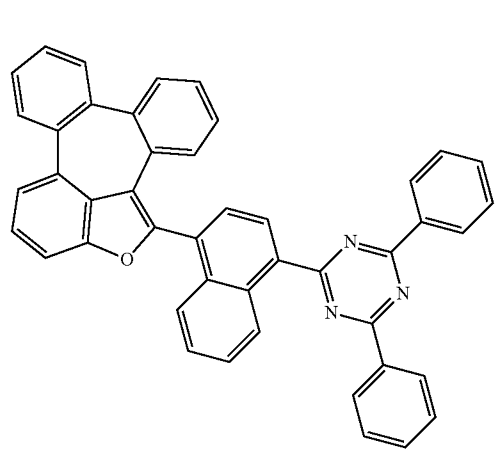
C-190
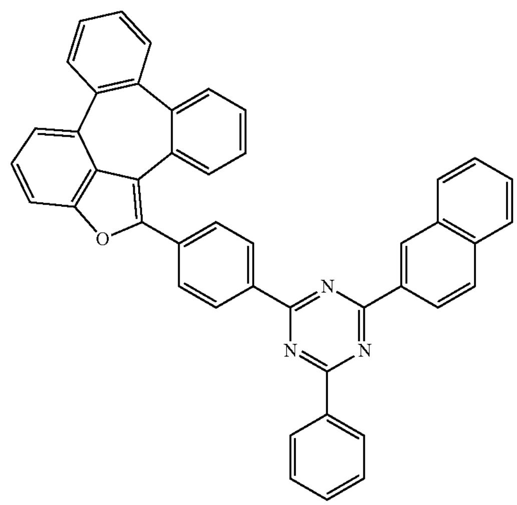

-continued
C-191
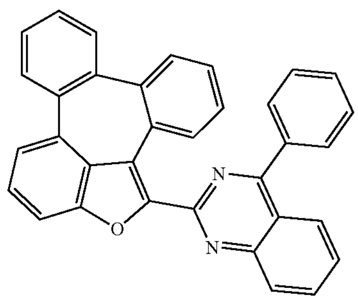
C-192
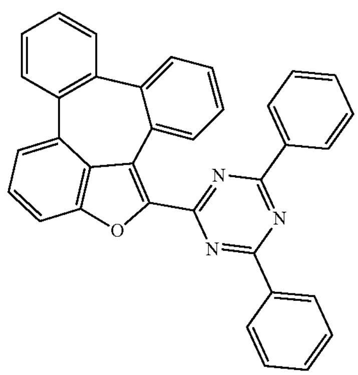
C-193
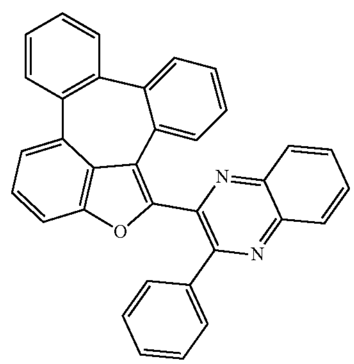
C-194
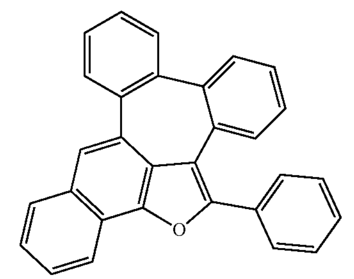
C-195
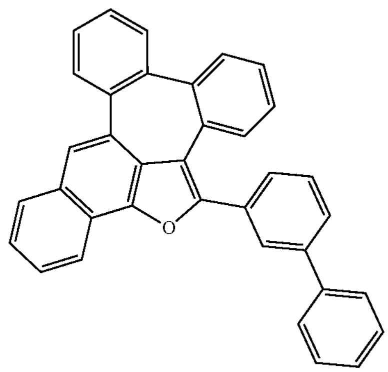
C-196
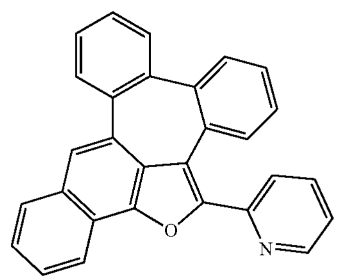
C-197
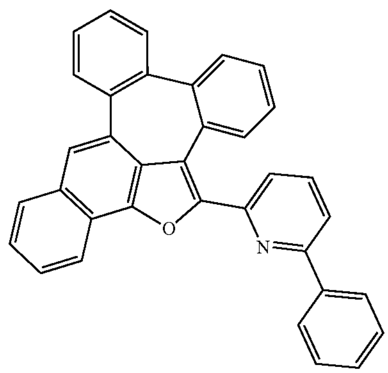
C-198
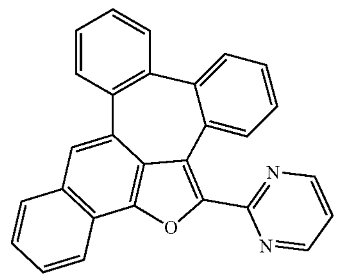

-continued
C-199
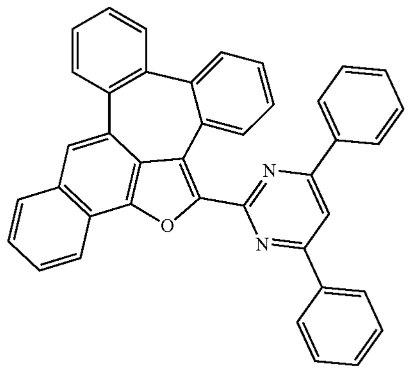
C-200
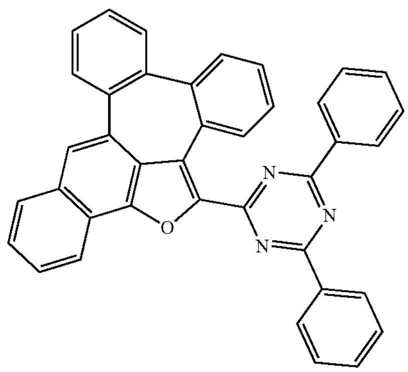
C-201
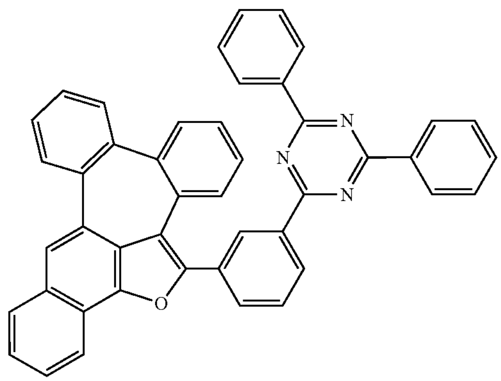
-continued
C-202
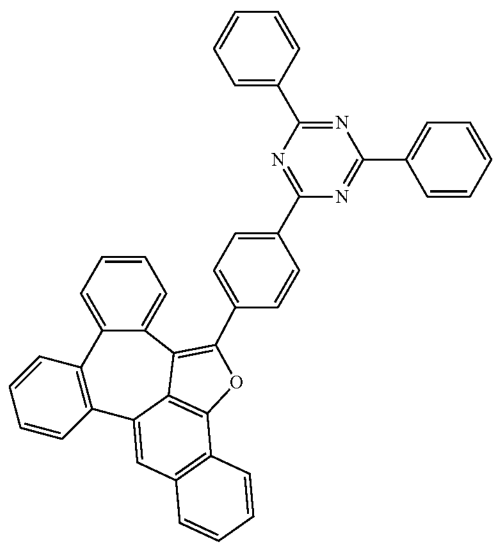
C-203
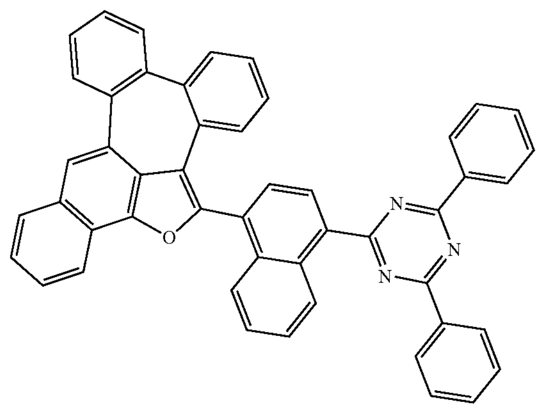
C-204
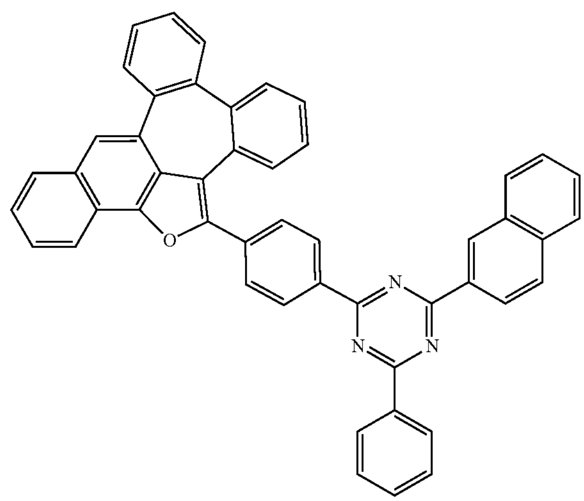

-continued
C-205
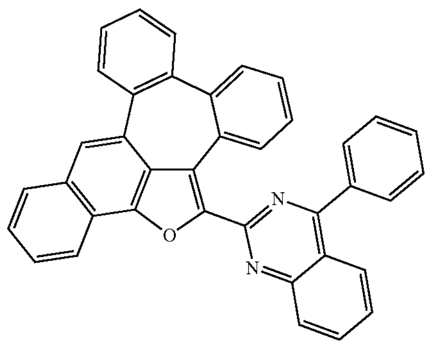
C-206
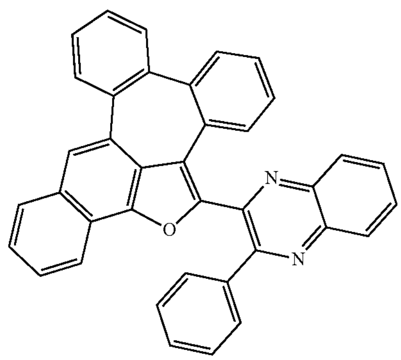
C-207
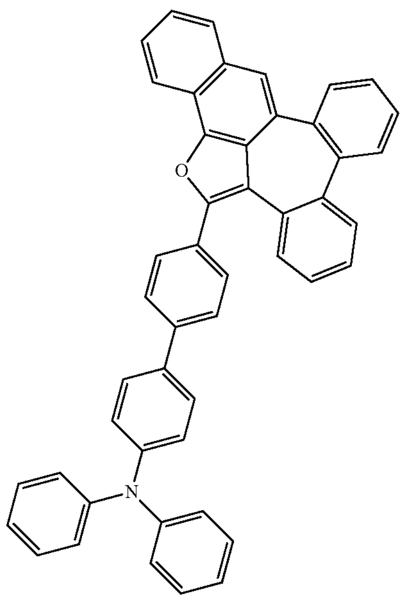
-continued
C-208
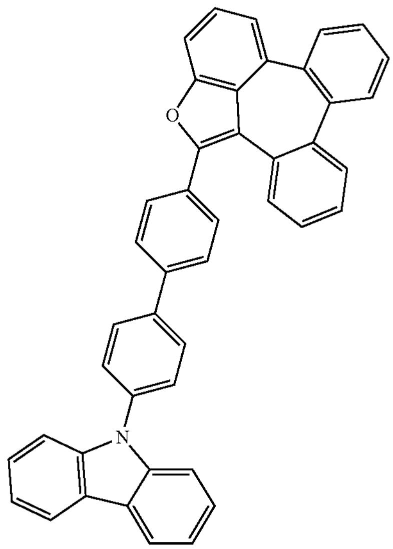
C-209
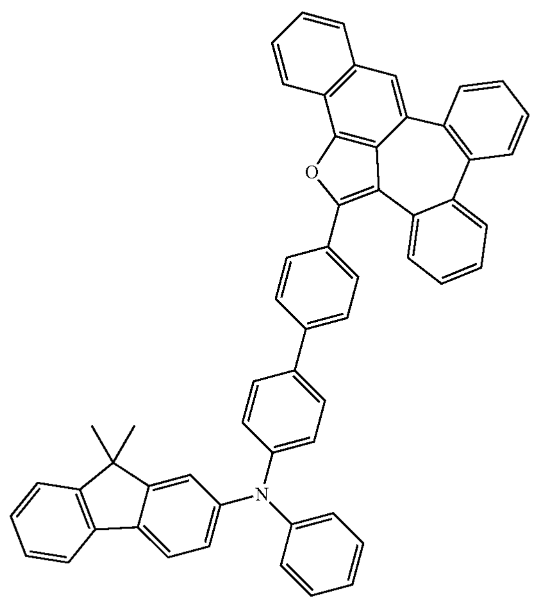

-continued
C-210
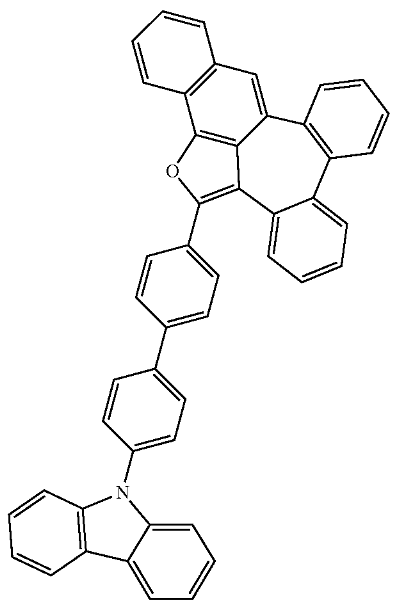
C-211
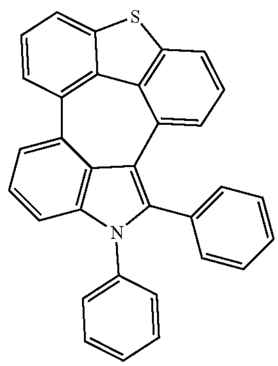
C-212
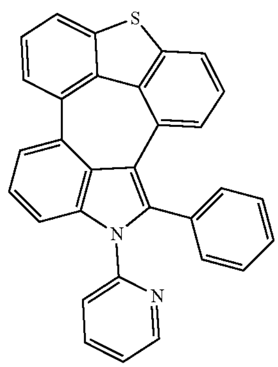
-continued
C-213
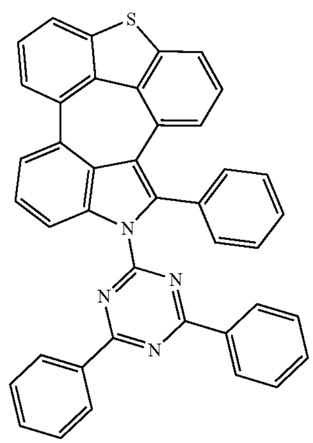
C-214
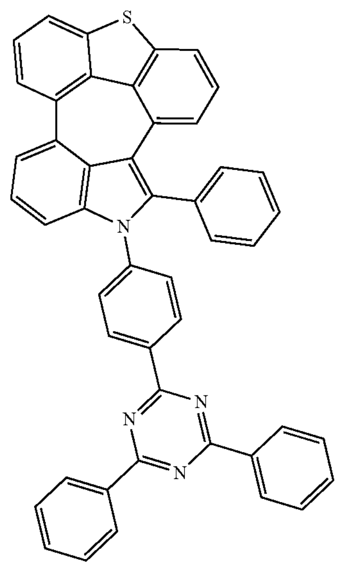
C-215
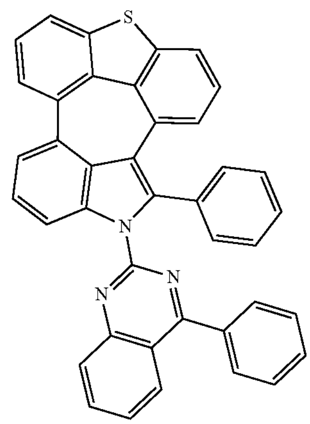

-continued
C-216
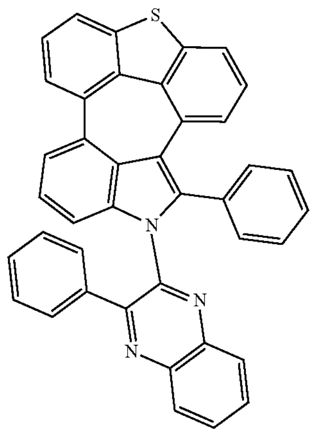
C-217
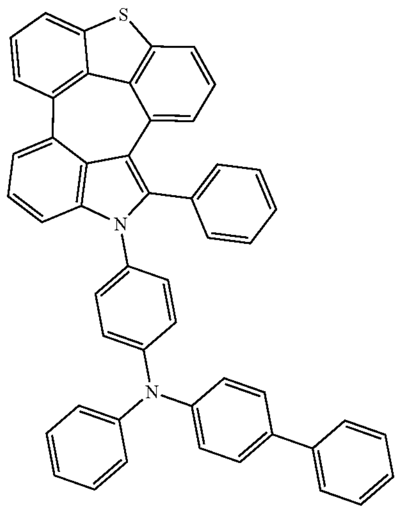
C-218
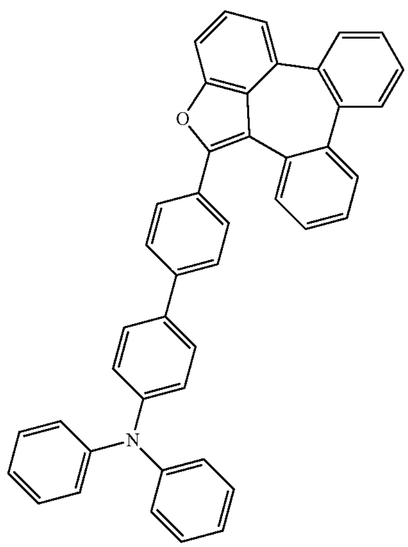
-continued
C-219
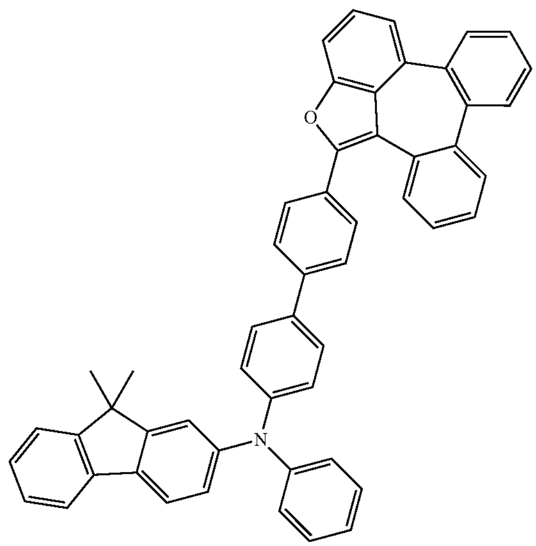
C-220
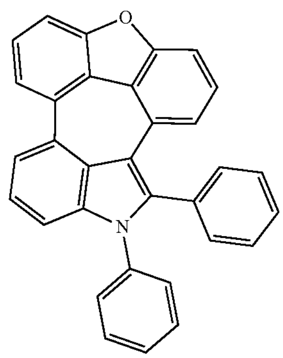
C-221
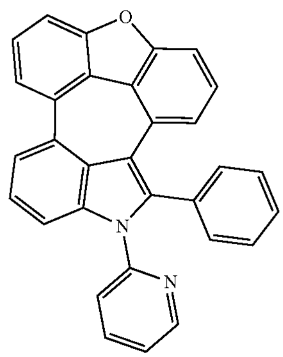

-continued
C-222
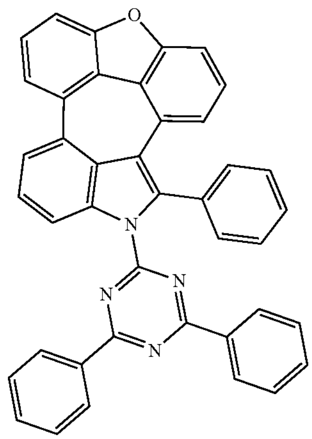
C-223
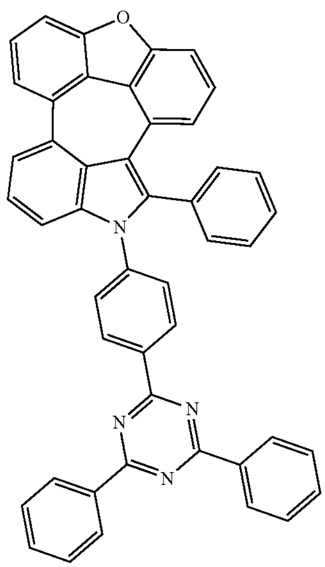
C-224
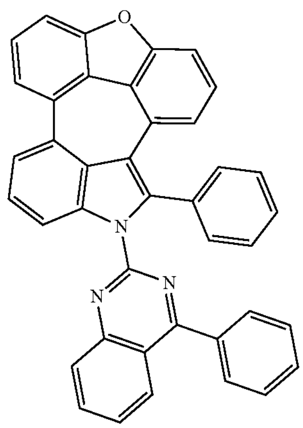
-continued
C-225
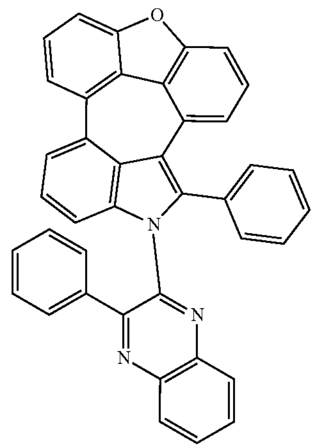
C-226
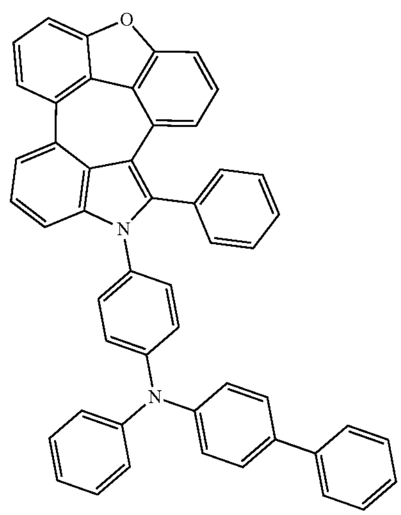
C-227
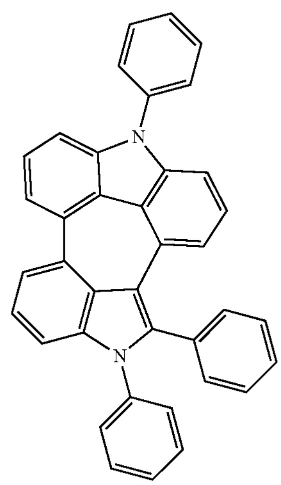

-continued
C-228
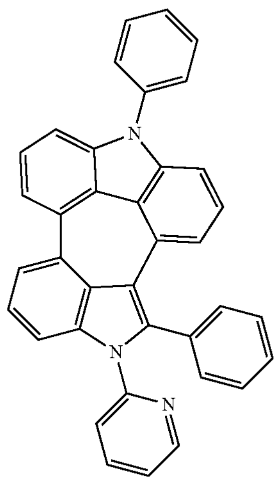
C-229
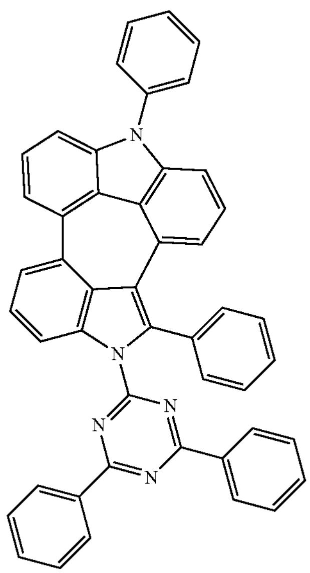
-continued
C-230
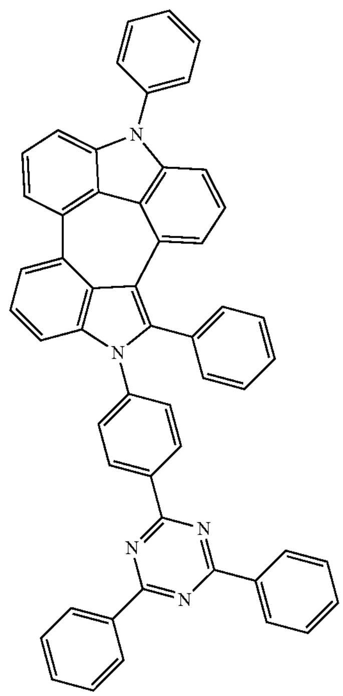
C-231
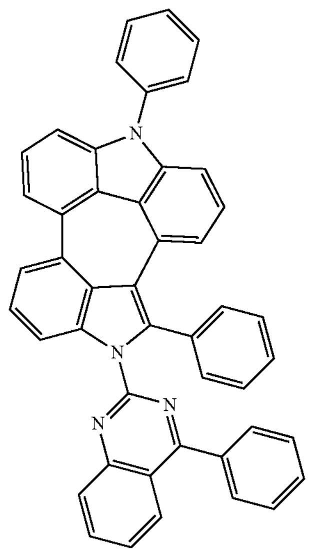

-continued
C-232
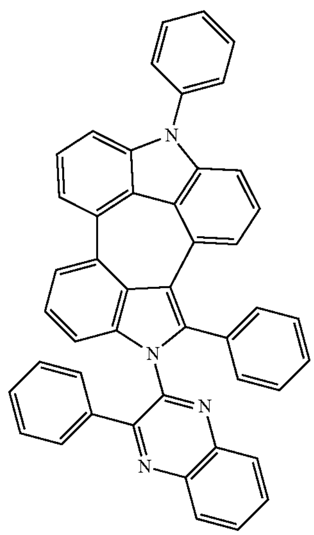
C-233
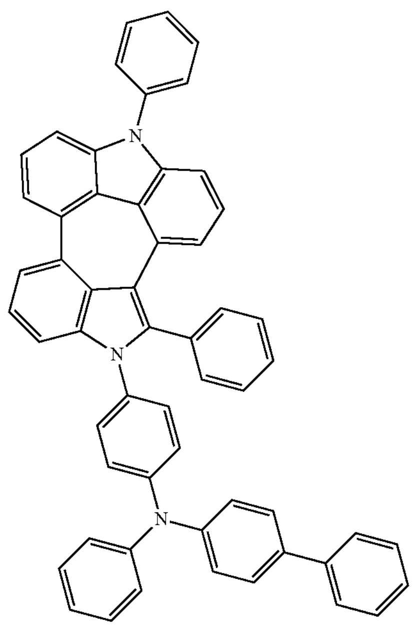
C-234
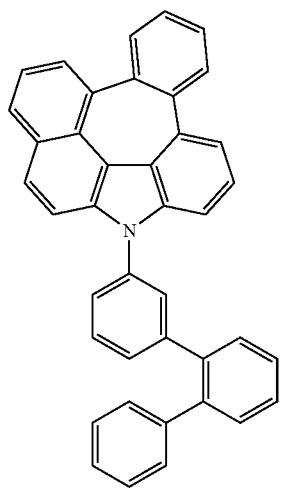
-continued
C-235
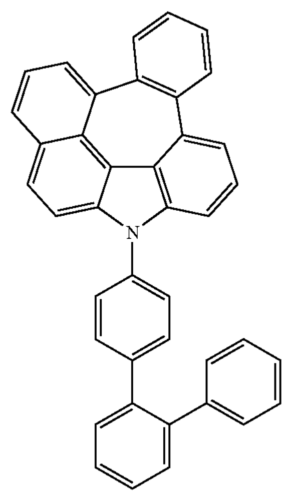
C-236
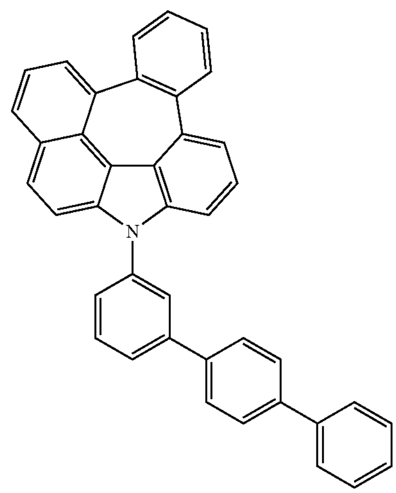
C-237
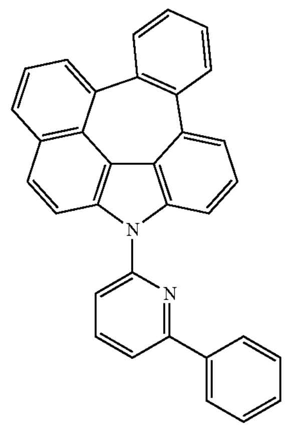

-continued
C-238
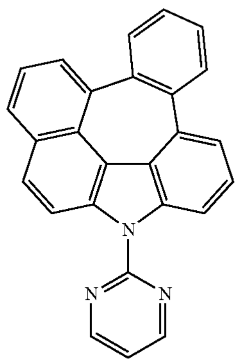
C-239
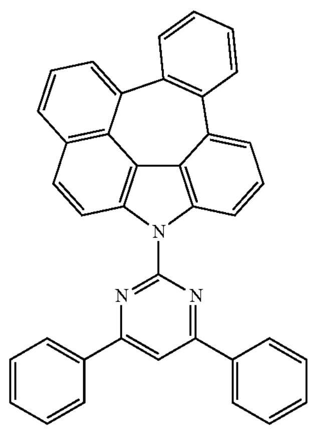
C-240
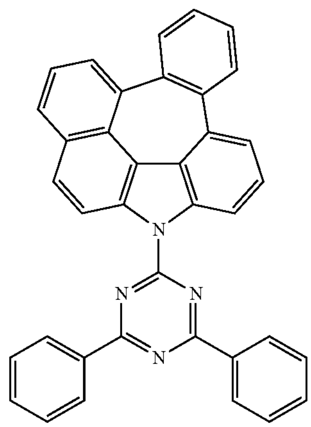
-continued
C-241
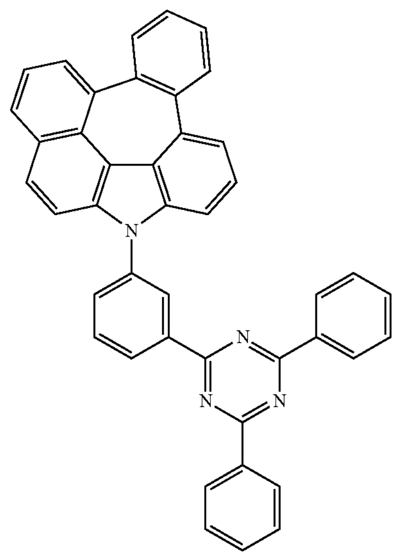
C-242
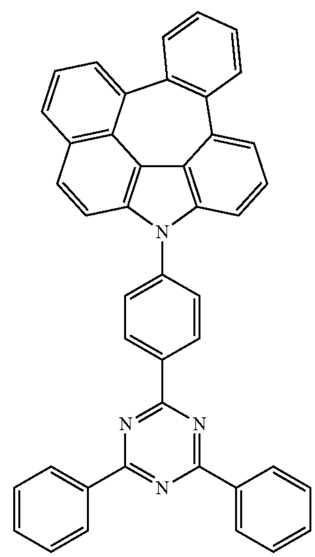
C-243
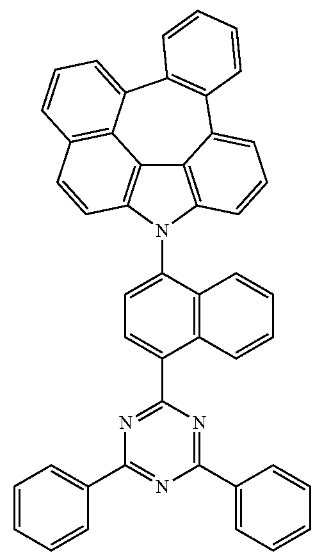

-continued
C-244
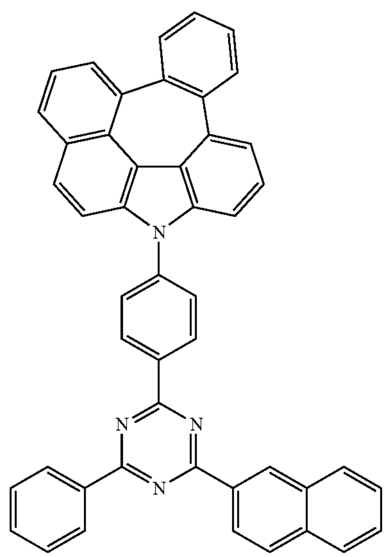
C-245
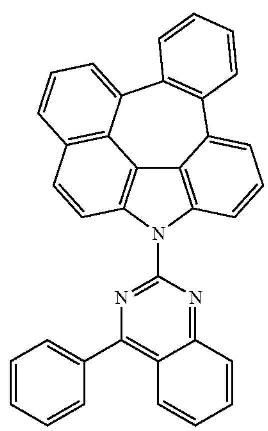
C-246
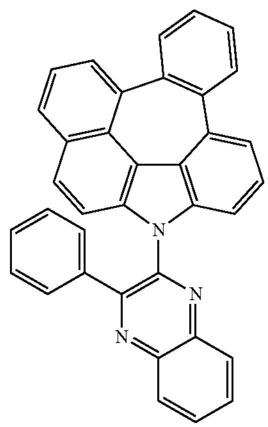
-continued
C-247
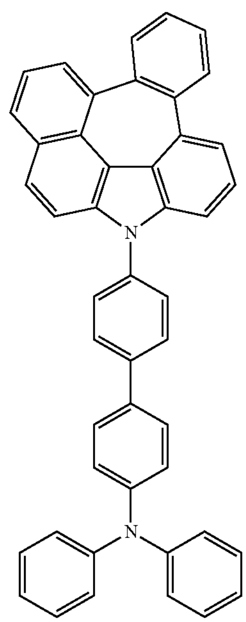
C-248
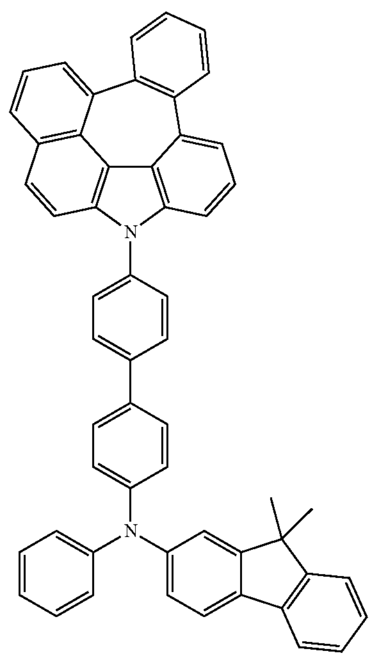

-continued
C-249
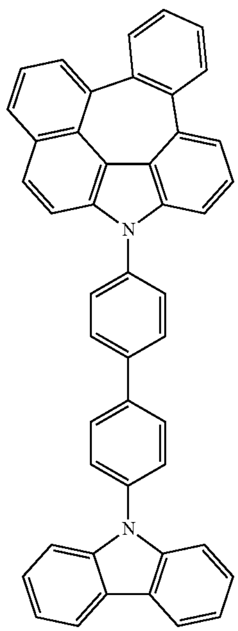
C-250
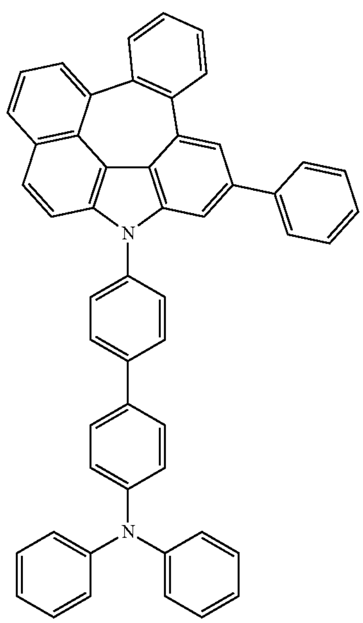
-continued
C-251
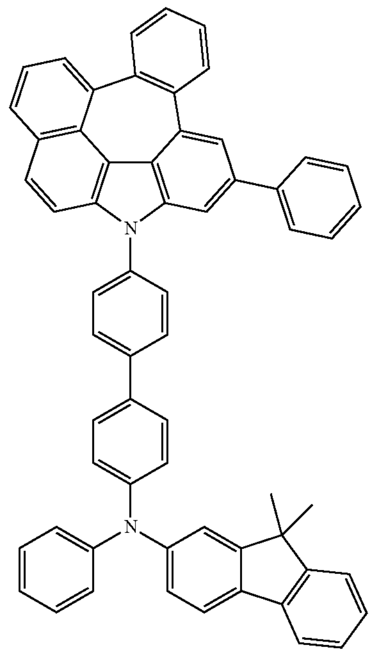
C-252
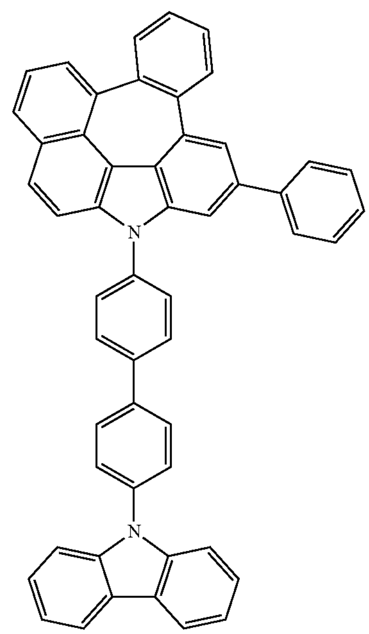

-continued
C-253
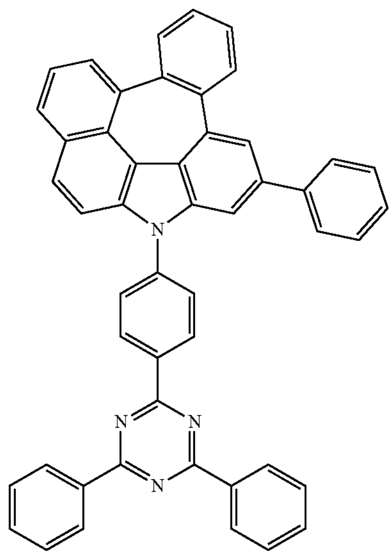
C-254
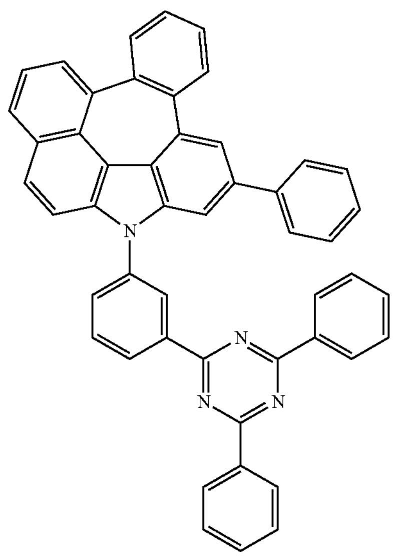
C-255
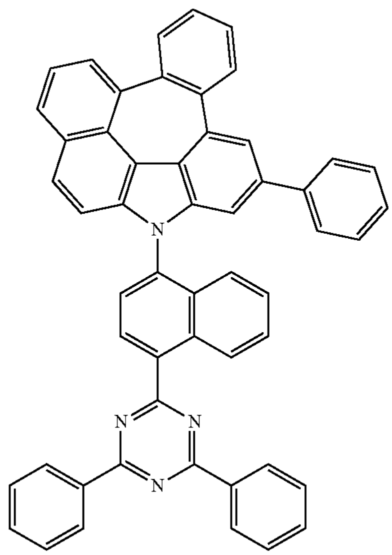
-continued
C-256
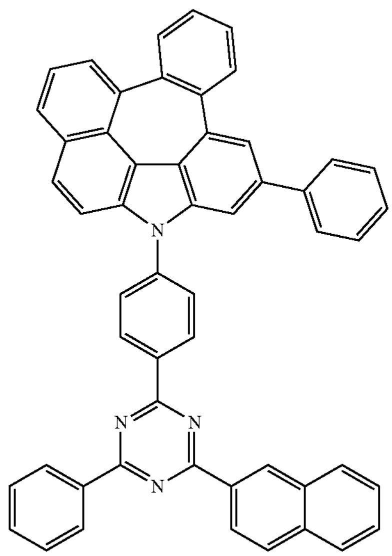
C-257
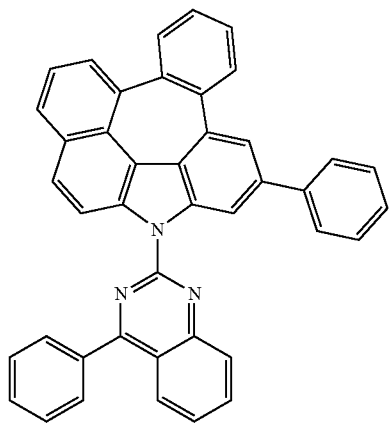
C-258
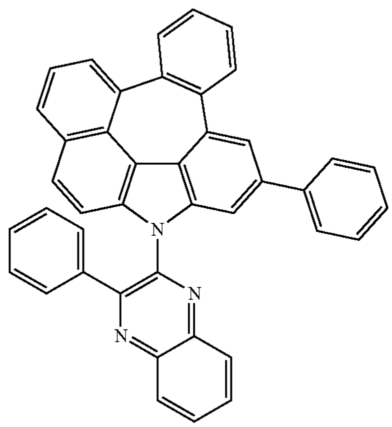

-continued
C-259
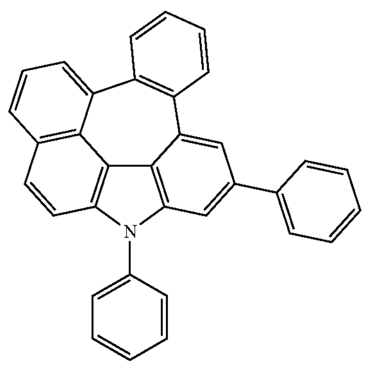
C-260
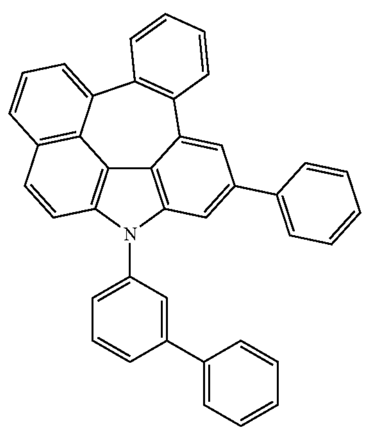
C-261
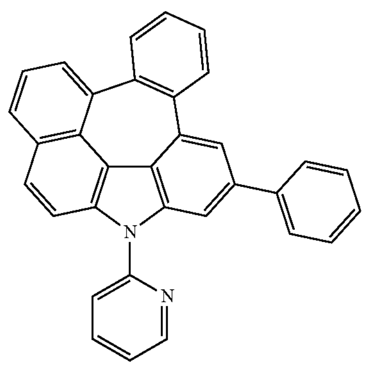
C-262
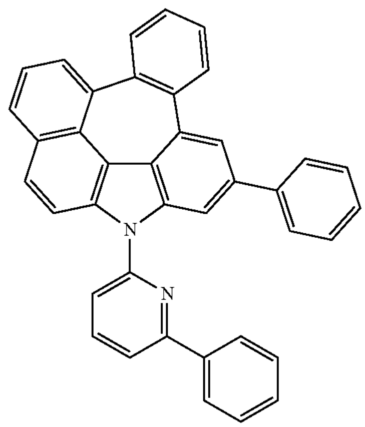
-continued
C-263
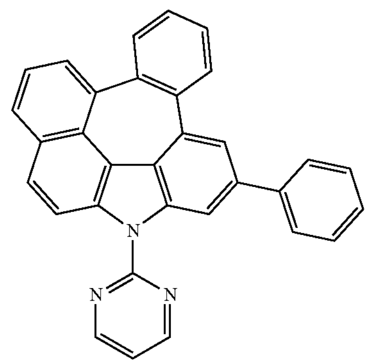
C-264
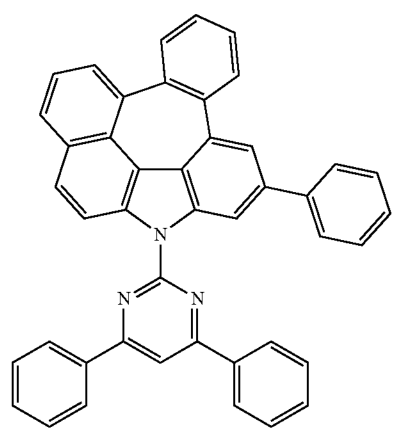
C-265
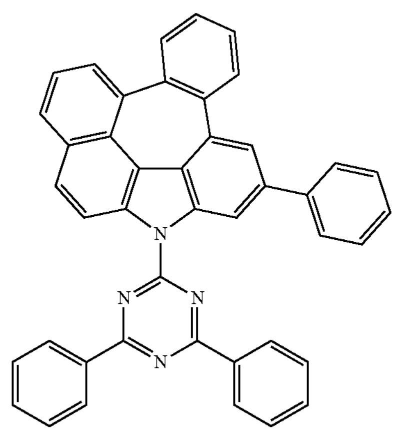
C-266
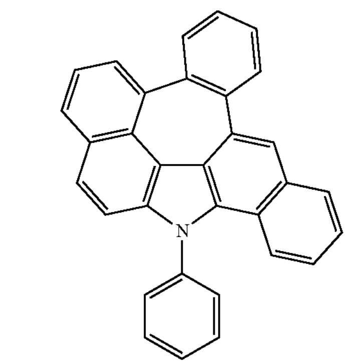

-continued
C-267
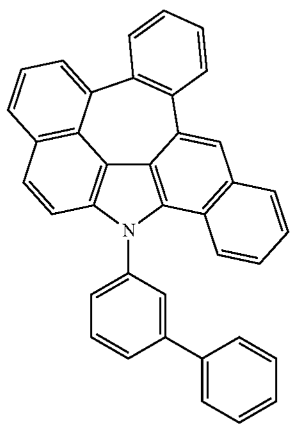
C-268
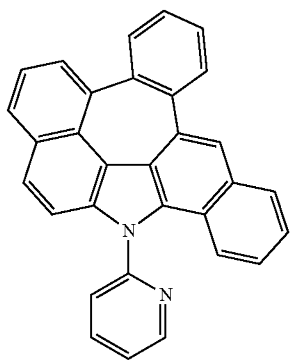
C-269
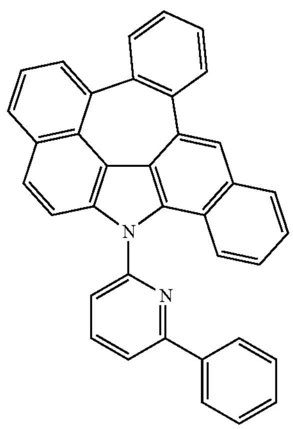
C-270
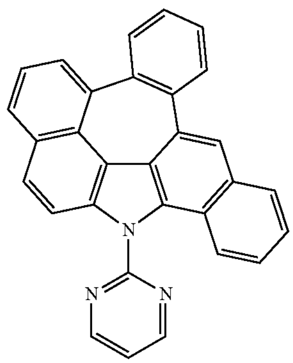
-continued
C-271
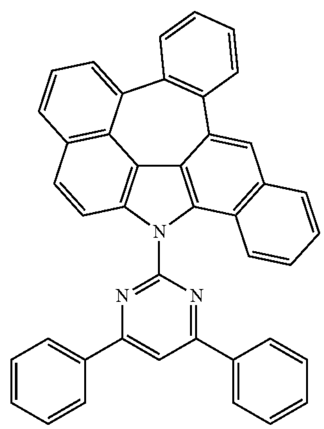
C-272
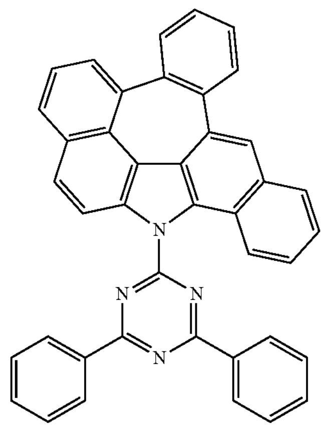
C-273
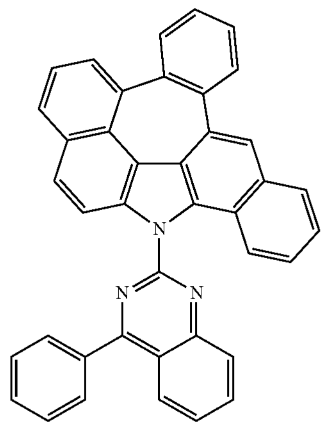

-continued
C-274
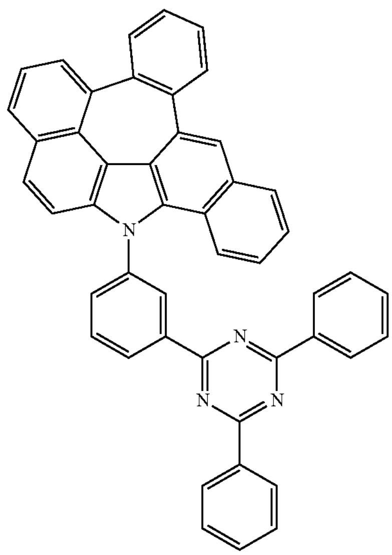
C-275
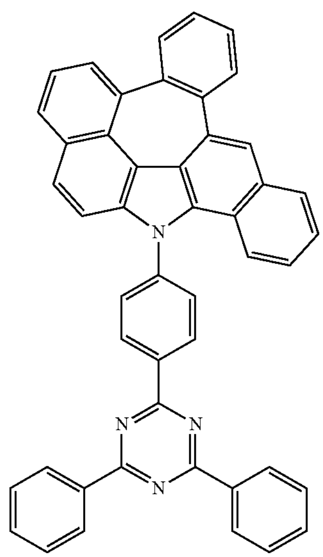
C-276
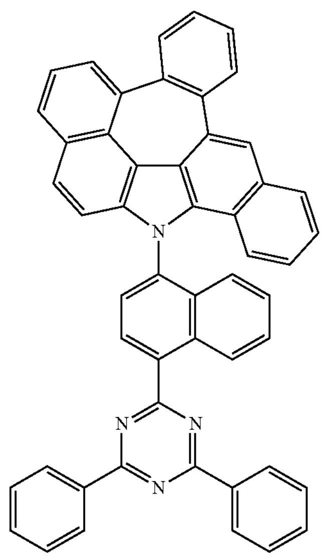
-continued
C-277
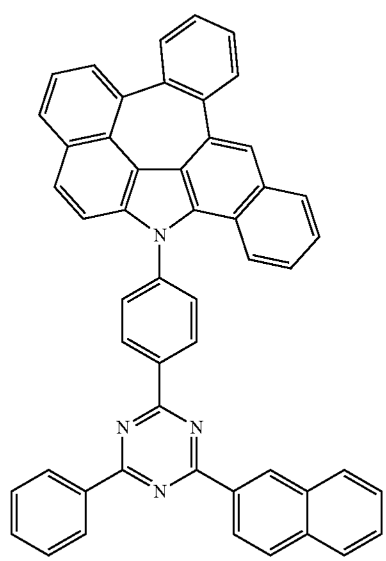
C-278
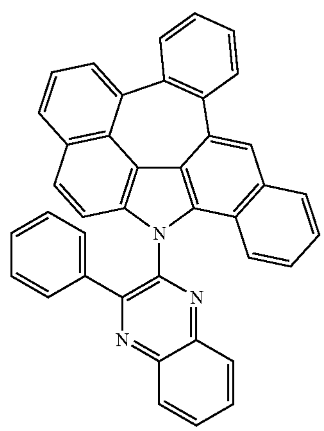
C-279
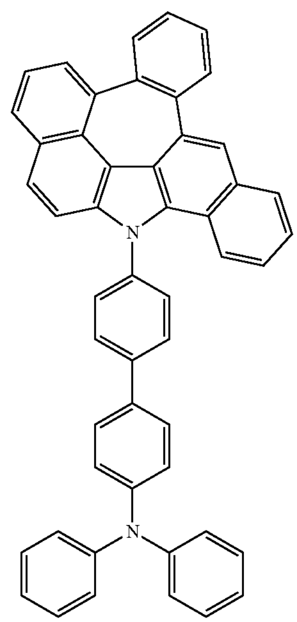

-continued
C-280
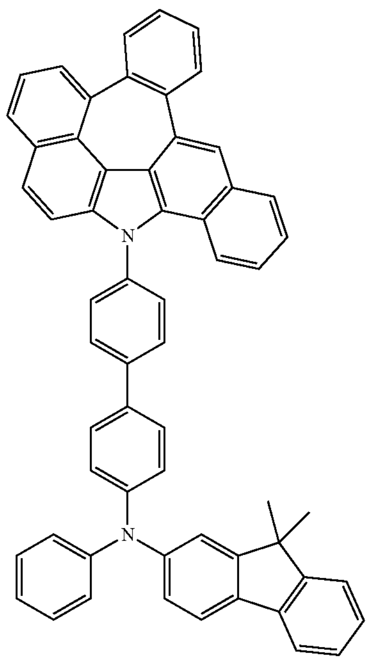
C-281
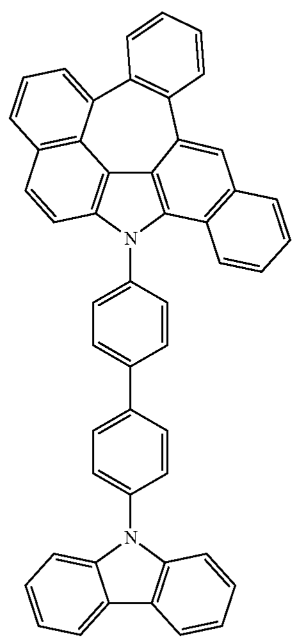
-continued
C-282
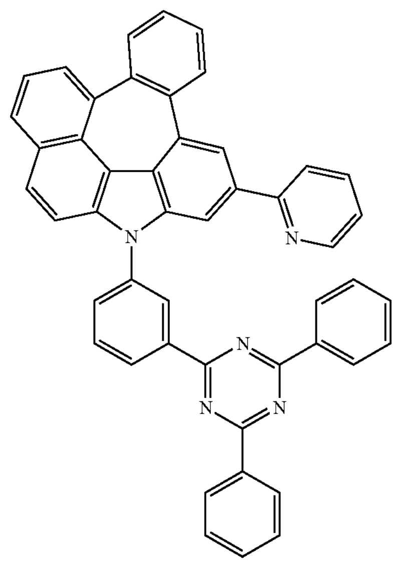
C-283
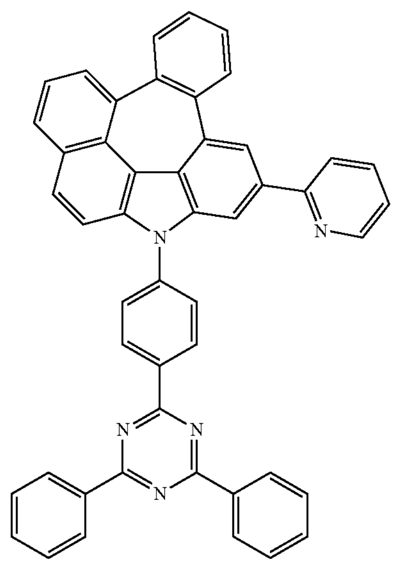
C-284
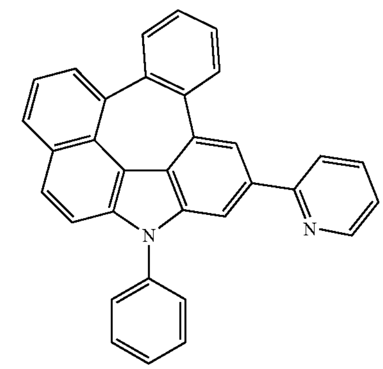

-continued
C-285
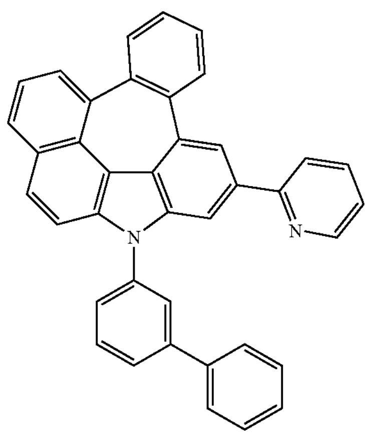
C-286
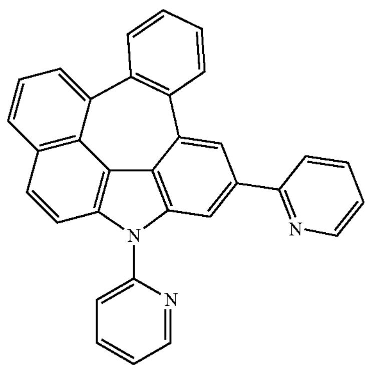
C-287
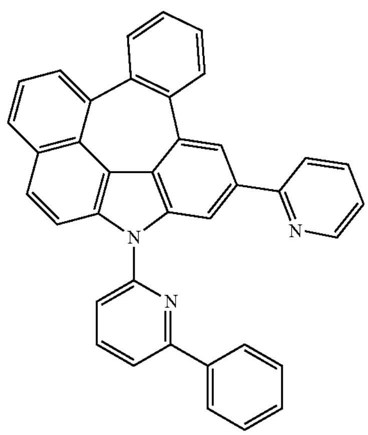
C-288
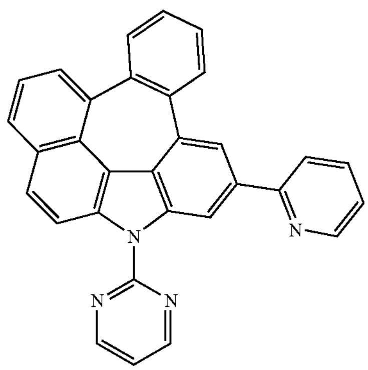
-continued
C-289
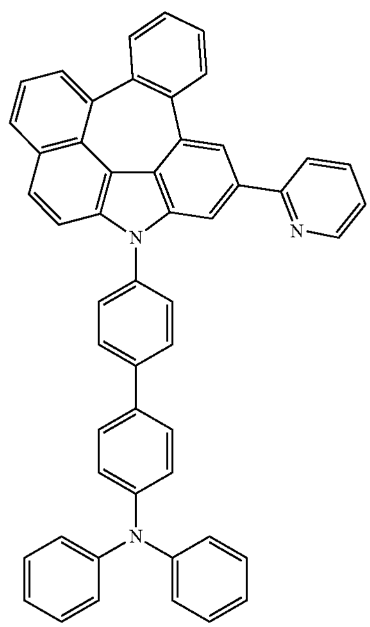
C-290
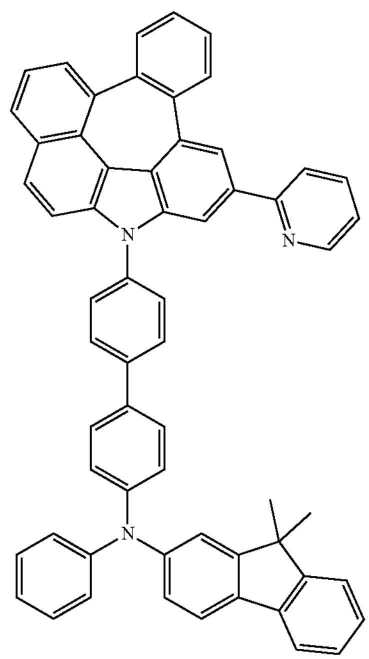

-continued
C-291
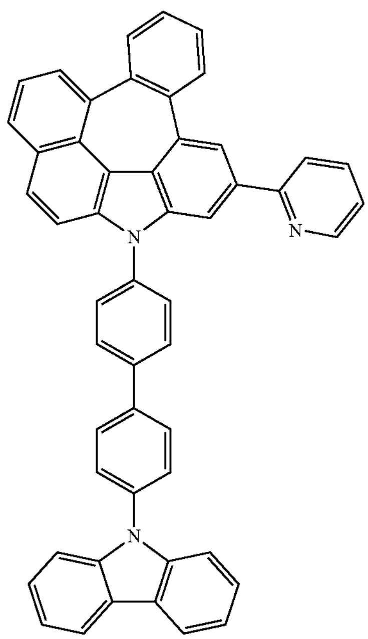
C-292
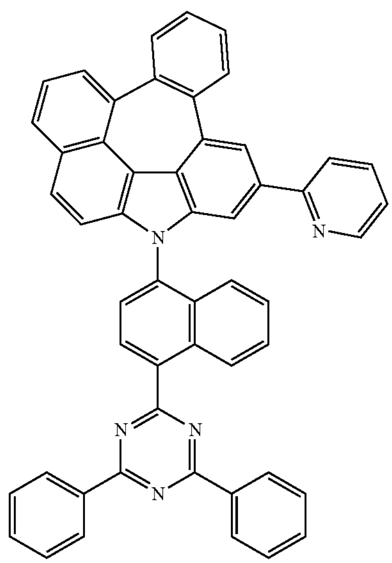
-continued
C-293
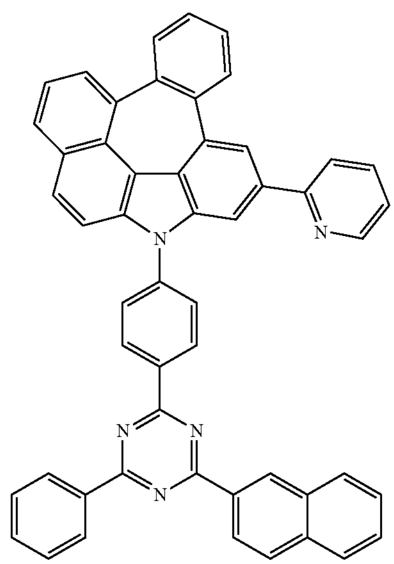
C-294
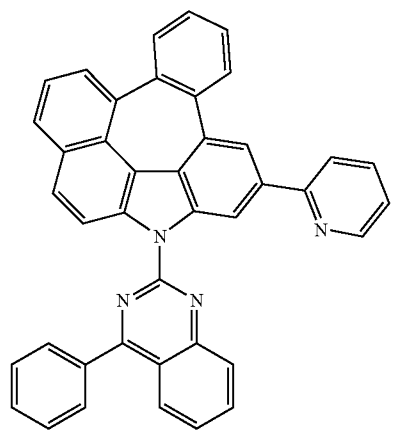
C-295
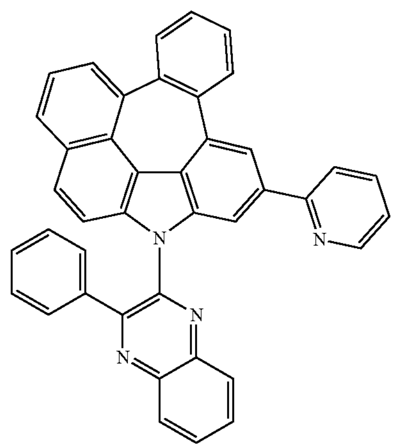

-continued
C-296
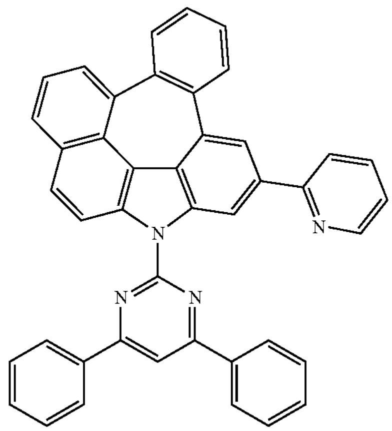
C-297
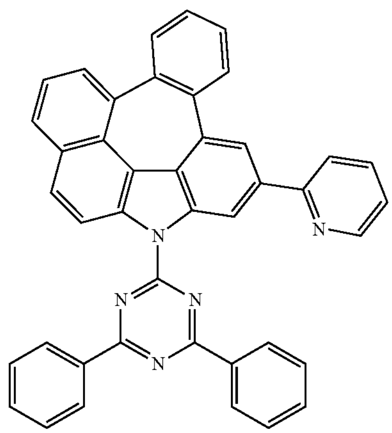
C-298
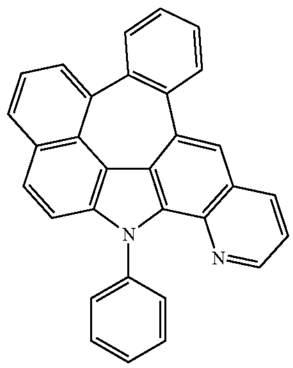
C-299
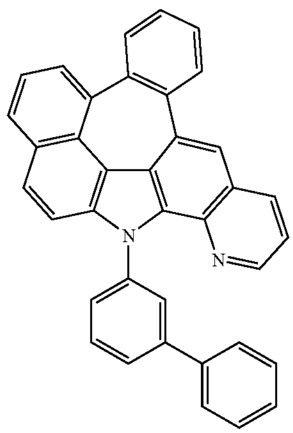
-continued
C-300
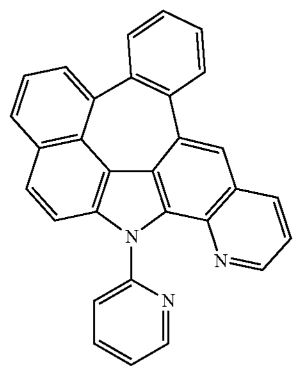
C-301
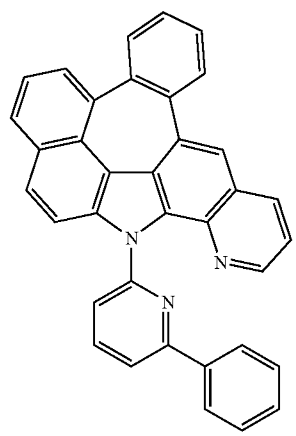
C-302
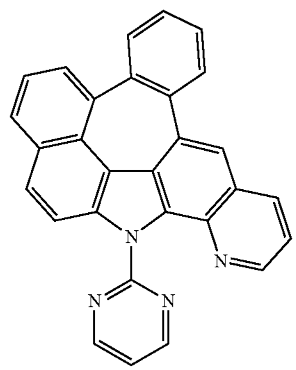
C-303
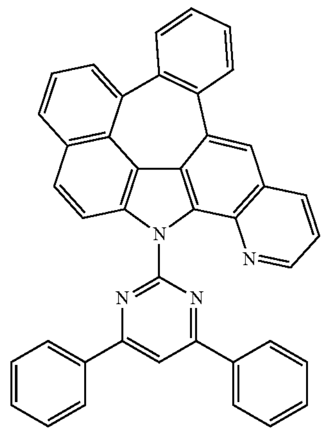

-continued
C-304
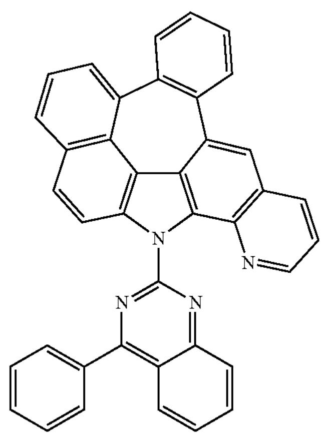
C-307
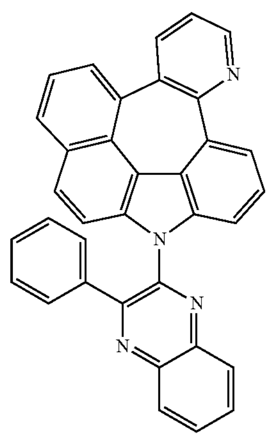
C-305
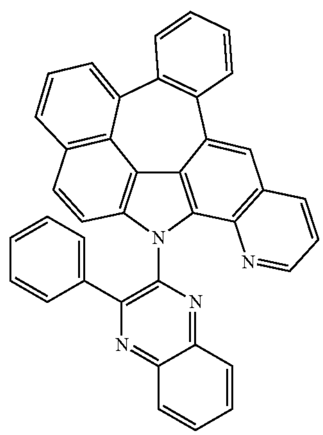
C-308
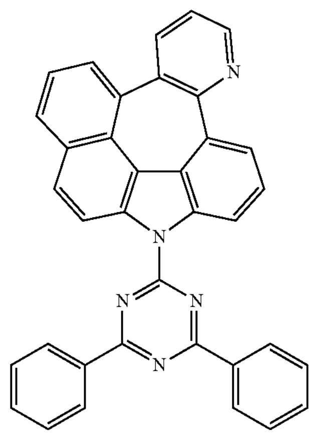
C-306
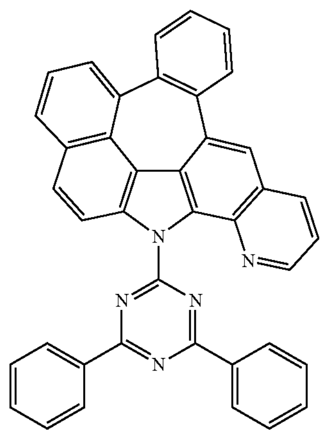
C-309
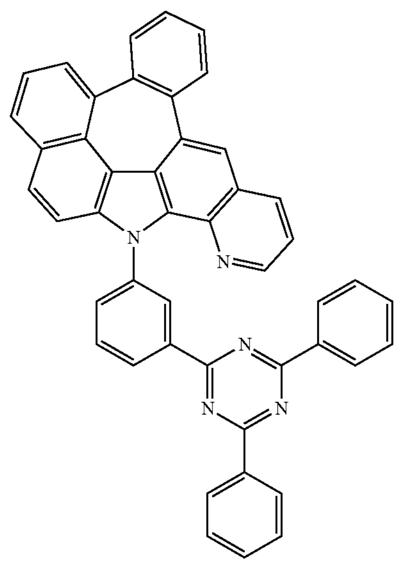

-continued
C-310
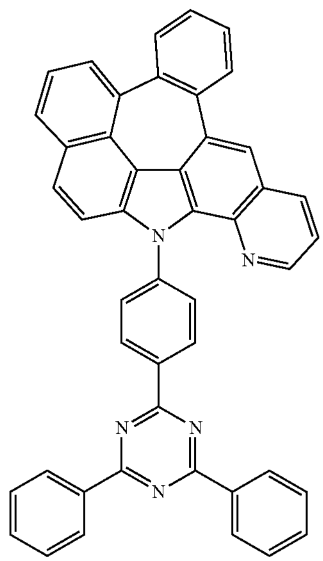
C-311
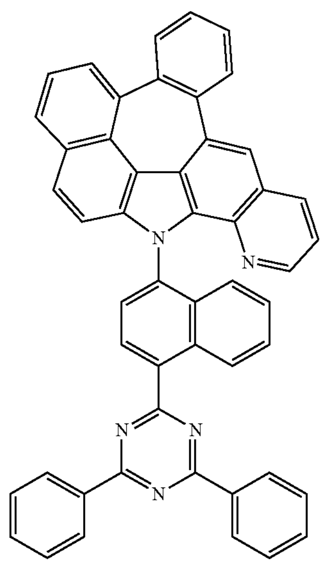
C-312
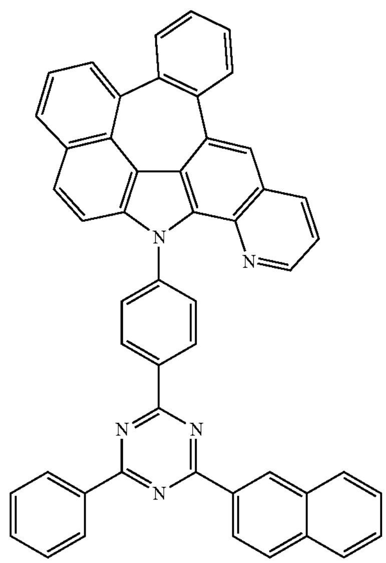
-continued
C-313
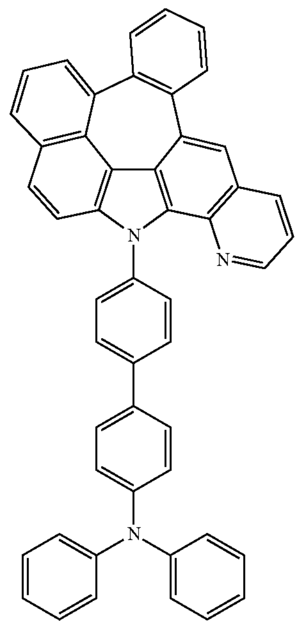
C-314
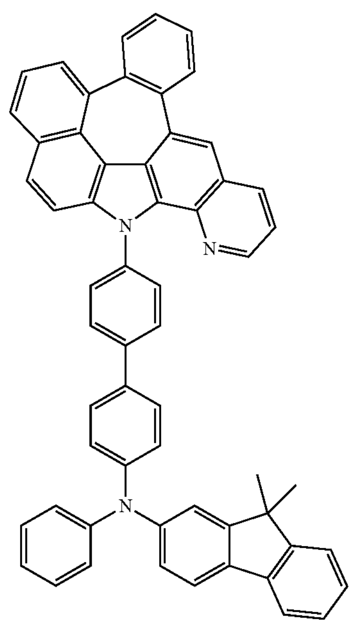

-continued
C-315
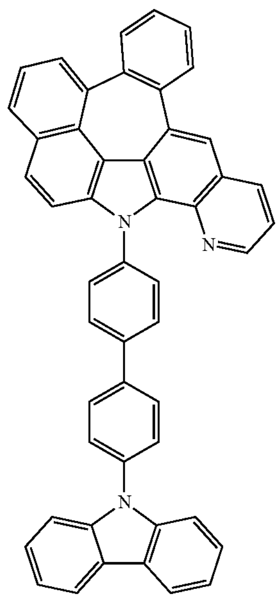
C-316
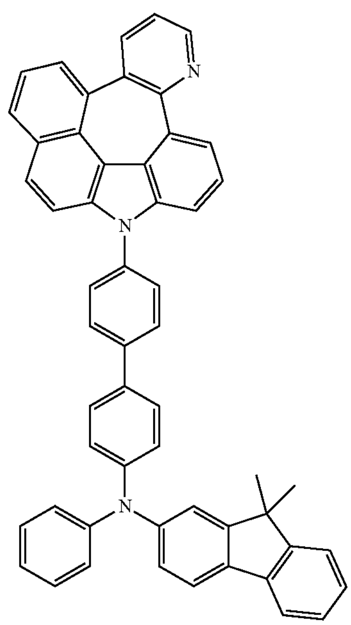
-continued
C-317
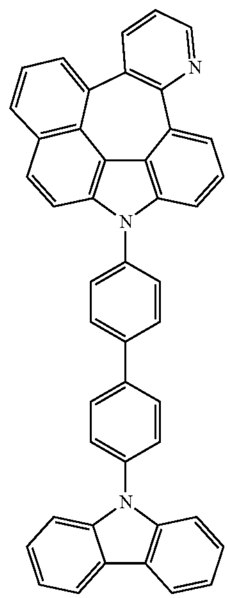
C-318
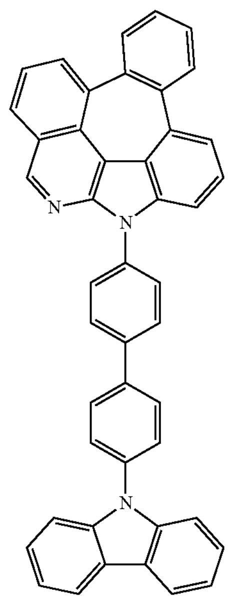
C-319
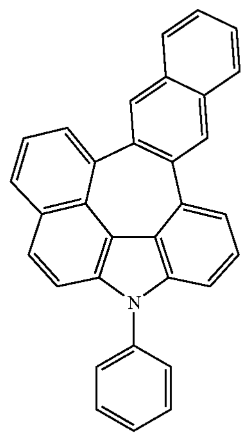

C-320
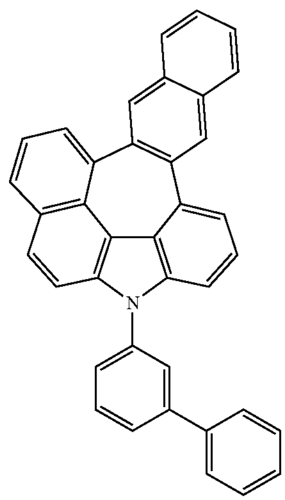
C-321
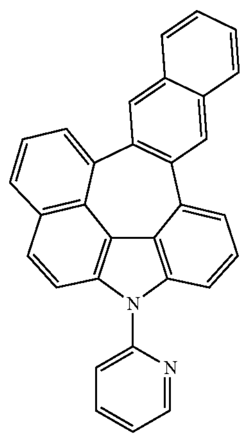
C-322
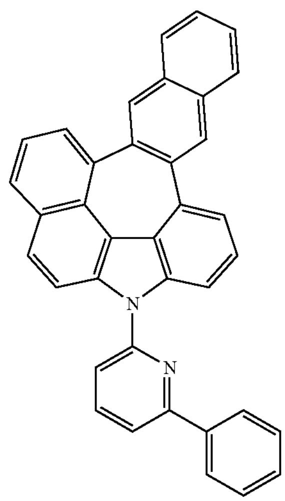
C-323
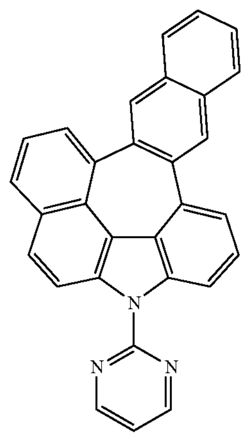
C-324
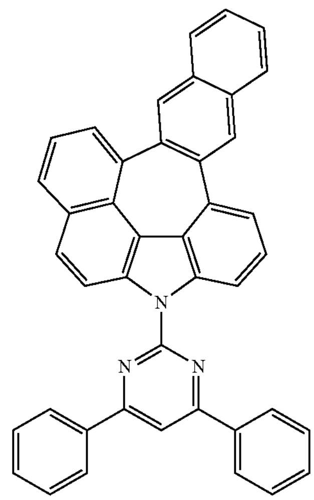
C-325
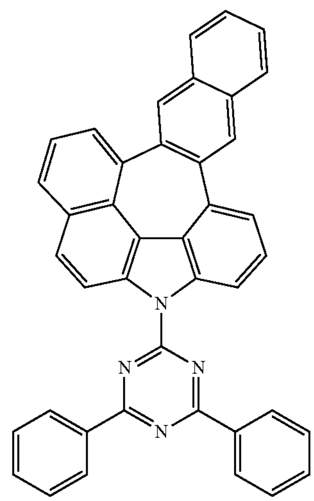

-continued
C-326
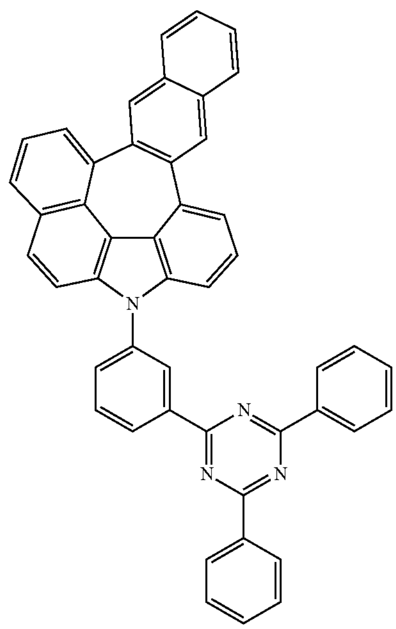
C-327
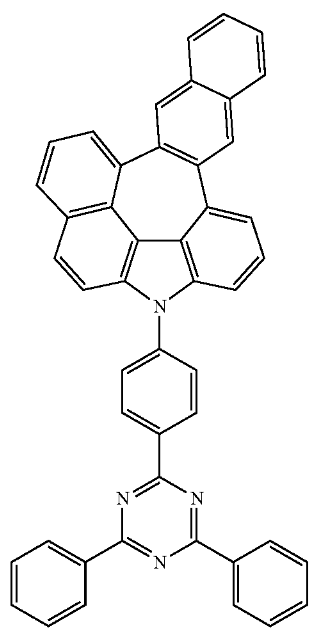
-continued
C-328
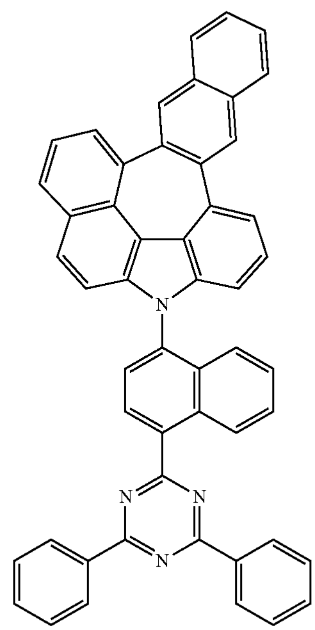
C-329
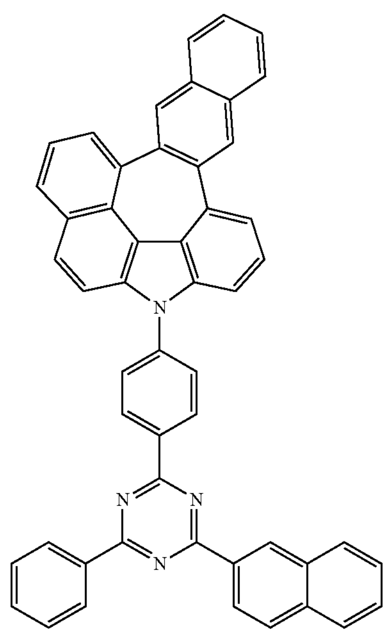

-continued
C-330
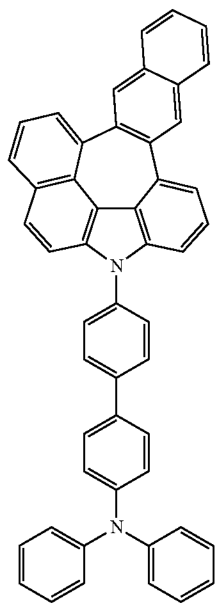
C-331
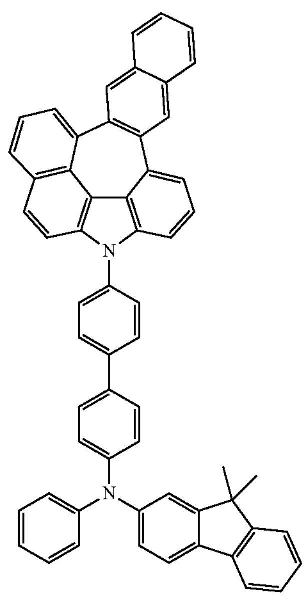
-continued
C-332
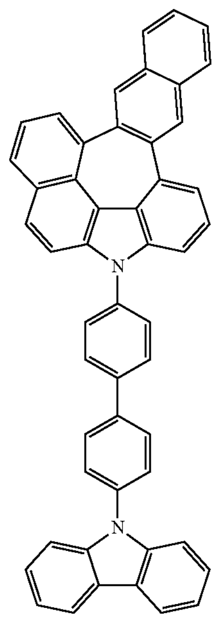
C-333
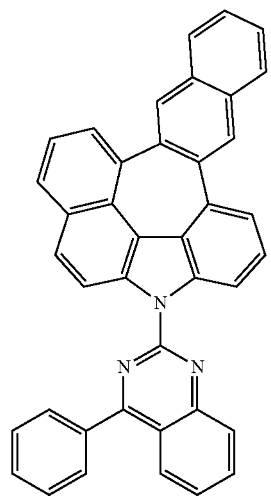
C-334
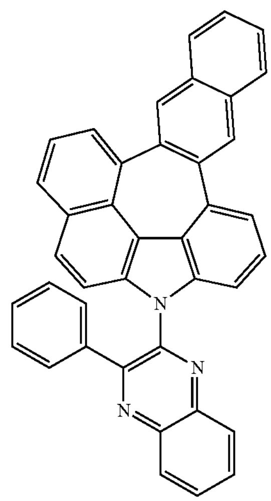

-continued
C-335
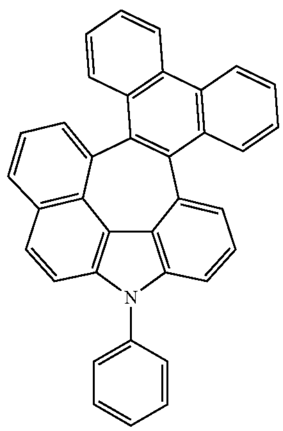
C-336
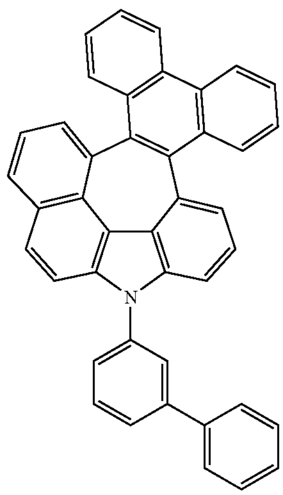
C-337
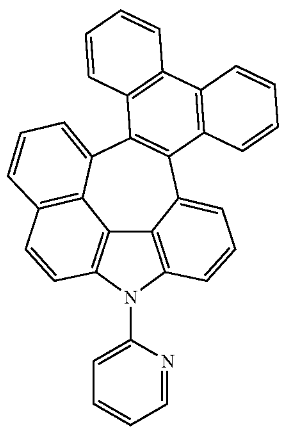
-continued
C-338
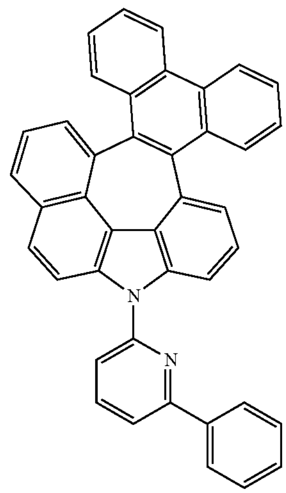
C-339
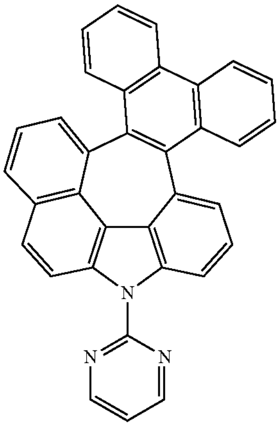
C-340
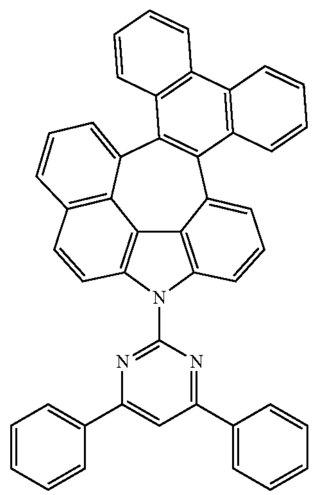

-continued
C-341
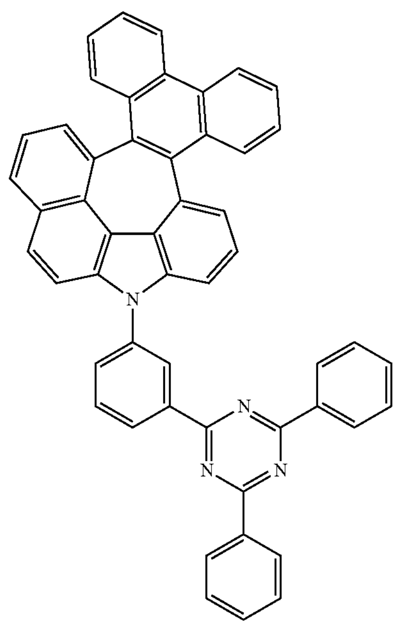
C-342
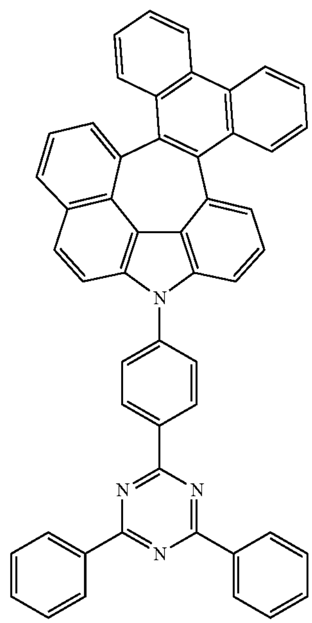
-continued
C-343
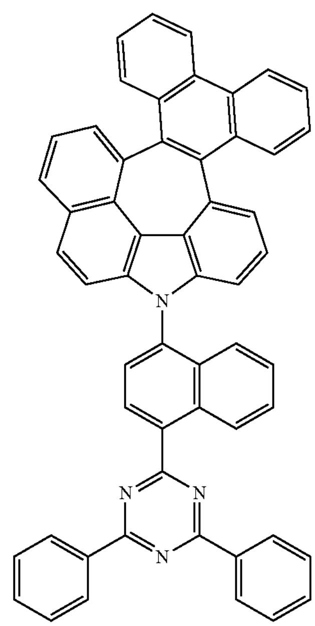
C-344
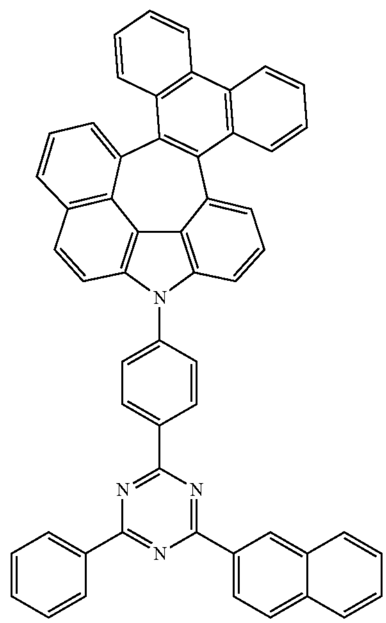

-continued
C-345
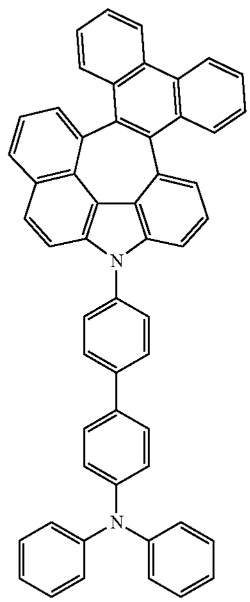
C-346
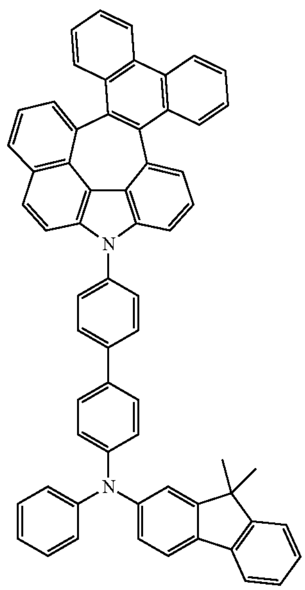
-continued
C-347
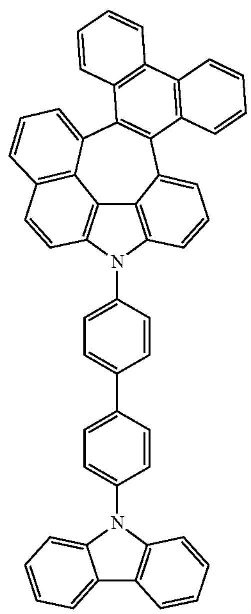
C-348
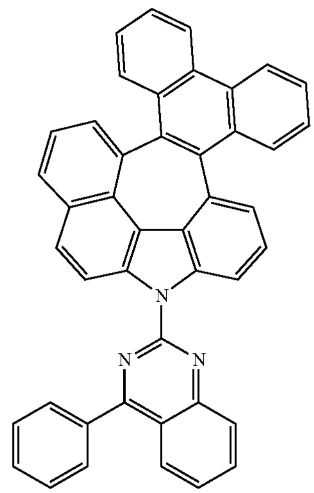
C-349
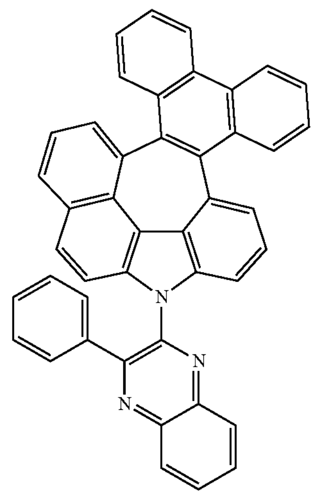

-continued
C-350
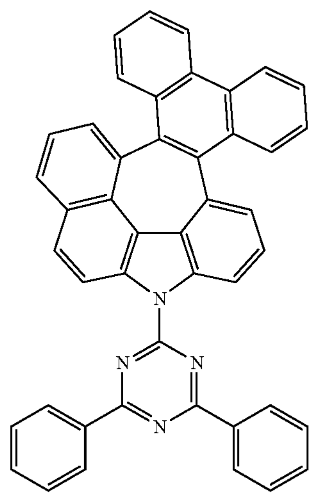
C-351
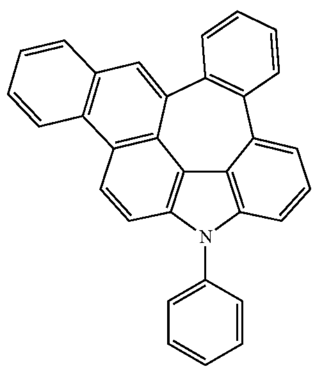
C-352
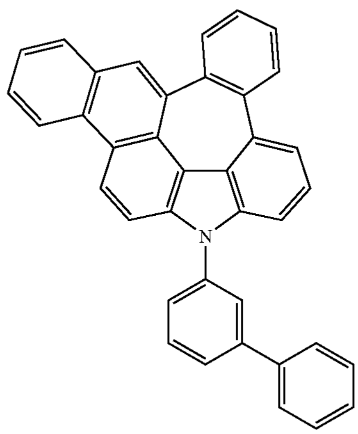
C-353
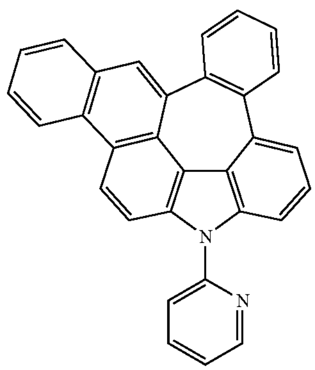
-continued
C-354
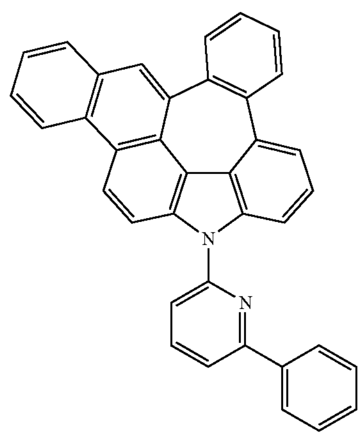
C-355
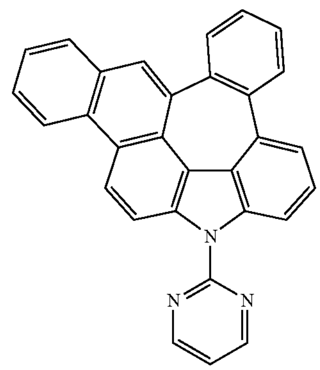
C-356
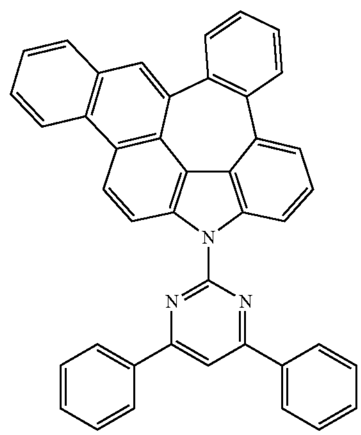

-continued
C-357
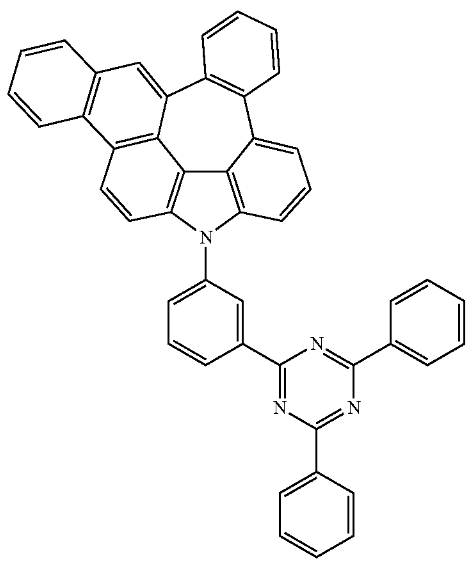
C-358
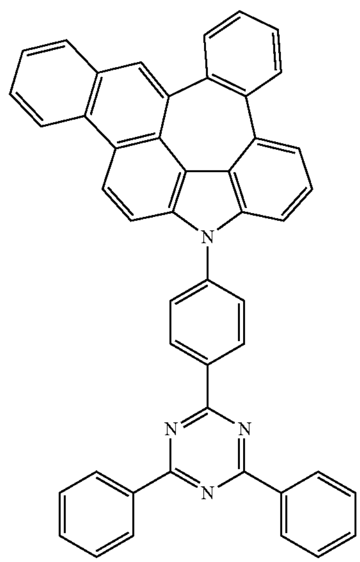
-continued
C-359
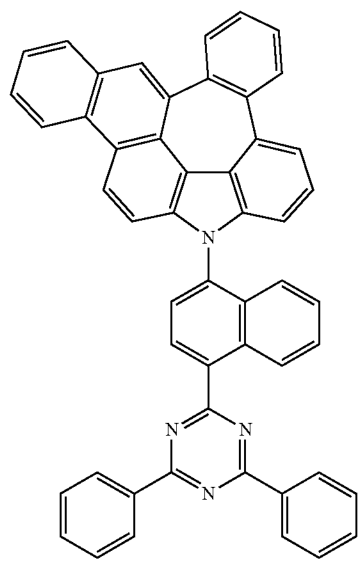
C-360
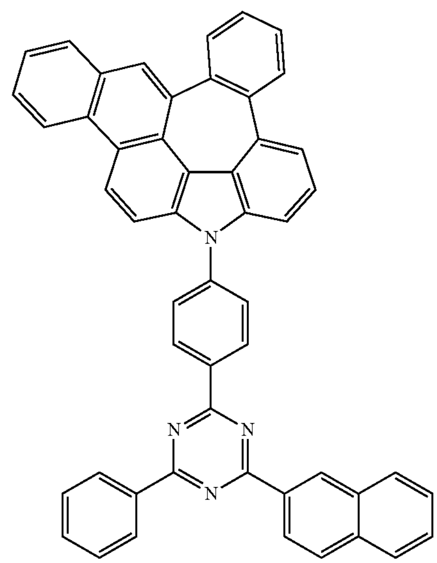
C-361
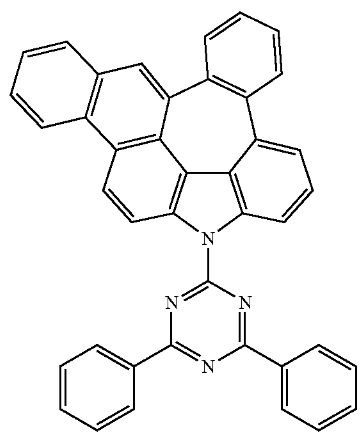

-continued
C-362
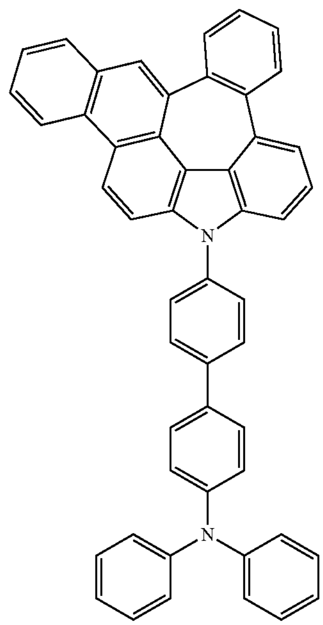
C-363
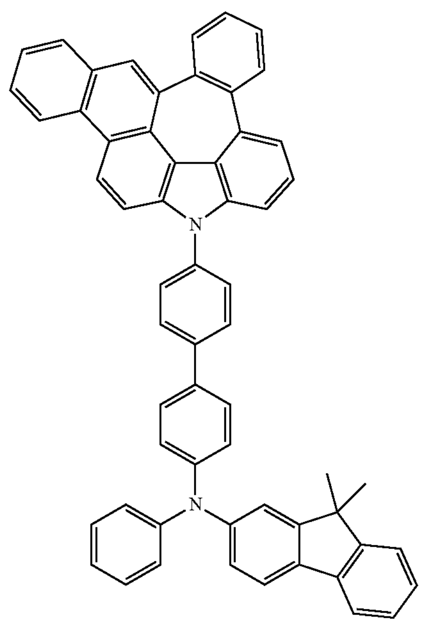
-continued
C-364
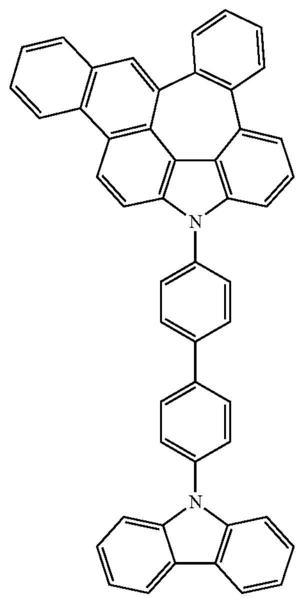
C-365
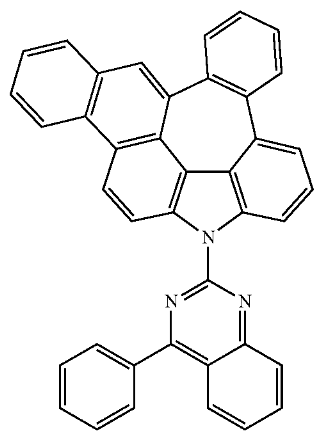
C-366
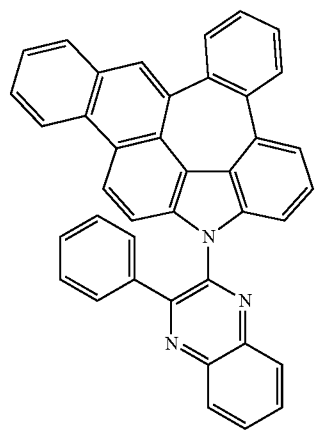

-continued
C-367
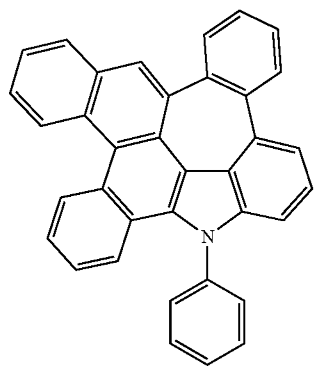
C-368
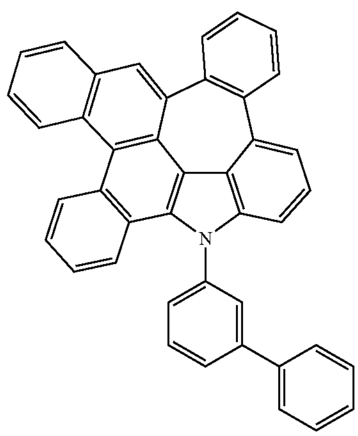
C-369
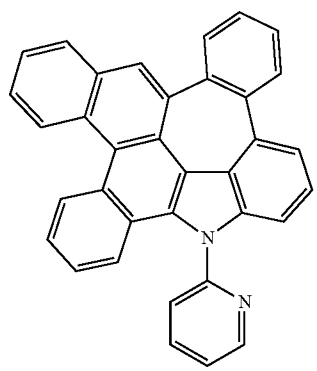
C-370
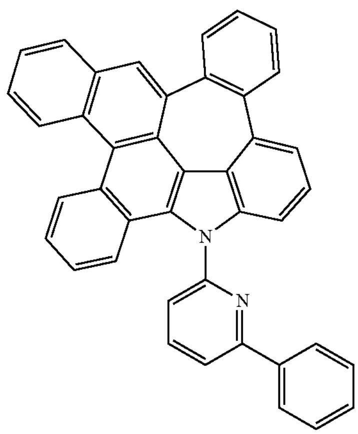
-continued
C-371
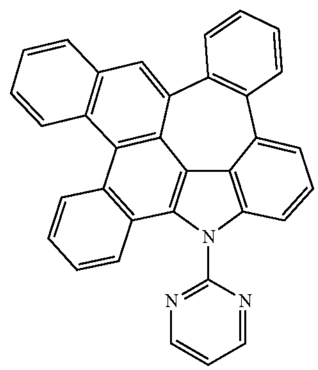
C-372
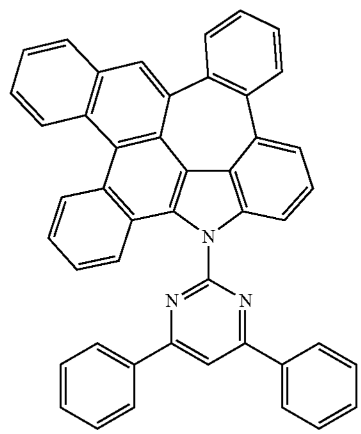
C-373
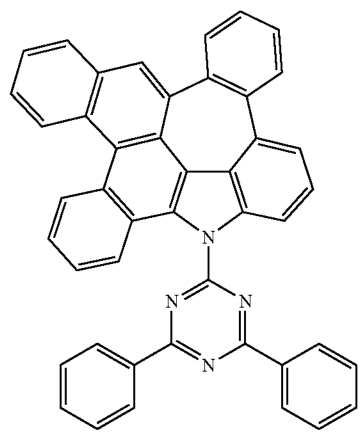

C-374
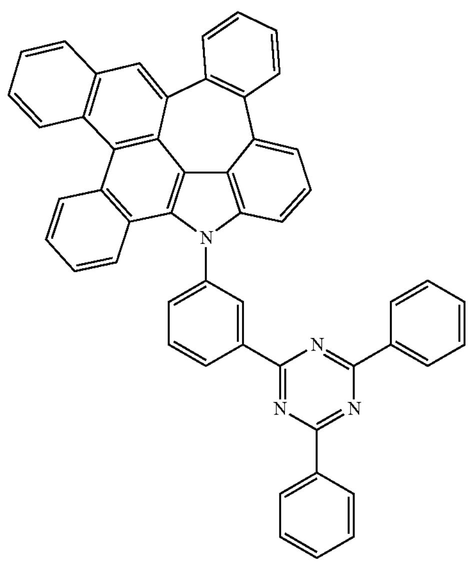
C-375
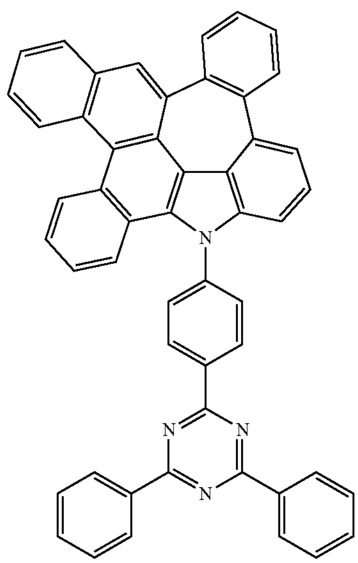
C-376
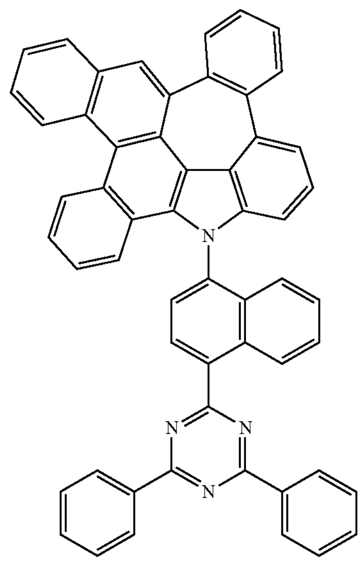
C-377
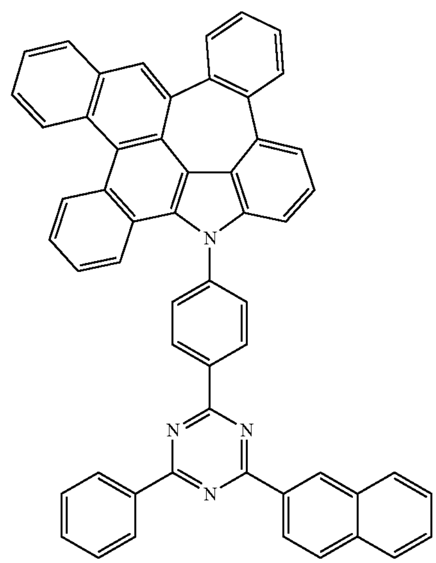
C-378
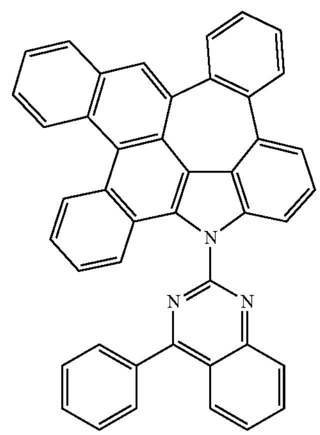

-continued
C-379
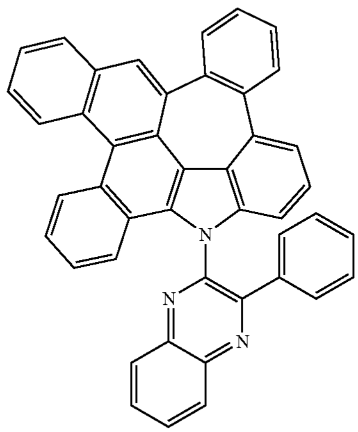
C-380
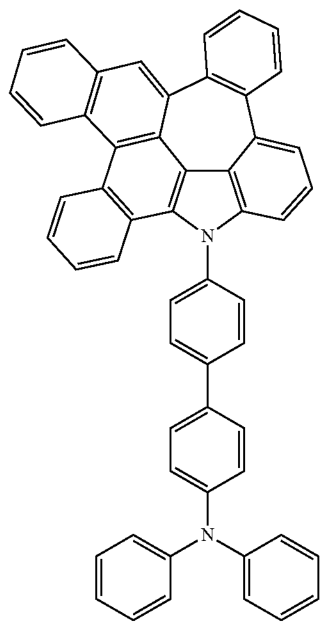
C-381
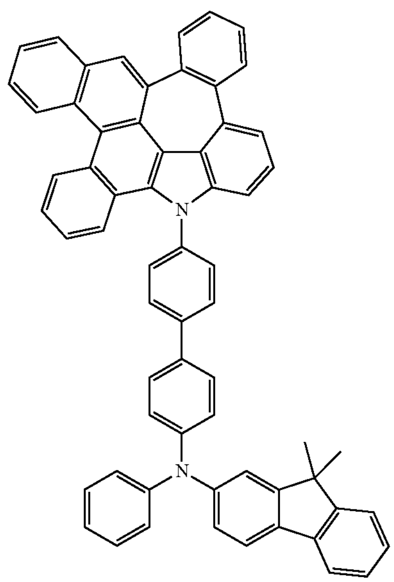
-continued
C-382
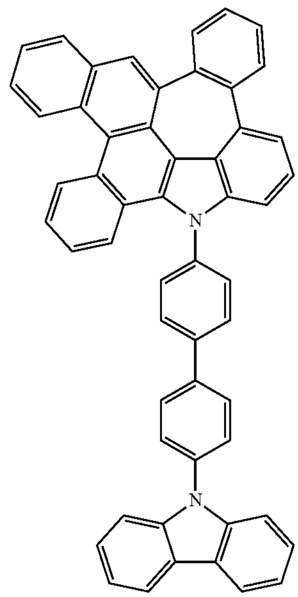
C-383
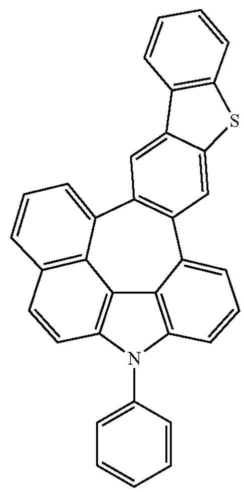
C-384
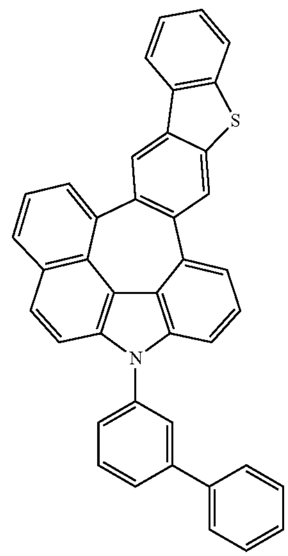

-continued
C-385
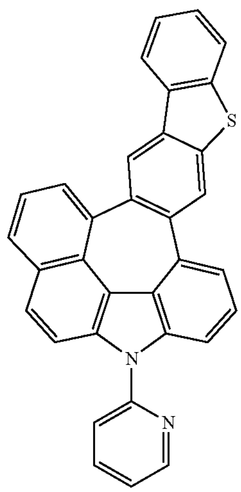
C-386
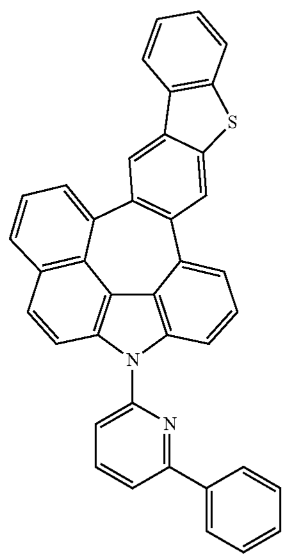
C-387
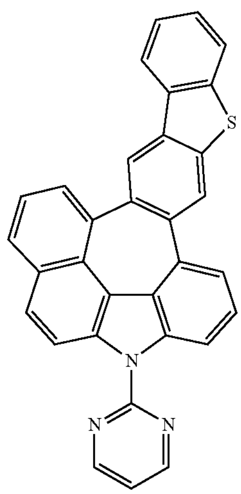
-continued
C-388
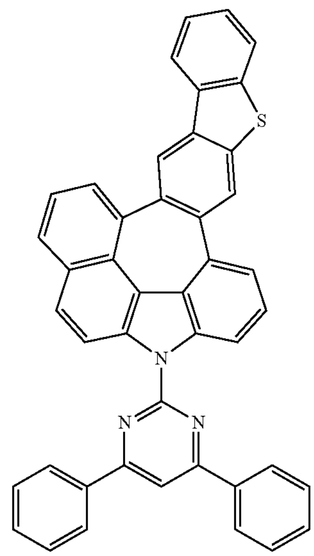
C-389
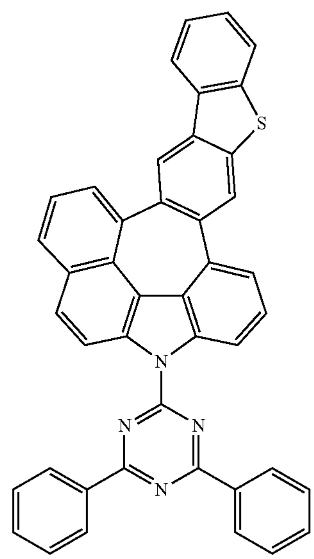

-continued
C-390
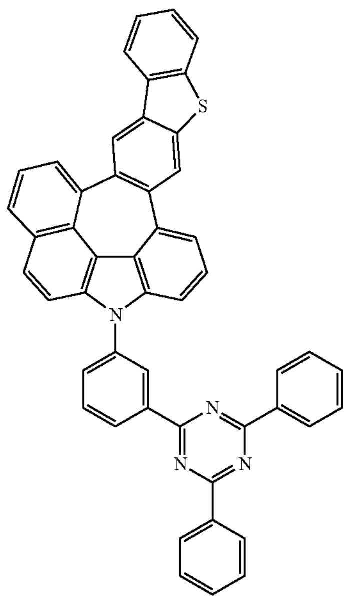
C-391
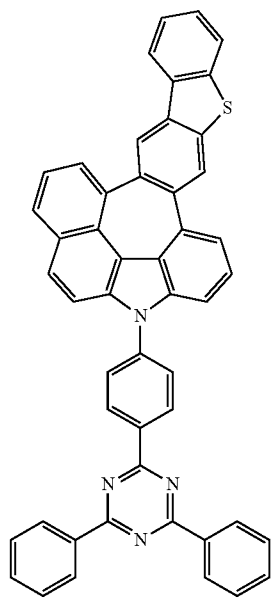
-continued
C-392
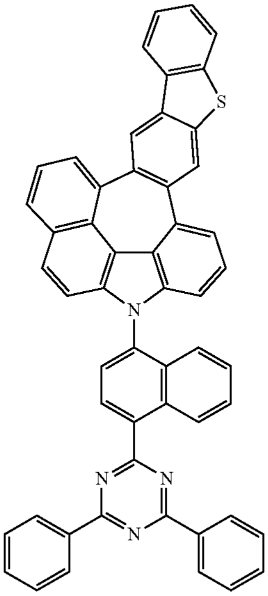
C-393
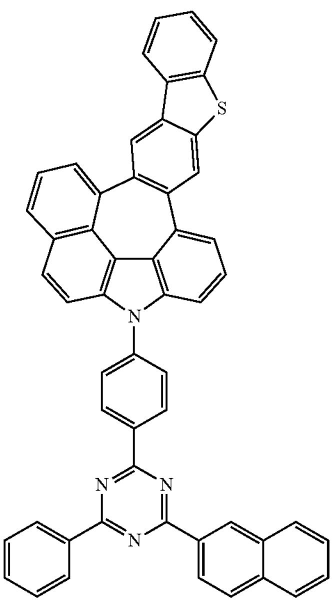

-continued
C-394
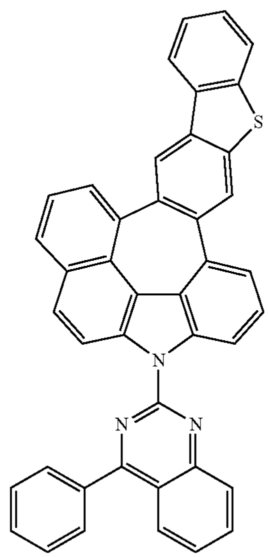
C-395
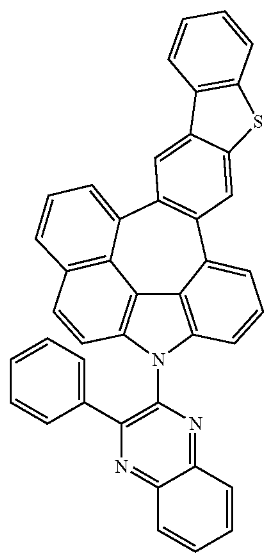
-continued
C-396
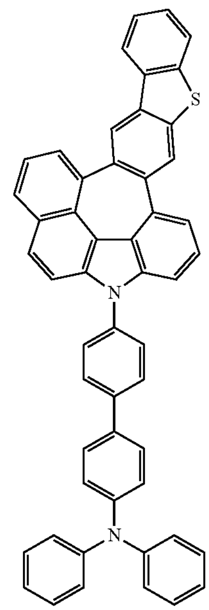
C-397
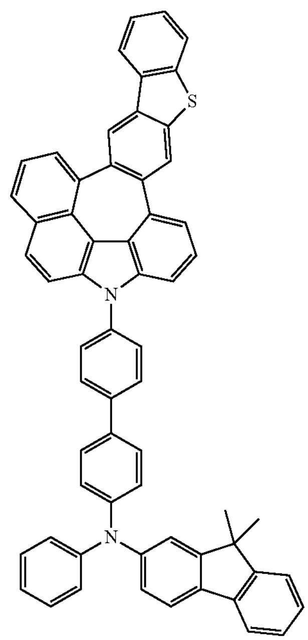

-continued
C-398
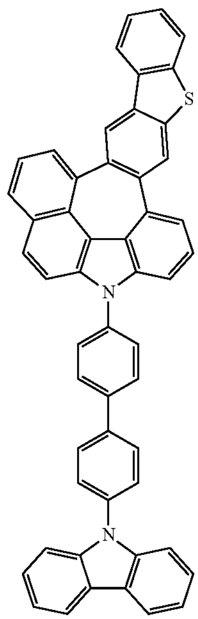
C-399
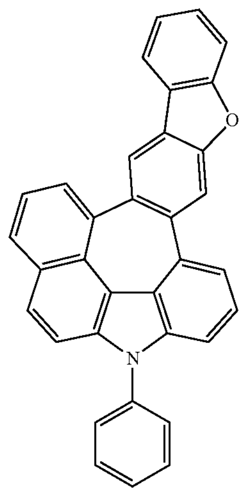
C-400
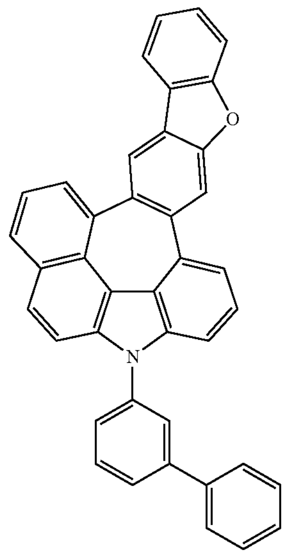
-continued
C-401
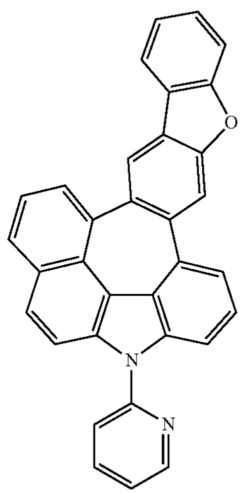
C-402
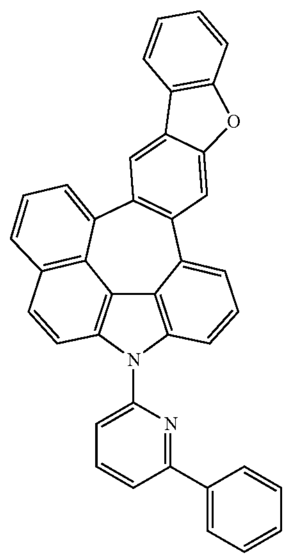
C-403
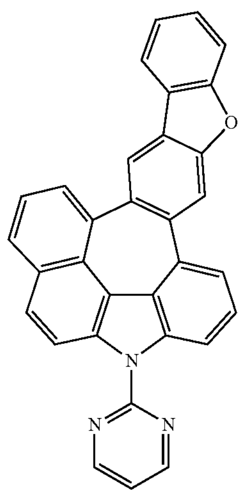

-continued
C-404
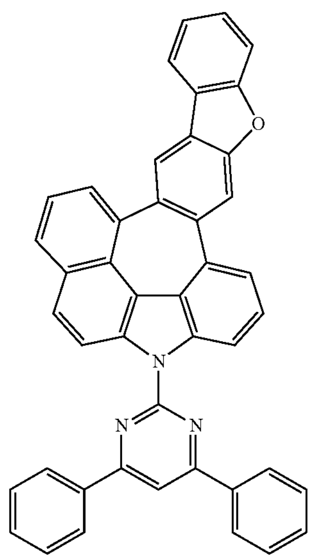
C-405
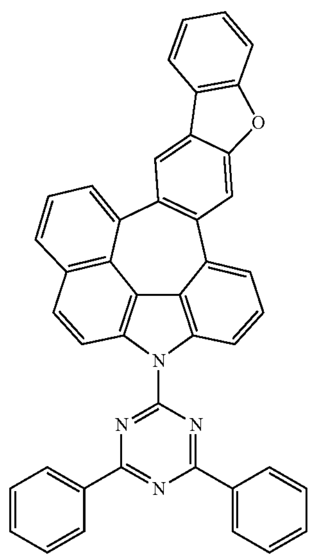
-continued
C-406
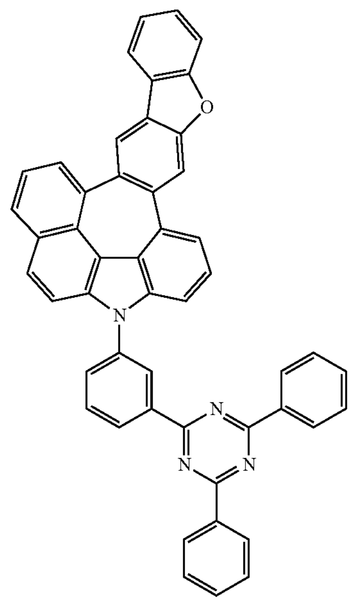
C-407
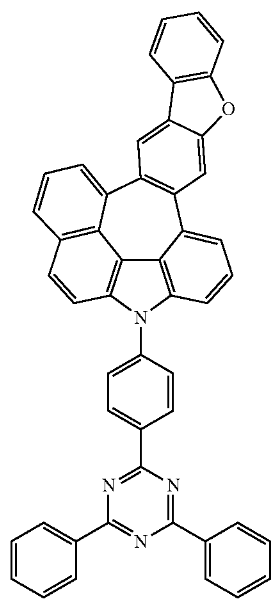

-continued
C-408
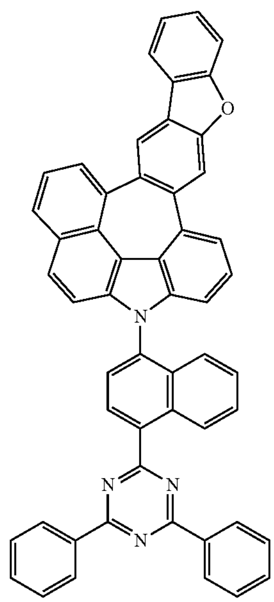
C-410
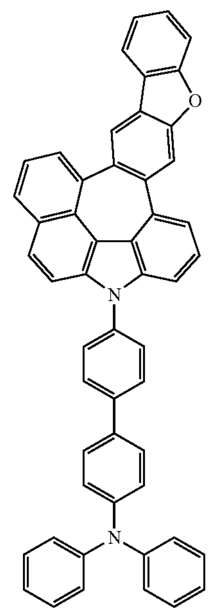
C-409
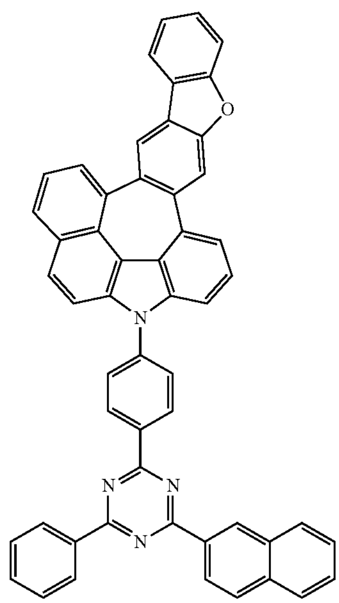
C-411
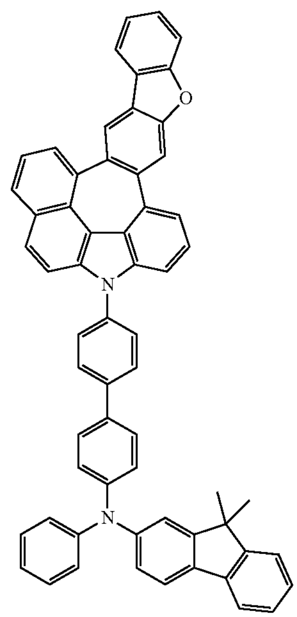

-continued
C-412
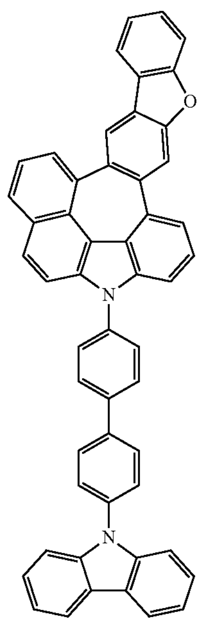
C-413
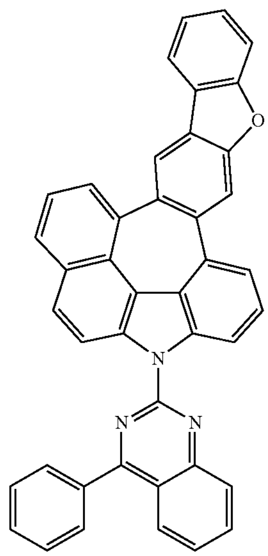
-continued
C-414
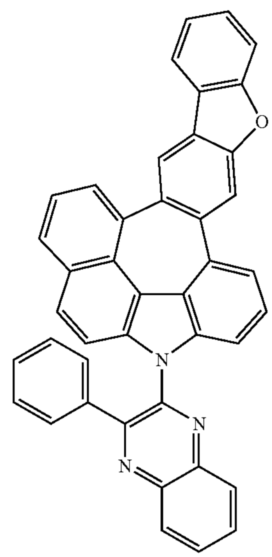
C-415
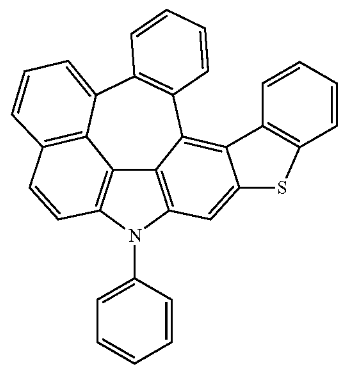
C-416
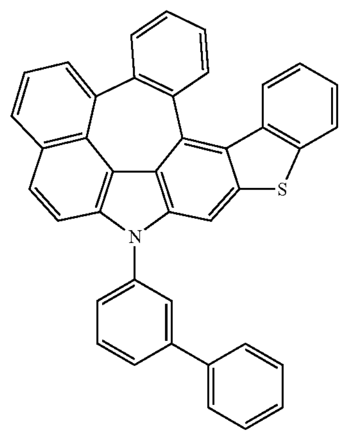

-continued
C-417
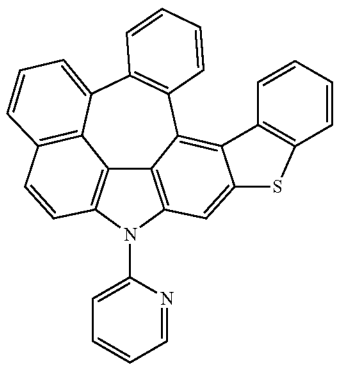
C-418
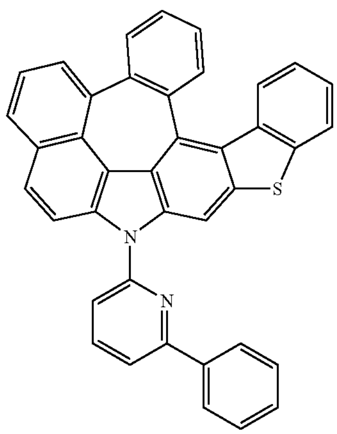
C-419
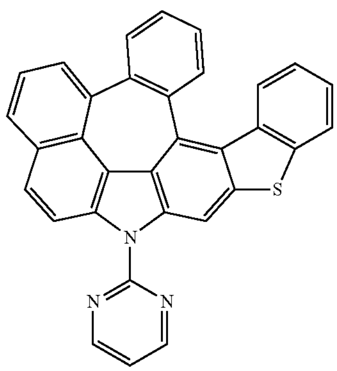
C-420
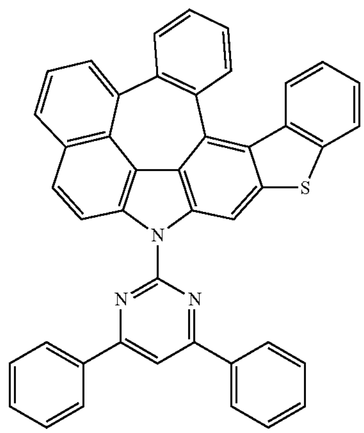
-continued
C-421
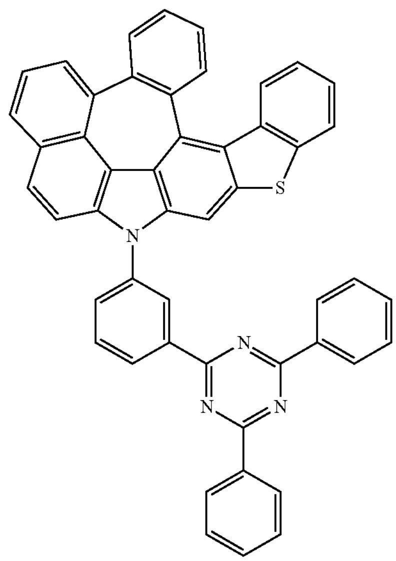
C-422
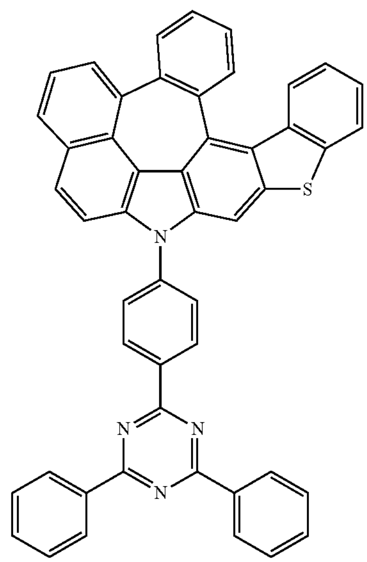

C-423
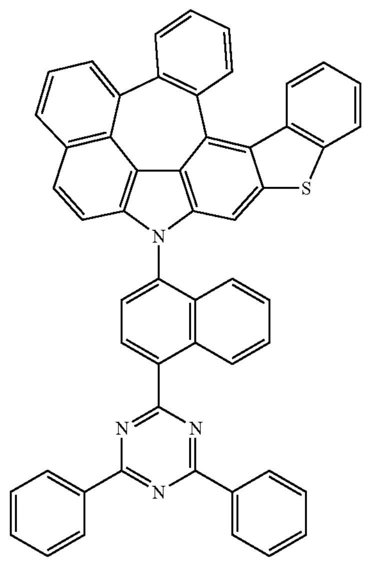
C-424
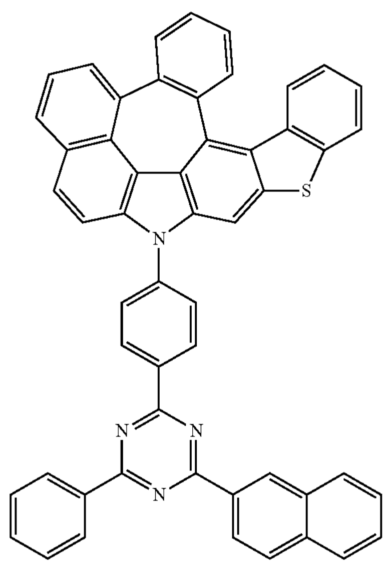
C-425
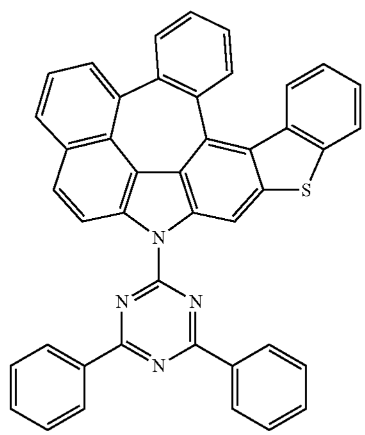
C-426
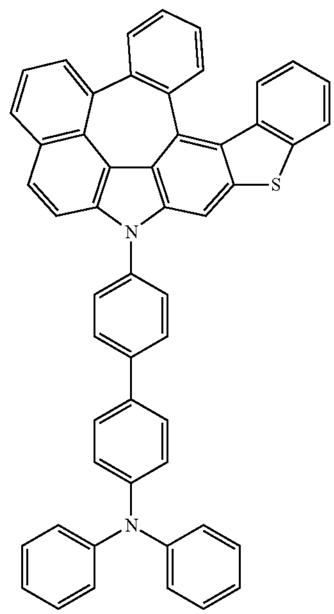
C-427
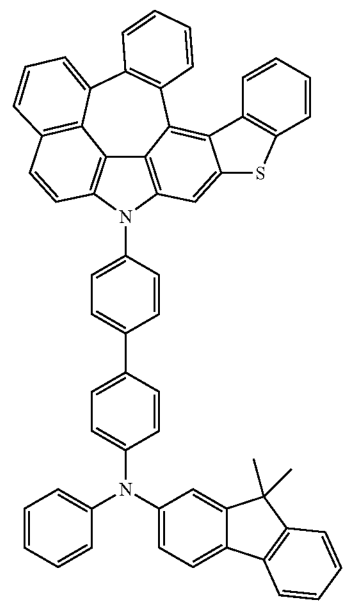

-continued
C-428
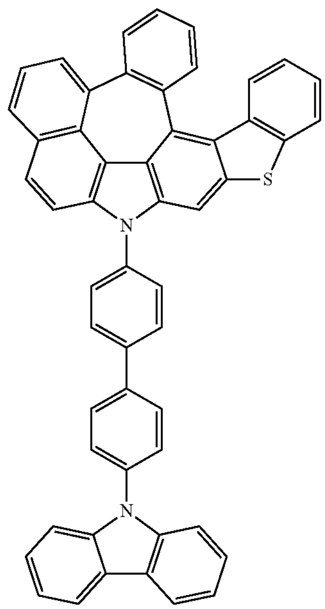
C-429
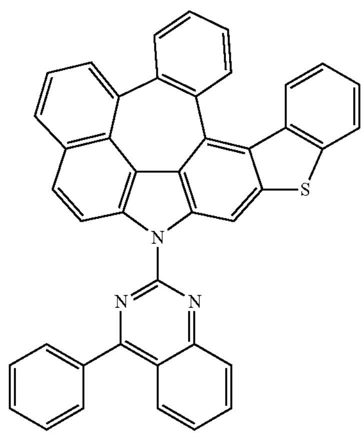
C-430
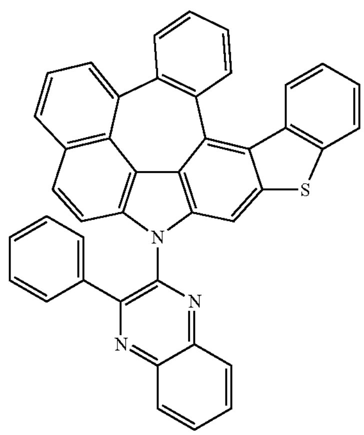
-continued
C-431
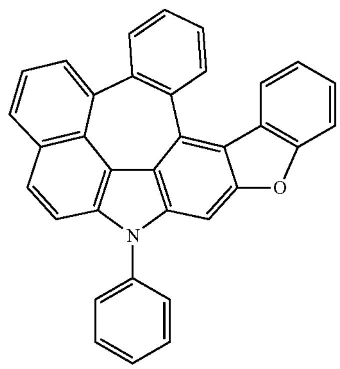
C-432
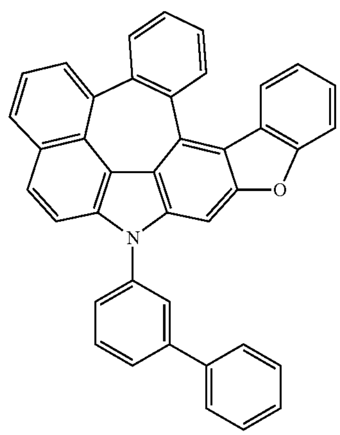
C-433
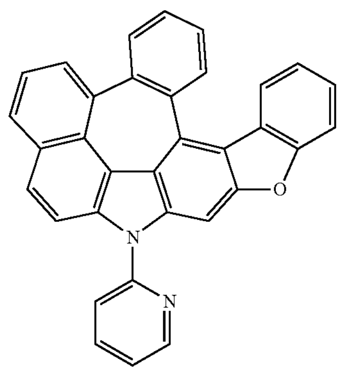
C-434
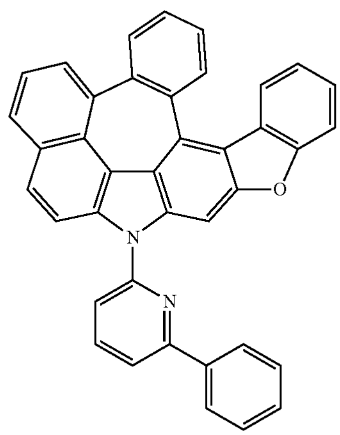

-continued
C-435
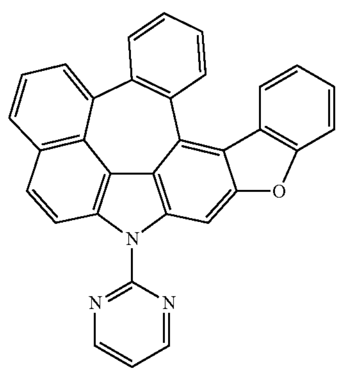
C-436
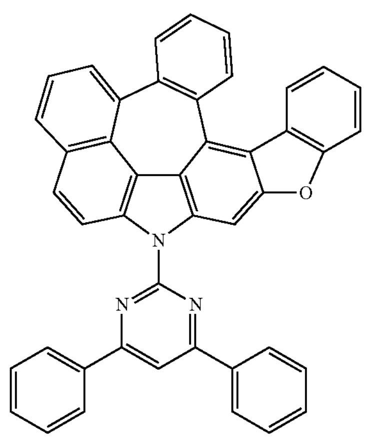
C-437
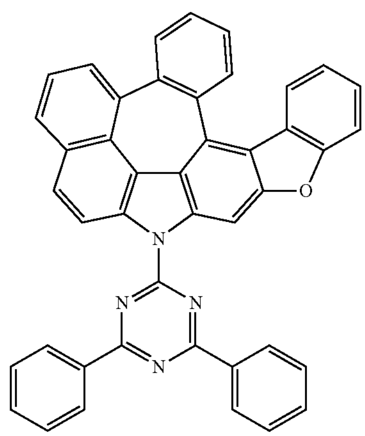
-continued
C-438
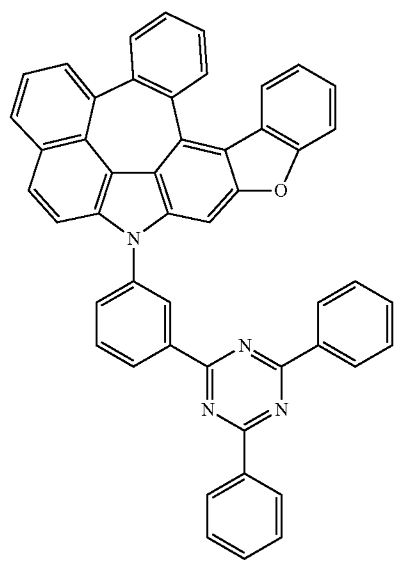
439
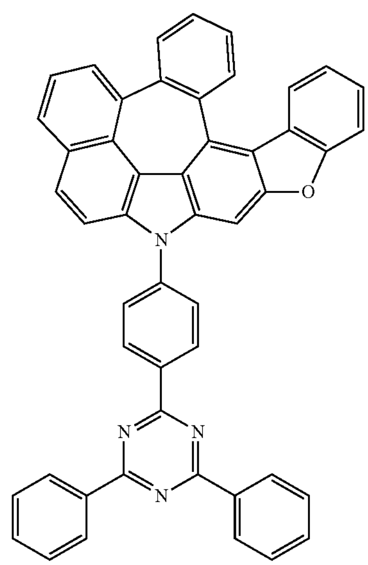
440
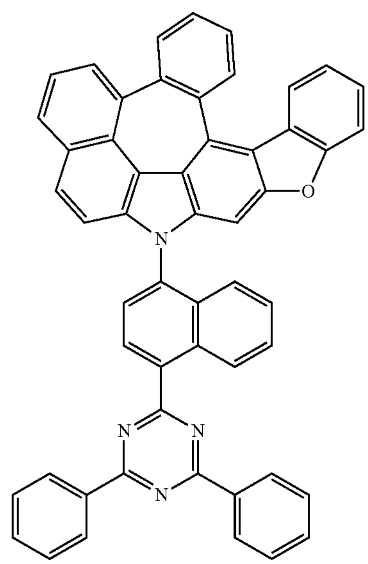

-continued
C-441
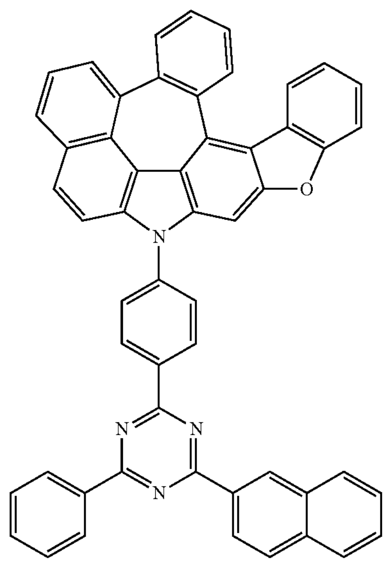
C-442
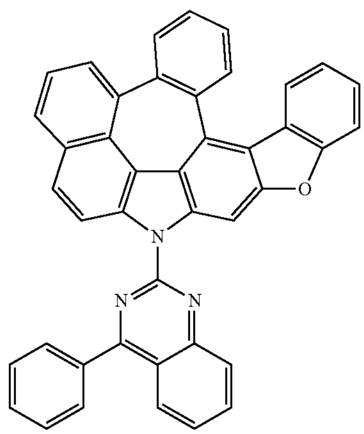
C-443
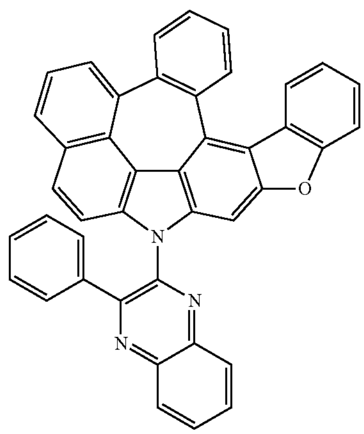
-continued
C-444
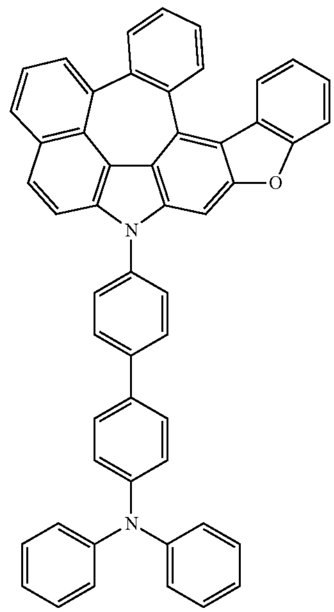
C-445
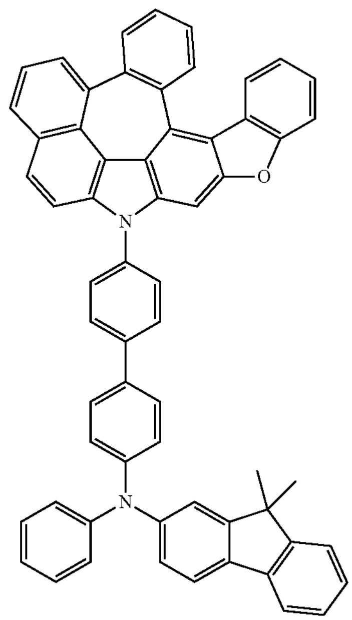

-continued
C-446
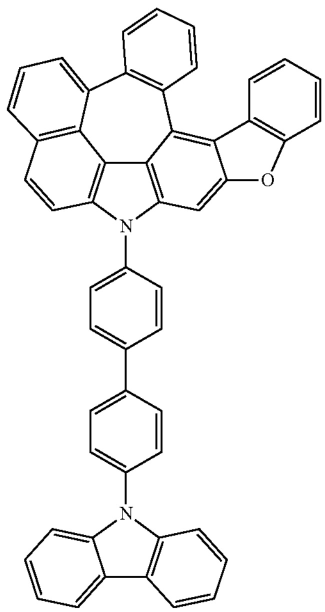
C-447
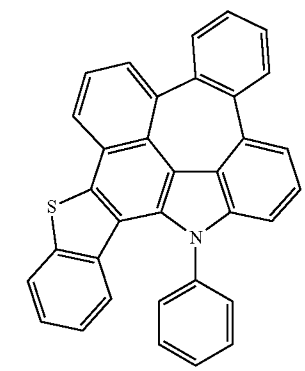
C-448
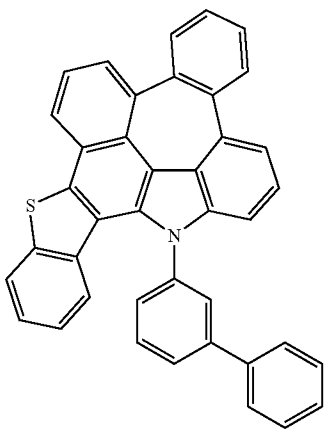
-continued
C-449
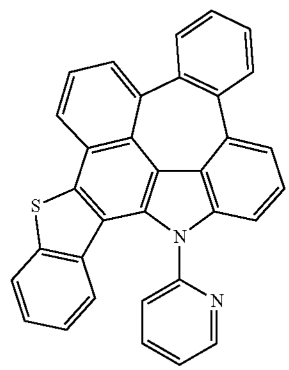
C-450
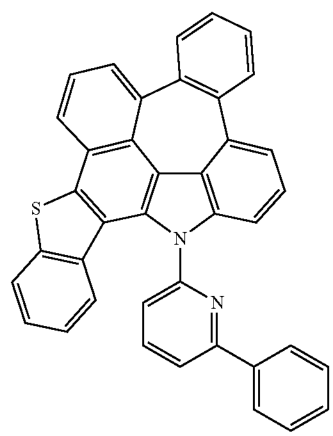
C-451
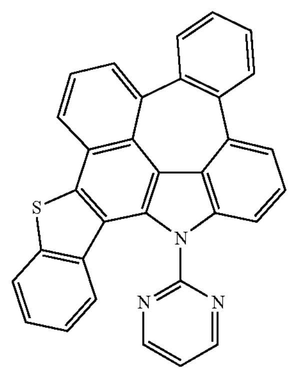
C-452
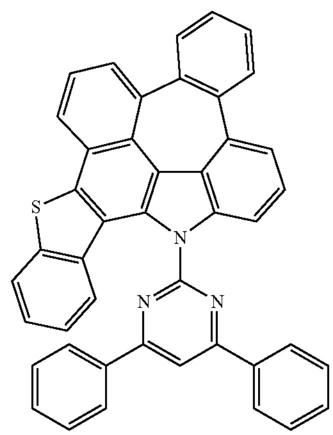

-continued
C-453
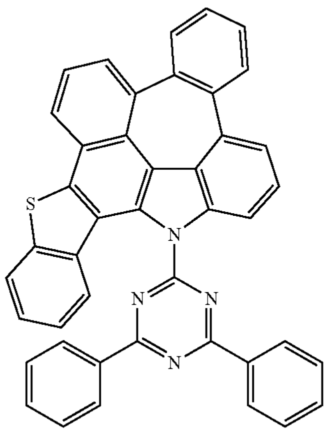
C-454
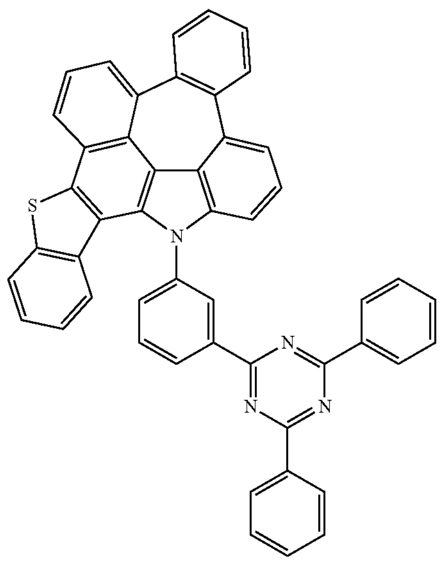
C-455
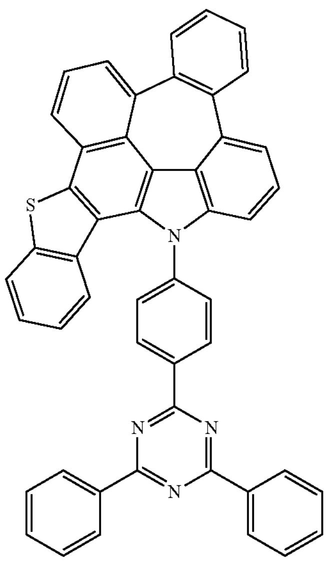
-continued
C-456
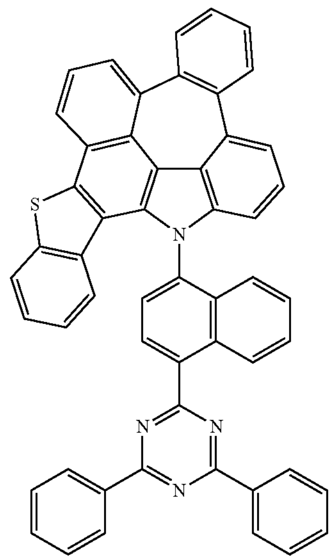
C-457
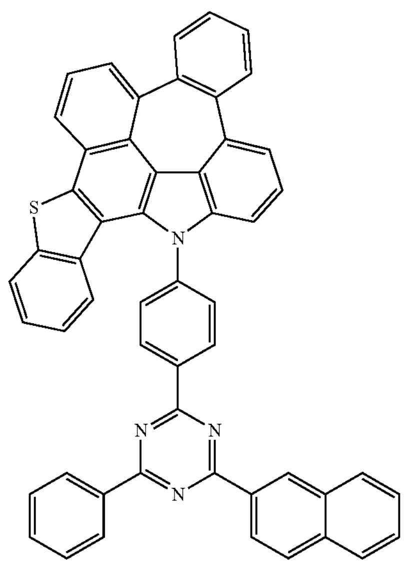
C-458
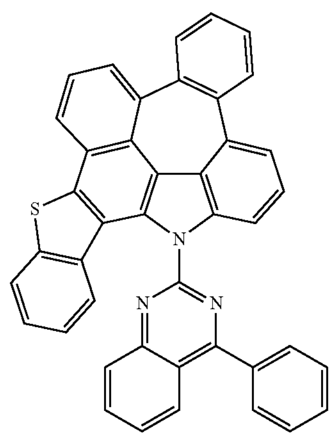

-continued
C-459
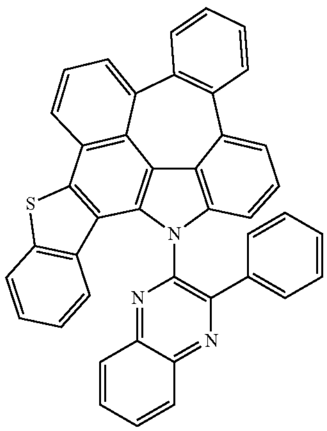
C-460
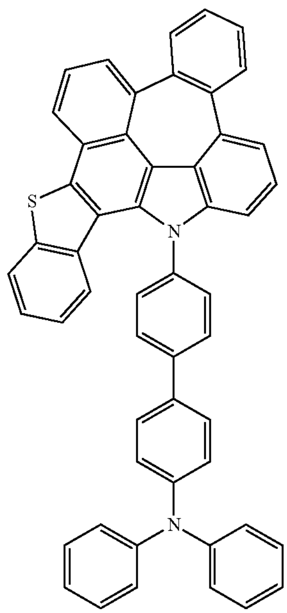
C-461
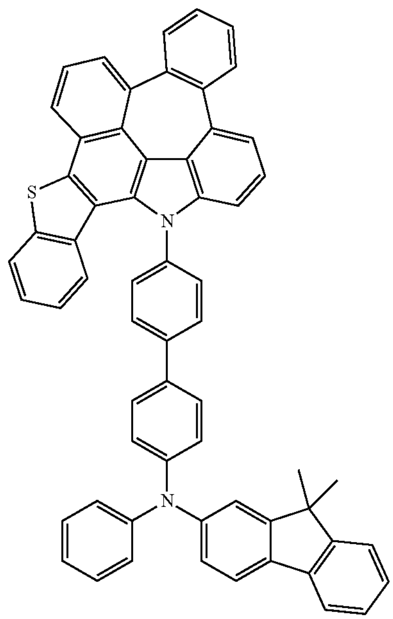
-continued
C-462
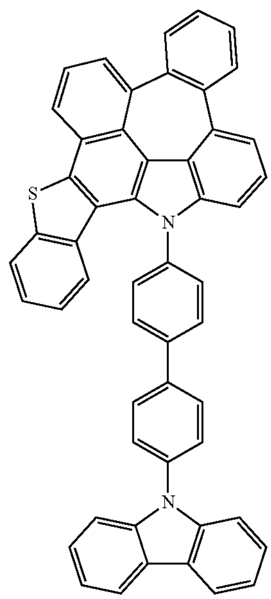
C-463
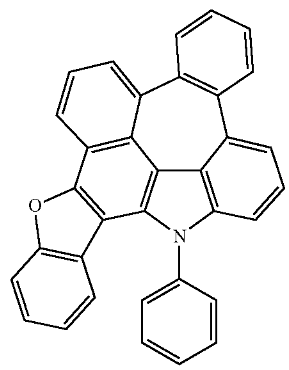
C-464
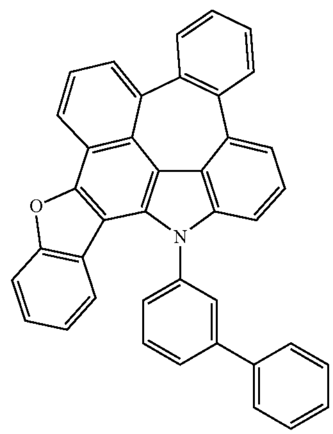

-continued
C-465
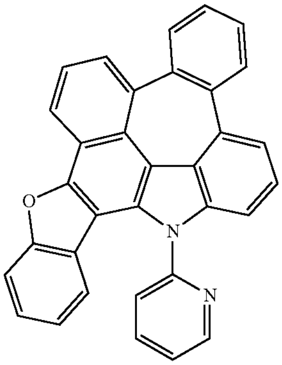
C-466
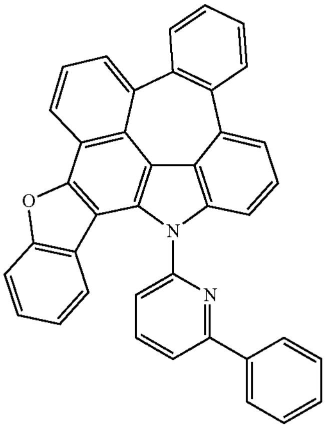
C-467
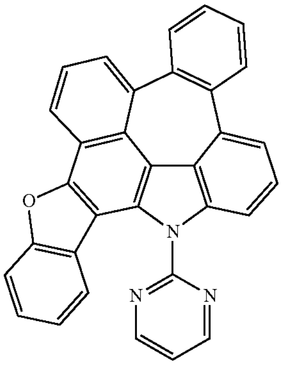
C-468
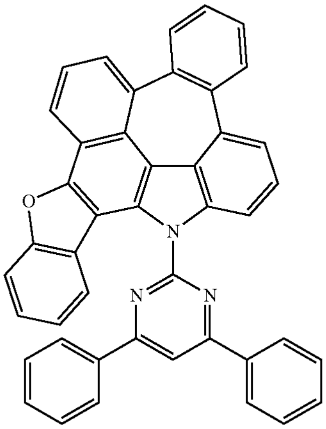
-continued
C-469
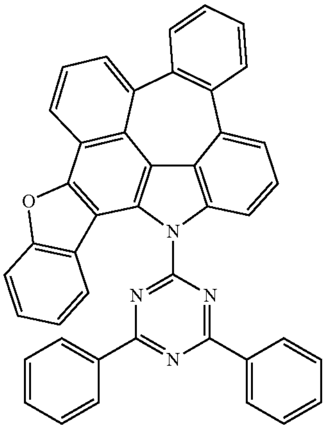
C-470
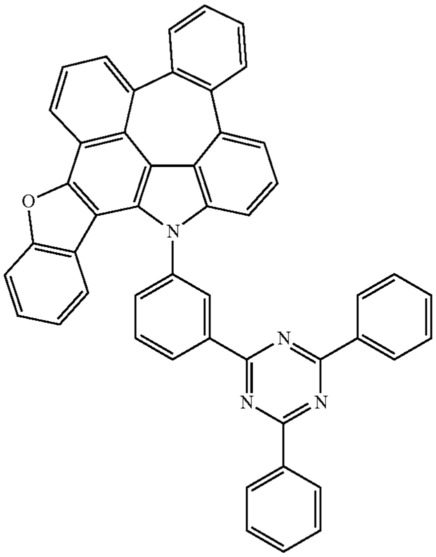
C-471
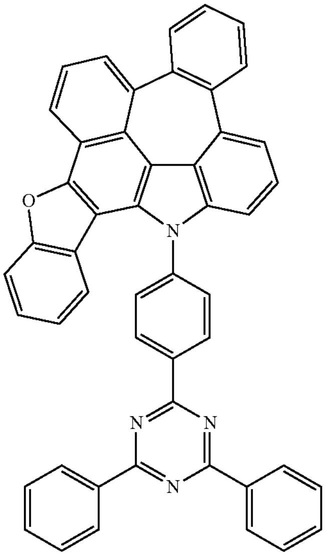

-continued
C-472
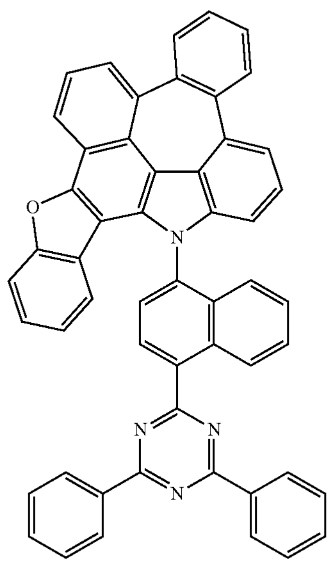
C-473
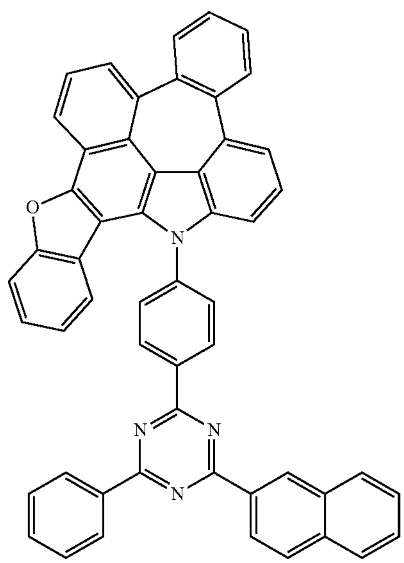
C-474
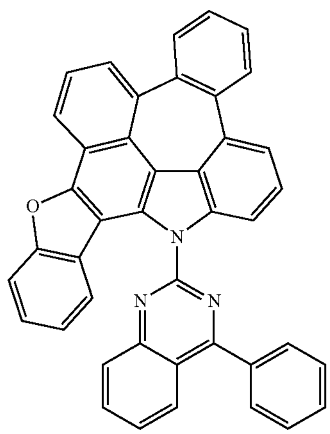
-continued
C-475
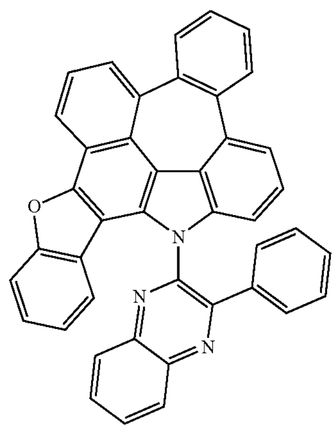
C-476
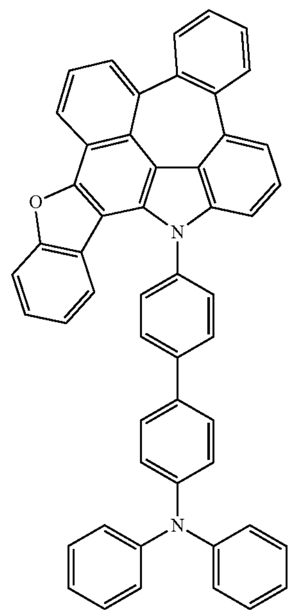
C-477
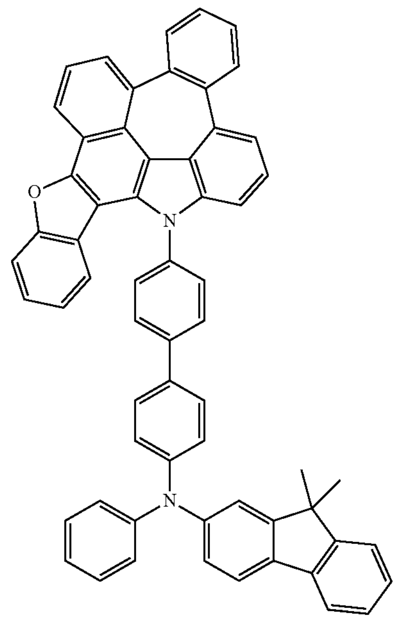

-continued
C-478
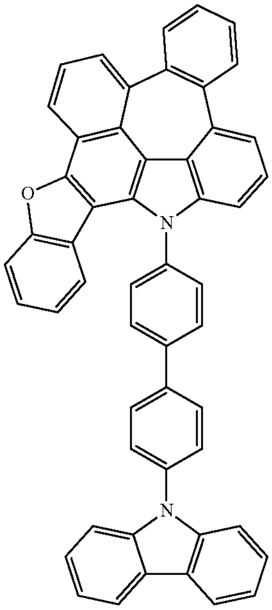
C-479
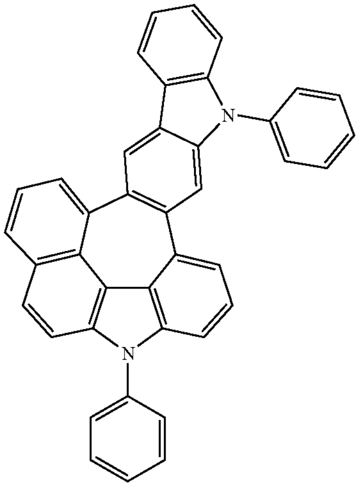
C-480
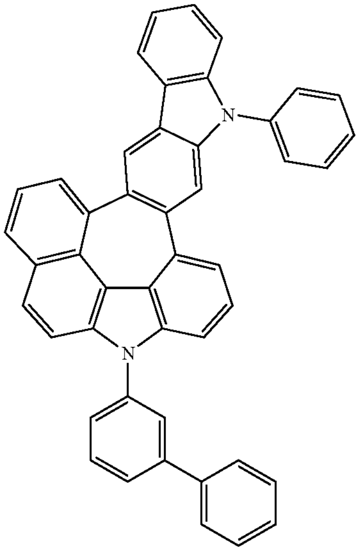
-continued
C-481
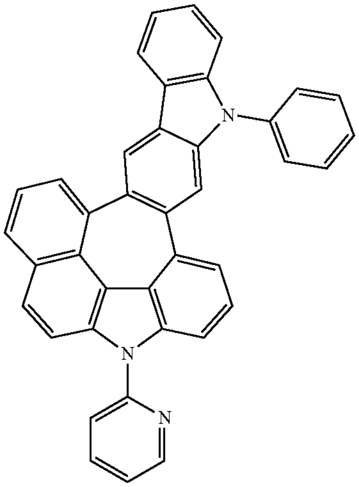
C-482
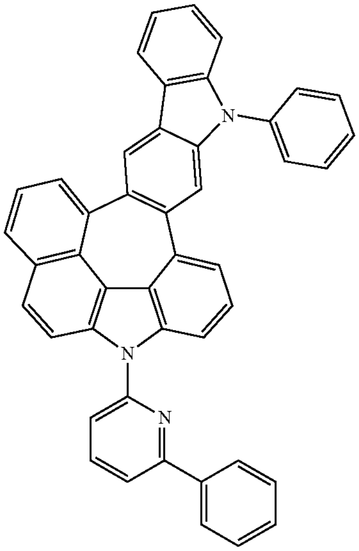
C-483
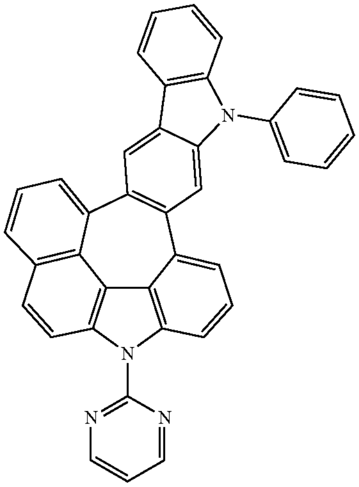

-continued
C-484
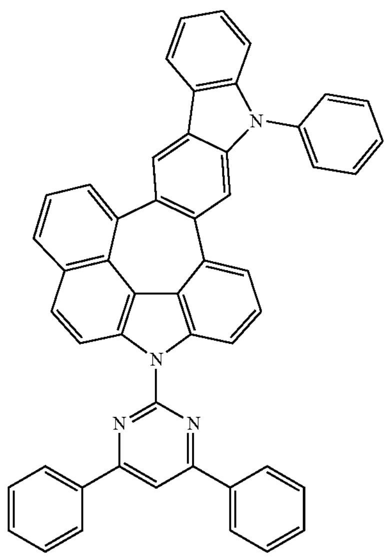
C-485
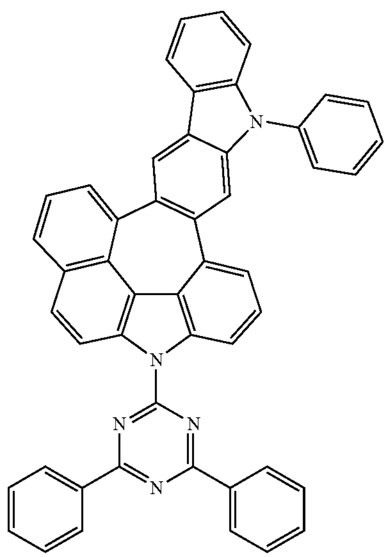
-continued
C-486
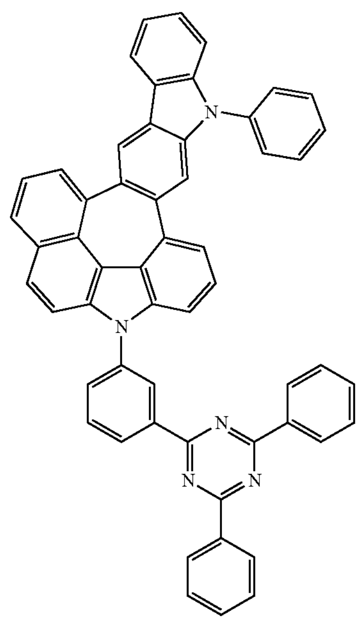
C-487
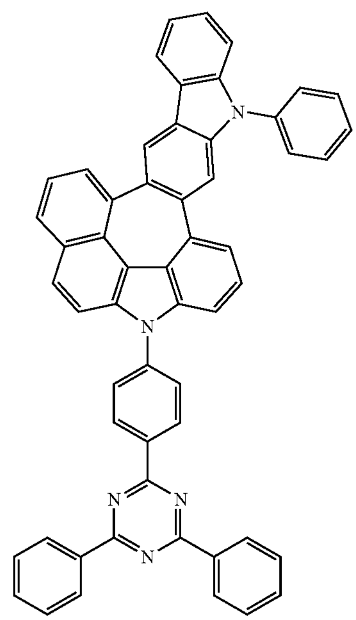

C-488
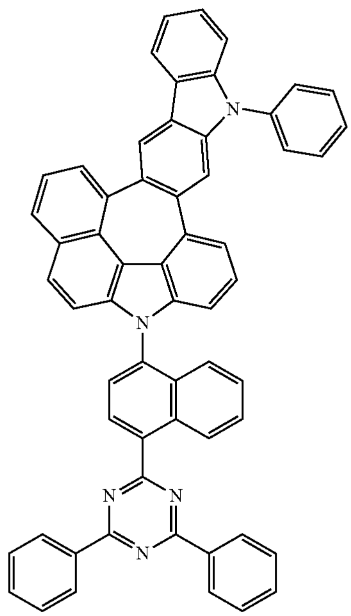
C-489
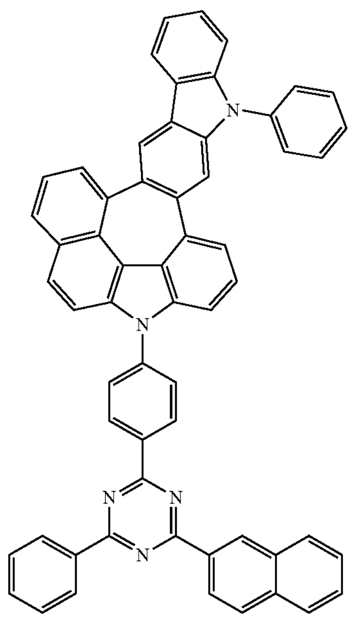
C-490
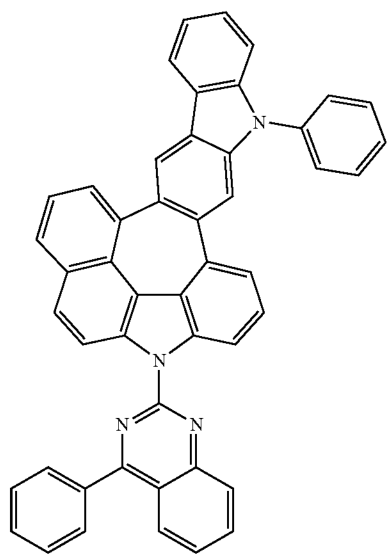
C-491
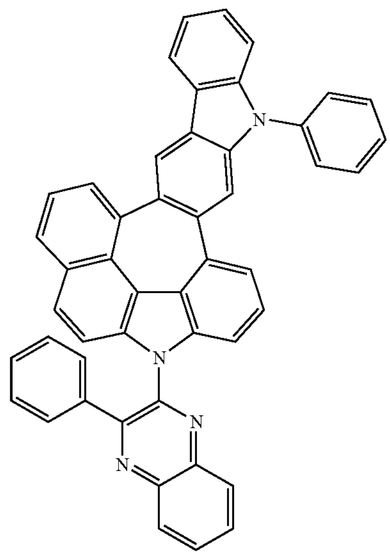

-continued
C-492
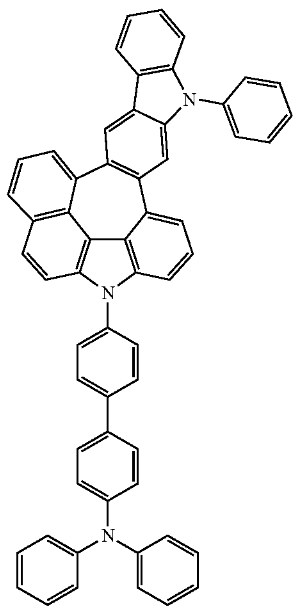
C-493
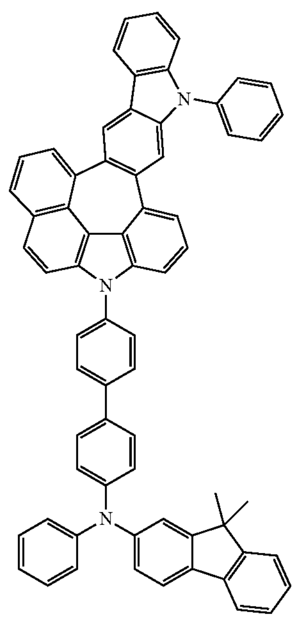
-continued
C-494
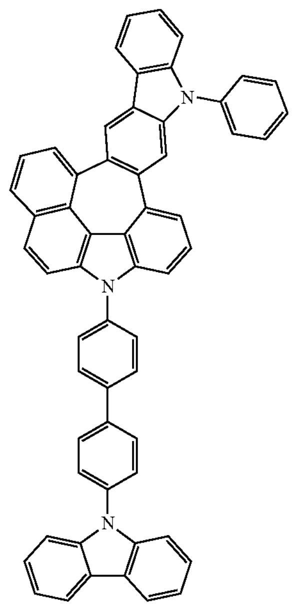
C-495
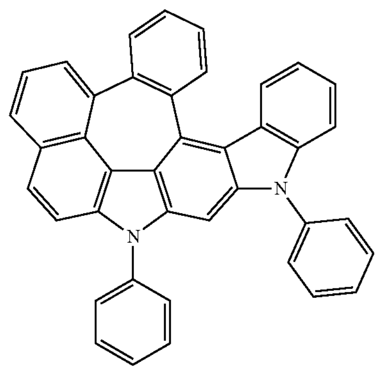
C-496
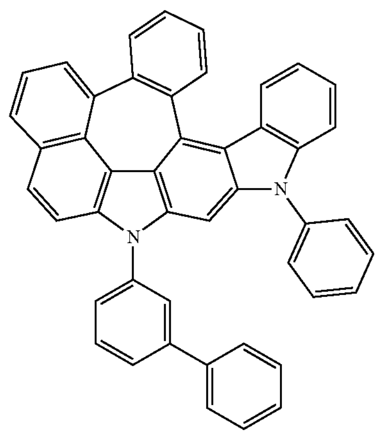

-continued
C-497
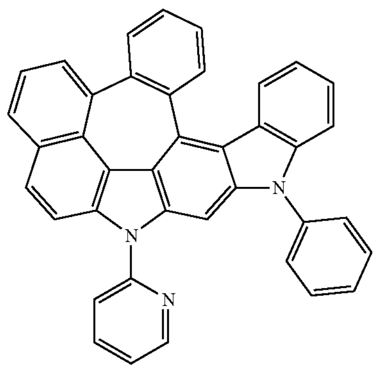
C-498
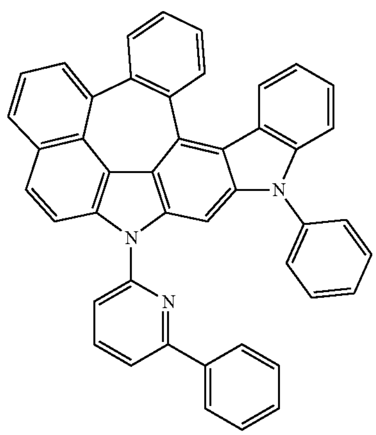
C-499
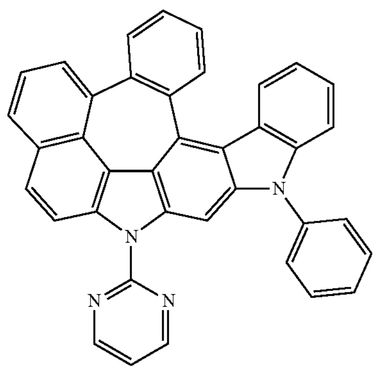
C-500
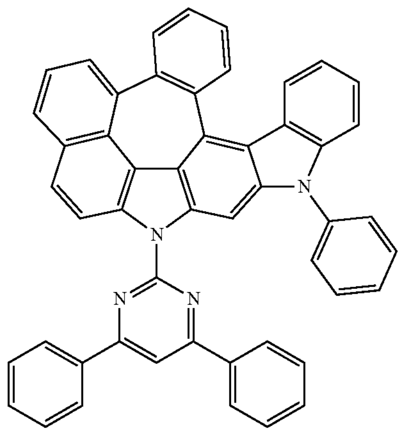
-continued
C-501
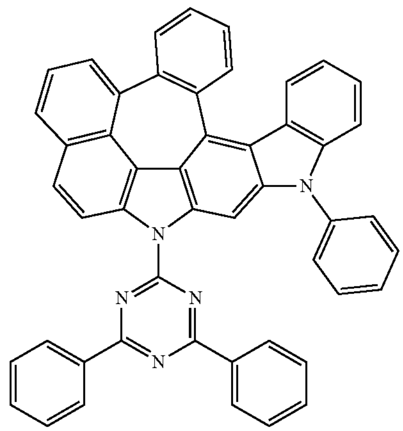
C-502
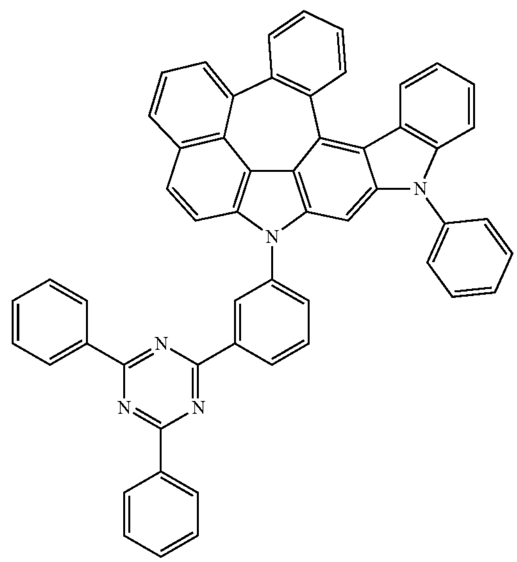
C-503
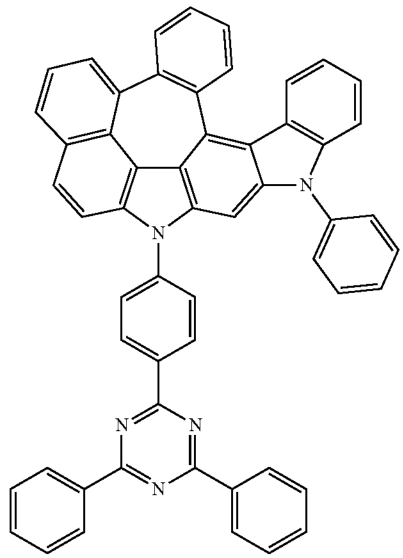

-continued
C-504
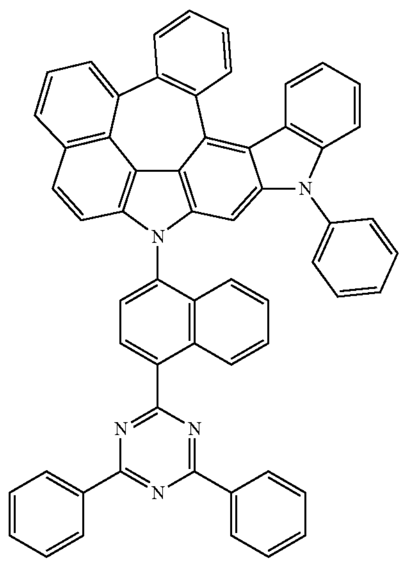
C-505
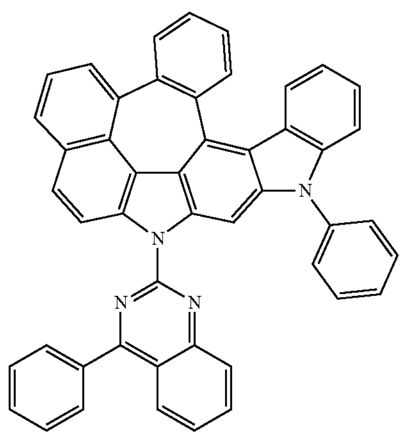
C-506
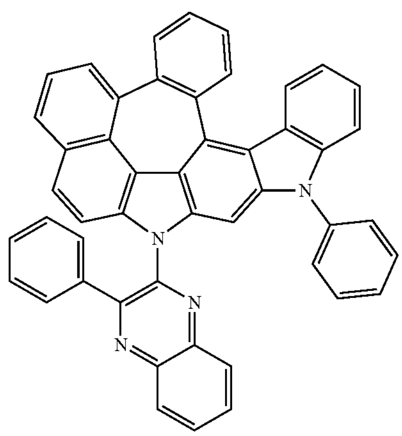
-continued
C-507
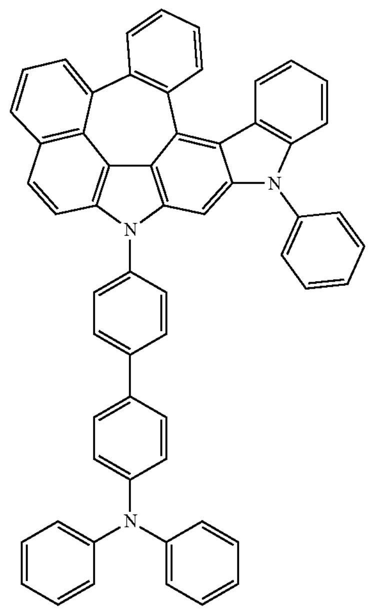
C-508
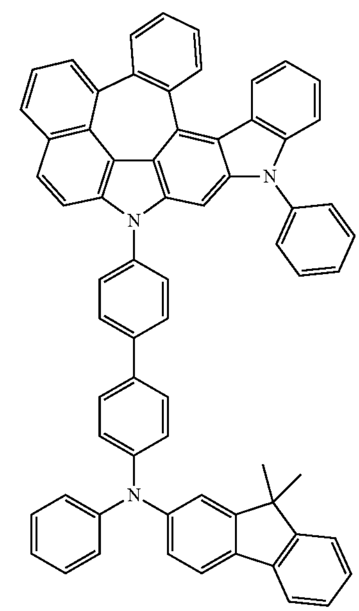

-continued
C-509
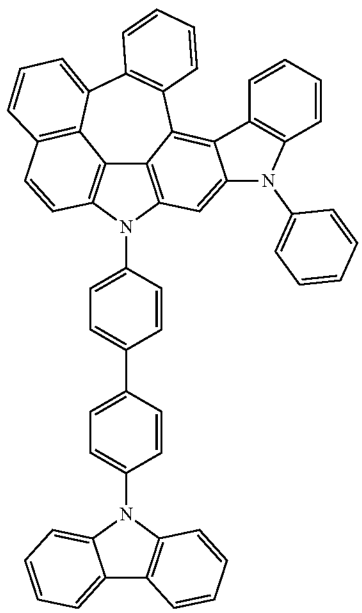
C-510
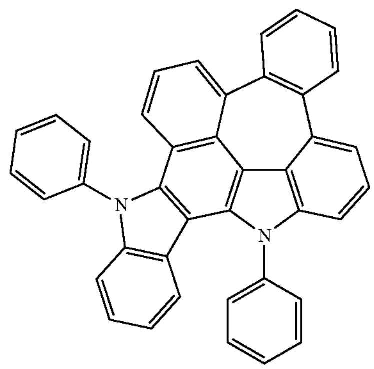
C-511
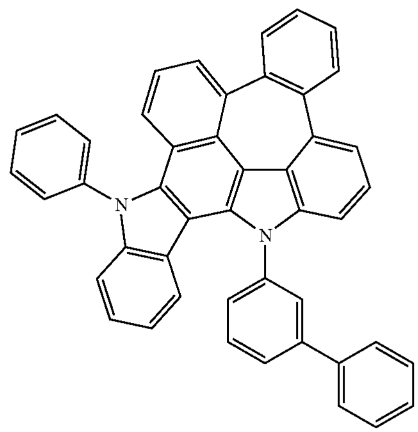
-continued
C-512
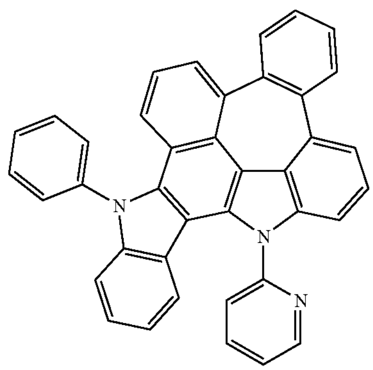
C-513
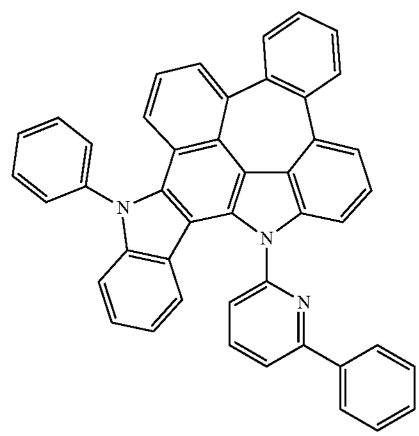
C-514
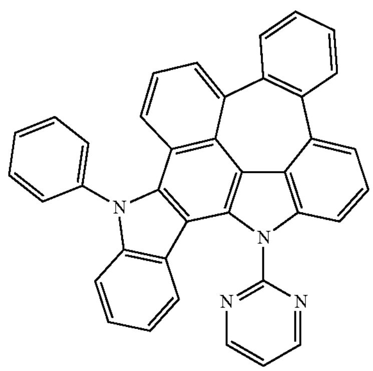
C-515
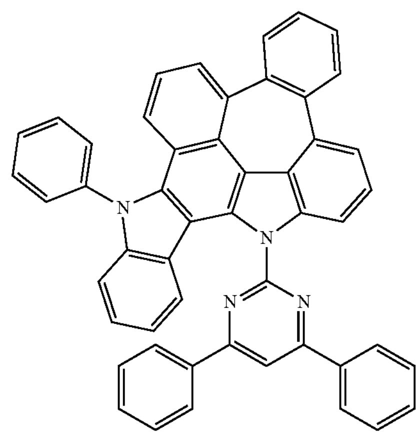

-continued
C-516
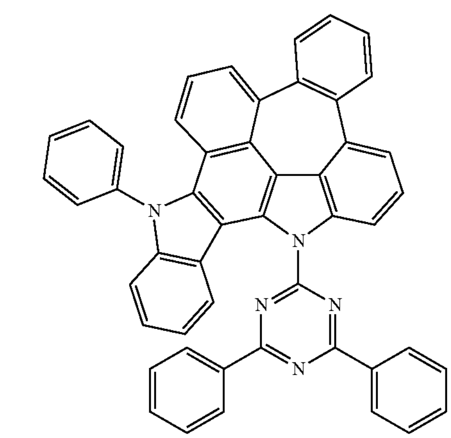
C-517
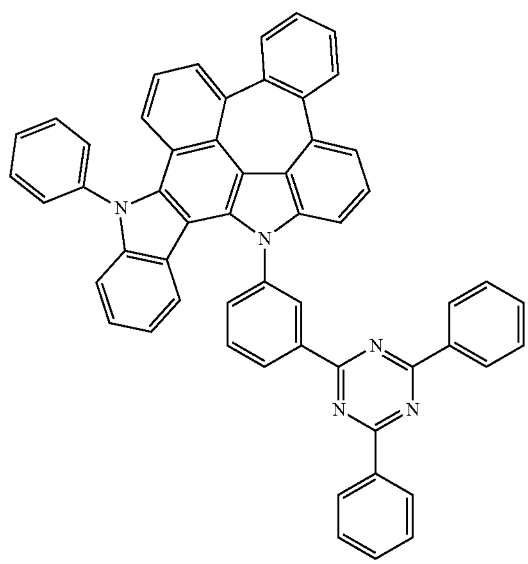
C-518
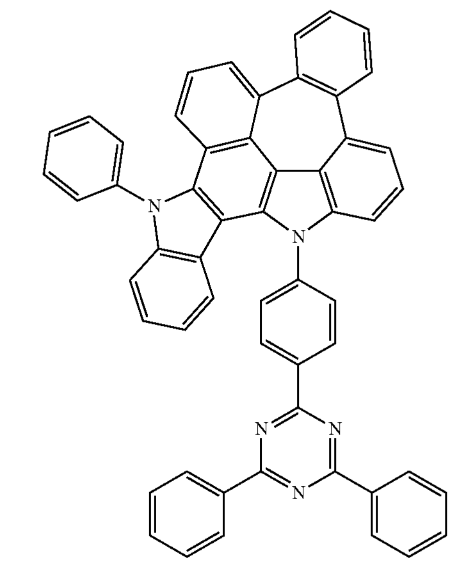
-continued
C-519
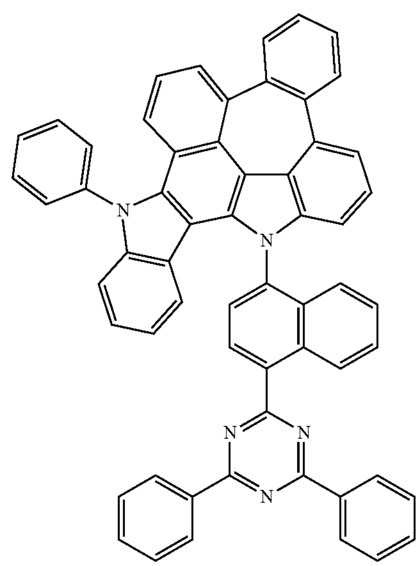
C-520
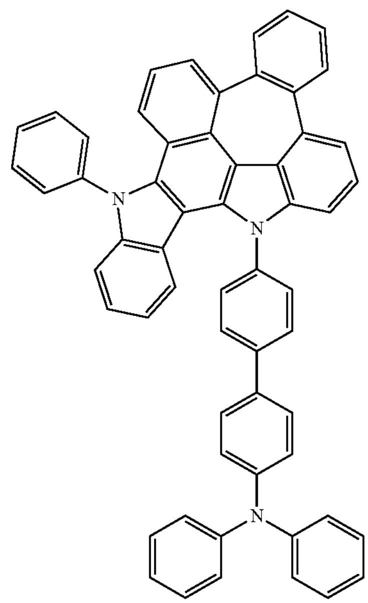

-continued
C-521
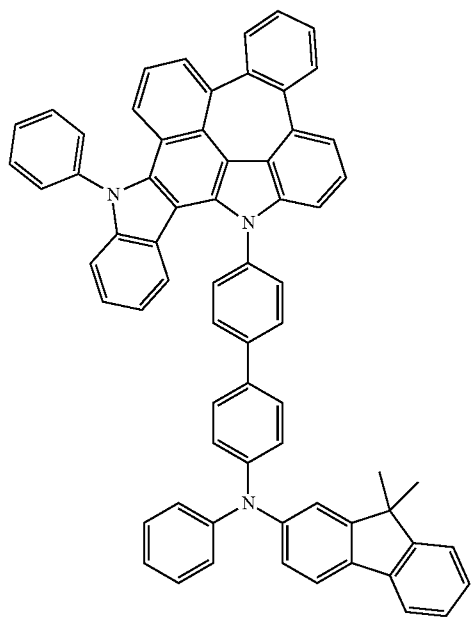
C-522
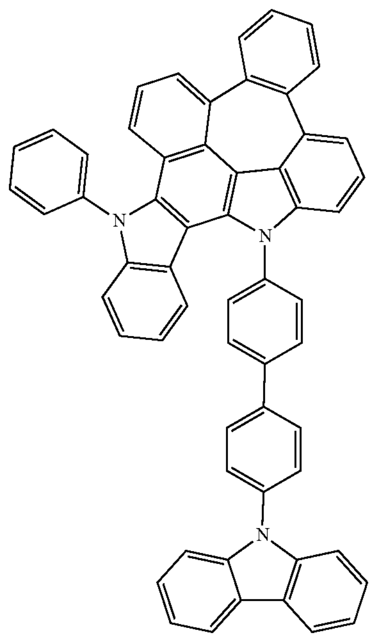
C-523
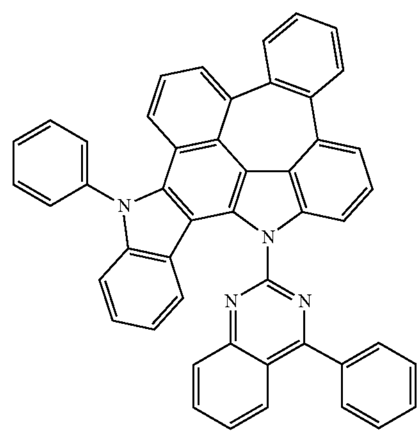
C-522
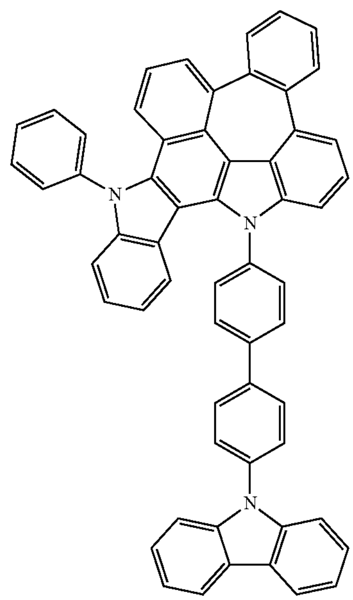
C-524
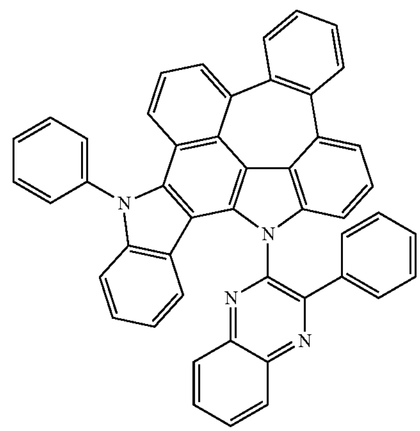

-continued
C-525
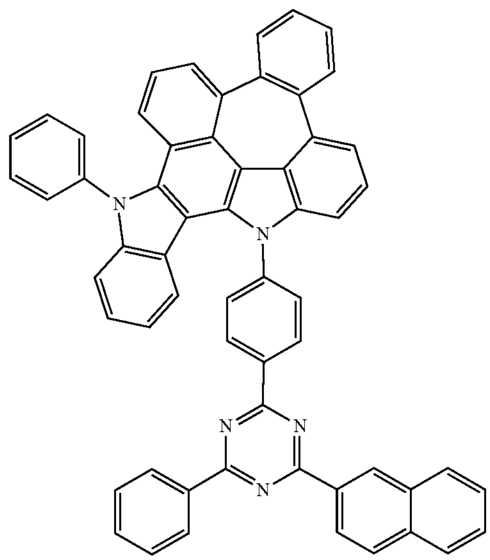
C-526
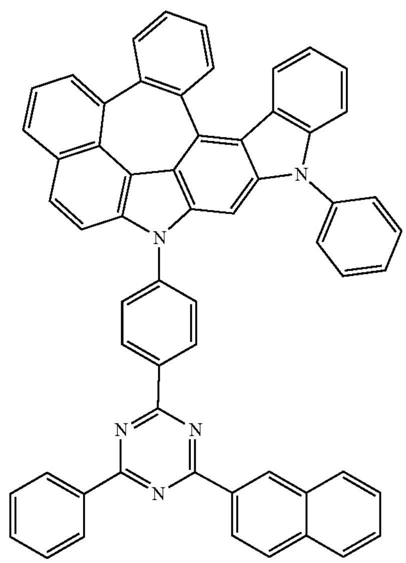
C-527
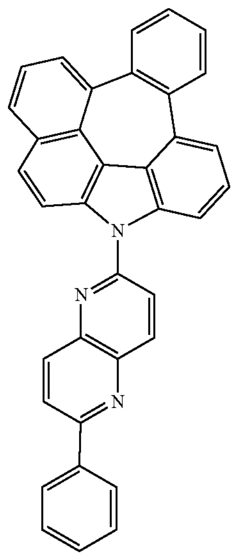
-continued
C-528
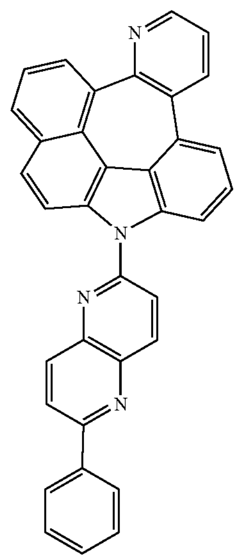
C-529
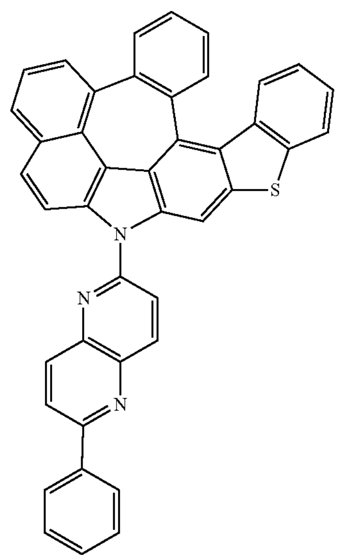
C-530
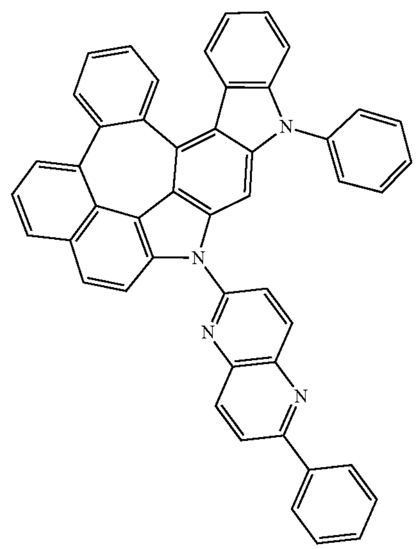

-continued
C-531
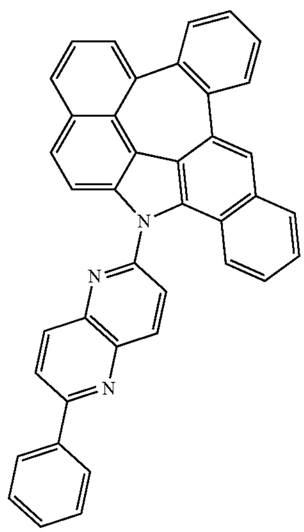
C-532
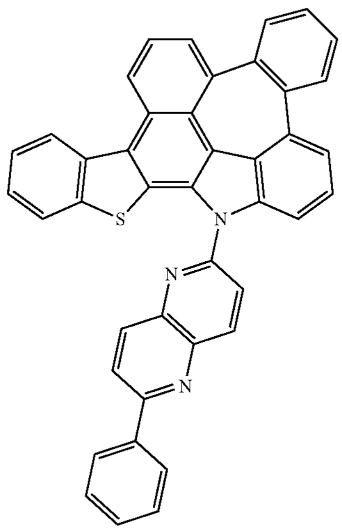
C-533
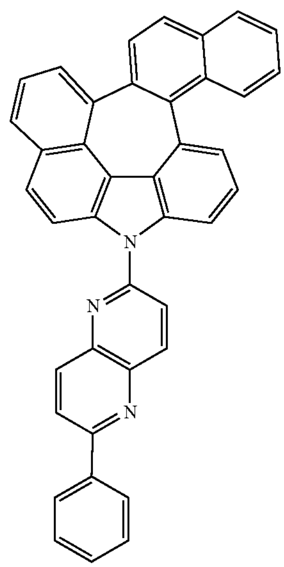
-continued
C-534
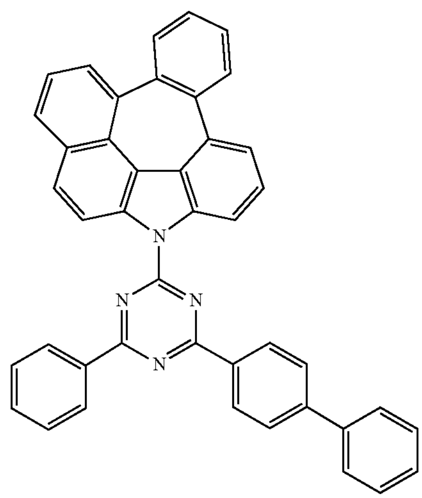
C-535
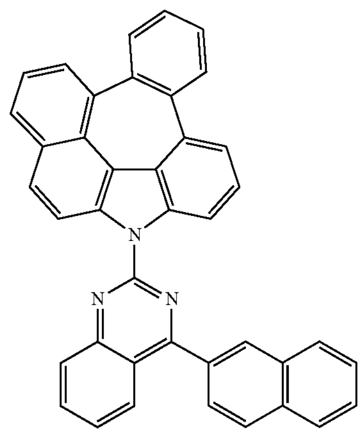
C-536
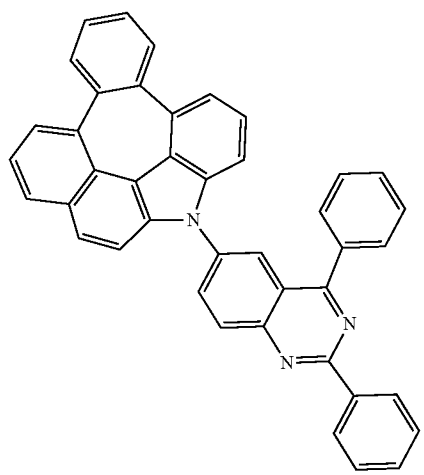

-continued
C-537
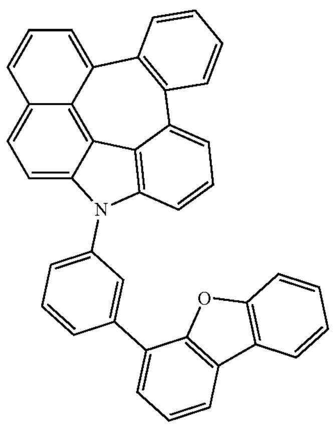
C-538
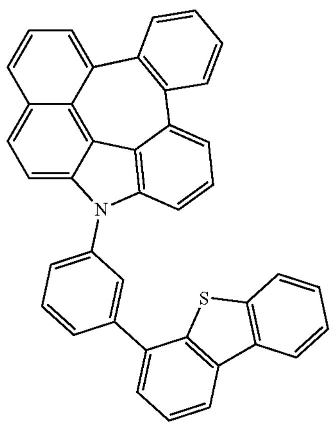
C-539
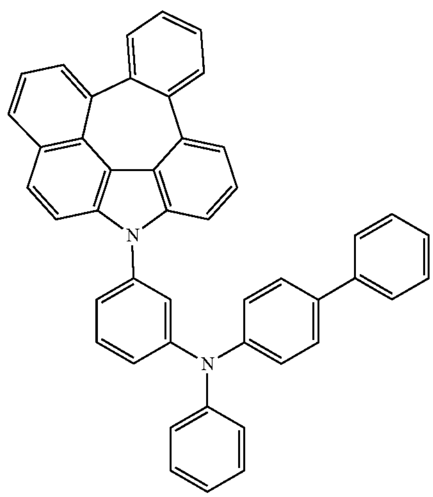
-continued
C-540
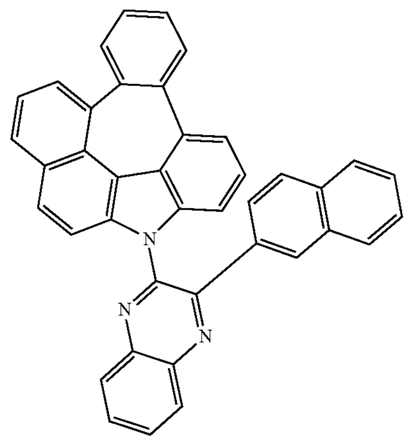
C-541
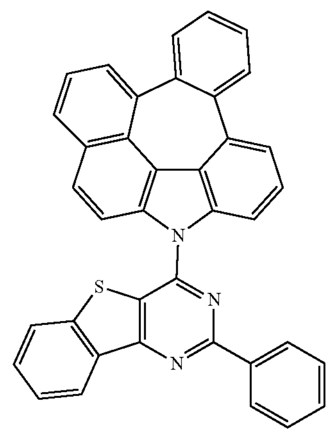
C-542
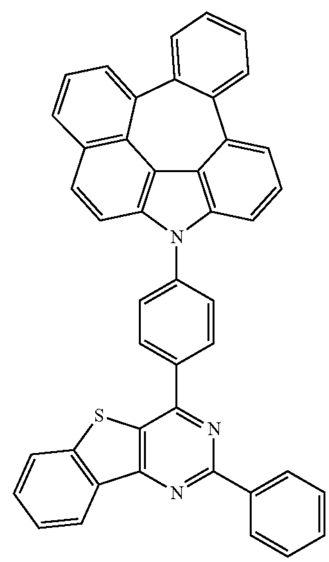

-continued
C-543
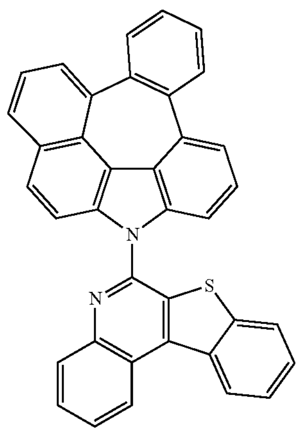
C-544
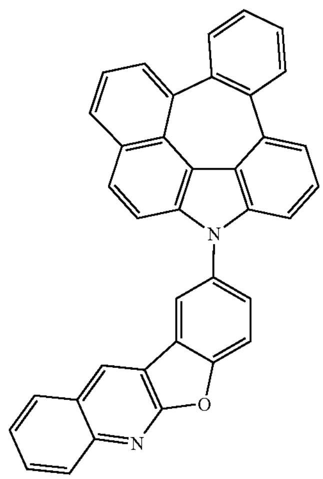
C-545
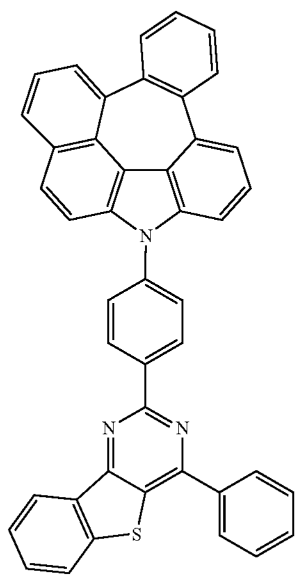
-continued
C-546
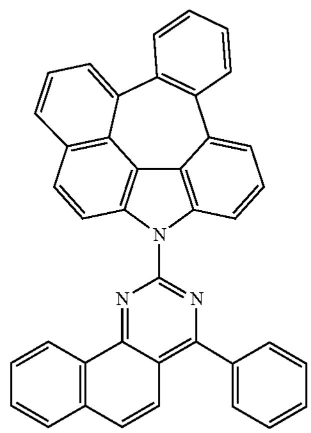
C-547
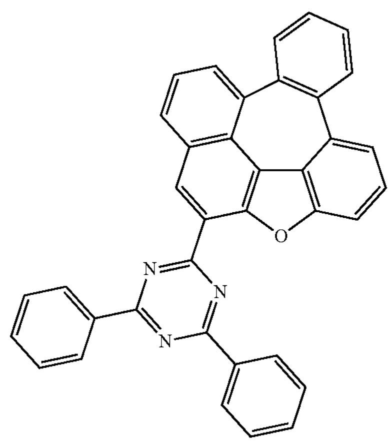
C-548
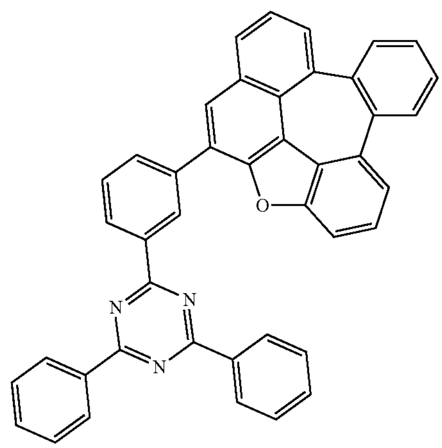

-continued
C-549
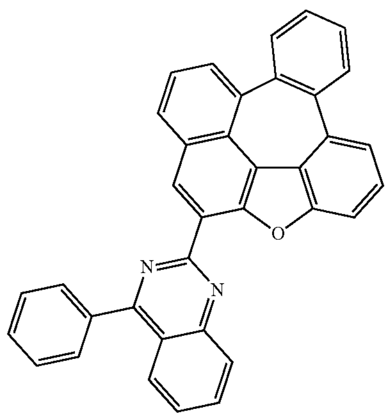
C-550
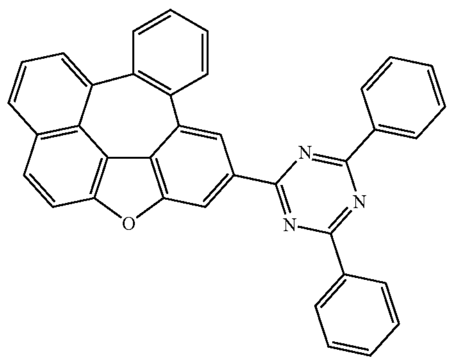
C-551
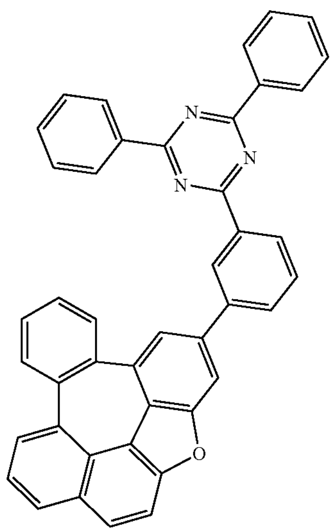
-continued
C-552
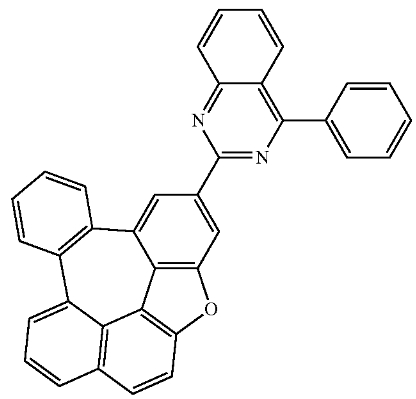
C-553
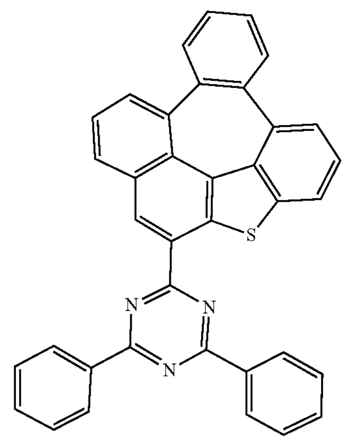
C-554
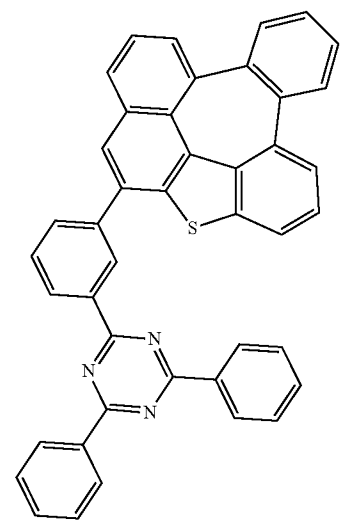

-continued
C-555
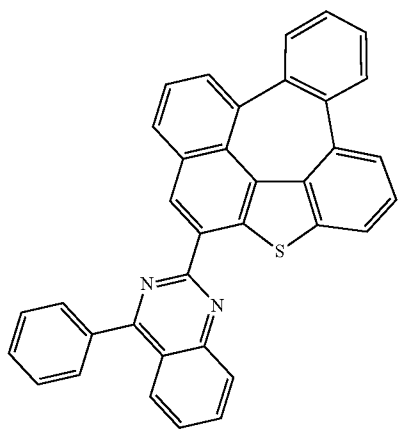
C-556
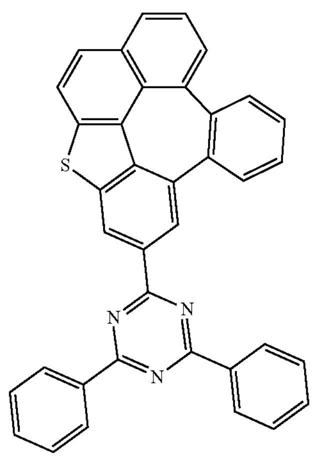
C-557
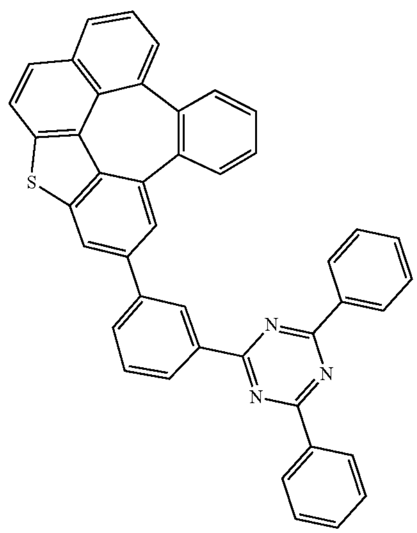
-continued
C-558
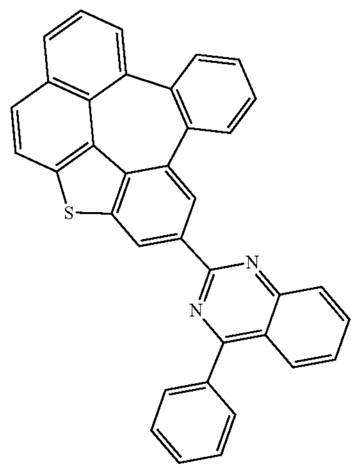
C-559
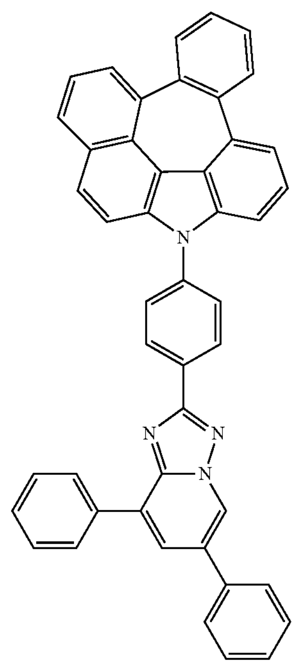
C-560
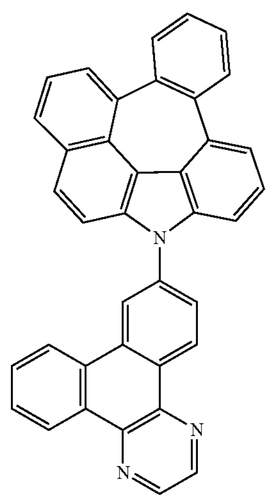

-continued
C-561
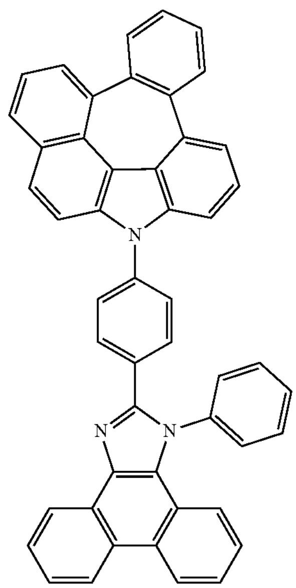
C-562
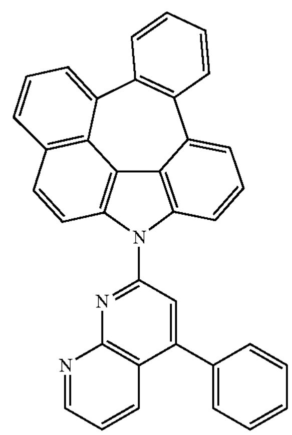
C-563
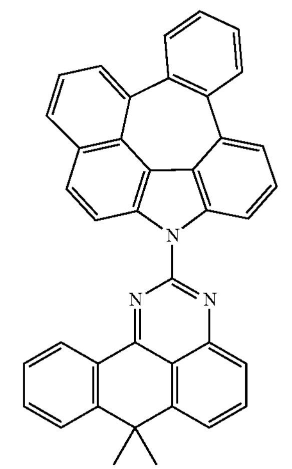
-continued
C-564
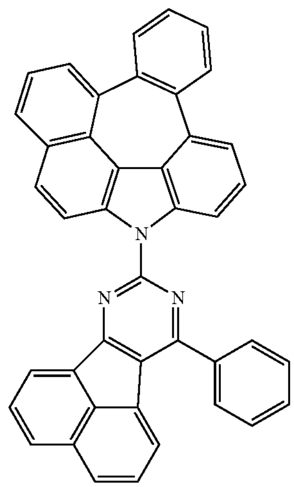
C-565
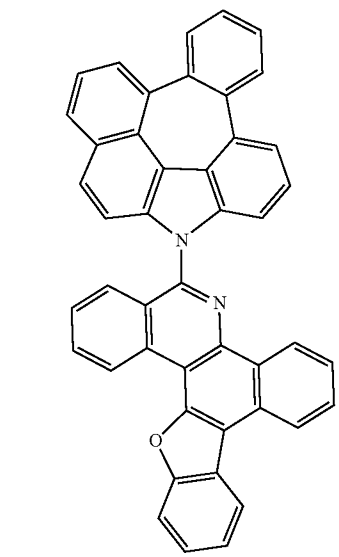
C-566
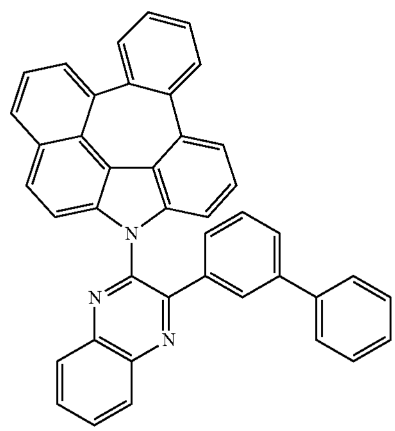

-continued
C-567
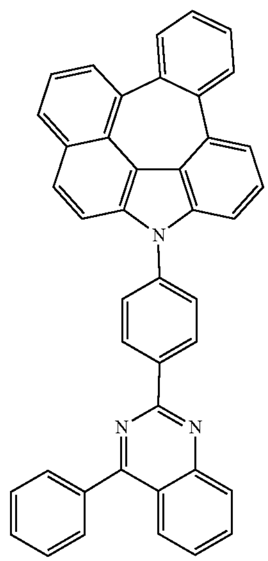
C-568
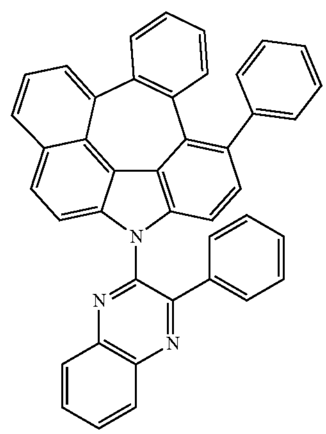
C-569
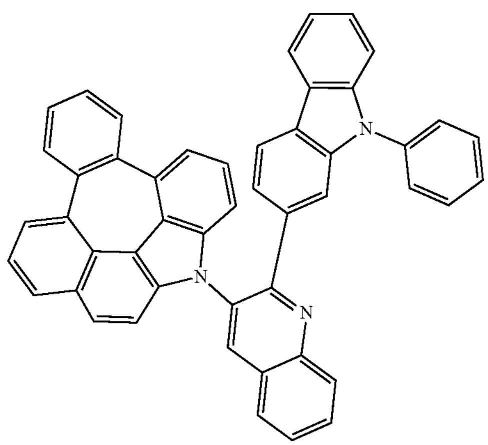
-continued
C-570
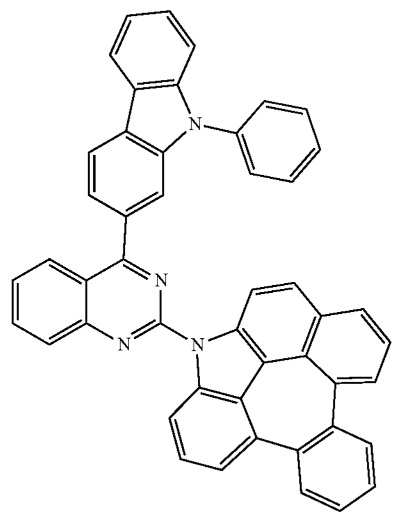
C-571
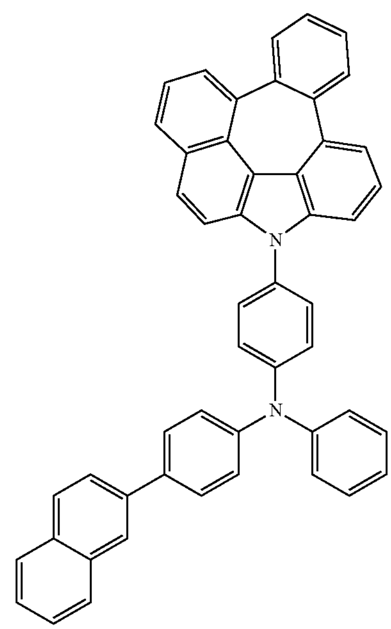

-continued
C-572
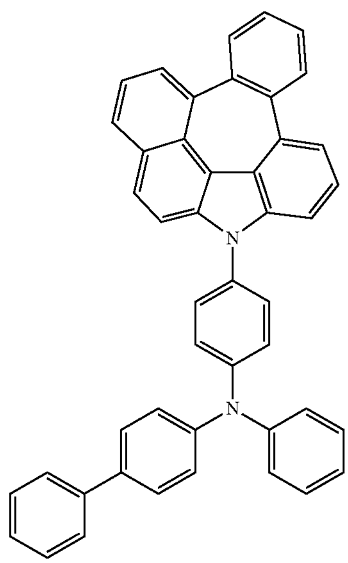
C-573
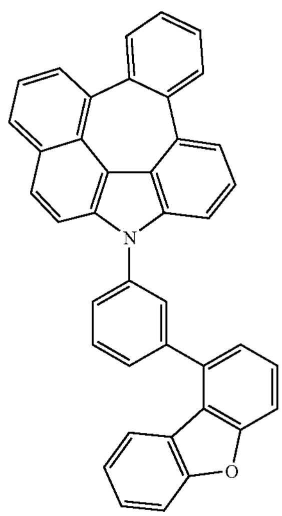
C-574
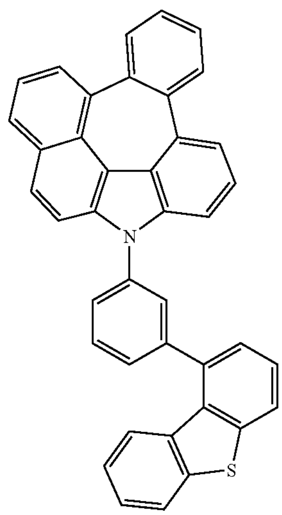
-continued
C-575
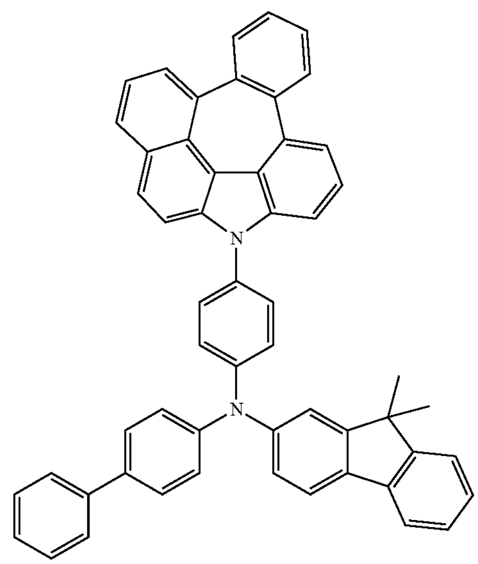
C-576
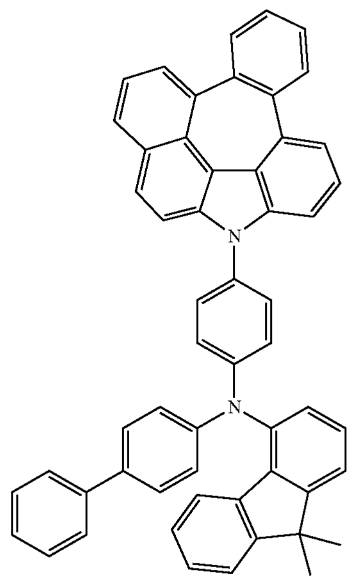

-continued
C-577
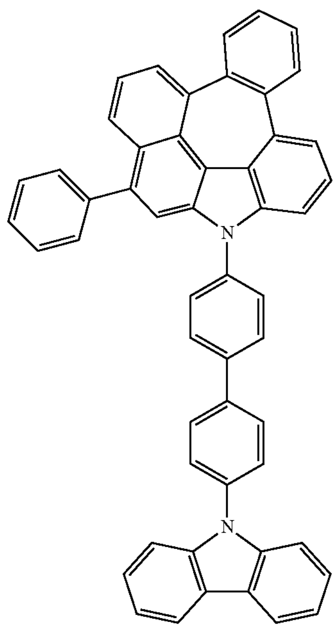
C-578
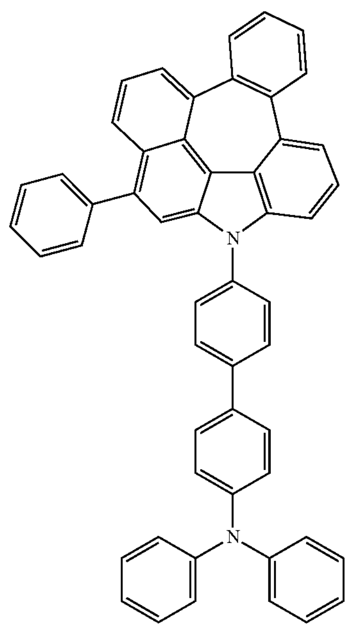
-continued
C-579
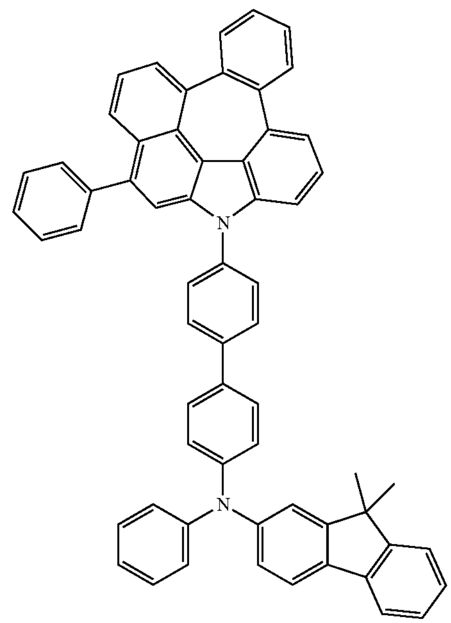
C-580
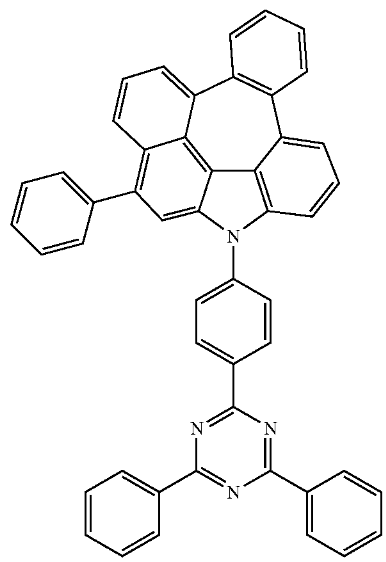

-continued
C-581
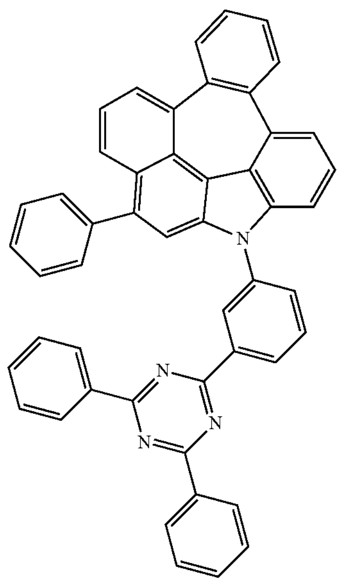
C-582
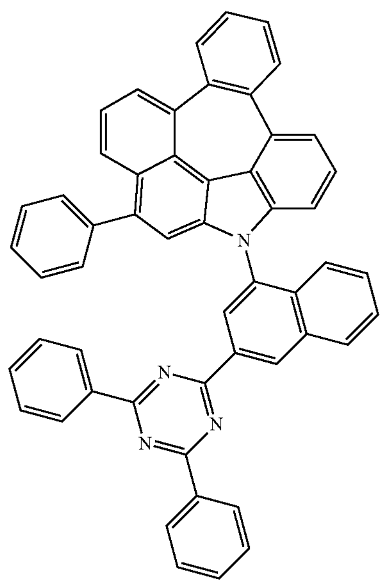
-continued
C-583
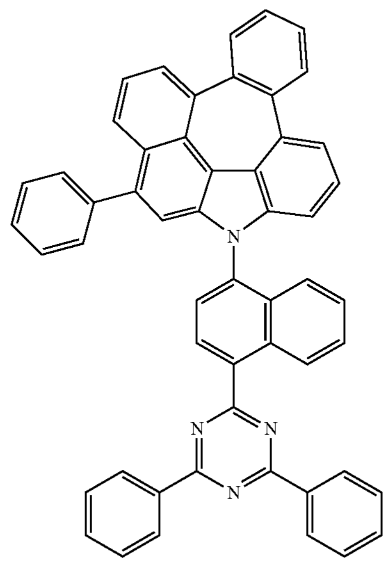
C-584
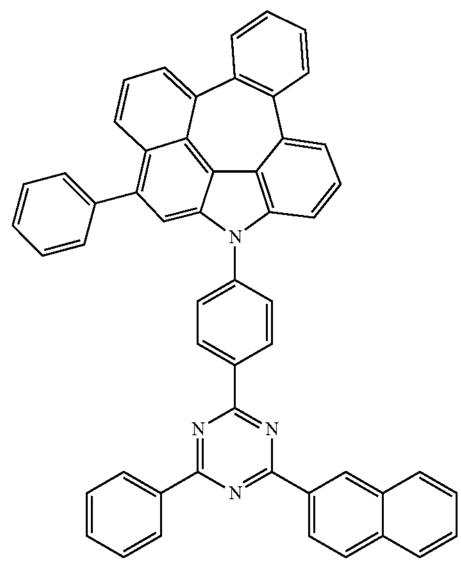

C-585
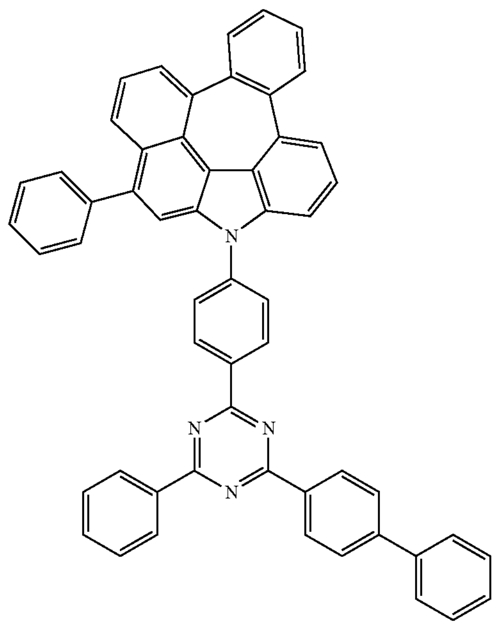
C-586
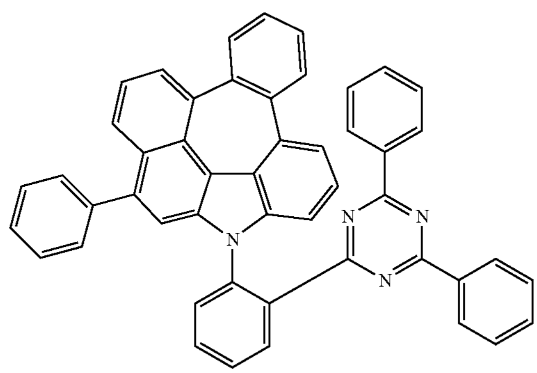
C-587
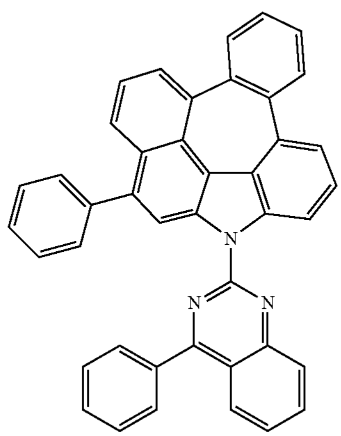
C-588
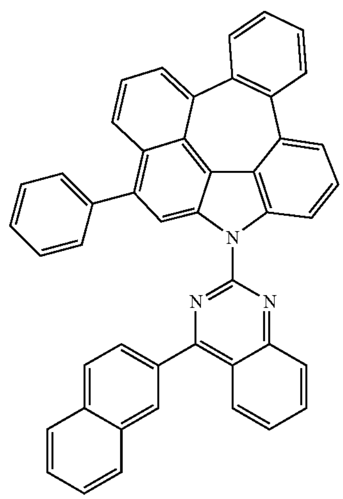
C-589
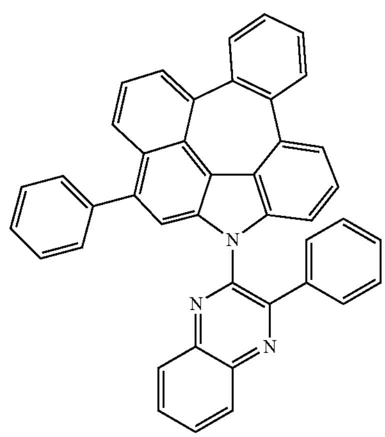
C-590
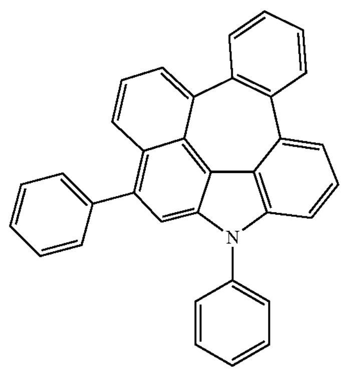

-continued
C-591
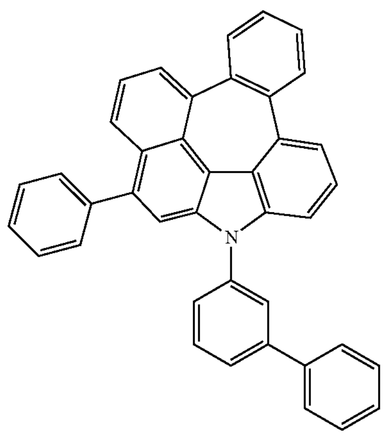
C-592
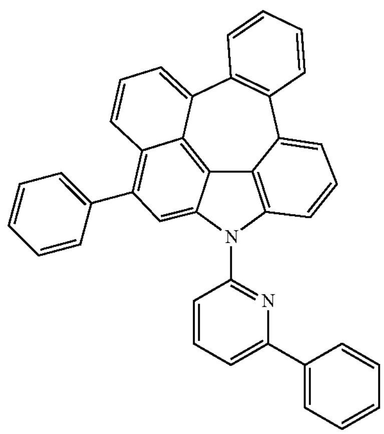
C-593
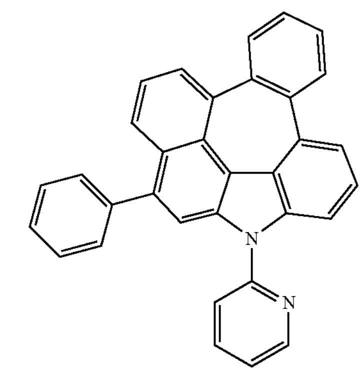
-continued
C-594
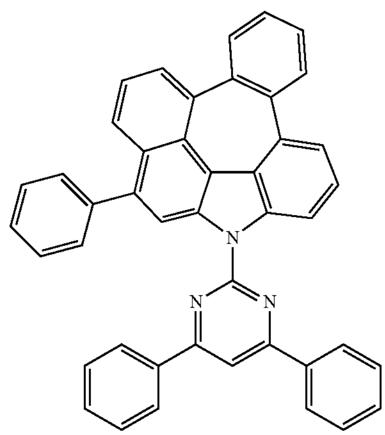
C-595
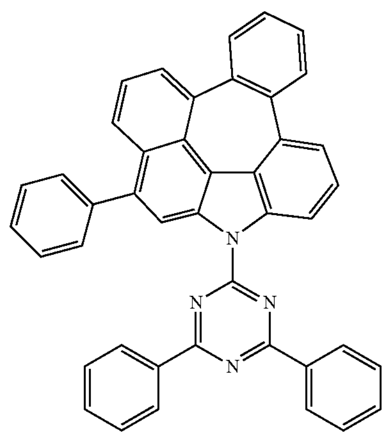
C-596
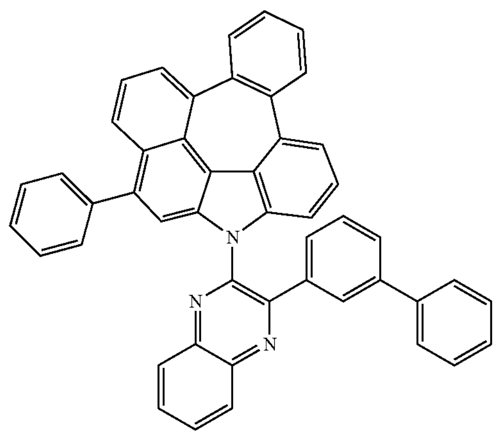

-continued
C-597
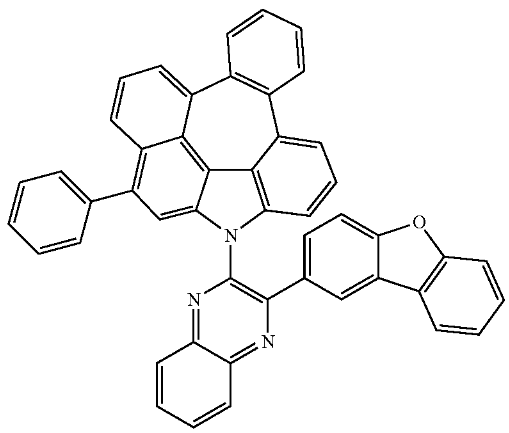
C-598
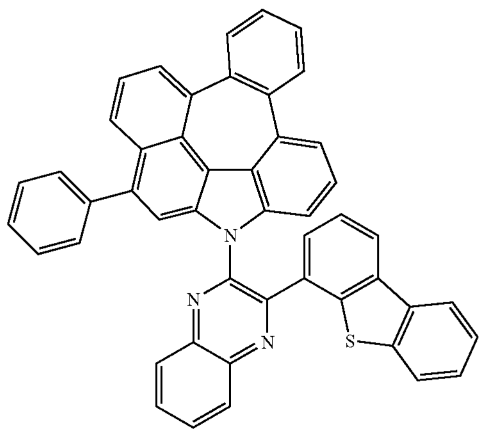
C-599
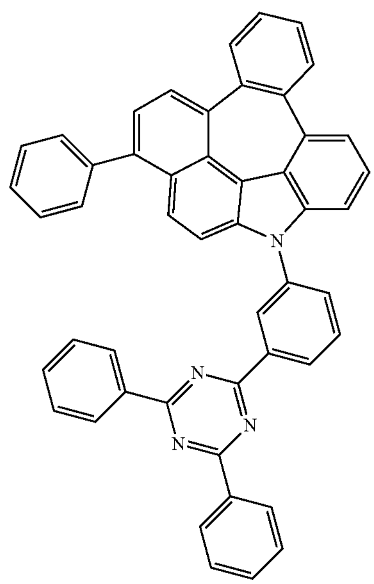
-continued
C-600
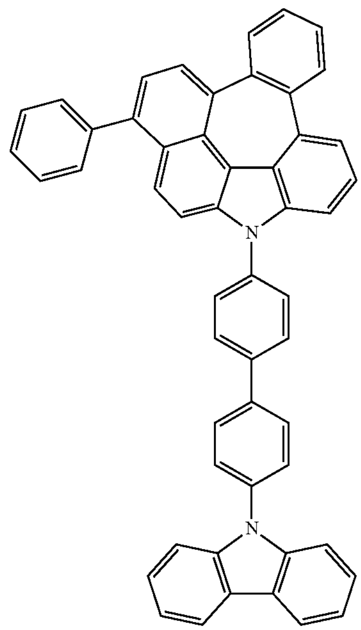
C-601
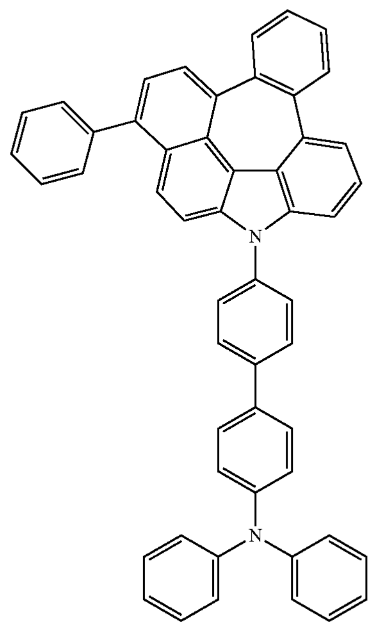

-continued
C-602
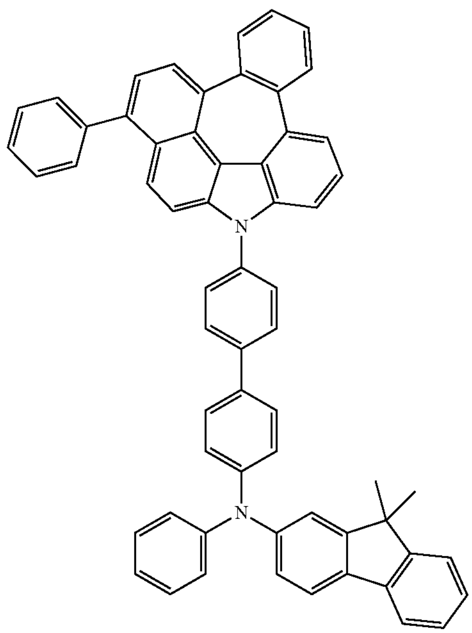
C-603
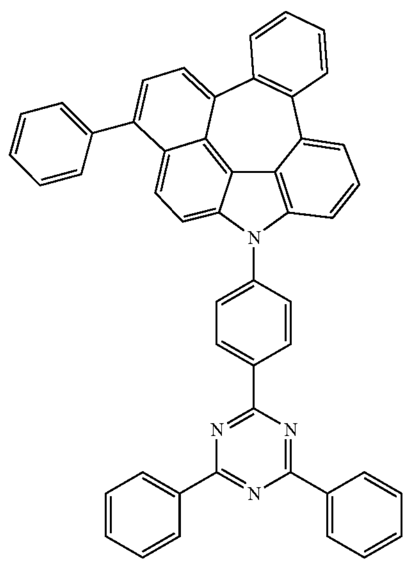
-continued
C-604
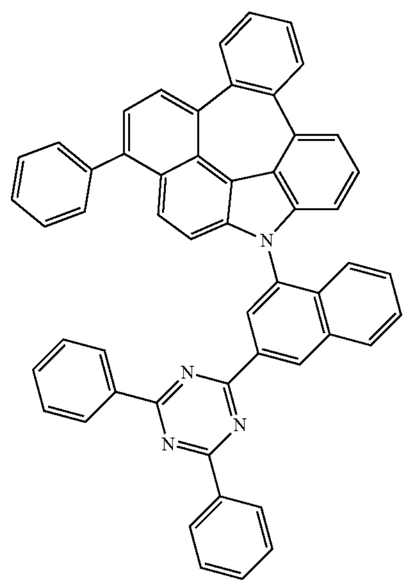
C-605
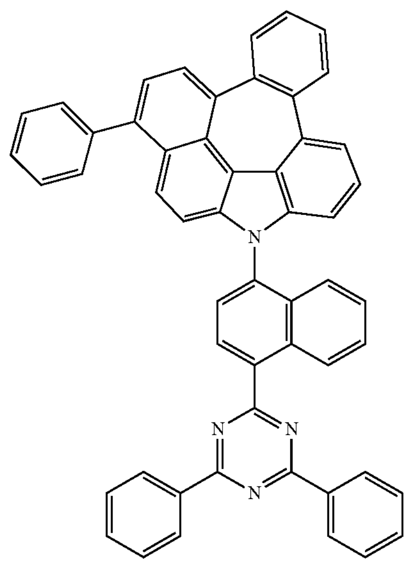

-continued
C-606
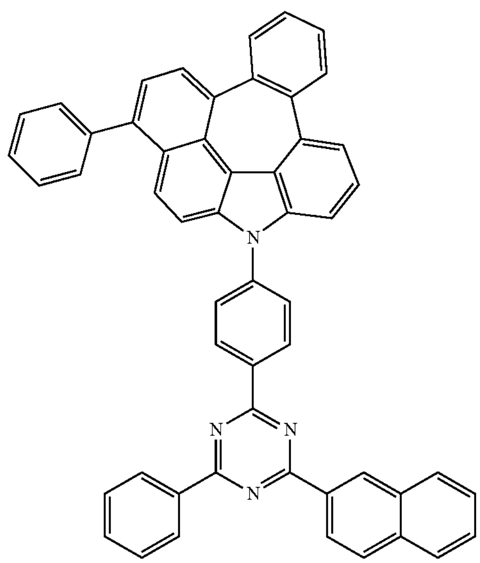
C-607
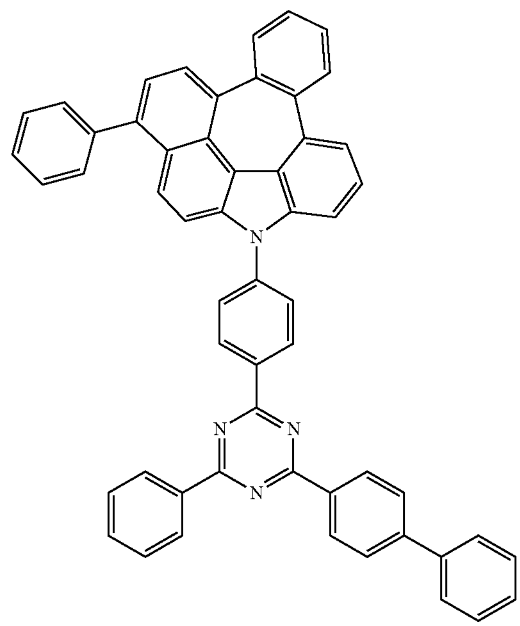
C-608
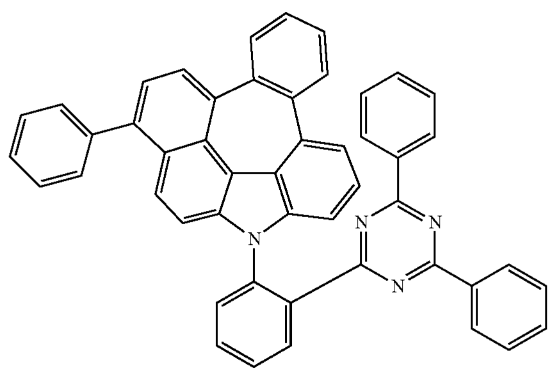
-continued
C-609
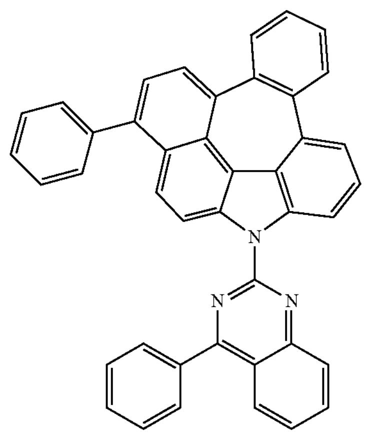
C-610
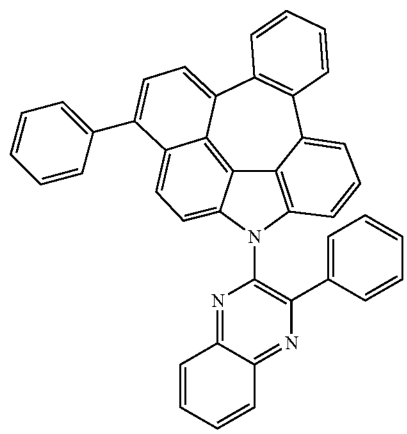
C-611
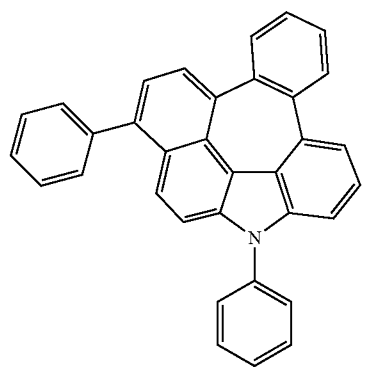

-continued
C-612
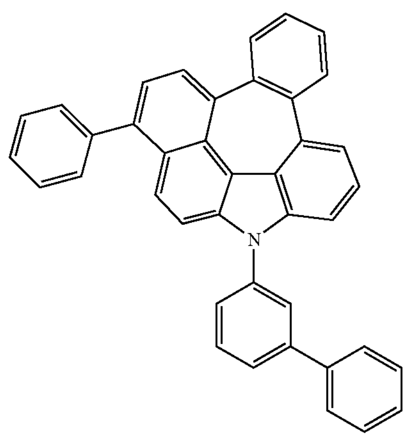
C-613
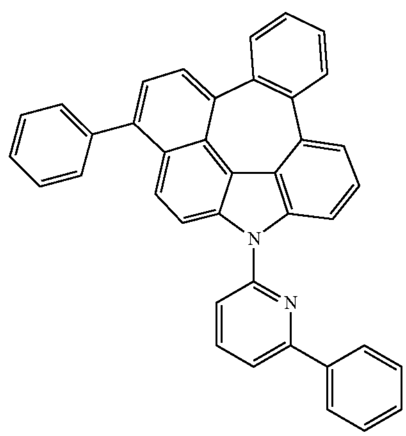
C-614
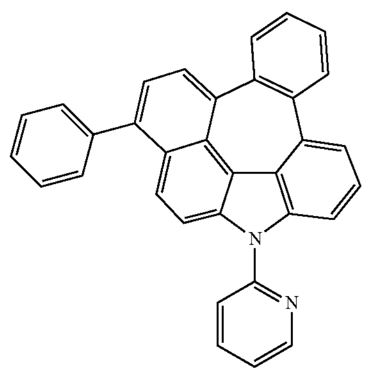
-continued
C-615
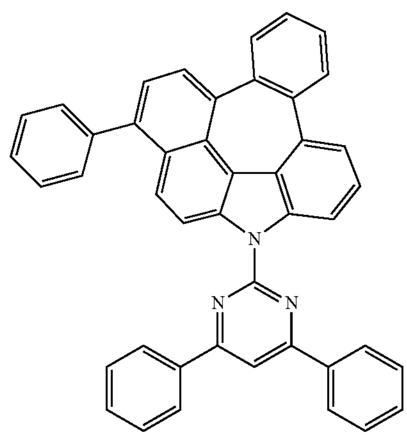
C-616
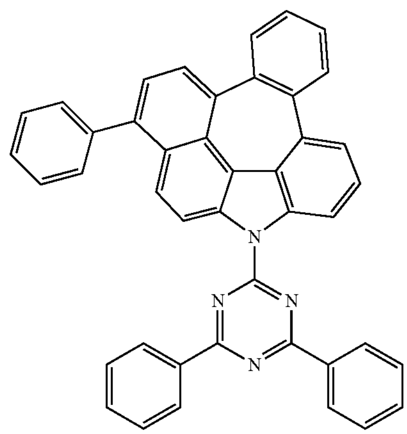
C-617
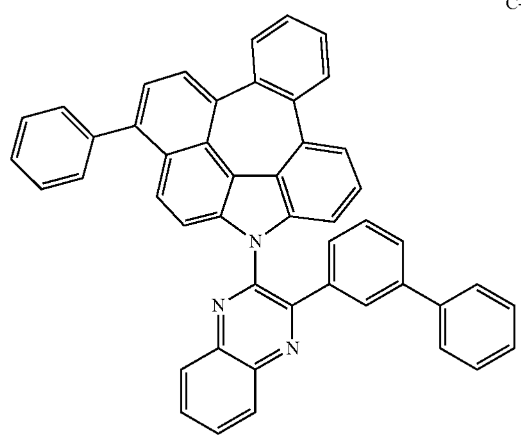

-continued
C-618
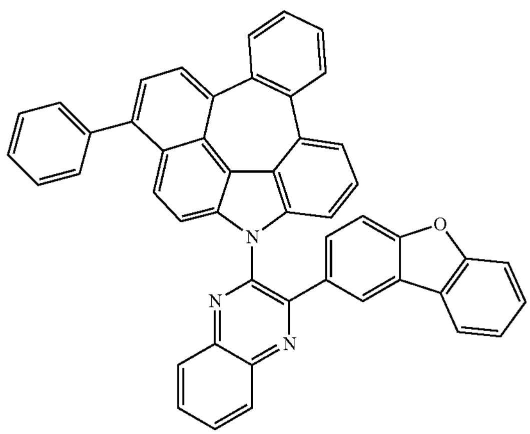
C-619
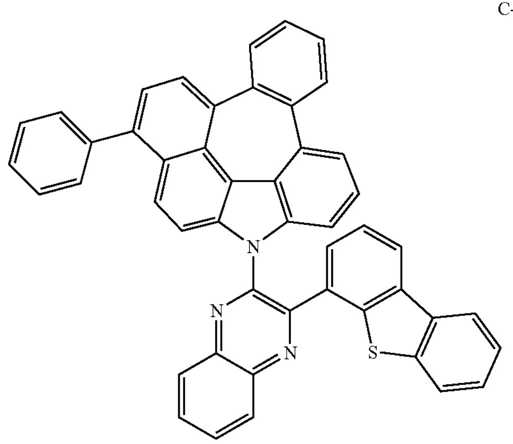
C-620
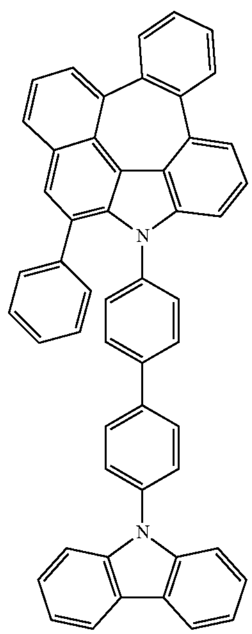
-continued
C-621
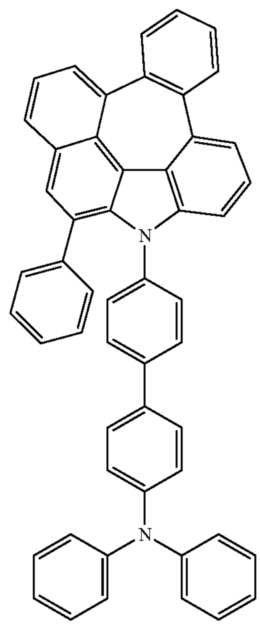
C-622
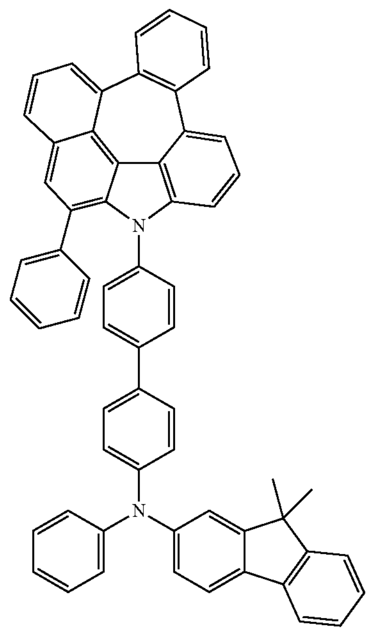

C-623
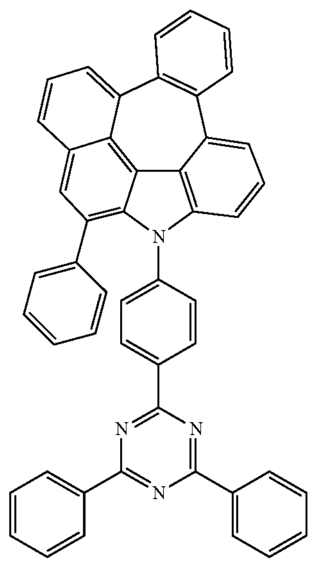
C-624
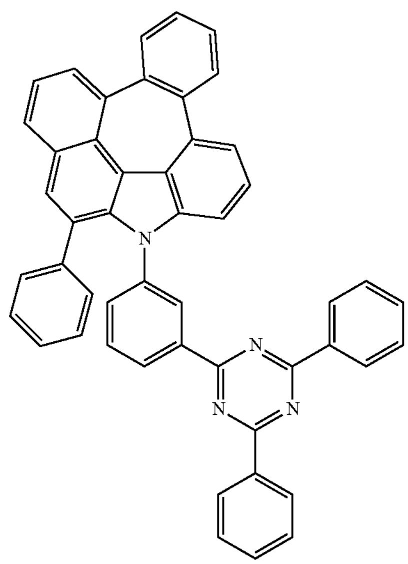
C-625
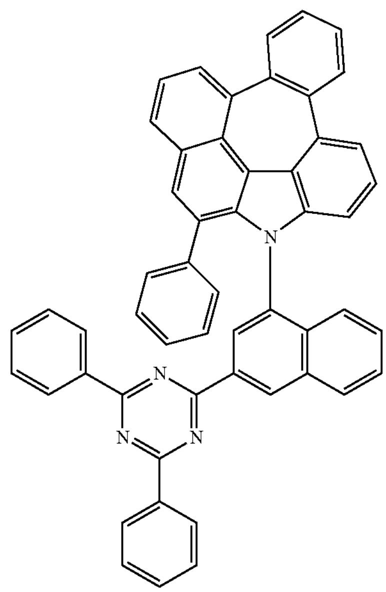
C-626
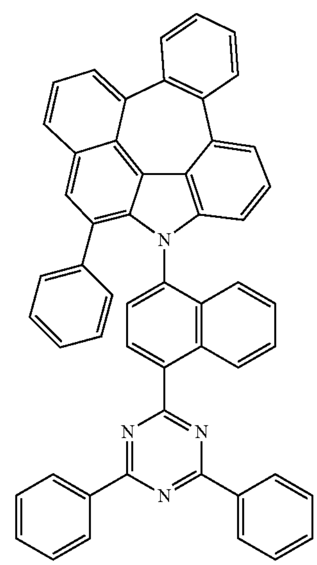

-continued
C-627
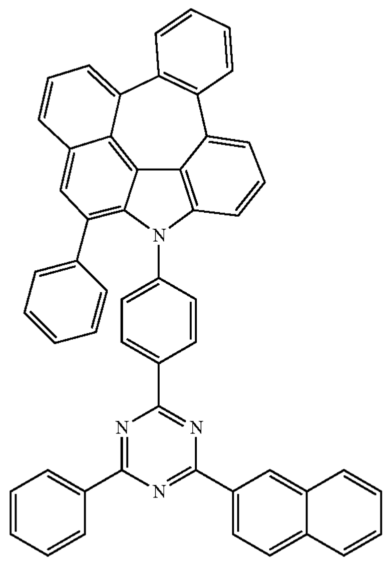
C-628
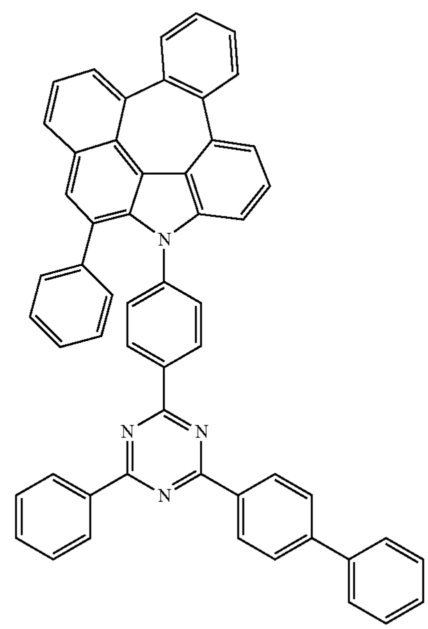
C-629
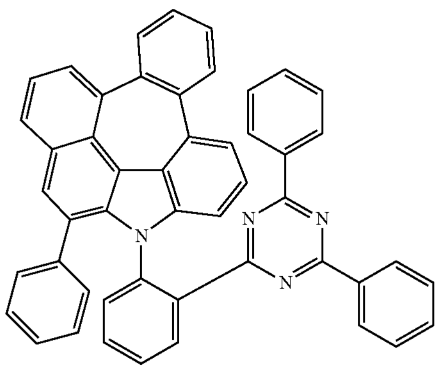
-continued
C-630
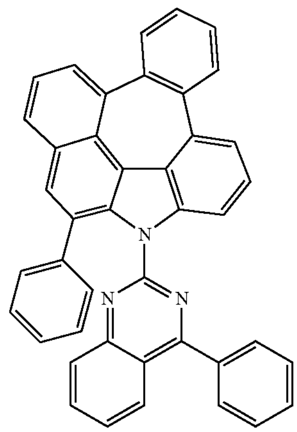
C-631
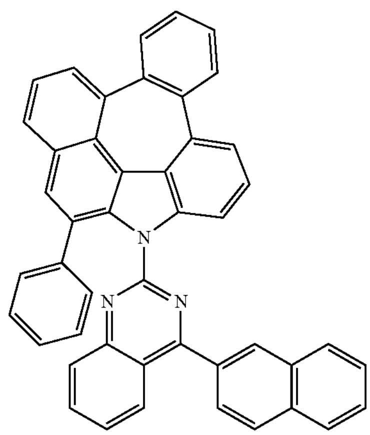
C-632
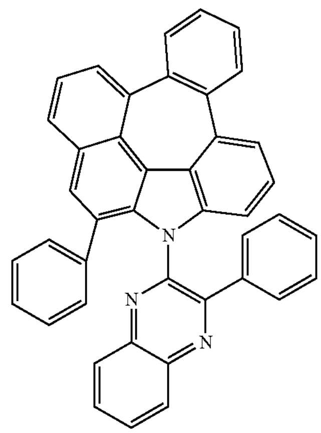

-continued
C-633
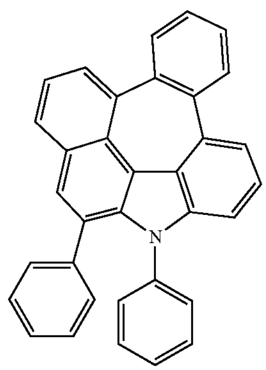
C-634
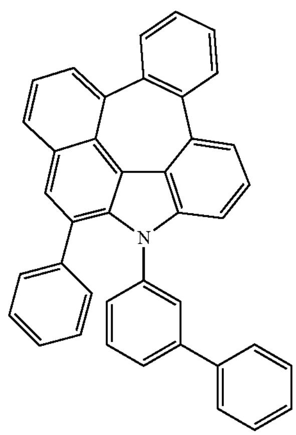
C-635
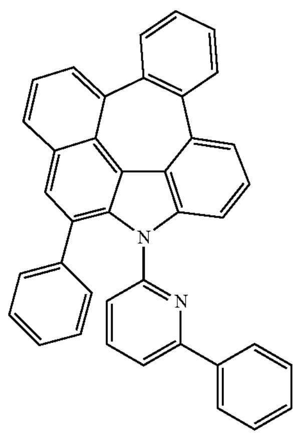
C-636
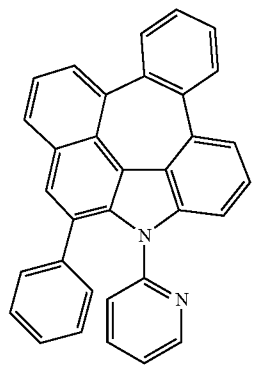
-continued
C-637
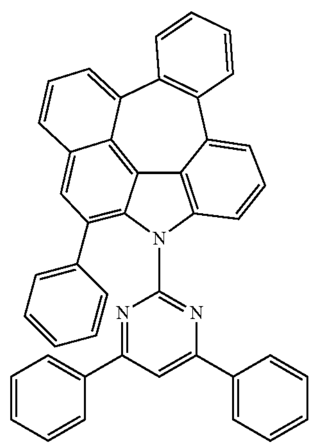
C-638
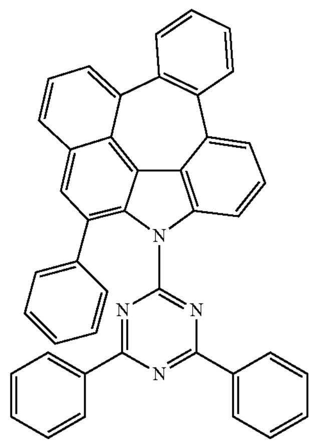
C-639
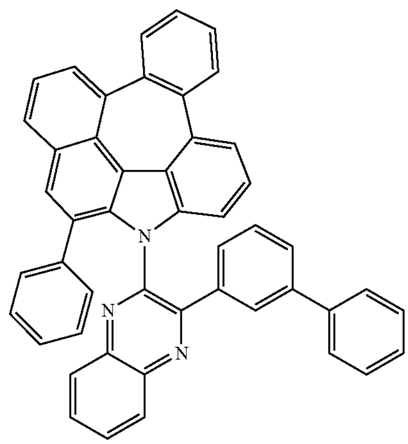

-continued
C-640
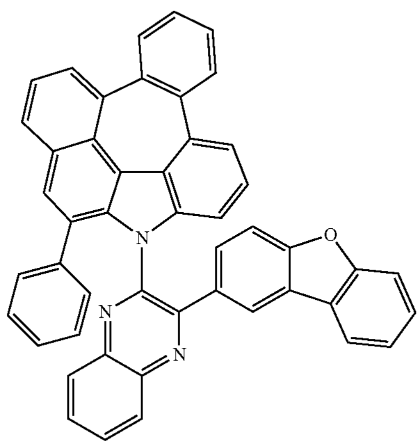
C-641
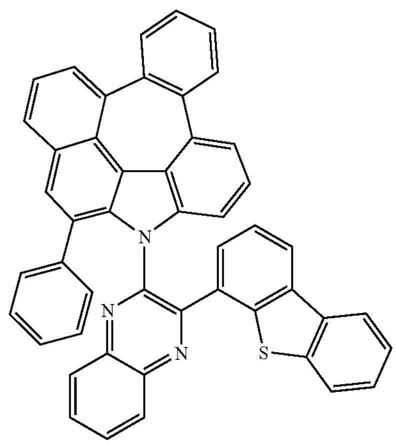
C-642
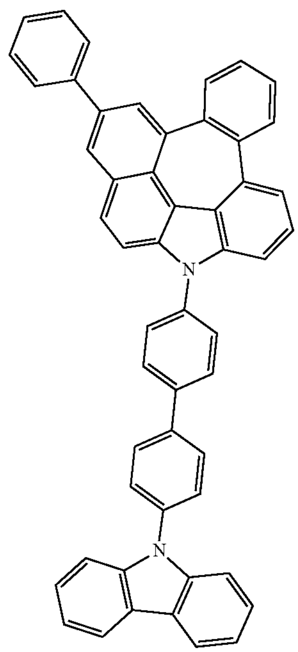
-continued
C-643
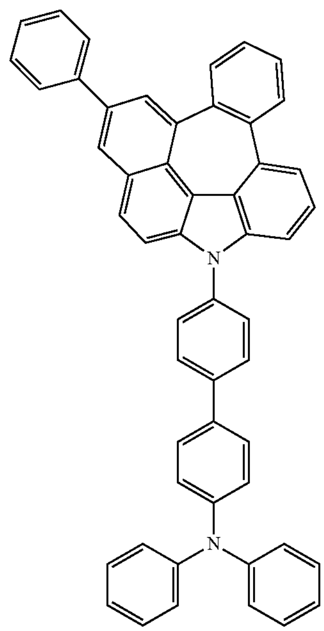
C-644
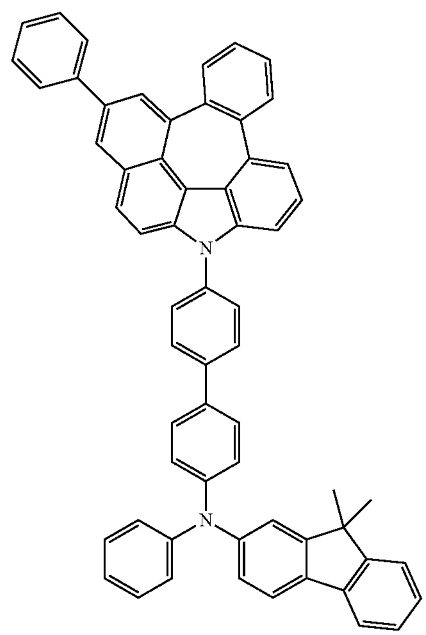

-continued
C-645
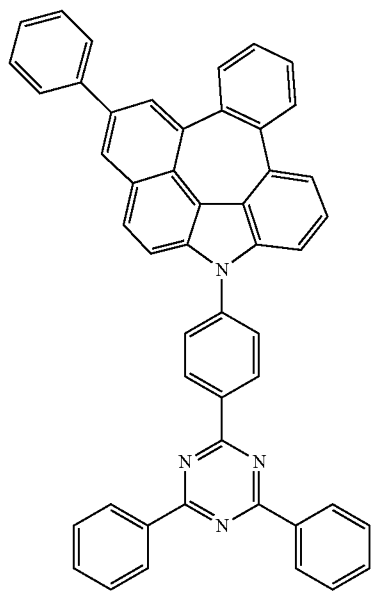
C-647
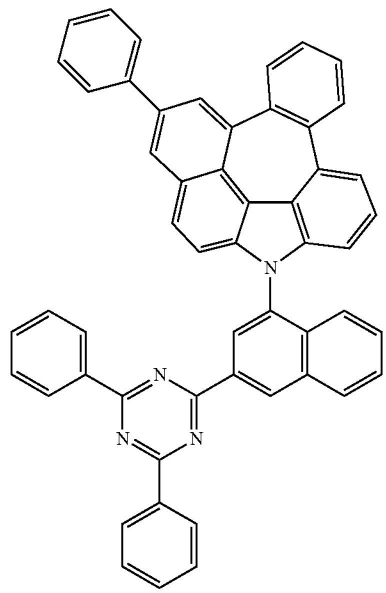
C-646
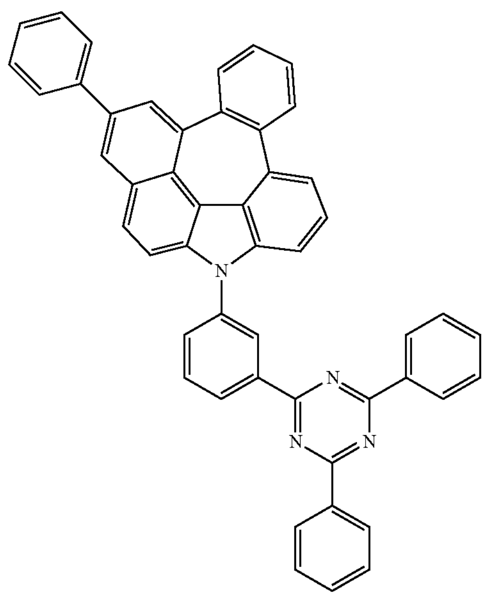
C-648
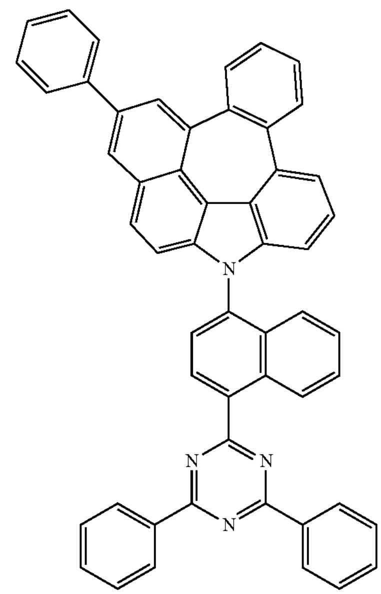

C-649
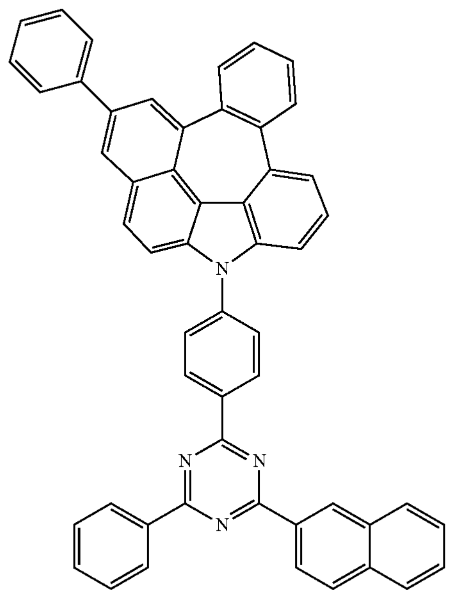
C-650
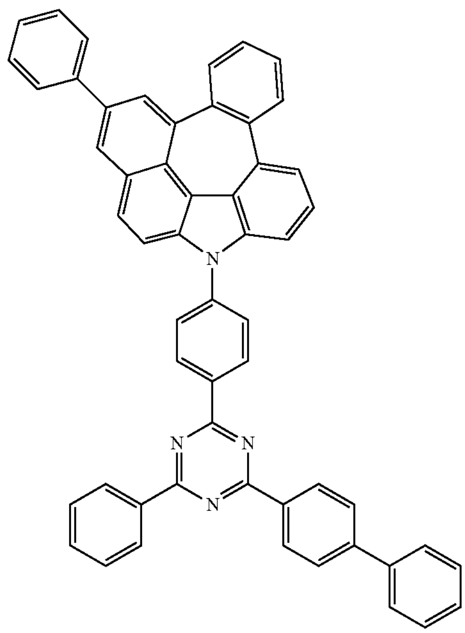
C-651
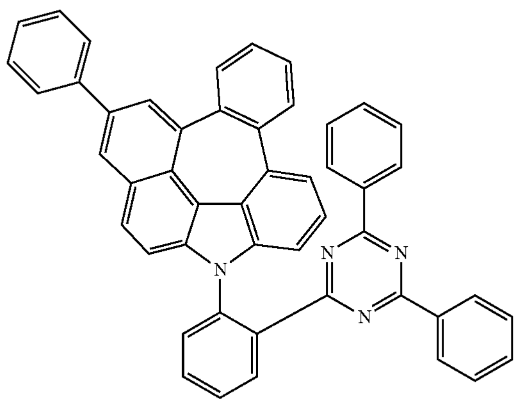
C-652
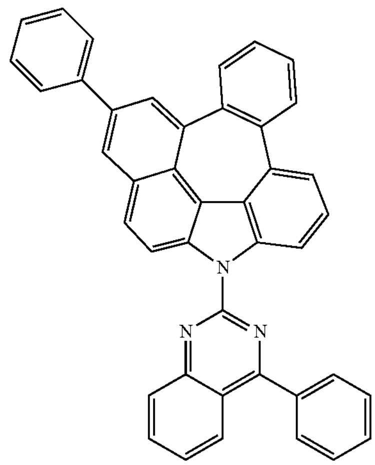
C-653
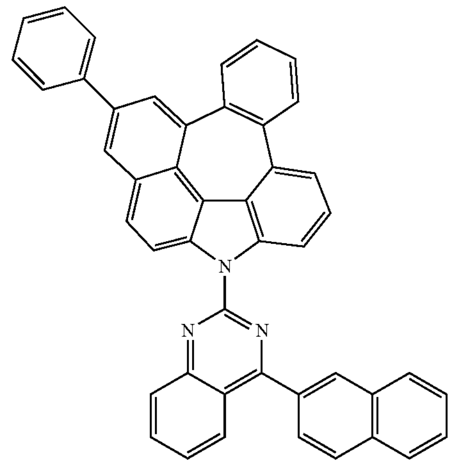
C-654
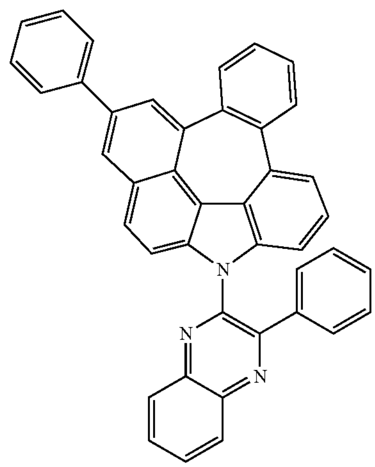

-continued
C-655
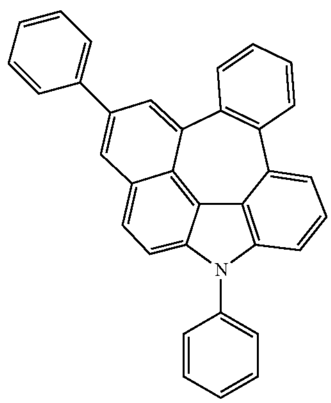
C-656
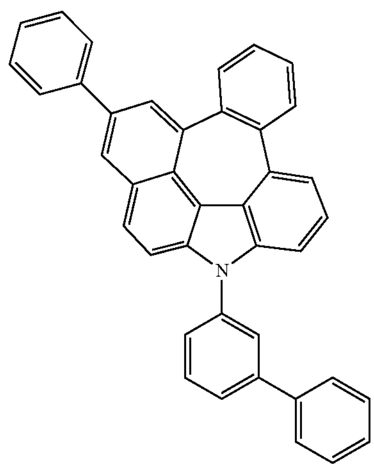
C-657
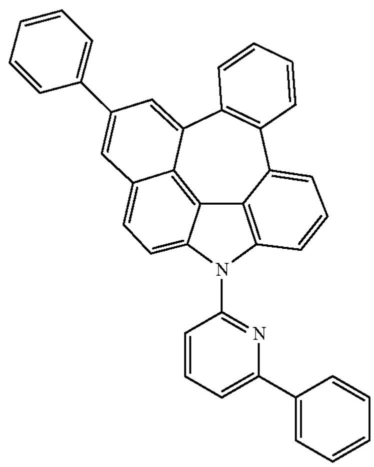
-continued
C-658
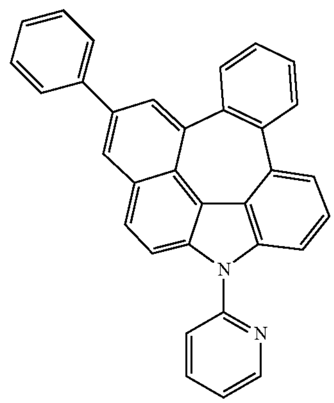
C-659
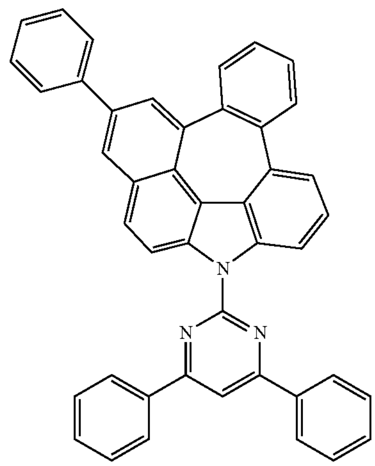
C-660
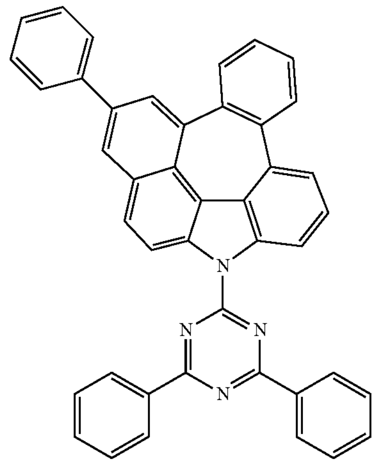

-continued
C-661
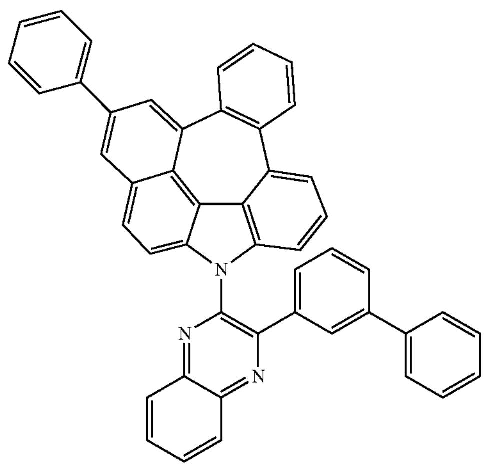
C-662
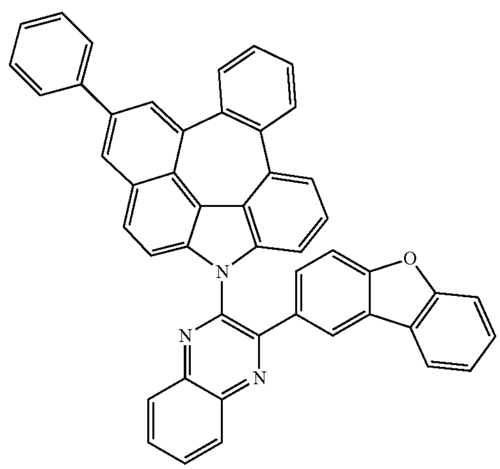
C-663
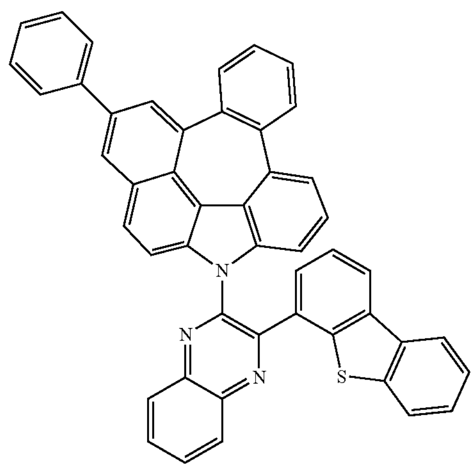
-continued
C-664
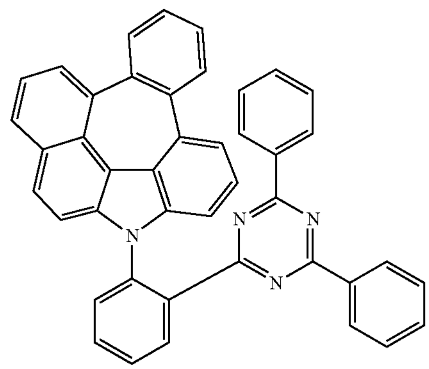
C-665
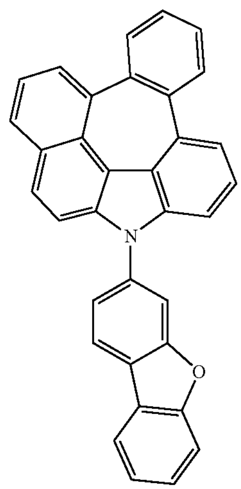
C-666
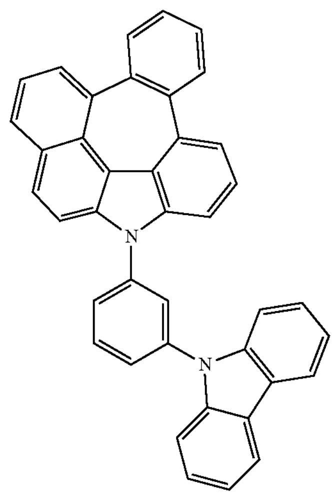

-continued
C-667
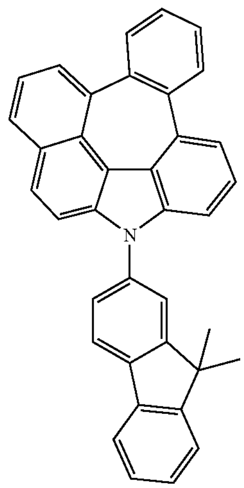
C-668
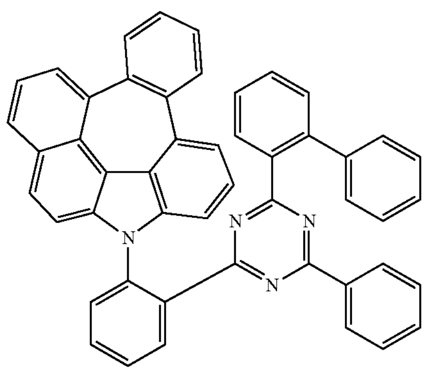
The compound represented by formula 2 may be at least one selected from the following compounds, but is not limited thereto.
H-1
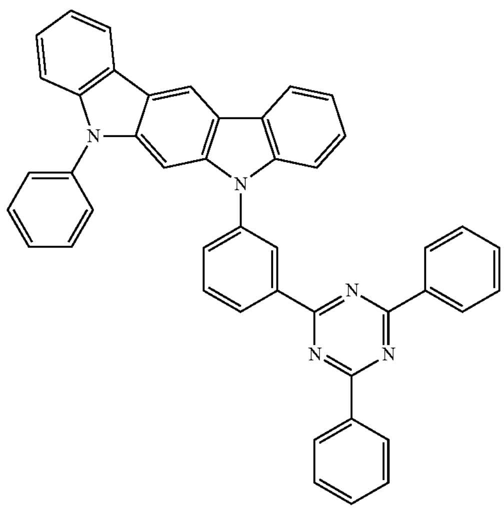
-continued
H-2
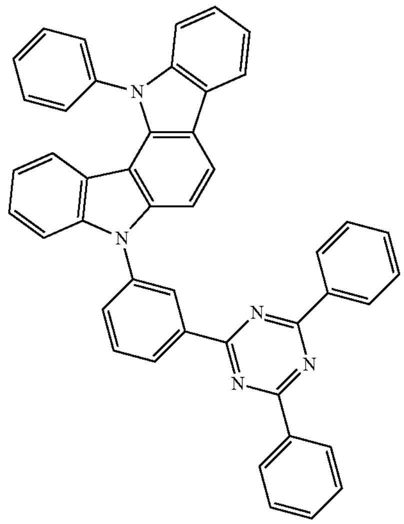
H-3
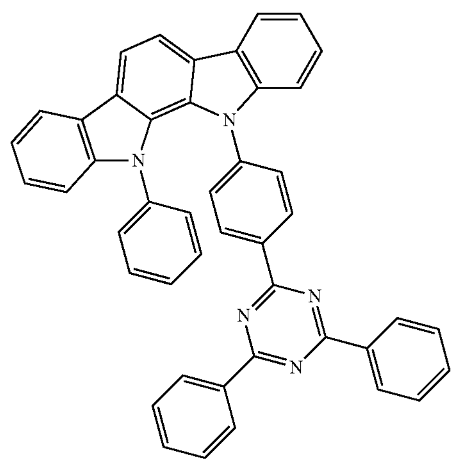
H-4
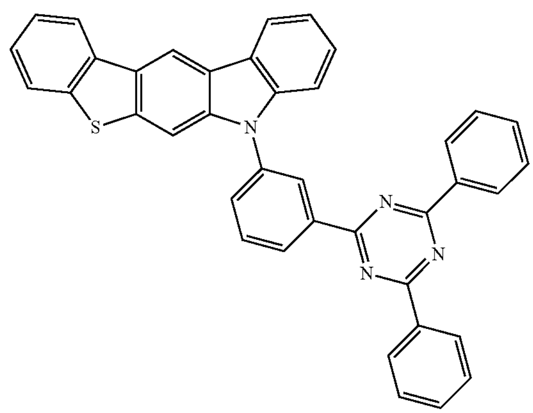

-continued
H-5
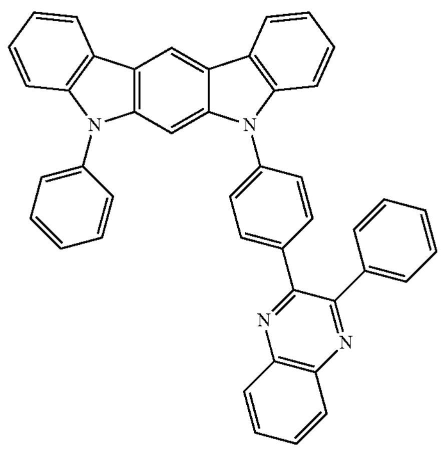
H-6
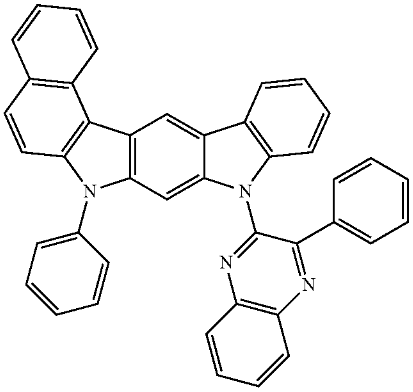
H-7
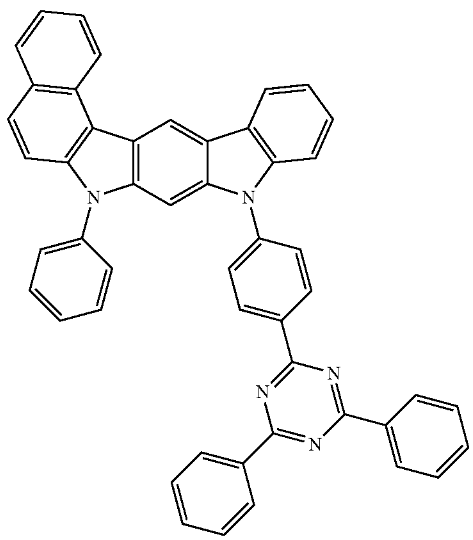
-continued
H-8
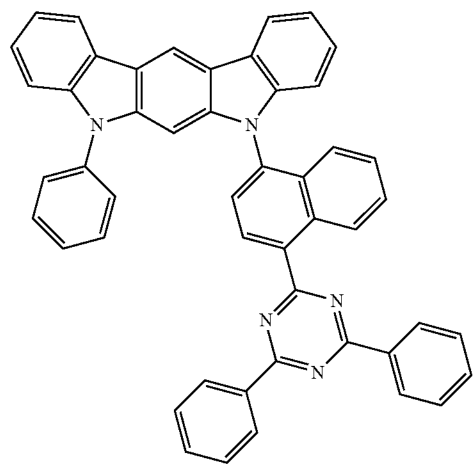
H-9
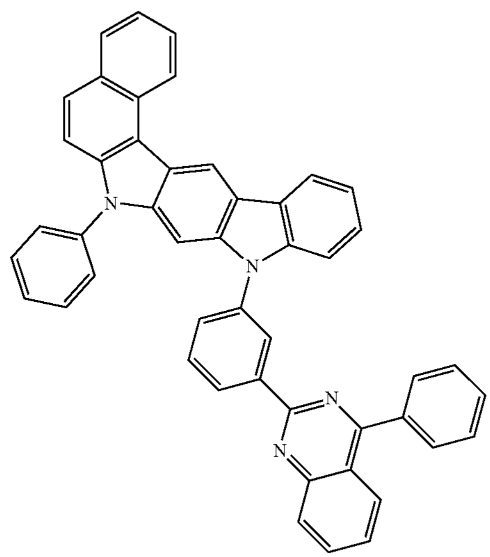
H-10
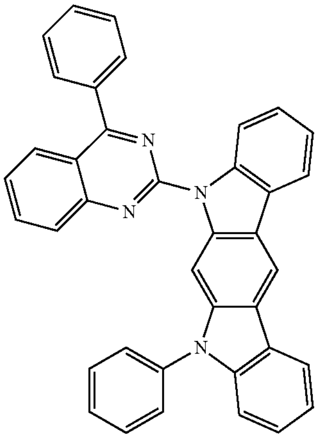

-continued
H-11
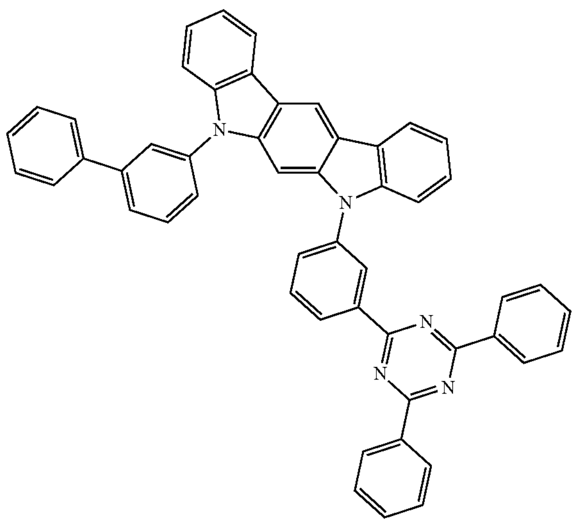
H-12
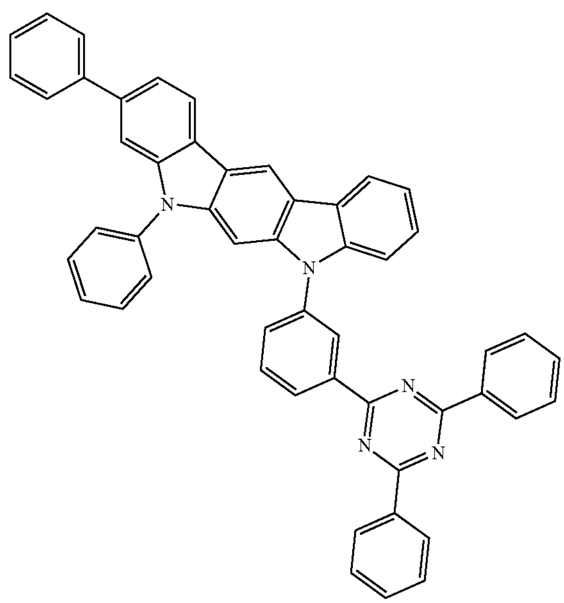
-continued
H-13
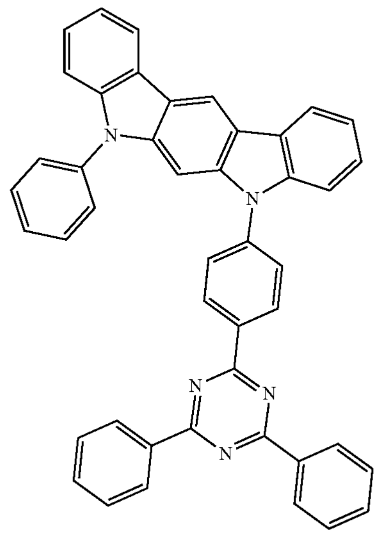
H-14
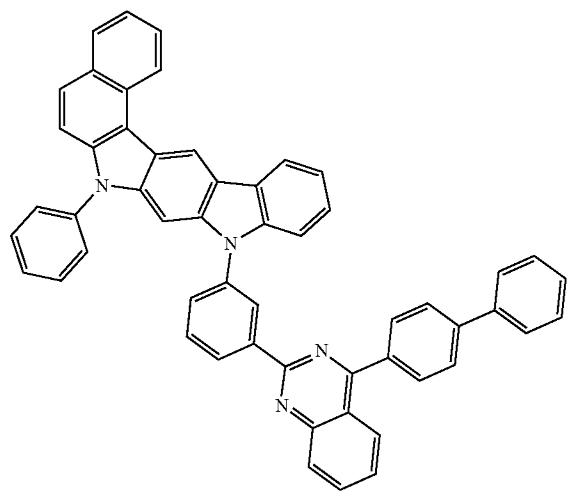
H-15
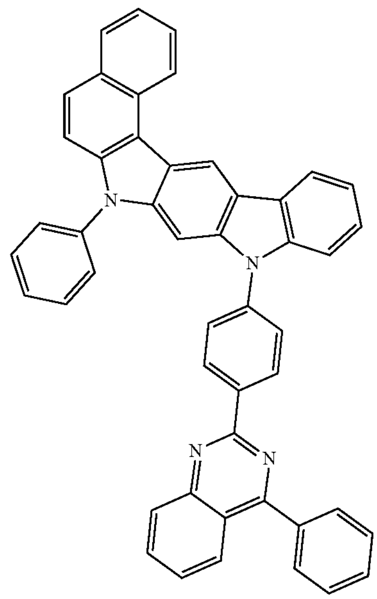

-continued
H-16
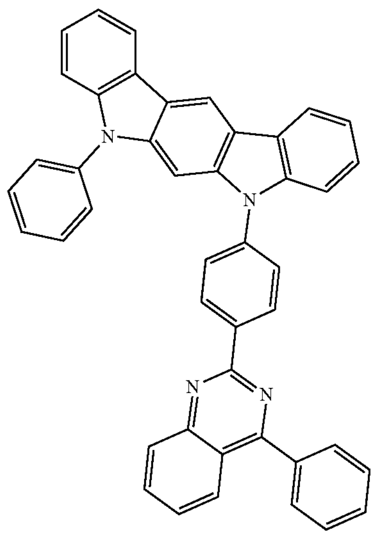
H-17
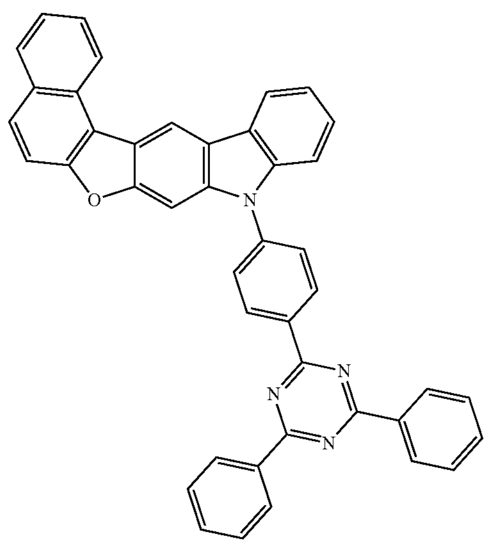
H-18
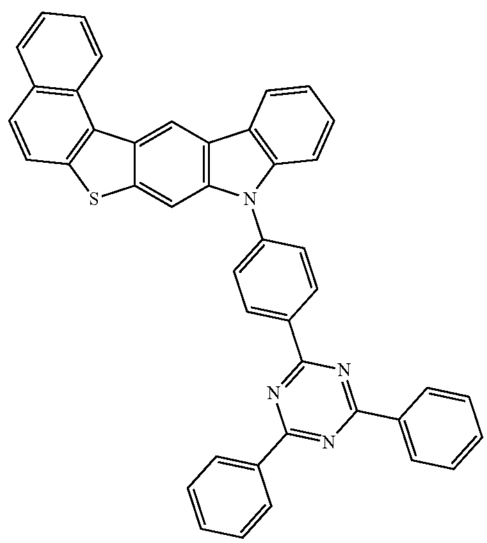
-continued
H-19
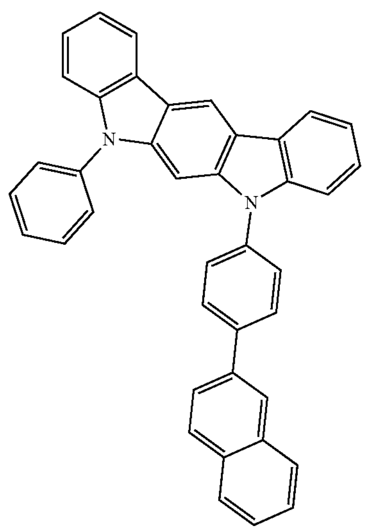
H-20
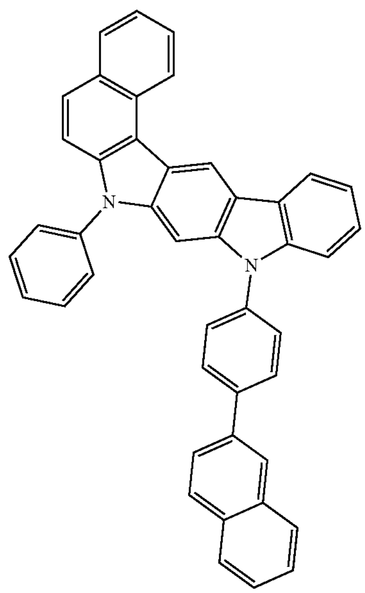
H-21
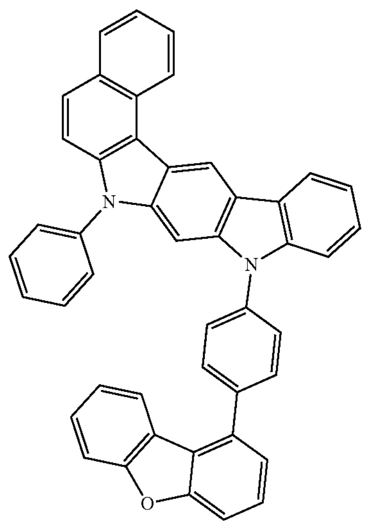

-continued
H-22
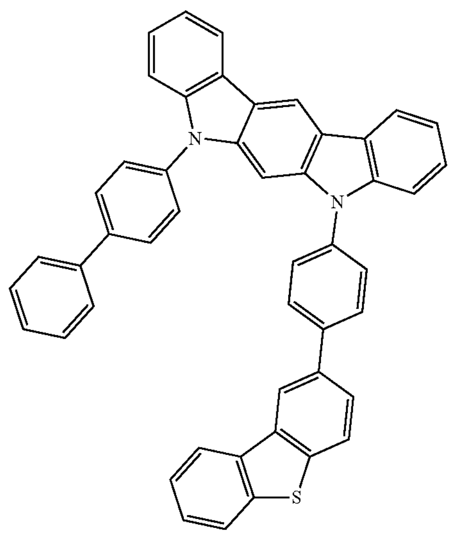
H-23
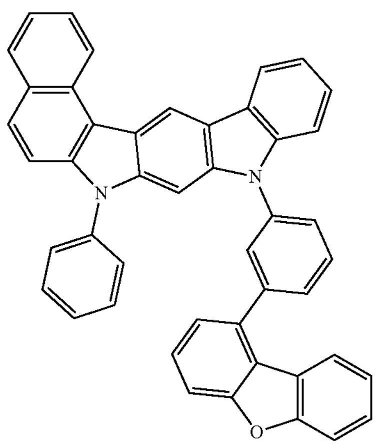
H-24
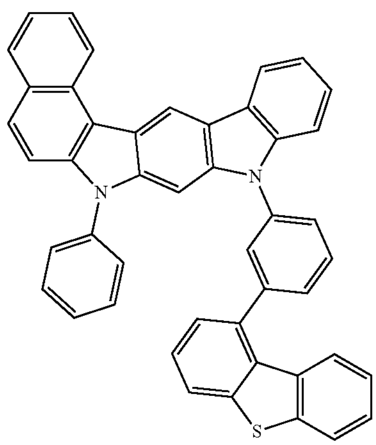
-continued
H-25
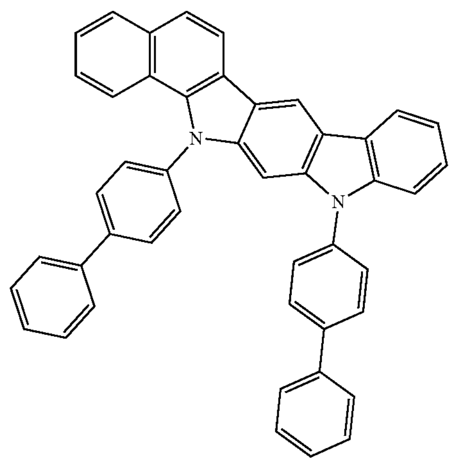
H-26
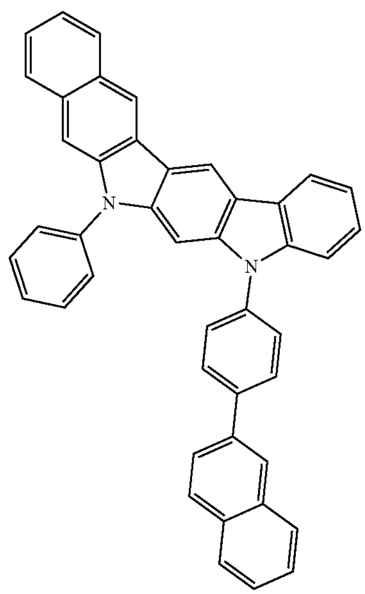
H-27
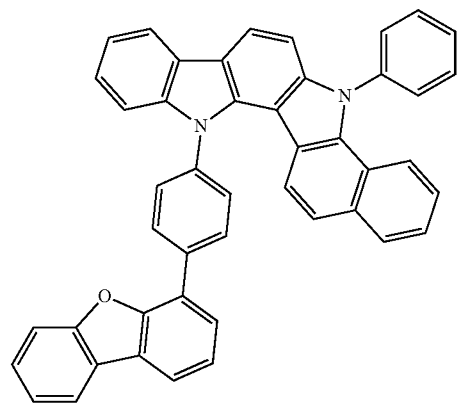

-continued
H-28
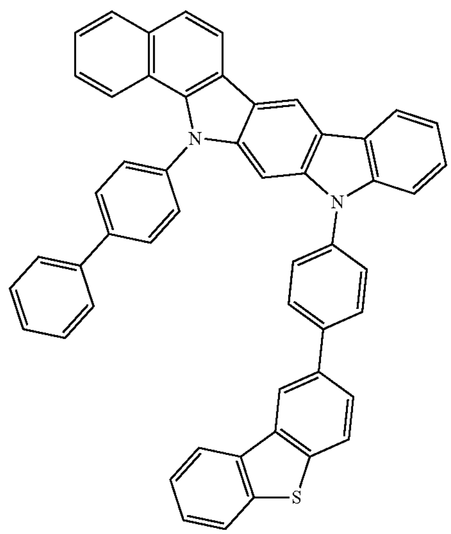
H-29
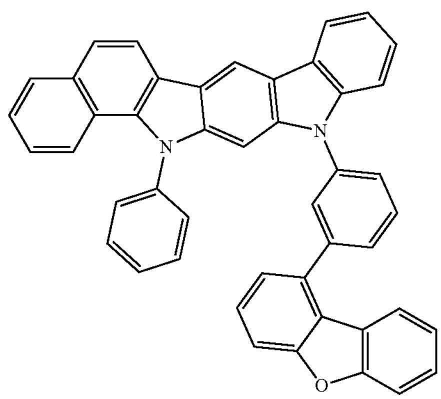
H-30
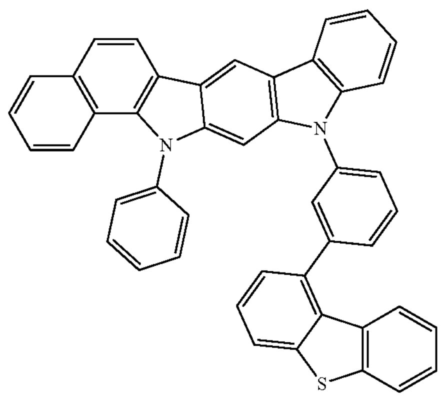
-continued
H-31
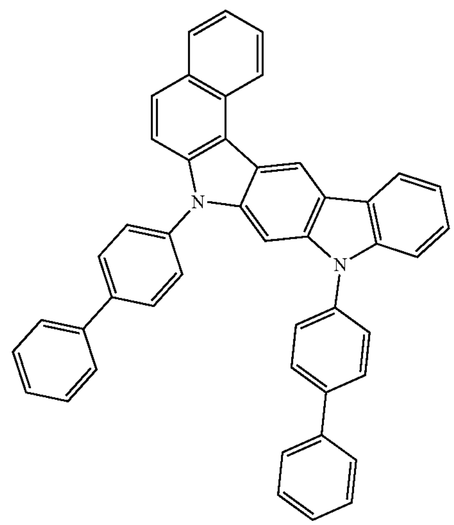
H-32
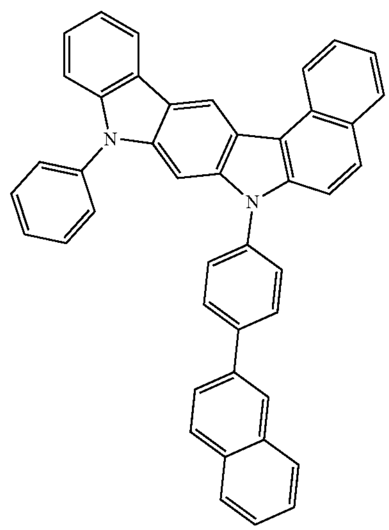
H-33
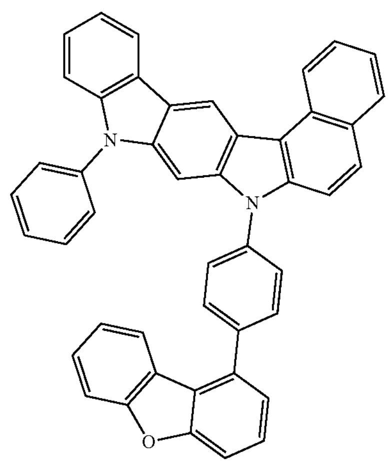

-continued
H-34
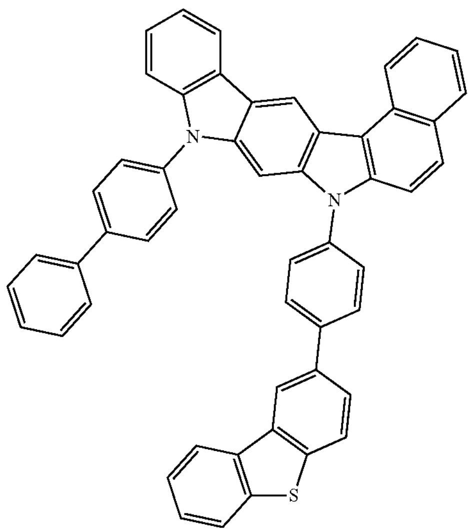
H-35
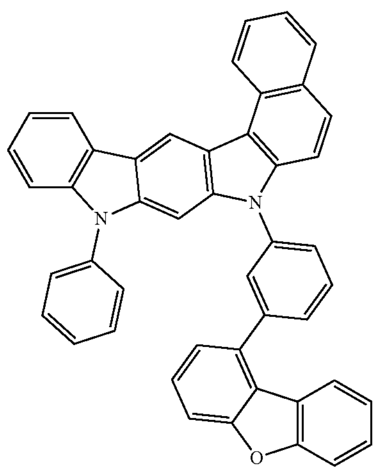
H-36
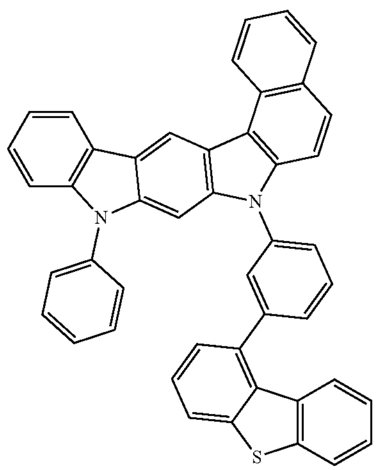
-continued
H-37
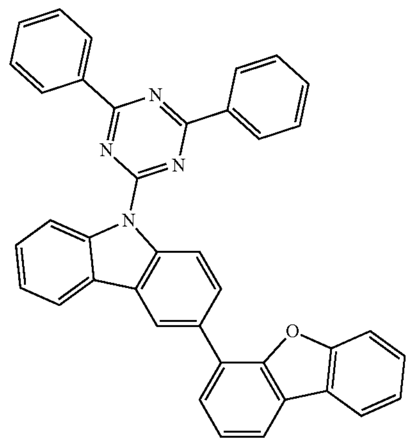
H-38
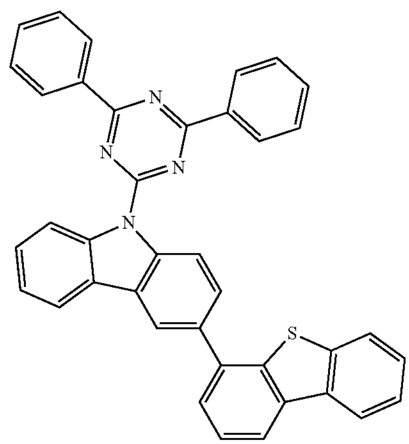
H-39
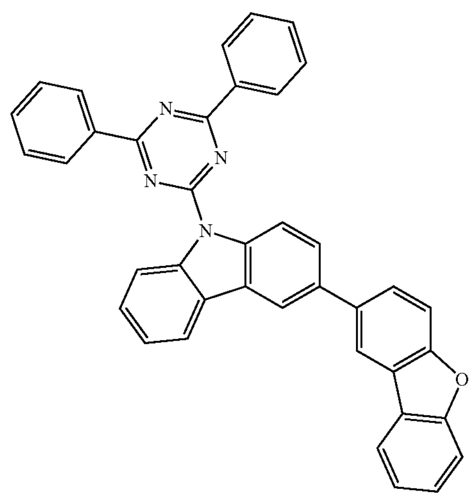

-continued
H-40
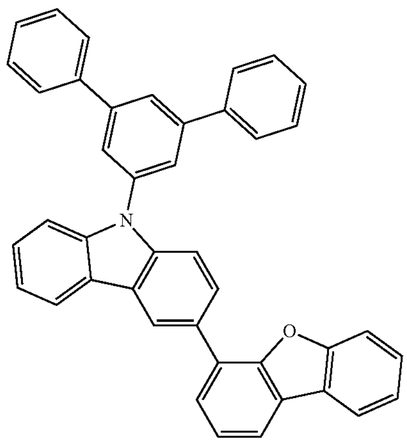
H-41
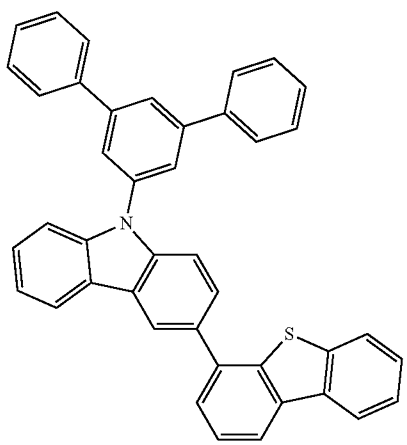
H-42
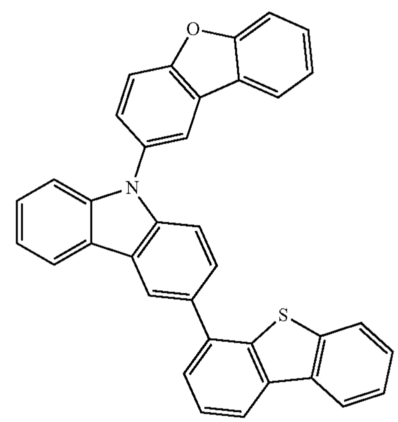
-continued
H-43
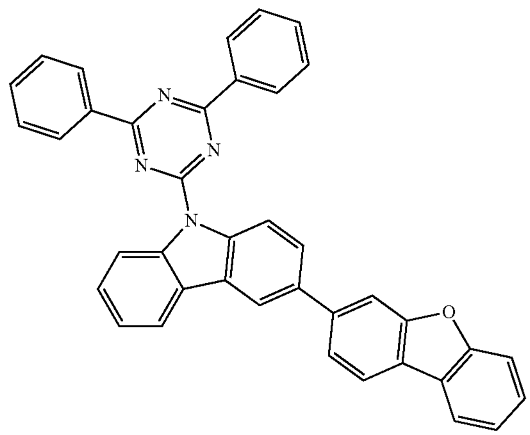
H-44
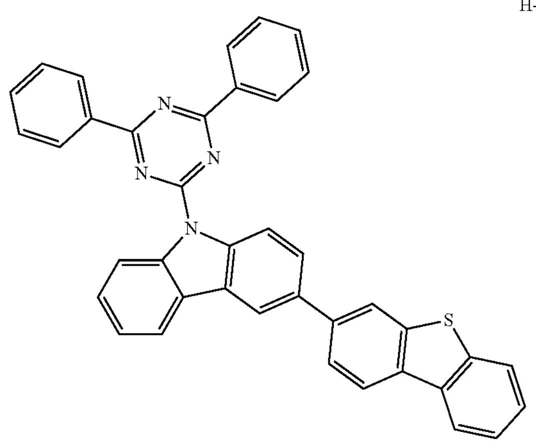
H-45
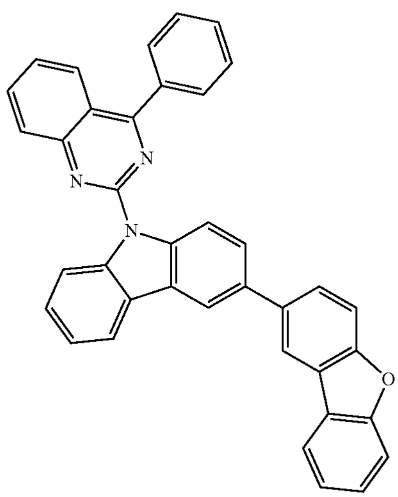

-continued
H-46
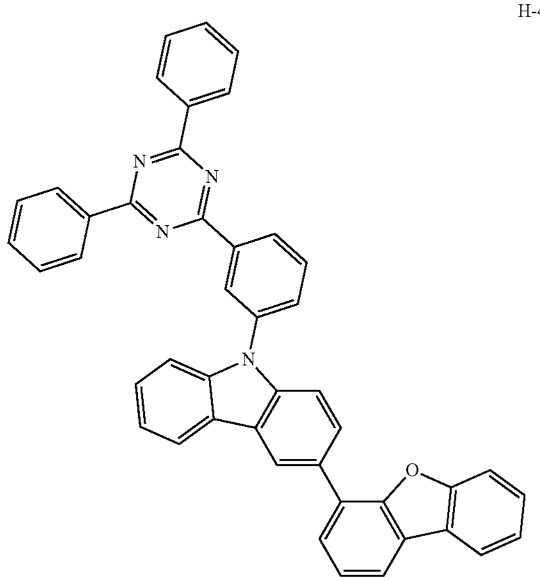
H-47
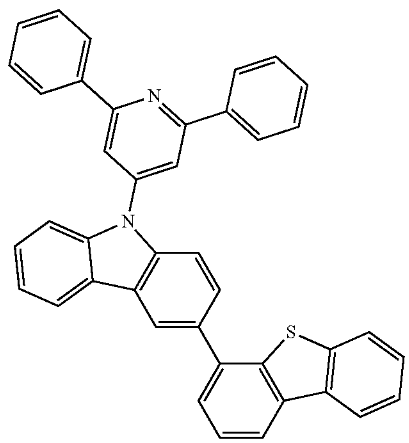
H-48
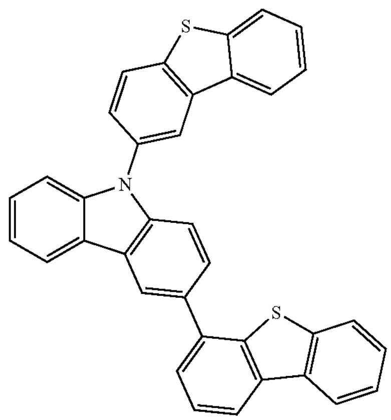
-continued
H-49
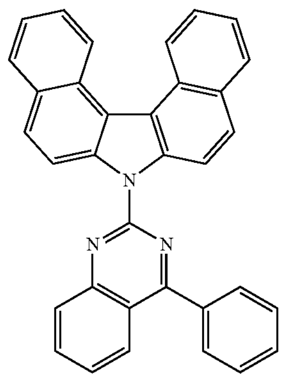
H-50
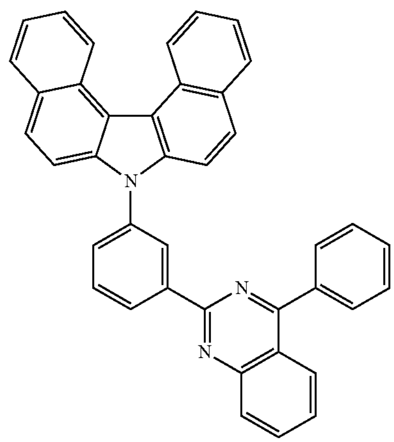
H-51
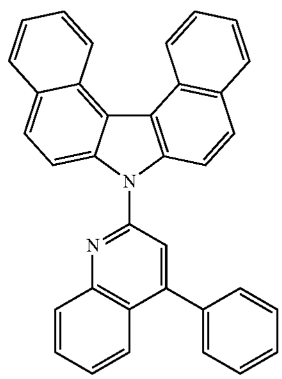
H-52
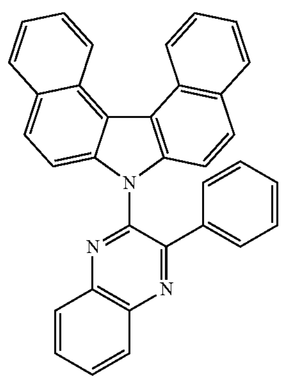

-continued
H-53
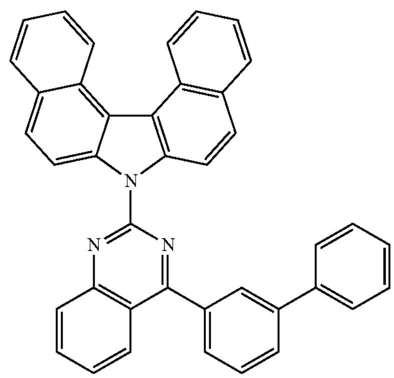
H-54
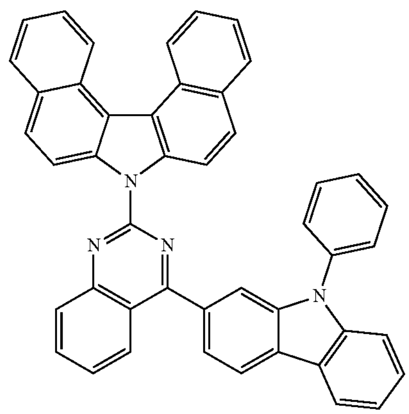
H-55
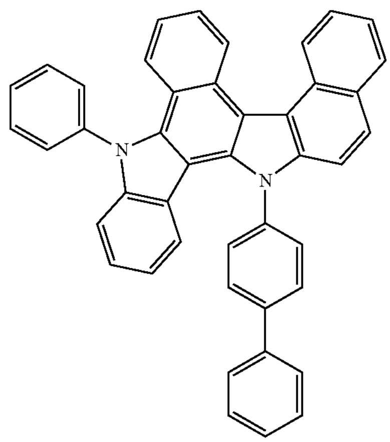
H-56
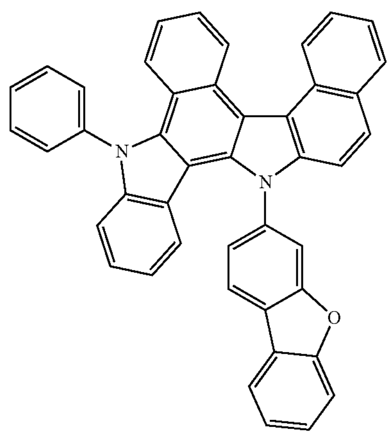
-continued
H-57
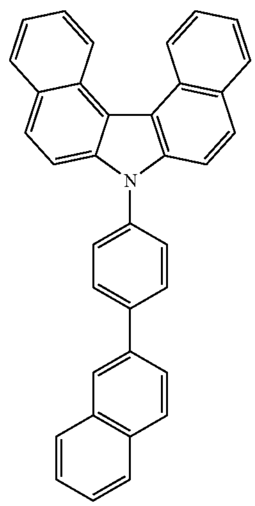
H-58
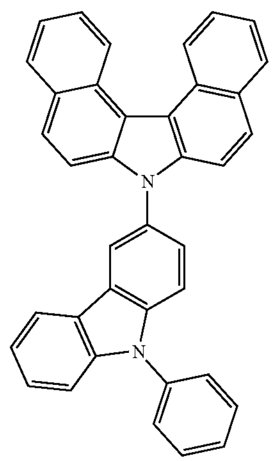
H-59
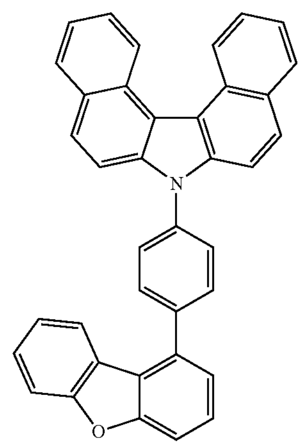

-continued
H-60
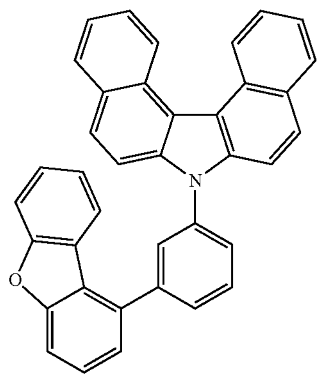
H-61
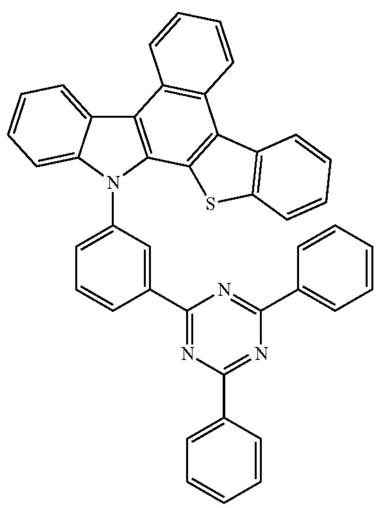
H-62
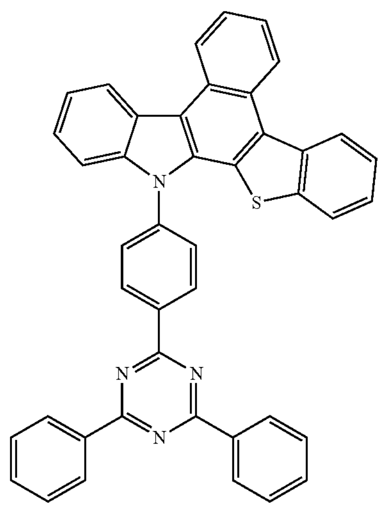
-continued
H-63
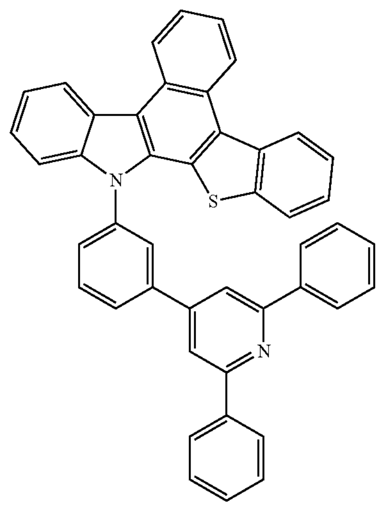
H-64
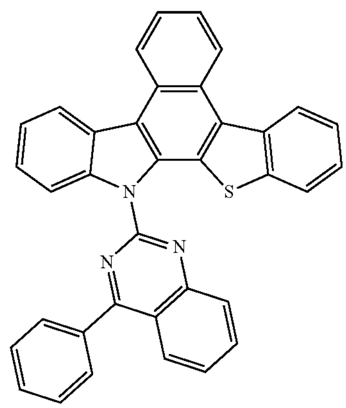
H-65
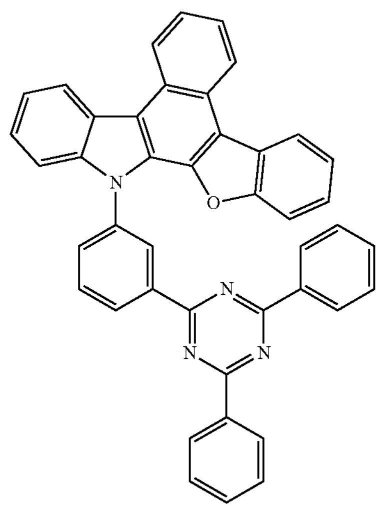

-continued
H-66
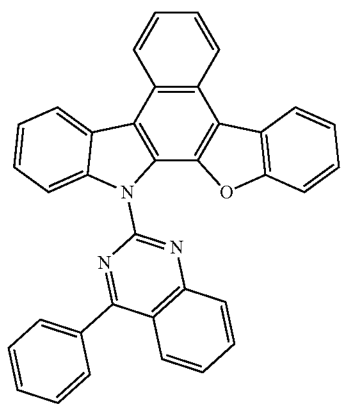
H-67
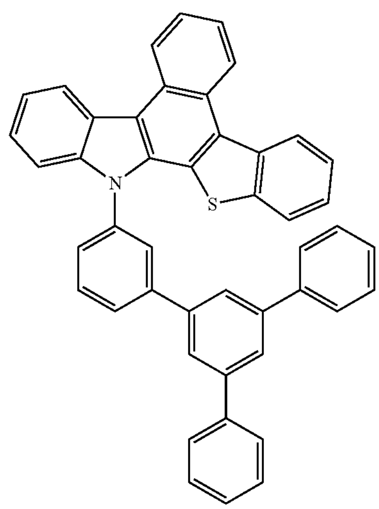
H-68
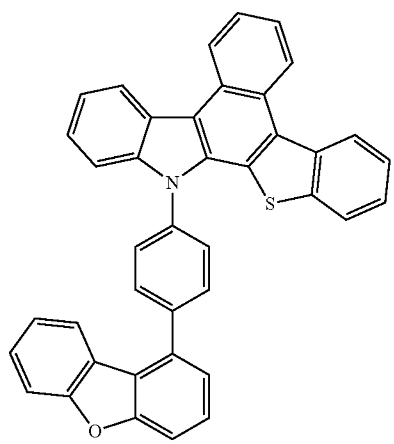
-continued
H-69
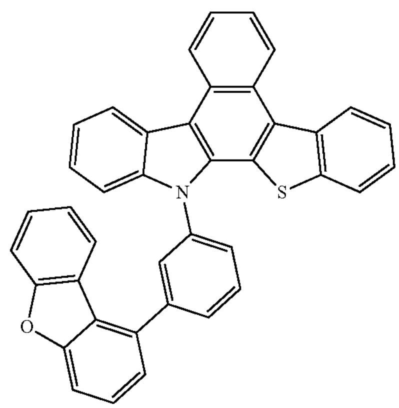
H-70
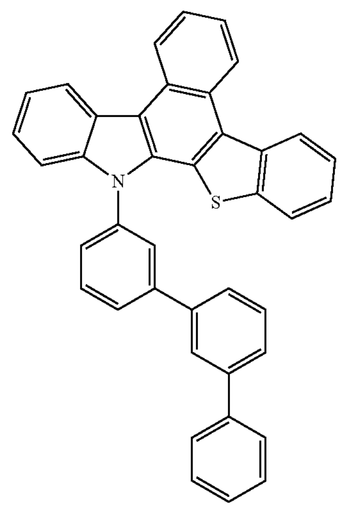
H-71
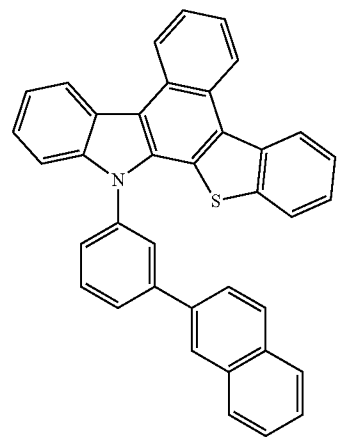

-continued
H-72
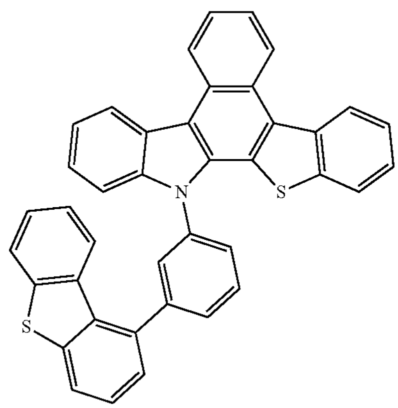
H-73
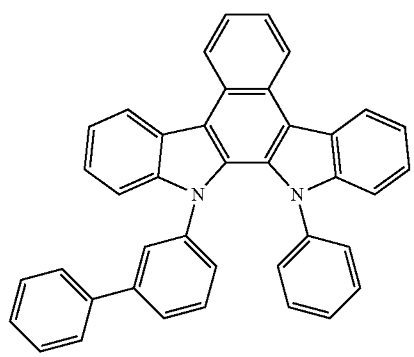
H-74
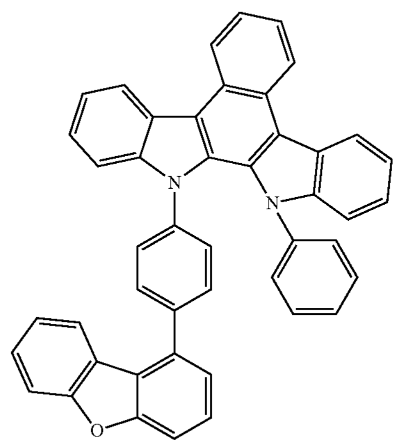
H-75
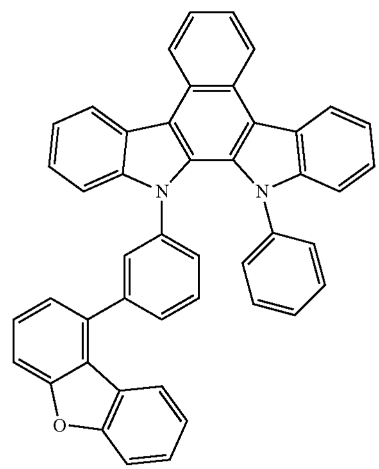
-continued
H-76
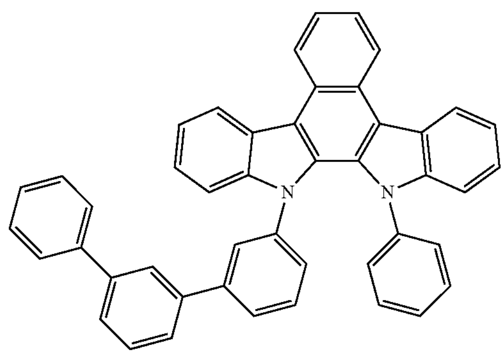
H-77
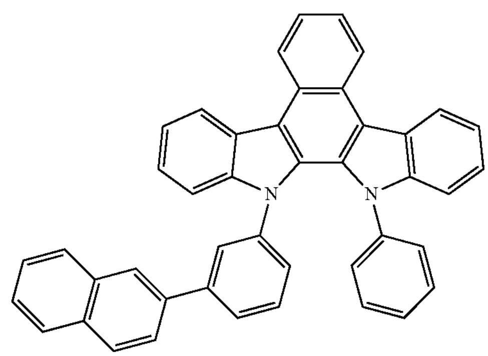
H-78
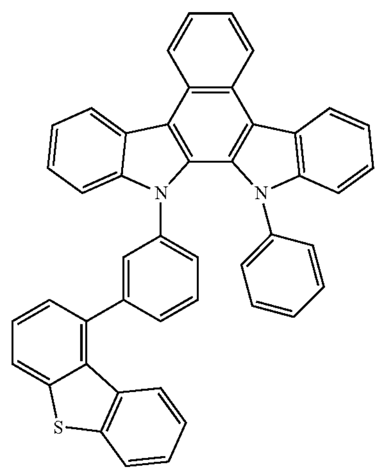

-continued
H-79
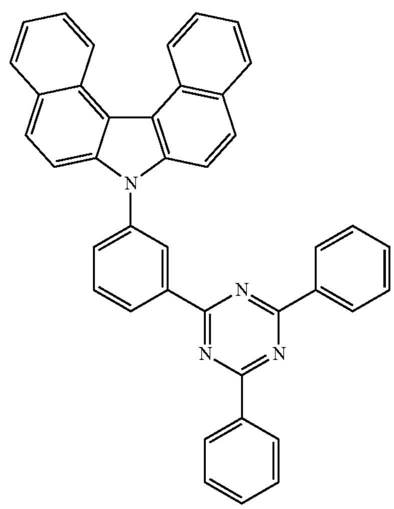
H-80
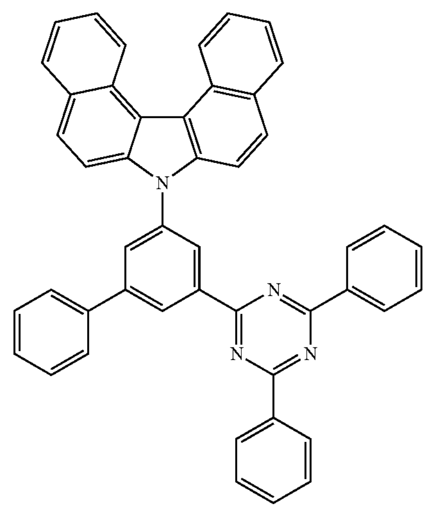
H-81
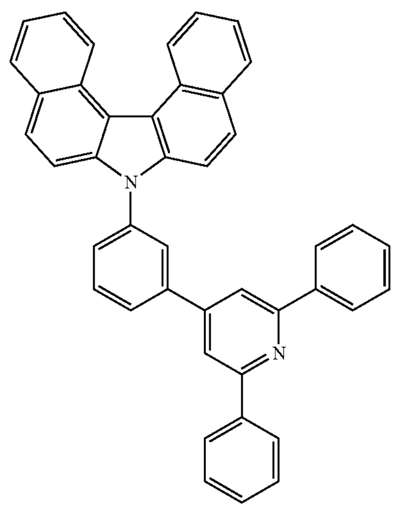
-continued
H-82
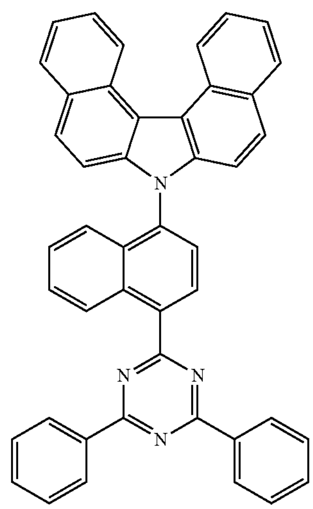
H-83
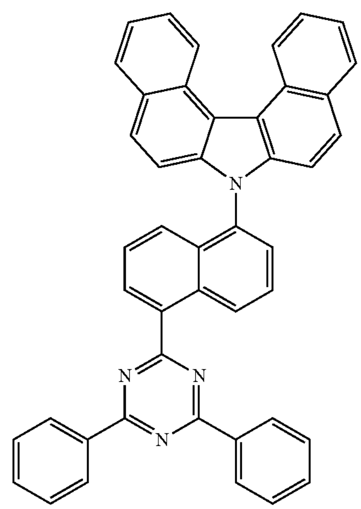
H-84
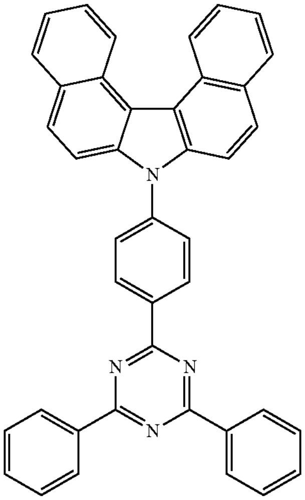

H-85
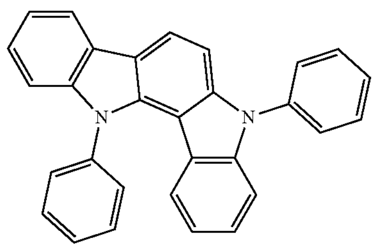
H-86
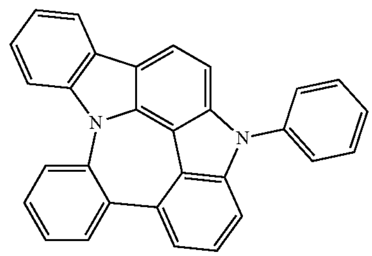
H-87
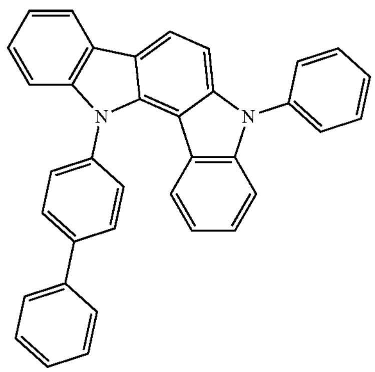
H-88
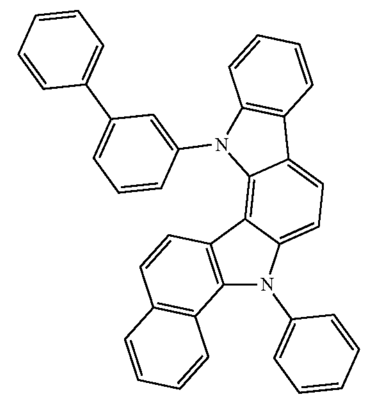
H-89
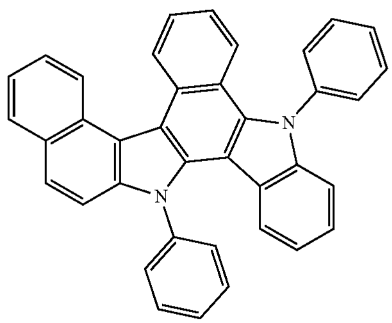
H-90
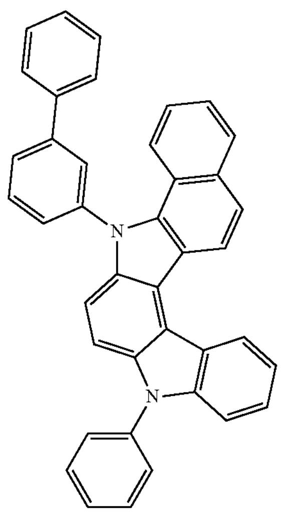
H-91
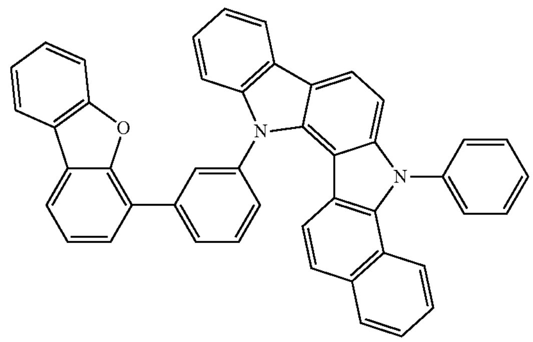
H-92
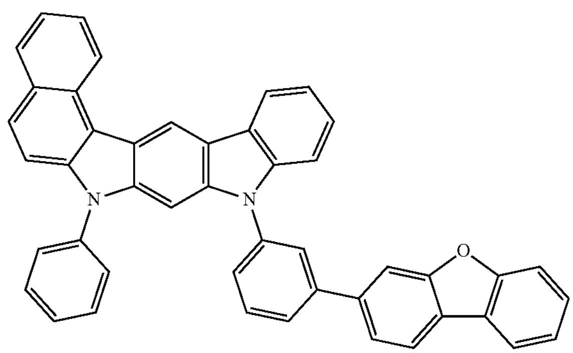
H-93
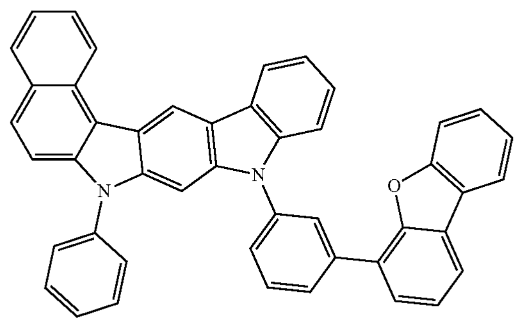

-continued
H-94
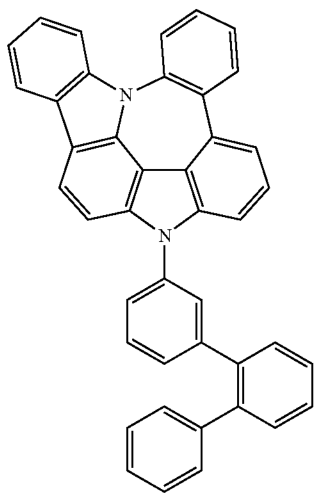
H-95
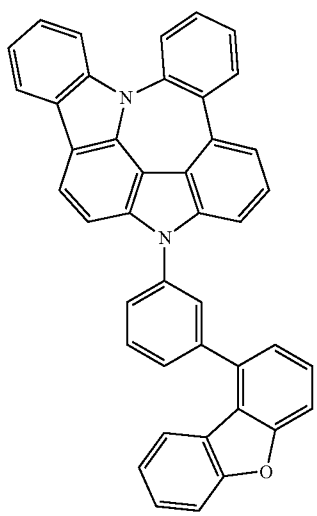
H-96
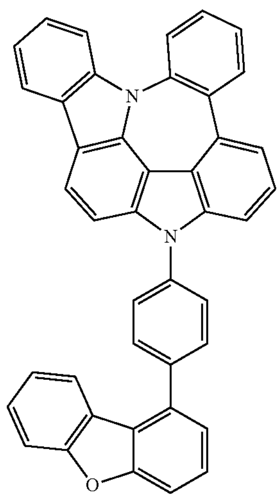
-continued
H-97
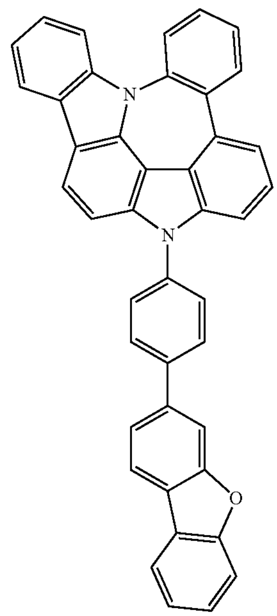
H-98
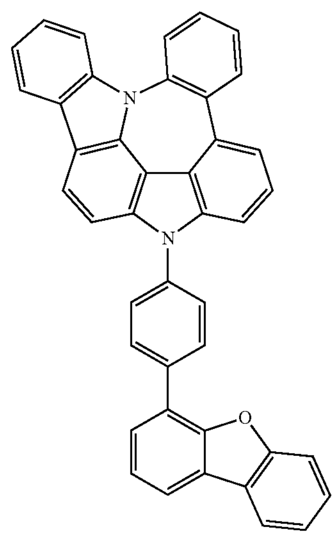

-continued
H-99
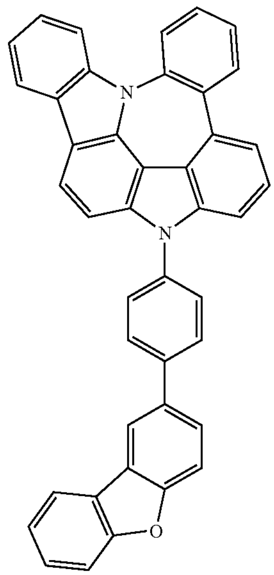
H-100
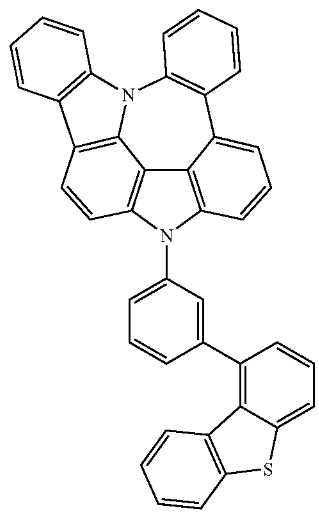
H-101
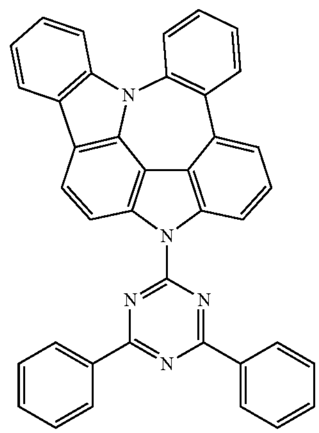
-continued
H-102
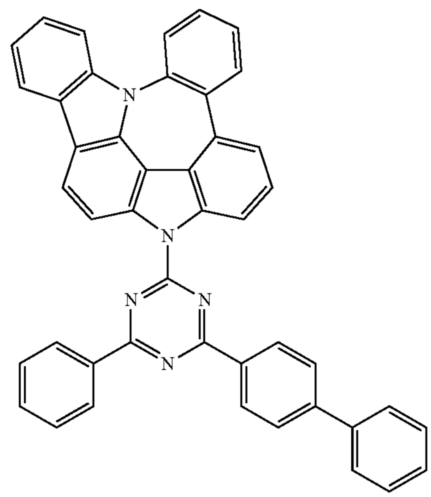
H-103
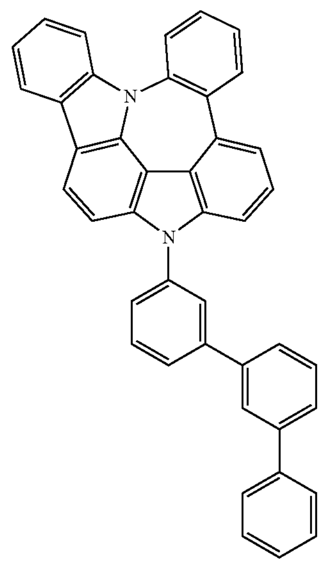
H-104
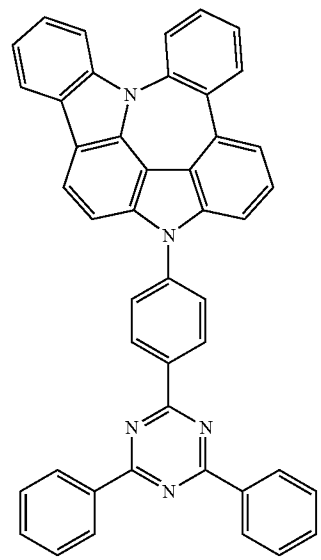

-continued
H-105
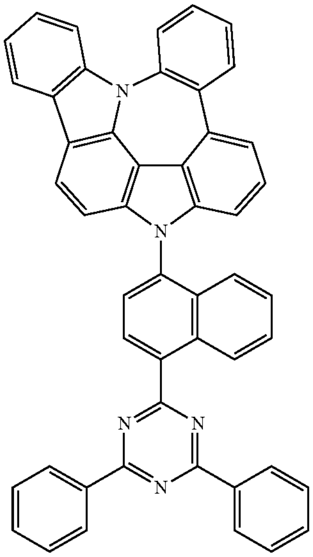
H-106
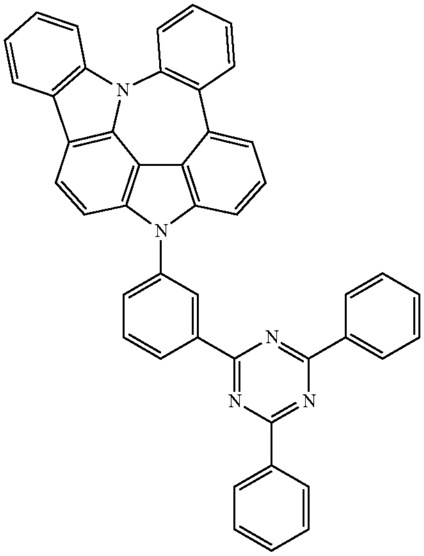
H-107
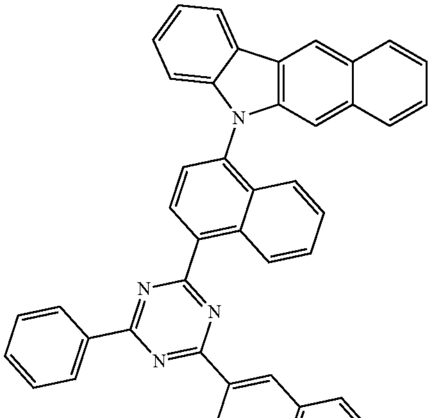
-continued
H-108
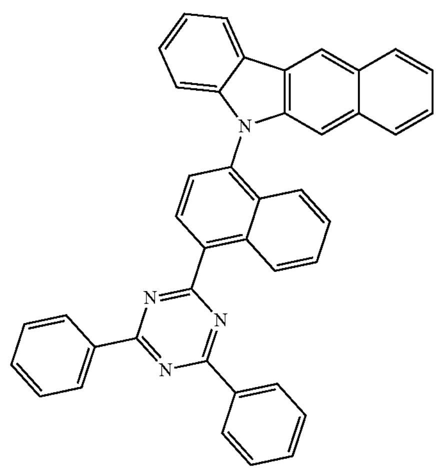
H-109
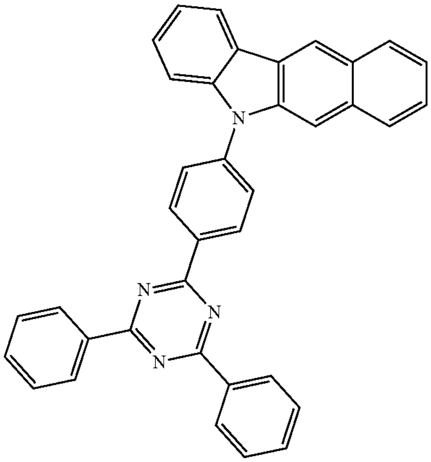
H-110
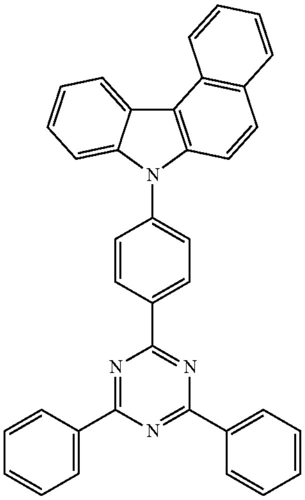

-continued
H-111
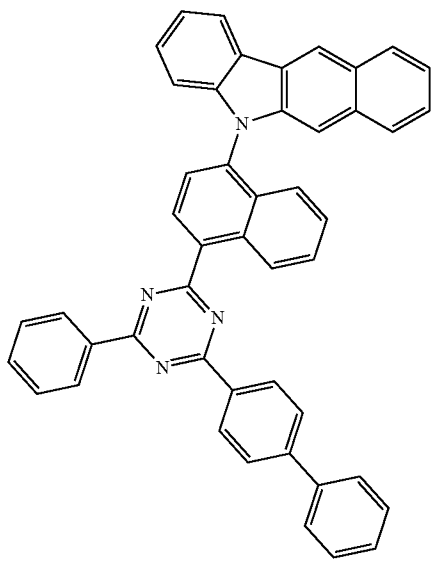
H-112
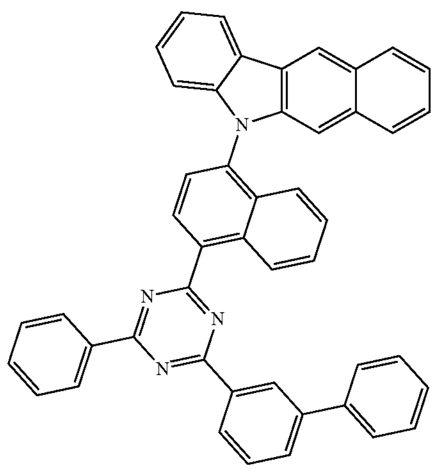
H-113
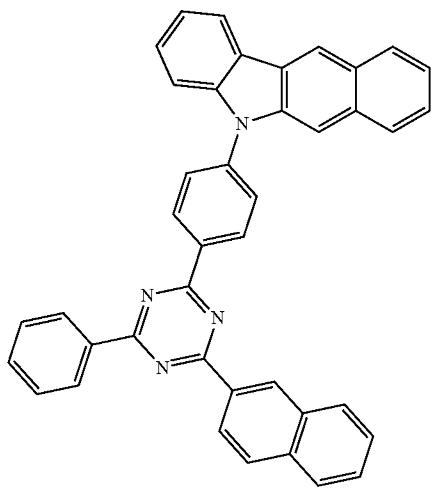
-continued
H-114
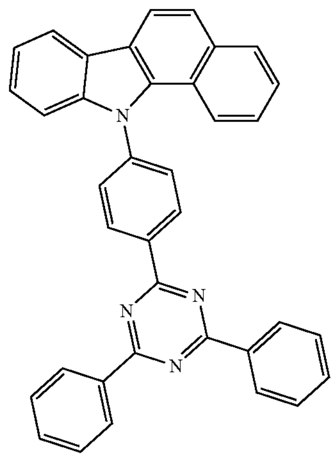
H-115
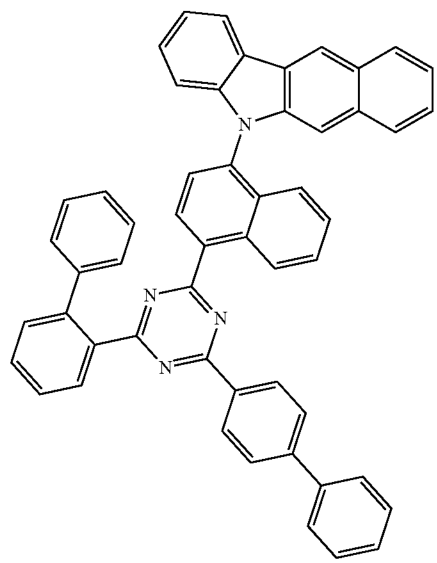
H-116
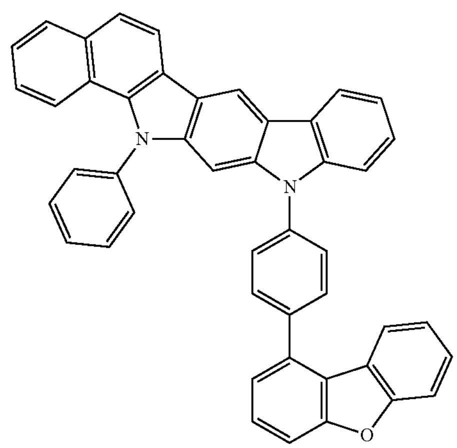

-continued
H-117
H-118
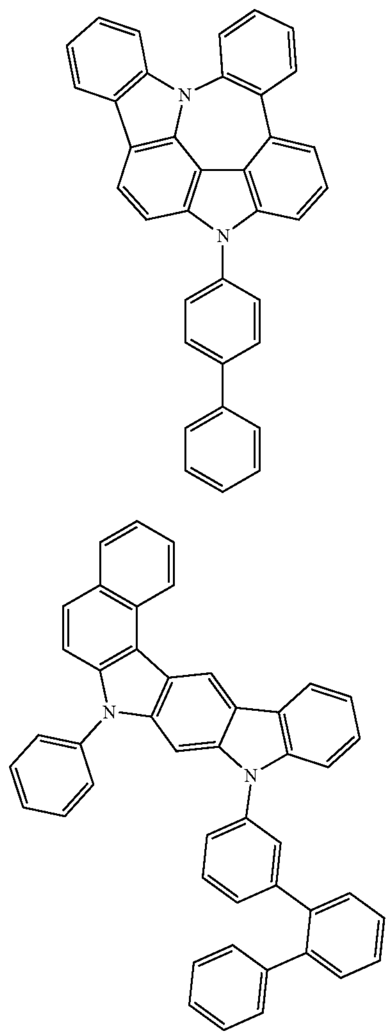
-continued
H-119
H-120
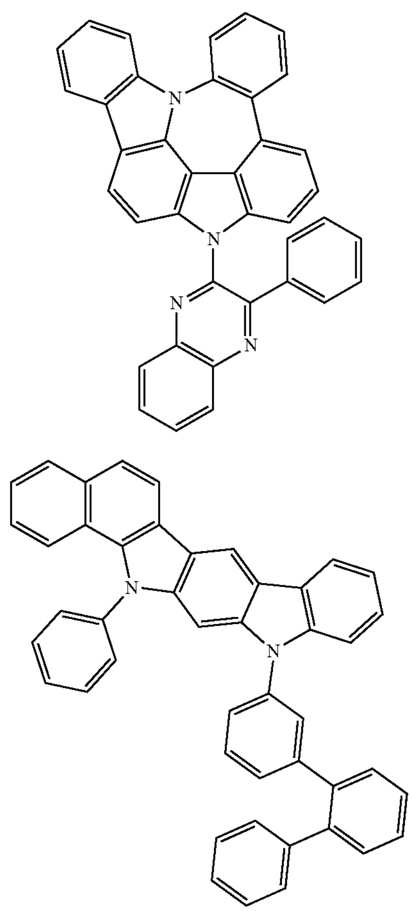
The compound represented by formula 1 according to the present disclosure can be prepared by a synthetic method known to one skilled in the art. For example, it can be prepared according to the following reaction schemes.
[Reaction Scheme 1]
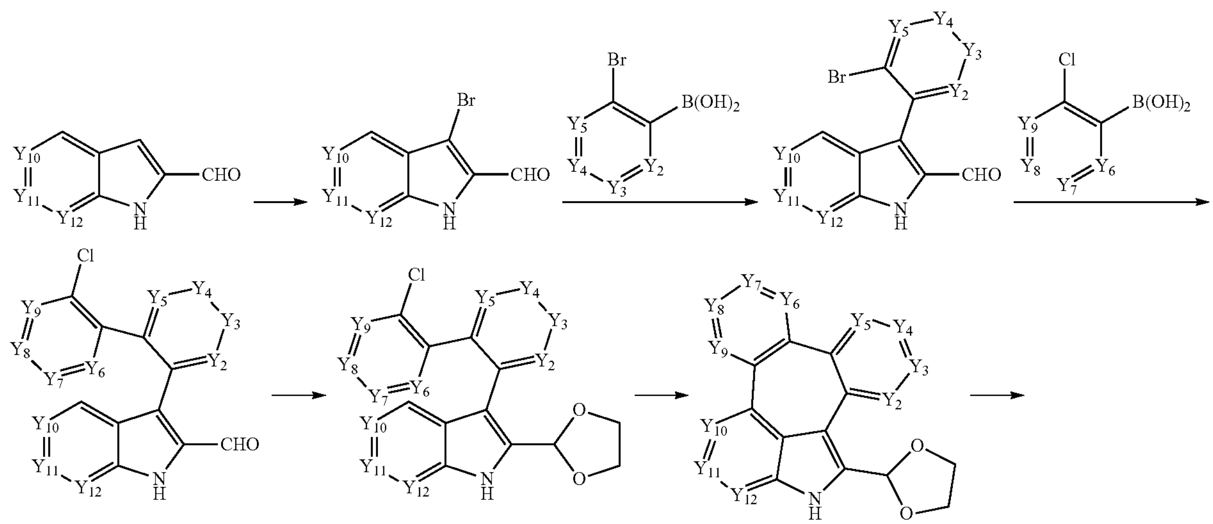

-continued
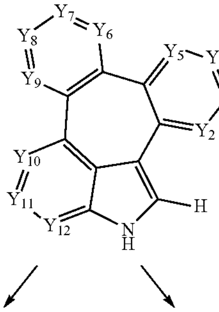
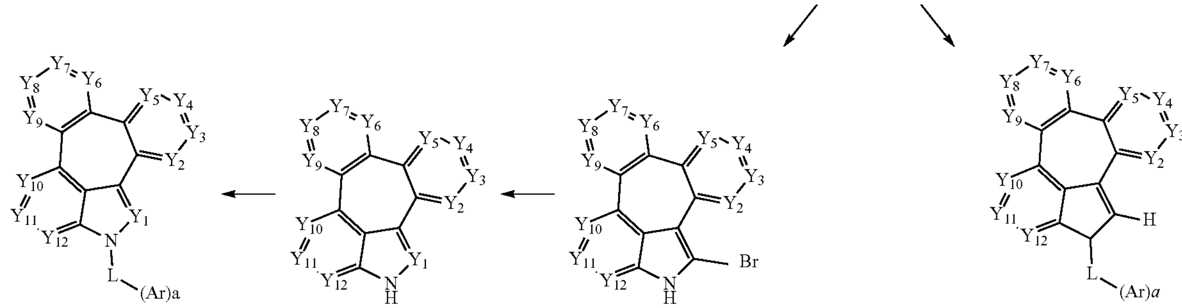
[Reaction Scheme 2]
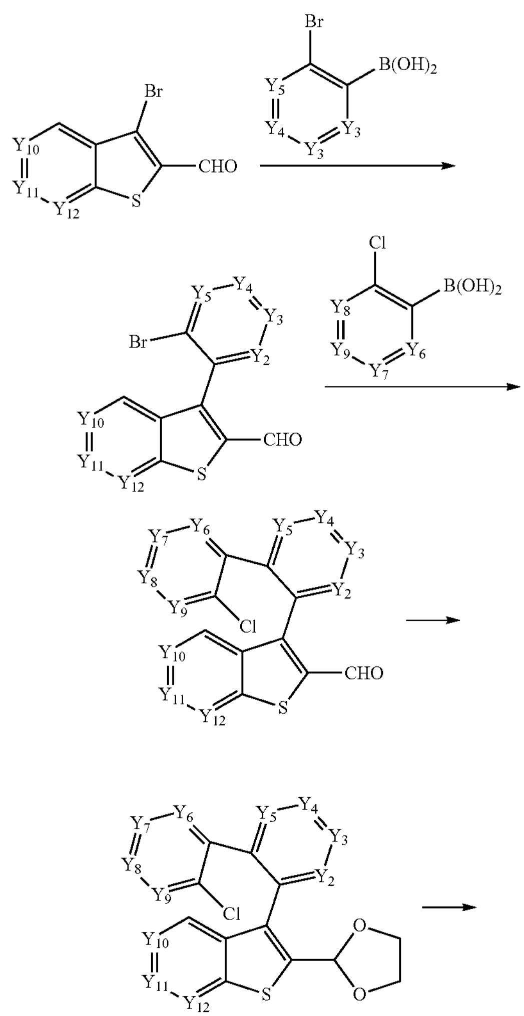
-continued
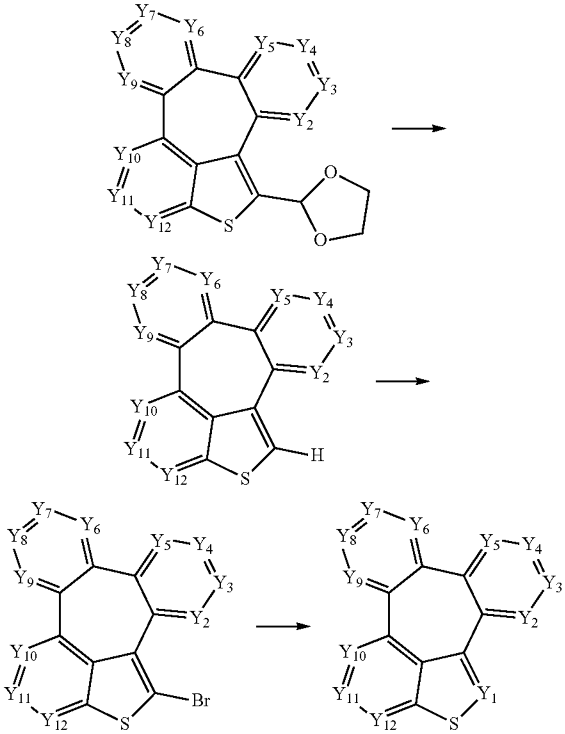
[Reaction Scheme 3]
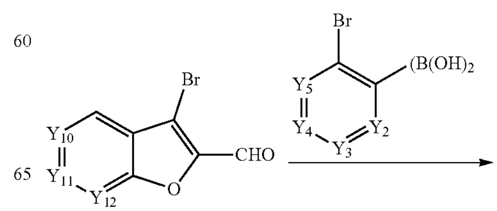

-continued
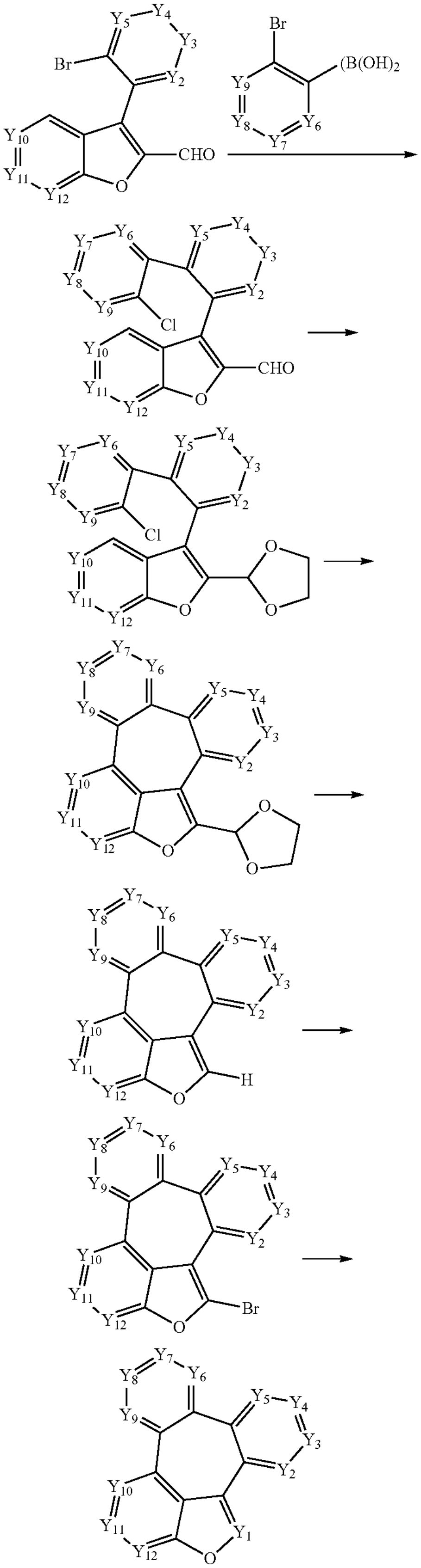
[Reaction Scheme 4]
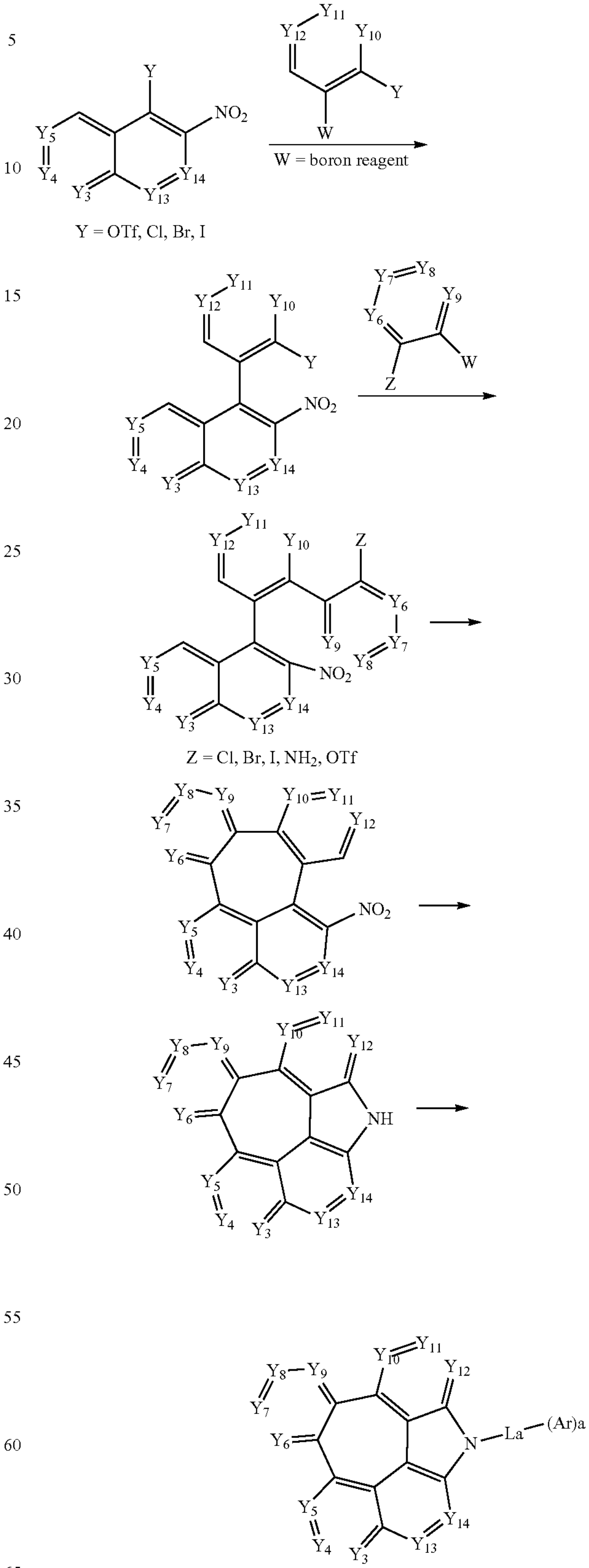

[Reaction Scheme 5]
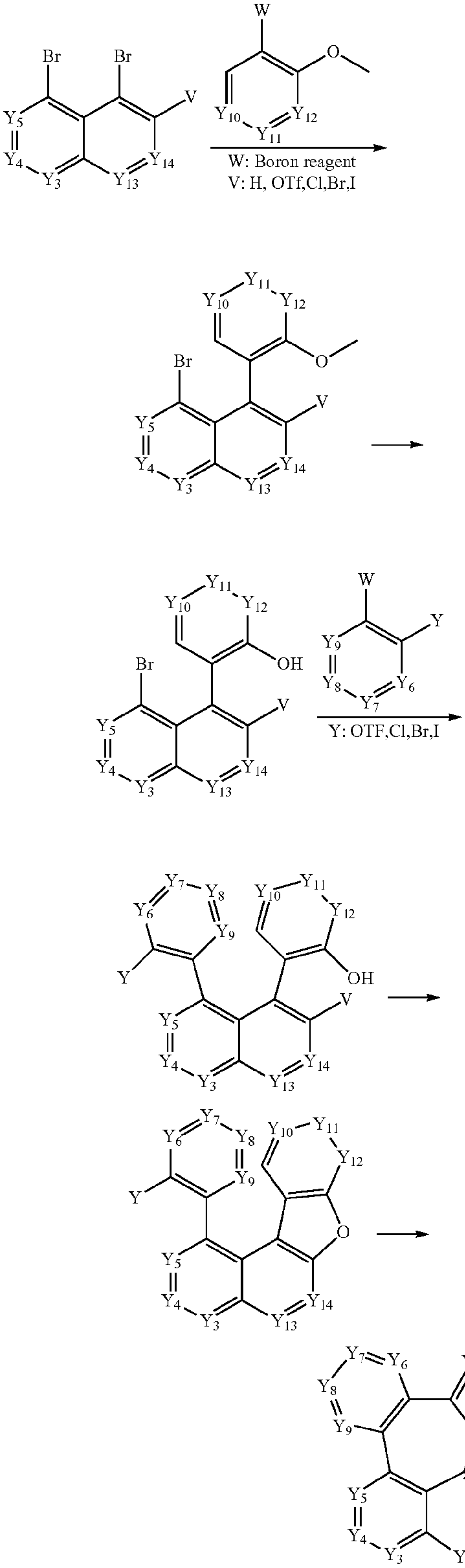
[Reaction Scheme 6]
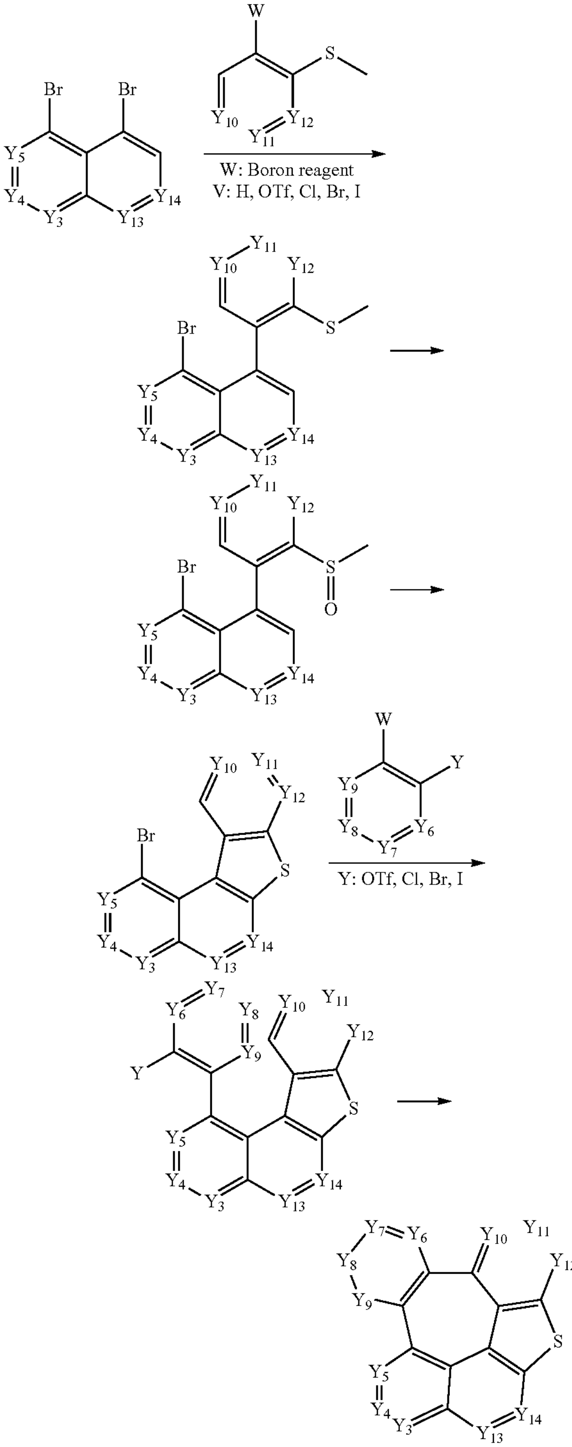
In reaction schemes 1 to 6, L, Ar, $Y_1$ to $Y_{12}$, and a are as defined in formula 1.
The compound represented by formula 2 of the present disclosure can be prepared by a synthetic method known to one skilled in the art. For example, it can be prepared by reference to Korean Patent Application Laid-Open Nos. 2015-0135109 (published on Dec. 2, 2015), 2015-0032447 (published on Mar. 26, 2015), 2016-0099471 (published on Aug. 22, 2016), and 2018-0012709 (published on Feb. 6, 2018), but is not limited thereto.

Meanwhile, the composition material for an organic electroluminescent device of the present disclosure may be a plurality of host materials, in which the compound represented by formula 1 may be the first host material and the compound represented by formula 2 may be the second host material. The composition material for an organic electroluminescent device of the present disclosure may consist of only the first host material represented by formula 1 and the second host material represented by formula 2, or may further comprise conventional materials included in the host material. The composition material for an organic electroluminescent device of the present disclosure may comprise the compound represented by formula 1 and the compound represented by formula 2 in the ratio of about 1:99 to about 99:1, preferably about 10:90 to about 90:10, and more preferably about 30:70 to about 70:30. Further, the compound represented by formula 1 and the compound represented by formula 2 may be combined in an amount of a desired ratio by placing them in a shaker and then mixing them, by placing them in a glass tube, dissolving them by heating, and then collecting the resultant, or by dissolving them in a solvent, etc. According to an embodiment of the present disclosure, an organic electroluminescent material comprising the plurality of host materials of the present disclosure is provided.

In addition, an organic electroluminescent device comprising the compound represented by formula 1 and the compound represented by formula 2 of the present disclosure may be provided. Specifically, the organic electroluminescent device of the present disclosure may comprise at least one light-emitting layer between the anode and cathode, in which the light-emitting layer may comprise a host and a dopant, and the host may comprise the composition material for an organic electroluminescent device of the present disclosure. The organic electroluminescent device of the present disclosure may comprise the compound represented by formula 1 as the first host material, and the compound represented by formula 2 as the second host material.

Herein, the light-emitting layer is a layer from which light is emitted, and can be a single layer or a multi-layer of which two or more layers are stacked. According to an embodiment of the present disclosure, the doping concentration of the dopant compound with respect to the host compound in the light-emitting layer may be less than 20 wt %.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer.

The dopant comprised in the organic electroluminescent device of the present disclosure is at least one phosphorescent or fluorescent dopant, preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device according to the present disclosure may include the compound represented by the following formula 101, but is not limited thereto.

(101)

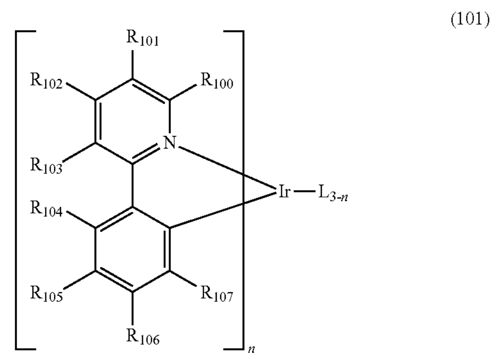

In formula 101, L is selected from the following structures 1 to 3:

[Structure 1]

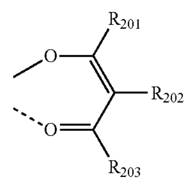

[Structure 2]

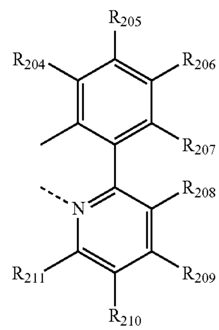

[Structure 3]

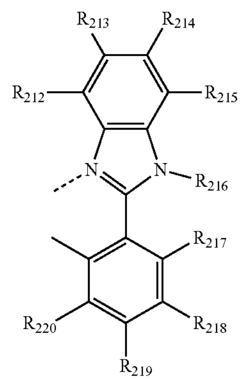

$R_{100}$ to $R_{103}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, a substituted or unsubstituted (C3-C30)heteroaryl, or a substituted or unsubstituted (C1-C30)alkoxy; or may be linked to adjacent $R_{100}$ to $R_{103}$ to form a substituted or unsubstituted fused ring, e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a substituted or unsubstituted (C3-C30)heteroaryl, a cyano, or a substituted or unsubstituted (C1-C30)alkoxy; or may be linked to adjacent $R_{104}$ to $R_{107}$ to form a substituted or unsubstituted fused ring, e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{220}$, each independently, represent hydrogen, deuterium, a halogen, a (C1-C30)alkyl unsubstituted or substituted with deuterium or a halogen, a substituted or unsubstituted (C3-C30)cycloalkyl, or a substituted or unsubstituted (C6-C30)aryl; or may be linked to adjacent $R_{201}$ to $R_{220}$ to form a substituted or unsubstituted fused ring; and n represents an integer of 1 to 3.

Specifically, the dopant compound includes the following compounds, but is not limited thereto.

D-1

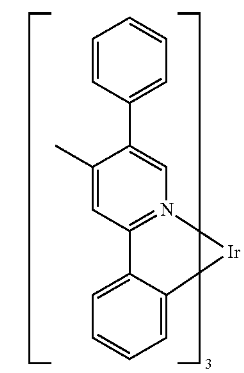

D-2

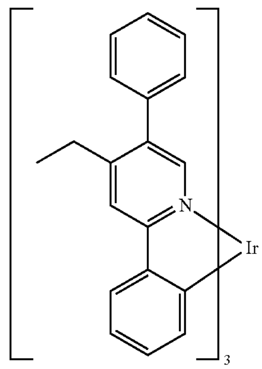

-continued

D-3

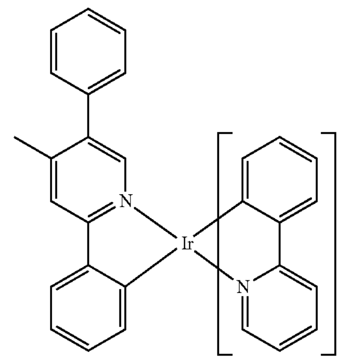

D-4

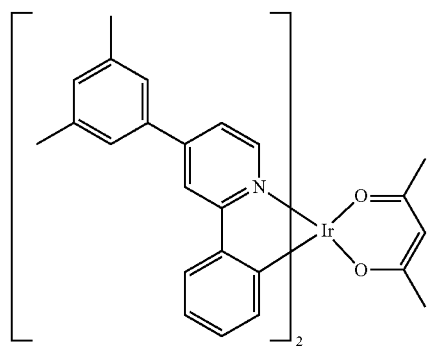

D-5

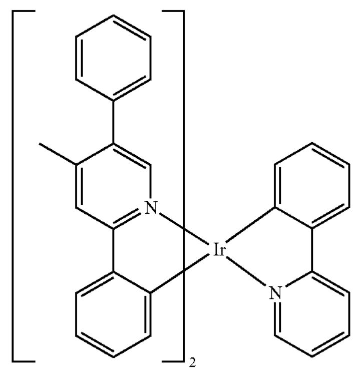

D-6

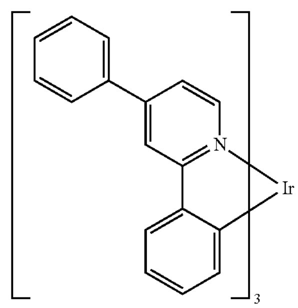

-continued
D-7
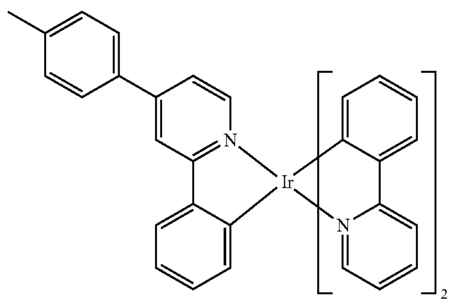
D-8
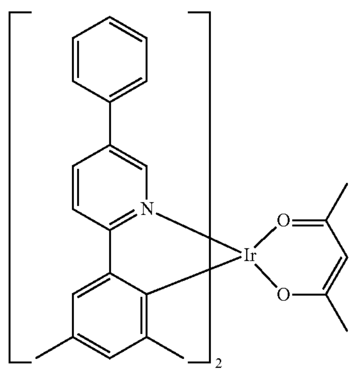
D-9
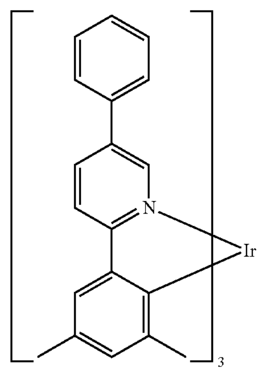
D-10
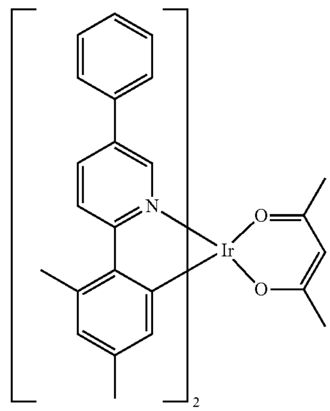
-continued
D-11
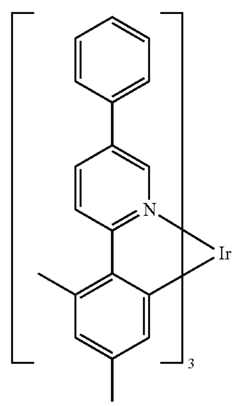
D-12
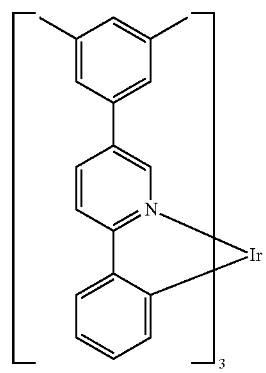
D-13
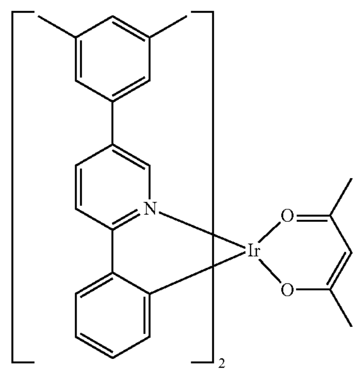
D-14
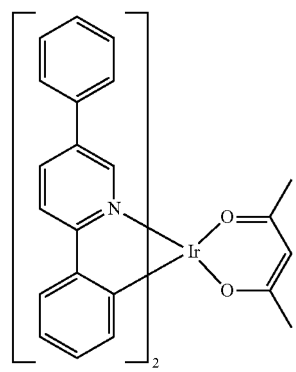

-continued
D-15
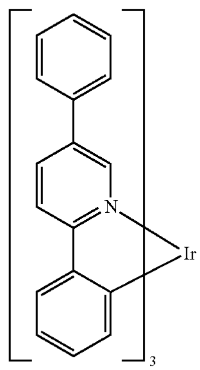
D-16
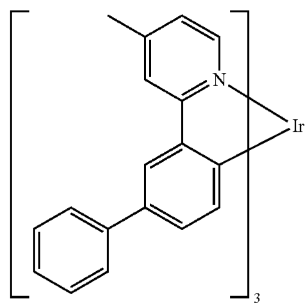
D-17
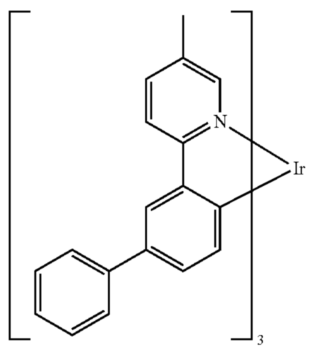
D-18
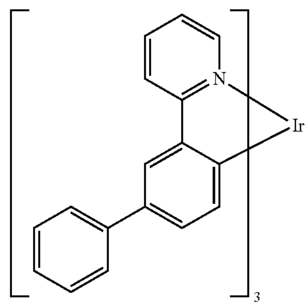
-continued
D-19
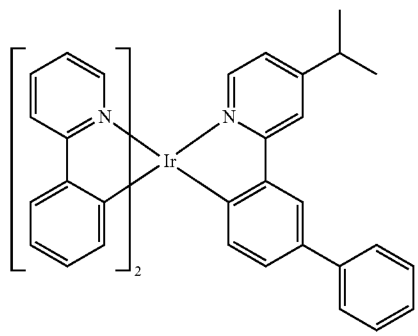
D-20
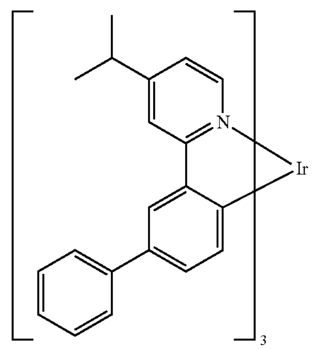
D-21
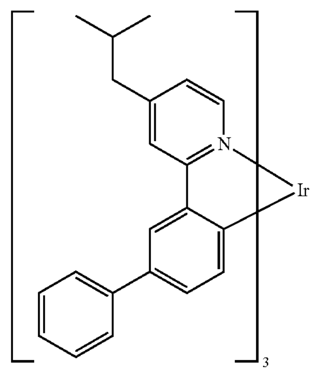
D-22
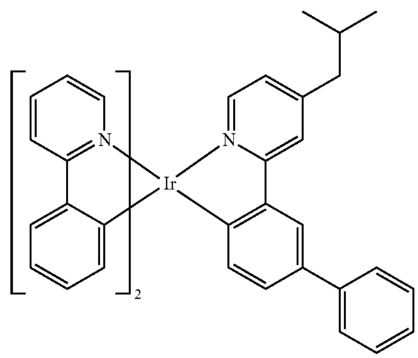

-continued
D-23
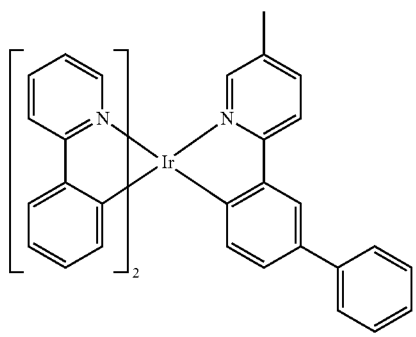
D-24
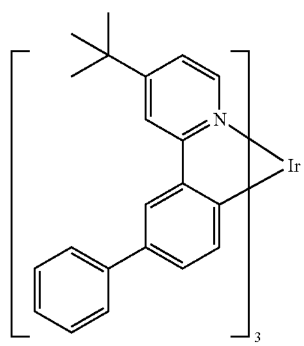
D-25
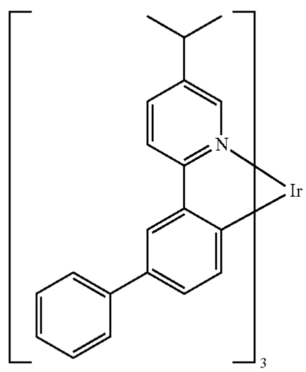
D-26
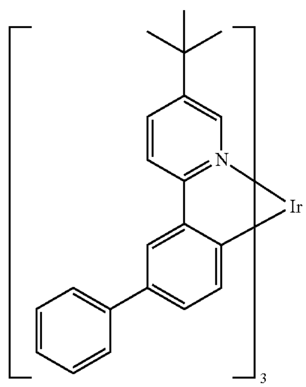
-continued
D-27
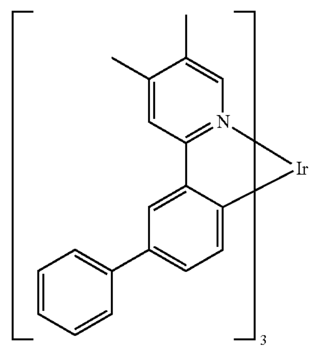
D-28
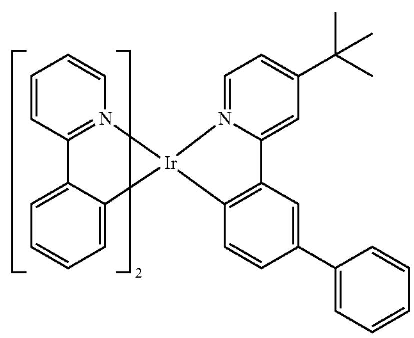
D-29
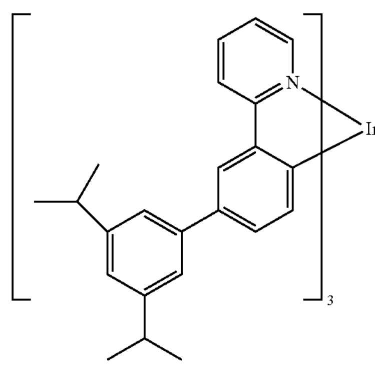
D-30
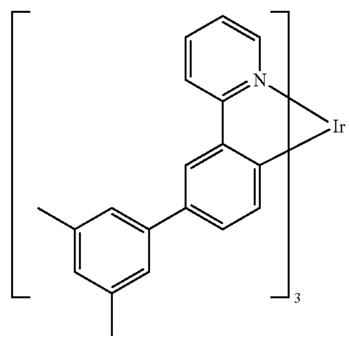

-continued
D-31
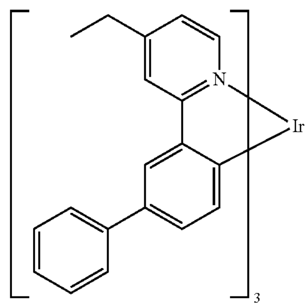
D-32
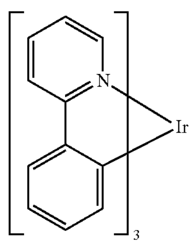
D-33
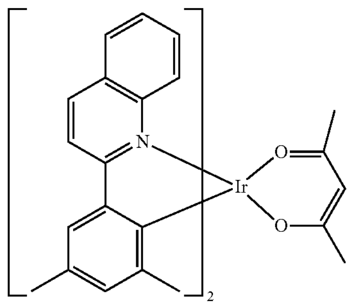
D-34
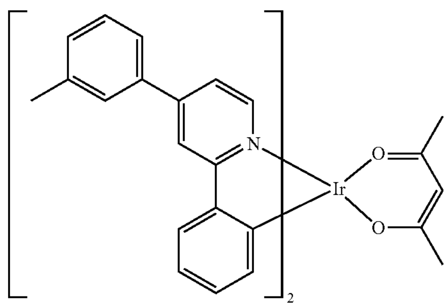
D-35
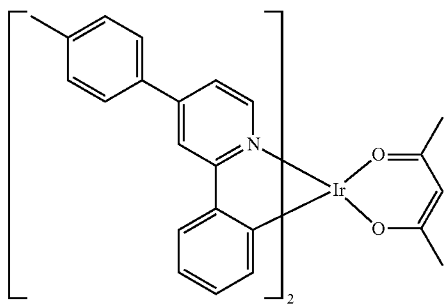
-continued
D-36
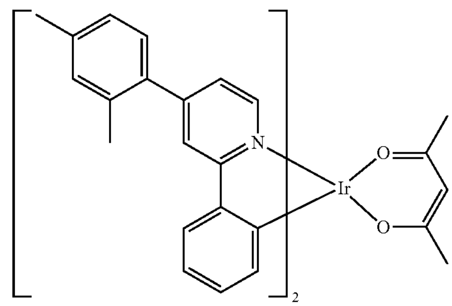
D-37
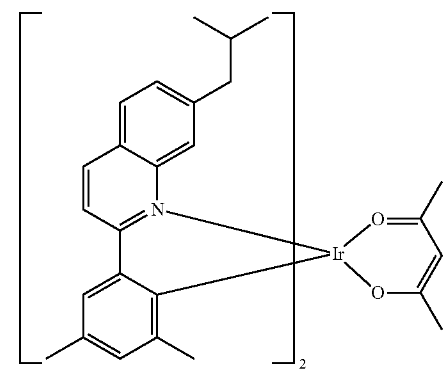
D-38
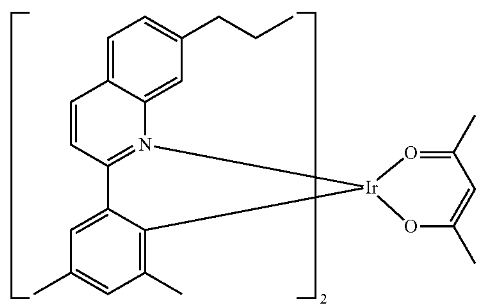
D-39
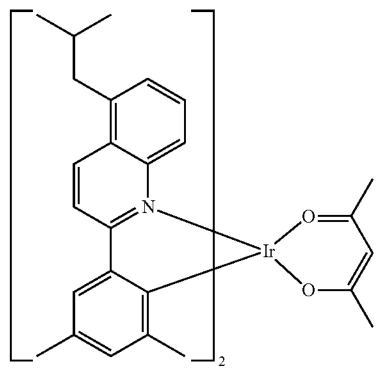

-continued
D-40
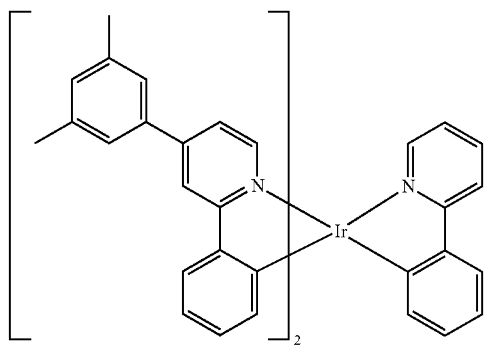
D-41
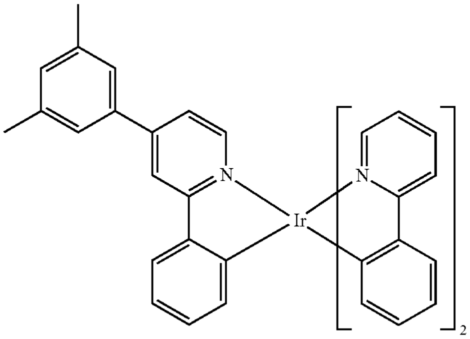
D-42
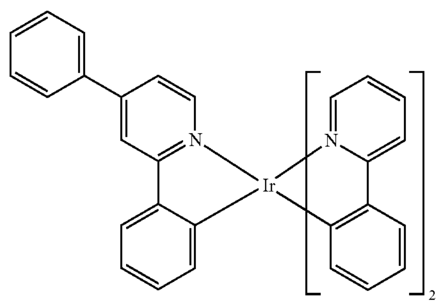
D-43
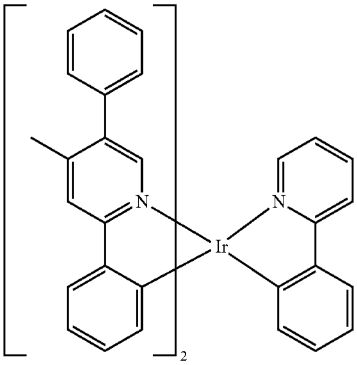
-continued
D-44
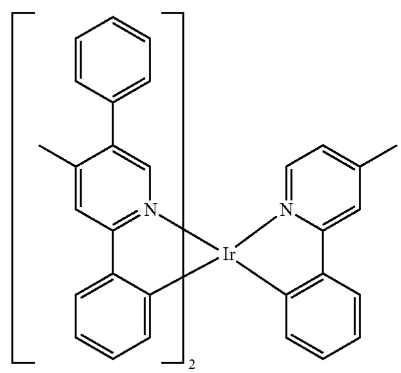
D-45
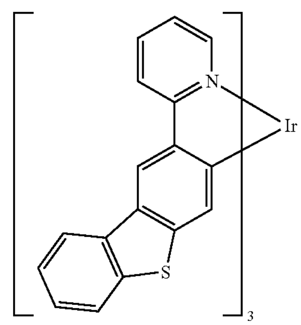
D-46
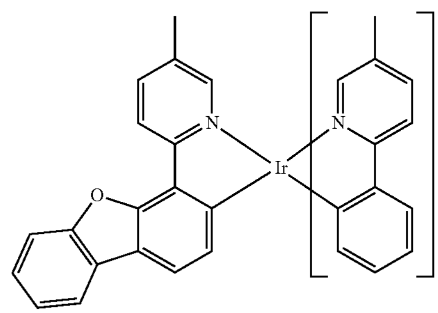
D-47
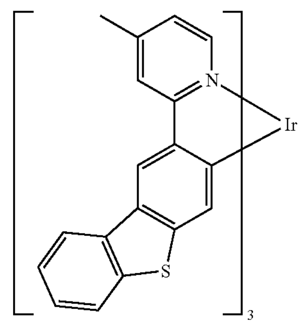
D-48
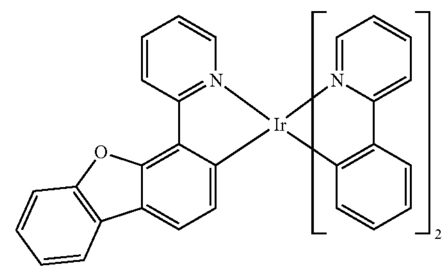

-continued
D-49
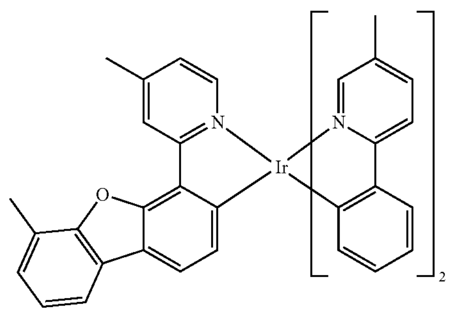
D-50
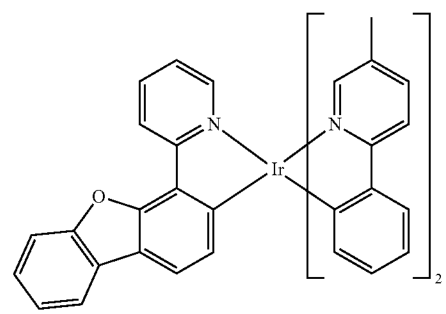
D-51
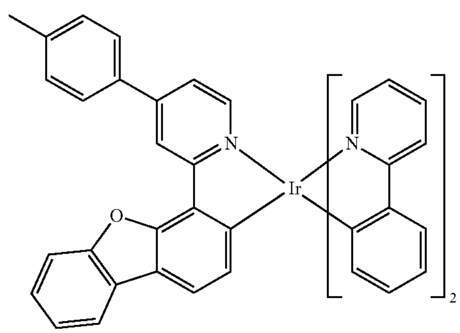
D-52
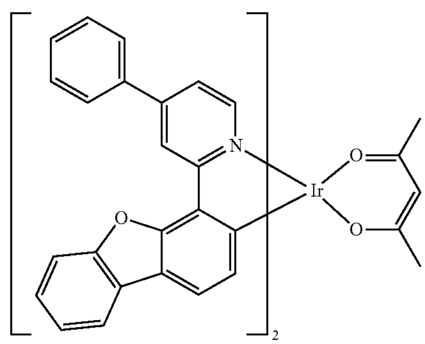
D-53
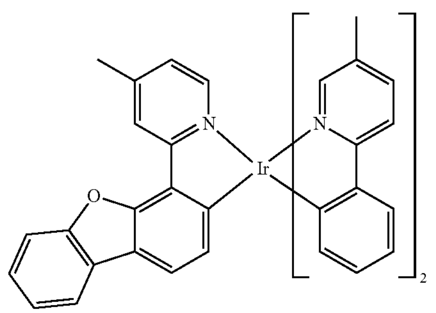
-continued
D-54
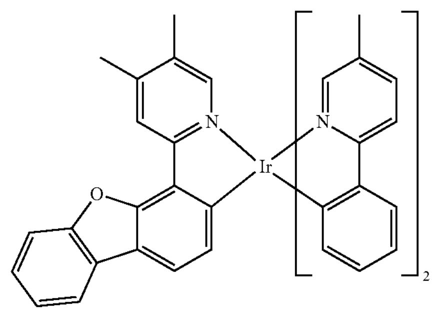
D-55
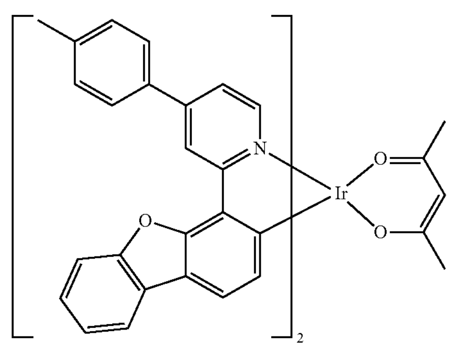
D-56
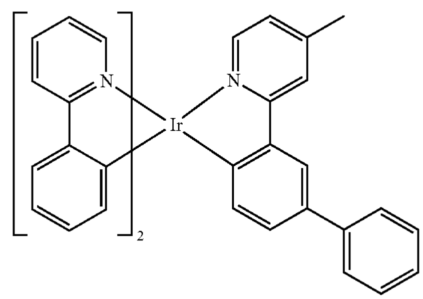
D-57
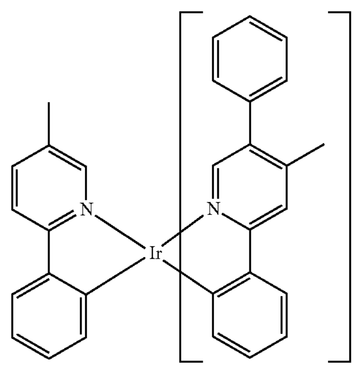

-continued
D-58
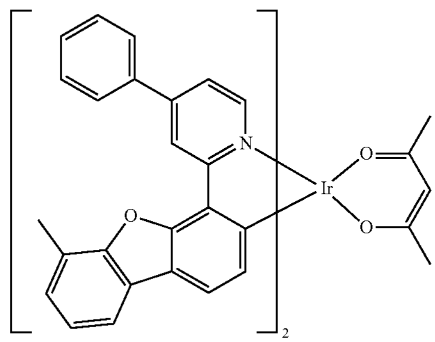
D-59
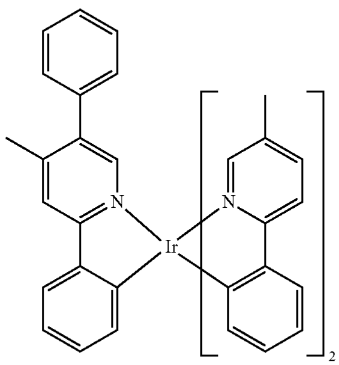
D-60
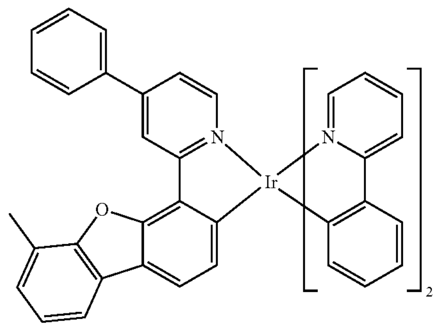
D-61
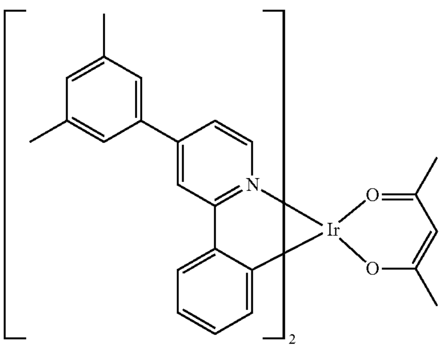
D-62
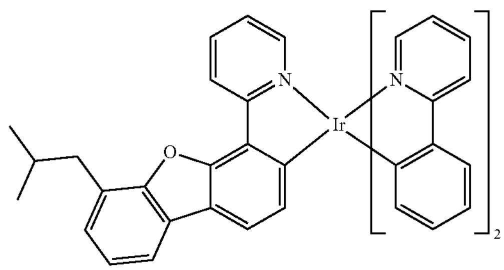
-continued
D-63
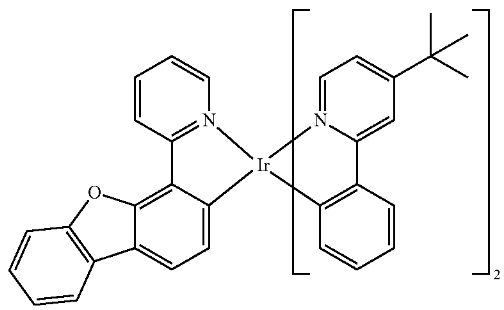
D-64
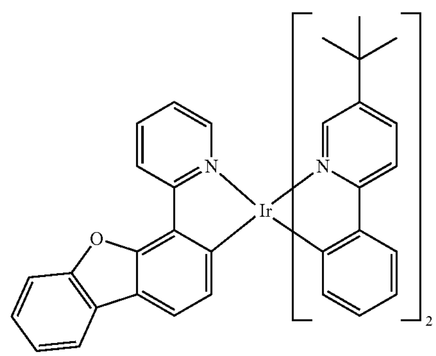
D-65
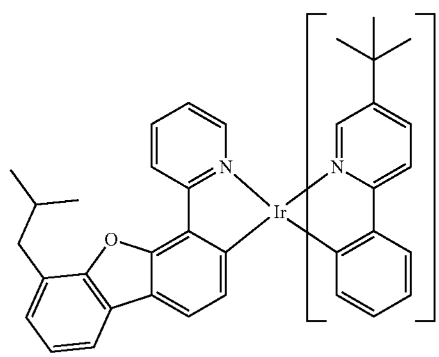
D-66
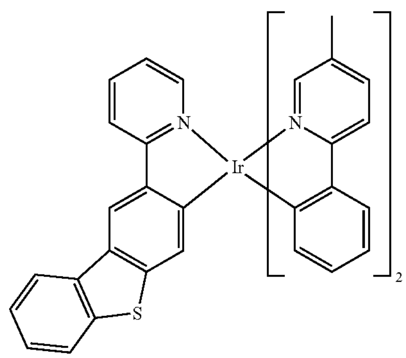

-continued
D-67
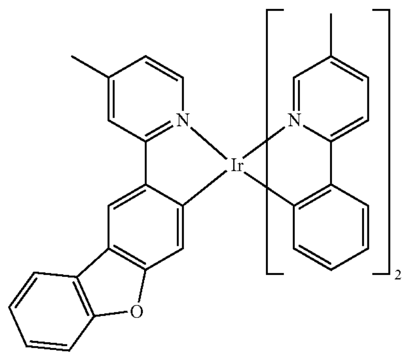
D-68
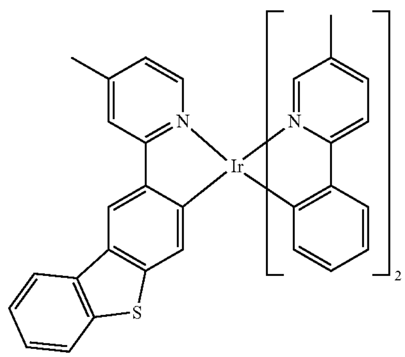
D-69
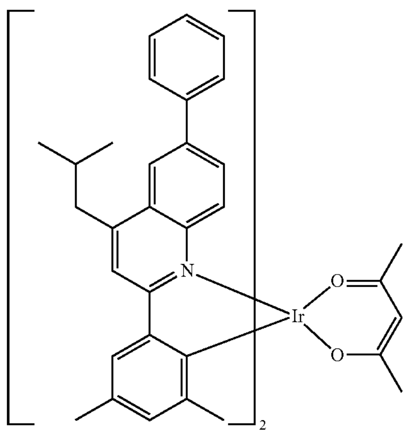
D-70
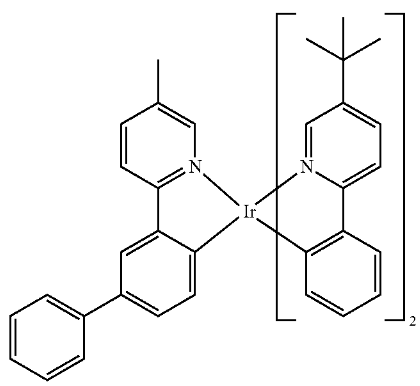
-continued
D-71
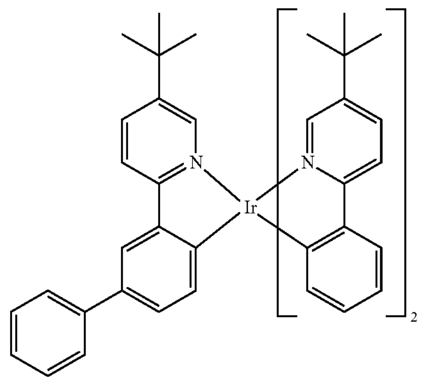
D-72
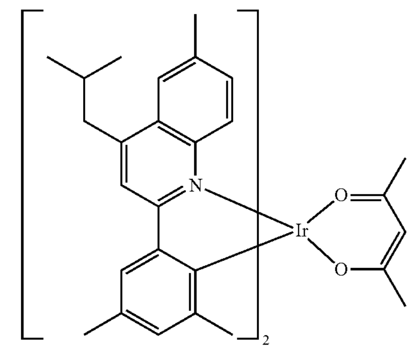
D-73
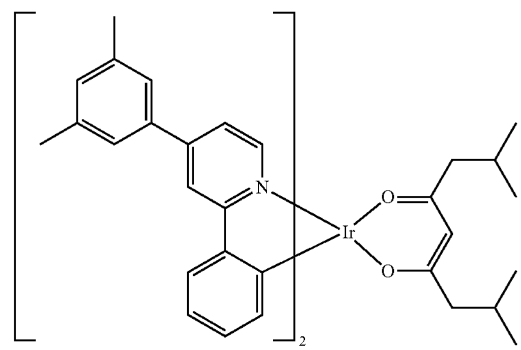
D-74
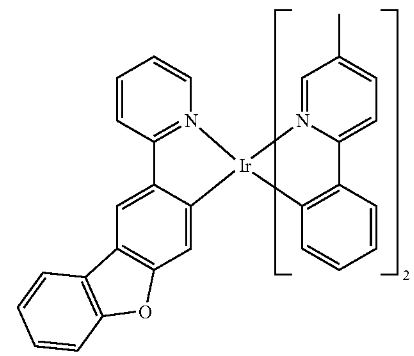

-continued
D-75
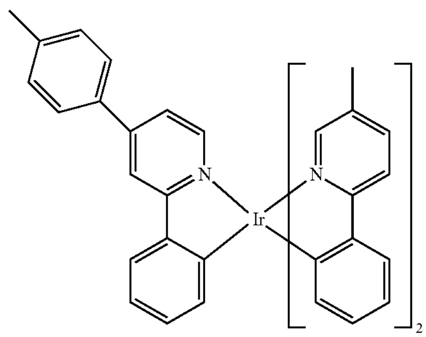
D-76
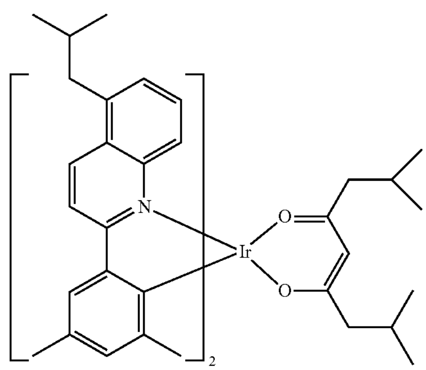
D-77
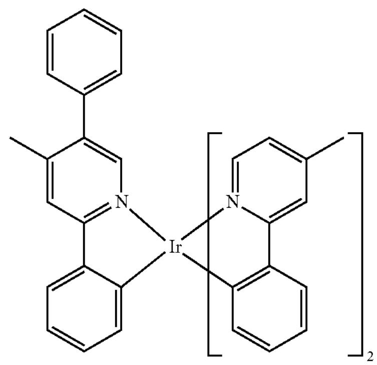
D-78
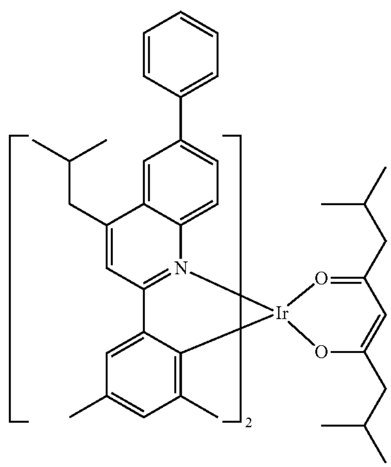
-continued
D-79
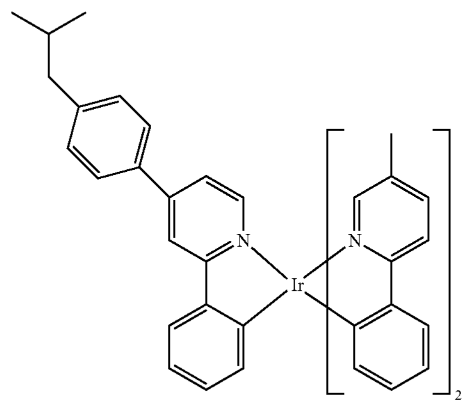
D-80
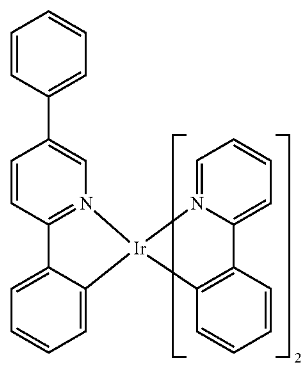
D-81
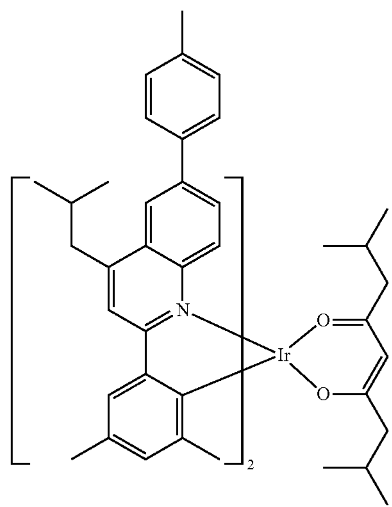

D-82
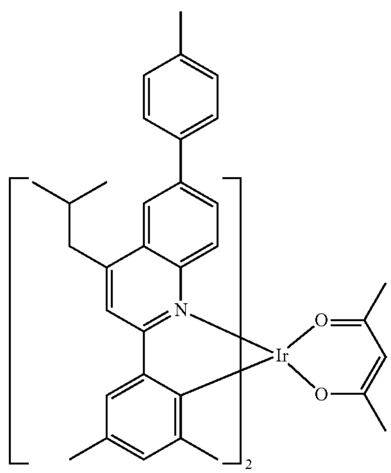
D-83
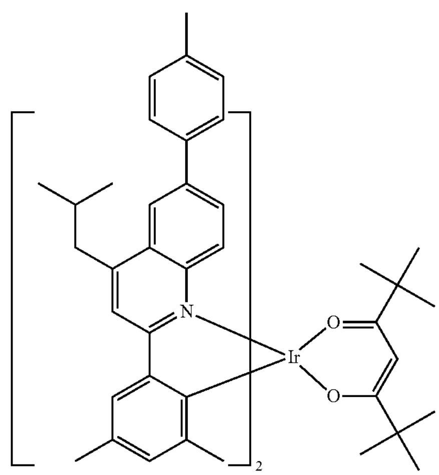
D-84
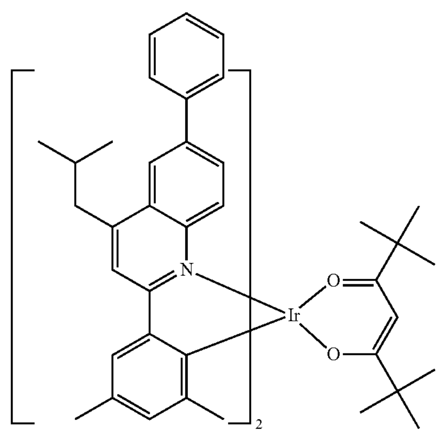
D-85
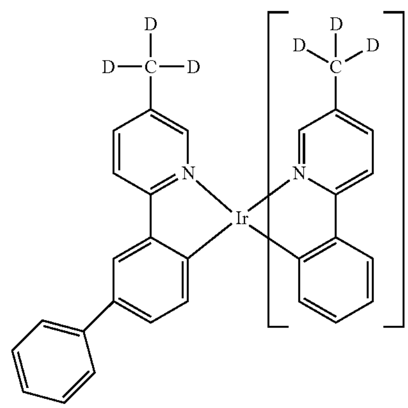
D-86
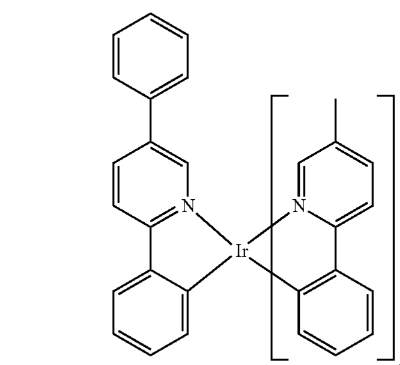
D-87
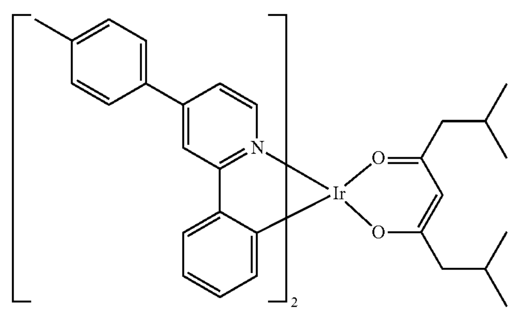
D-88
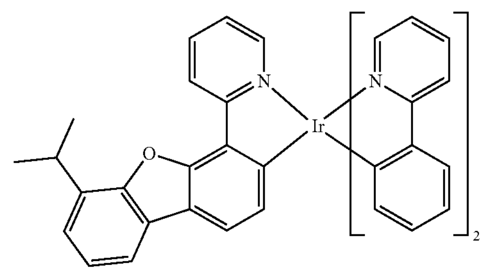
D-89
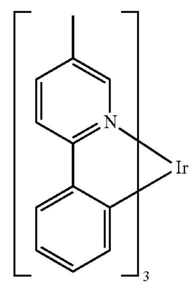

-continued
D-90
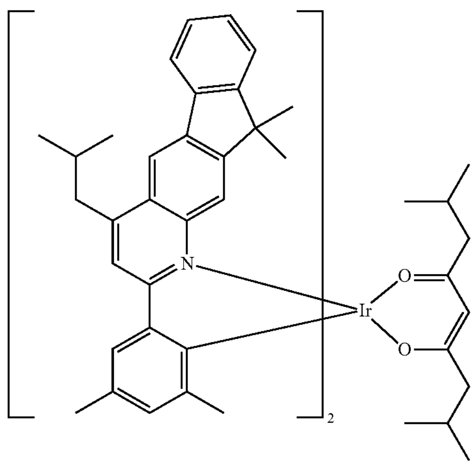
D-91
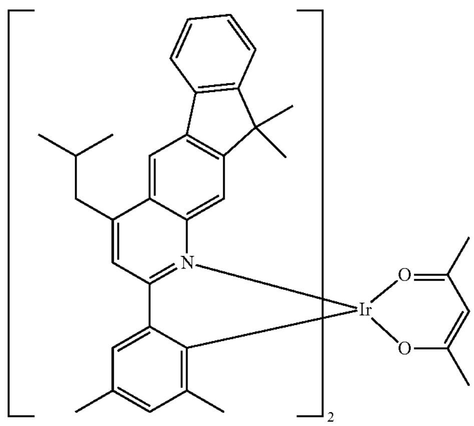
D-92
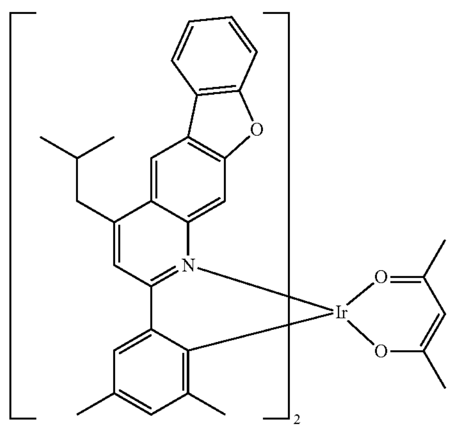
-continued
D-93
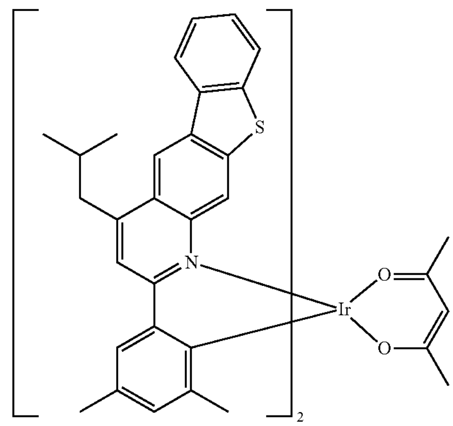
D-94
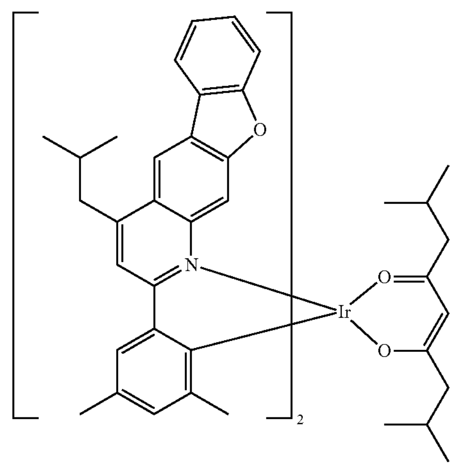
D-95
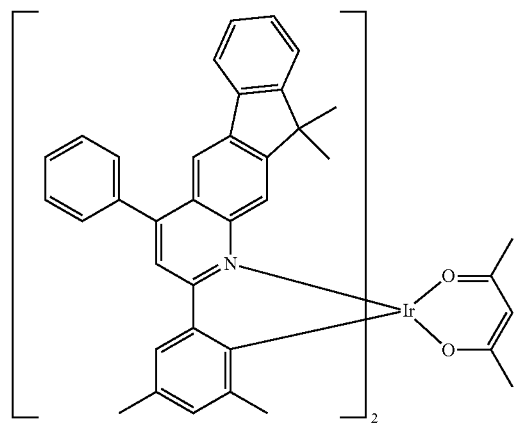

-continued
D-96
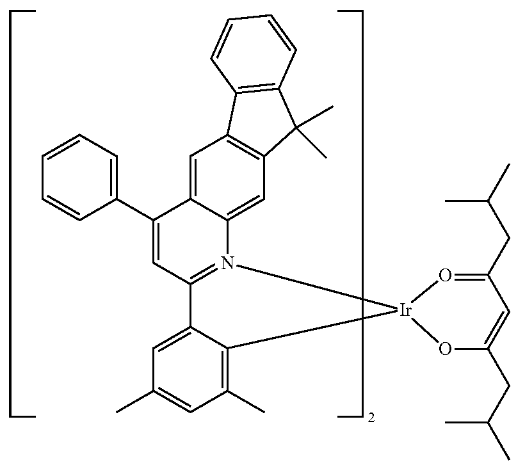
D-97
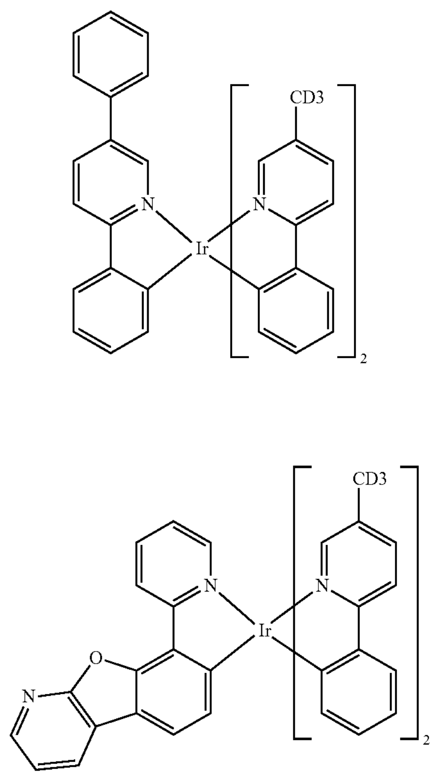
D-98
D-99
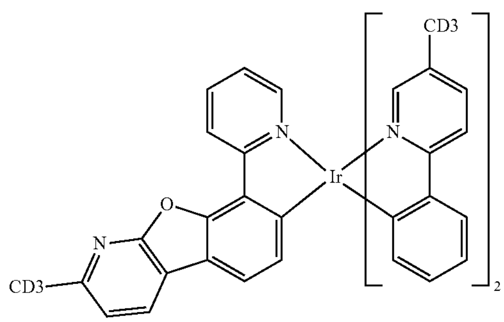
-continued
D-100
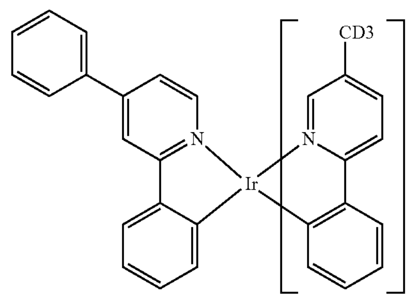
D-101
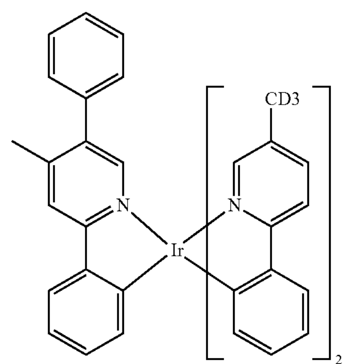
D-102
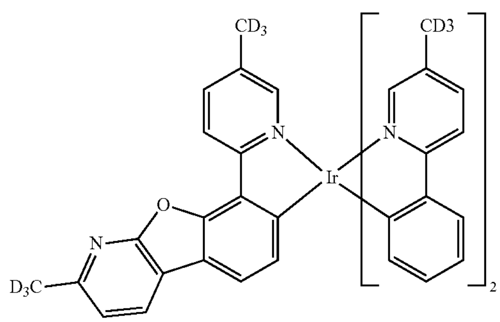
D-103
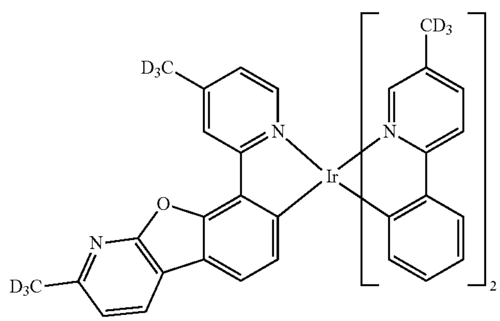
D-104
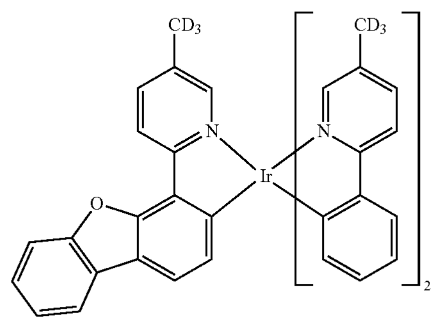

D-105
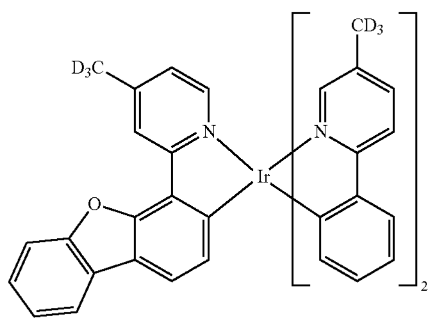
D-106
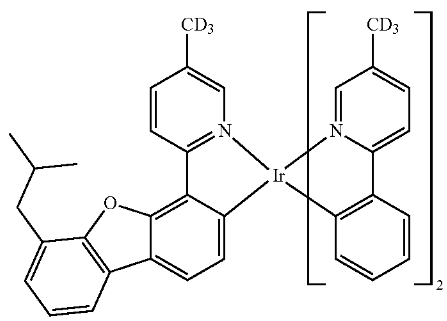
D-107
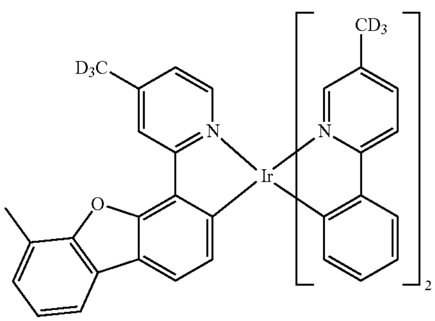
D-108
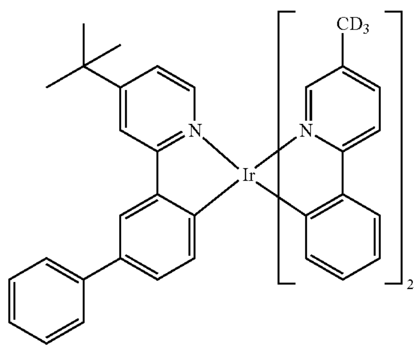
D-109
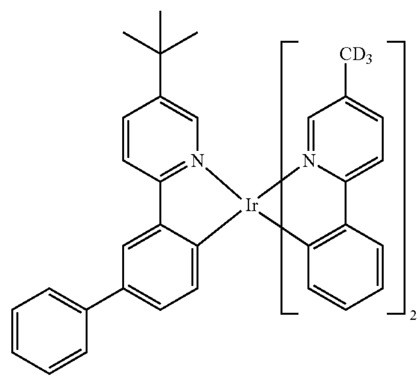
D-110
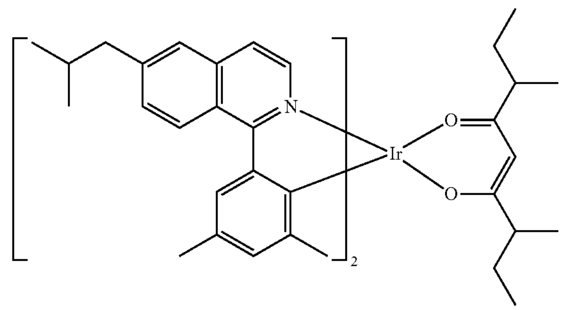
D-111
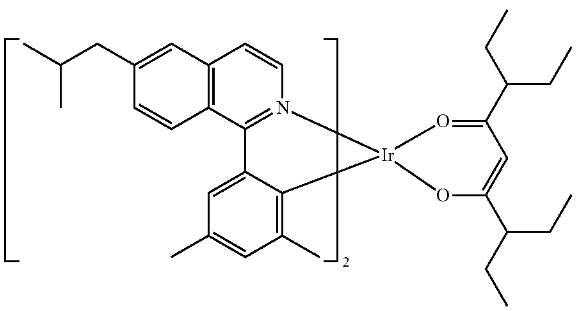
D-112
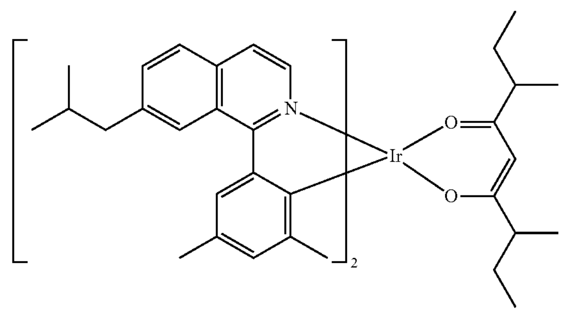

-continued
D-113
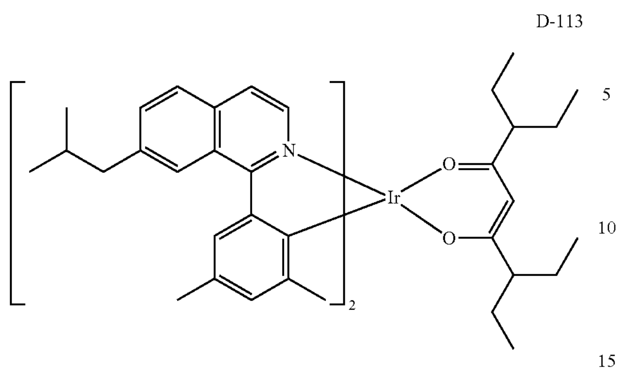
D-114
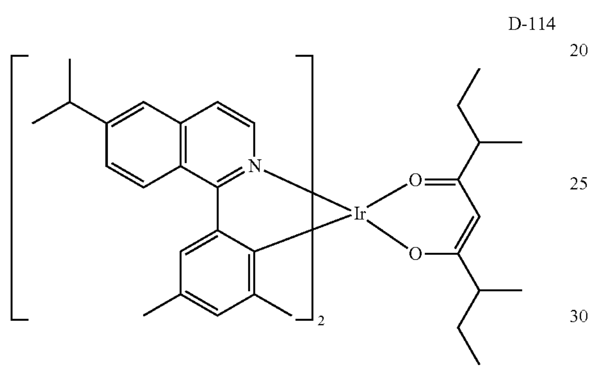
D-115
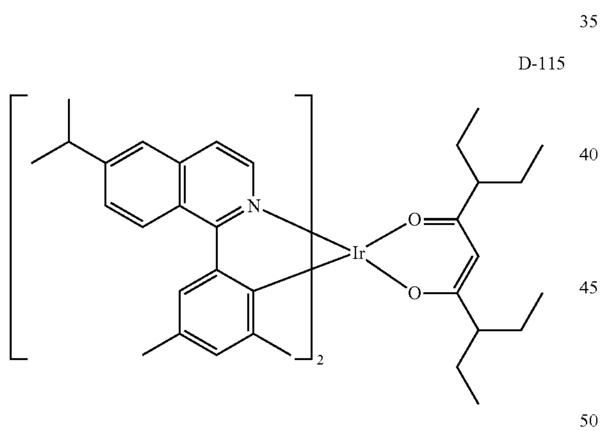
D-116
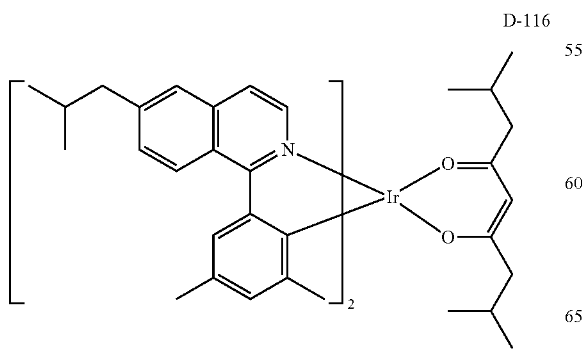
-continued
D-117
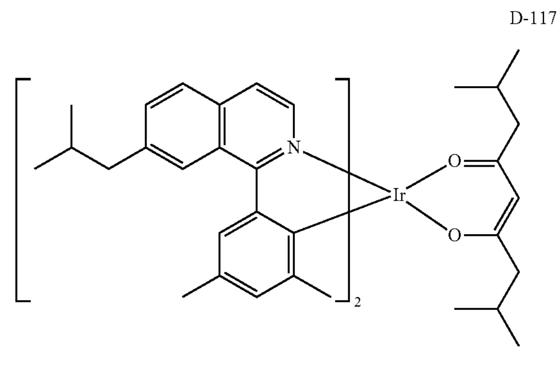
D-118
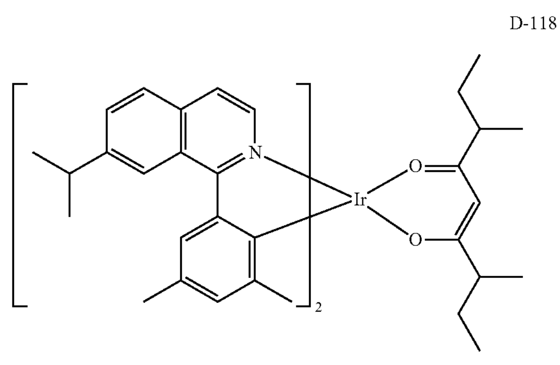
D-119
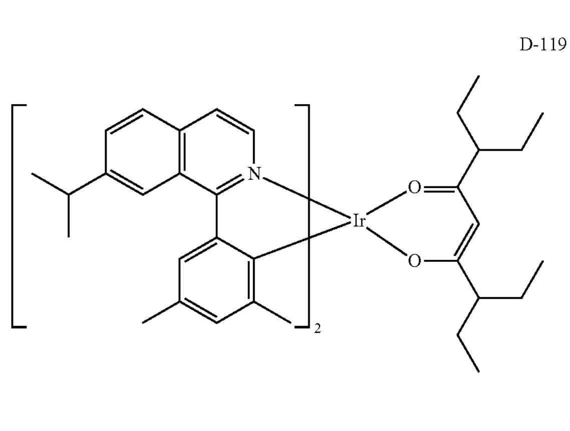
D-120
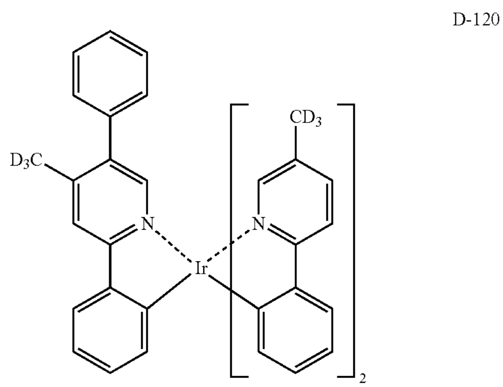

-continued

D-121

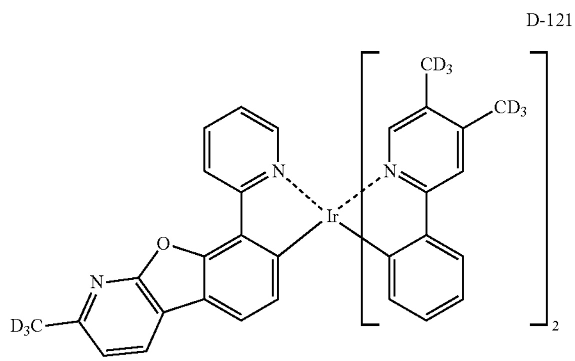

D-122

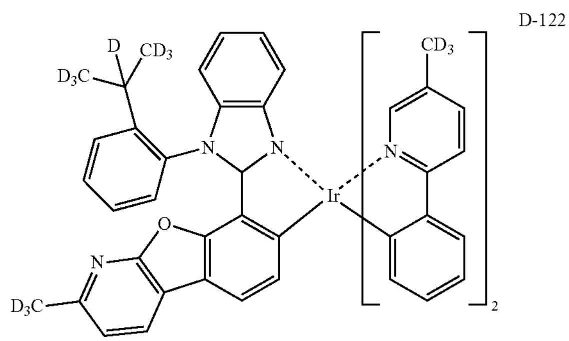

D-123

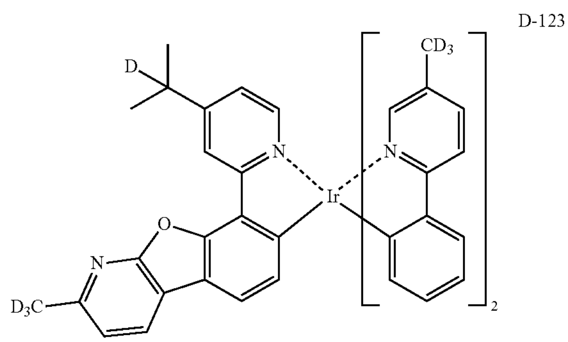

D-124

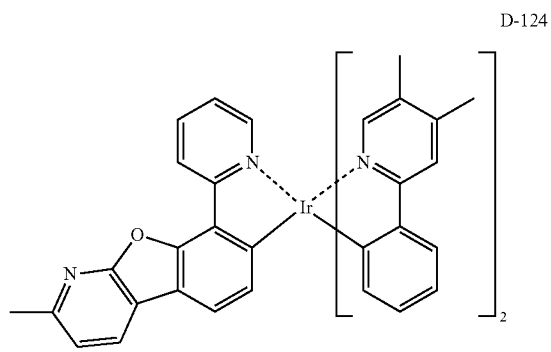

D-125

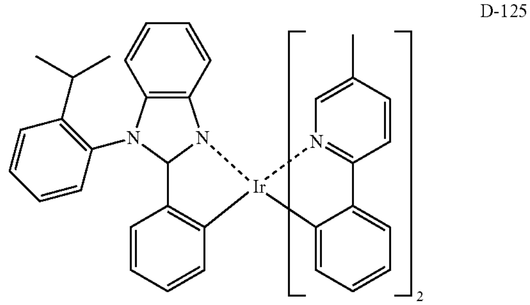

-continued

D-126

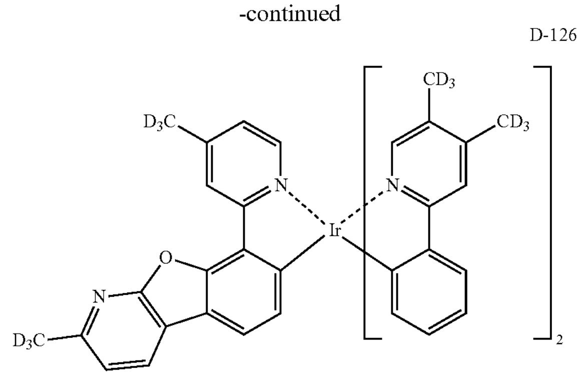

D-127

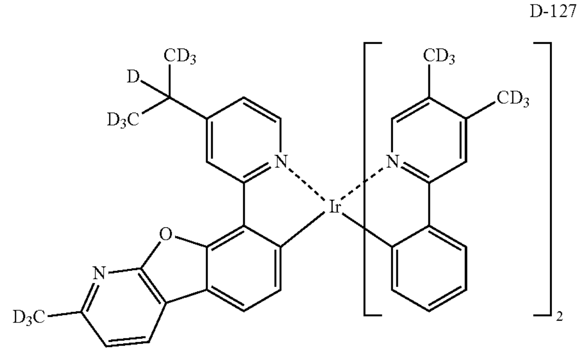

The organic electroluminescent device according to the present disclosure comprises a first electrode; a second electrode; and at least one organic layer between the first and second electrodes.

One of the first and second electrodes may be an anode, and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Each of the layers may further consist of multi-layers.

The first electrode and the second electrode may be formed with a transmissive conductive material, a transflective conductive material, or a reflective conductive material, respectively. The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

The organic layer may further comprise at least one compound selected from the group consisting of arylamine-based compounds and styrylarylamine-based compounds.

In addition, in the organic electroluminescent device according to the present disclosure, the organic layer may further comprise at least one metal selected from the group consisting of metals of Group 1, metals of Group 2, transition metals of the 4th period, transition metals of the 5th period, lanthanides and organic metals of d-transition elements of the Periodic Table, or at least one complex compound comprising said metal.

In addition, the organic electroluminescent device according to the present disclosure may emit white light by further comprising at least one light-emitting layer which comprises a blue electroluminescent compound, a red electroluminescent compound or a green electroluminescent compound known in the field, besides the compound according to the present disclosure. In addition, it may further include a yellow or orange light-emitting layer, if necessary.

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_X$ ($1 \leq X \leq 2$), $AlO_X$ ($1 \leq X \leq 1.5$), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective in promoting or blocking the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of an organic electroluminescent device.

In the organic electroluminescent device according to the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic electroluminescent device having two or more light-emitting layers which emits white light.

An organic electroluminescent material according to an embodiment of the present disclosure may be used as light-emitting materials for a white organic light-emitting device. The white organic light-emitting device has been suggested to have various structures such as a parallel arrangement (side-by-side) method, a stacking method, or color conversion material (CCM) method, etc., according to the arrangement of R (red), G (green), B (blue), or YG (yellowish green) light-emitting units. In addition, the organic electroluminescent material according to an embodiment of the present disclosure may also be applied to the organic electroluminescent device comprising QD (quantum dot).

In order to form each layer constituting the organic electroluminescent device of the present disclosure, dry film-forming methods such as vacuum deposition, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not particularly limited as long as the material constituting each layer is soluble or dispersible in the solvents, which do not cause any problems in forming a film.

The present disclosure can provide a display device using the composition material for an organic electroluminescent device comprising the compound represented by formula 1 and the compound represented by formula 2. That is, the composition material for an organic electroluminescent device of the present disclosure can be used to produce a display system or a lighting system. Specifically, it is possible to produce a display system, e.g., a display system for smartphones, tablets, notebooks, PCs, TVs, or cars, or a lighting system, e.g., an outdoor or indoor lighting system, by using the composition material for an organic electroluminescent device of the present disclosure.

Hereinafter, the improved luminous efficiency and lifespan characteristics of the OLED device by comprising the composition material for an organic electroluminescent device of the present disclosure will be explained. However, the following Examples are intended to explain the characteristics of the OLED device comprising the composition material for an organic electroluminescent device of the present disclosure, and the present disclosure is not limited to the Examples below.

Device Examples 1 to 18: Production of an OLED Device Comprising the Composition Material for an OLED Device According to the Present Disclosure An organic light-emitting diode (OLED) device was produced comprising the composition material for an OLED device according to the present disclosure. A transparent electrode indium tin oxide (ITO) thin film (10 Ω/sq) on a glass substrate for an OLED device (Geomatec, Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound HT-2 was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. The first and second host compounds shown in Table 1 below were introduced into one cell of the vacuum vapor depositing apparatus as a host, and compound D-39 was introduced into another cell. The two host materials were evaporated at a rate of 1:1 and the dopant material was simultaneously evaporated at a different rate and these were deposited in a doping amount of 3 wt % based on the total amount of the host and dopant to form a light-emitting layer having a thickness of 40 nm on the second hole transport layer. Compound ET-1 and compound EI-1 were then introduced into two other cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced.

Comparative Example 1: Production of an OLED Device Comprising a Conventional Compound An OLED device was produced in the same manner as in Device Example 1, except that compound A was used as the second host compound.

The luminous efficiency at a luminance of 5,000 nits, and the time taken for luminance to decrease from 100% to 95% at a constant current and at a luminance of 5,000 nits (lifespan; T95) of the produced OLED devices are provided in Table 1 below.

TABLE 1

| | First Host | Second Host | Efficiency (cd/A) | Increase in Efficiency (%) | Lifespan (T95, hr) |
|---|---|---|---|---|---|
| Comparative Example 1 | C-241 | A | 20.8 | — | 241 |
| Device Example 1 | C-241 | H-21 | 23.9 | 14.9 | 345 |
| Device Example 2 | C-536 | H-27 | 24.0 | 15.4 | 444 |
| Device Example 3 | C-536 | H-23 | 23.3 | 12.0 | 377 |
| Device Example 4 | C-241 | H-92 | 22.6 | 8.7 | 379 |
| Device Example 5 | C-241 | H-93 | 21.6 | 3.8 | 309 |
| Device Example 6 | C-539 | H-108 | 23.8 | 14.4 | 346 |
| Device Example 7 | C-573 | H-108 | 25.7 | 23.6 | 284 |
| Device Example 8 | C-234 | H-108 | 23.3 | 12.0 | 332 |
| Device Example 9 | C-235 | H-108 | 21.8 | 4.8 | 376 |
| Device Example 10 | C-236 | H-108 | 22.8 | 9.6 | 249 |
| Device Example 11 | C-241 | H-116 | 22.5 | 8.2 | 247 |
| Device Example 12 | C-241 | H-94 | 24.6 | 18.3 | 420 |
| Device Example 13 | C-664 | H-117 | 25.5 | 22.6 | 846 |
| Device Example 14 | C-664 | H-118 | 22.3 | 7.2 | 250 |
| Device Example 15 | C-664 | H-119 | 26.1 | 25.5 | 364 |
| Device Example 16 | C-665 | H-108 | 27.0 | 29.8 | 876 |
| Device Example 17 | C-572 | H-108 | 24.1 | 15.9 | 742 |
| Device Example 18 | C-666 | H-108 | 25.5 | 22.6 | 343 |

From Table 1 above, it can be seen that the organic electroluminescent device comprising the compounds represented by formulas 1 and 2 of the present disclosure as a host exhibits higher luminous efficiency and longer lifespan characteristics than the organic electroluminescent device comprising the conventional organic electroluminescent compound. By using the composition material for an organic electroluminescent device of the present disclosure, both luminous efficiency and lifespan characteristics in an organic electroluminescent device, which conflict with each other, can be improved.

The compounds used in the Device Examples and the Comparative Example are shown in Table 2 below.

TABLE 2

| | |
|---|---|
| Hole Injection Layer/ Hole Transport Layer | 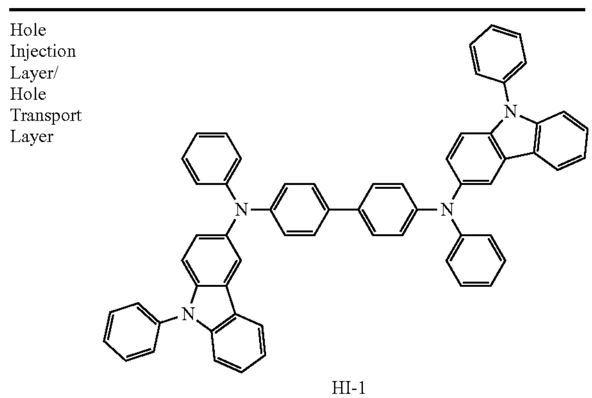 HI-1 |

TABLE 2-continued
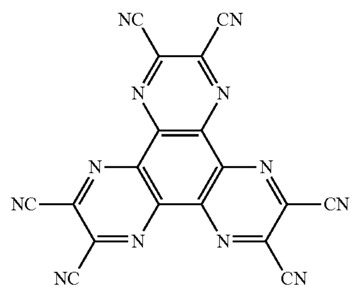
HI-2
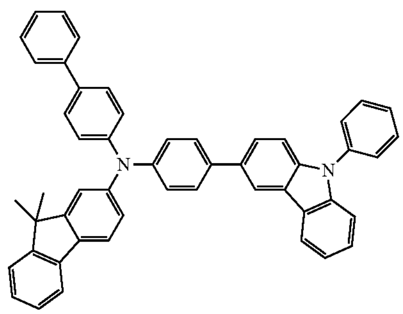
HT-1
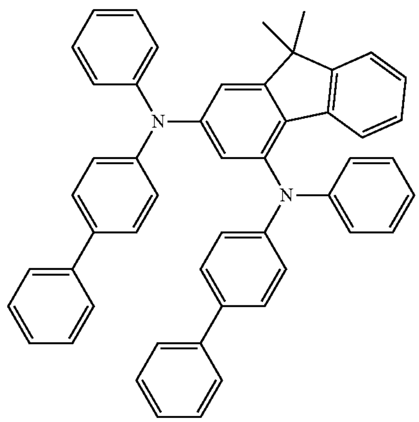
HT-2
Light-Emitting Layer
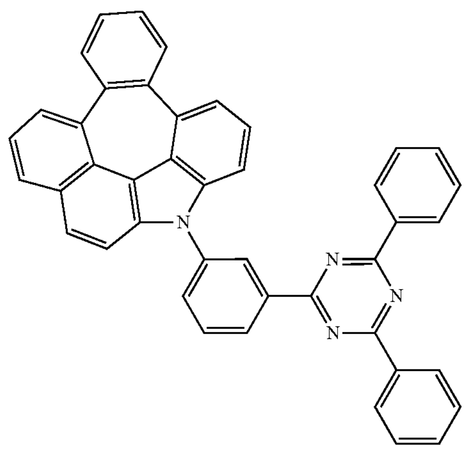
C-241
TABLE 2-continued
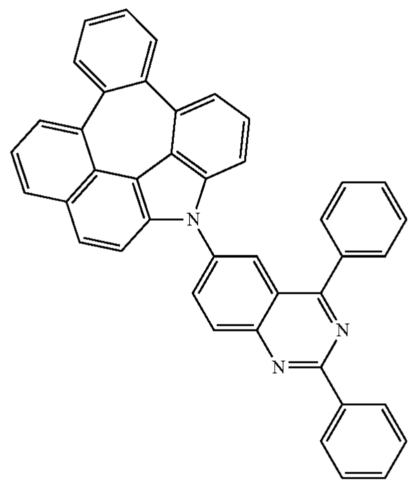
C-536
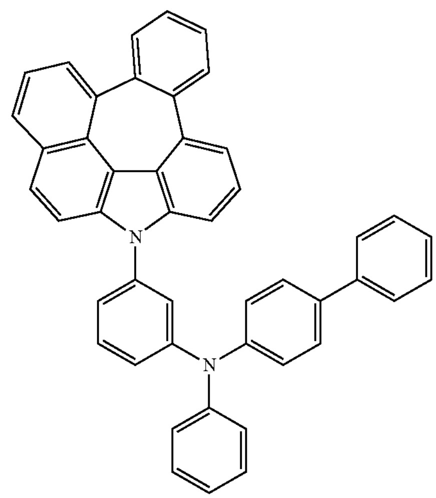
C-539
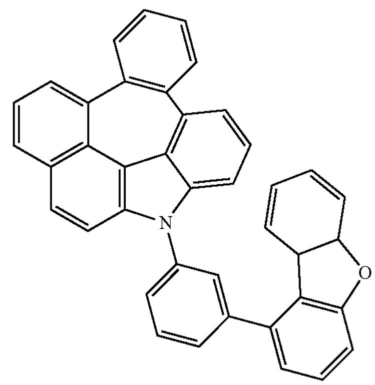
C-573

TABLE 2-continued
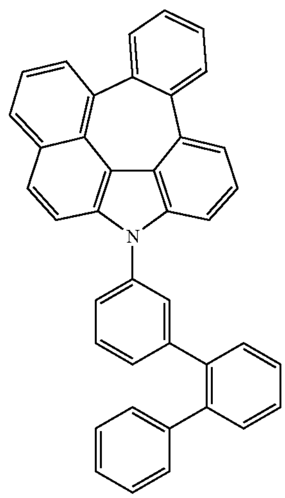
C-234
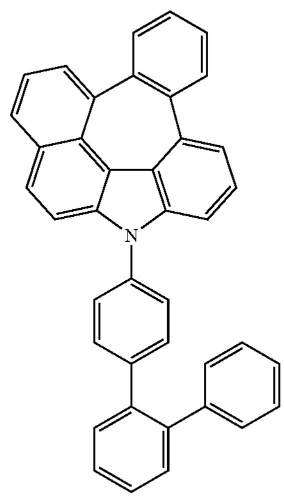
C-235
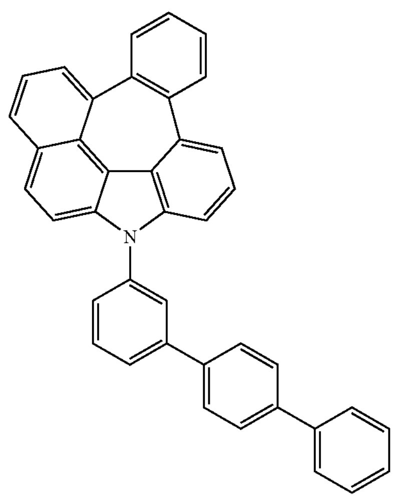
C-236
TABLE 2-continued
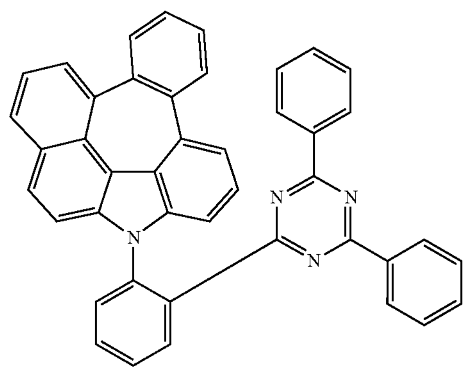
C-664
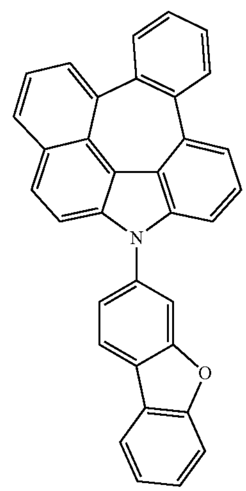
C-665
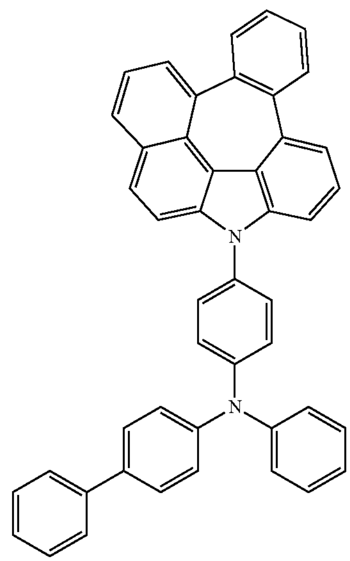
C-572

TABLE 2-continued
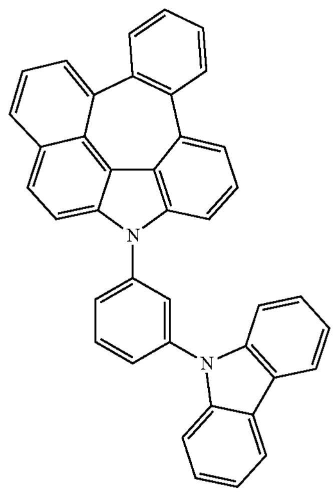
C-666
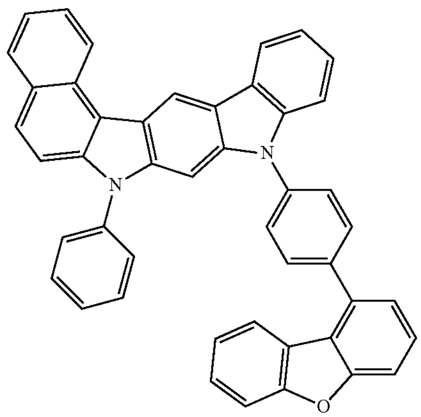
H-21
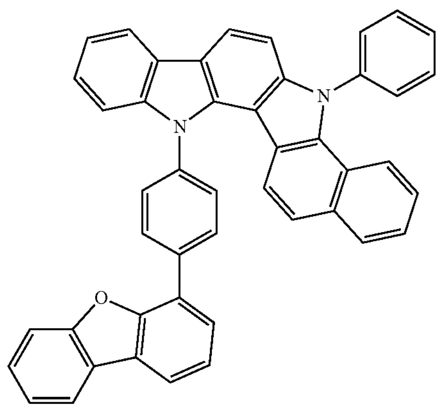
H-27
TABLE 2-continued
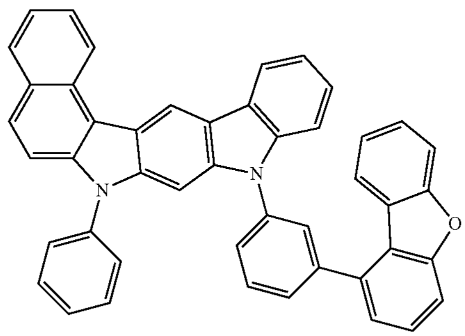
H-23
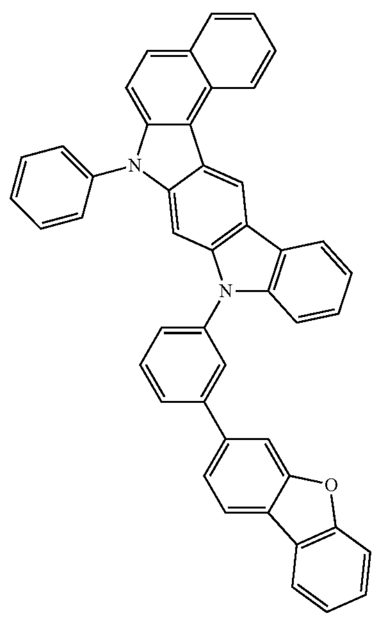
H-92
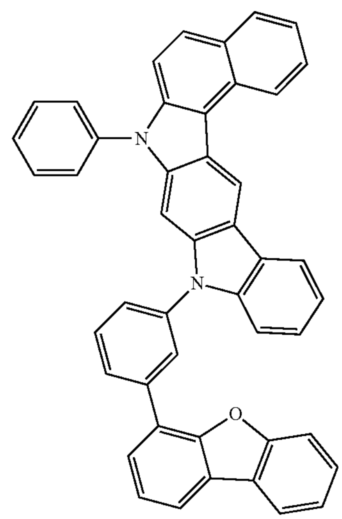
H-93

TABLE 2-continued
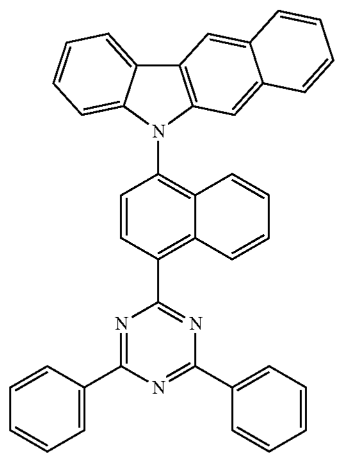
H-108
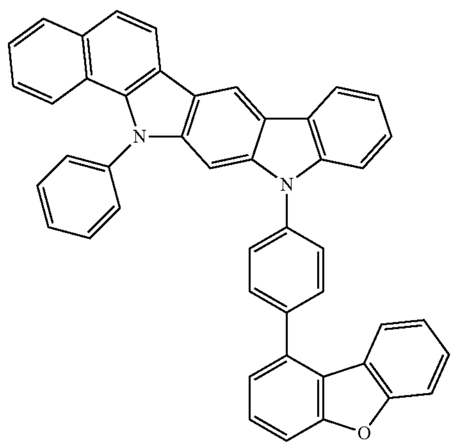
H-116
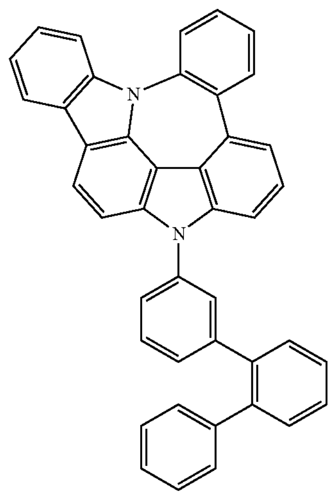
H-94
TABLE 2-continued
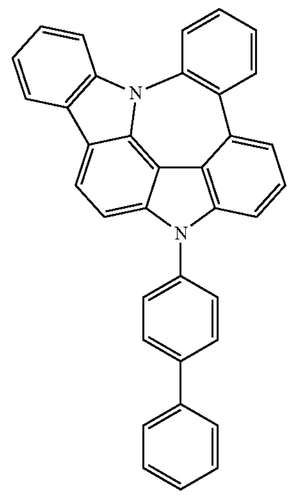
H-117
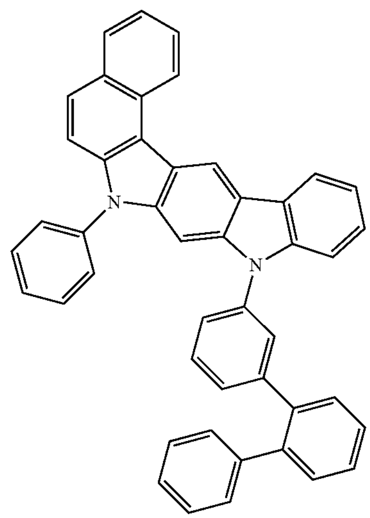
H-118
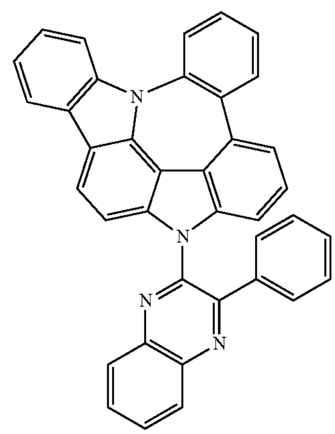
H-119

TABLE 2-continued

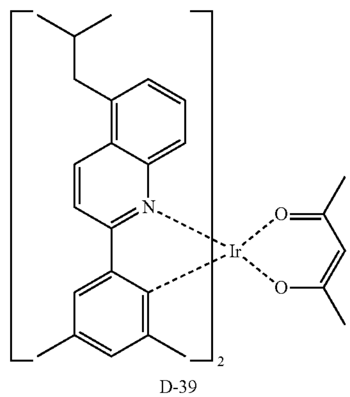

D-39

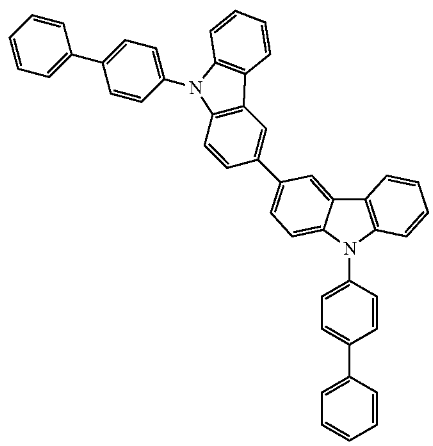

A

Electron Transport Layer/ Electron Injection Layer

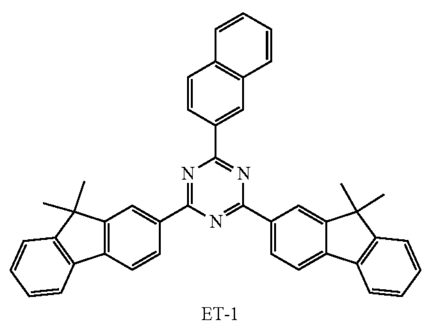 [SMILES: CC1(C)c2ccccc2-c2ccc(-c3nc(-c4ccc5c(c4)C(C)(C)c4ccccc4-5)nc(-c4ccc5ccccc5c4)n3)cc21]

ET-1

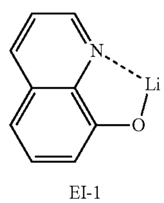

EI-1

The invention claimed is:

1. A composition material for an organic electroluminescent device, comprising the compound represented by the following formula 1-2 and the compound represented by the following formula 2:

(1-2)

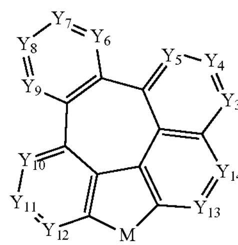

wherein

M represents N-L-$(Ar)_a$, S, or O;

L represents a single bond, a substituted or unsubstituted (C6-C30)arylene, or a substituted or unsubstituted (3- to 30-membered)heteroarylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$Y_3$ to $Y_{14}$, each independently, represent N or $CR_1$;

$R_1$ in $Y_3$ to $Y_8$ and $Y_{11}$ to $Y_{14}$, each independently, represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or adjacent $R_1$'s in $Y_3$ to $Y_8$ and $Y_{11}$ to $Y_{14}$ may be fused with each other to form a substituted or unsubstituted ring;

$R_1$ in $Y_9$ and $Y_{10}$, each independently, represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri(C6-C30)arylsilyl; and a represents an integer of 1 to 4, in which if a is an integer of 2 or more, each of Ar may be the same or different;

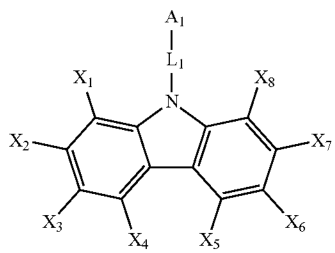

(2)

wherein $A_1$ represents a substituted or unsubstituted (C6-C30)aryl, or a substituted or unsubstituted (5- to 30-membered) heteroaryl;

$L_1$ represents a single bond, a substituted or unsubstituted (C6-C30)arylene, or a substituted or unsubstituted (3- to 30-membered)heteroarylene;

$X_1$ to $X_8$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered) heteroaryl, $—NR_5R_6$, or $—SiR_7R_8R_9$; or may be fused with adjacent $X_1$ to $X_8$ to form a ring, with the proviso that any one of $X_1$ to $X_8$ is not a substituted or unsubstituted carbazolyl; and $R_5$ to $R_9$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered) heteroaryl; or may be fused with adjacent $R_5$ to $R_9$ to form a ring.

2. A composition material for an organic electroluminescent device, comprising the compound represented by the following formula 1-1 and the compound represented by the following formula 2:

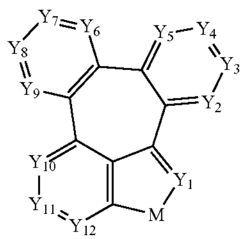

(1-1)

wherein

M represents N-L-$(Ar)_a$, S, or O;

L represents a single bond, a substituted or unsubstituted (C6-C30)arylene, or a substituted or unsubstituted (3- to 30-membered)heteroarylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino;

$Y_1$ represents N or $CR_2$, in which $R_2$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino;

$Y_2$ to $Y_{12}$, each independently, represent N or $CR_1$;

$R_1$, each independently, represents hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; or adjacent $R_1$'s may be fused with each other to form a substituted or unsubstituted ring; and a represents an integer of 1 to 4, in which if a is an integer of 2 or more, each of Ar may be the same or different;

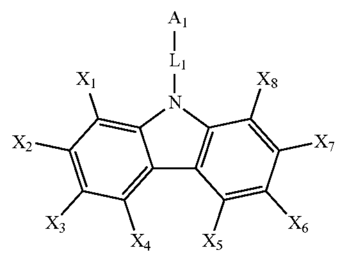

(2)

wherein $A_1$ represents a substituted or unsubstituted (C6-C30)aryl, or a substituted or unsubstituted (5- to 30-membered) heteroaryl;

$L_1$ represents a single bond, a substituted or unsubstituted (C6-C30)arylene, or a substituted or unsubstituted (3- to 30-membered)heteroarylene;

$X_1$ to $X_8$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered) heteroaryl, —$NR_5R_6$, or —$SiR_7R_8R_9$; or may be fused with adjacent $X_1$ to $X_8$ to form a ring, with the proviso that any one of $X_1$ to $X_8$ is not a substituted or unsubstituted carbazolyl; and $R_5$ to $R_9$, each independently, represent hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered) heteroaryl; or may be fused with adjacent $R_5$ to $R_9$ to form a ring.

3. The composition material for an organic electroluminescent device according to claim 1, wherein in formula 1-2, at least an adjacent pair of $Y_3$ to $Y_{14}$ represent $CR_1$, and $R_1$'s of the two adjacent $CR_1$'s are fused with each other to independently form the ring represented by any one of the following formulas 1-11 to 1-15:

(1-11)

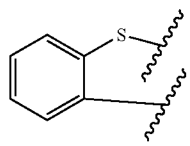

(1-12)

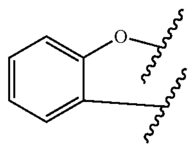

(1-13)

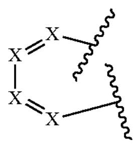

(1-14)

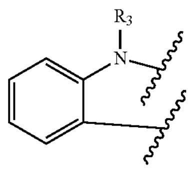

(1-15)

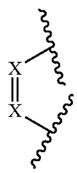

wherein

X represents N or $CR_4$;

$R_3$ and $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl (C6-C30)arylamino; and

 represents a fused site of C and $R_1$ in the adjacent $CR_1$'s.

4. The composition material for an organic electroluminescent device according to claim 1, wherein Ar represents a substituted or unsubstituted phenyl, a substituted or unsubstituted naphthyl, a substituted or unsubstituted biphenyl, a substituted or unsubstituted terphenyl, a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzothienopyrimidinyl, a substituted or unsubstituted benzothienoquinolinyl, a substituted or unsubstituted benzofuroquinolinyl, a substituted or unsubstituted triaindenyl, a substituted or unsubstituted phenanthroimidazolyl, a substituted or unsubstituted (9- to 25-membered)heteroaryl containing at least one of nitrogen, oxygen, and sulfur, a substituted or unsubstituted diphenylamino, a substituted or unsubstituted phenylbiphenylamino, or a substituted or unsubstituted fluorenylphenylamino.

5. The composition material for an organic electroluminescent device according to claim 1, wherein formula 2 is represented by any one of the following formulas 2-1 to 2-8:

(2-1)

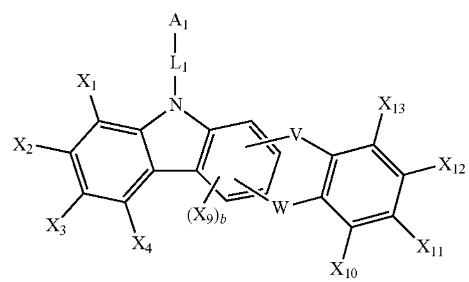

-continued (2-2)

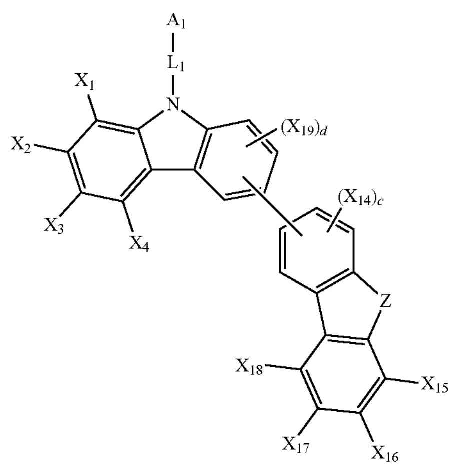

(2-3)

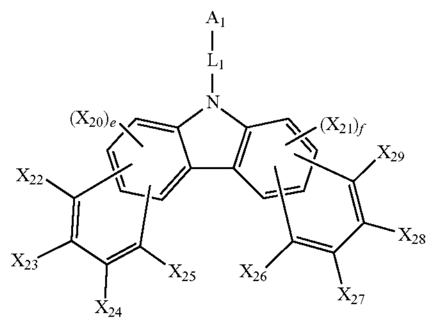

(2-4)

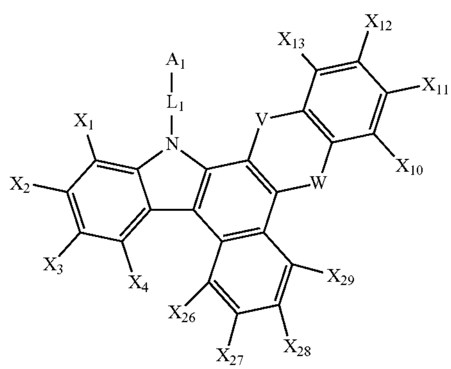

(2-5)

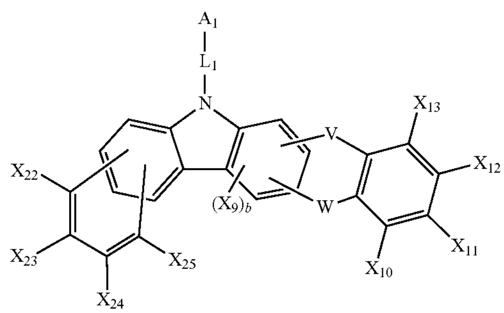

-continued (2-6)

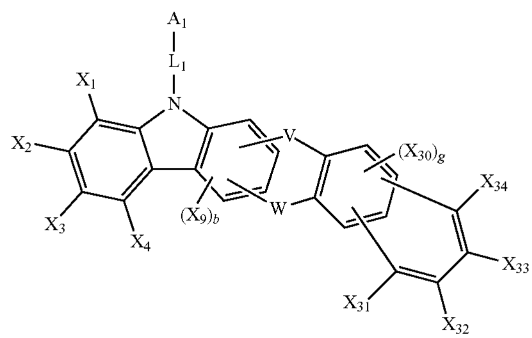

(2-7)

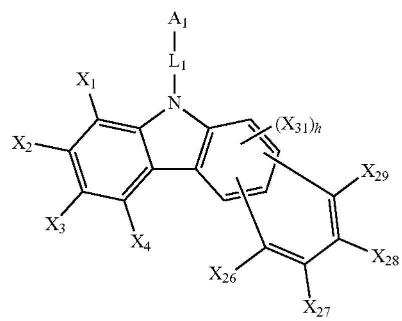

(2-8)

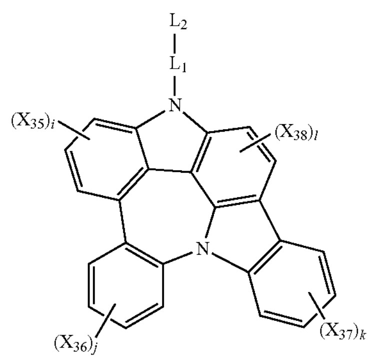

wherein $A_1$, $L_1$, and $X_1$ to $X_4$ are as defined in claim 1;

$X_9$ to $X_{38}$, each independently, are as defined for $X_1$;

b, e, f, g, h, and l, each independently, represent 1 or 2; c, d, and i, each independently, represent an integer of 1 to 3; j and k, each independently, represent an integer of 1 to 4; in which if b to l are an integer of 2 or more, each of $X_9$, $X_{14}$, $X_{19}$, $X_{20}$, $X_{21}$, $X_{30}$, $X_{31}$, and $X_{35}$ to $X_{38}$ may be the same or different;

Z represents O or S;

V and W, each independently, represent a single bond, $NR_{16}$, O, or S, with the proviso that both V and W are not a single bond, and both V and W are not $NR_{16}$, and $R_{16}$ represents hydrogen, deuterium, a halogen, a cyano, a carboxyl, a nitro, a hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl.

6. The composition material for an organic electroluminescent device according to claim 1, wherein the substituents of the substituted alkyl, the substituted alkoxy, the substituted cycloalkyl, the substituted cycloalkenyl, the substituted heterocycloalkyl, the substituted aryl(ene), the substituted heteroaryl(ene), the substituted trialkylsilyl, the substituted triarylsilyl, the substituted dialkylarylsilyl, the substituted alkyldiarylsilyl, the substituted mono- or dialkylamino, the substituted mono- or di-arylamino, and the substituted alkylarylamino in Ar, L, $R_1$, $A_1$, $L_1$, $X_1$ to $X_8$, and $R_5$ to $R_9$, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (3- to 7-membered)heterocycloalkyl; a (C6-C30)aryloxy; a (C6-C30)arylthio; a (3- to 50-membered)heteroaryl unsubstituted or substituted with a (C1-C30)alkyl, a (C6-C30)aryl, or a di(C6-C30)arylamino; a (C6-C30)aryl unsubstituted or substituted with a cyano, a (3- to 50-membered)heteroaryl, or a tri(C6-C30)arylsily; a tri(C1-C30)alkylsilyl, a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

7. The composition material for an organic electroluminescent device according to claim 1, wherein the compound represented by formula 1-2 is at least one selected from the group consisting of:

C-234

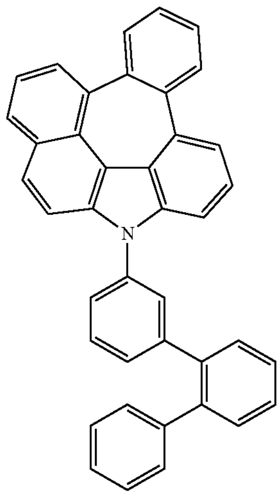

-continued

C-235

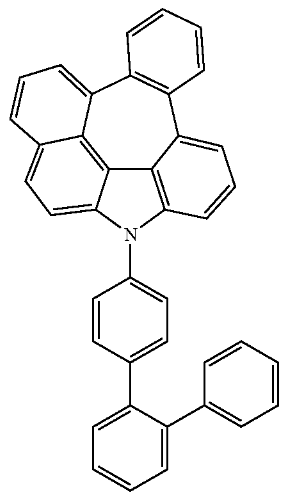

C-236

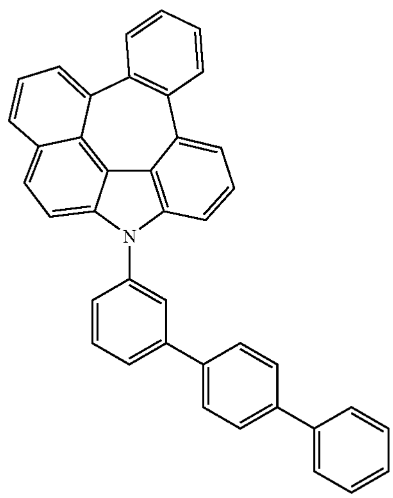

C-237

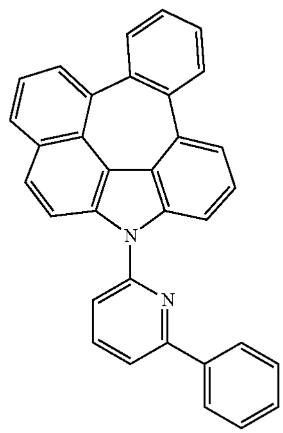

C-238
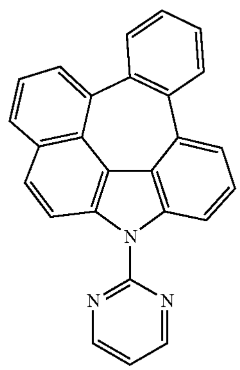
C-239
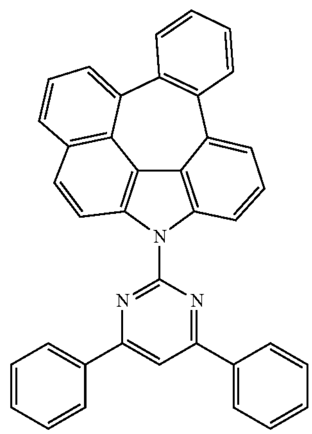
C-240
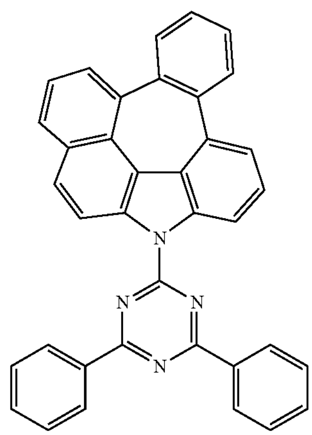
C-241
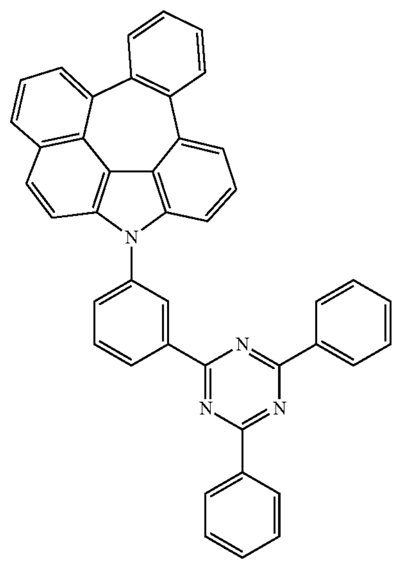
C-242
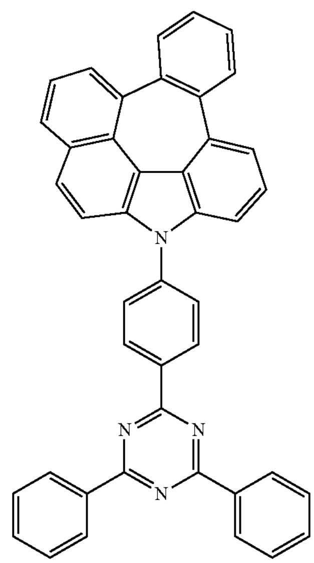

-continued
C-243
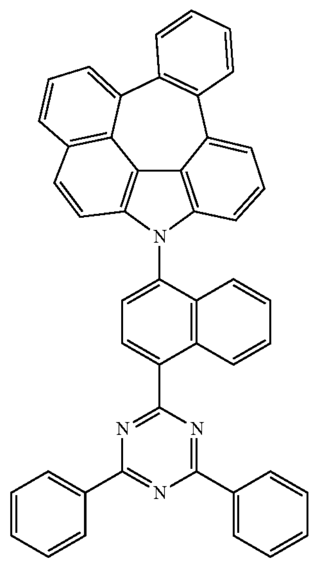
C-244
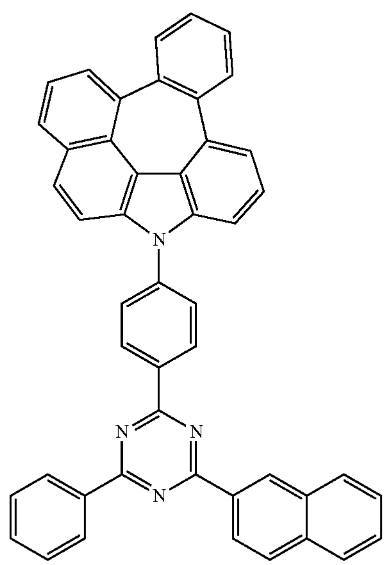
C-245
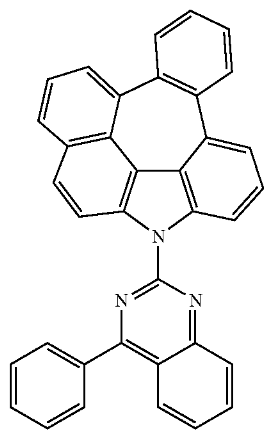
-continued
C-246
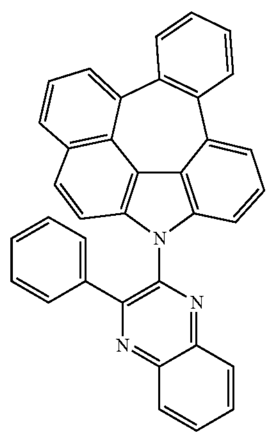
C-247
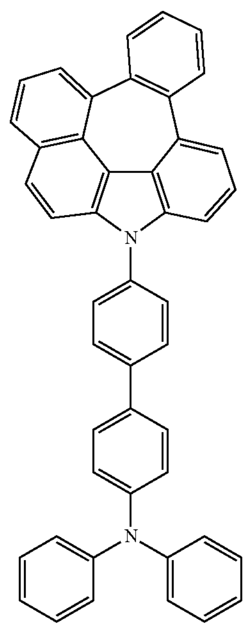

-continued
C-248
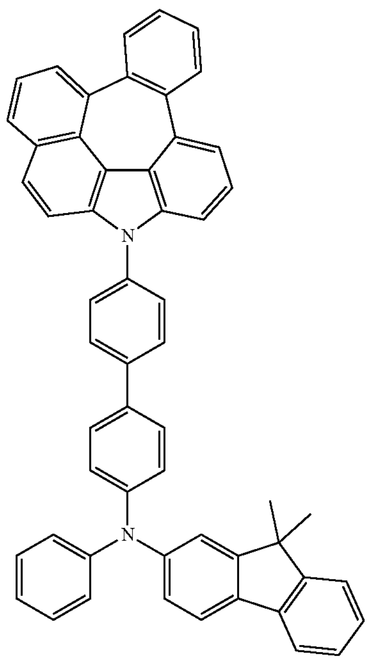
C-249
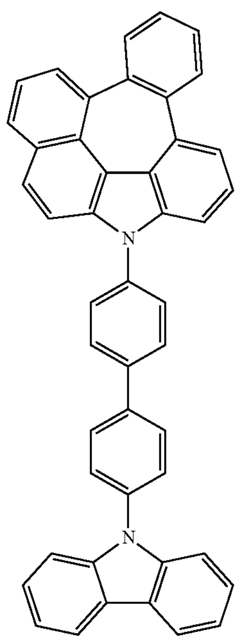
-continued
C-250
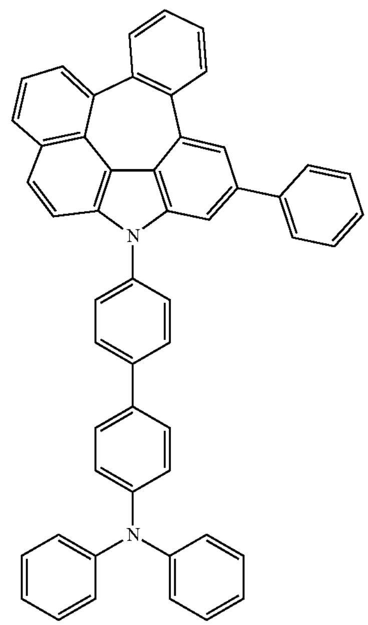
C-251
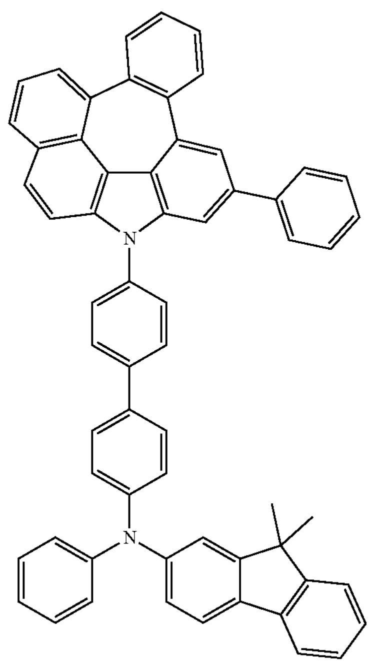

C-252
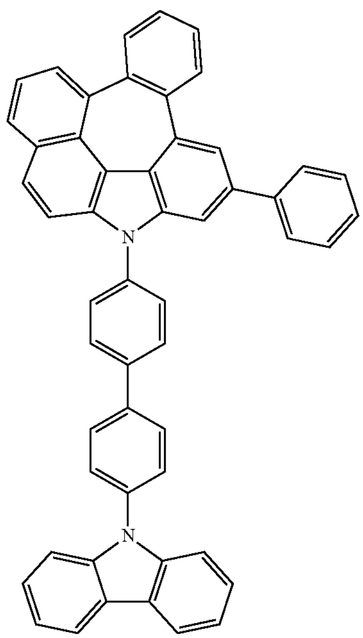
C-253
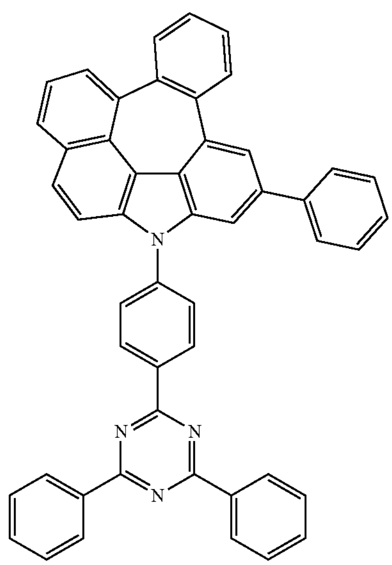
C-254
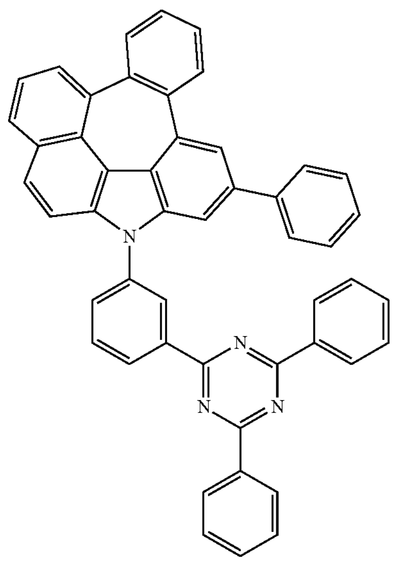
C-255
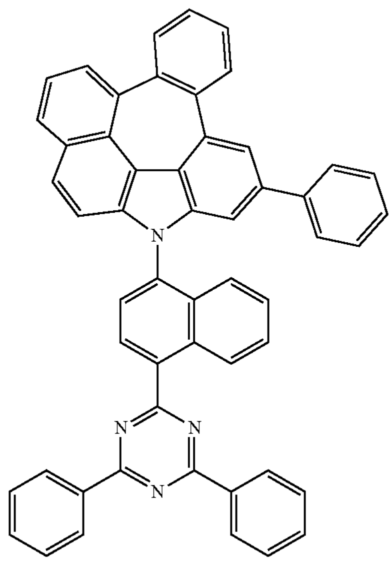

-continued
C-256
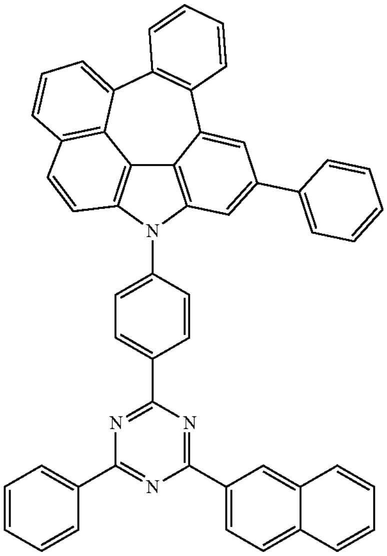
C-257
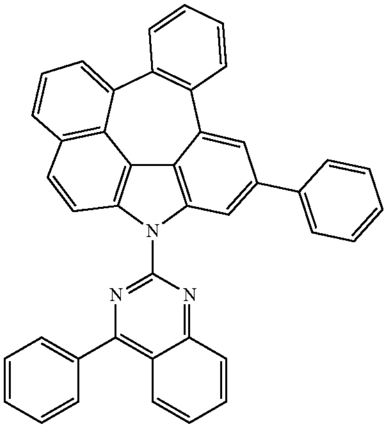
C-258
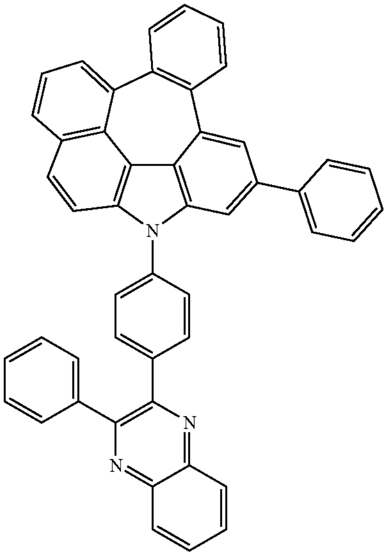
-continued
C-259
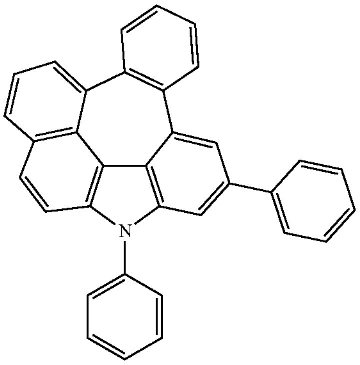
C-260
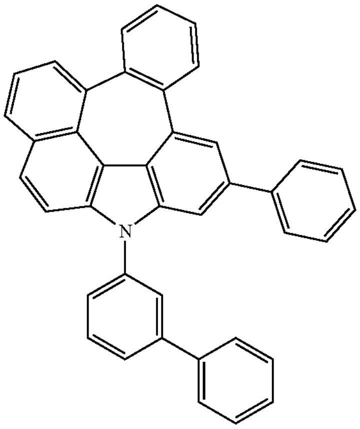
C-261
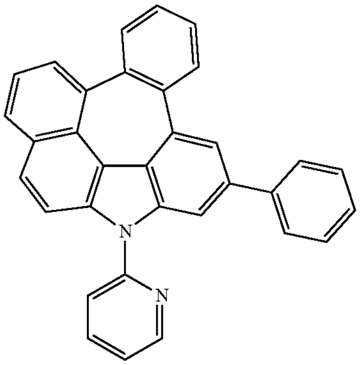
C-262
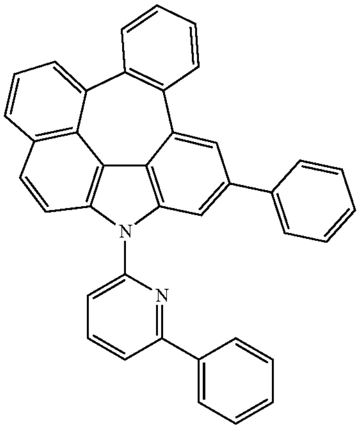

-continued
C-263
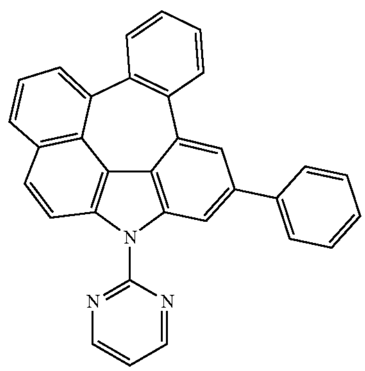
C-264
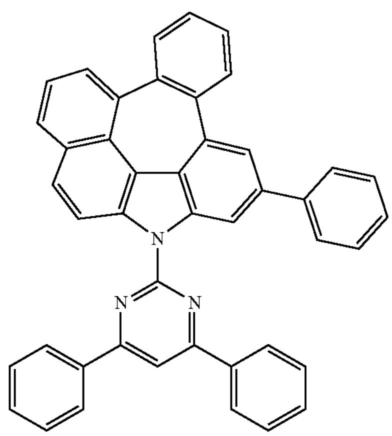
C-265
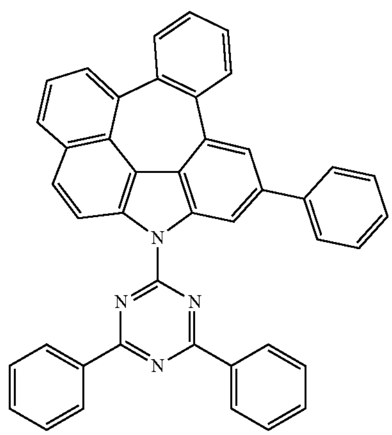
C-266
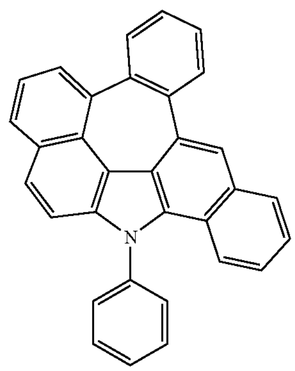
-continued
C-267
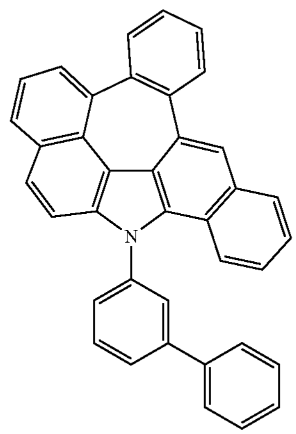
C-268
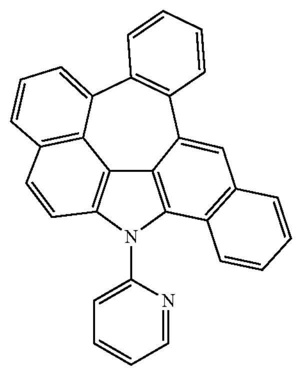
C-269
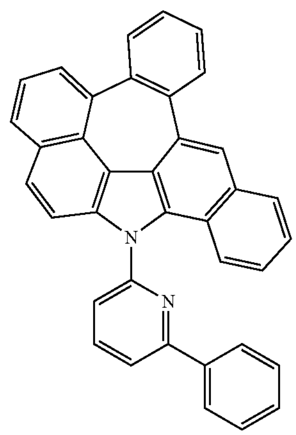
C-270
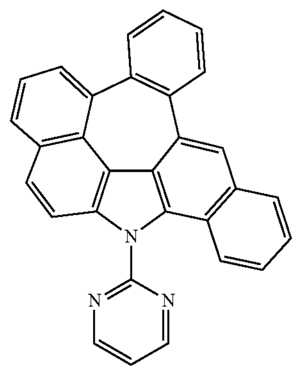

-continued
C-271
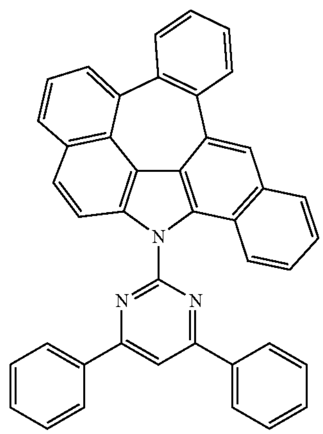
C-272
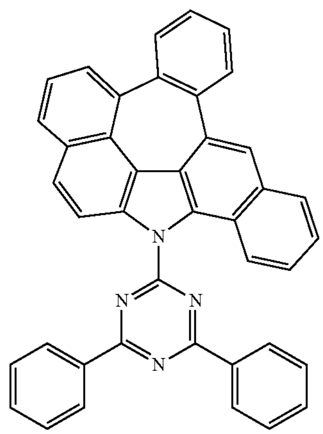
C-273
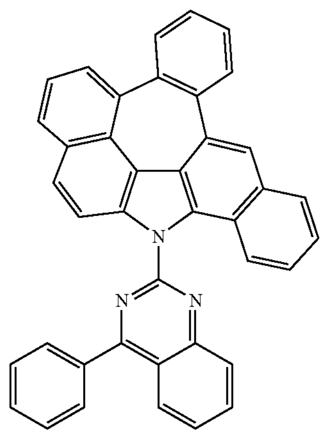
-continued
C-274
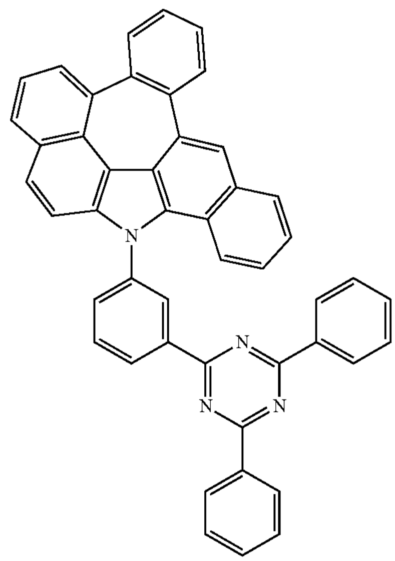
C-275
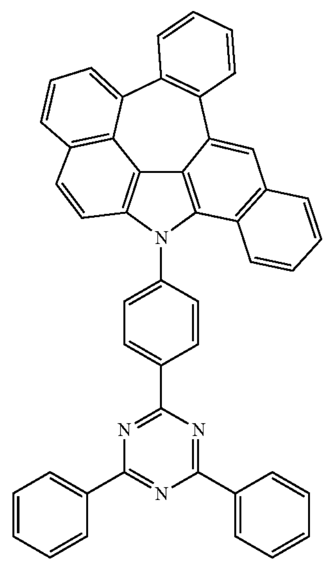

-continued
C-276
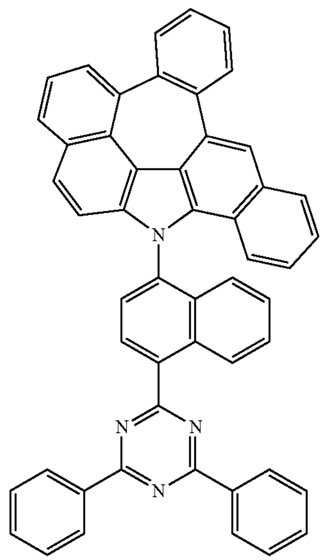
C-277
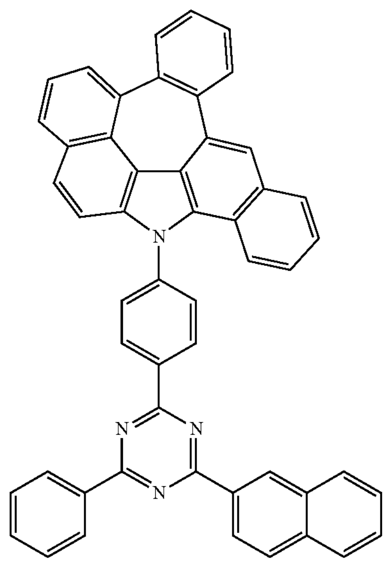
C-278
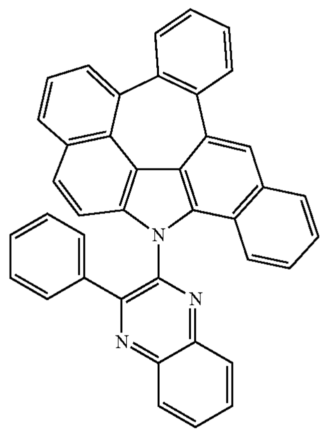
-continued
C-279
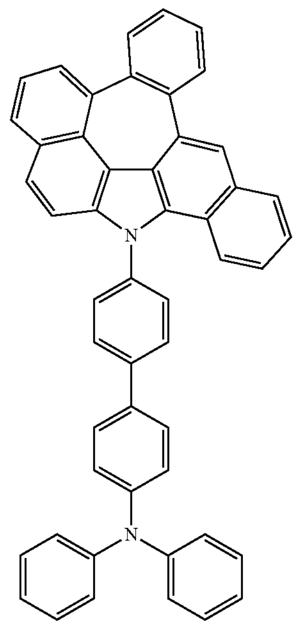
C-280
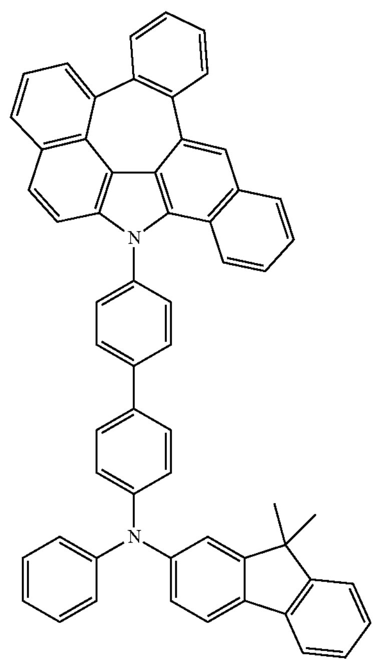

-continued
C-281
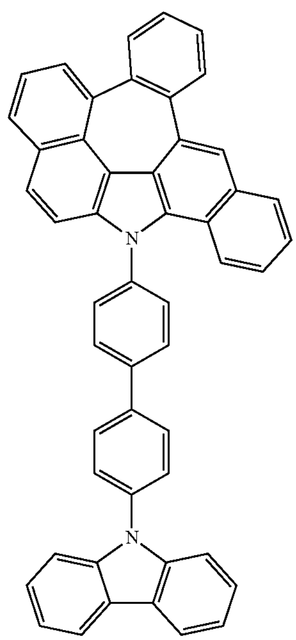
C-282
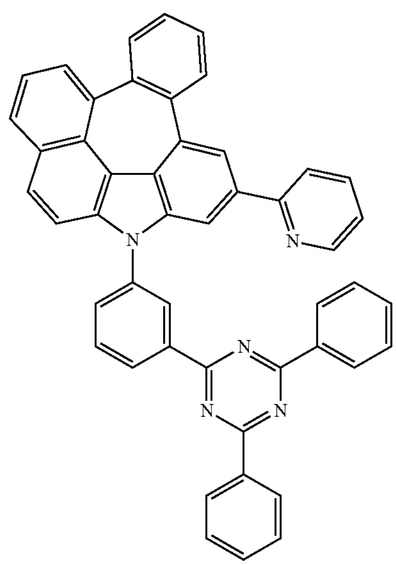
-continued
C-283
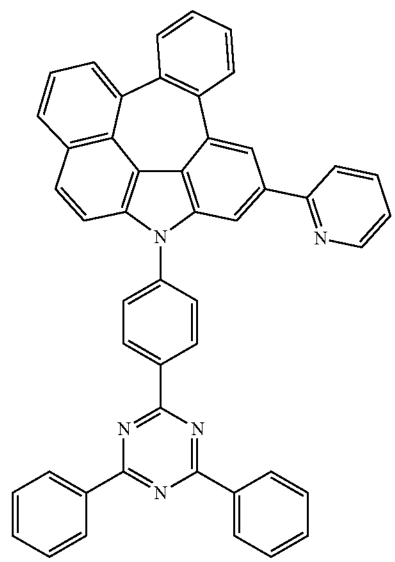
C-284
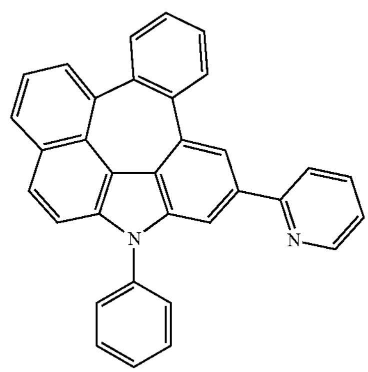
C-285
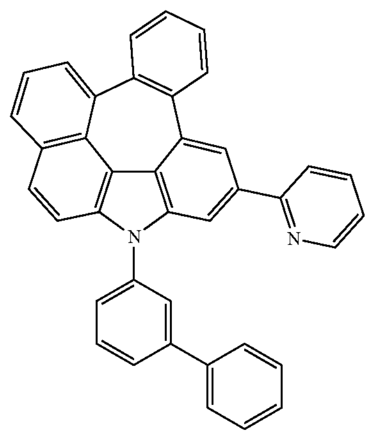

-continued
C-286
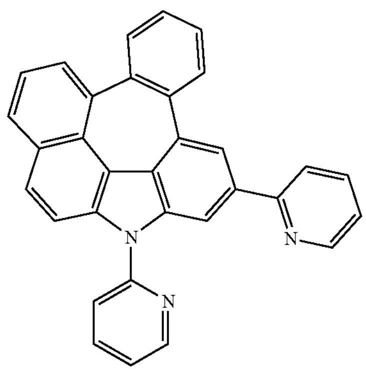
C-287
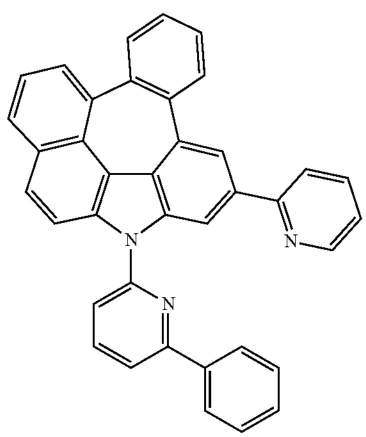
C-288
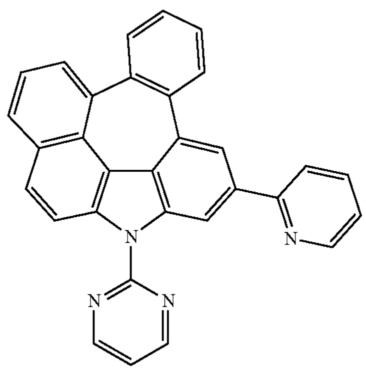
-continued
C-289
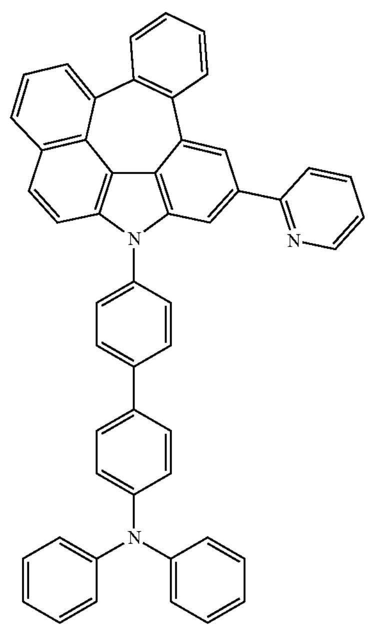
C-290
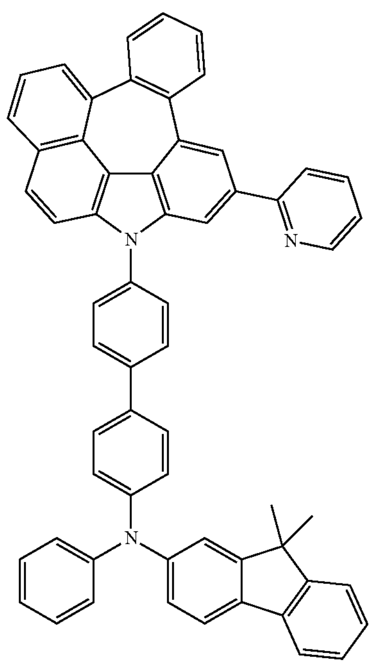

-continued
C-291
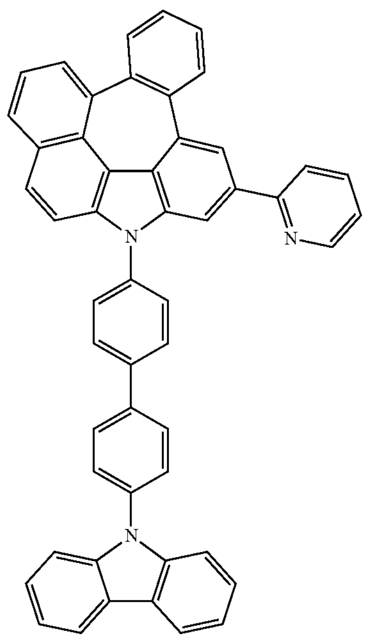
C-292
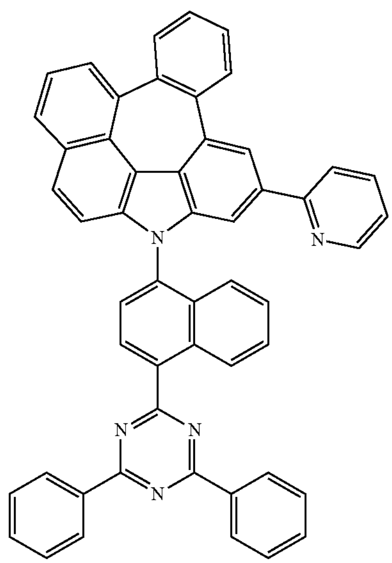
-continued
C-293
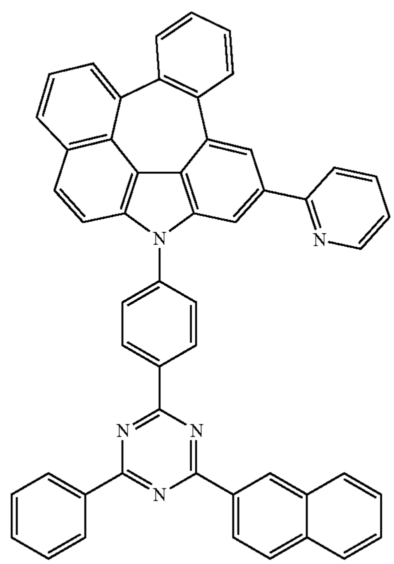
C-294
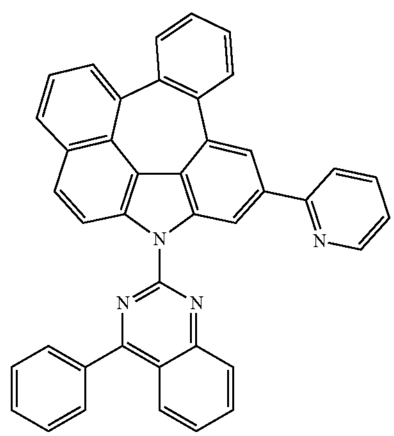
C-295
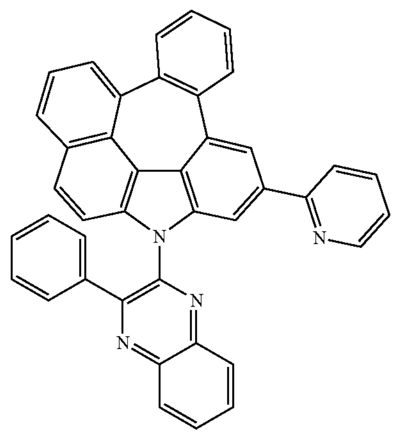

-continued
C-296
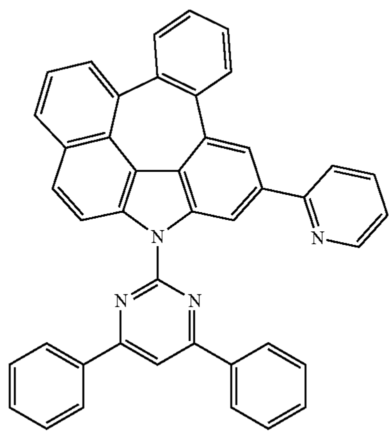
C-297
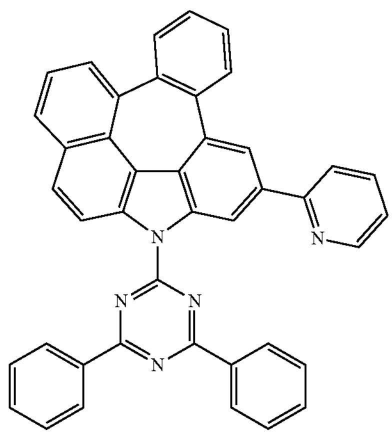
C-298
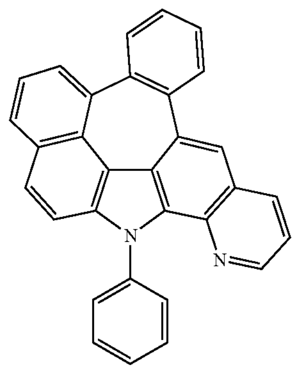
-continued
C-299
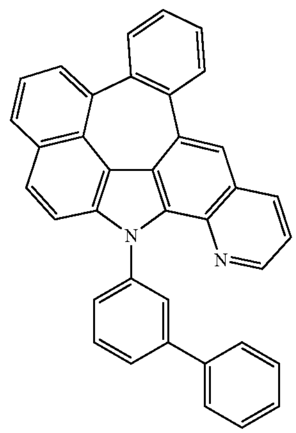
C-300
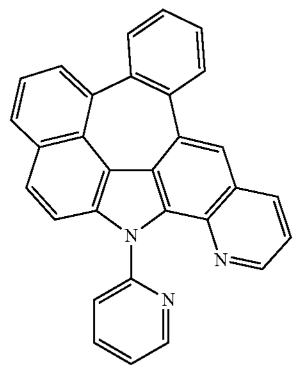
C-301
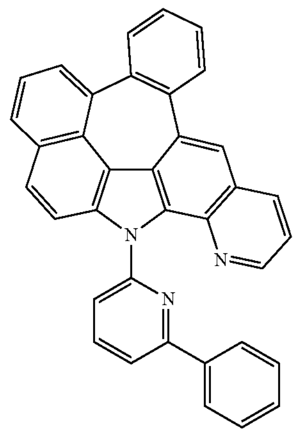
C-302
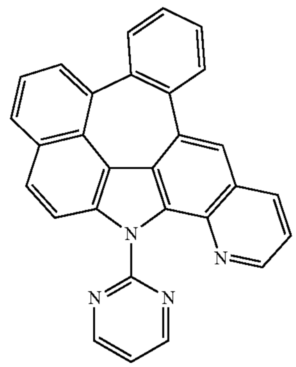

-continued
C-303
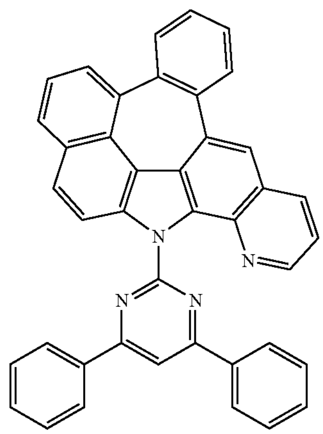
C-304
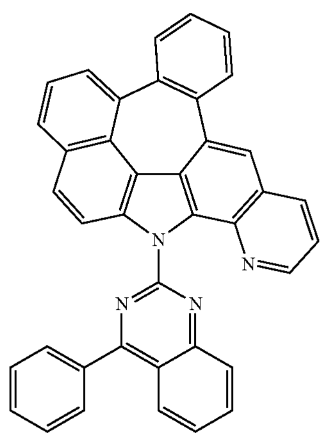
C-305
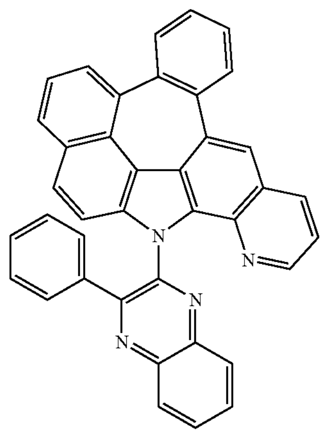
-continued
C-306
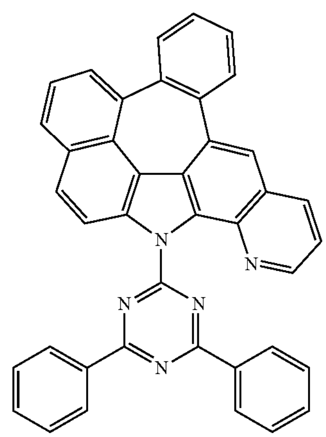
C-307
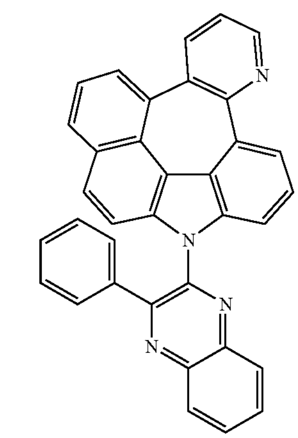
C-308
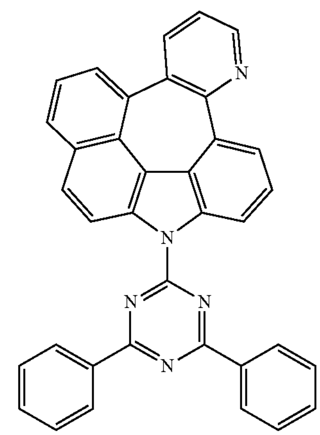

-continued
C-309
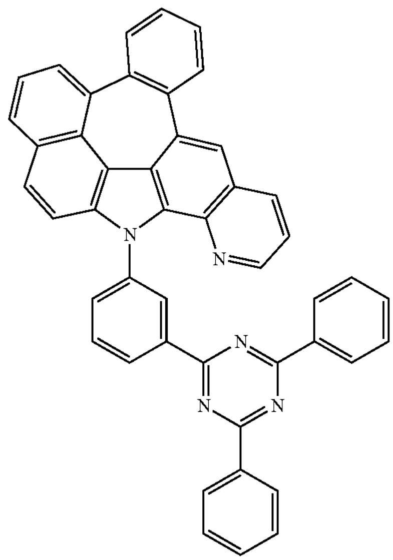
C-310
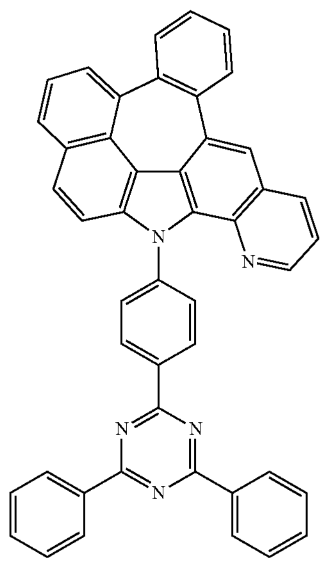
C-311
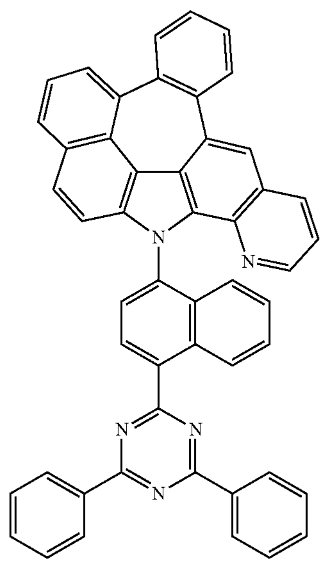
-continued
C-312
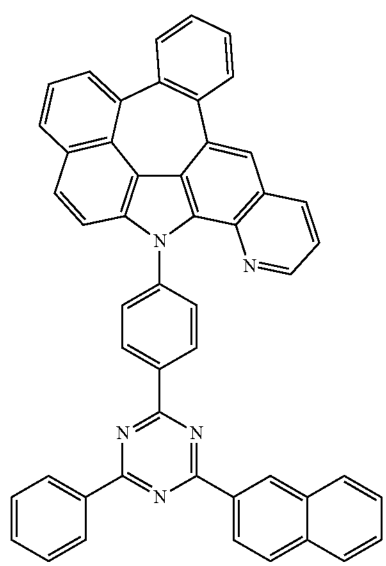
C-313
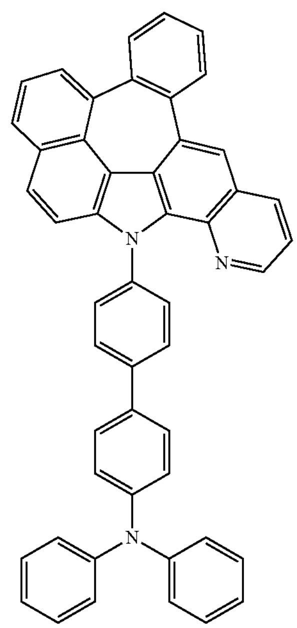

-continued
C-314
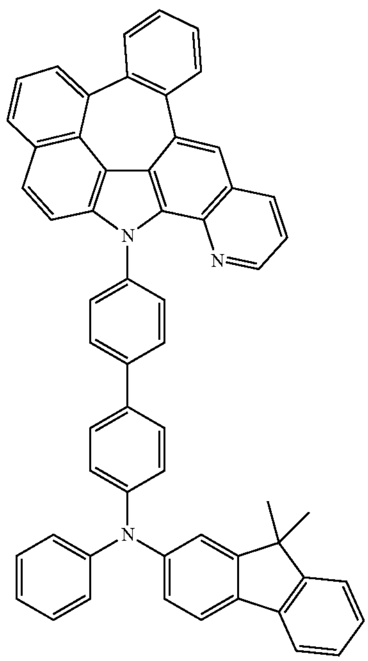
C-315
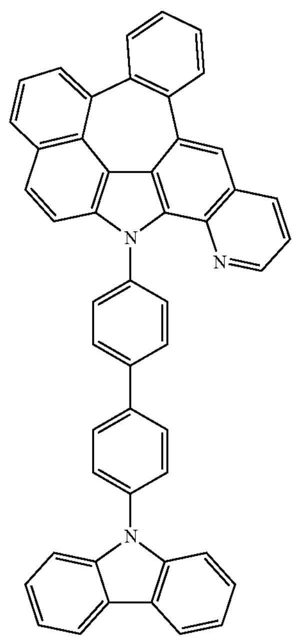
-continued
C-316
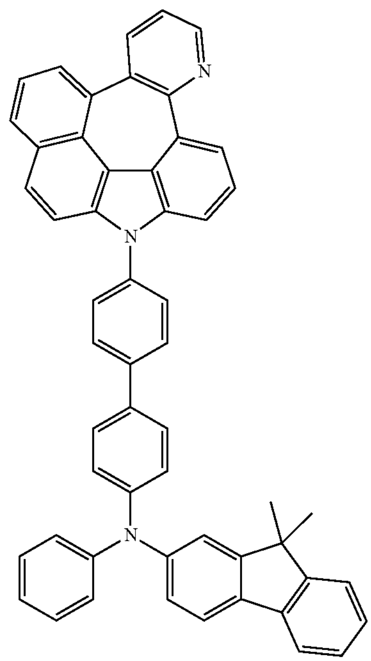
C-317
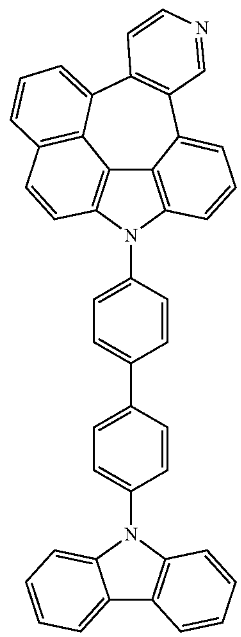

-continued
C-318
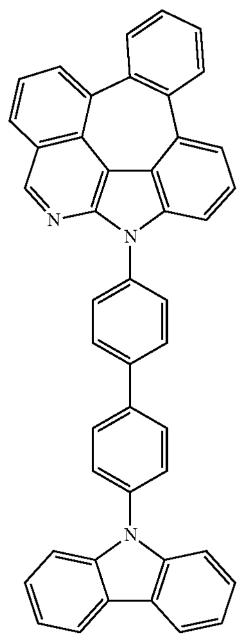
C-319
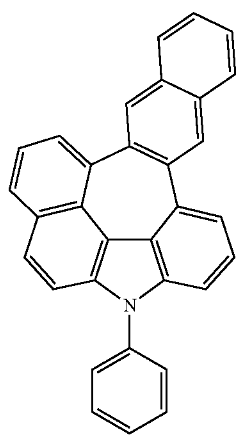
C-320
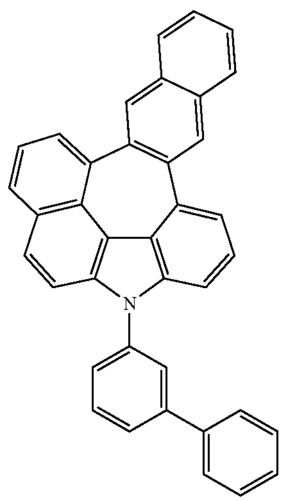
-continued
C-321
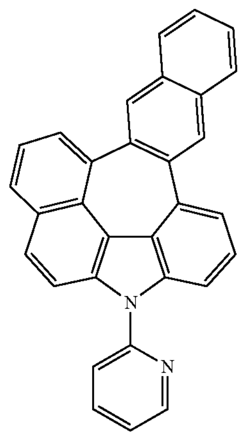
C-322
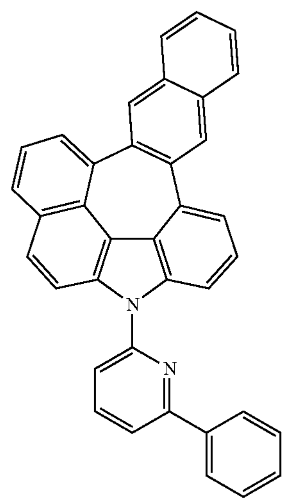
C-323
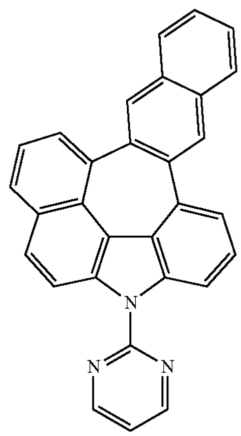

-continued
C-324
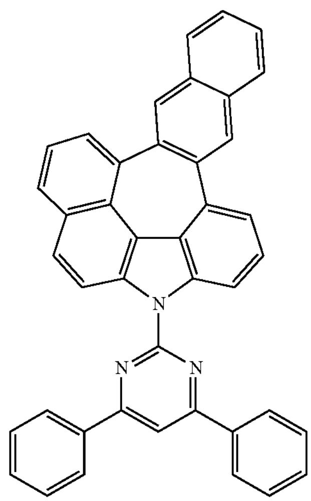
C-325
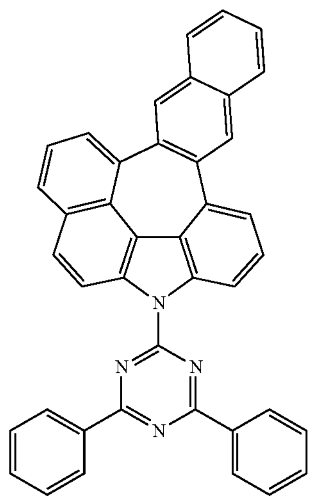
C-326
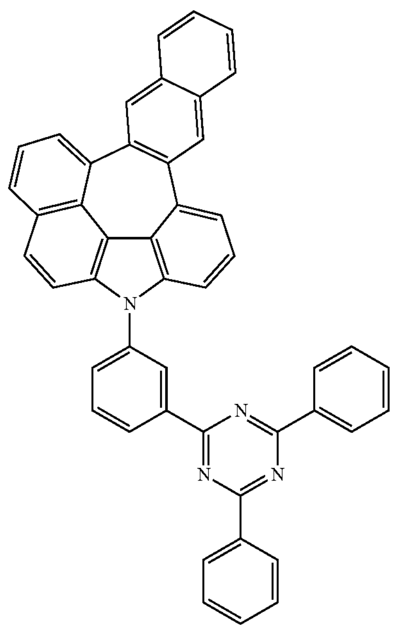
-continued
C-327
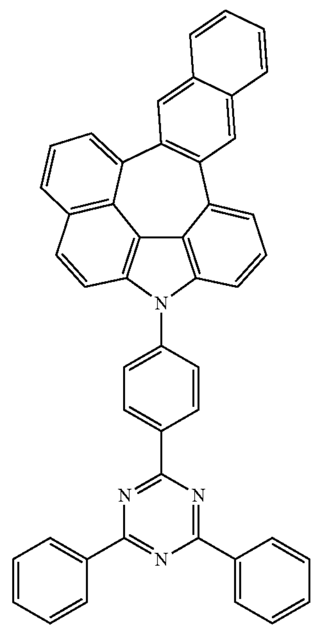
C-328
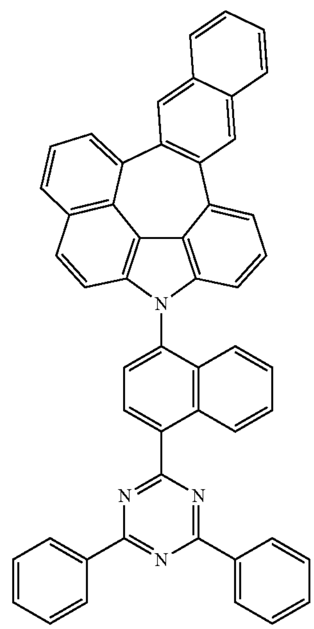

C-329
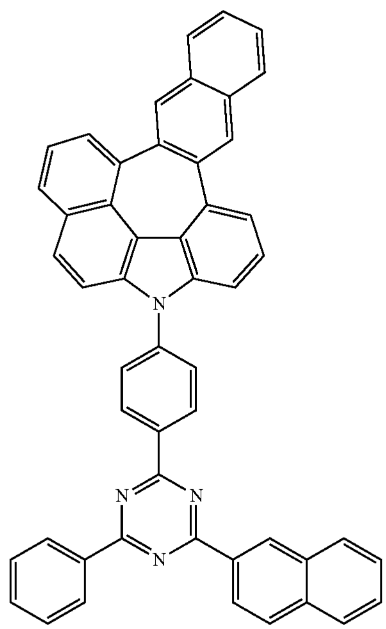
C-330
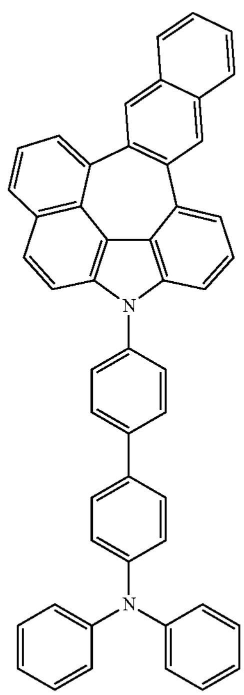
C-331
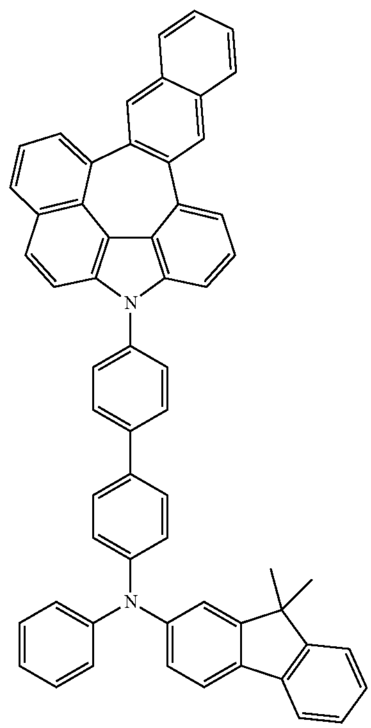
C-332
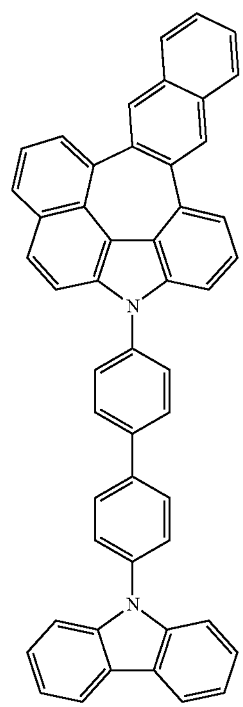

-continued
C-333
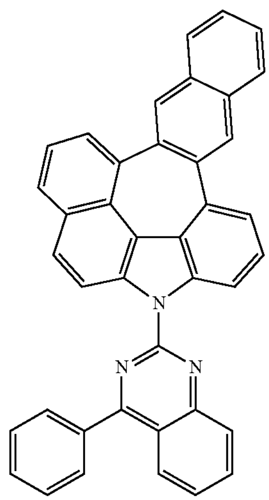
C-334
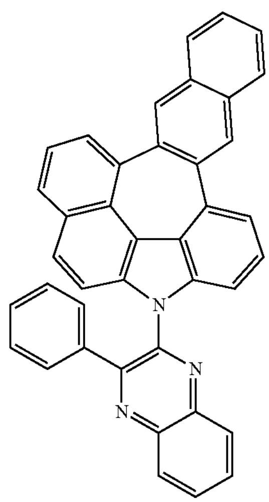
C-335
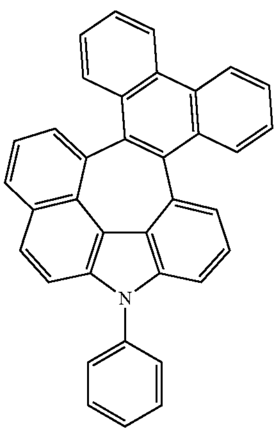
-continued
C-336
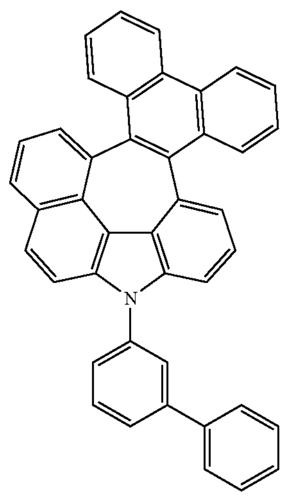
C-337
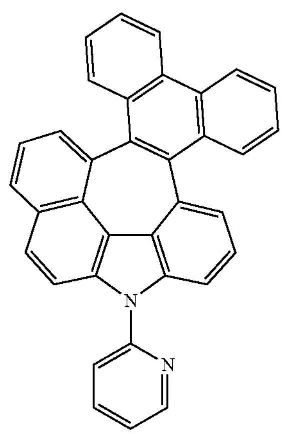
C-338
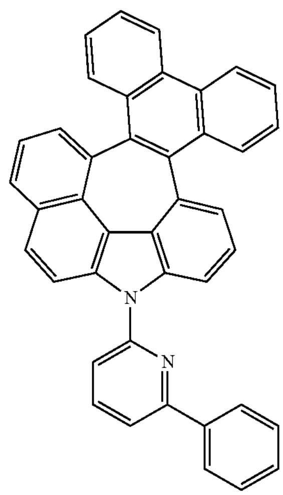

-continued
C-339
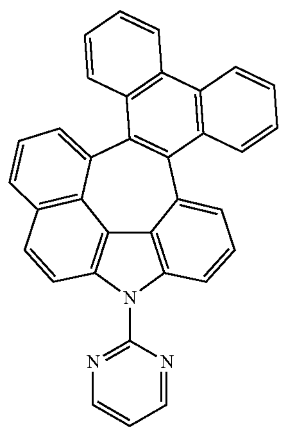
C-340
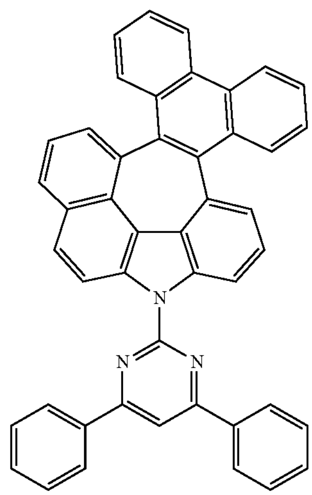
C-341
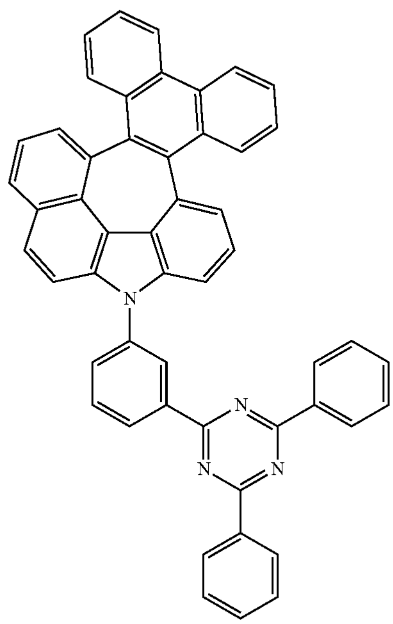
-continued
C-342
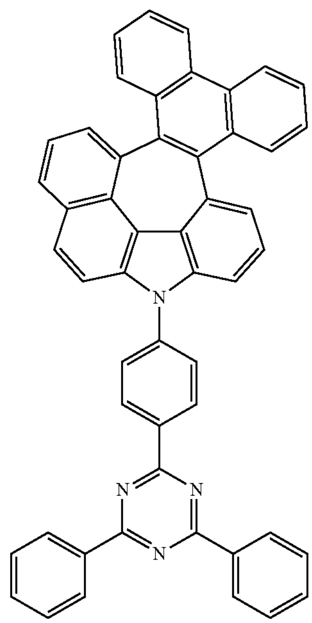
C-343
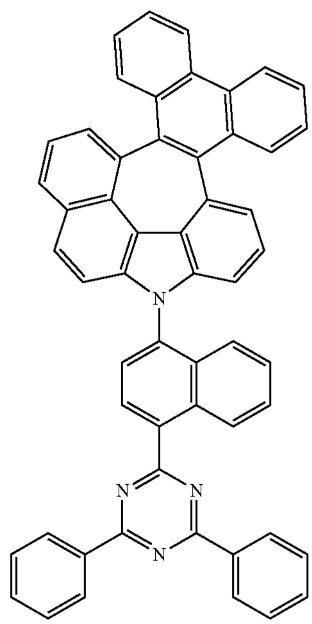

C-344
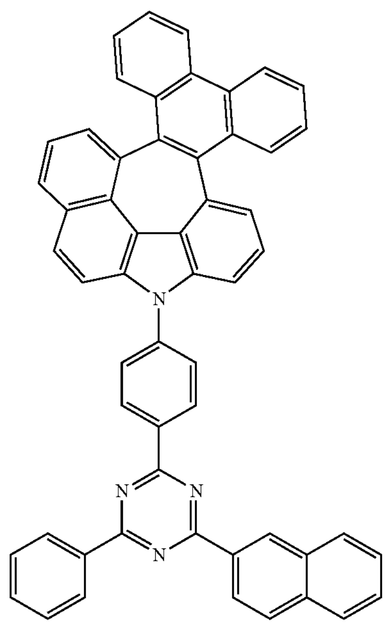
C-345
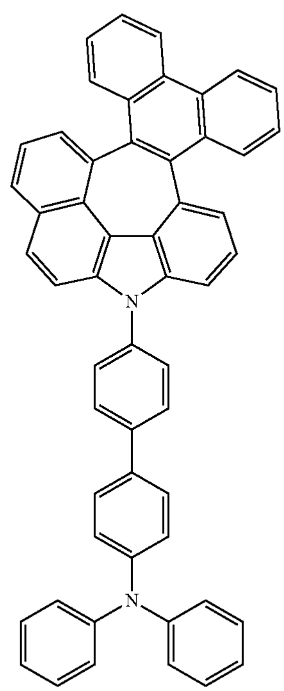
C-346
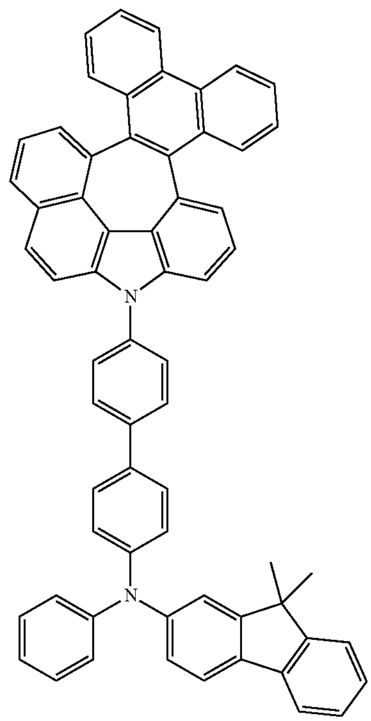
C-347
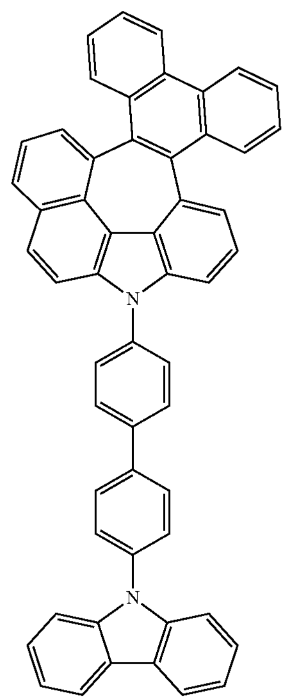

-continued
C-348
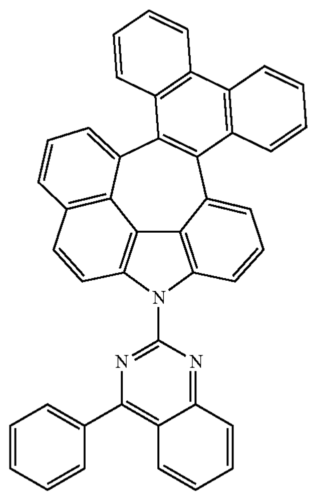
C-349
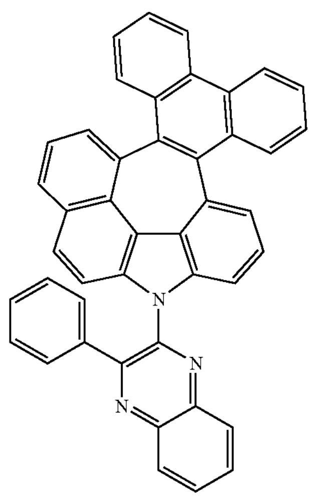
C-350
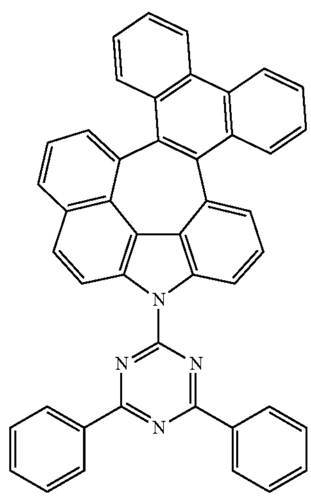
-continued
C-351
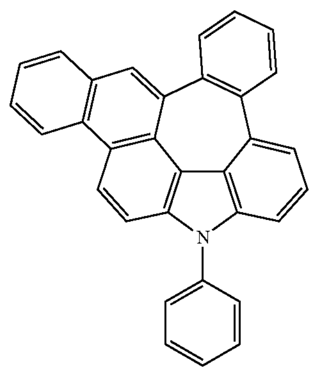
C-352
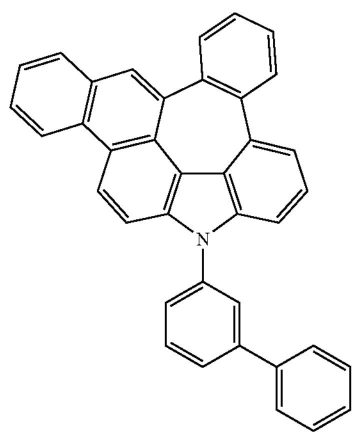
C-353
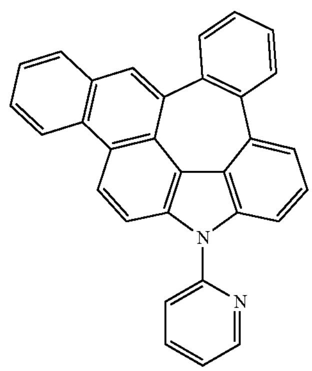
C-354
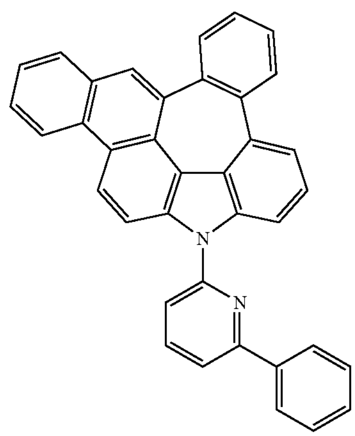

-continued
C-355
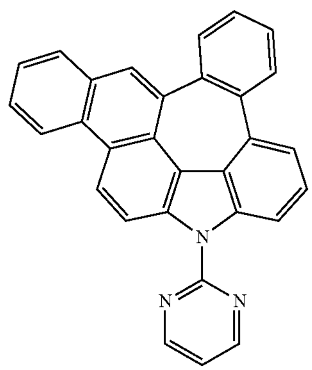
C-356
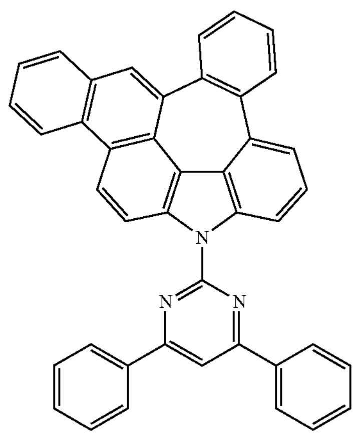
C-357
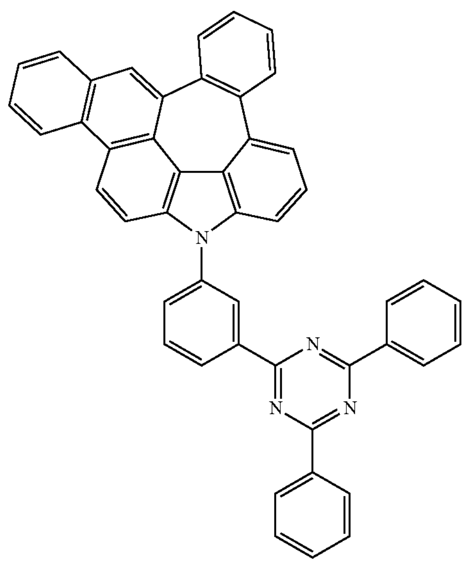
-continued
C-358
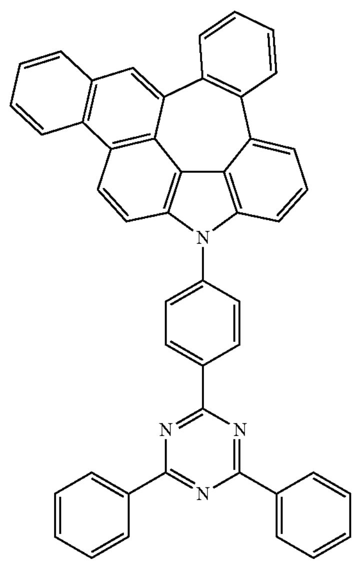
C-359
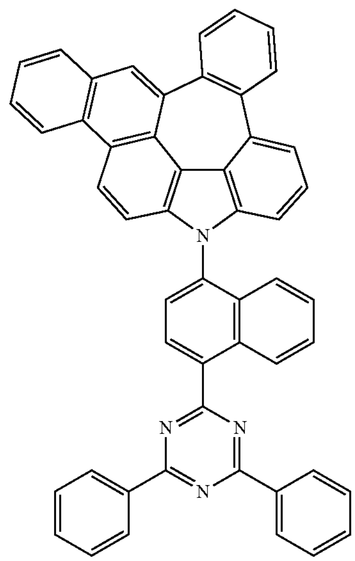
C-360
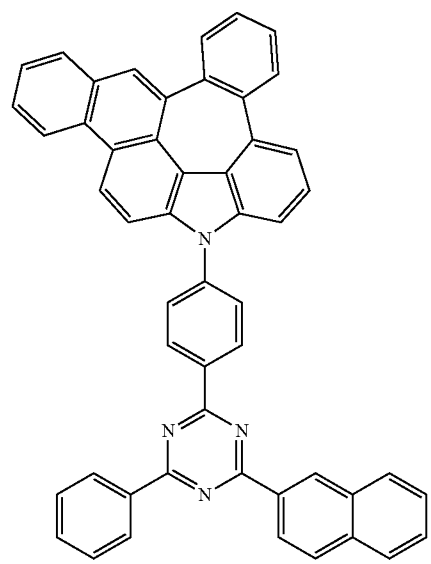

-continued
C-361
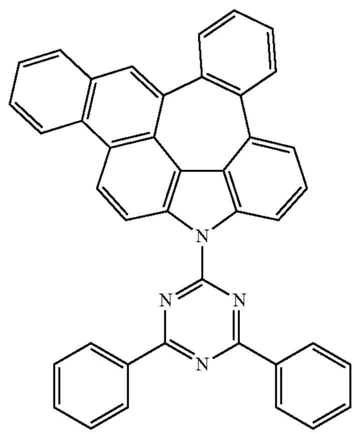
C-362
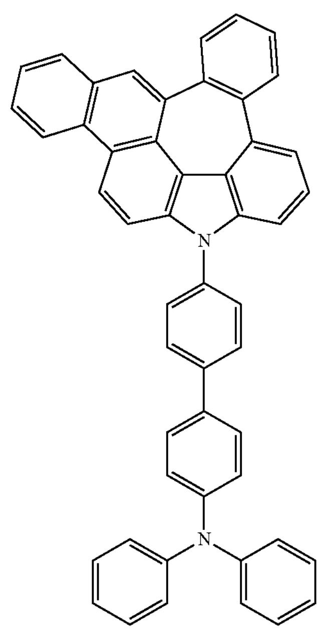
-continued
C-363
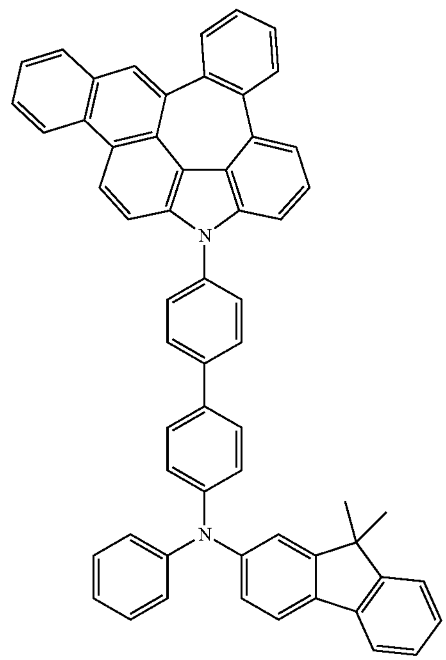
C-364
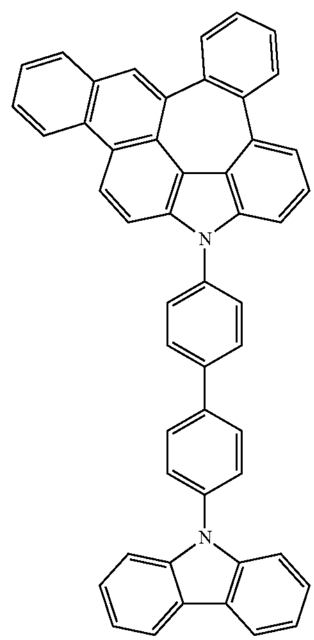

-continued
C-365
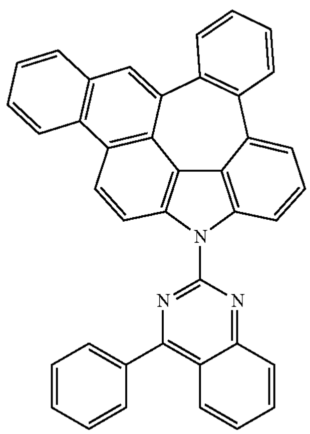
C-366
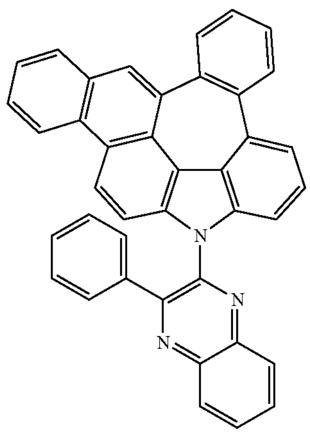
C-367
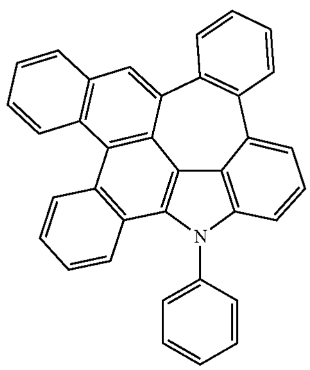
-continued
C-368
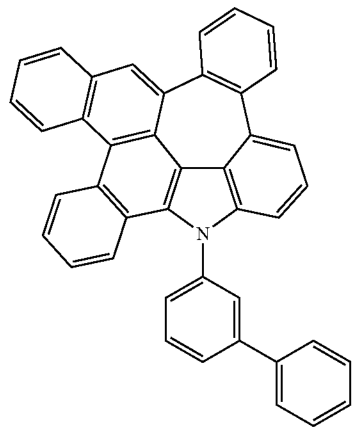
C-369
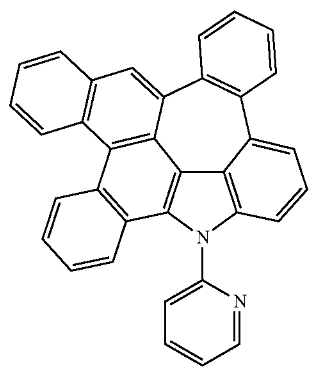
C-370
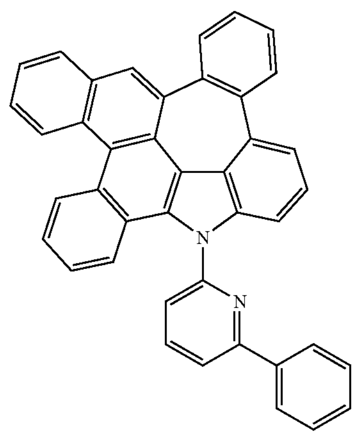
C-371
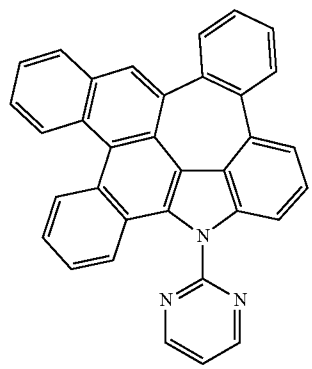

-continued
C-372
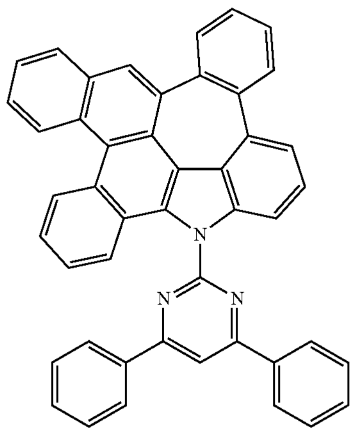
C-373
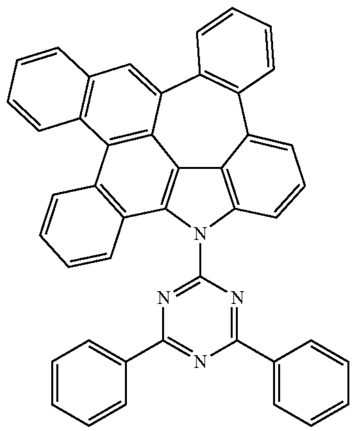
C-374
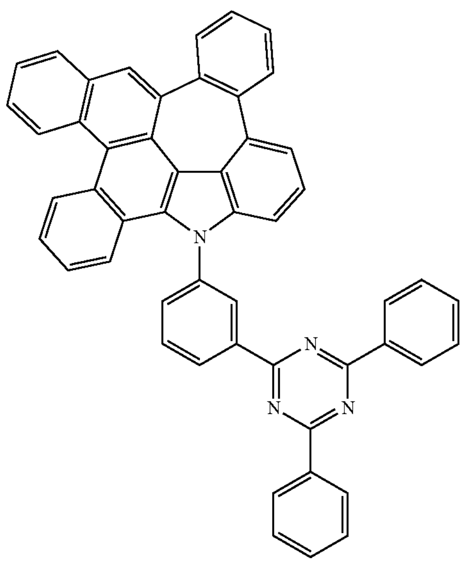
-continued
C-375
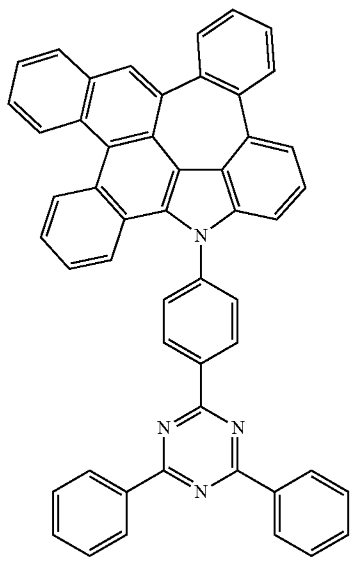
C-376
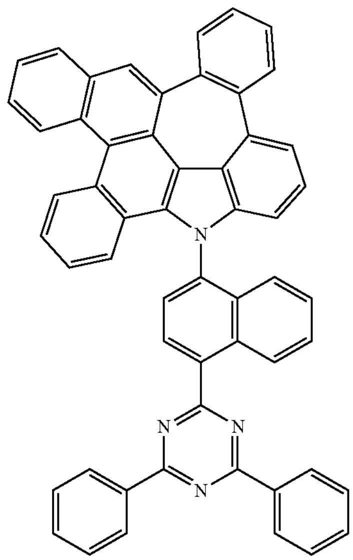
C-377
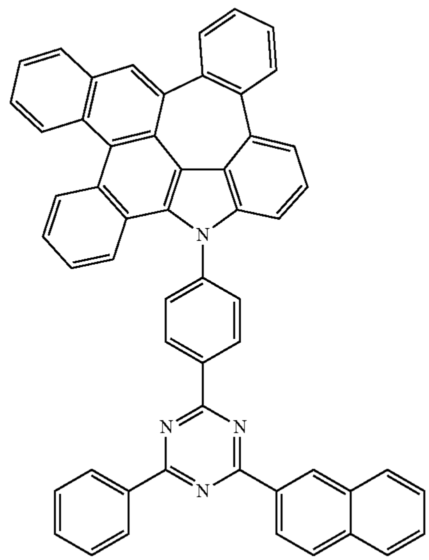

-continued
C-378
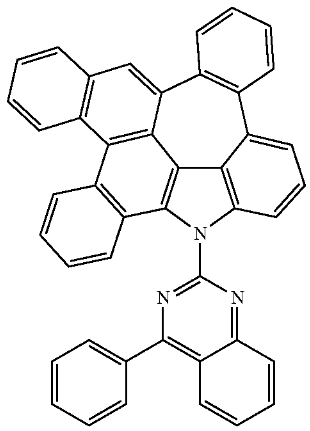
C-379
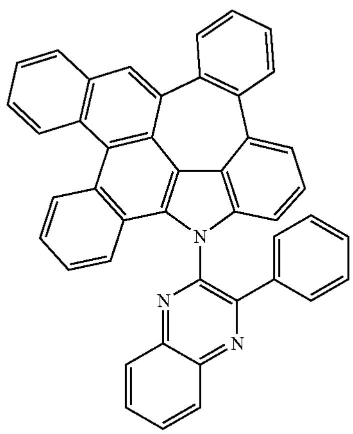
C-380
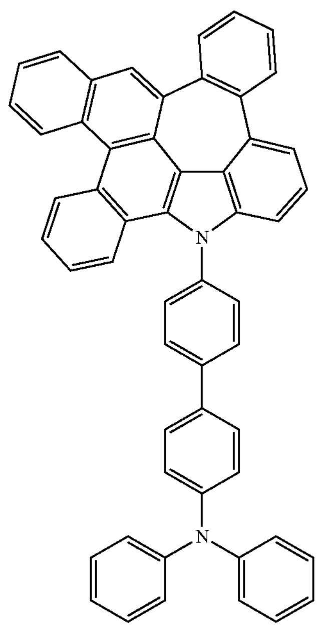
-continued
C-381
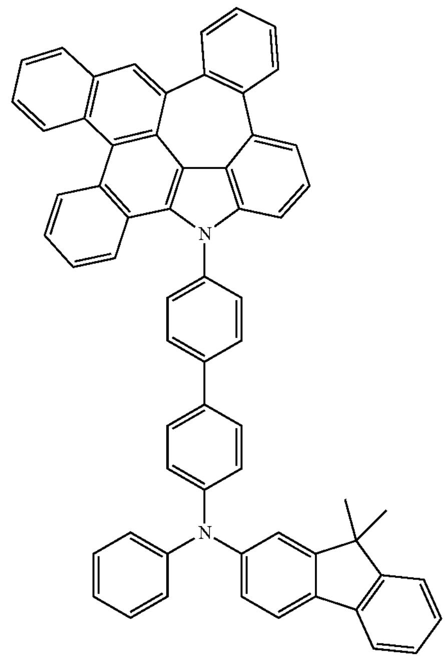
C-382
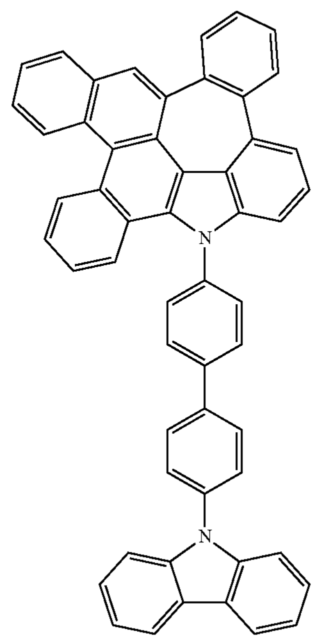

-continued
C-383
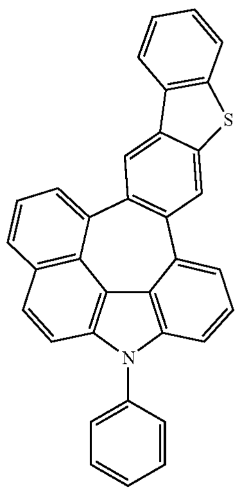
C-384
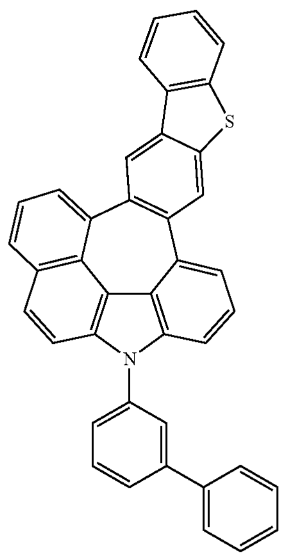
C-385
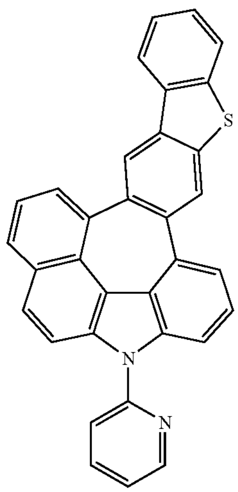
-continued
C-386
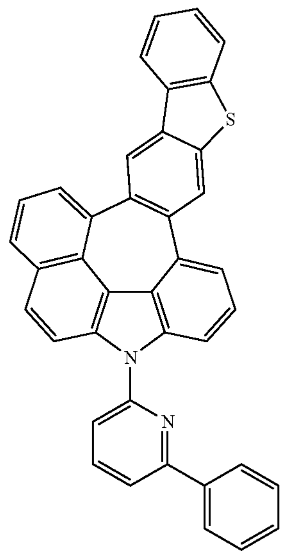
C-387
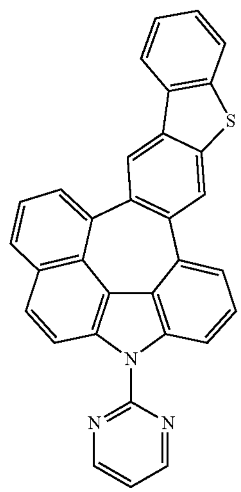
C-388
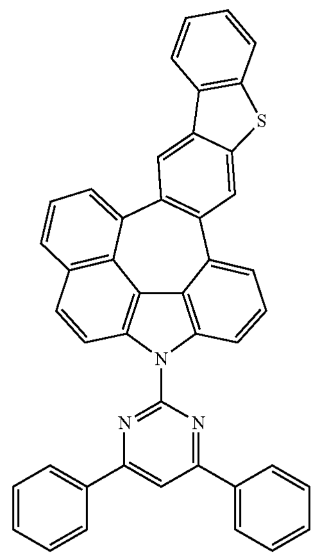

-continued
C-389
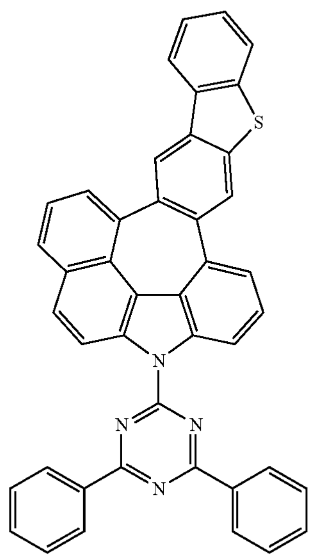
C-390
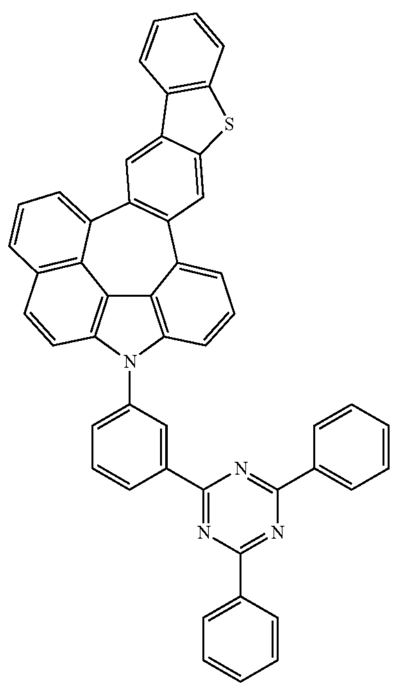
-continued
C-391
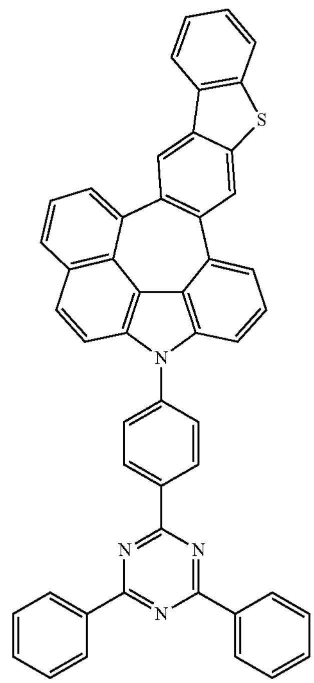
C-392
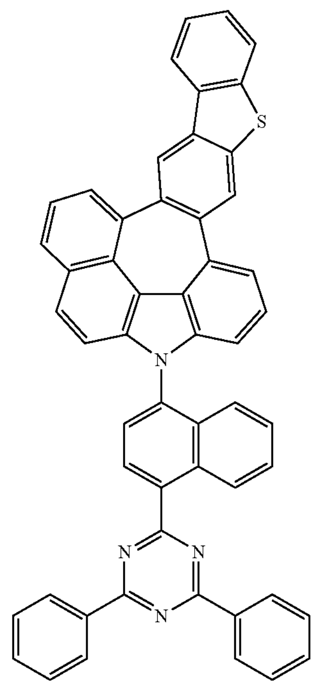

-continued
C-393
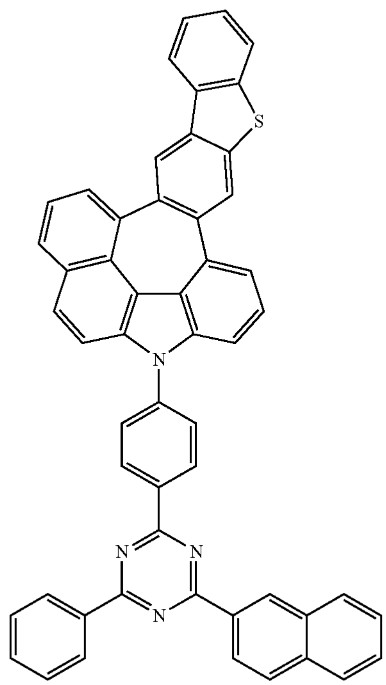
C-394
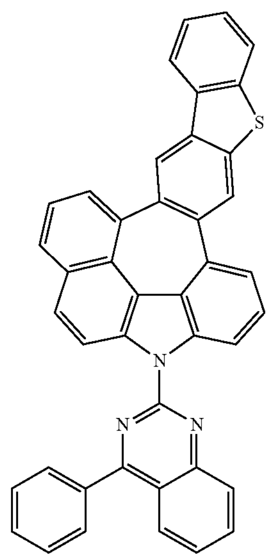
-continued
C-395
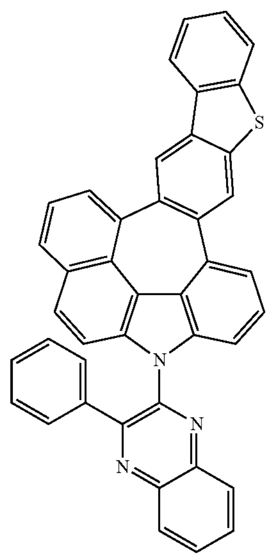
C-396
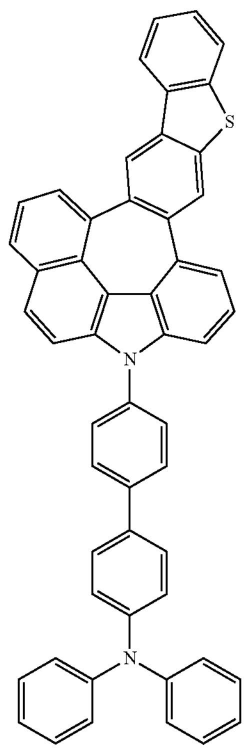

-continued
C-397
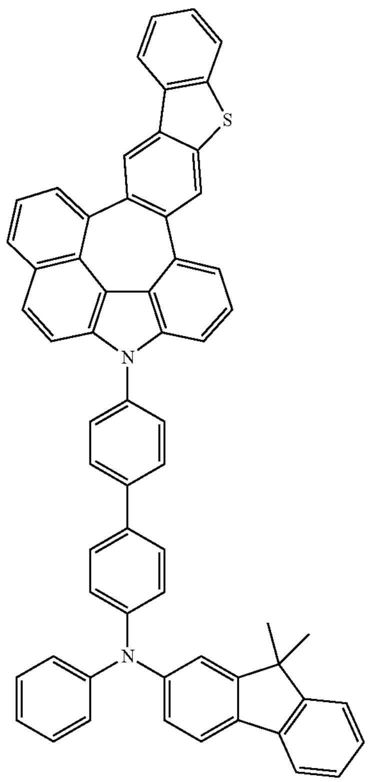
C-398
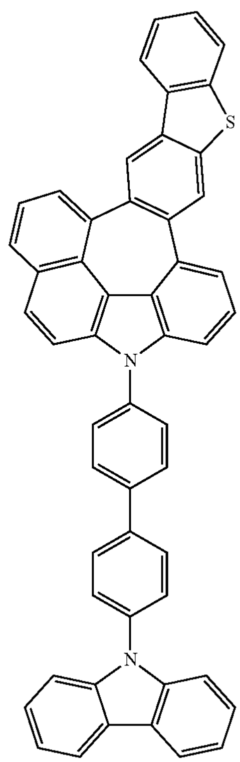
-continued
C-399
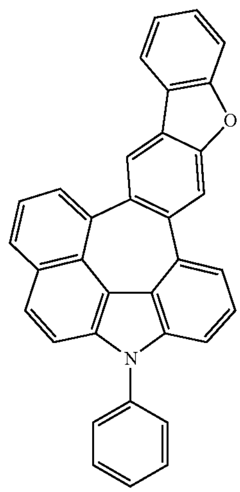
C-400
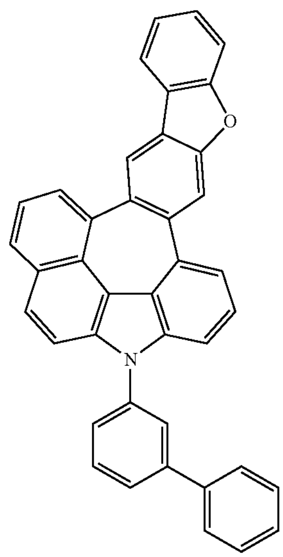
C-401
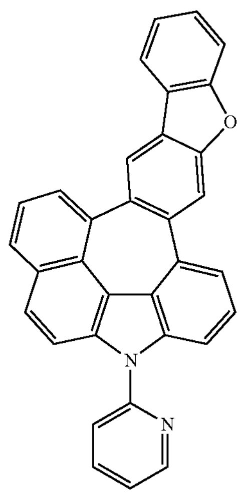

-continued
C-402
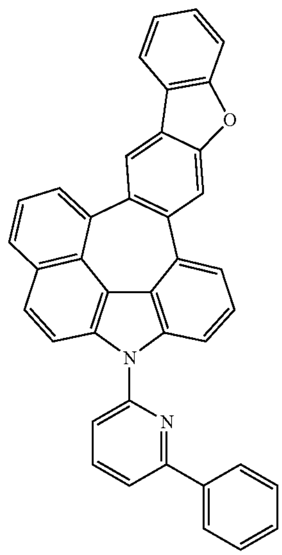
C-403
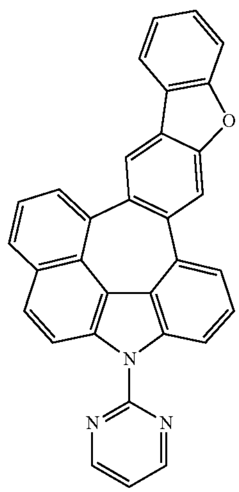
C-404
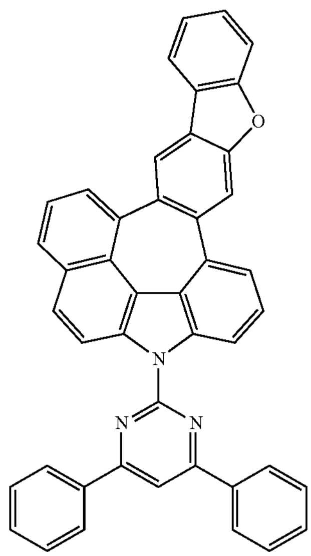
-continued
C-405
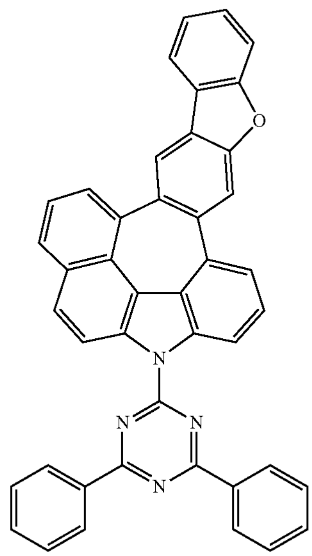
C-406
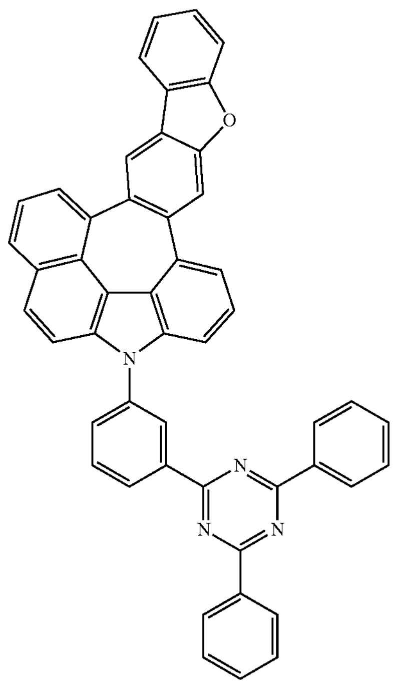

-continued
C-407
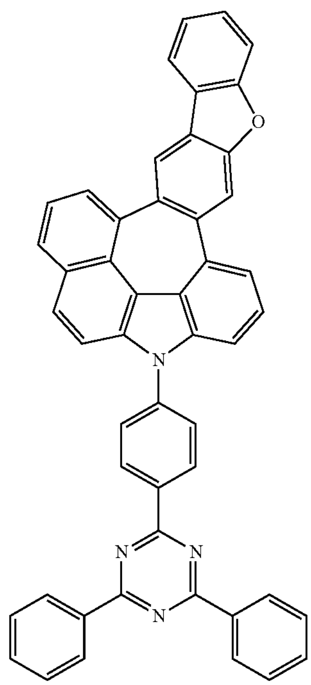
C-408
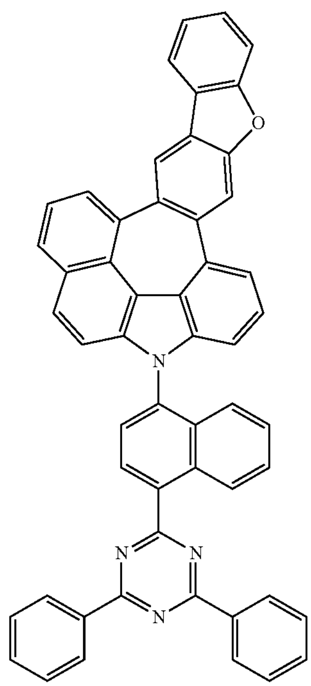
-continued
C-409
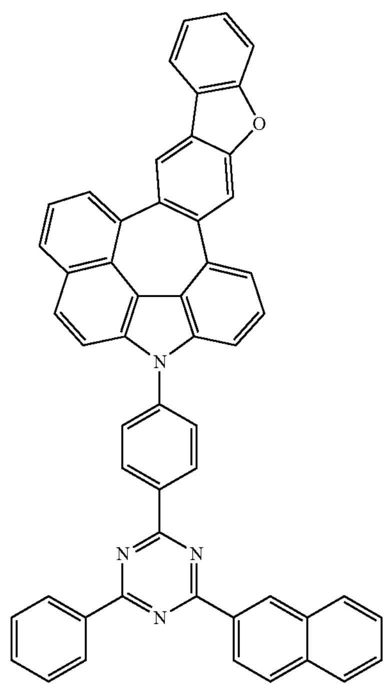
C-410
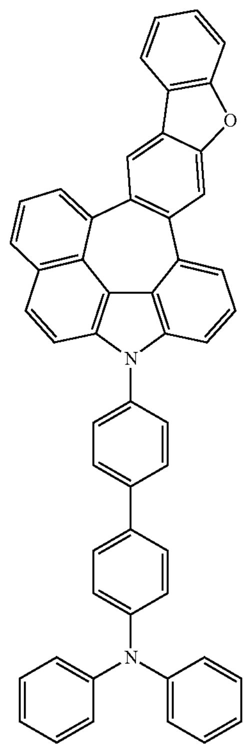

-continued
C-411
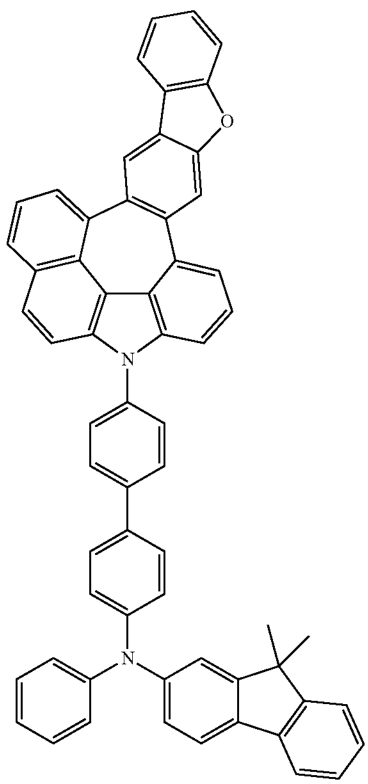
C-412
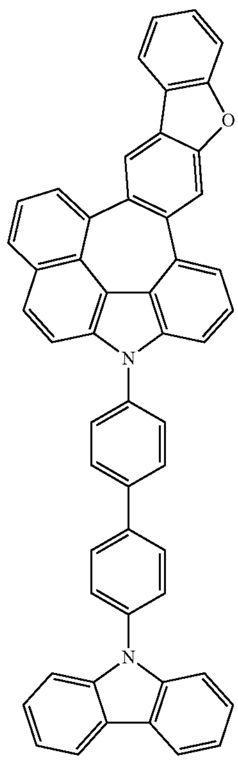
-continued
C-413
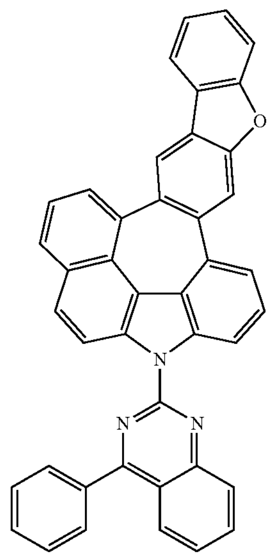
C-414
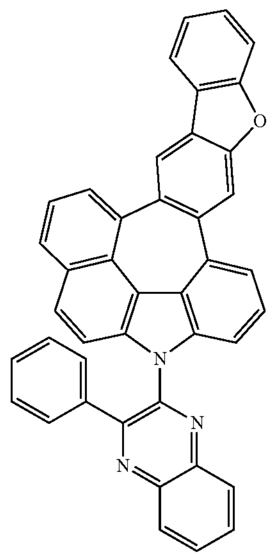
C-415
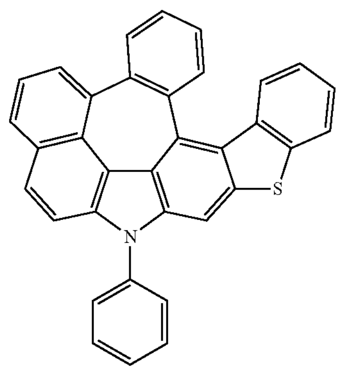

-continued
C-416
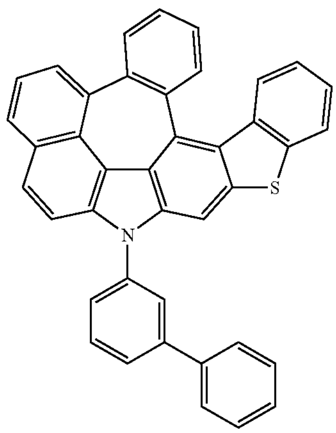
C-417
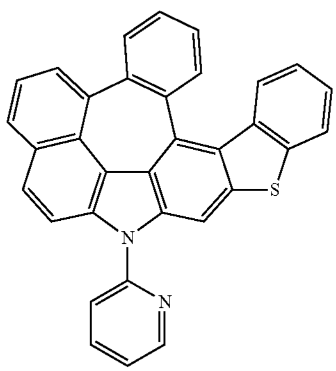
C-418
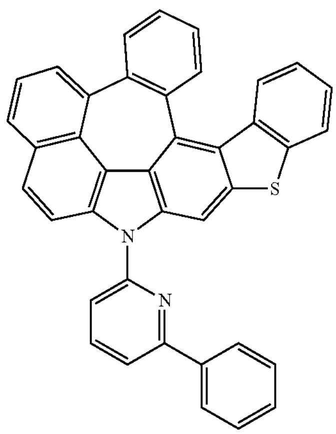
C-419
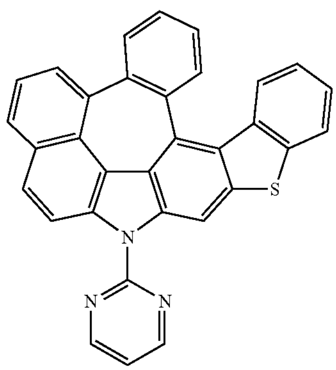
-continued
C-420
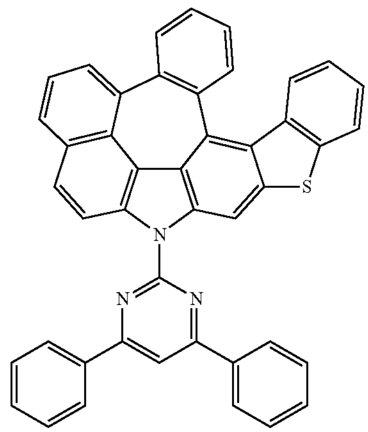
C-421
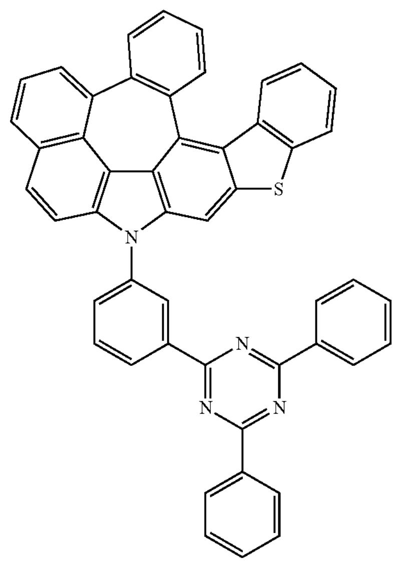
C-422
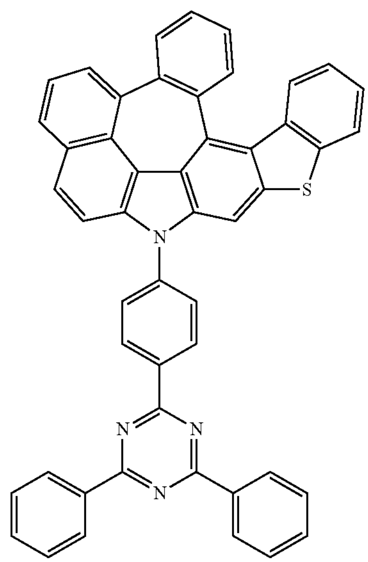

C-423
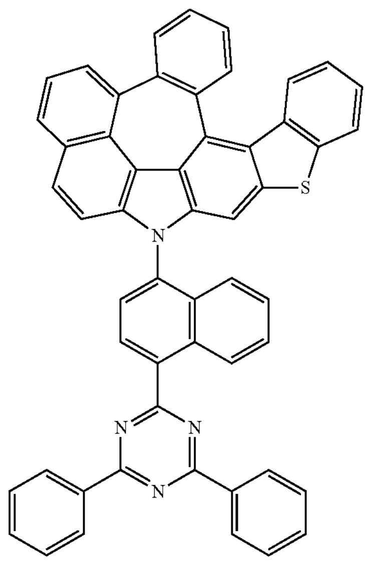
C-424
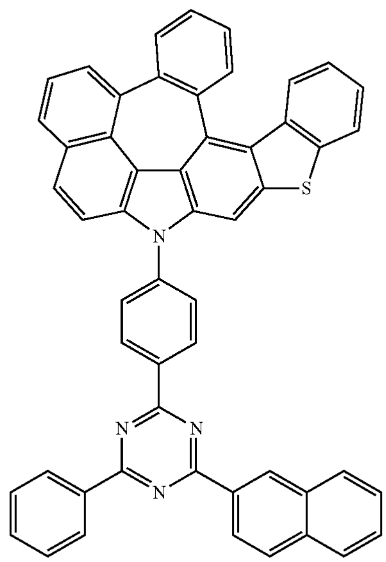
C-425
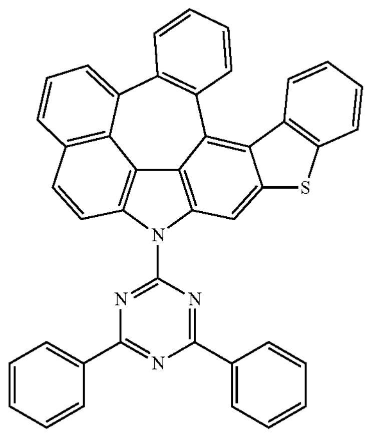
C-426
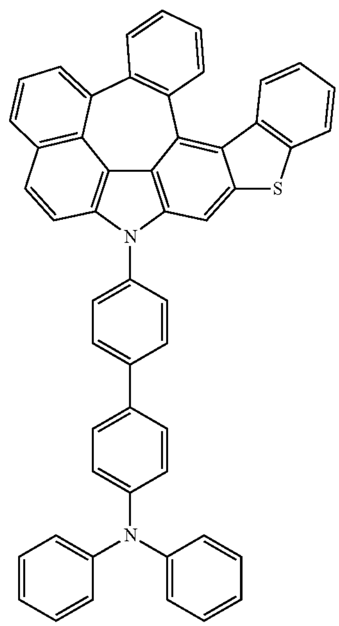
C-427
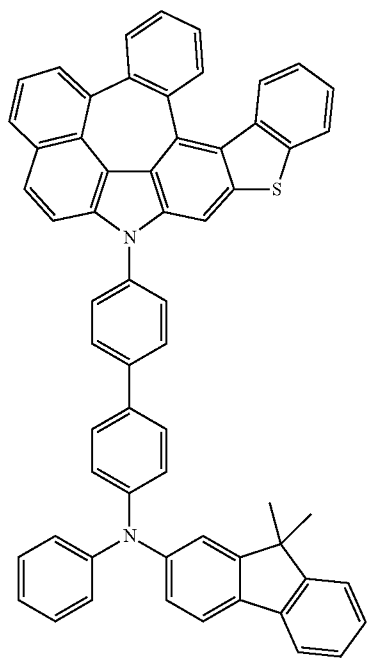

-continued
C-428
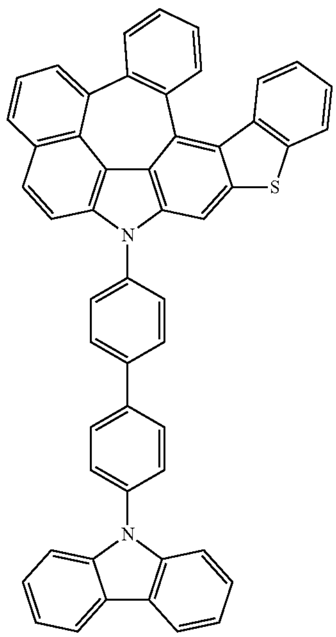
C-429
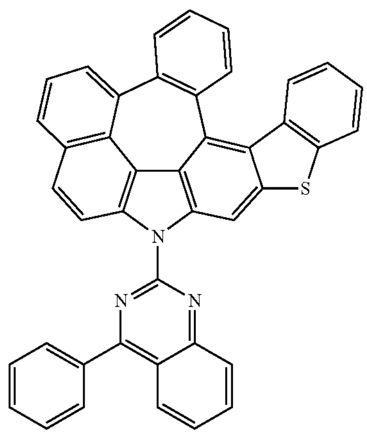
C-430
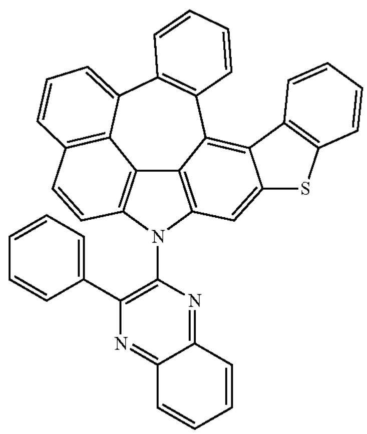
-continued
C-431
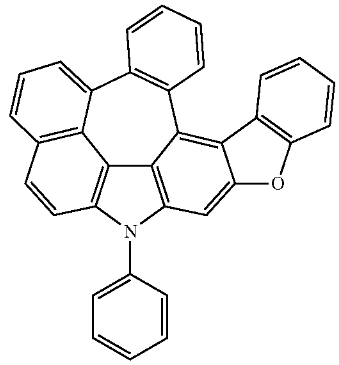
C-432
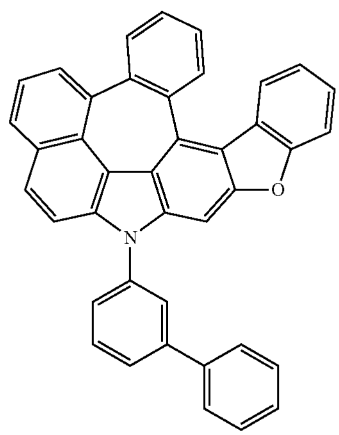
C-433
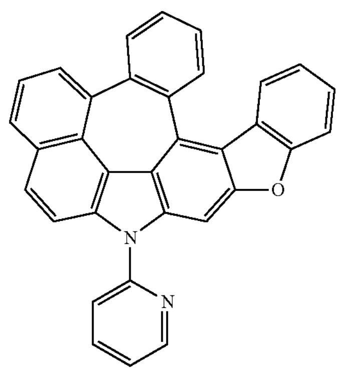
C-434
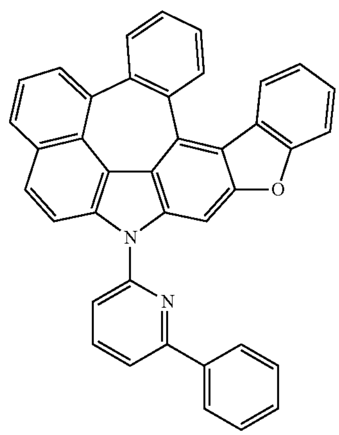

-continued
C-435
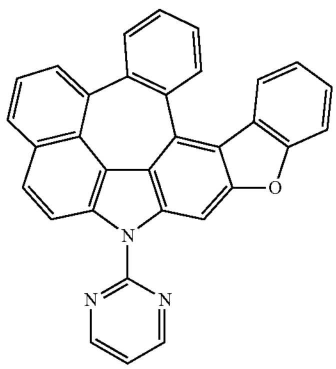
C-436
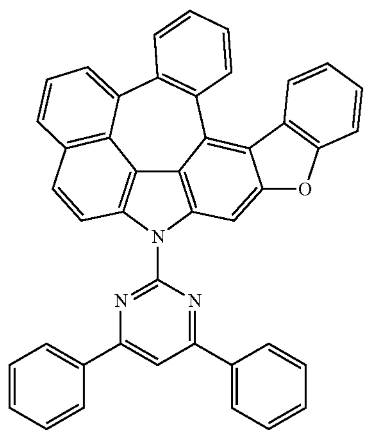
C-437
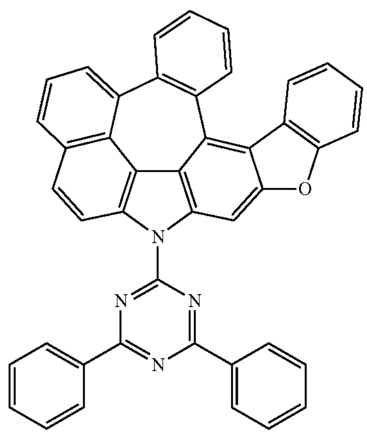
-continued
C-438
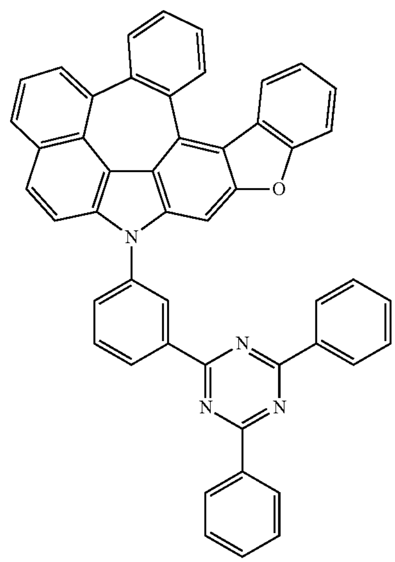
C-439
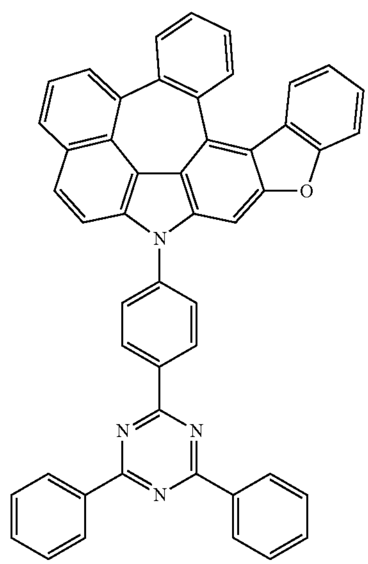

-continued
C-440
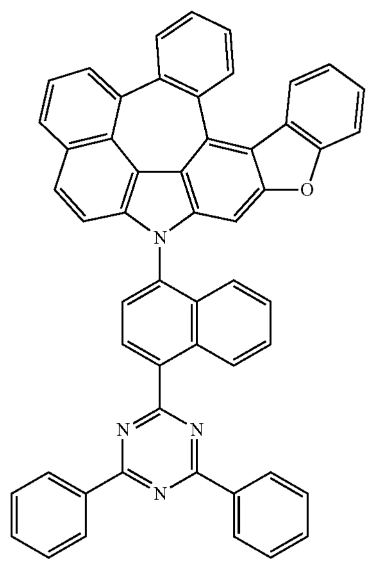
C-441
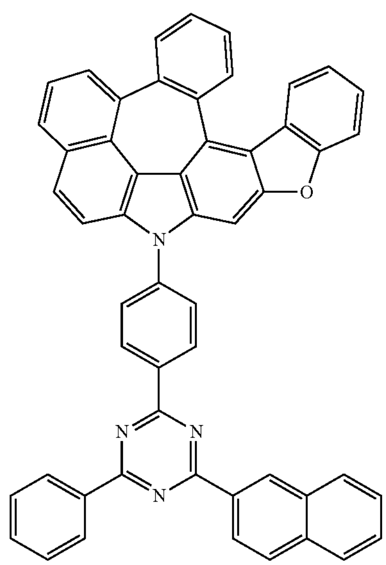
C-442
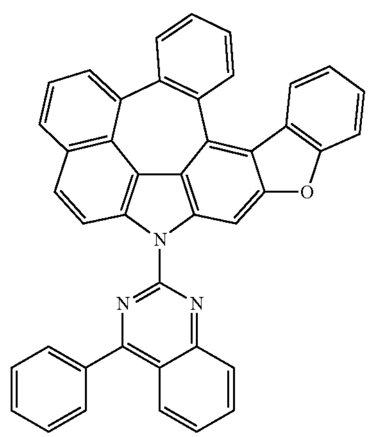
-continued
C-443
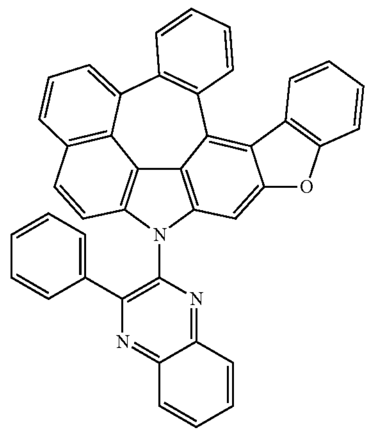
C-444
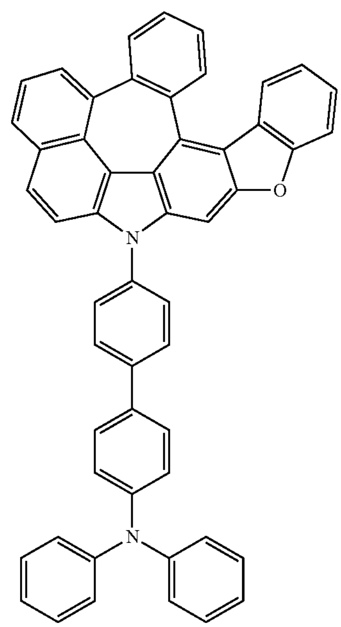

-continued
C-445
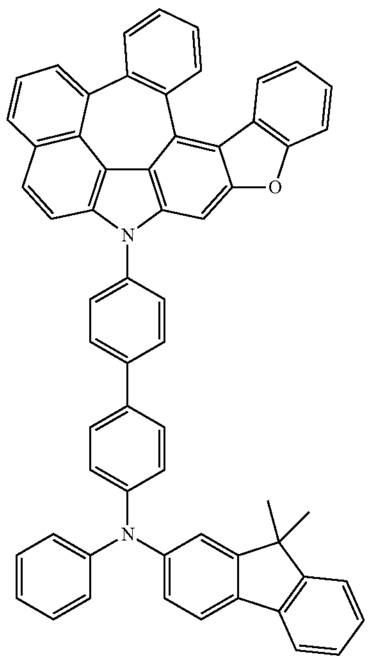
C-446
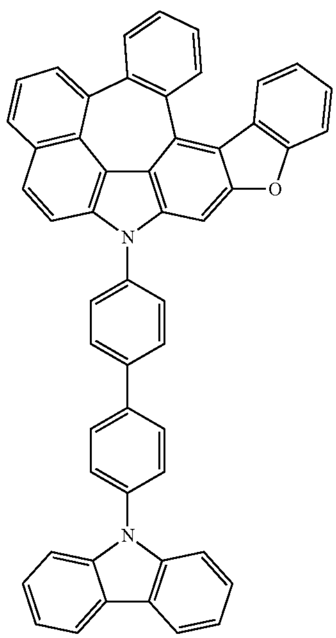
C-447
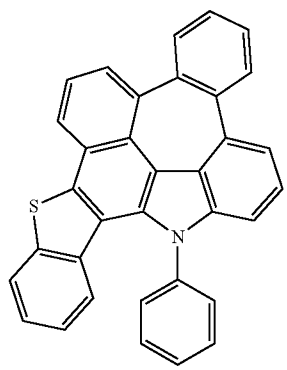
-continued
C-448
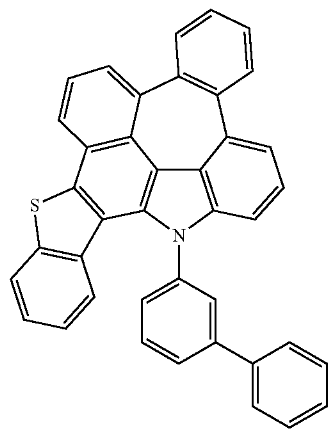
C-449
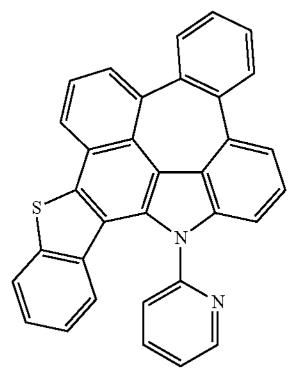
C-450
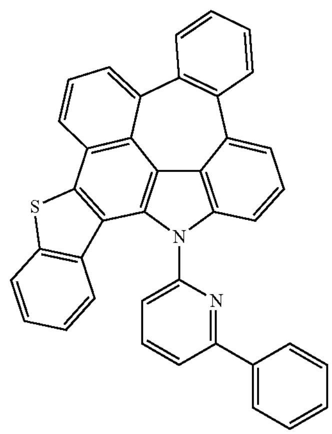
C-451
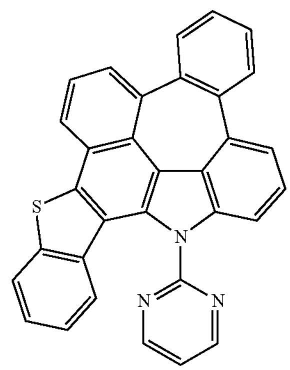

-continued
C-452
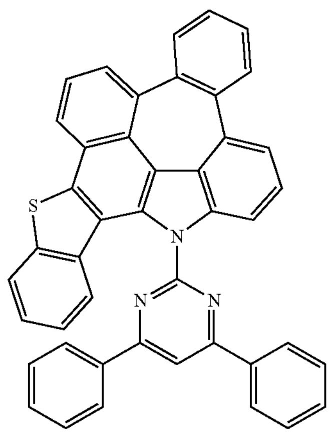
C-453
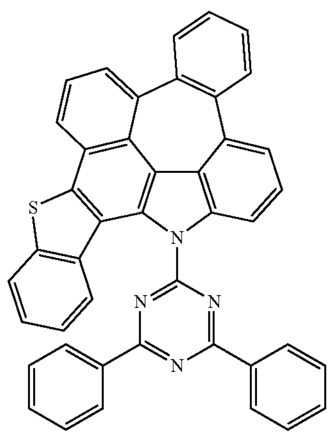
C-454
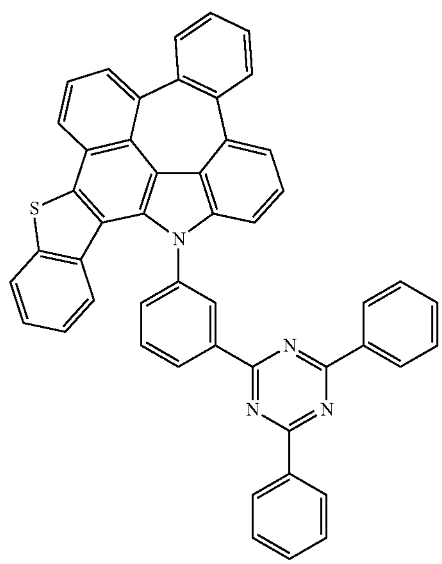
-continued
C-455
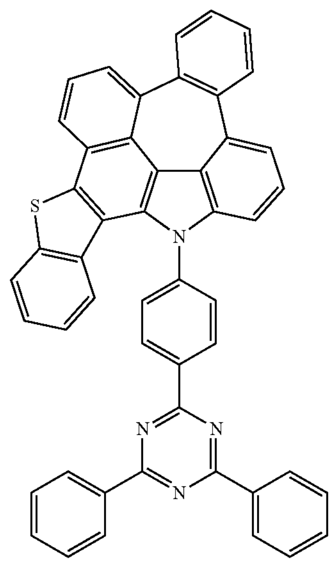
C-456
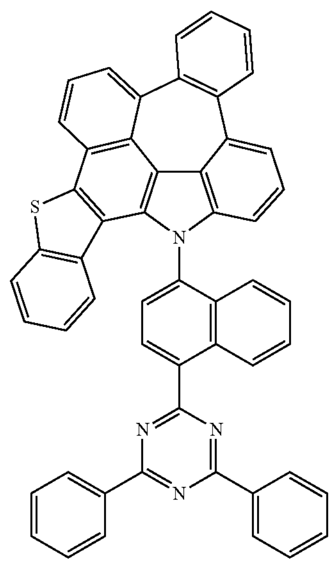

-continued
C-457
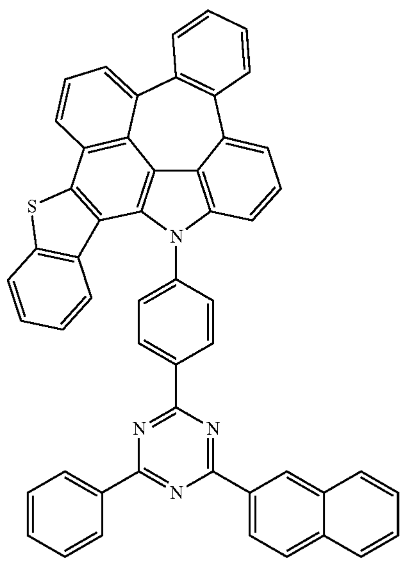
C-458
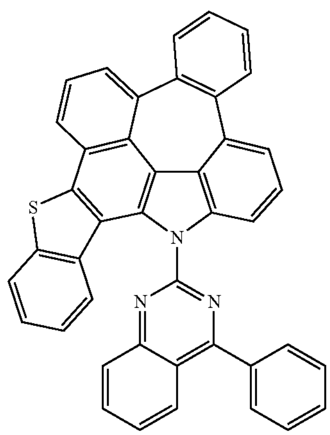
C-459
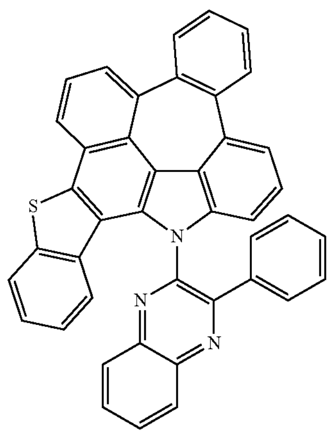
-continued
C-460
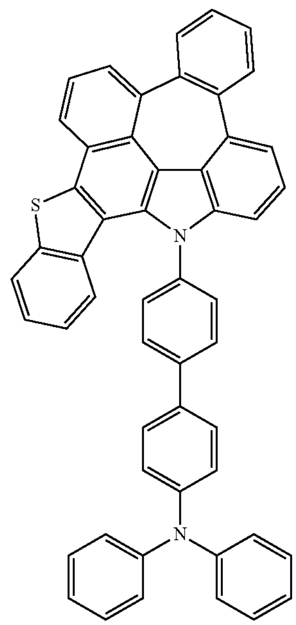
C-461
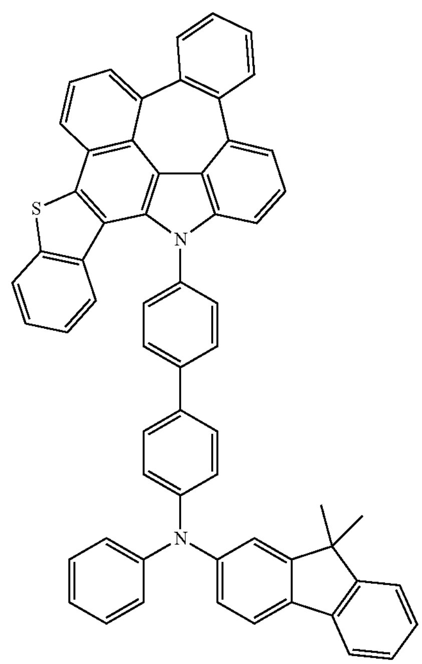

-continued
C-462
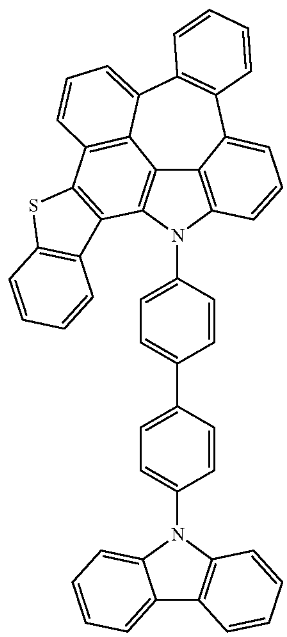
C-463
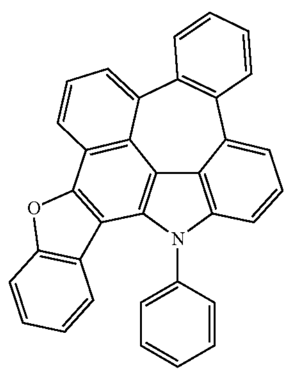
C-464
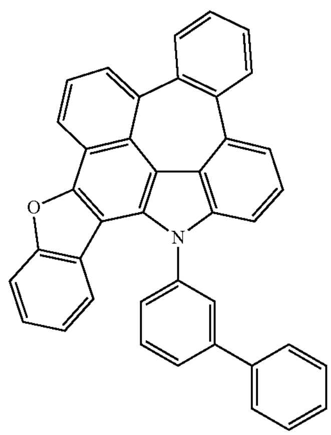
-continued
C-465
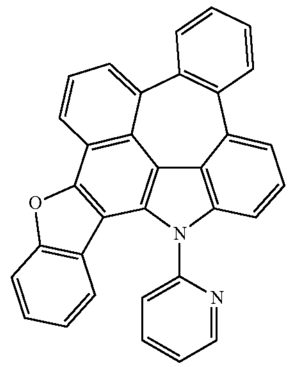
C-466
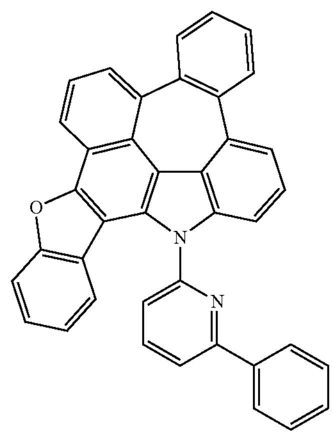
C-467
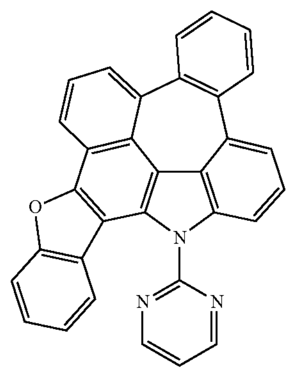
C-468
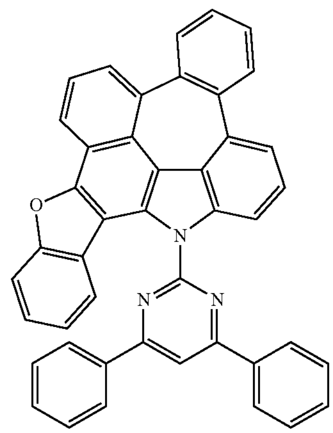

-continued
C-469
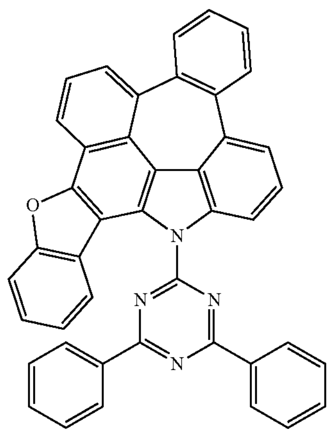
C-470
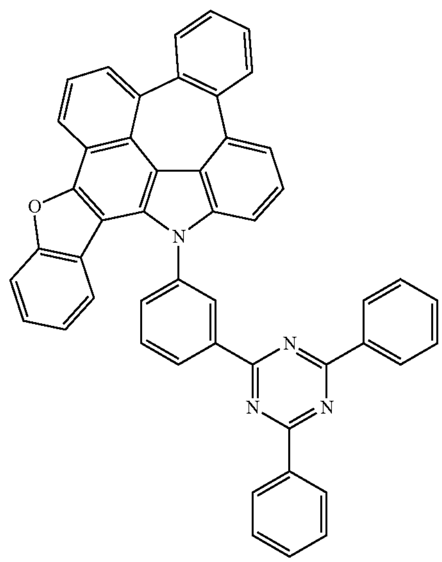
C-471
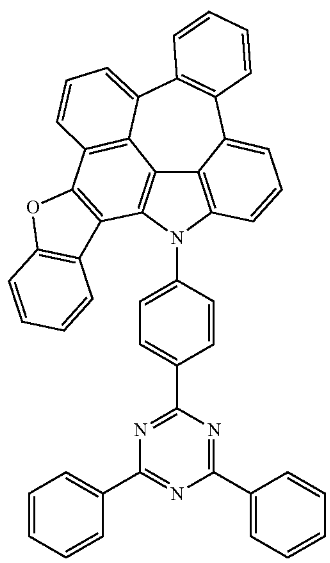
-continued
C-472
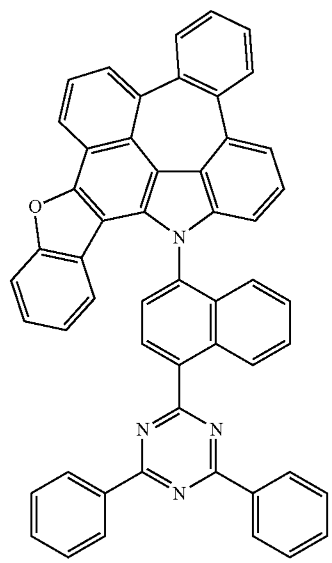
C-473
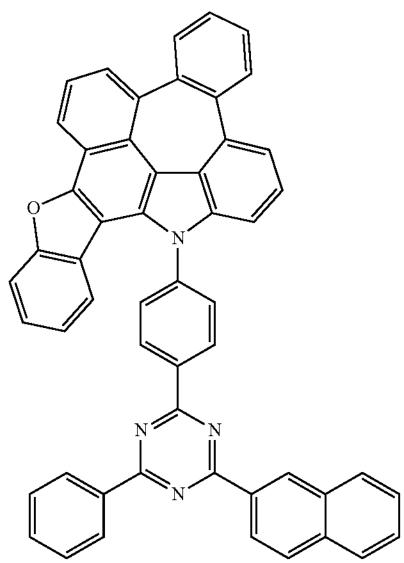
C-474
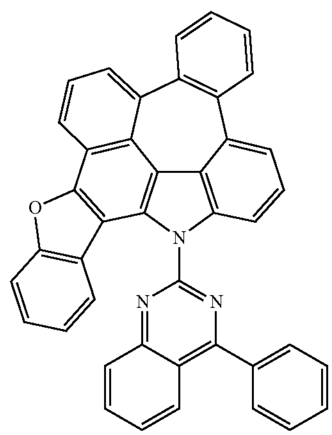

-continued
C-475
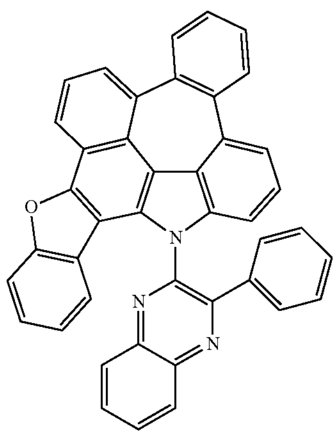
C-476
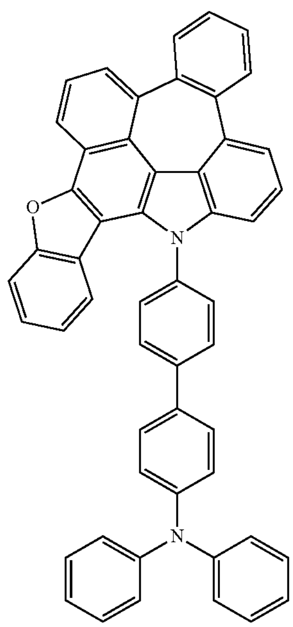
-continued
C-477
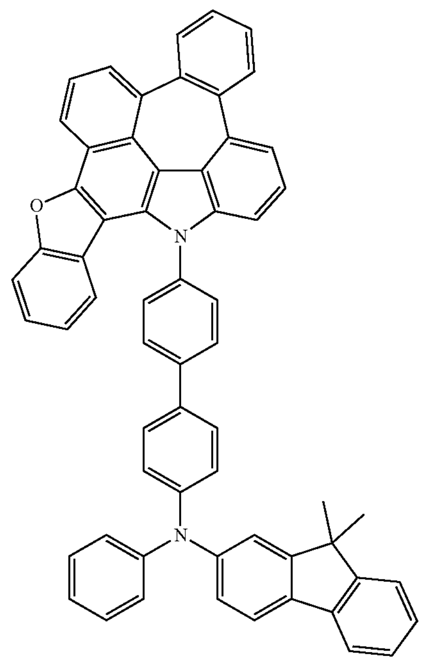
C-478
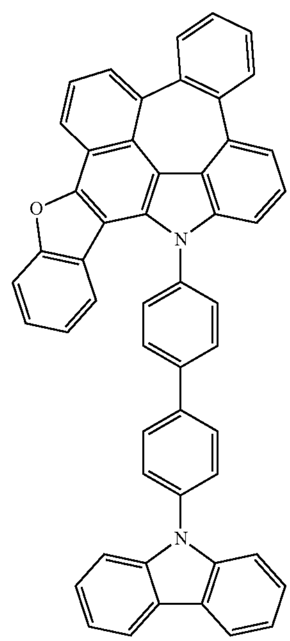

-continued
C-479
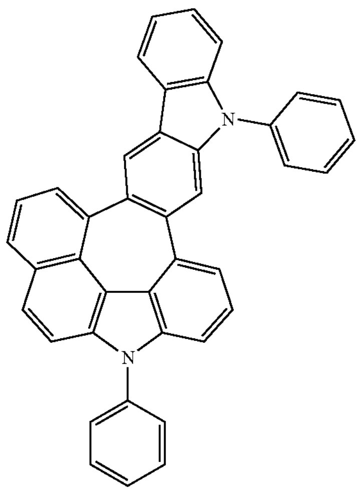
C-480
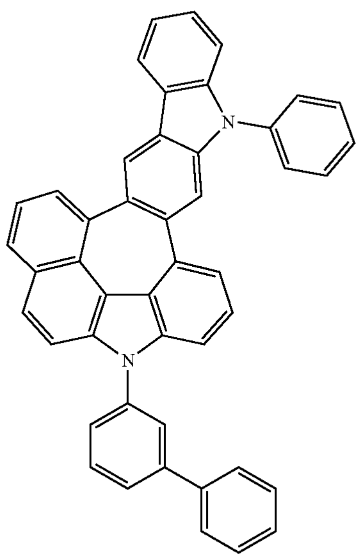
C-481
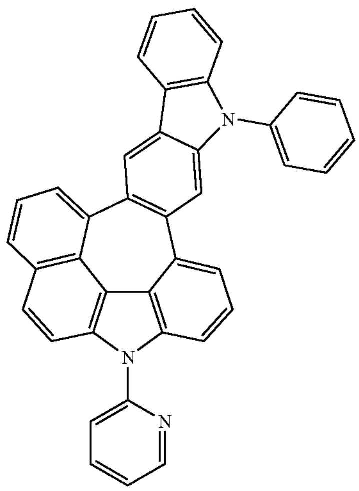
-continued
C-482
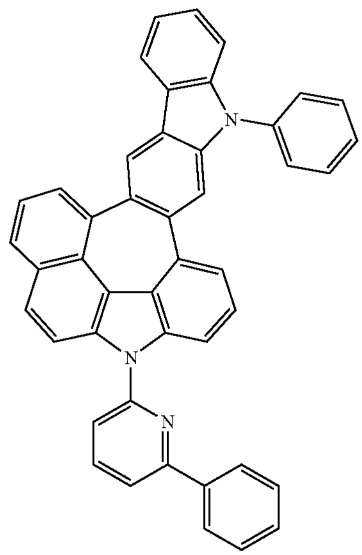
C-483
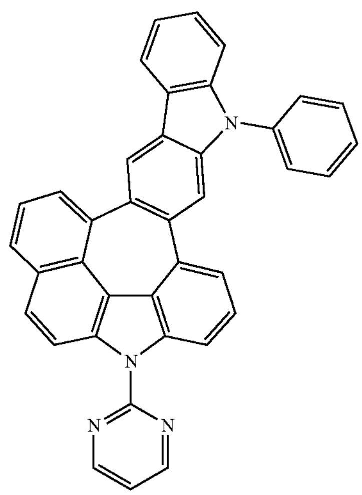
C-484
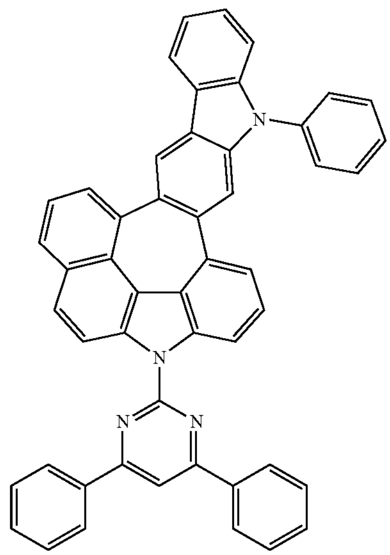

-continued
C-485
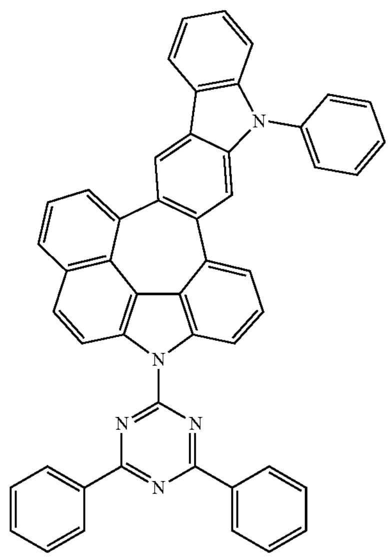
C-486
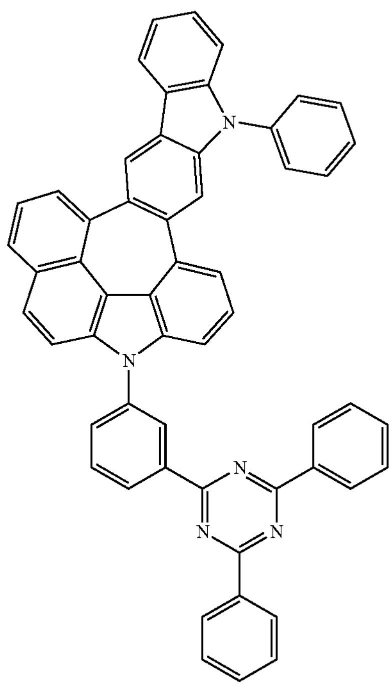
-continued
C-487
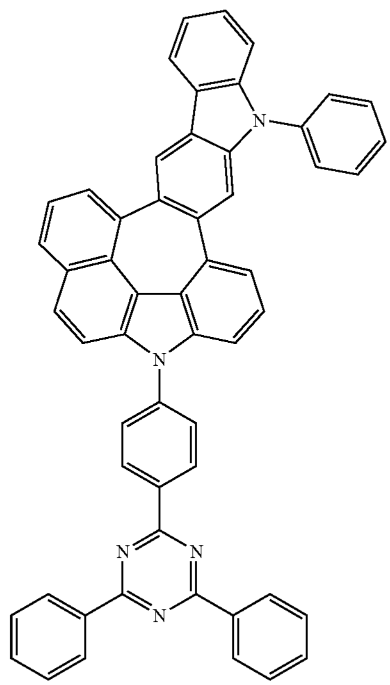
C-488
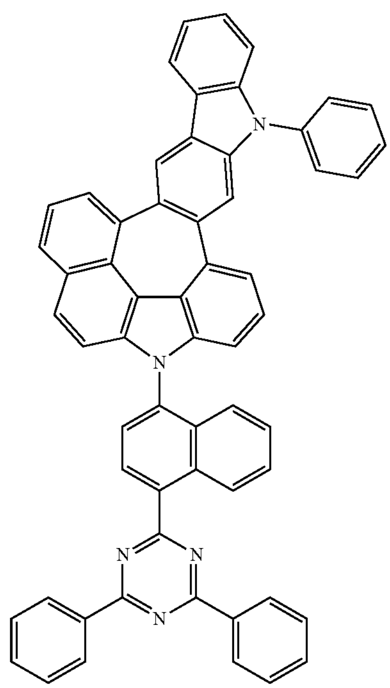

-continued
C-489
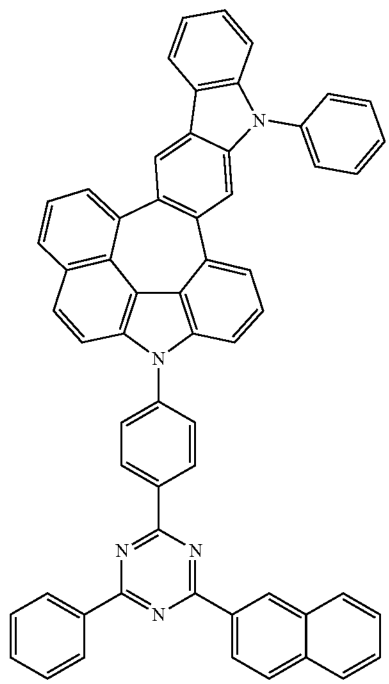
C-490
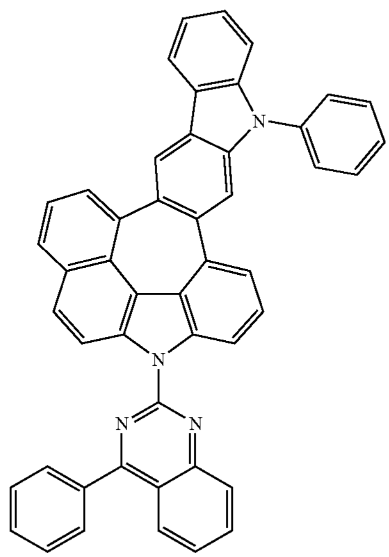
-continued
C-491
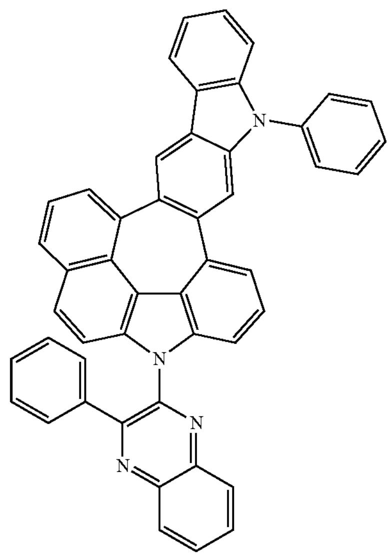
C-492
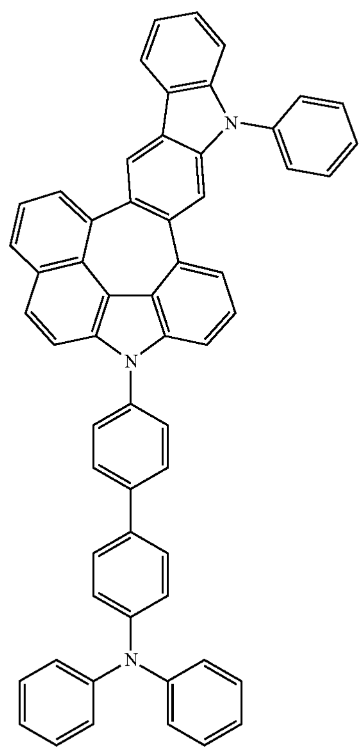

-continued
C-493
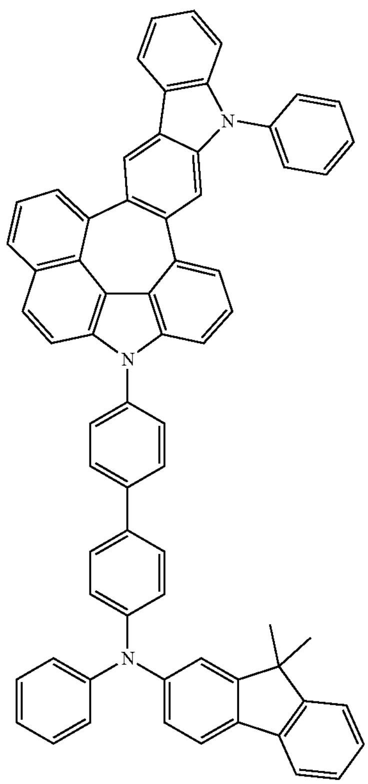
C-494
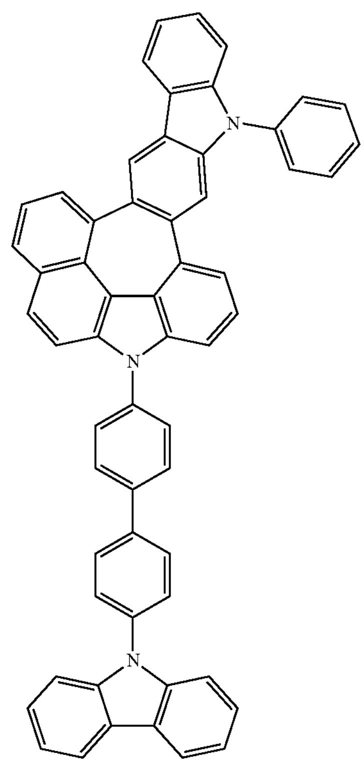
-continued
C-495
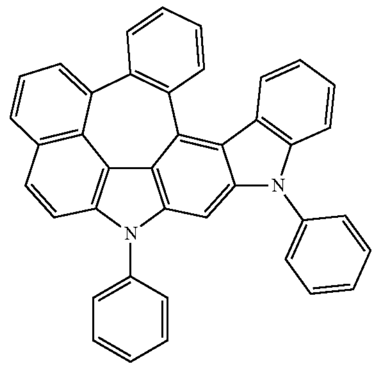
C-496
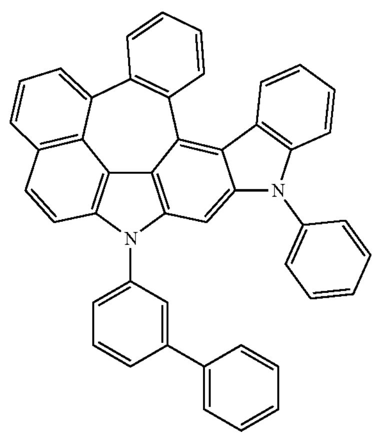
C-497
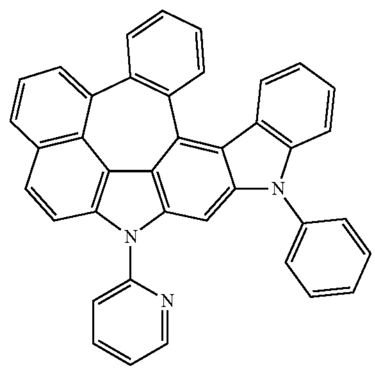
C-498
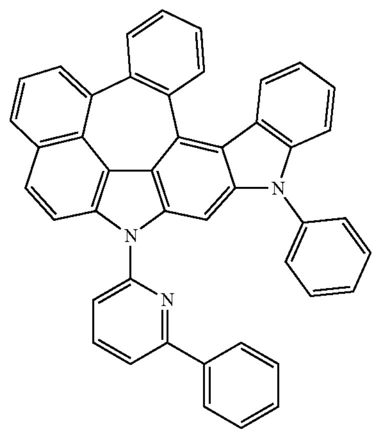

-continued
C-499
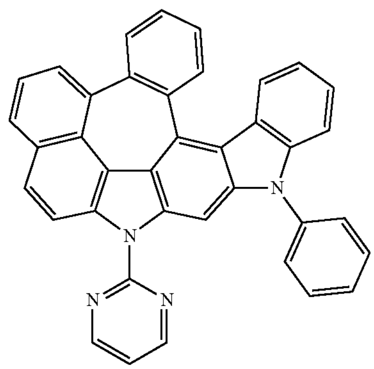
C-500
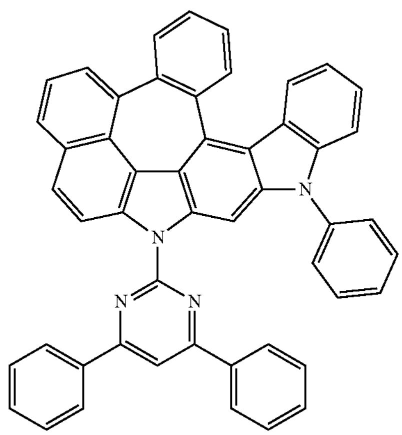
C-501
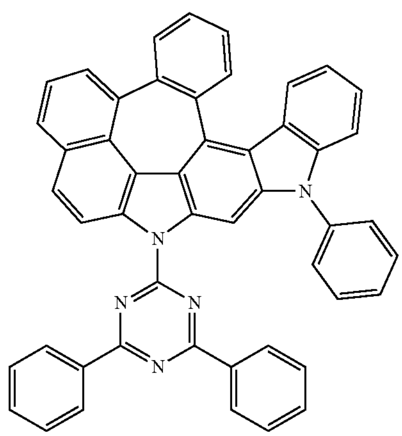
-continued
C-502
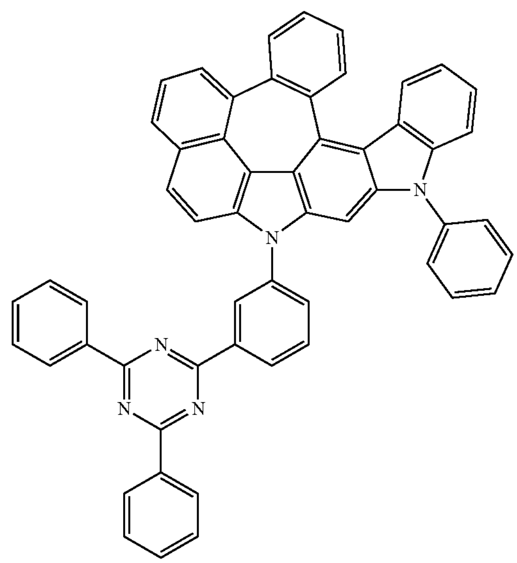
C-503
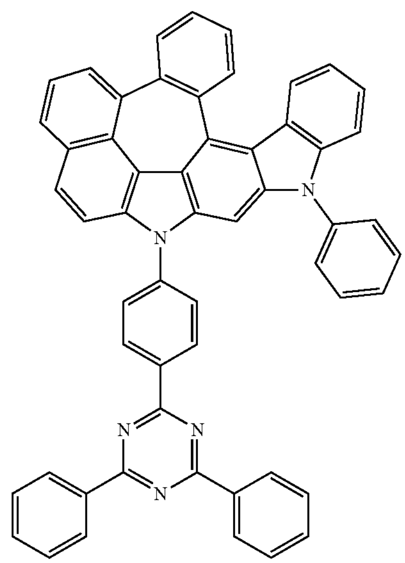

-continued
C-504
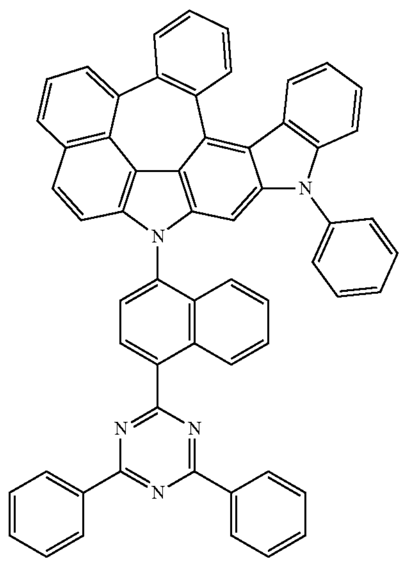
C-505
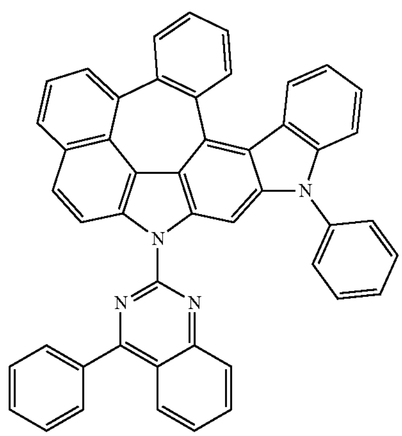
C-506
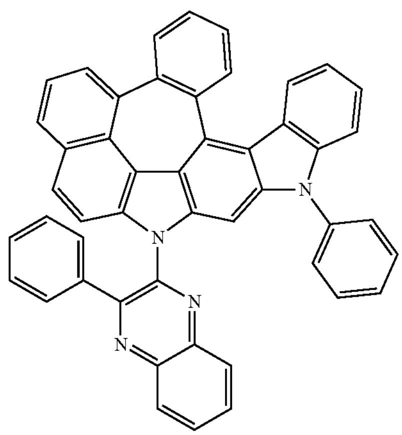
-continued
C-507
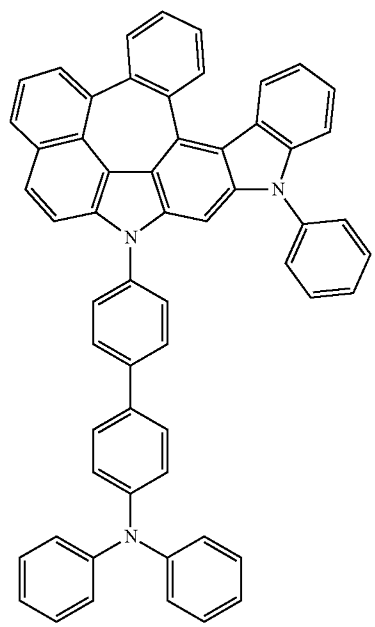
C-508
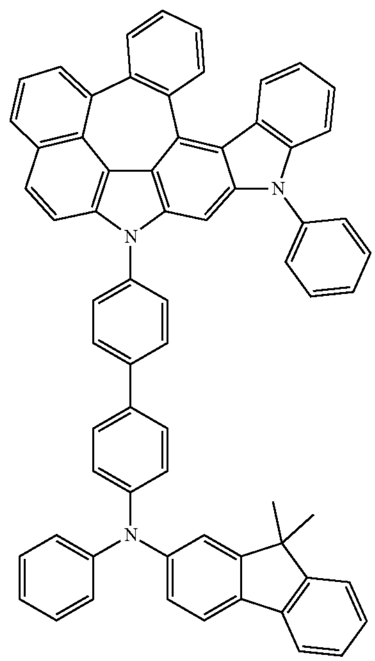

-continued
C-509
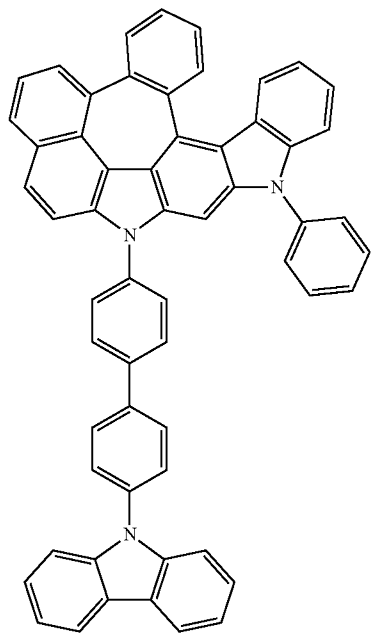
C-510
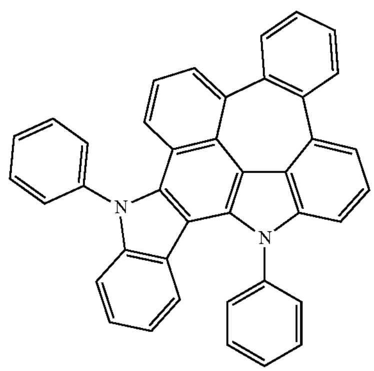
C-511
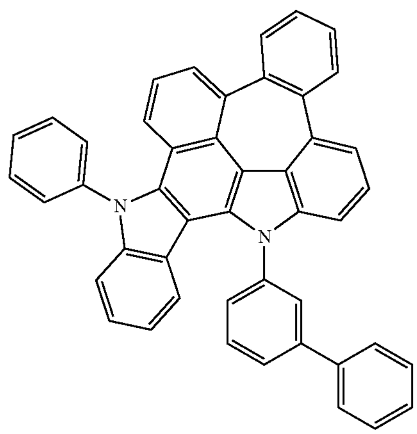
-continued
C-512
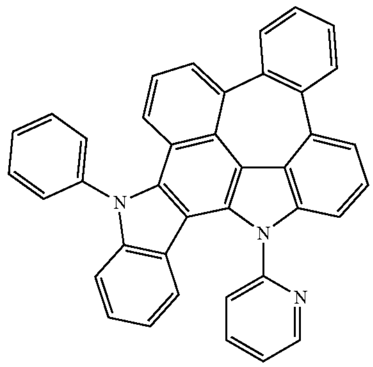
C-513
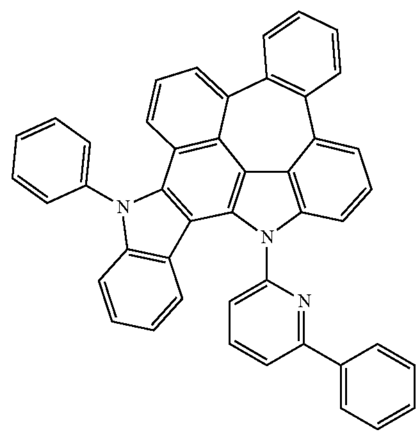
C-514
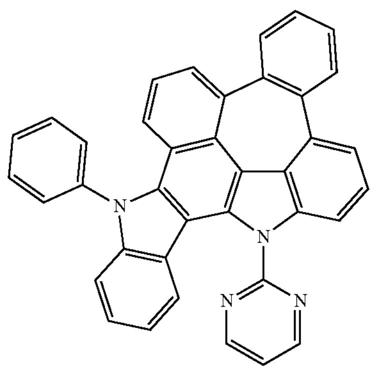
C-515
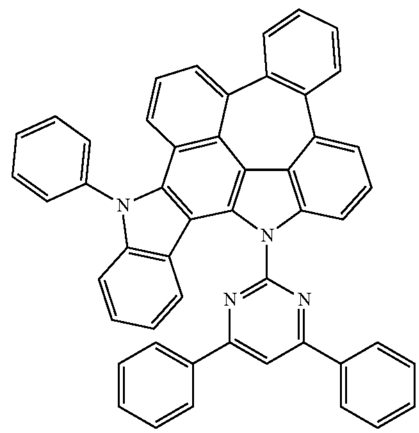

-continued
C-516
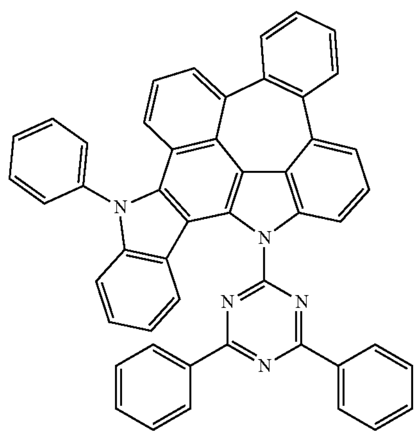
C-517
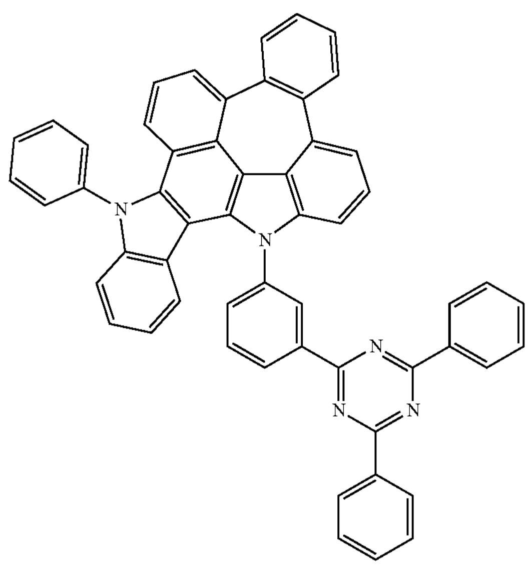
C-518
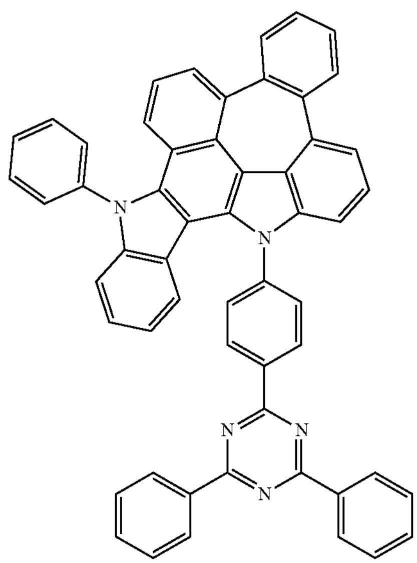
-continued
C-519
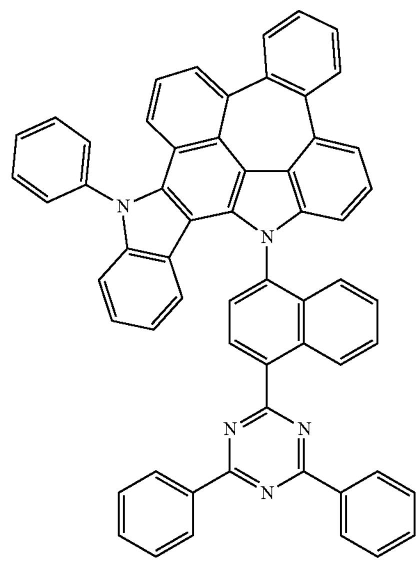
C-520
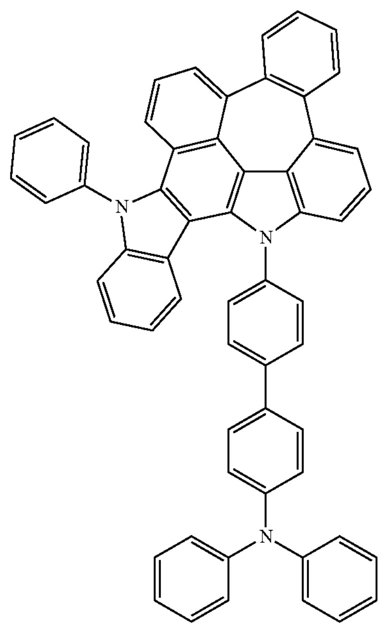

-continued
C-521
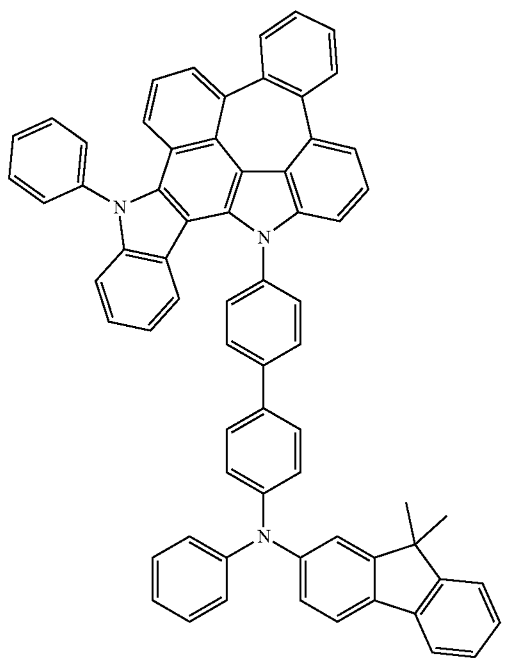
C-522
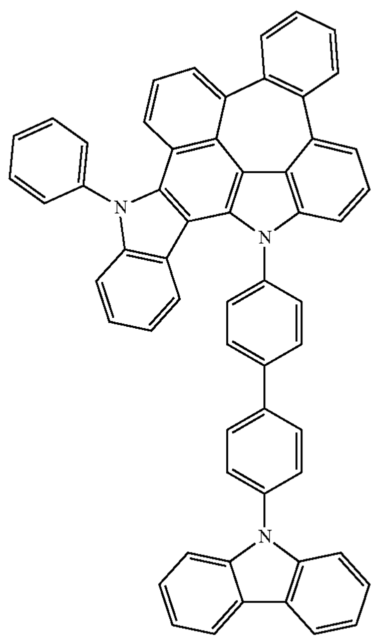
-continued
C-523
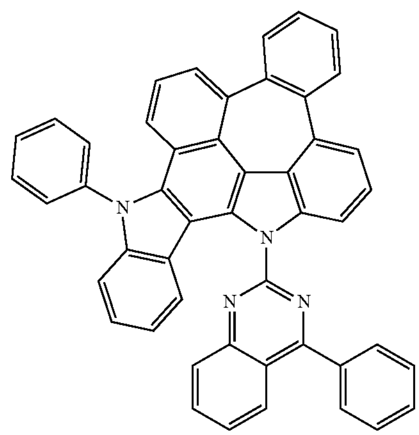
C-524
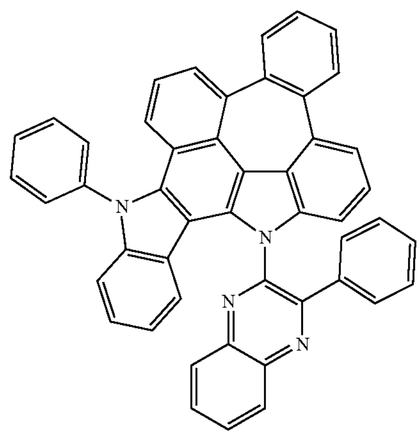
C-525
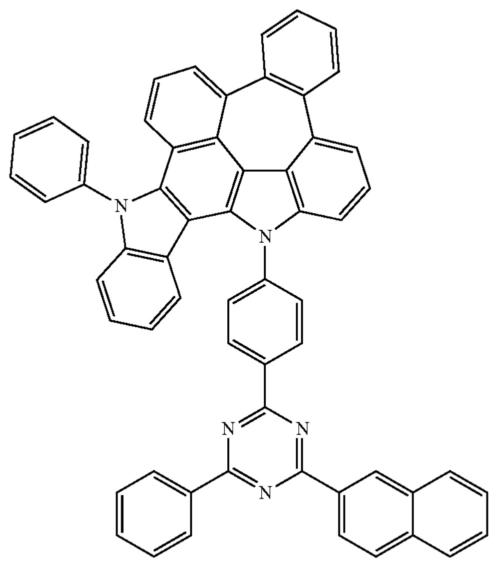

-continued
C-526
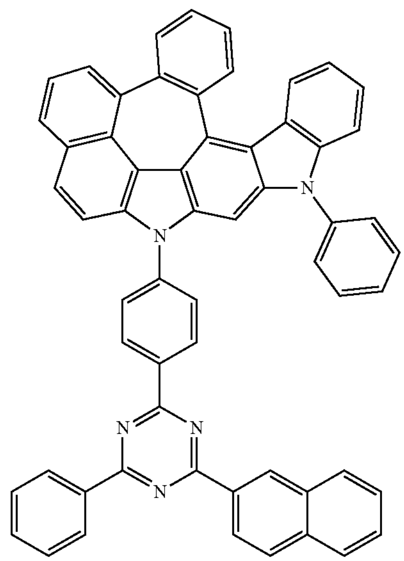
C-527
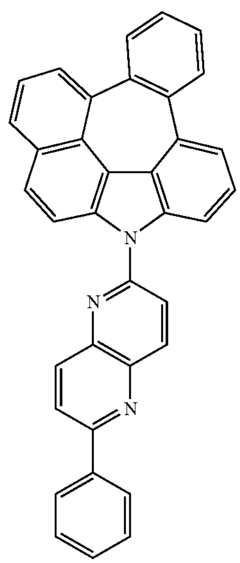
C-528
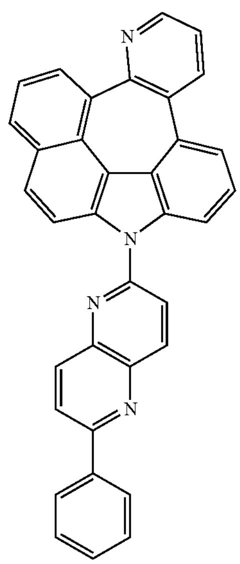
-continued
C-529
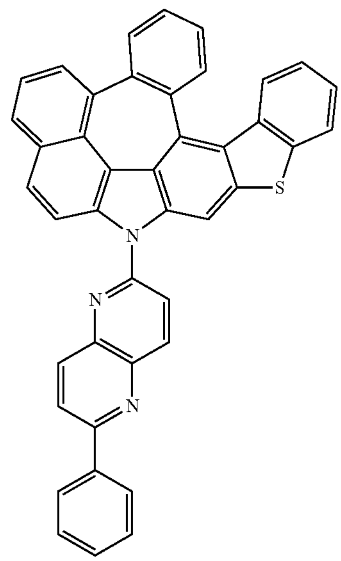
C-530
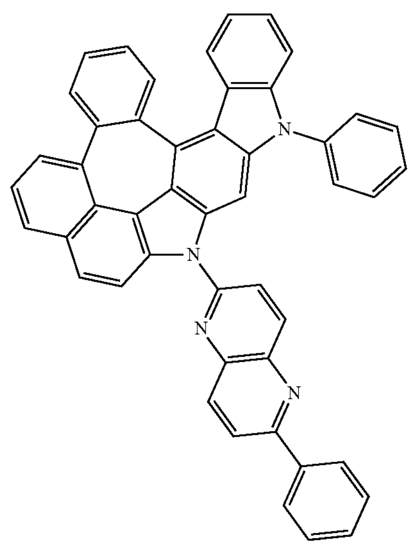
C-531
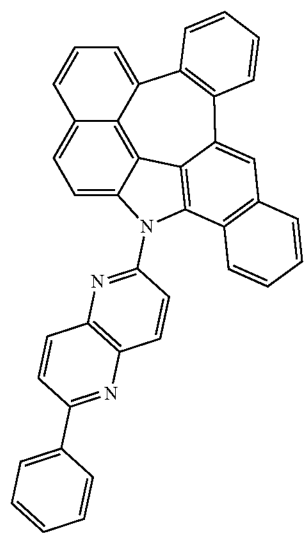

-continued
C-532
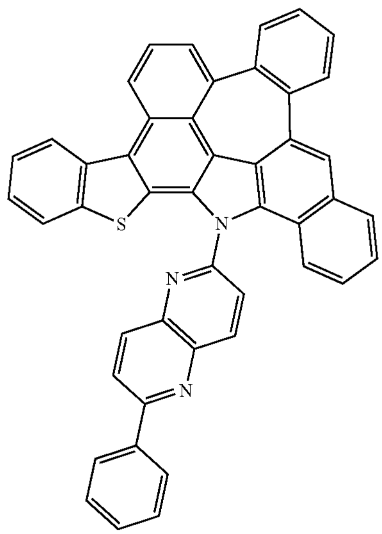
C-533
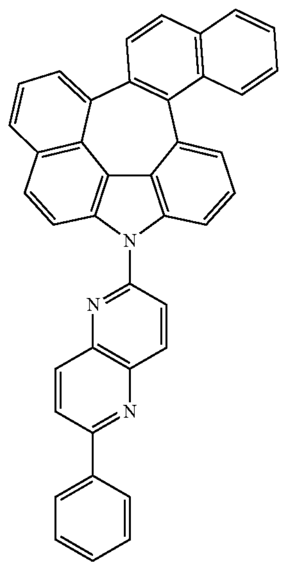
C-534
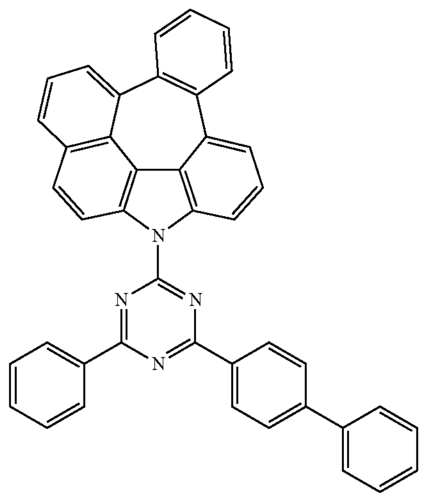
-continued
C-535
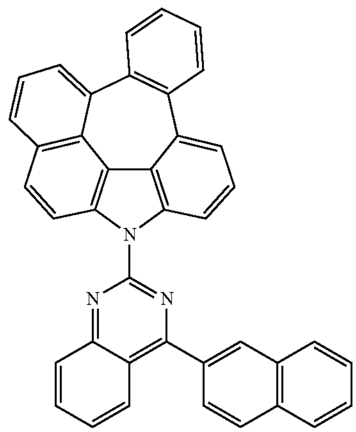
C-536
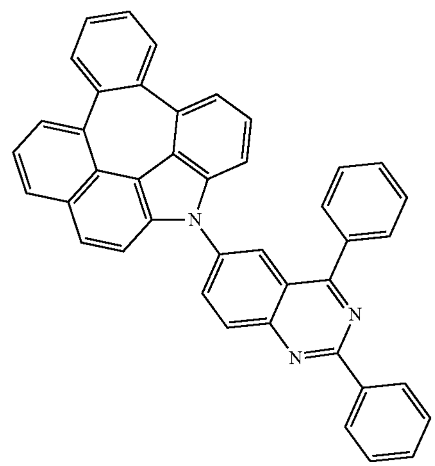
C-537
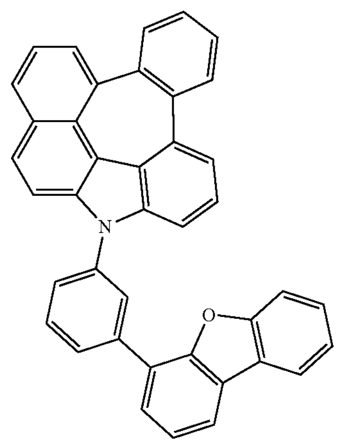

-continued
C-538
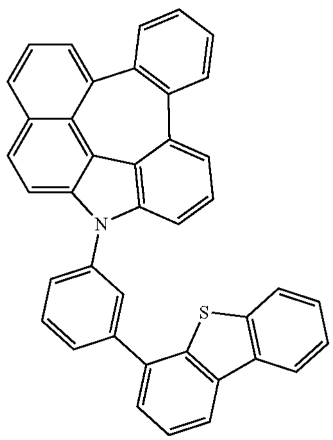
C-539
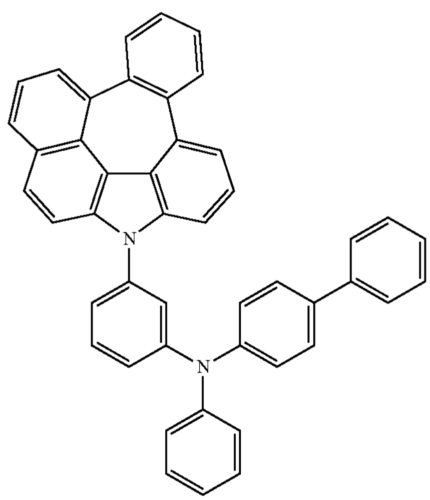
C-540
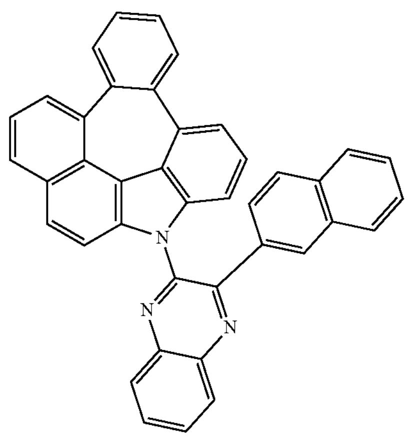
-continued
C-541
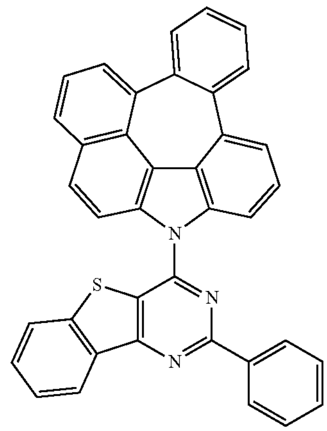
C-542
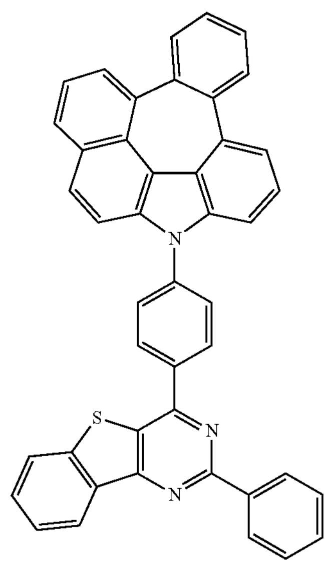
C-543
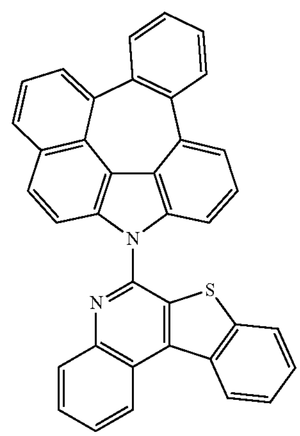

-continued
C-544
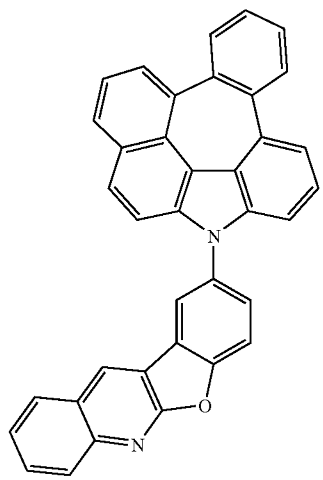
C-545
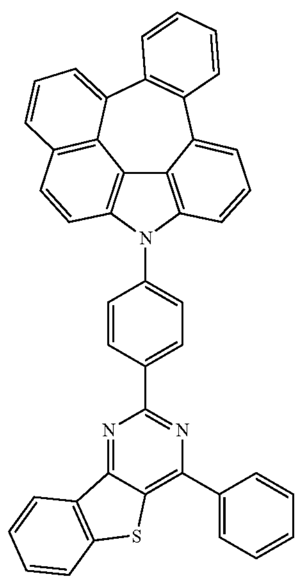
C-546
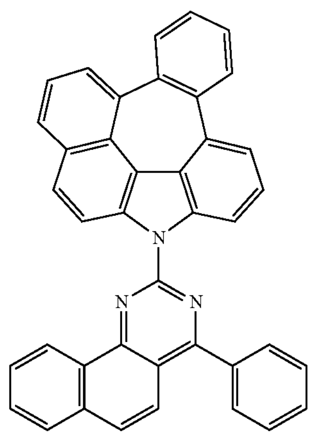
-continued
C-547
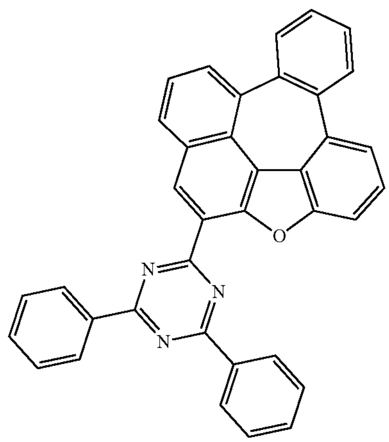
C-548
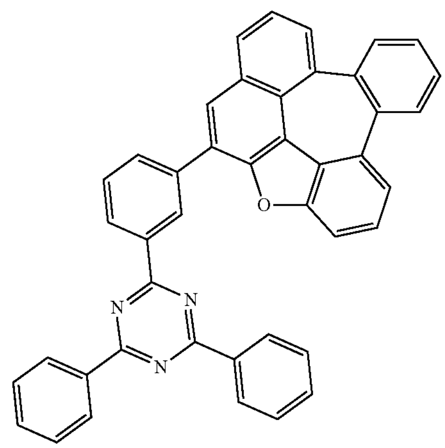
C-549
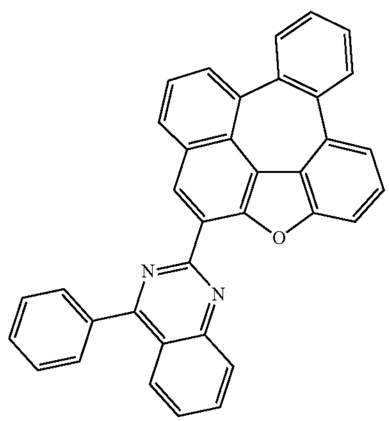

C-550
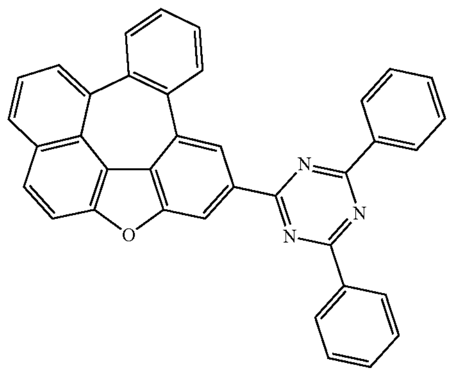
C-551
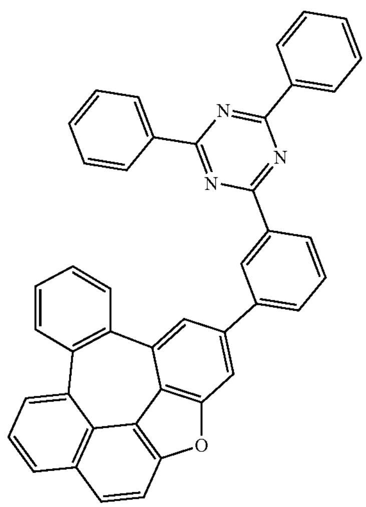
C-552
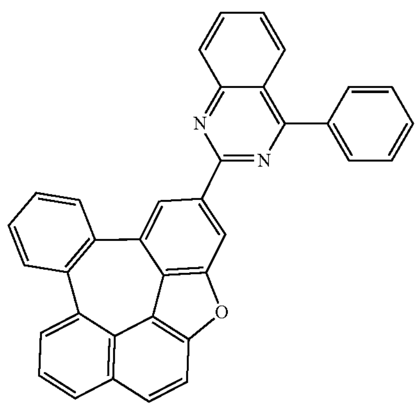
C-553
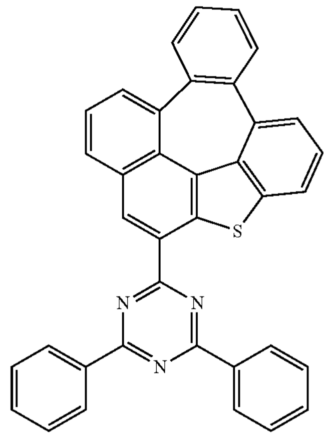
C-554
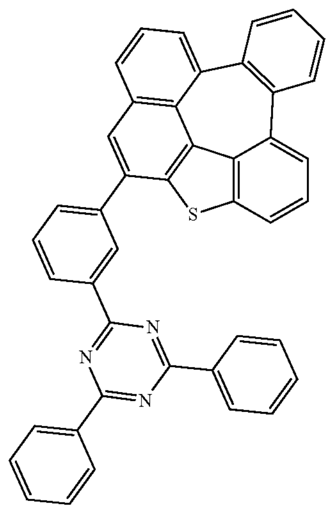
C-555
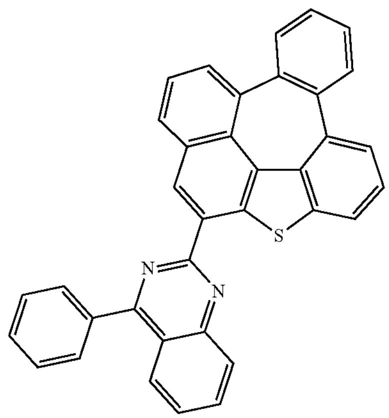

-continued
C-556
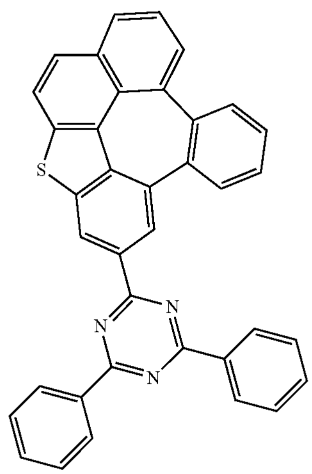
C-557
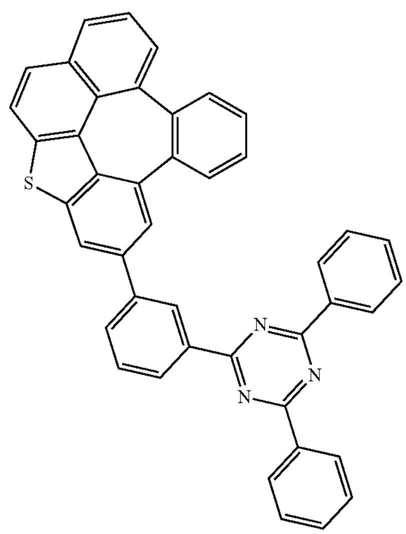
C-558
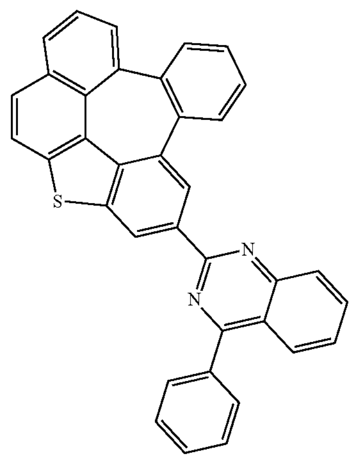
-continued
C-559
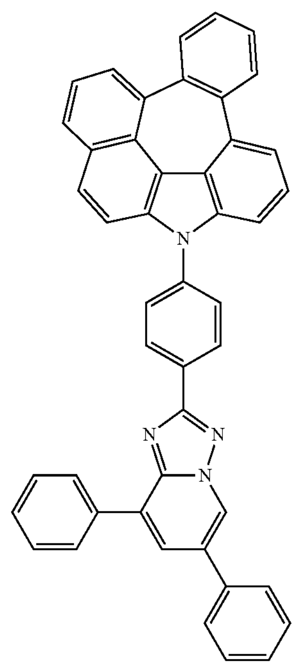
C-560
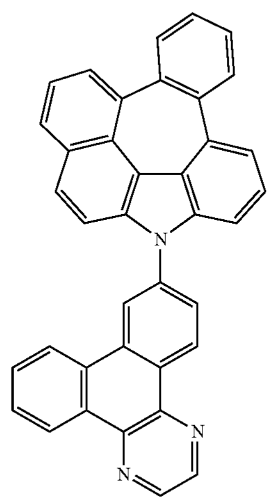

-continued
C-561
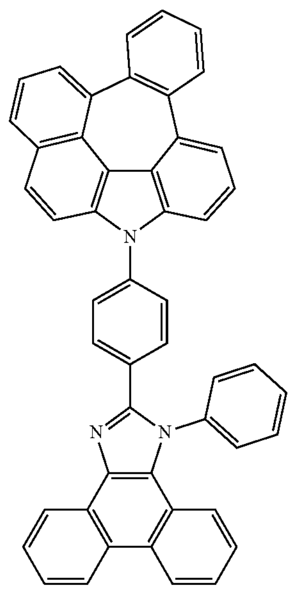
C-562
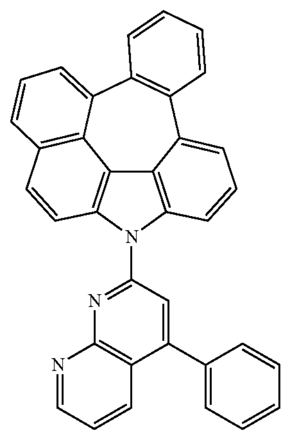
C-563
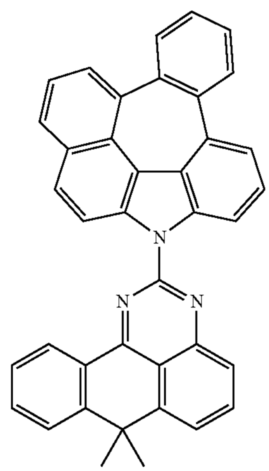
-continued
C-564
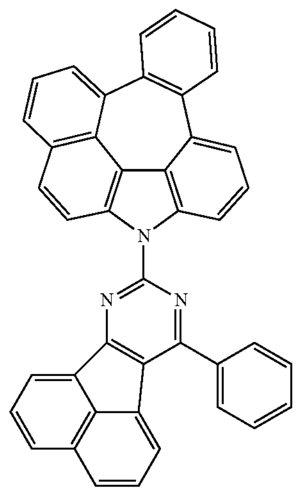
C-565
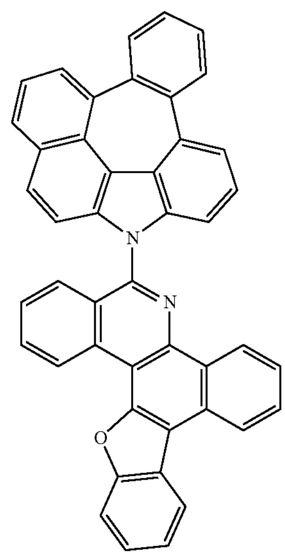
C-566
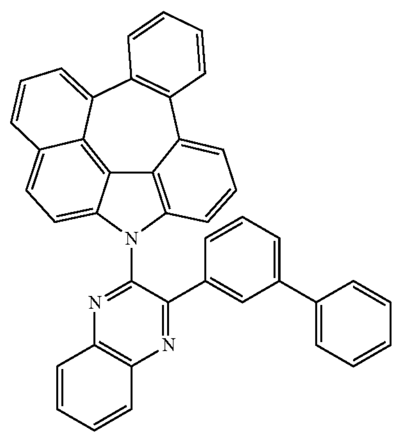

-continued
C-567
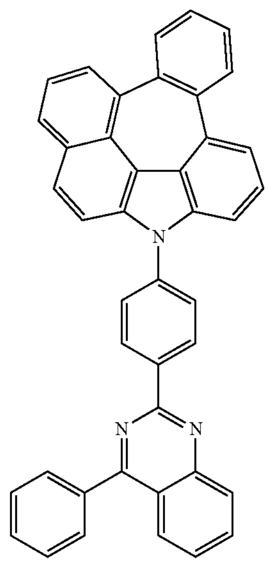
C-568
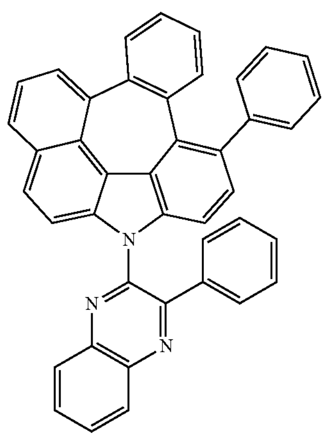
C-569
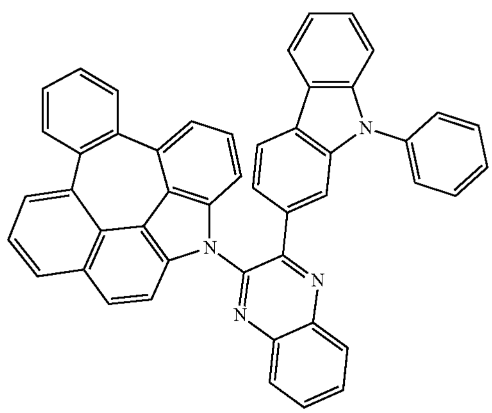
-continued
C-570
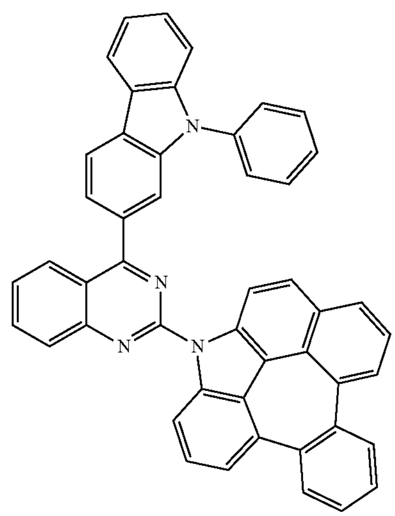
C-571
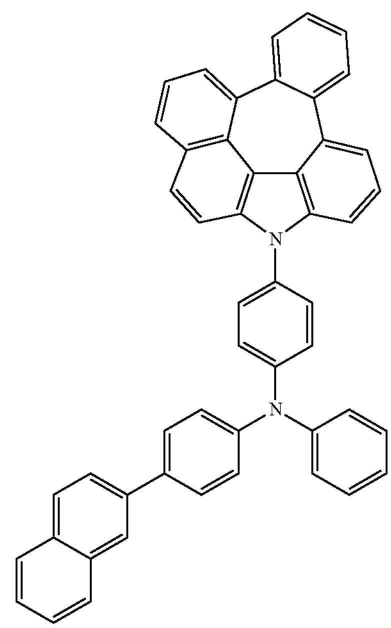

-continued
C-572
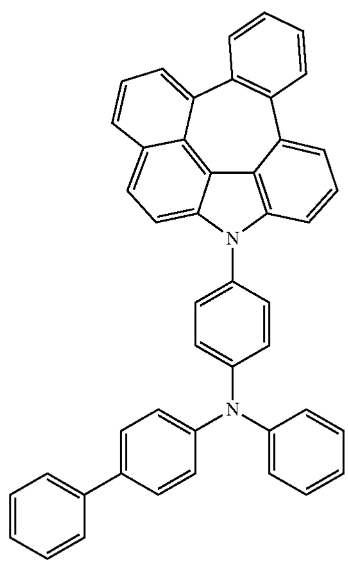
C-573
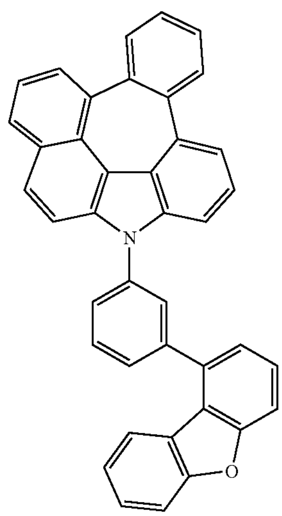
C-574
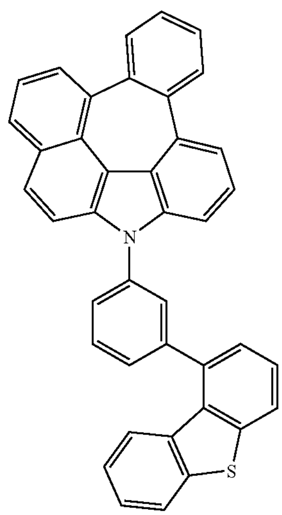
-continued
C-575
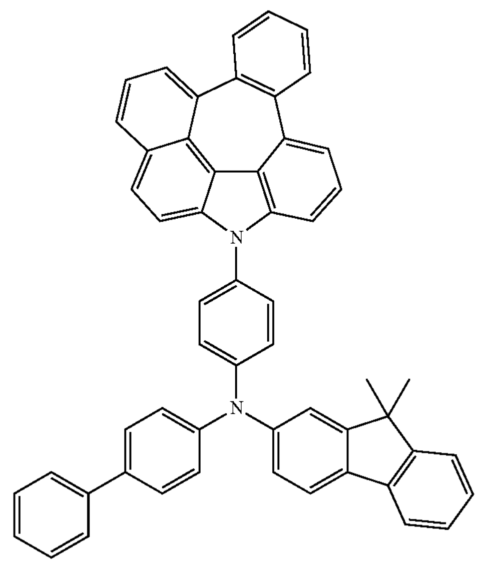
C-576
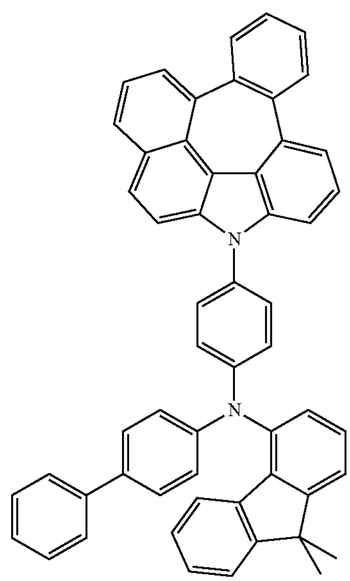

-continued
C-577
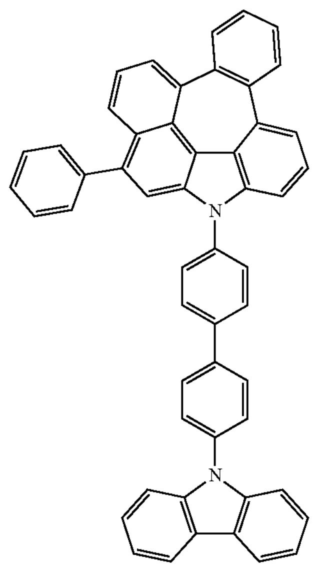
C-578
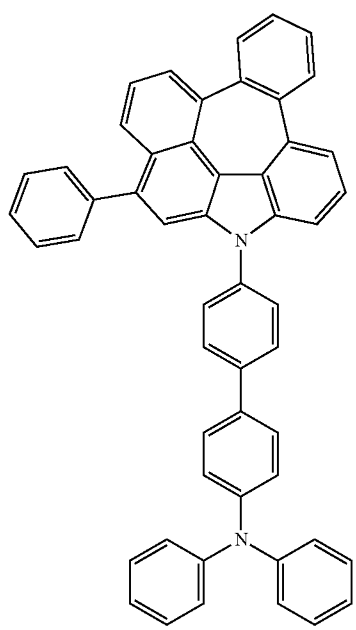
-continued
C-579
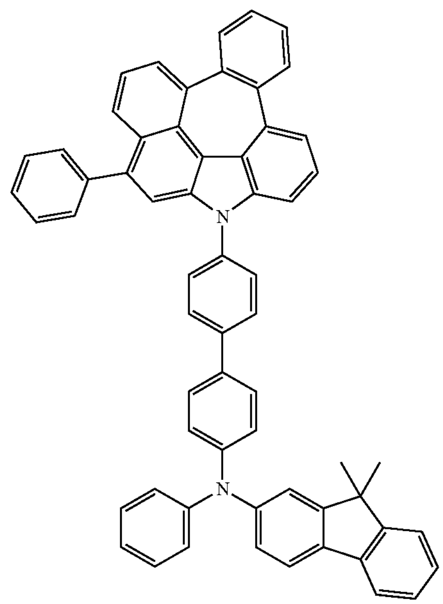
C-580
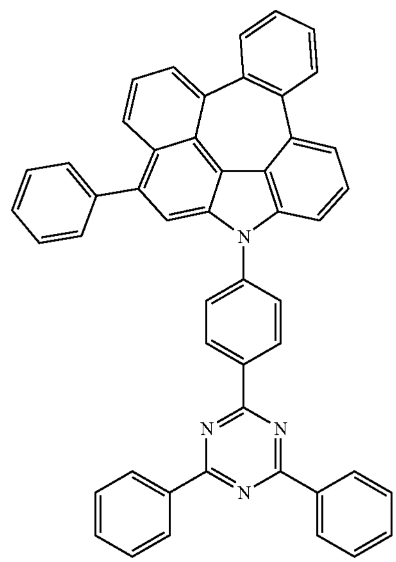

-continued
C-581
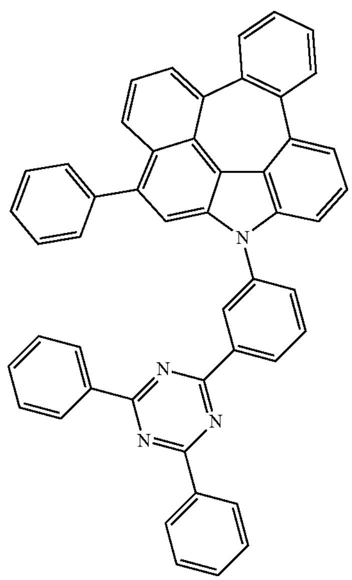
C-582
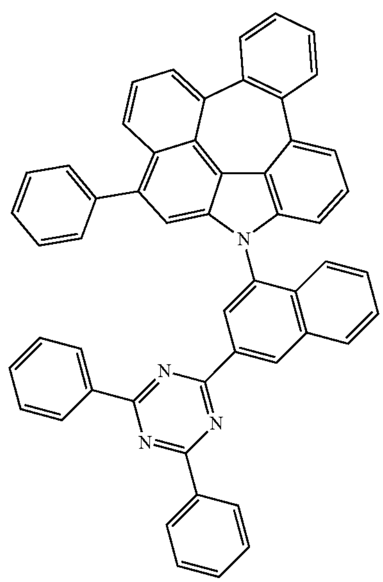
-continued
C-583
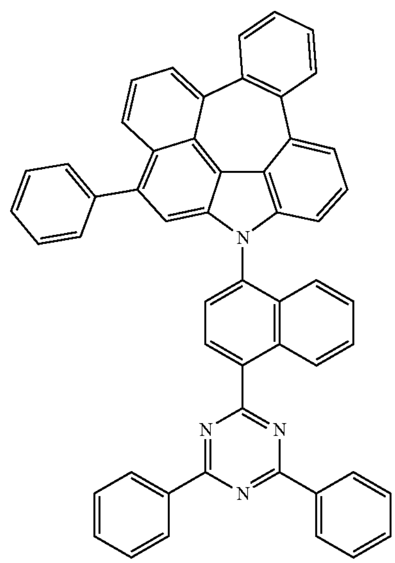
C-584
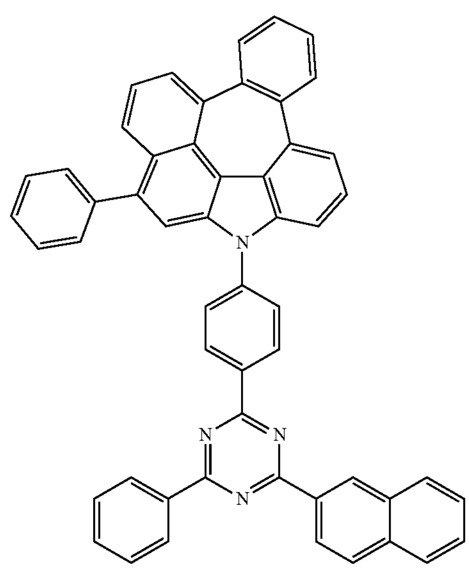

-continued
C-585
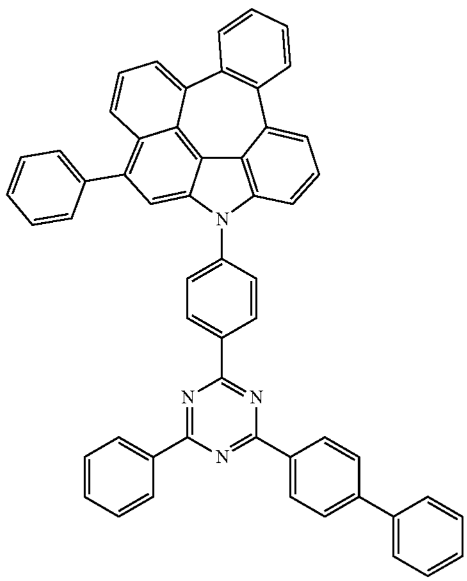
C-586
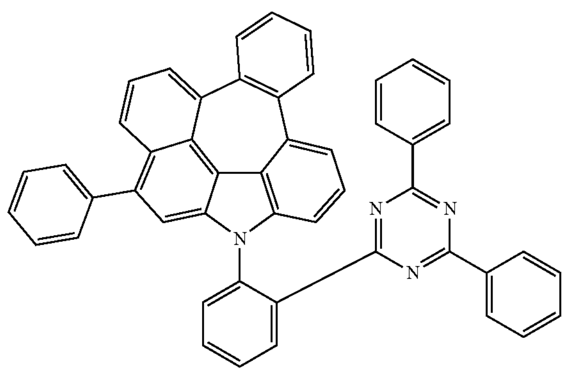
C-587
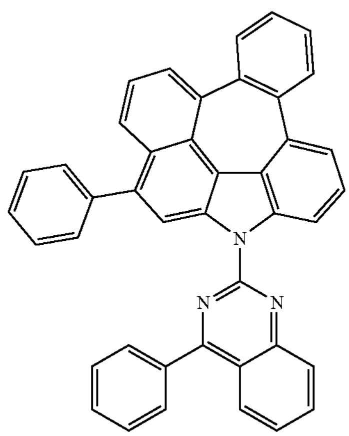
-continued
C-588
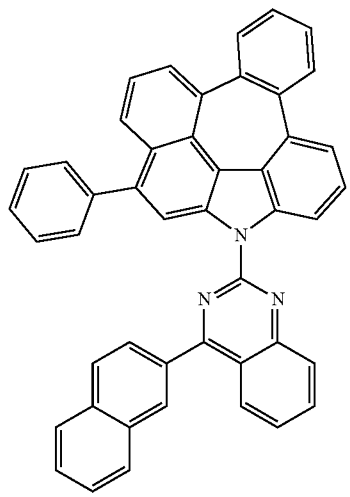
C-589
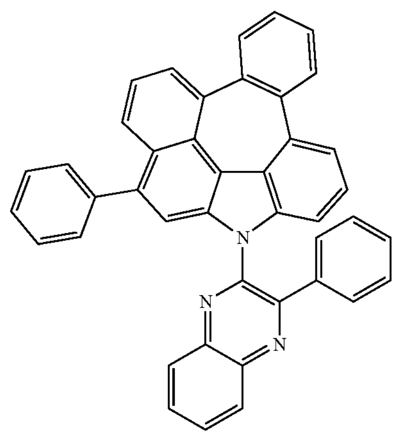
C-590
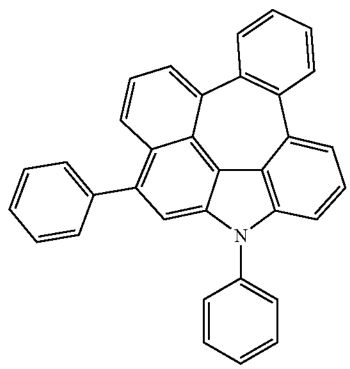

-continued
C-591
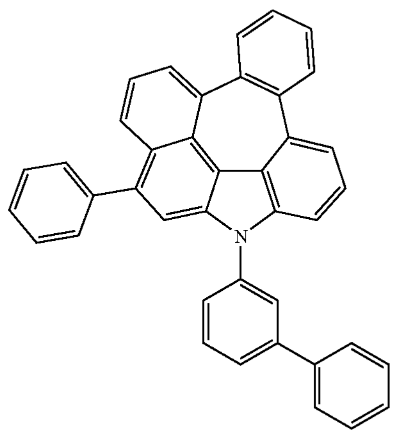
C-592
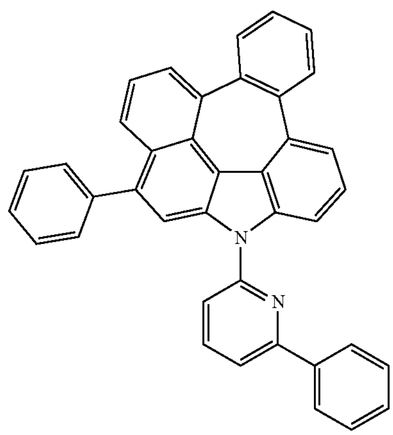
C-593
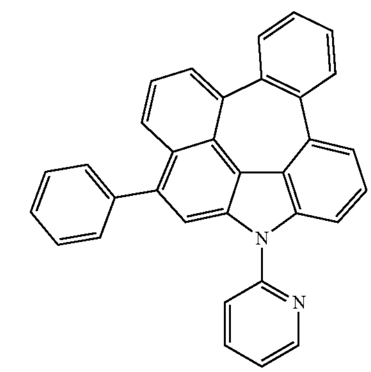
-continued
C-594
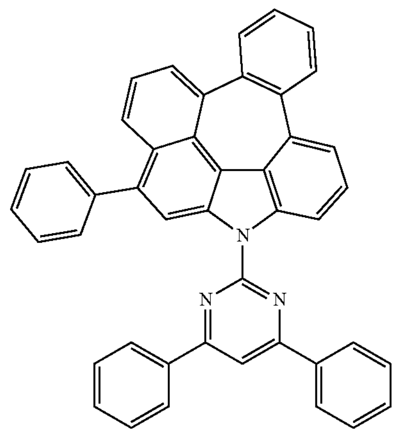
C-595
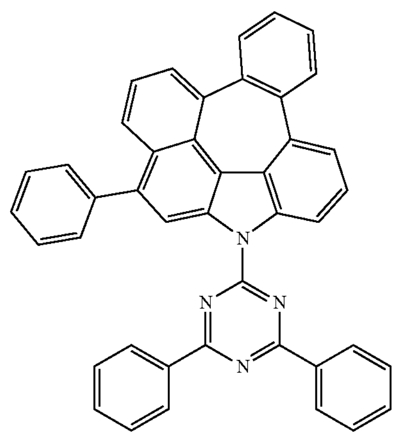
C-596
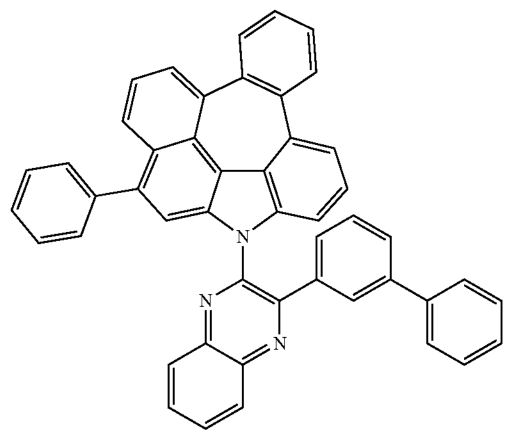

-continued
C-597
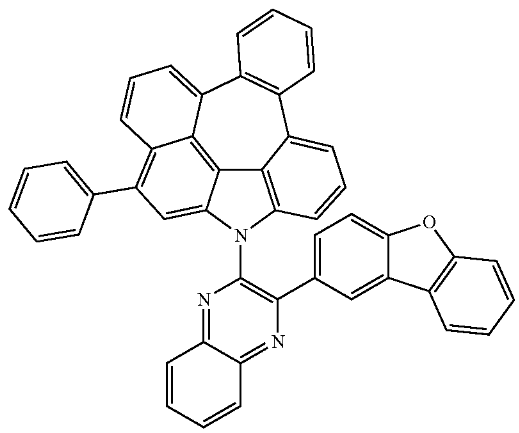
C-598
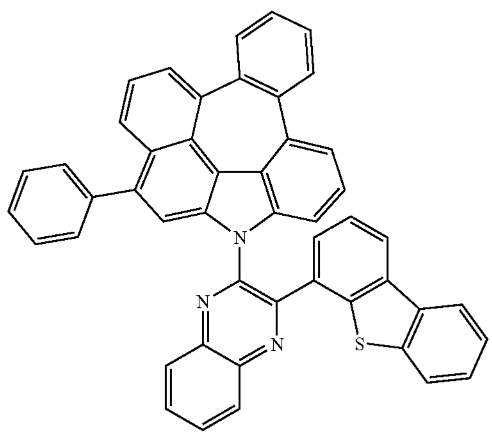
C-599
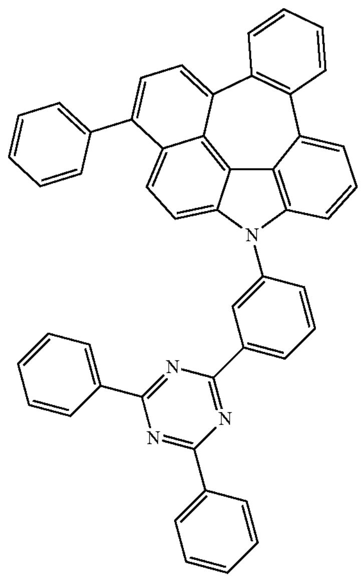
-continued
C-600
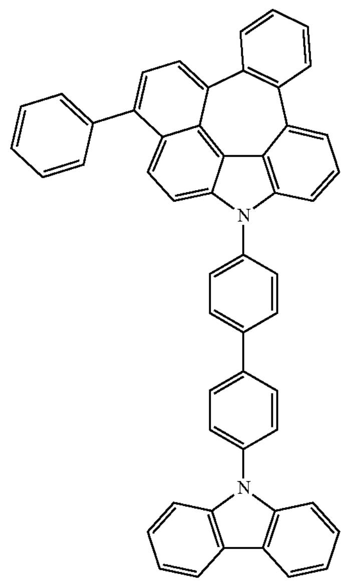
C-601
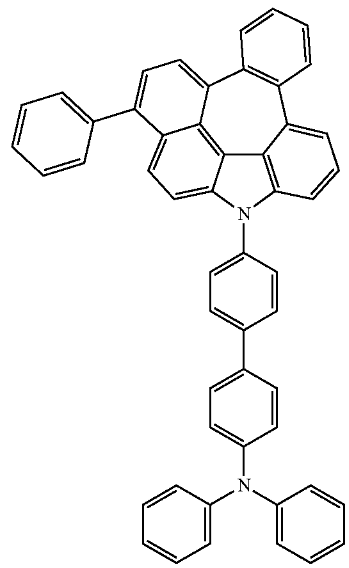

-continued
C-602
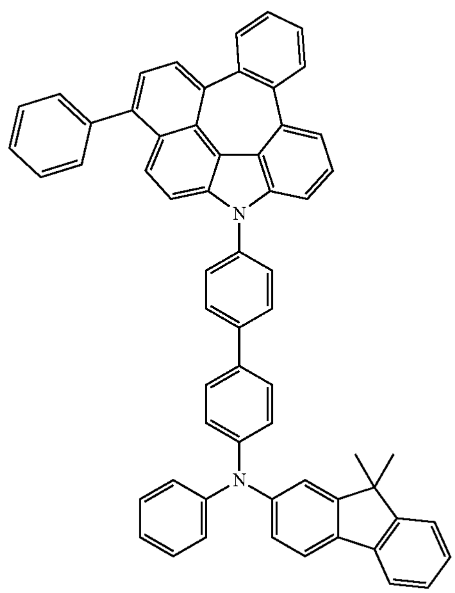
C-603
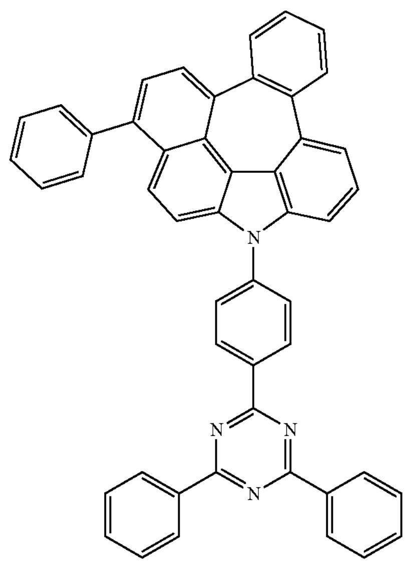
-continued
C-604
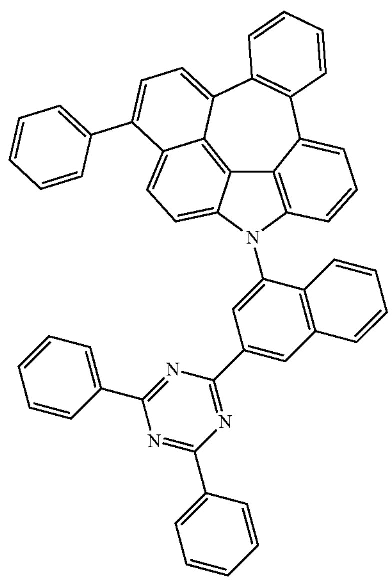
C-605
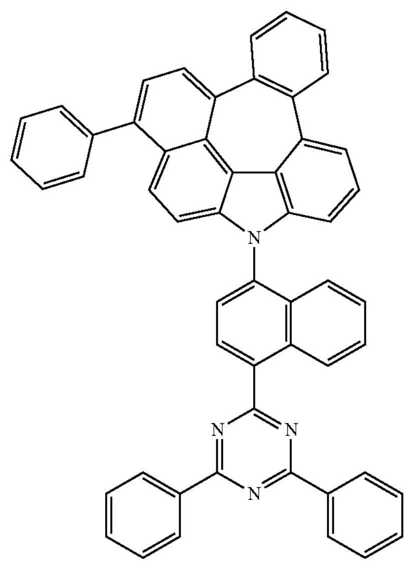

-continued
C-606
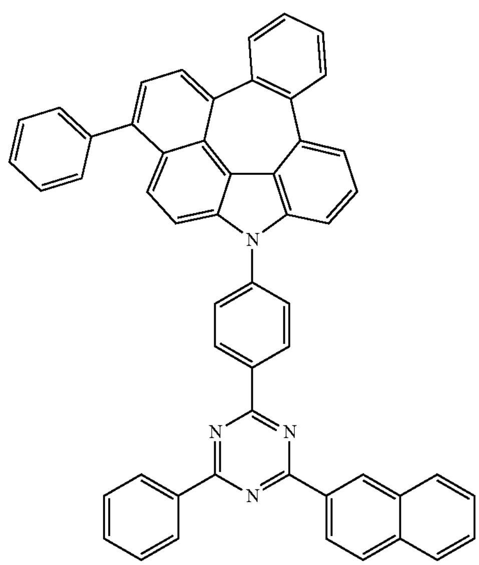
C-607
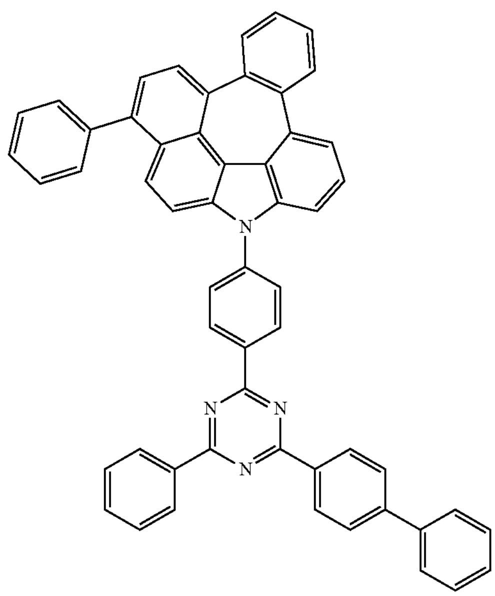
C-608
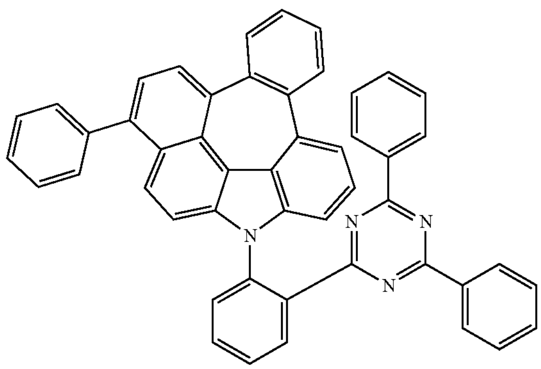
-continued
C-609
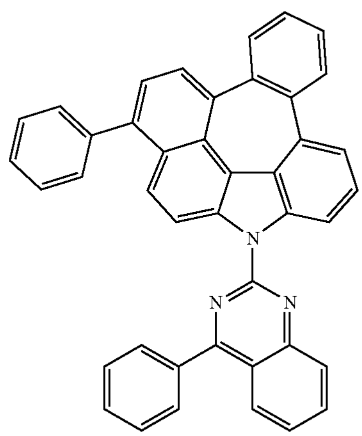
C-610
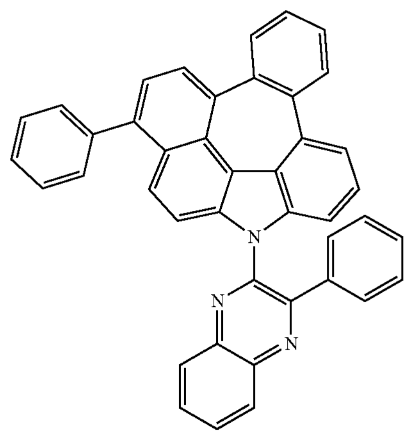
C-611
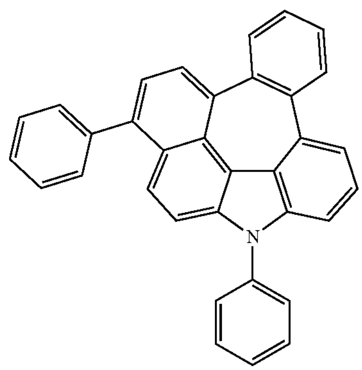

-continued
C-612
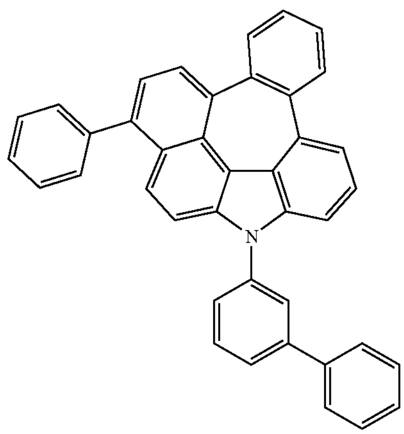
C-613
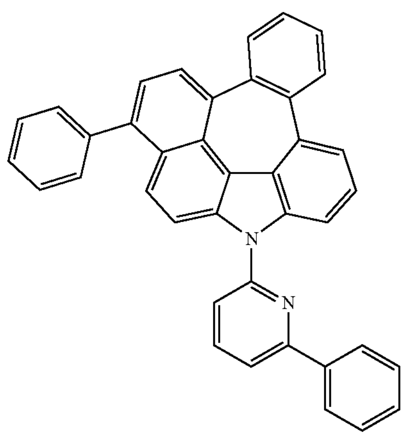
C-614
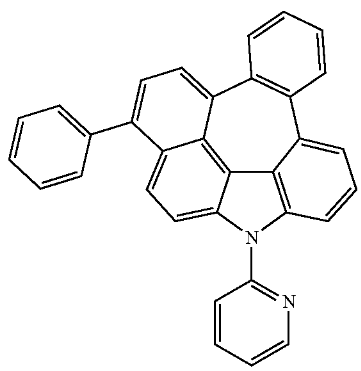
-continued
C-615
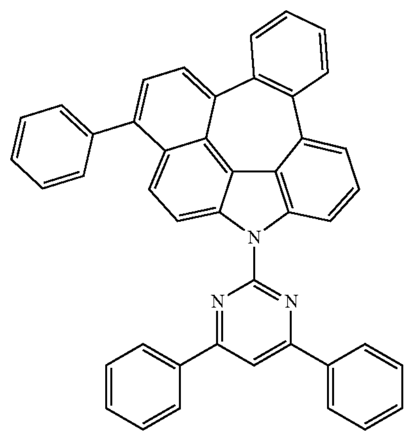
C-616
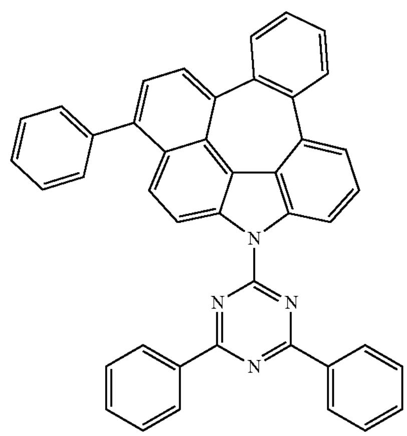
C-617
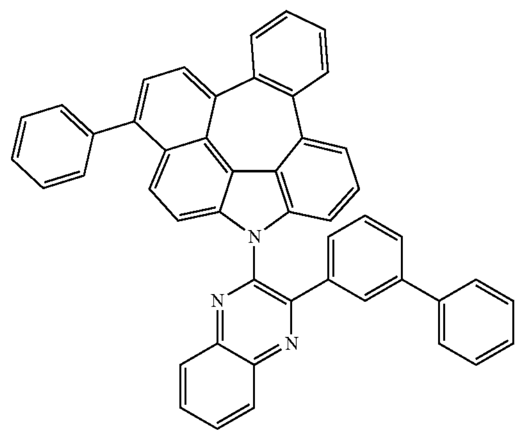

-continued
C-618
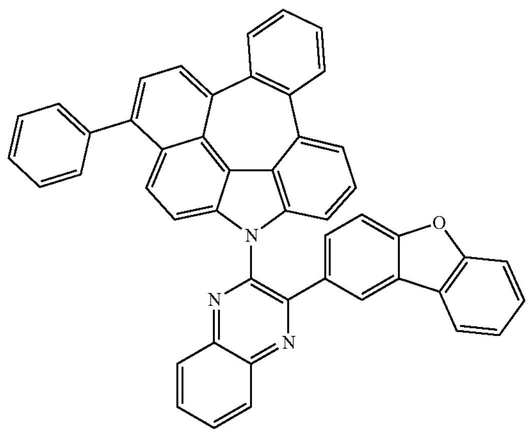
C-619
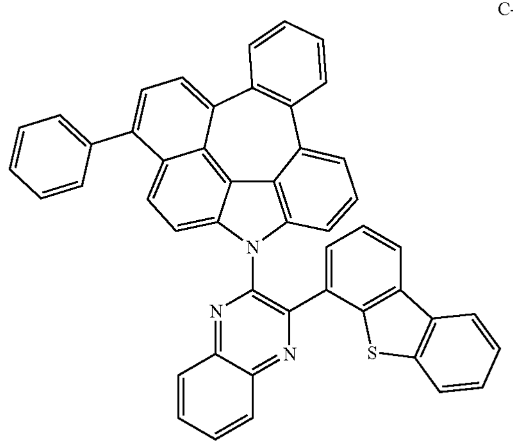
C-620
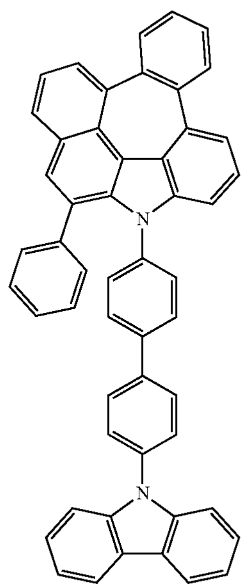
-continued
C-621
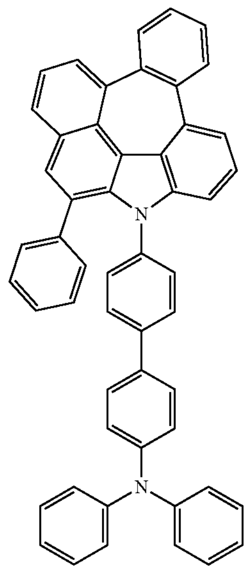
C-622
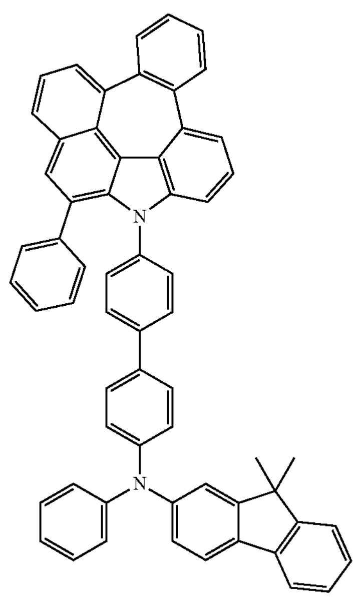

-continued
C-623
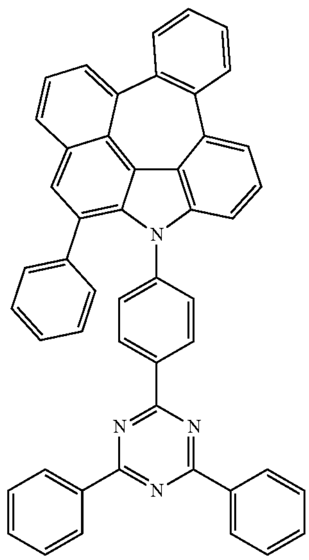
C-624
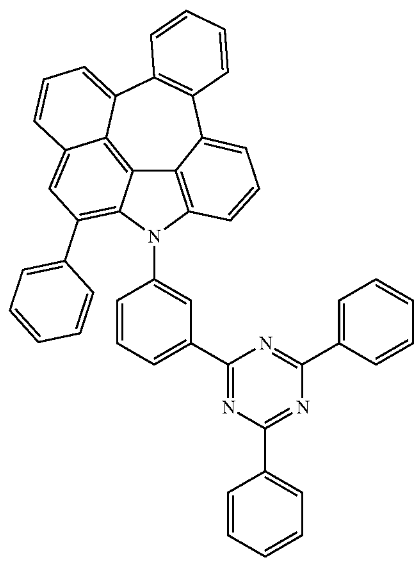
-continued
C-625
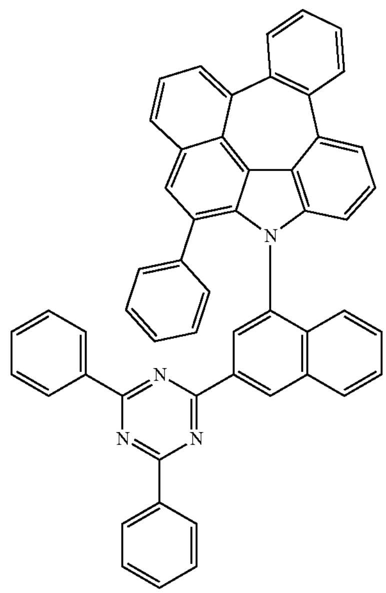
C-626
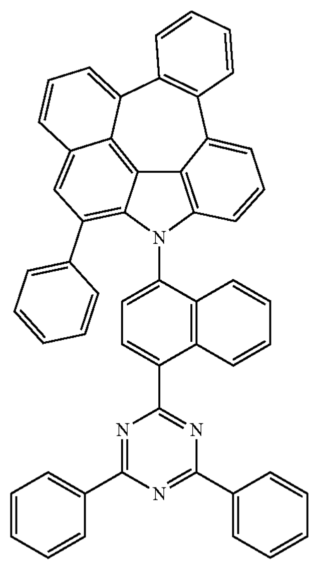

-continued
C-627
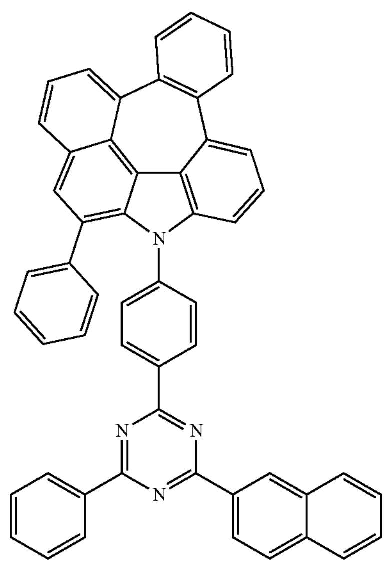
C-628
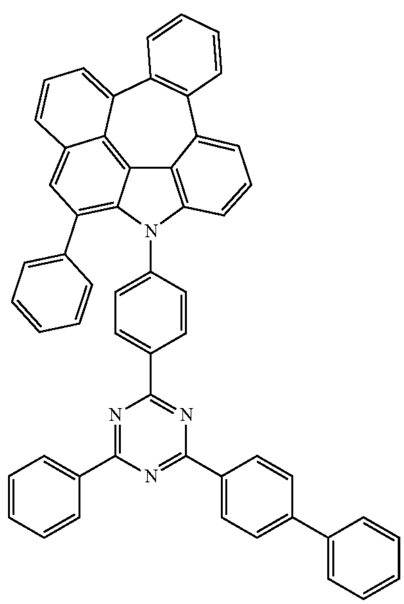
C-629
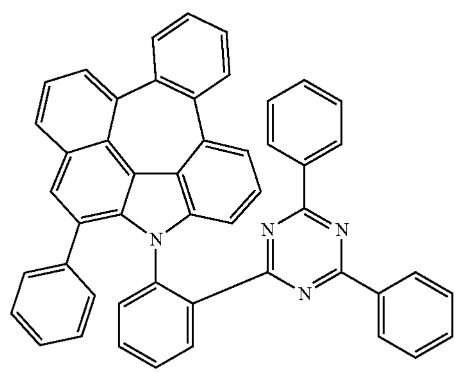
-continued
C-630
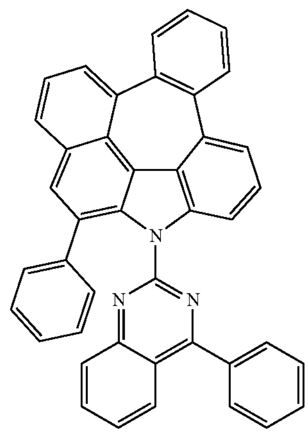
C-631
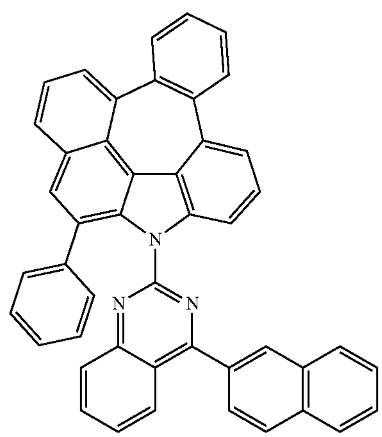
C-632
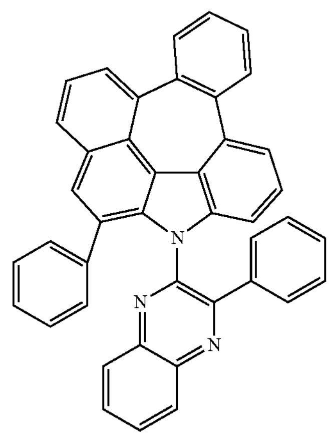
C-633
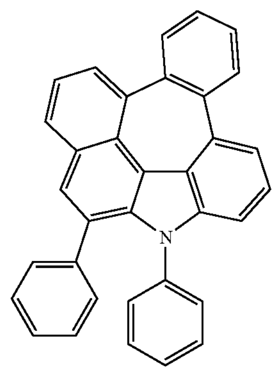

-continued
C-634
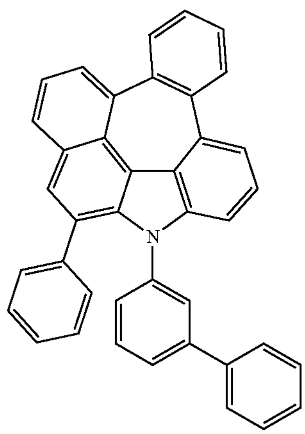
C-635
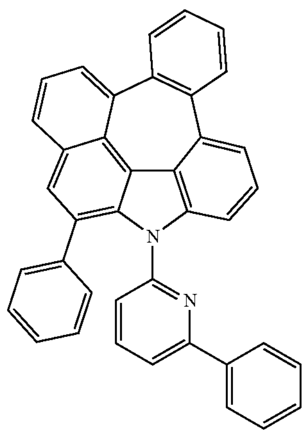
C-636
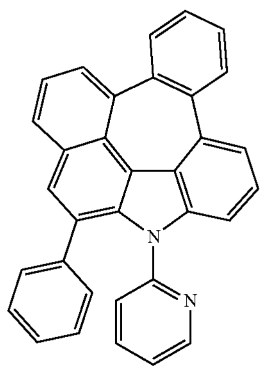
-continued
C-637
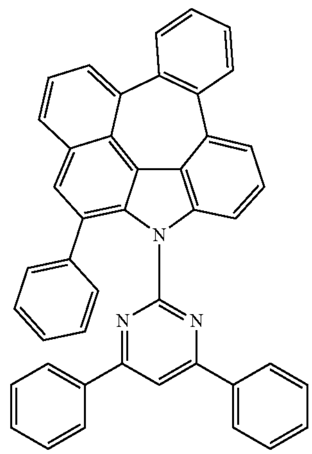
C-638
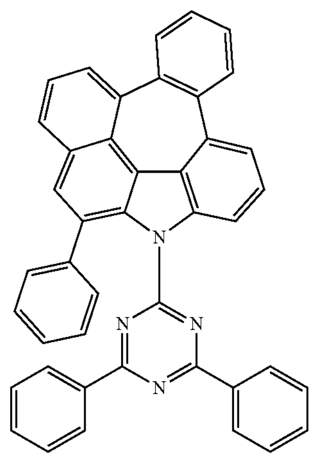
C-639
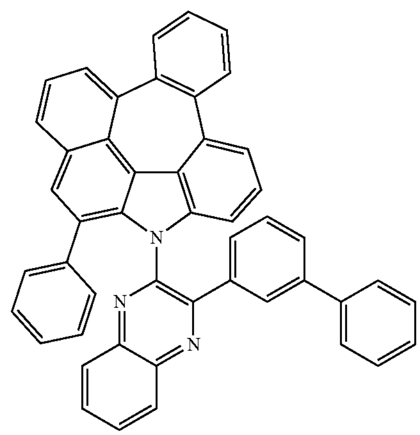

-continued
C-640
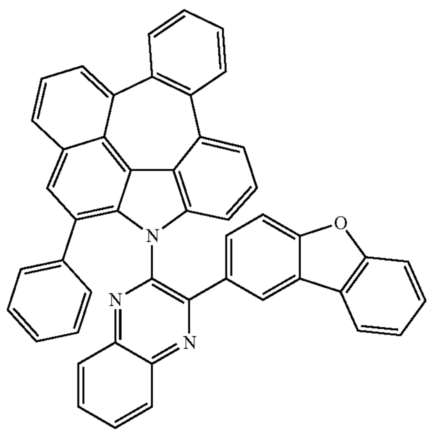
C-641
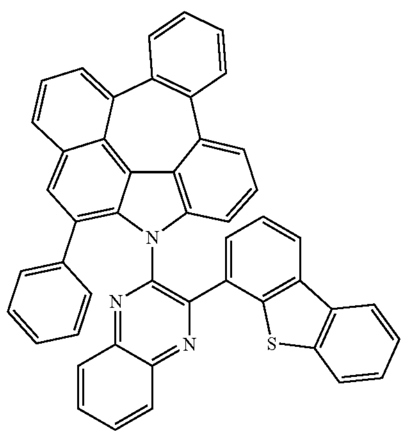
C-642
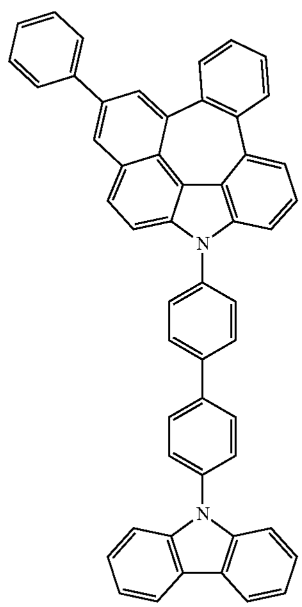
-continued
C-643
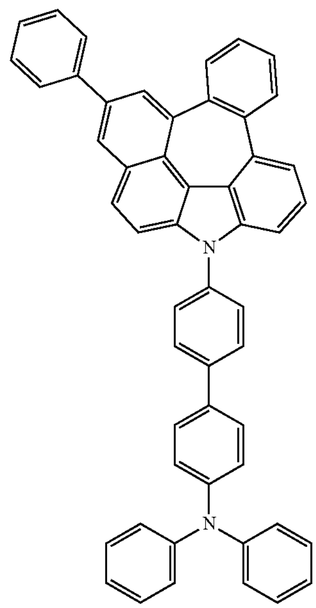
C-644
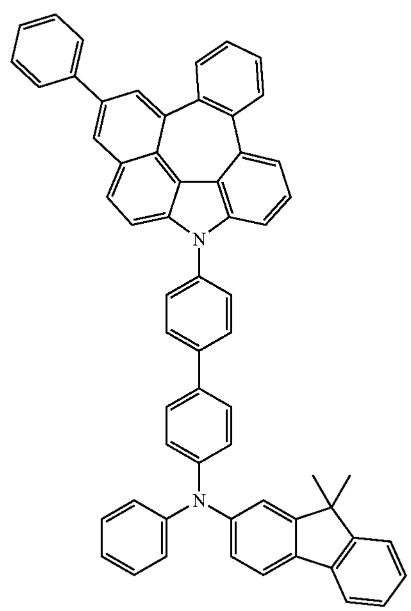

-continued
C-645
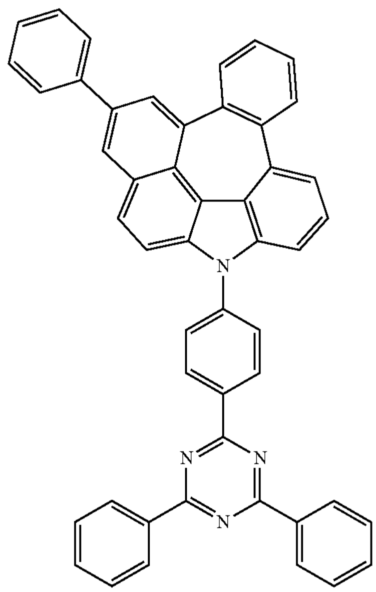
C-646
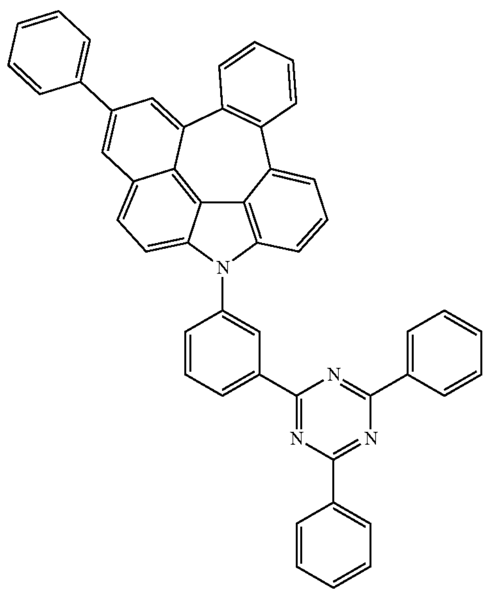
-continued
C-647
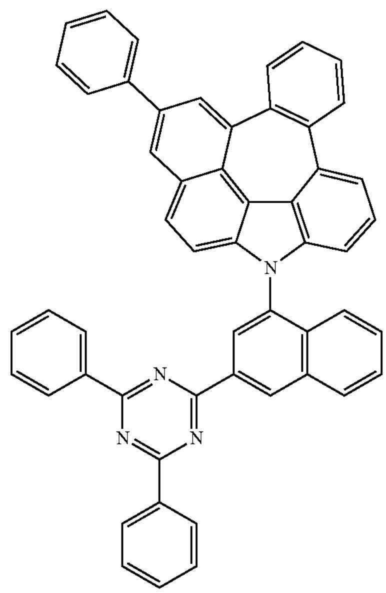
C-648
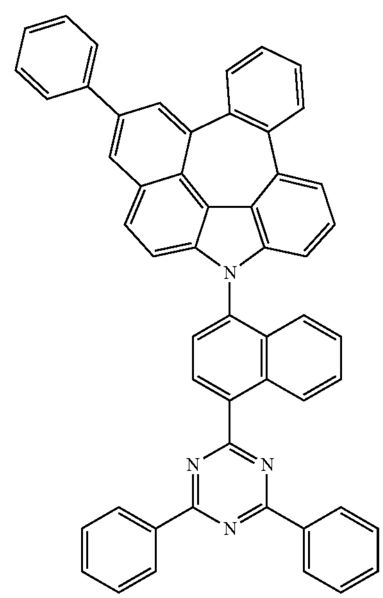

-continued
C-649
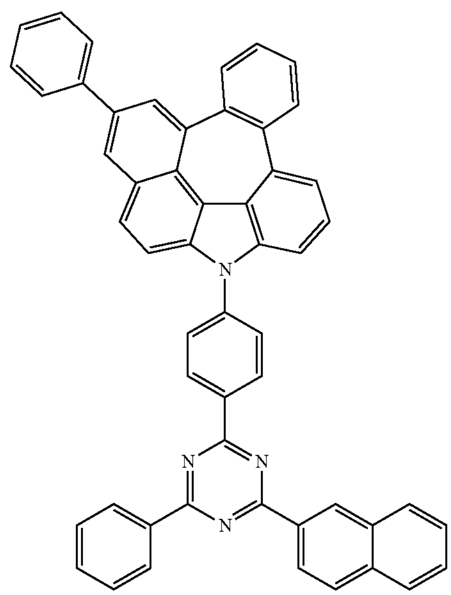
C-650
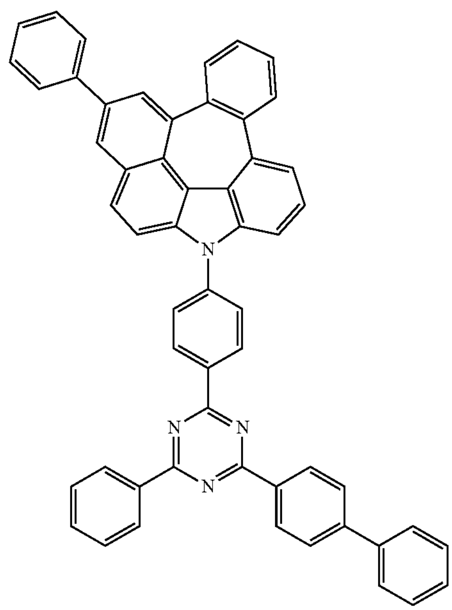
C-651
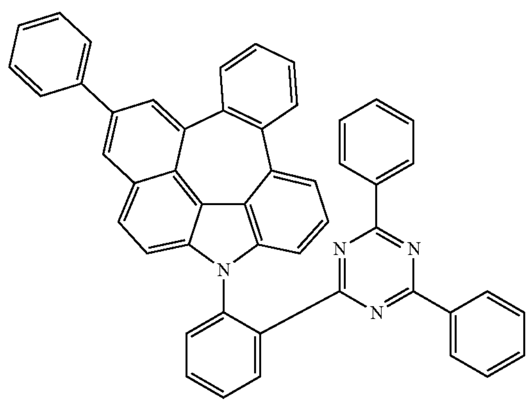
-continued
C-652
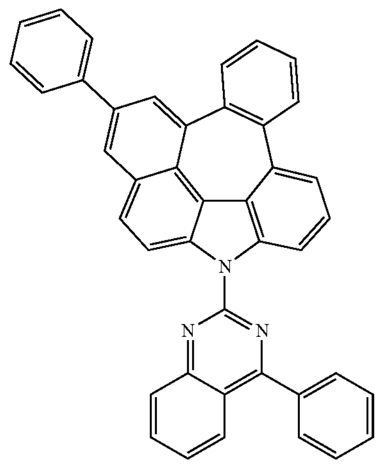
C-653
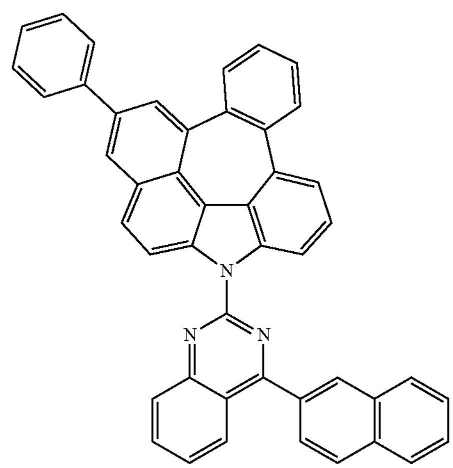
C-654
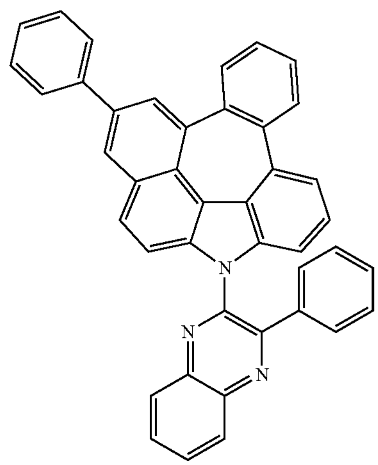

-continued
C-655
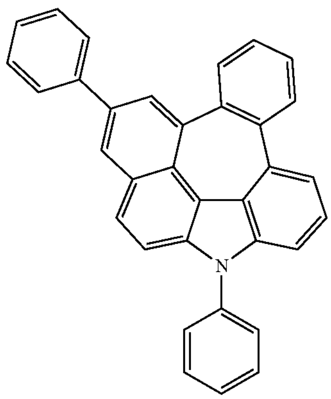
C-656
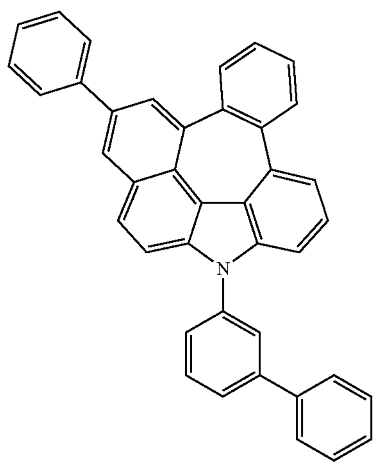
C-657
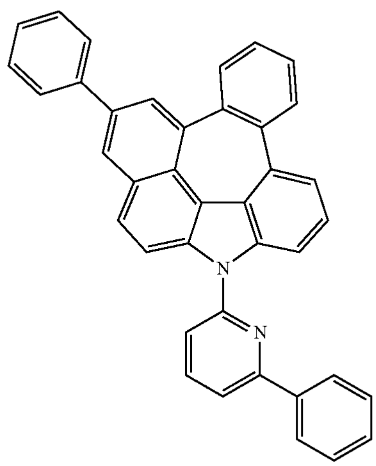
-continued
C-658
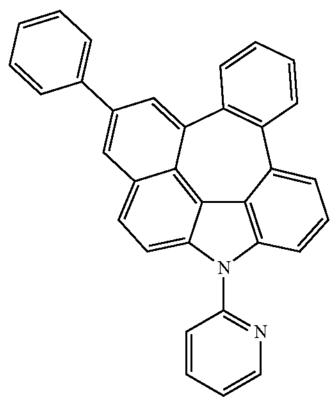
C-659
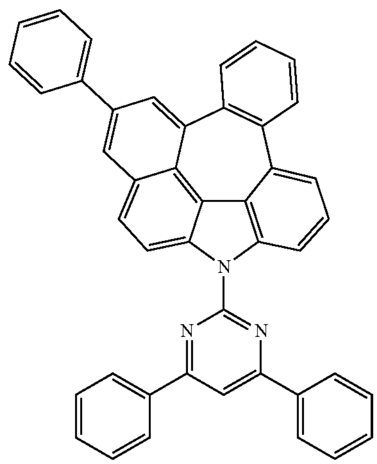
C-660
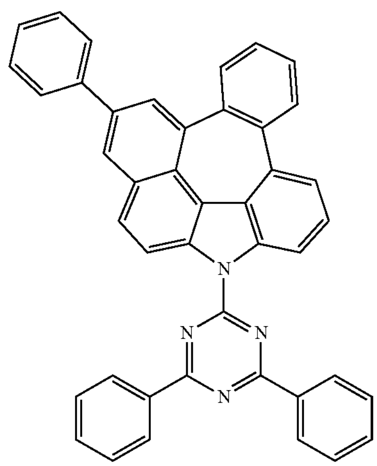

-continued
C-661
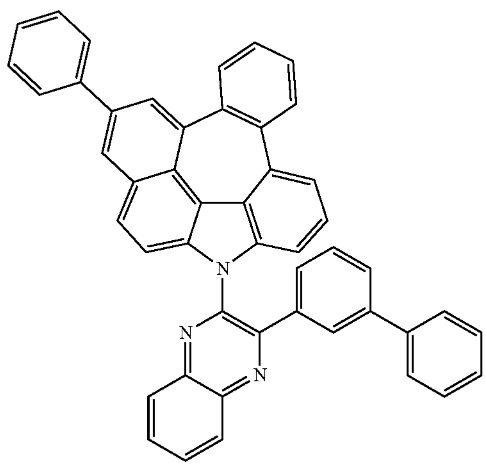
C-662
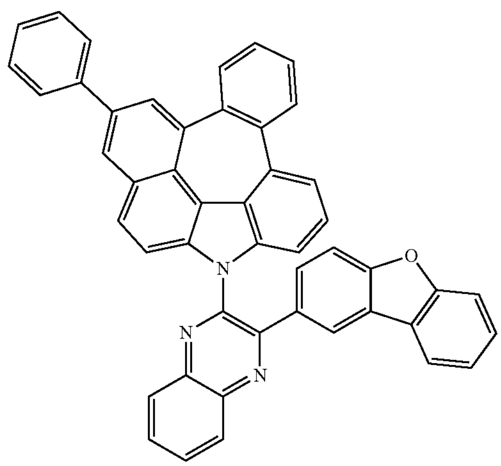
C-663
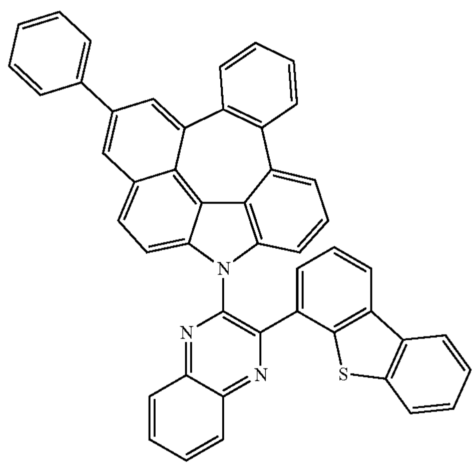
-continued
C-664
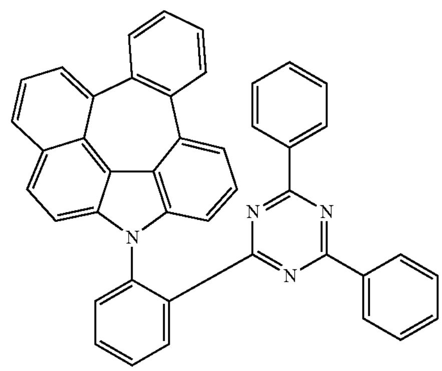
C-665
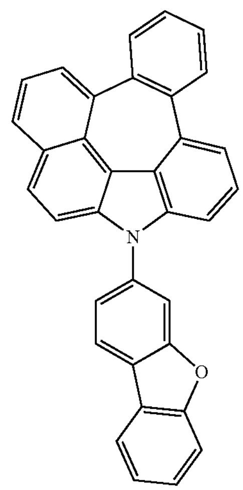
C-666
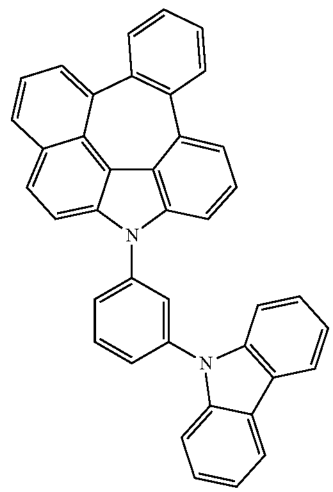

-continued
C-667
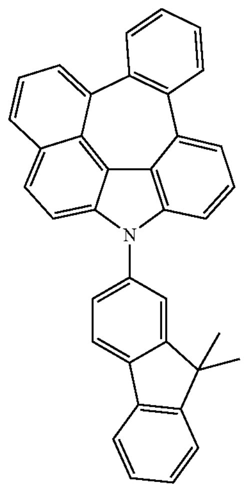
and
C-668
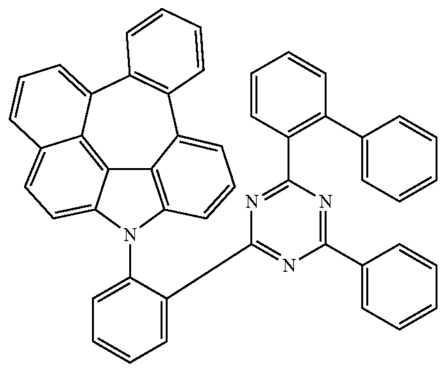
.
8. The composition material for an organic electroluminescent device according to claim 1, wherein the compound represented by formula 2 is at least one selected from the group consisting of:
H-1
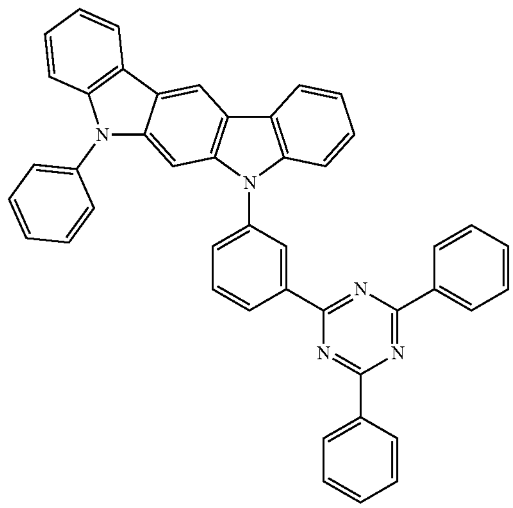
-continued
H-2
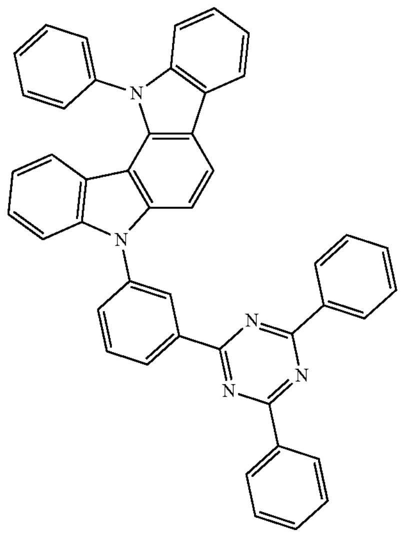
H-3
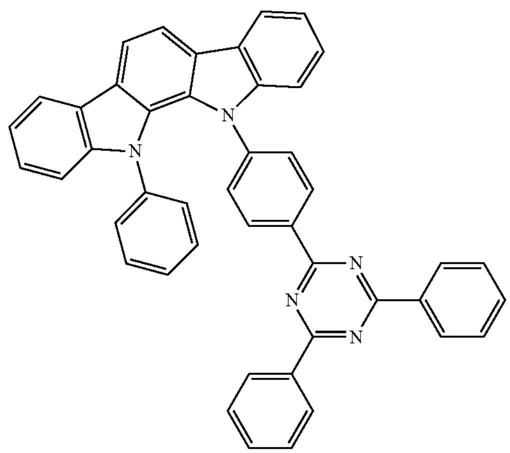
H-4
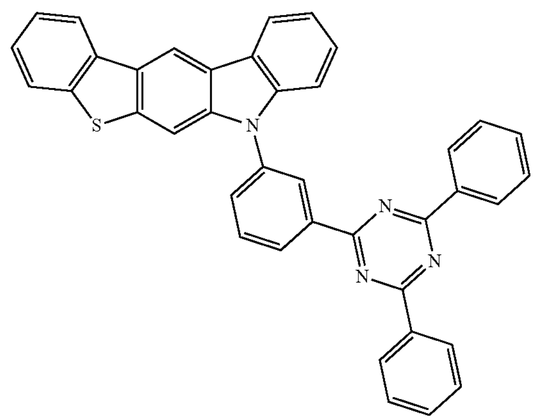

-continued
H-5
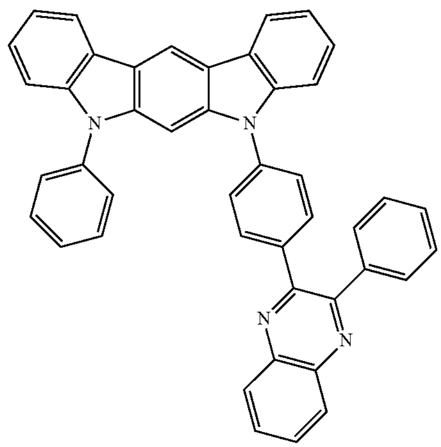
H-6
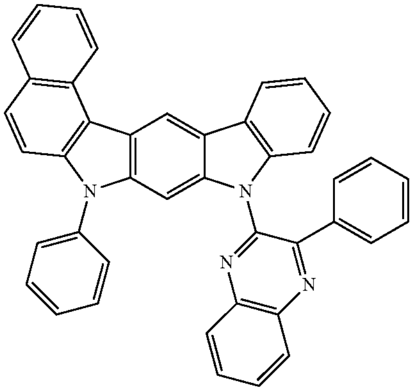
H-7
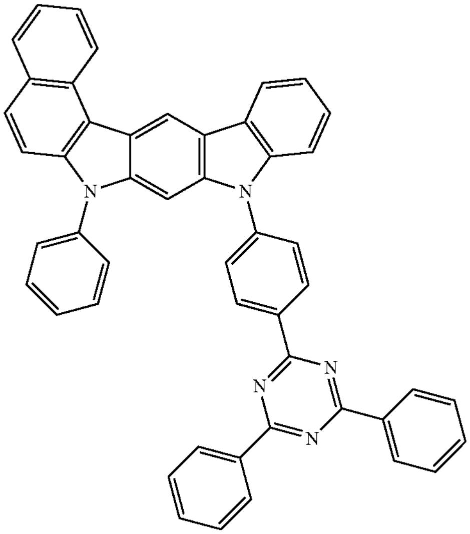
-continued
H-8
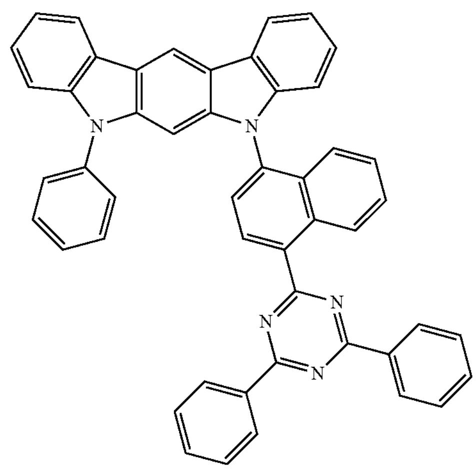
H-9
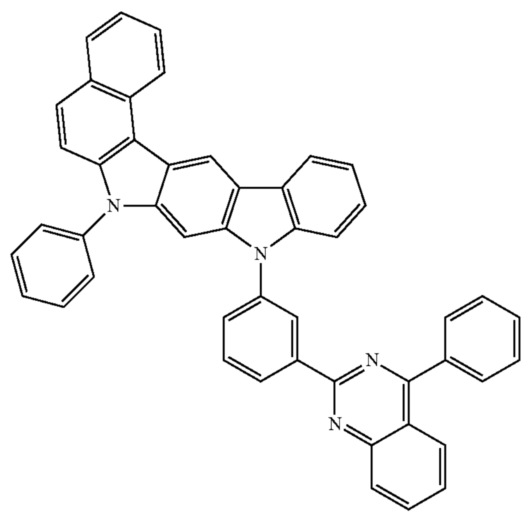
H-10
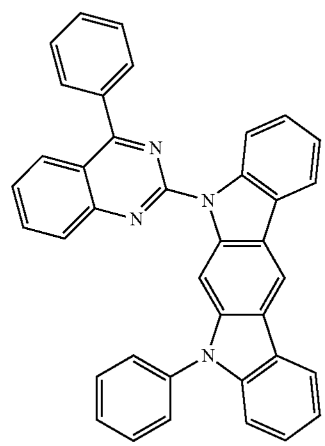

-continued
H-11
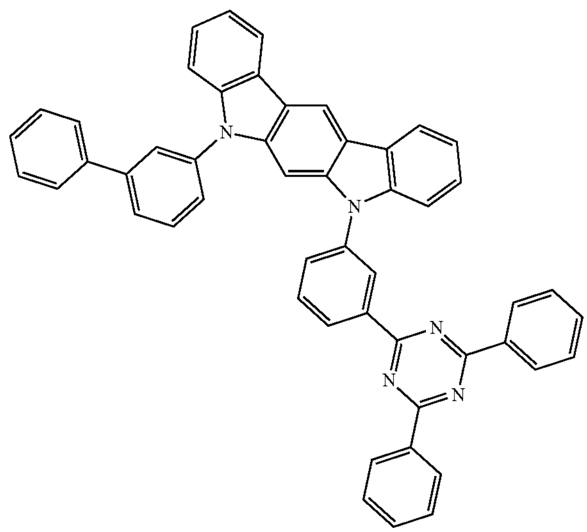
H-12
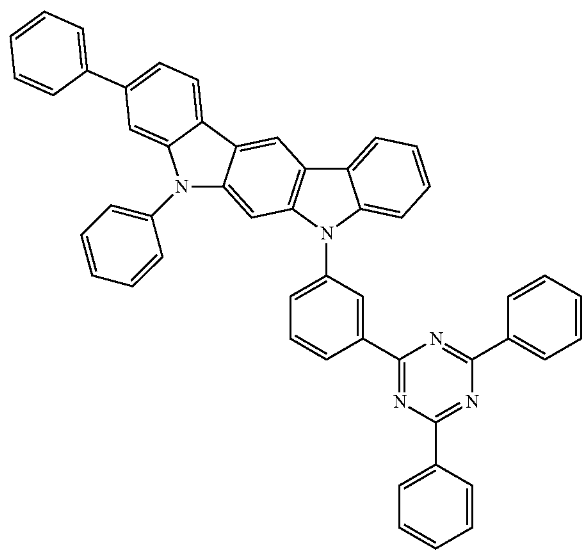
H-13
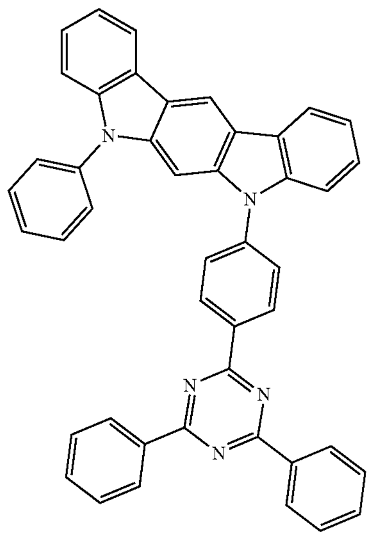
-continued
H-14
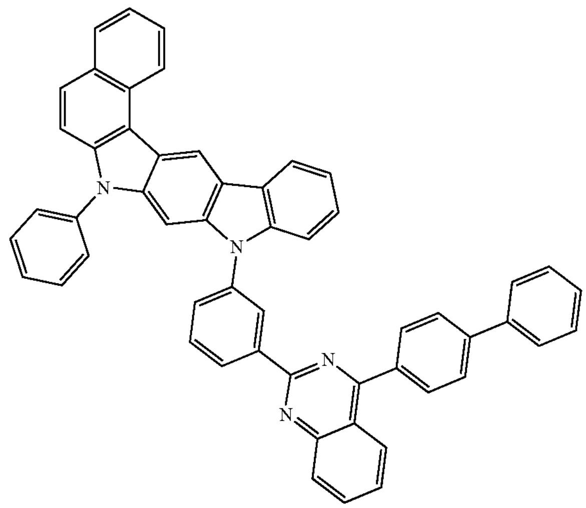
H-15
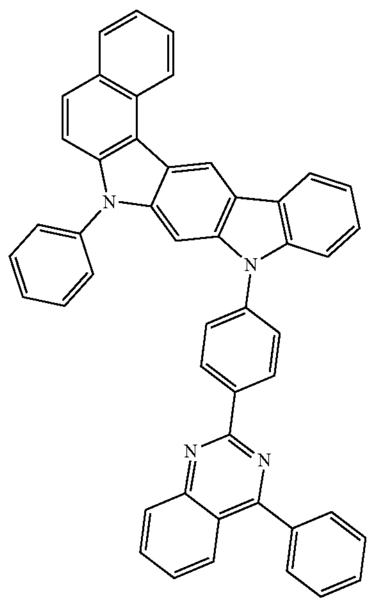
H-16
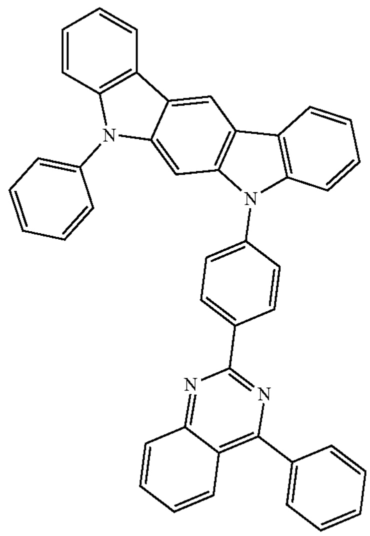

-continued
H-17
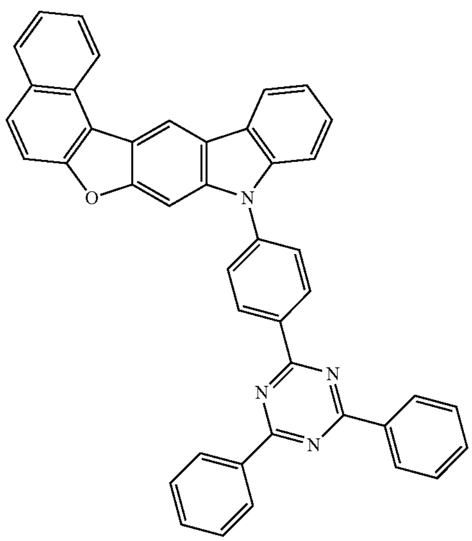
H-18
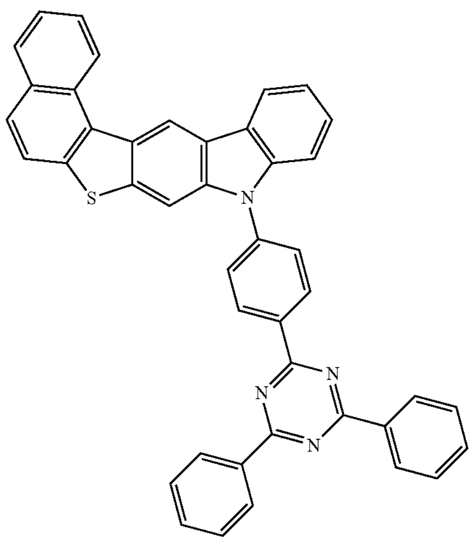
H-19
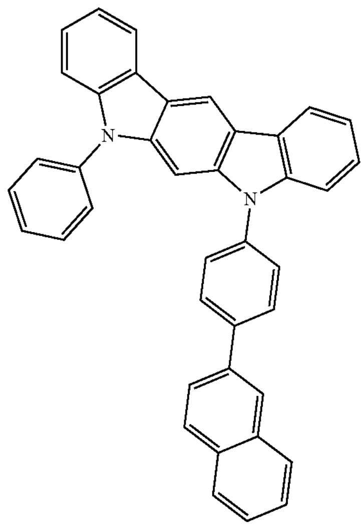
-continued
H-20
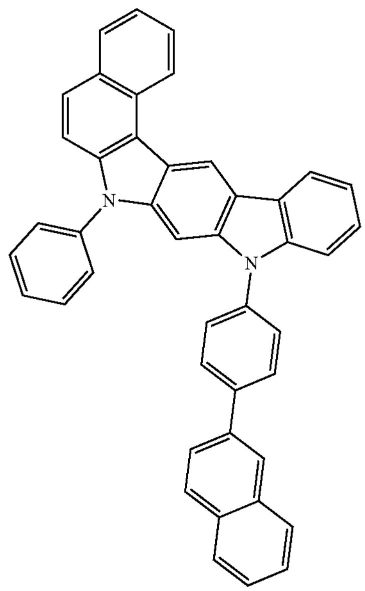
H-21
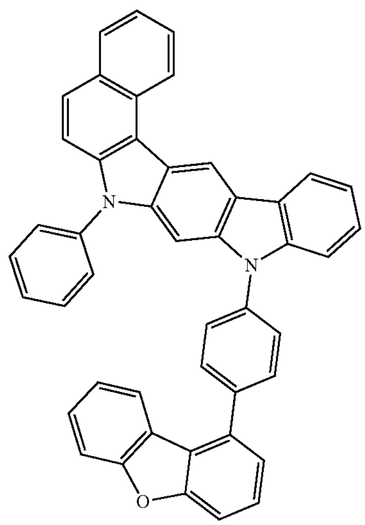
H-22
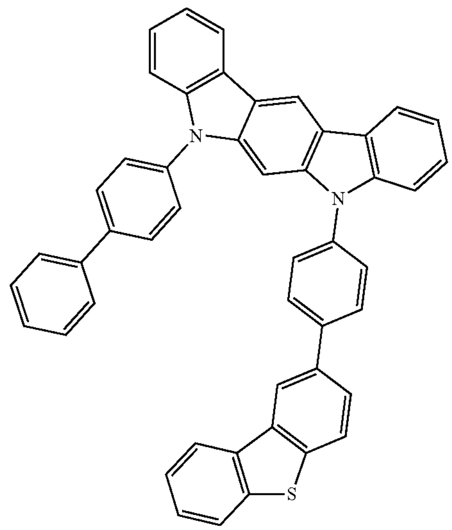

-continued
H-23
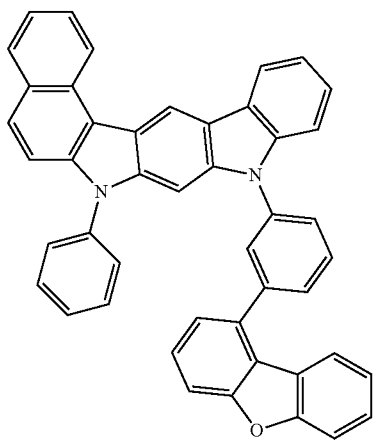
H-24
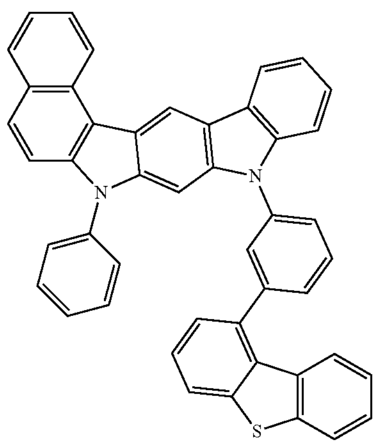
H-25
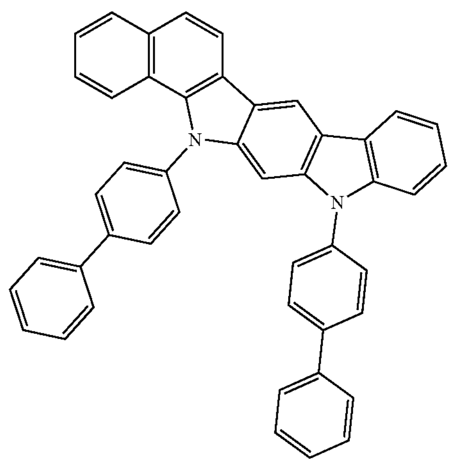
-continued
H-26
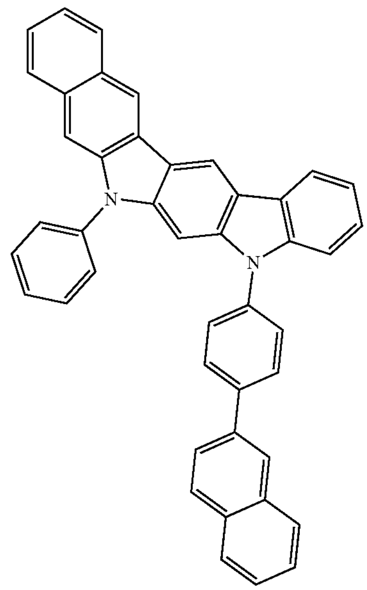
H-27
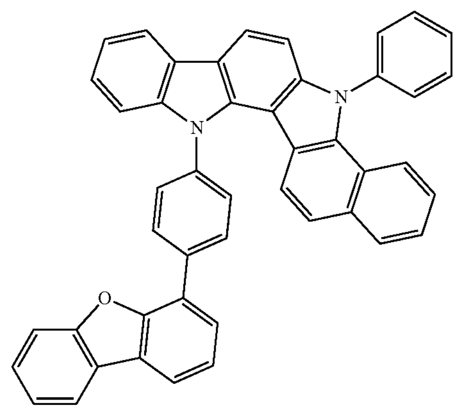
H-28
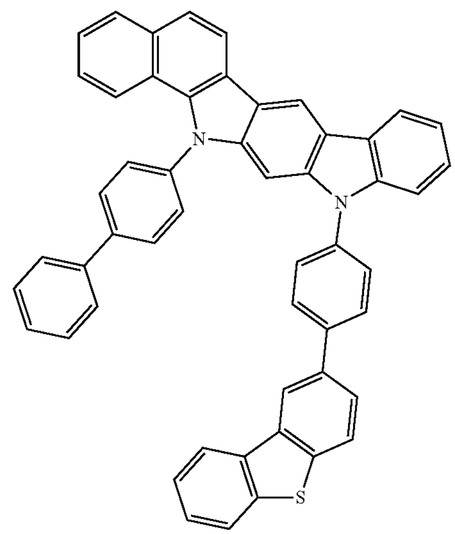

-continued
H-29
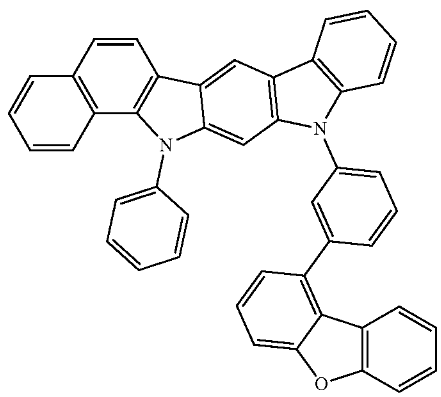
H-30
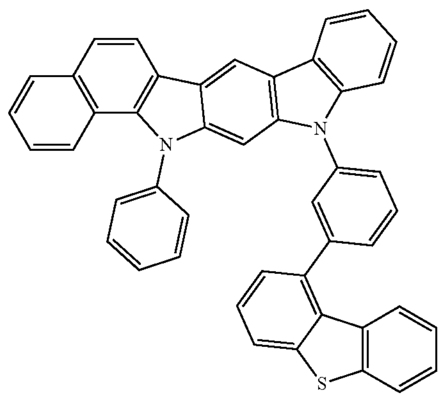
H-31
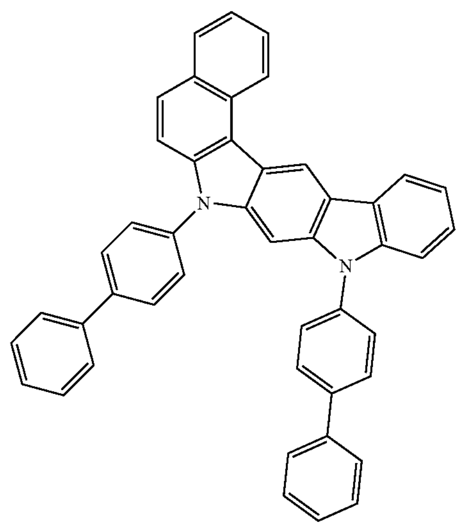
-continued
H-32
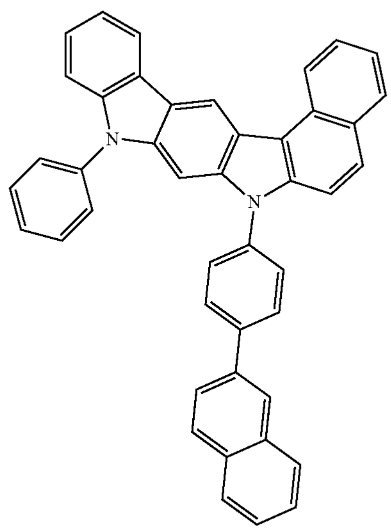
H-33
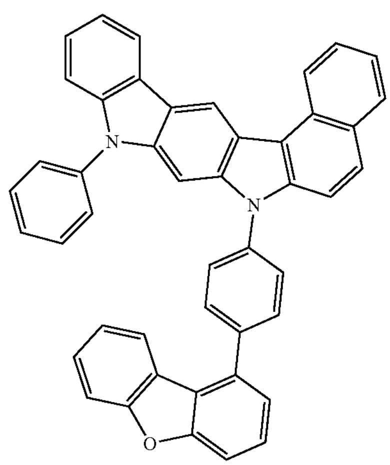
H-34
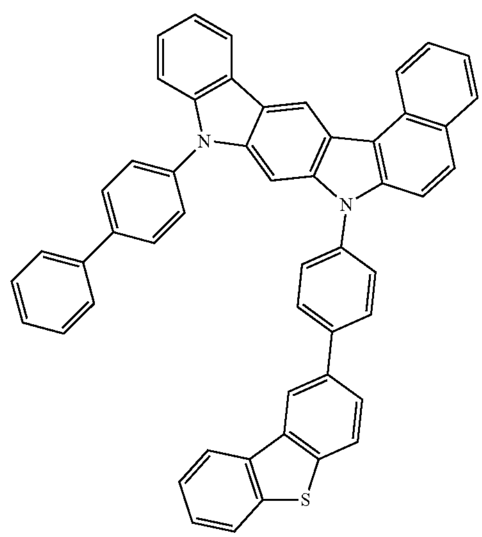

-continued
H-35
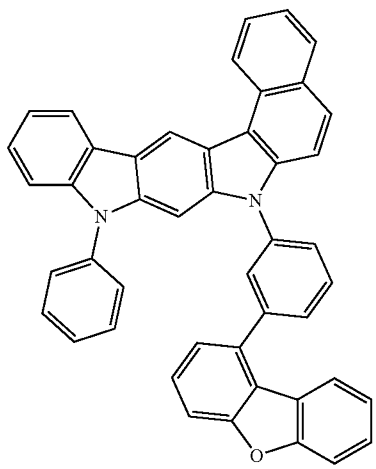
H-36
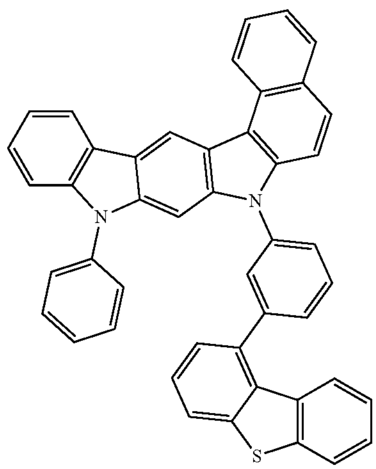
H-37
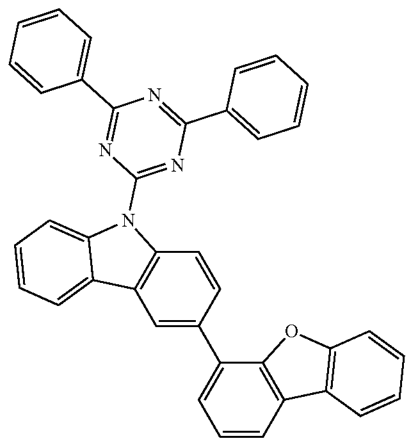
-continued
H-38
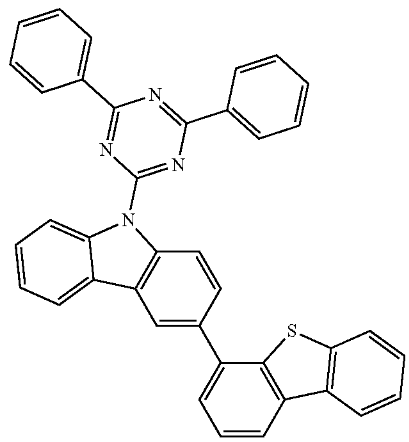
H-39
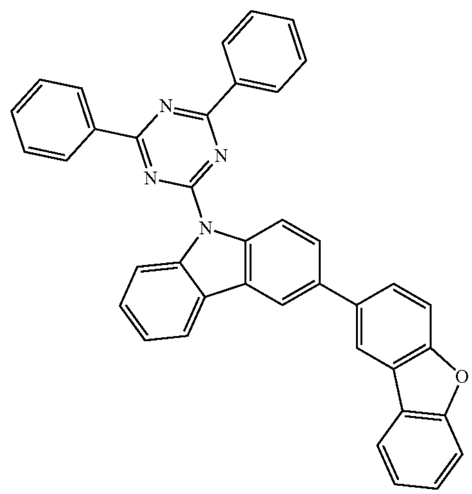
H-40
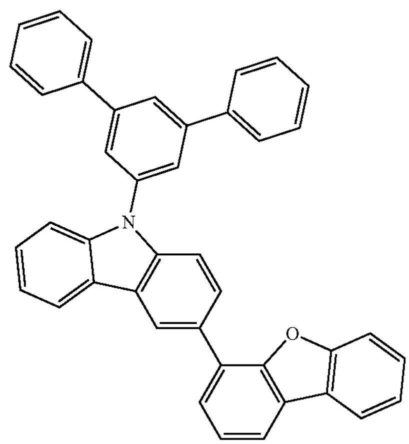

-continued
H-41
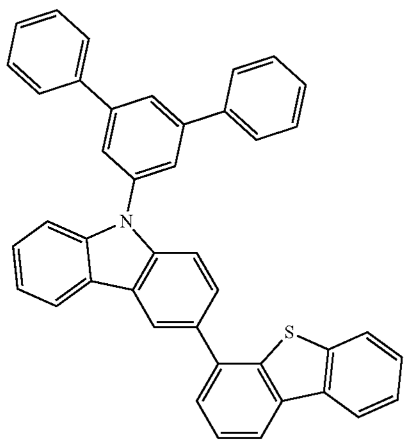
H-42
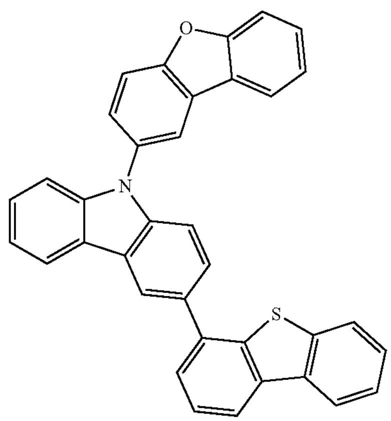
H-43
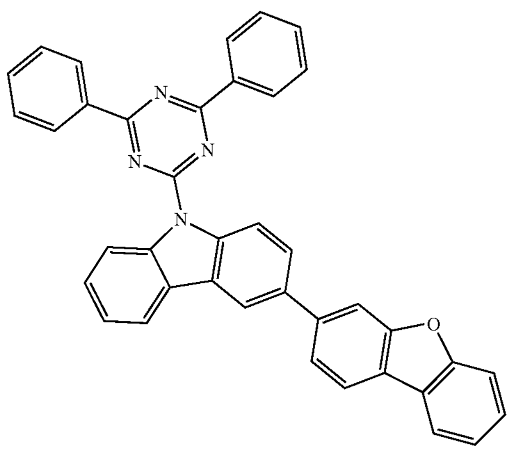
-continued
H-44
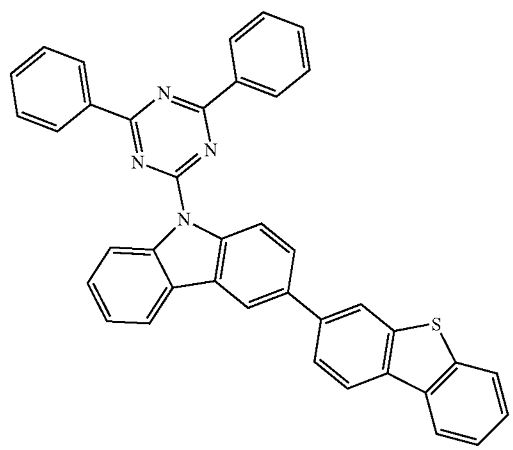
H-45
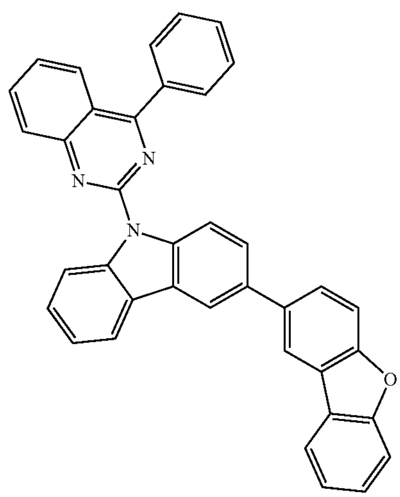
H-46
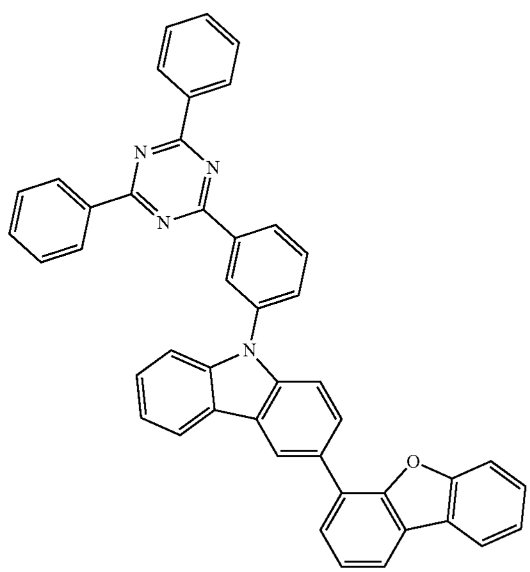

-continued
H-47
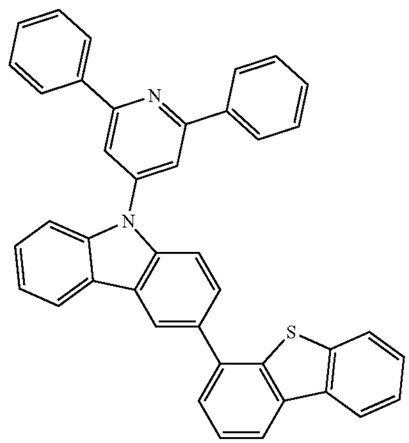
H-48
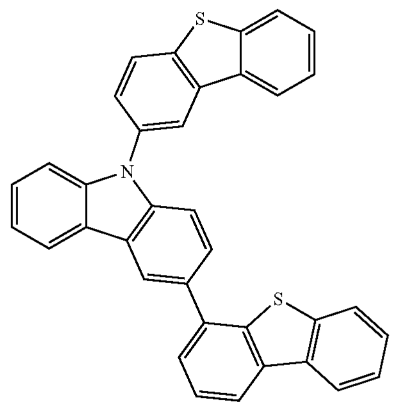
H-49
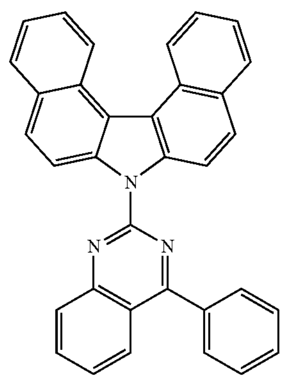
H-50
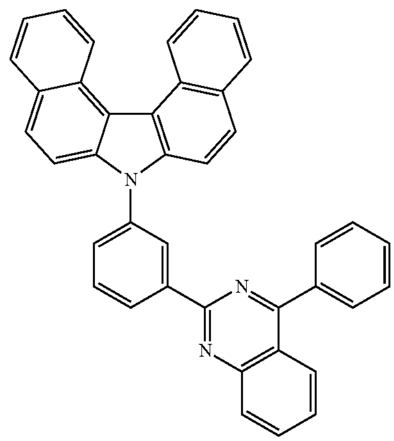
-continued
H-51
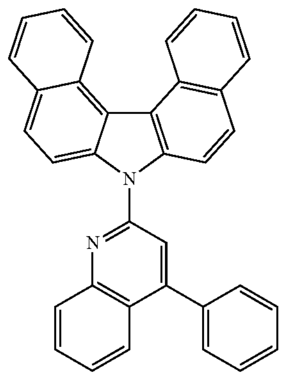
H-52
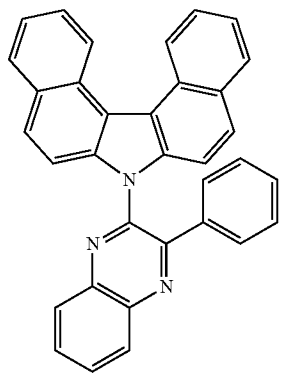
H-53
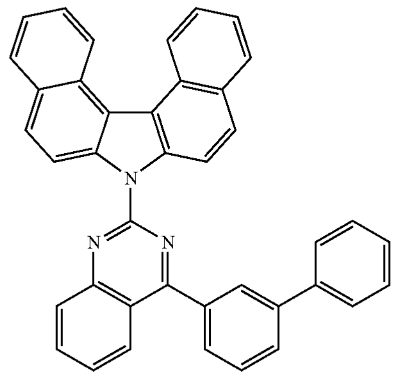
H-54
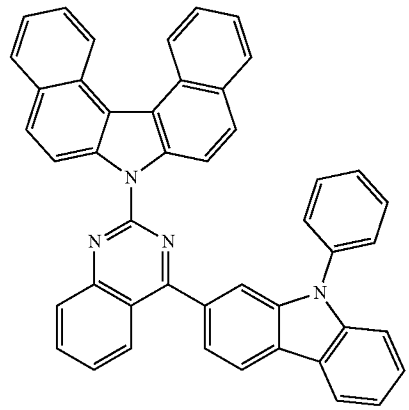

-continued
H-55
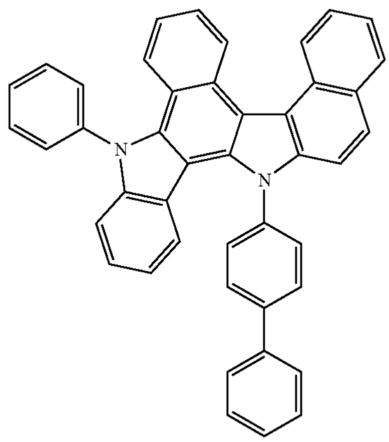
H-56
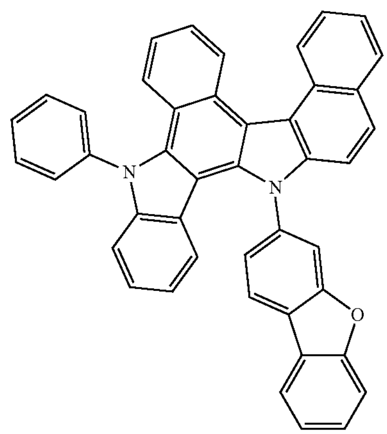
H-57
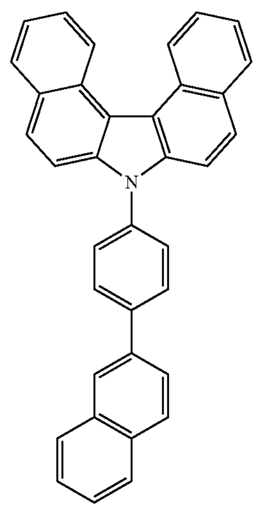
-continued
H-58
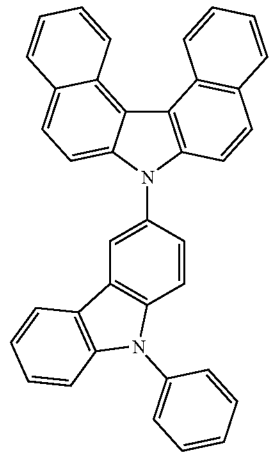
H-59
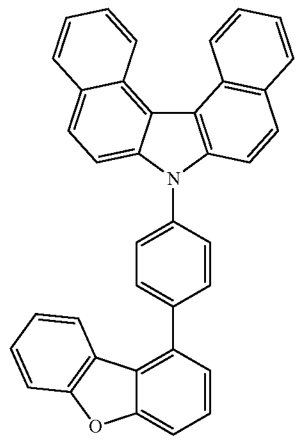
H-60
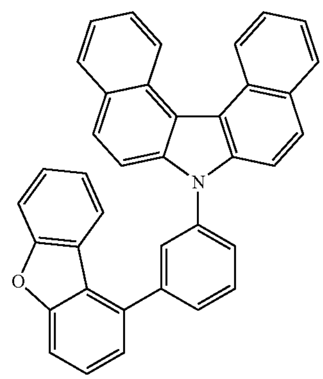

-continued
H-61
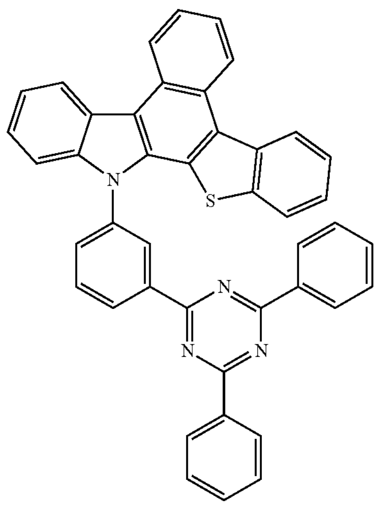
H-62
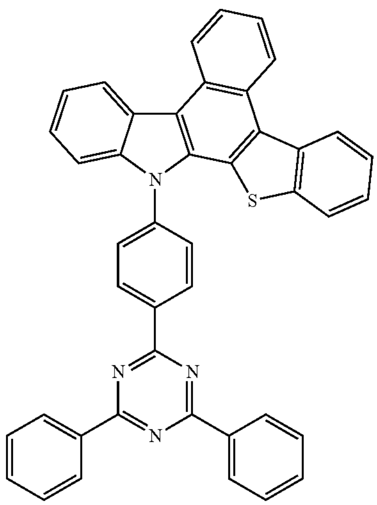
H-63
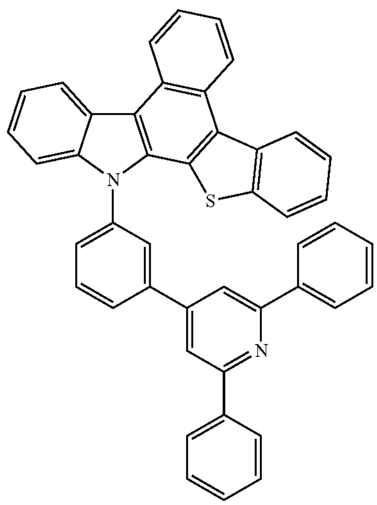
-continued
H-64
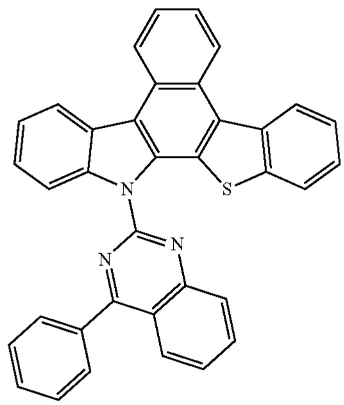
H-65
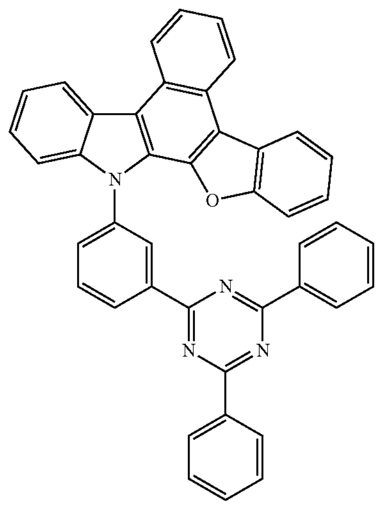
H-66
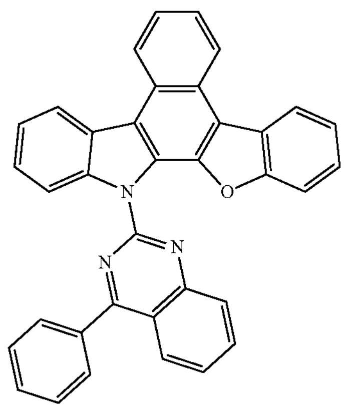

-continued
H-67
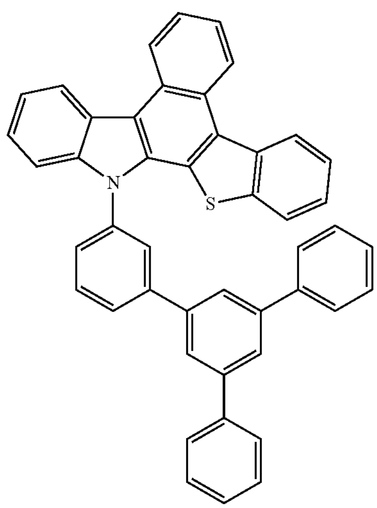
H-68
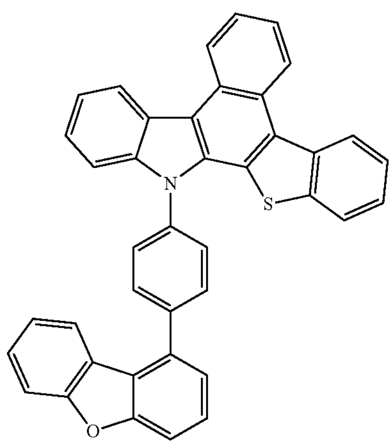
H-69
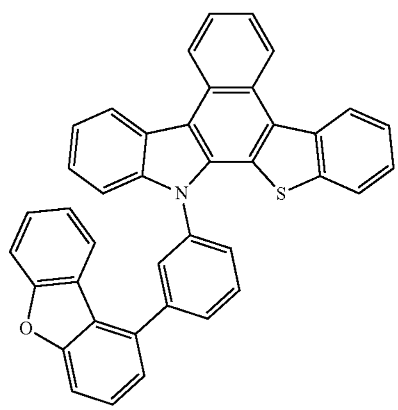
-continued
H-70
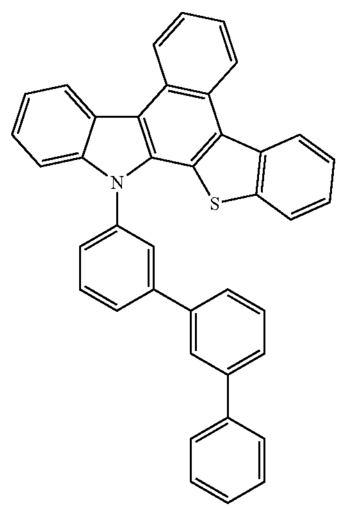
H-71
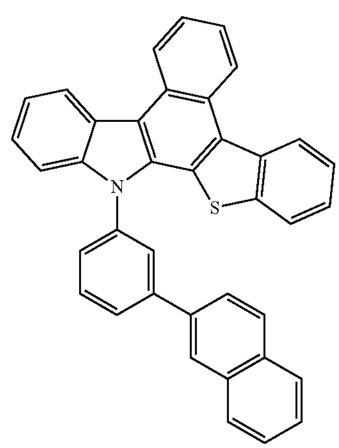
H-72
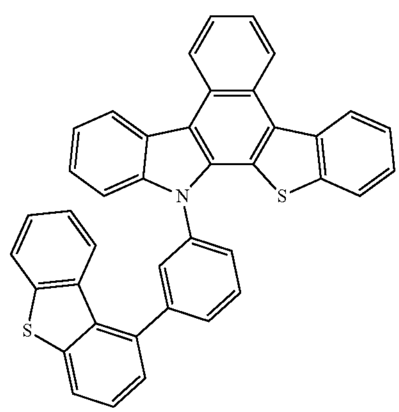

-continued
H-73
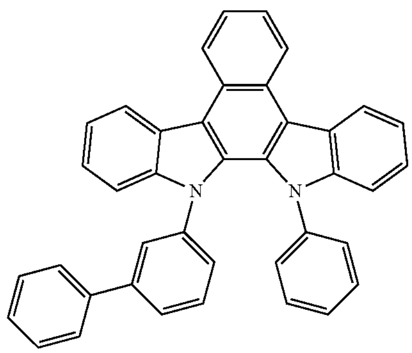
H-74
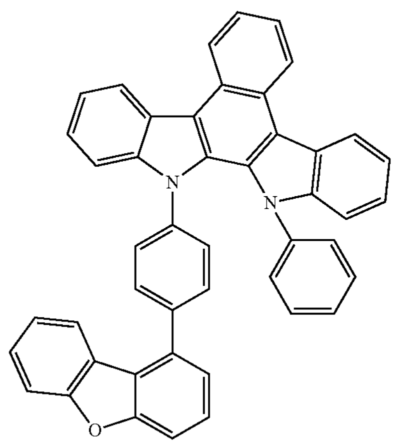
H-75
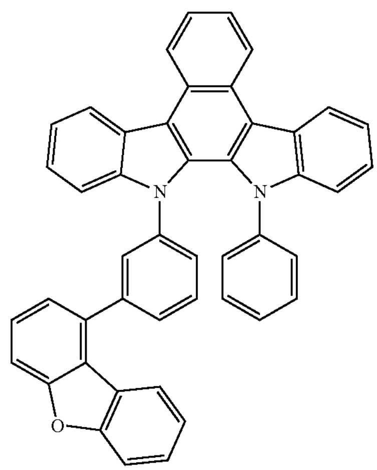
H-76
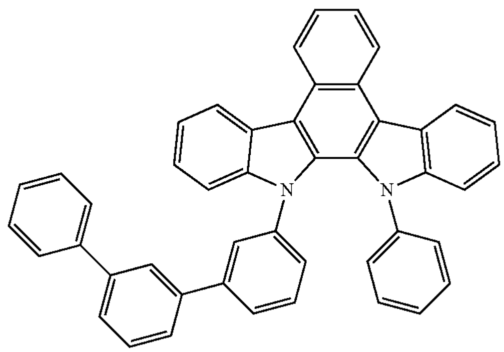
-continued
H-77
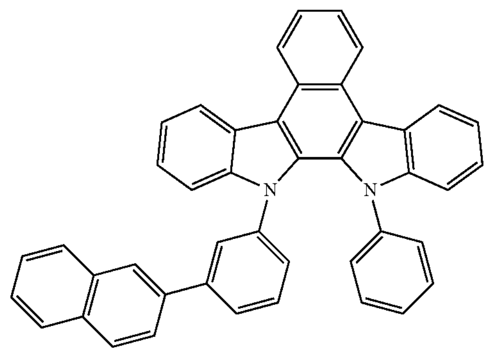
H-78
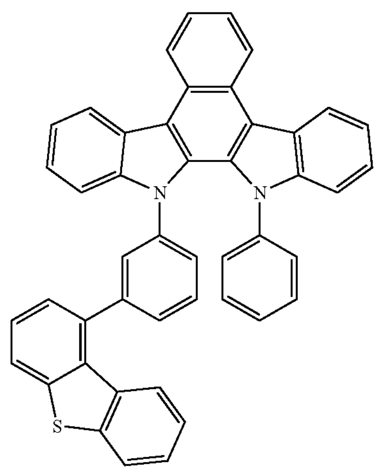
H-79
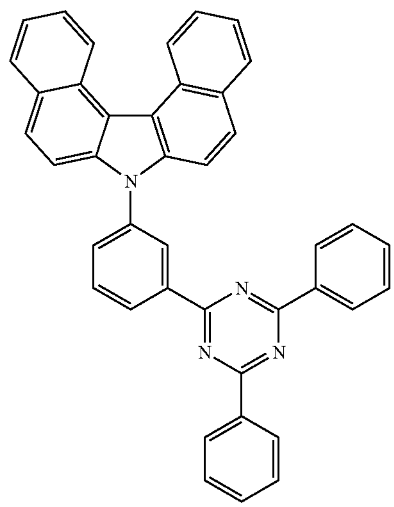

-continued
H-80
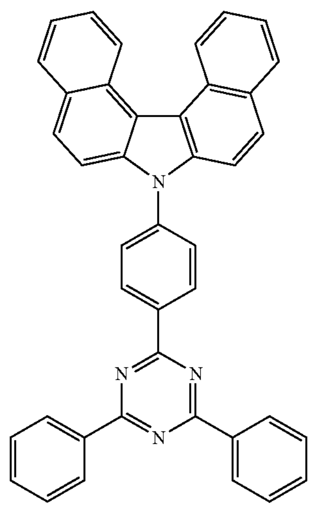
H-81
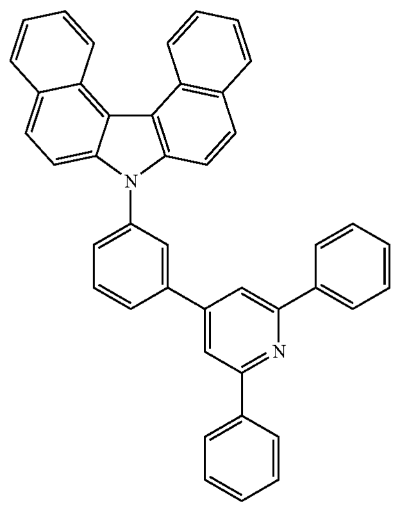
H-82
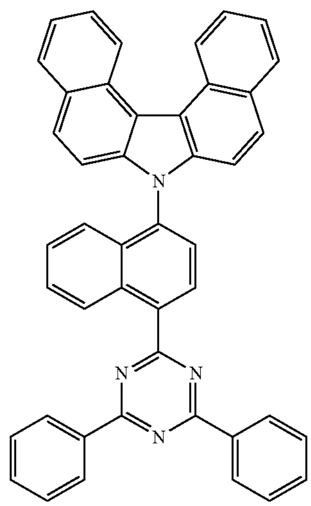
-continued
H-83
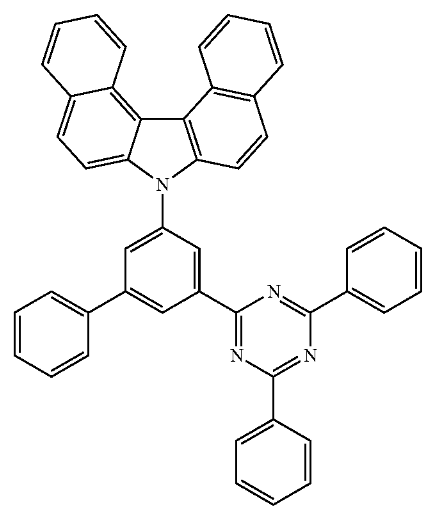
H-84
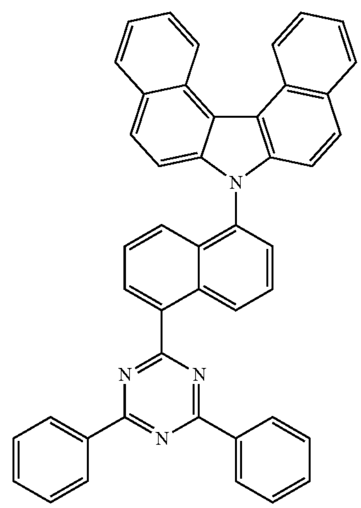
H-85
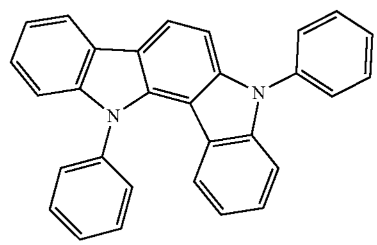
H-86
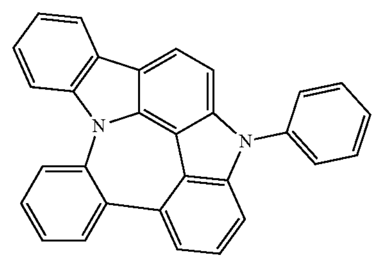

-continued
H-87
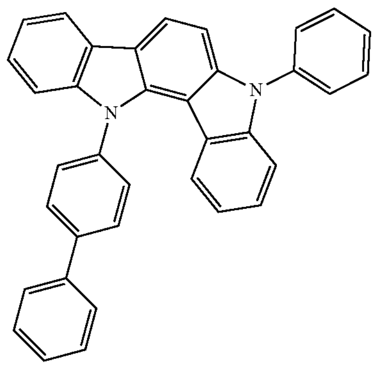
H-88
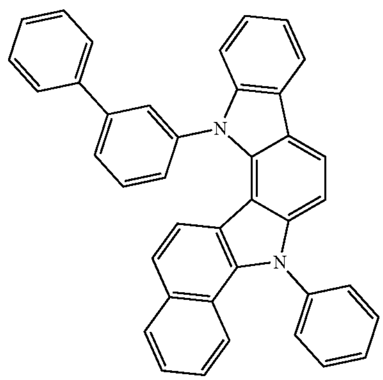
H-89
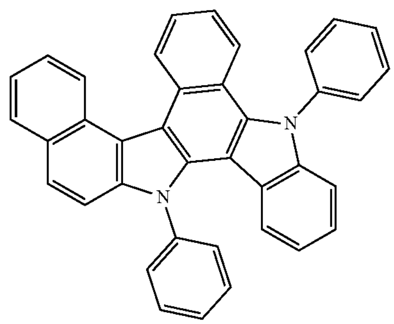
H-90
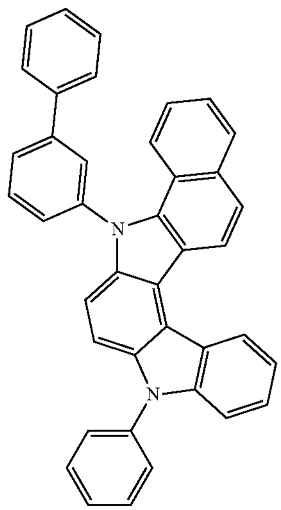
-continued
H-91
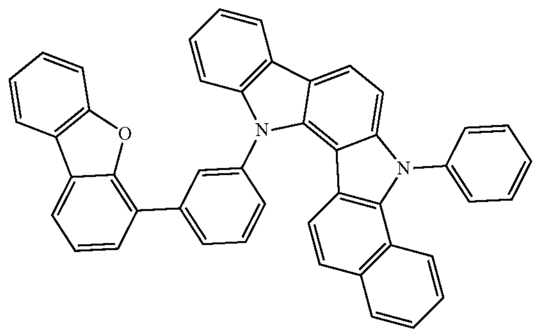
H-92
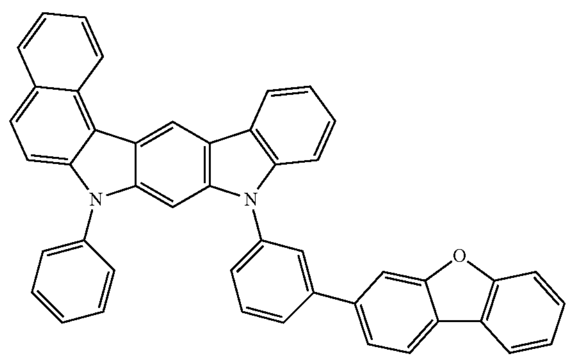
H-93
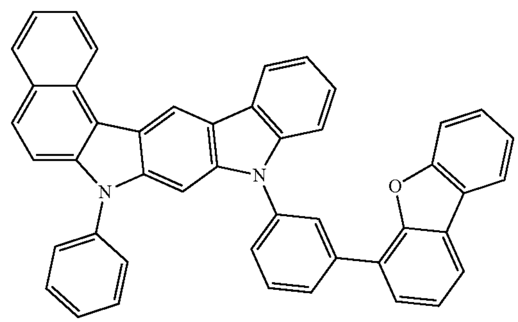
H-94
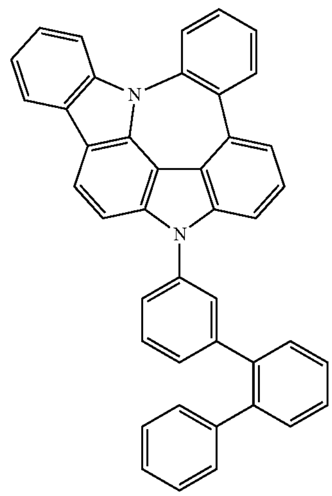

-continued
H-95
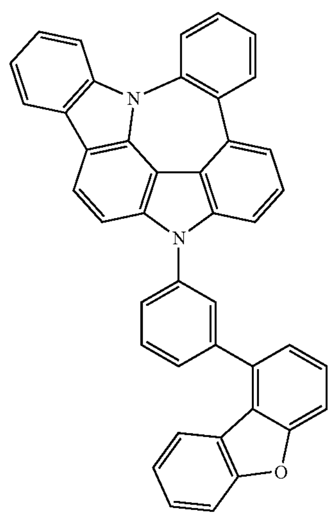
H-96
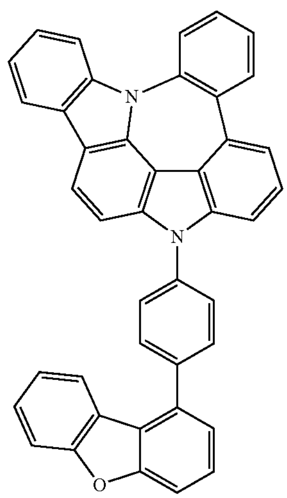
H-97
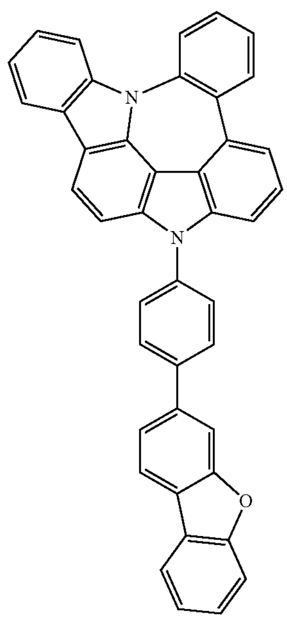
-continued
H-98
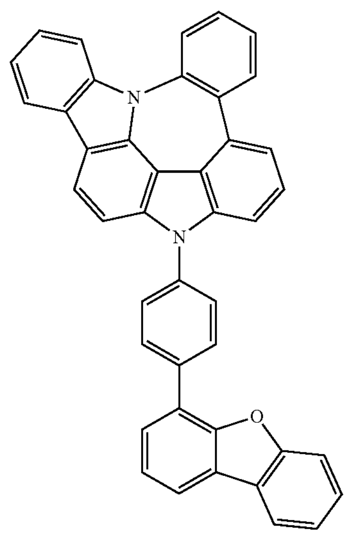
H-99
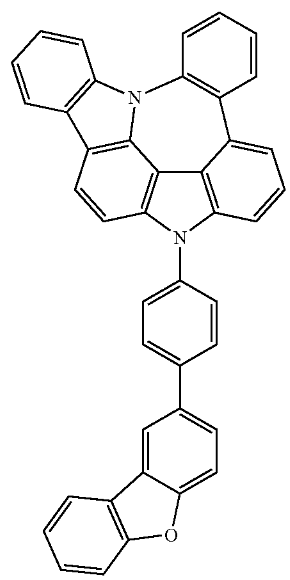
H-100
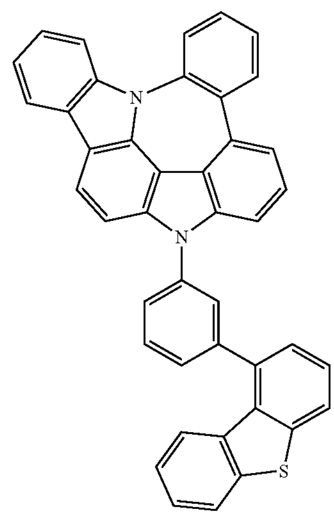

-continued
H-101
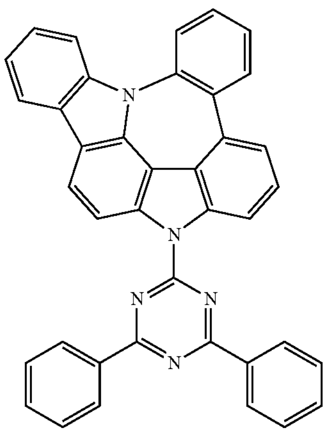
H-102
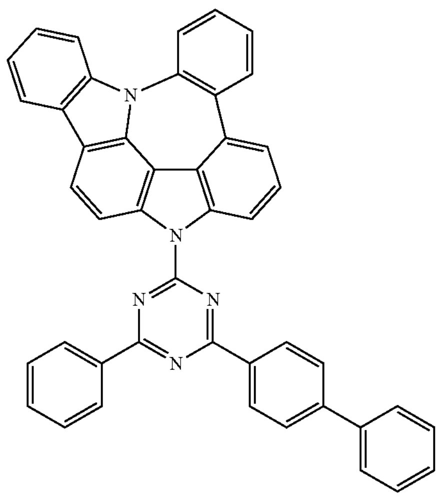
H-103
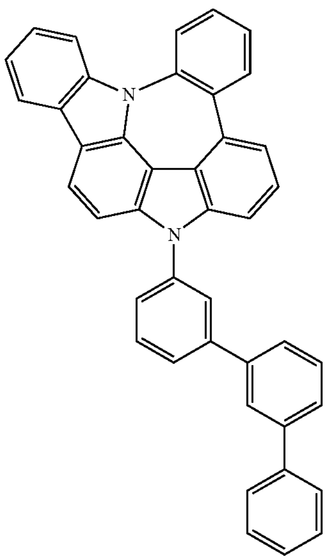
-continued
H-104
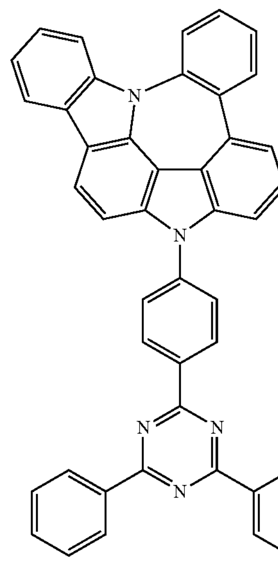
H-105
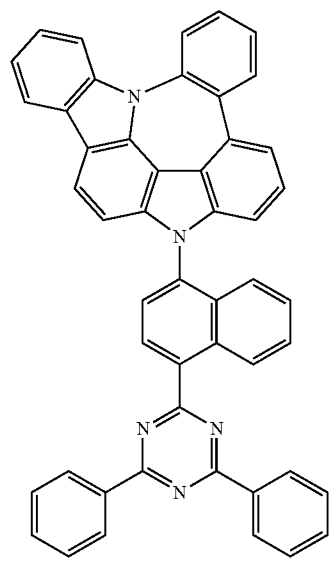
H-106
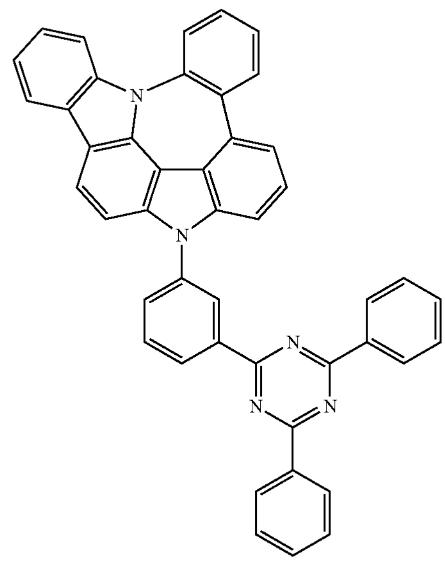

-continued
H-107
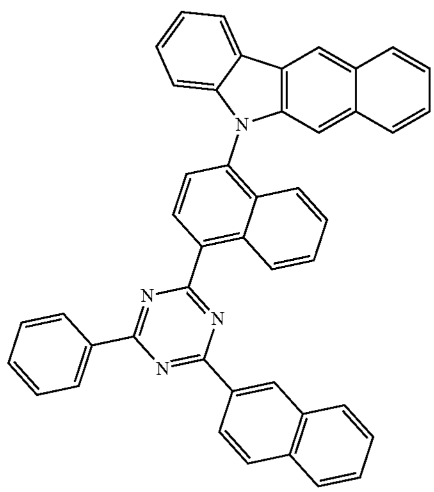
H-108
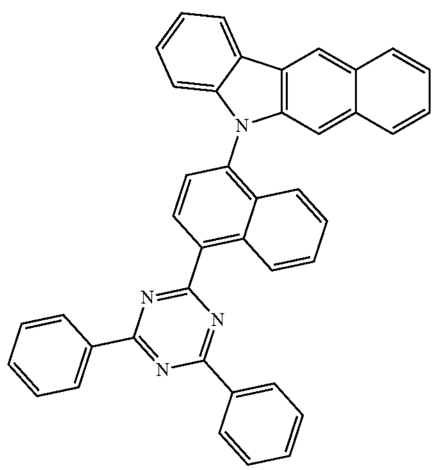
H-109
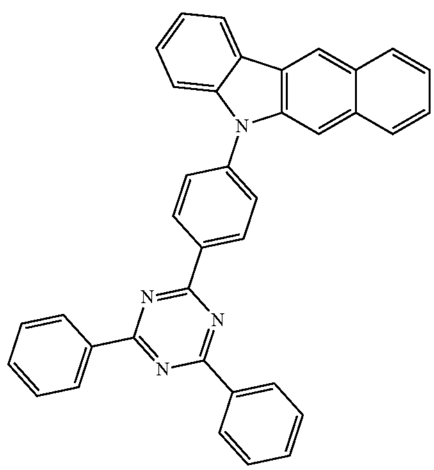
-continued
H-110
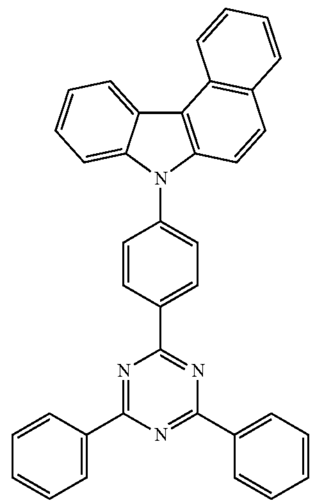
H-111
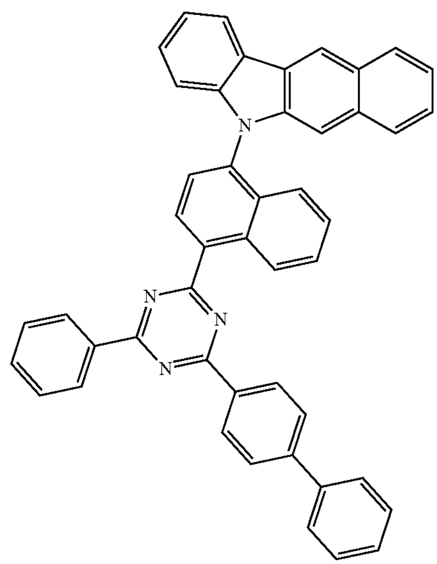
H-112
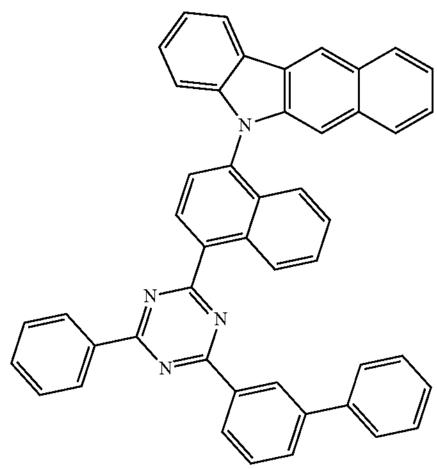

-continued
H-113
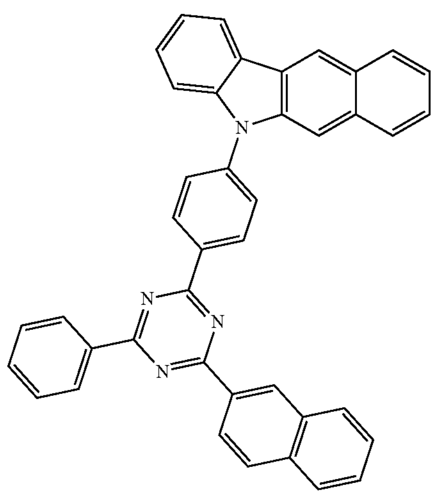
H-114
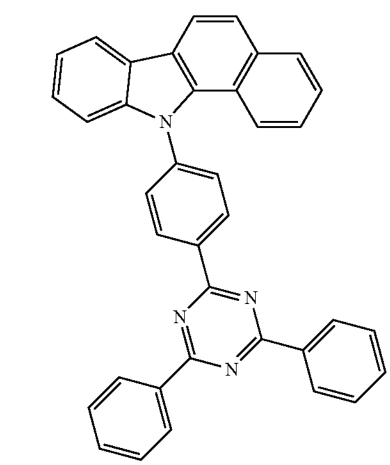
H-115
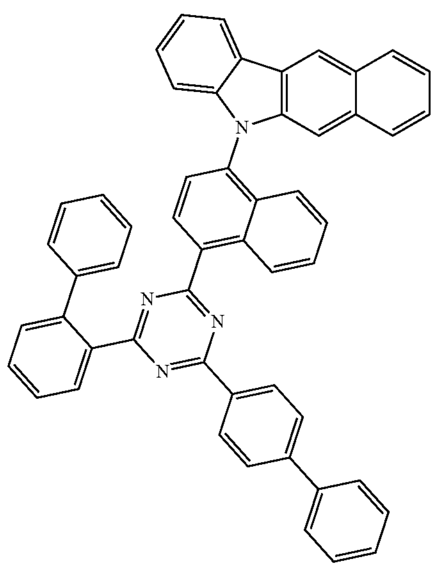
-continued
H-116
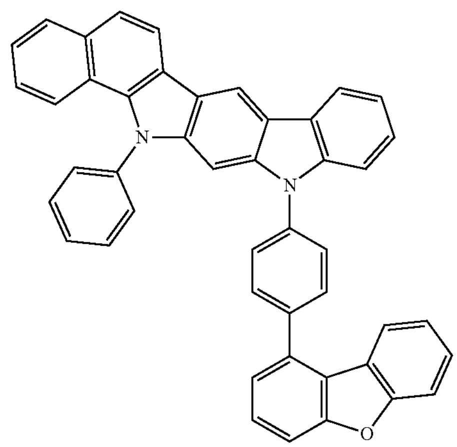
H-117
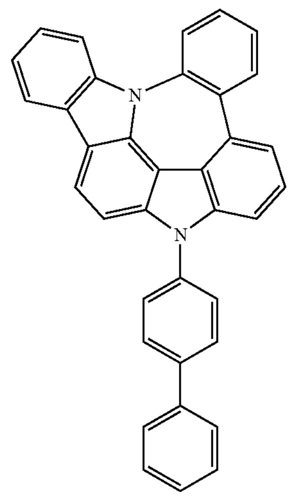

-continued

H-118

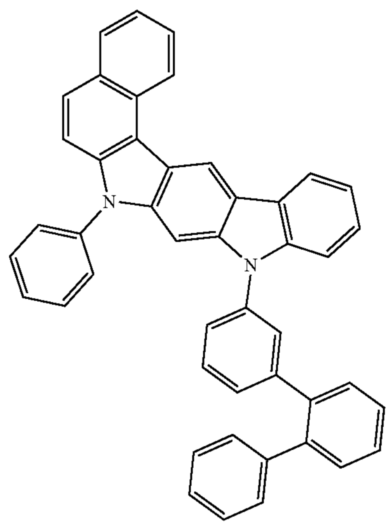

H-119

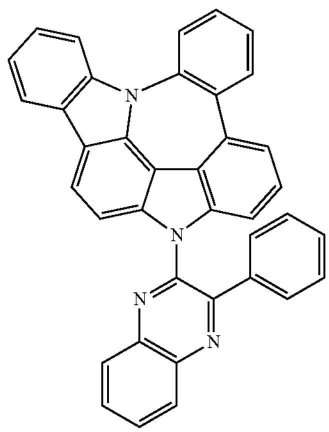

and

-continued

H-120

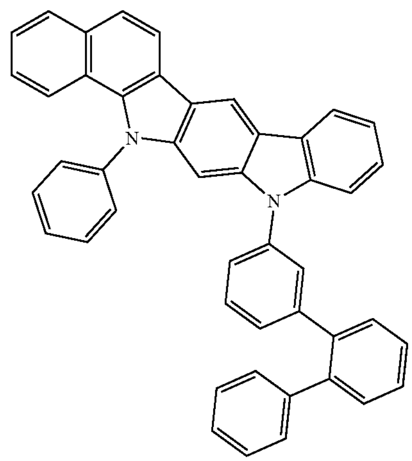

.

9. A plurality of host materials comprising a first host material and a second host material, wherein the first host material comprises the compound represented by formula 1-2 as described in claim 1, and the second host material comprises the compound represented by formula 2 as described in claim 1.

10. An organic electroluminescent device comprising the composition material as described in claim 1.

11. A plurality of host materials comprising a first host material and a second host material, wherein the first host material comprises the compound represented by formula 1-1 as described in claim 2, and the second host material comprises the compound represented by formula 2 as described in claim 2.

12. An organic electroluminescent device comprising the composition material as described in claim 2.

* * * * *